United States Patent
Bellenie et al.

(10) Patent No.: US 12,110,286 B2
(45) Date of Patent: Oct. 8, 2024

(54) BENZIMIDAZOLONE DERIVED INHIBITORS OF BCL6

(71) Applicants: Cancer Research Technology Limited, London (GB); The Institute of Cancer Research: Royal Cancer Hospital, London (GB)

(72) Inventors: Benjamin Richard Bellenie, London (GB); Michael K. Carter, London (GB); Kwai Ming Jack Cheung, London (GB); Owen Alexander Davis, London (GB); Swen Hoelder, London (GB); Matthew Garth Lloyd, London (GB); Ana Varela Rodriguez, London (GB); Hannah Woodward, London (GB); Paolo Innocenti, London (GB)

(73) Assignees: Cancer Research Technology Limited, London (GB); The Institute of Cancer Research, London (GB)

( * ) Notice: Subject to any disclaimer, the term of this patent is extended or adjusted under 35 U.S.C. 154(b) by 0 days.

(21) Appl. No.: 16/616,901

(22) PCT Filed: May 25, 2018

(86) PCT No.: PCT/GB2018/051447
§ 371 (c)(1),
(2) Date: Nov. 25, 2019

(87) PCT Pub. No.: WO2018/215801
PCT Pub. Date: Nov. 29, 2018

(65) Prior Publication Data
US 2021/0147382 A1    May 20, 2021

(30) Foreign Application Priority Data
May 26, 2017  (GB) ...................... 1708502
Apr. 13, 2018  (GB) ...................... 1806130

(51) Int. Cl.
| | | |
|---|---|---|
| C07D 401/14 | (2006.01) |
| C07D 401/12 | (2006.01) |
| C07D 403/12 | (2006.01) |
| C07D 403/14 | (2006.01) |
| C07D 405/14 | (2006.01) |
| C07D 409/14 | (2006.01) |
| C07D 413/14 | (2006.01) |
| C07D 417/14 | (2006.01) |
| C07D 471/04 | (2006.01) |
| C07D 471/08 | (2006.01) |
| C07D 487/04 | (2006.01) |

(52) U.S. Cl.
CPC ......... C07D 401/14 (2013.01); C07D 401/12 (2013.01); C07D 403/12 (2013.01); C07D 403/14 (2013.01); C07D 405/14 (2013.01); C07D 409/14 (2013.01); C07D 413/14 (2013.01); C07D 417/14 (2013.01); C07D 471/04 (2013.01); C07D 471/08 (2013.01); C07D 487/04 (2013.01)

(58) Field of Classification Search
CPC .. C07D 401/14; C07D 401/12; C07D 403/12; C07D 403/14; C07D 405/14; C07D 409/14; C07D 413/14; C07D 417/14; C07D 471/04; C07D 471/08; C07D 487/04
See application file for complete search history.

(56) References Cited

U.S. PATENT DOCUMENTS

| | | |
|---|---|---|
| 8,338,464 B2 | 12/2012 | Melnick et al. |
| 11,161,839 B2 | 11/2021 | Bellenie et al. |
| 2005/0256157 A1 | 11/2005 | Gesner et al. |
| 2021/0206756 A1 | 7/2021 | Bellenie et al. |

FOREIGN PATENT DOCUMENTS

| | | |
|---|---|---|
| CN | 105017159 A | 11/2015 |
| EP | 2565193 A1 | 3/2013 |
| JP | H0259572 A | 2/1990 |

(Continued)

OTHER PUBLICATIONS

Chemical Abstracts Registry No. 1821048-93-4, indexed in the Registry file on Nov. 20, 2015. (Year: 2015).*
International Search Report for International Application No. PCT/GB2018/051447 dated Aug. 2, 2018.
International Search Report for International Application No. PCT/GB2018/051444 dated Aug. 13, 2018.

(Continued)

Primary Examiner — Laura L Stockton
(74) Attorney, Agent, or Firm — Goodwin Procter LLP

(57) ABSTRACT

The present invention relates to compounds of Formula I that function as inhibitors of BCL6 (B-cell lymphoma 6) activity: wherein $X_1$, $X_2$, $R^1$, $R^2$ and $R^3$ are each as defined herein. The present invention also relates to processes for the preparation of these compounds, to pharmaceutical compositions comprising them, and to their use in the treatment of proliferative disorders, such as cancer, as well as other diseases or conditions in which BCL6 activity is implicated.

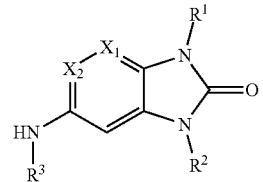

Formula I

15 Claims, No Drawings

(56) References Cited

FOREIGN PATENT DOCUMENTS

| | | |
|---|---|---|
| JP | 2012/515793 A | 7/2012 |
| JP | 2013/517273 A | 5/2013 |
| JP | 2014/520767 A | 8/2014 |
| WO | WO-2004/046118 A2 | 6/2004 |
| WO | WO-2008/066887 A2 | 6/2008 |
| WO | WO-2009/063240 A1 | 5/2009 |
| WO | WO-2010/085684 A1 * 7/2010 ........... C07D 401/12 |
| WO | WO-2016/033100 A1 | 3/2016 |
| WO | WO-2016/033416 A1 | 3/2016 |
| WO | WO-2017/007658 A1 | 1/2017 |
| WO | WO-2018/108704 A1 | 6/2018 |

OTHER PUBLICATIONS

Chemical Abstracts RN: 1436344-98-7., "2H-Benzimidazol-2-one, 5-[(5,6-dimethyl [1,2,4] triazolo [1,5-a]pyrimidin-7-yl)amino]-1,3-dihydro-1,3-dimethyl-," Chemical Library, Ukrorgsyntez Ltd.: 1 page (Entered STN: Jun. 9, 2013).

Hanan et al., "Discovery of Selective and Noncovalent Diaminopyrimidine-Based Inhibitors of Epidermal Growth Factor Receptor Containing the T790M Resistance Mutation," Journal of Medicinal Chemistry, 57(23): 10176-10191 w/ Supporting Information (2014).

Kamada et al., "Discovery of a B-Cell Lymphoma 6 Protein-Protein Interaction Inhibitor by a Biophysics-Driven Fragment-Based Approach," Journal of Medicinal Chemistry, 60(10): 4358-4368 (2017).

U.S. Appl. No. 16/616,906 U.S. Pat. No. 11,161,839, Quinolone Derived Inhibitors of BCL6, filed Nov. 25, 2019, Granted.

U.S. Appl. No. 17/046,650 U.S. Pat. No. 11,512,095, BCL6 Inhibitors, filed Oct. 9, 2020, Granted.

U.S. Appl. No. 17/968,159 US 2023/0287003, BCL6 Inhibitors, filed Oct. 18, 2022, Published.

U.S. Appl. No. 17/768,174,[1,4]Oxazepino[2,3-C]Quinolinone Derivatives as BLC6 Inhibitors, filed Apr. 11, 2022, Pending.

* cited by examiner

BENZIMIDAZOLONE DERIVED INHIBITORS OF BCL6

RELATED APPLICATIONS

This application is a U.S. National Stage application of International Application No. PCT/GB2018/051447 filed May 25, 2018, which claims priority from Great Britain Application No. 1806130.9 filed Apr. 13, 2018 and Great Britain Application No. 1708502.8 filed May 26, 2017.

INTRODUCTION

The present invention relates to certain compounds that function as inhibitors of BCL6 (B-cell lymphoma 6) activity. The present invention also relates to processes for the preparation of these compounds, to pharmaceutical compositions comprising them, and to their use in the treatment of proliferative disorders, such as cancer, as well as other diseases or conditions in which BCL6 activity is implicated.

BACKGROUND OF THE INVENTION

BCL6 is a zinc finger transcription repressor that plays a key role in the formation and development of germinal centres, in which B cells undergo somatic hypermutation and recombination of the immunoglobulin genes, in order to generate diversity in antibodies against a variety of foreign antigens (Dent et al., *Science*, 1997, 276, 589-592). BCL6 allows the proliferation of antibody producing B cells by repressing genes involved in DNA damage response, cell cycle arrest and apoptosis. BCL6 mediates this repression by recruiting the corepressor proteins SMRT, NCoR and BCoR to an extended groove motif that forms along the dimer interface of the BCL6 BTB (BR-C, Ttk and Bab) domain (Ahmad et al., *Mol Cell*, 2003, 12, 1551-1564; Ghetu et al., *Mol Cell*, 2008, 29, 384-391). Genetic upregulation of the BCL6 gene, as seen in many lymphomas, leads to malignant B cell proliferation (Hatzi & Melnick, *Trends Mol Med*, 2014, 20, 343-352). Therefore, there exists a need to develop agents that inhibit the tumourigenic effects of BCL6, either by selectively binding to the BTB domain and preventing corepressor recruitment, or by binding to the BTB domain and inducing protein degradation (Kerres et al. *Cell Rep.*, 2017, 20, 2860-2875).

SUMMARY OF THE INVENTION

According to a first aspect of the present invention, there is provided a compound, or a pharmaceutically acceptable salt, hydrate or solvate thereof, as defined herein.

According to a further aspect of the present invention, there is provided a pharmaceutical composition comprising a compound as defined herein, or a pharmaceutically acceptable salt, hydrate or solvate thereof, in admixture with a pharmaceutically acceptable diluent or carrier.

According to a further aspect of the present invention, there is provided a method of inhibiting BCL6 activity, in vitro or in vivo, said method comprising contacting a cell with an effective amount of a compound or a pharmaceutically acceptable salt, hydrate or solvate thereof as defined herein.

According to a further aspect of the present invention, there is provided a method of inhibiting cell proliferation, in vitro or in vivo, said method comprising contacting a cell with an effective amount of a compound or a pharmaceutically acceptable salt, hydrate or solvate thereof as defined herein, or a pharmaceutical composition as defined herein.

According to a further aspect of the present invention, there is provided a method of treating a disease or disorder in which BCL6 activity is implicated in a patient in need of such treatment, said method comprising administering to said patient a therapeutically effective amount of a compound or a pharmaceutically acceptable salt, hydrate or solvate thereof as defined herein, or a pharmaceutical composition as defined herein.

According to a further aspect of the present invention, there is provided a method of treating a proliferative disorder in a patient in need of such treatment, said method comprising administering to said patient a therapeutically effective amount of a compound or a pharmaceutically acceptable salt, hydrate or solvate thereof as defined herein, or a pharmaceutical composition as defined herein.

According to a further aspect of the present invention, there is provided a method of treating cancer in a patient in need of such treatment, said method comprising administering to said patient a therapeutically effective amount of a compound or a pharmaceutically acceptable salt, hydrate or solvate thereof as defined herein, or a pharmaceutical composition as defined herein.

According to a further aspect of the present invention, there is provided a compound, or a pharmaceutically acceptable salt, hydrate or solvate thereof, or a pharmaceutical composition as defined herein for use in therapy.

According to a further aspect of the present invention, there is provided a compound or a pharmaceutically acceptable salt, hydrate or solvate thereof as defined herein, or a pharmaceutical composition as defined herein, for use in the treatment of a proliferative condition.

According to a further aspect of the present invention, there is provided a compound, or a pharmaceutically acceptable salt, hydrate or solvate thereof, or a pharmaceutical composition as defined herein for use in the treatment of cancer. In a particular embodiment, the cancer is human cancer.

According to a further aspect of the present invention, there is provided a compound, or a pharmaceutically acceptable salt, hydrate or solvate thereof, as defined herein for use in the inhibition of BCL6 activity.

According to a further aspect of the present invention, there is provided a compound, or a pharmaceutically acceptable salt, hydrate or solvate thereof, as defined herein for use in the treatment of a disease or disorder in which BCL6 activity is implicated.

According to a further aspect of the present invention, there is provided the use of a compound, or a pharmaceutically acceptable salt, hydrate or solvate thereof, as defined herein in the manufacture of a medicament for the treatment of a proliferative condition.

Suitably, the proliferative disorder is cancer, suitably a human cancer (for example haematological cancers such as lymphomas (including diffuse large B-cell lymphoma (DLBCL), follicular lymphoma (FL), Burkitt lymphoma (BL) and angioimmunoblastic T-cell lymphoma (AITL)), leukaemias (including acute lymphoblastic leukaemia (ALL) and chronic myeloid leukaemia (CML)) and multiple myeloma, and solid tumours (including glioma, breast cancer, non-small cell lung cancer (NSCLC) and squamous cell carcinomas (SCC) (including SCC of the head and neck, oesophagus, lung and ovary))).

According to a further aspect of the present invention, there is provided the use of a compound, or a pharmaceutically acceptable salt, hydrate or solvate thereof, as defined herein in the manufacture of a medicament for the treatment of cancer.

According to a further aspect of the present invention, there is provided a use of a compound, or a pharmaceutically acceptable salt, hydrate or solvate thereof, as defined herein in the manufacture of a medicament for the inhibition of BCL6 activity.

According to a further aspect of the present invention, there is provided a use of a compound, or a pharmaceutically acceptable salt, hydrate or solvate thereof, as defined herein in the manufacture of a medicament for the treatment of a disease or disorder in which BCL6 activity is implicated.

According to a further aspect of the present invention, there is provided a process for preparing a compound, or a pharmaceutically acceptable salt, hydrate or solvate thereof, as defined herein.

According to a further aspect of the present invention, there is provided a compound, or a pharmaceutically acceptable salt, hydrate or solvate thereof, obtainable by, or obtained by, or directly obtained by a process of preparing a compound as defined herein.

According to a further aspect of the present invention, there are provided novel intermediates as defined herein which are suitable for use in any one of the synthetic methods set out herein.

Features, including optional, suitable, and preferred features in relation to one aspect of the invention may also be features, including optional, suitable and preferred features in relation to any other aspect of the invention.

DETAILED DESCRIPTION OF THE INVENTION

Definitions

Unless otherwise stated, the following terms used in the specification and claims have the following meanings set out below.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

In this specification the term "alkyl" includes both straight and branched chain alkyl groups. References to individual alkyl groups such as "propyl" are specific for the straight chain version only and references to individual branched chain alkyl groups such as "isopropyl" are specific for the branched chain version only. For example, "(1-6C)alkyl" includes (1-4C)alkyl, (1-3C)alkyl, propyl, isopropyl and t-butyl.

The term "(m-nC)" or "(m-nC) group" used alone or as a prefix, refers to any group having m to n carbon atoms.

An "alkylene" group is an alkyl group that is positioned between and serves to connect two other chemical groups. Thus, "(1-6C)alkylene" means a linear saturated divalent hydrocarbon radical of one to six carbon atoms or a branched saturated divalent hydrocarbon radical of three to six carbon atoms, for example, methylene ($—CH_2—$), ethylene ($—CH_2CH_2—$), propylene ($—CH_2CH_2CH_2—$), 2-methylpropylene ($—CH_2CH(CH_3)CH_2—$), pentylene ($—CH_2CH_2CH_2CH_2CH_2—$), and the like.

"(3-10C)cycloalkyl" means a hydrocarbon ring containing from 3 to 10 carbon atoms, for example, cyclopropyl, cyclobutyl, cyclopentyl, cyclohexyl, cycloheptyl and bicyclo[2.2.1]heptyl.

"(3-10C)cycloalkenyl" means a hydrocarbon ring containing from 3 to 10 carbon atoms and at least one double bond, for example, cyclobutenyl, cyclopentenyl, cyclohexenyl or cycloheptenyl, such as 3-cyclohexen-1-yl, or cyclooctenyl.

The term "halo" or "halogeno" refers to fluoro, chloro, bromo and iodo, suitably fluoro, chloro and bromo, more suitably, fluoro and chloro.

The term "heterocyclyl", "heterocyclic" or "heterocycle" means a non-aromatic saturated or partially saturated monocyclic, fused, bridged, or spiro bicyclic heterocyclic ring system(s). Monocyclic heterocyclic rings contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles contain from 7 to 17 member atoms, suitably 7 to 12 member atoms, in the ring. Bicyclic heterocyclic(s) rings may be fused, spiro, or bridged ring systems. Examples of heterocyclic groups include cyclic ethers such as oxiranyl, oxetanyl, tetrahydrofuranyl, dioxanyl, and substituted cyclic ethers. Heterocycles containing nitrogen include, for example, azetidinyl, pyrrolidinyl, piperidinyl, piperazinyl, tetrahydrotriazinyl, tetrahydropyrazolyl, and the like. Typical sulfur containing heterocycles include tetrahydrothienyl, dihydro-1,3-dithiol, tetrahydro-2H-thiopyran, and hexahydrothiepine. Other heterocycles include dihydro-oxathiolyl, tetrahydro-oxazolyl, tetrahydro-oxadiazolyl, tetrahydrodioxazolyl, tetrahydro-oxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo ($=O$) or thioxo ($=S$) substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. However, reference herein to piperidino or morpholino refers to a piperidin-1-yl or morpholin-4-yl ring that is linked via the ring nitrogen.

By "bridged ring systems" is meant ring systems in which two rings share more than two atoms, see for example *Advanced Organic Chemistry*, by Jerry March, 4th Edition, Wiley Interscience, pages 131-133, 1992. Examples of bridged heterocyclyl ring systems include, aza-bicyclo[2.2.1]heptane, 2-oxa-5-azabicyclo[2.2.1]heptane, aza-bicyclo[2.2.2]octane, aza-bicyclo[3.2.1]octane and quinuclidine.

By "spiro bi-cyclic ring systems" we mean that the two ring systems share one common spiro carbon atom, i.e. the heterocyclic ring is linked to a further carbocyclic or heterocyclic ring through a single common spiro carbon atom. Examples of spiro ring systems include 6-azaspiro[3.4]octane, 2-oxa-6-azaspiro[3.4]octane, 2-azaspiro[3.3]heptanes, 2-oxa-6-azaspiro[3.3]heptanes, 7-oxa-2-azaspiro[3.5]nonane, 6-oxa-2-azaspiro[3.4]octane, 2-oxa-7-azaspiro[3.5]nonane and 2-oxa-6-azaspiro[3.5]nonane.

The term "heteroaryl" or "heteroaromatic" means an aromatic mono-, bi-, or polycyclic ring incorporating one or more (for example 1-4, particularly 1, 2 or 3) heteroatoms selected from nitrogen, oxygen or sulfur. The term heteroaryl includes both monovalent species and divalent species. Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydropyrido[2,3-b]pyrazinyl and 3,4-dihydro-2H-pyrido[3,2-b][1,4]oxazinyl.

Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

A bicyclic heteroaryl group may be, for example, a group selected from:

a benzene ring fused to a 5- or 6-membered ring containing 1, 2 or 3 ring heteroatoms;

a pyridine ring fused to a 5- or 6-membered ring containing 1, 2 or 3 ring heteroatoms;

a pyrimidine ring fused to a 5- or 6-membered ring containing 1 or 2 ring heteroatoms;

a pyrrole ring fused to a 5- or 6-membered ring containing 1, 2 or 3 ring heteroatoms;

a pyrazole ring fused to a 5- or 6-membered ring containing 1 or 2 ring heteroatoms;

a pyrazine ring fused to a 5- or 6-membered ring containing 1 or 2 ring heteroatoms;

an imidazole ring fused to a 5- or 6-membered ring containing 1 or 2 ring heteroatoms;

an oxazole ring fused to a 5- or 6-membered ring containing 1 or 2 ring heteroatoms;

an isoxazole ring fused to a 5- or 6-membered ring containing 1 or 2 ring heteroatoms;

a thiazole ring fused to a 5- or 6-membered ring containing 1 or 2 ring heteroatoms;

an isothiazole ring fused to a 5- or 6-membered ring containing 1 or 2 ring heteroatoms;

a thiophene ring fused to a 5- or 6-membered ring containing 1, 2 or 3 ring heteroatoms;

a furan ring fused to a 5- or 6-membered ring containing 1, 2 or 3 ring heteroatoms;

a cyclohexyl ring fused to a 5- or 6-membered heteroaromatic ring containing 1, 2 or 3 ring heteroatoms; and a cyclopentyl ring fused to a 5- or 6-membered heteroaromatic ring containing 1, 2 or 3 ring heteroatoms.

Particular examples of bicyclic heteroaryl groups containing a six membered ring fused to a five membered ring include but are not limited to benzfuranyl, benzthiophenyl, benzimidazolyl, benzoxazolyl, benzisoxazolyl, benzthiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl and pyrazolopyridinyl groups.

Particular examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

The term "aryl" means a cyclic or polycyclic aromatic ring having from 5 to 12 carbon atoms. The term aryl includes both monovalent species and divalent species. Examples of aryl groups include, but are not limited to, phenyl, biphenyl, naphthyl and the like. In a particular embodiment, an aryl is phenyl.

The term "optionally substituted" refers to either groups, structures, or molecules that are substituted and those that are not substituted. The term "wherein a/any CH, CH$_2$, CH$_3$ group or heteroatom (i.e. NH) within a $R^1$ group is optionally substituted" suitably means that (any) one of the hydrogen radicals of the $R^1$ group is substituted by a relevant stipulated group.

Where optional substituents are chosen from "one or more" groups it is to be understood that this definition includes all substituents being chosen from one of the specified groups or the substituents being chosen from two or more of the specified groups.

The phrase "compound of the invention" means those compounds which are disclosed herein, both generically and specifically.

Compounds of the Invention

In one aspect, the present invention relates to compounds, or pharmaceutically acceptable salts, hydrates or solvates thereof, having the structural formula (I), shown below:

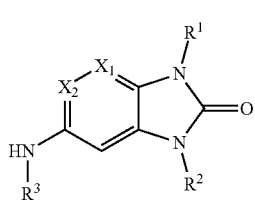

Formula (I)

wherein:

$X_1$ is selected from N or $CR^a$, wherein $R^a$ is selected from hydrogen, (1-2C)alkyl, halogen, hydroxy, (1-2C)alkoxy, (1-2C)haloalkyl, (1-2C)haloalkoxy, (2-4C)alkenyl, (2-4C)alkynyl, nitro, cyano or $NR^bR^c$, wherein $R^b$ and $R^c$ are independently selected from hydrogen or (1-2C)alkyl;

$X_2$ is selected from N or $CR^d$, wherein $R^d$ is selected from hydrogen, (1-2C)alkyl, fluoro, chloro, bromo, hydroxy, (1-2C)alkoxy, (1-2C)haloalkyl or (1-2C)haloalkoxy;

$R^1$ is selected from hydrogen or a group of the formula:

-L-Y—Z wherein:

L is absent or (1-5C)alkylene optionally substituted by one or more substituents selected from (1-2C)alkyl or oxo;

Y is absent or O, S, SO, $SO_2$, $N(R^e)$, C(O), C(O)O, OC(O), $C(O)N(R^e)$, $N(R^e)C(O)$, $N(R^e)C(O)N(R^f)$, $N(R^e)C(O)O$, $OC(O)N(R^e)$, $S(O)_2N(R^e)$, or $N(R^e)SO_2$, wherein $R^e$ and $R^f$ are each independently selected from hydrogen or (1-4C)alkyl; and Z is hydrogen, (1-6C)alkyl, (2-6C)alkenyl, (2-6C)alkynyl, aryl, (3-10C)cycloalkyl, (3-10C)cycloalkenyl, heteroaryl or heterocyclyl; wherein Z is optionally further substituted by one or more substituent groups independently selected from (1-4C)alkyl, halo, (1-4C)haloalkyl, (1-4C)haloalkoxy, amino, (1-4C)aminoalkyl, cyano, hydroxy, carboxy, carbamoyl, sulphamoyl, mercapto, ureido, $NR^gR^h$, $OR^g$, $C(O)R^g$, $C(O)OR^g$, $OC(O)R^g$, $C(O)N(R^g)R^h$, $N(R^g)C(O)R^h$, $S(O)_yR^g$ (where y is 0, 1 or 2), $SO_2N(R^g)R^h$, $N(R^g)SO_2R^g$, $Si(R^g)(R^h)R^i$ or $(CH_2)_zNR^gR^h$ (where z is 1, 2 or 3); wherein $R^{g'}$ $R^h$ and $R^i$ are each independently selected from hydrogen, (1-6C)alkyl or (3-6C)cycloalkyl; or $R^g$ and $R^h$ can be linked such that, together with the nitrogen atom to which they are attached, they form a 4-9 membered heterocyclic ring which is optionally substituted by one or more substituents selected from (1-4C)alkyl, halo, (1-4C) haloalkyl, (1-4C)haloalkoxy, (1-4C)alkoxy, (1-4C) alkylamino, amino, cyano or hydroxy;

$R^2$ is selected from:
(i) hydrogen or methyl;
(ii) a group of the formula:

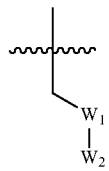

wherein:

denotes the point of attachment;

$W_1$ is selected from $CR^4R^5$ or C(O), wherein $R^4$ and $R^5$ are independently selected from hydrogen, (1-2C) alkyl, fluoro, hydroxy, cyano, nitro, (1-2C)alkoxy, (1-2C)haloalkyl, (1-2C)haloalkoxy or $NR^jR^k$, wherein $R^j$ and $R^k$ are independently selected from hydrogen or (1-2C)alkyl; or $R^4$ and $R^5$ can be linked such that, together with the carbon atom to which they are attached, they form a 3-6-membered carbocyclic ring or a 3-6-membered heterocyclic ring, which is optionally substituted by one or more substituents selected from (1-2C)alkyl, halo, (1-2C)haloalkyl, (1-2C)haloalkoxy, (1-2C)alkoxy, (1-2C)alkylamino, amino, cyano or hydroxy;

$W_2$ is selected from cyano, a 5- or 6-membered heteroaryl, phenyl, $C(O)R^l$, $SO_2R^l$, $C(O)OCH_3$, $C(O)N(H)CH_3$, $CR^6R^7R^8$ or $NR^lR^m$, wherein $R^l$ and $R^m$ are independently selected from hydrogen or (1-4C) alkyl, and wherein:

$R^6$ is selected from hydrogen, (1-2C)alkyl, fluoro, chloro, bromo, hydroxy, amino, cyano, nitro, (1-2C)alkoxy, (1-2C)haloalkyl or (1-2C)haloalkoxy;

$R^7$ is selected from hydrogen, (1-2C)alkyl, fluoro, chloro, bromo, hydroxy, cyano, nitro, (1-2C) alkoxy, (1-2C)haloalkyl, (1-2C)haloalkoxy or a group of the formula:

—$Y_2$-$L_2$-$Z_2$ wherein:

$Y_2$ is absent or selected from O, $N(R^n)$, S, SO, $SO_2$, C(O), C(O)O, OC(O), $C(O)N(R^n)$, $N(R^n)$ C(O), $S(O)_2N(R^n)$, or $N(R^n)SO_2$, wherein $R^n$ is selected from hydrogen or (1-2C)alkyl;

$L_2$ is absent or (1-2C)alkylene; and $Z_2$ is hydrogen, (1-6C)alkyl, (2-4C)alkenyl, (2-4C)alkynyl, phenyl, (3-6C)cycloalkyl, 5-6 membered heteroaryl or a 4-6-membered heterocyclyl; wherein $Z_2$ is optionally substituted by one or more substituents selected from (1-4C)alkyl, halo, (1-4C)haloalkyl, (1-4C)haloalkoxy, (1-4C)alkoxy, (1-4C)alkylamino, amino, cyano, nitro, hydroxy, $C(O)R^o$, $C(O)OR^o$, $OC(O)R^o$, $C(O)N(R^o)R^p$, $NR^oC(O)R^p$, wherein R° and R^p are independently selected from hydrogen or (1-4C)alkyl; and R^8 is selected from (1-2C)alkyl, —C(O)OR^q, OR^q, —C(O)NR^q, NR^qR^r, phenyl or a 5-membered heteroaryl, wherein R^q and R^r are independently selected from hydrogen or (1-2C)alkyl;

or R^6 and R^7 can be linked such that, together with the carbon atom to which they are attached, they form a 3-6-membered carbocyclic ring or a 3-6-membered heterocyclic ring, which is optionally substituted by one or more substituents selected from (1-2C)alkyl, halo, (1-2C)haloalkyl, (1-2C)haloalkoxy, (1-2C)alkoxy, (1-2C)alkylamino, amino, cyano or hydroxyl; or (iii) a group of the formula:

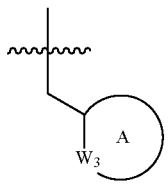

wherein:

denotes the point of attachment;

ring A is a 4 to 6 membered cycloalkyl or heterocyclyl ring, optionally substituted with one or more substituent groups selected from (1-2C)alkyl, halo, hydroxy, cyano or (1-2C)alkoxy;

$W_3$ is selected from $NR^{100}$ or $CR^{101}R^{102}$, wherein $R^{100}$ is selected from hydrogen, (1-2C)alkyl, (1-4C)haloalkyl, (1-4C)hydroxyalkyl, —C(O)—CH$_3$ or —C(O)OR^{ab} wherein R^{ab} is (1-4C)alkyl, $R^{101}$ and $R^{102}$ are each independently selected from hydrogen, (1-2C)alkyl, cyclopropyl, fluoro, chloro, bromo, hydroxy, amino, cyano, nitro, (1-2C)alkoxy, (1-2C)haloalkyl, (1-2C)haloalkoxy, —C(O)OR^{ac}, —NR^{ac}R^{ad}, phenyl or a 5-membered heteroaryl, wherein R^{ac} and R^{ad} are independently selected from hydrogen or (1-2C)alkyl; and $R^3$ is selected from:

i) a group of Formula A shown below:

Formula A

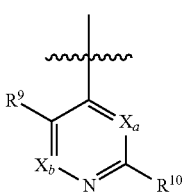

wherein:

denotes the point of attachment;

$X_a$ and $X_b$ are independently selected from N or $CR^{x1}$, wherein $R^{x1}$ is selected from hydrogen, fluoro, chloro, bromo, (1-2C)alkyl, (1-2C)alkoxy, cyano, nitro, acetylenyl, CH$_2$F, CF$_2$H or CF$_3$;

$R^9$ is selected from hydrogen, fluoro, chloro, bromo, (1-2C)alkyl, (1-2C)alkoxy, cyano, nitro, acetylenyl, CH$_2$F, CF$_2$H or CF$_3$;

$R^{10}$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—$Y_3$—$Z_3$ wherein:

$Y_3$ is absent or O, $N(R^s)(CR^sR^t)_{q1}$ (where $q_1$ is 0, 1 or 2), S, SO, SO$_2$, C(O), C(O)O, OC(O), C(O)N(R^s), N(R^s)C(O), N(R^s)C(O)N(R^t), N(R^s)C(O)O, OC(O)N(R^s), S(O)$_2$N(R^s), N(R^s)SO$_2$, wherein R^s and R^t are each independently selected from hydrogen or (1-4C)alkyl; and $Z_3$ is hydrogen, (1-6C)alkyl, aryl, (3-6C)cycloalkyl, (2-4C)alkenyl, (2-4C)alkynyl, (3-6C)cycloalkenyl, heteroaryl or 4 to 11-membered heterocyclyl; wherein $Z_3$ is optionally further substituted by one or more substituent groups independently selected from oxo, (1-4C)alkyl, (3-6C)cycloalkyl, halo, (1-4C)haloalkyl, (1-4C)haloalkoxy, (1-4C)hydroxyalkyl, amino, cyano, hydroxy, amido, carboxy, carbamoyl, sulphamoyl, mercapto, C(O)NR^uR^v, NR^uR^v or OR^u, wherein R^u and R^v are each independently selected from hydrogen, (1-4C)alkyl or (3-6C)cycloalkyl; and/or $Z^3$ is optionally further substituted by a group of the formula:

-$L_Z$-$W_Z$ wherein:

$L_Z$ is absent or a (1-5C)alkylene optionally substituted by one or more substituents selected from (1-2C)alkyl or oxo; and $W_Z$ is aryl, heteroaryl, 4- to 7-membered heterocyclyl, 3- to 6-membered carbocycyl, halo, (1-4C)haloalkyl, (1-4C)haloalkoxy, cyano, hydroxy, (1-4C)alkoxy, C(O)R^{xa}, COOR^{xa}, C(O)NR^{xa}R^{xb} or NR^{xa}R^{xb}, wherein R^{xa} and R^{xb} are each independently selected from hydrogen or (1-4C)alkyl; and wherein each aryl, heteroaryl, 4- to 7-membered heterocyclyl or 3- to 6-membered carbocycyl is optionally further substituted by one or more substituent groups independently selected from (1-4C)alkyl, halo, (1-4C)haloalkyl, amino, cyano or hydroxy;

ii) a group of Formula B shown below:

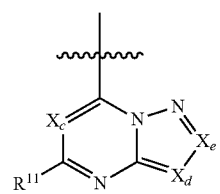

wherein:

denotes the point of attachment;

$X_c$, $X_d$ and $X_e$ are independently selected from N, CH, CF, CCl, C—CN or CCH$_3$;

$R^{11}$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y$_5$—Z$_5$ wherein:

Y$_5$ is absent or O, N(R$^w$), C(O), C(O)O, OC(O), C(O)N(R$^w$), N(R$^w$)C(O), N(R$^w$)C(O)N(R$^x$), N(R$^w$)C(O)O, OC(O)N(R$^w$), S(O)$_2$N(R$^w$), N(R$^w$)SO$_2$, wherein R$^w$ and R$^x$ are each independently selected from hydrogen or (1-4C)alkyl; and Z$_5$ is hydrogen, (1-6C)alkyl, aryl, (3-8C)cycloalkyl, (3-8C)cycloalkenyl, heteroaryl or heterocyclyl; wherein Z$_5$ is optionally further substituted by one or more substituent groups independently selected from (1-4C)alkyl, halo, (1-4C)haloalkyl, (1-4C)haloalkoxy, (1-4C)hydroxyalkyl, amino, cyano, hydroxy, amido, carboxy, carbamoyl, sulphamoyl, mercapto, NR$^y$R$^z$, OR$^y$, wherein R$^y$ and R$^z$ are each independently selected from hydrogen, (1-4C)alkyl or (3-6C)cycloalkyl;

iii) a group of Formula C shown below:

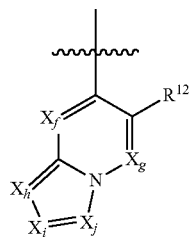

Formula C wherein:

denotes the point of attachment;

$R^{12}$ is selected from fluoro, chloro, bromo, (1-2C)alkyl, (1-2C)alkoxy, cyano, nitro, (2-4C)alkenyl, (2-4C)alkynyl, CH$_2$F, CF$_2$H or CF$_3$;

$X_f$ and $X_g$ are independently selected from N or CR$^{13}$, wherein R$^{13}$ is selected from hydrogen, fluoro, chloro, (1-2C)alkyl, (1-2C)haloalkyl or (1-2C)haloalkoxy;

$X_h$, $X_i$ and $X_j$ are independently selected from N or CR$^{14}$, wherein R$^{14}$ is selected from hydrogen, halo, (1-2C)alkyl, (1-2C)alkoxy, (1-2C)haloalkyl or (1-2C)haloalkoxy;

with the proviso that:

(i) when R$^3$ is a group of Formula B, no more than two of $X_c$, $X_d$ and $X_e$ are nitrogen;

(ii) when R$^3$ is a group of Formula C, no more than three of $X_f$, $X_g$, $X_h$, $X_i$ and $X_j$ are nitrogen;

(iii) when $X_1$ and $X_2$ are CH, R$^1$ and R$^2$ are hydrogen or methyl, R$^3$ is a group of Formula A, $X_a$ is N, $X_b$ is CH and R$^9$ is methyl or fluoro, R$^{10}$ is not a methylsulfonylaminophenyl or an aminosulfonylphenyl;

(iv) when Y$_3$ is NH, each of R$^1$ and R$^2$ are not hydrogen or methyl; and (v) the compound is not one of the following:

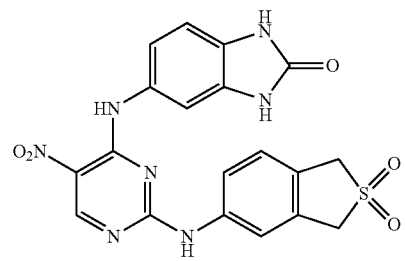

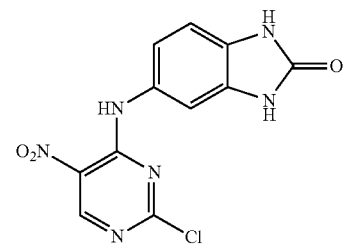

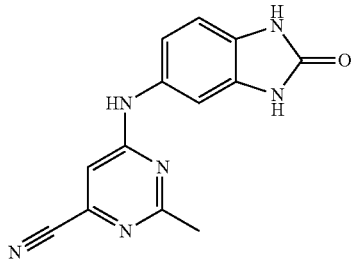

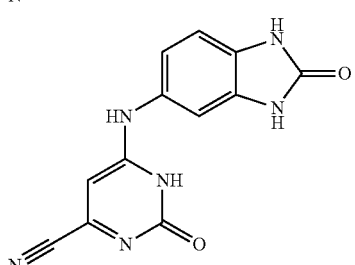

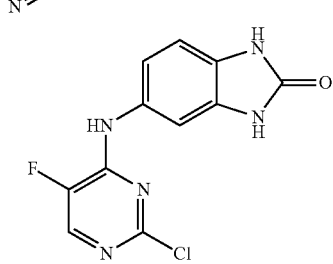

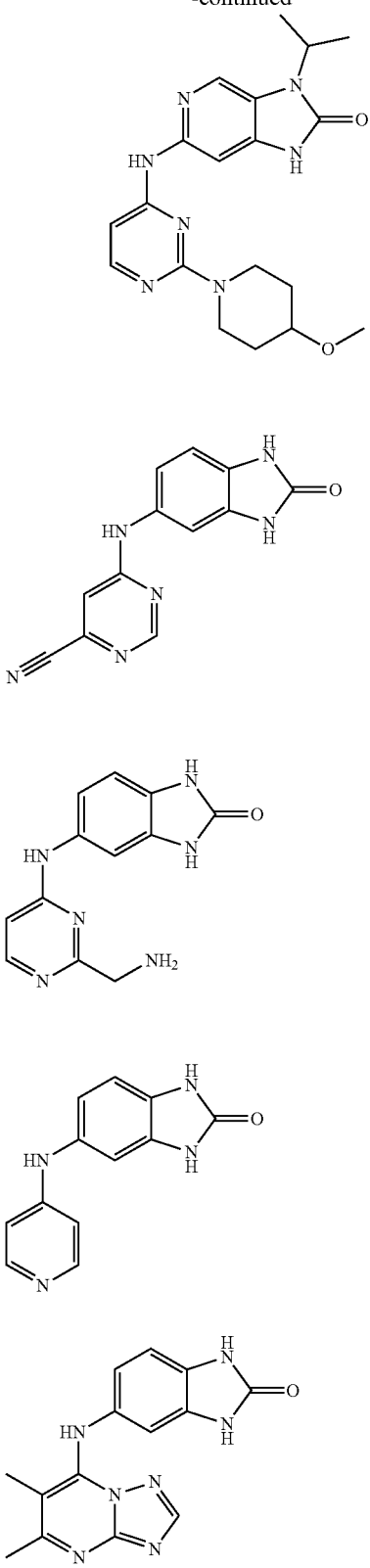

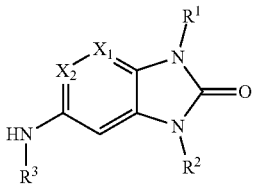

Formula (I)

wherein:
X₁ is selected from N or CR$^a$, wherein R$^a$ is selected from hydrogen, (1-2C)alkyl, halogen, hydroxy, (1-2C)alkoxy, (1-2C)haloalkyl, (1-2C)haloalkoxy, (2-4C)alkenyl, (2-4C)alkynyl, nitro, cyano or NR$^b$R$^o$, wherein R$^b$ and R$^o$ are independently selected from hydrogen or (1-2C)alkyl;

X₂ is selected from N or CR$^d$, wherein R$^d$ is selected from hydrogen, (1-2C)alkyl, fluoro, chloro, bromo, hydroxy, (1-2C)alkoxy, (1-2C)haloalkyl or (1-2C)haloalkoxy;

R¹ is selected from hydrogen or a group of the formula:

-L-Y—Z wherein:
L is absent or (1-5C)alkylene optionally substituted by one or more substituents selected from (1-2C)alkyl or oxo;

Y is absent or O, S, SO, SO₂, N(R$^e$), C(O), C(O)O, OC(O), C(O)N(R$^e$), N(R$^e$)C(O), N(R$^e$)C(O)N(R$^f$), N(R$^e$)C(O)O, OC(O)N(R$^e$), S(O)₂N(R$^e$), or N(R$^e$)SO₂, wherein R$^e$ and R$^f$ are each independently selected from hydrogen or (1-4C)alkyl; and Z is hydrogen, (1-6C)alkyl, (2-6C)alkenyl, (2-6C)alkynyl, aryl, (3-10C)cycloalkyl, (3-10C)cycloalkenyl, heteroaryl or heterocyclyl; wherein Z is optionally further substituted by one or more substituent groups independently selected from (1-4C)alkyl, halo, (1-4C)haloalkyl, (1-4C)haloalkoxy, amino, (1-4C)aminoalkyl, cyano, hydroxy, carboxy, carbamoyl, sulphamoyl, mercapto, ureido, NR$^g$R$^h$, OR$^g$, C(O)R$^g$, C(O)OR$^g$, OC(O)R$^g$, C(O)N(R$^g$)R$^h$, N(R$^g$)C(O)R$^h$, S(O)$_y$R$^9$ (where y is 0, 1 or 2), SO₂N(R$^g$)R$^h$, N(R$^g$)SO₂R$^g$, Si(R$^g$)(R$^h$)R$^i$ or (CH₂)$_z$NR$^g$R$^h$ (where z is 1, 2 or 3); wherein R$^{g'}$ R$^h$ and R$^i$ are each independently selected from hydrogen, (1-6C)alkyl or (3-6C)cycloalkyl; or R$^g$ and R$^h$ can be linked such that, together with the nitrogen atom to which they are attached, they form a 4-9 membered heterocyclic ring which is optionally substituted by one or more substituents selected from (1-4C)alkyl, halo, (1-4C)haloalkyl, (1-4C)haloalkoxy, (1-4C)alkoxy, (1-4C)alkylamino, amino, cyano or hydroxy; R² is selected from:
(i) hydrogen or methyl;
(ii) a group of the formula:

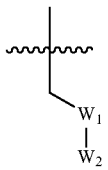

In an embodiment, the present invention relates to compounds, or pharmaceutically acceptable salts, hydrates or solvates thereof, having the structural formula (I), shown below:

wherein:

denotes the point of attachment;
$W_1$ is selected from $CR^4R^5$ or C(O), wherein $R^4$ and $R^5$ are independently selected from hydrogen, (1-2C)alkyl, fluoro, hydroxy, cyano, nitro, (1-2C)alkoxy, (1-2C)haloalkyl, (1-2C)haloalkoxy or $NR^jR^k$, wherein $R^j$ and $R^k$ are independently selected from hydrogen or (1-2C)alkyl; or
$R^4$ and $R^5$ can be linked such that, together with the carbon atom to which they are attached, they form a 3-6-membered carbocyclic ring or a 3-6-membered heterocyclic ring, which is optionally substituted by one or more substituents selected from (1-2C)alkyl, halo, (1-2C)haloalkyl, (1-2C)haloalkoxy, (1-2C)alkoxy, (1-2C)alkylamino, amino, cyano or hydroxy;
$W_2$ is selected from cyano, a 5- or 6-membered heteroaryl, phenyl, $C(O)R^l$, $SO_2R^l$, $C(O)OCH_3$, $C(O)N(H)CH_3$, $CR^6R^7R^8$ or $NR^lR^m$, wherein $R^l$ and $R^m$ are independently selected from hydrogen or (1-4C)alkyl, and wherein:
$R^6$ is selected from hydrogen, (1-2C)alkyl, fluoro, chloro, bromo, hydroxy, amino, cyano, nitro, (1-2C)alkoxy, (1-2C)haloalkyl or (1-2C)haloalkoxy;
$R^7$ is selected from hydrogen, (1-2C)alkyl, fluoro, chloro, bromo, hydroxy, cyano, nitro, (1-2C)alkoxy, (1-2C)haloalkyl, (1-2C)haloalkoxy or a group of the formula:

—$Y_2$-$L_2$-$Z_2$ wherein:
$Y_2$ is absent or selected from O, N(R″), S, SO, $SO_2$, C(O), C(O)O, OC(O), C(O)N(R″), N(R″)C(O), $S(O)_2N(R″)$, or $N(R″)SO_2$, wherein R″ is selected from hydrogen or (1-2C)alkyl;
$L_2$ is absent or (1-2C)alkylene; and
$Z_2$ is hydrogen, (1-6C)alkyl, (2-4C)alkenyl, (2-4C)alkynyl, phenyl, (3-6C)cycloalkyl, 5-6 membered heteroaryl or a 4-6-membered heterocyclyl; wherein $Z_2$ is optionally substituted by one or more substituents selected from (1-4C)alkyl, halo, (1-4C)haloalkyl, (1-4C)haloalkoxy, (1-4C)alkoxy, (1-4C)alkylamino, amino, cyano, nitro, hydroxy, $C(O)R^o$, $C(O)OR^o$, $OC(O)R^o$, $C(O)N(R^o)R^p$, $NR^oC(O)R^p$, wherein $R^o$ and $R^p$ are independently selected from hydrogen or (1-4C)alkyl; and
$R^8$ is selected from (1-2C)alkyl, —$C(O)OR^q$, $OR^q$, —$C(O)NR^q$, $NR^qR^r$, phenyl or a 5-membered heteroaryl, wherein $R^q$ and $R^r$ are independently selected from hydrogen or (1-2C)alkyl;
or $R^6$ and $R^7$ can be linked such that, together with the carbon atom to which they are attached, they form a 3-6-membered carbocyclic ring or a 3-6-membered heterocyclic ring, which is optionally substituted by one or more substituents selected from (1-2C)alkyl, halo, (1-2C)haloalkyl, (1-2C)haloalkoxy, (1-2C)alkoxy, (1-2C)alkylamino, amino, cyano or hydroxyl; or (iii) a group of the formula:

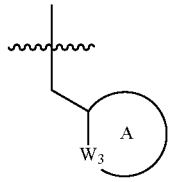

wherein:

denotes the point of attachment;
ring A is a 4 to 6 membered cycloalkyl or heterocyclyl ring, optionally substituted with one or more substituent groups selected from (1-2C)alkyl, halo, hydroxy, cyano or (1-2C)alkoxy;
$W_3$ is selected from $NR^{100}$ or $CR^{101}R^{102}$, wherein $R^{100}$ is selected from hydrogen, (1-2C)alkyl, (1-4C)haloalkyl, (1-4C)hydroxyalkyl, —C(O)—$CH_3$ or —$C(O)OR^{ab}$, wherein $R^{ab}$ is (1-2C)alkyl, $R^{101}$ and $R^{102}$ are each independently selected from hydrogen, (1-2C)alkyl, cyclopropyl, fluoro, chloro, bromo, hydroxy, amino, cyano, nitro, (1-2C)alkoxy, (1-2C)haloalkyl, (1-2C)haloalkoxy, —$C(O)OR^{ac}$, —$NR^{ac}R^{ad}$, phenyl or a 5-membered heteroaryl, wherein $R^{ac}$ and $R^{ad}$ are independently selected from hydrogen or (1-2C)alkyl; and
$R^3$ is selected from:
i) a group of Formula A shown below:

Formula A

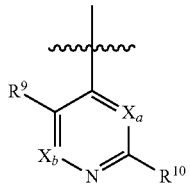

wherein:

denotes the point of attachment;
$X_a$ and $X_b$ are independently selected from N or $CR^{x1}$, wherein $R^{x1}$ is selected from hydrogen, fluoro, chloro, bromo, (1-2C)alkyl, (1-2C)alkoxy, cyano, nitro, acetylenyl, $CH_2F$, $CF_2H$ or $CF_3$;
$R^9$ is selected from hydrogen, fluoro, chloro, bromo, (1-2C)alkyl, (1-2C)alkoxy, cyano, nitro, acetylenyl, $CH_2F$, $CF_2H$ or $CF_3$;
$R^{10}$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—$Y_3$—$Z_3$ wherein:
Y$_3$ is absent or O, N(R$^s$)(CR$^s$R$^t$)$_{q^1}$ (where q is 0, 1 or 2), S, SO, SO$_2$, C(O), C(O)O, OC(O), C(O)N(R$^s$), N(R$^s$)C(O), N(R$^s$)C(O)N(R$^t$), N(R$^s$)C(O)O, OC(O)N(R$^s$), S(O)$_2$N(R$^s$), N(R$^s$)SO$_2$, wherein R$^s$ and R$^t$ are each independently selected from hydrogen or (1-4C)alkyl; and Z$_3$ is hydrogen, (1-6C)alkyl, aryl, (3-6C)cycloalkyl, (2-4C)alkenyl, (2-4C)alkynyl, (3-6C)cycloalkenyl, heteroaryl or 4 to 11-membered heterocyclyl; wherein Z$_3$ is optionally further substituted by one or more substituent groups independently selected from oxo, (1-4C)alkyl, (3-6C)cycloalkyl, halo, (1-4C)haloalkyl, (1-4C)haloalkoxy, amino, cyano, hydroxy, amido, carboxy, carbamoyl, sulphamoyl, mercapto, C(O)NR$^u$R$^v$, NR$^u$R$^v$ or OR$^u$, wherein R$^u$ and R$^v$ are each independently selected from hydrogen, (1-4C)alkyl or (3-6C)cycloalkyl; or Z$^3$ is optionally further substituted by a group of the formula:

-L$_Z$-W$_Z$ wherein:
L$_Z$ is a (1-5C)alkylene optionally substituted by one or more substituents selected from (1-2C)alkyl or oxo; and
W$_Z$ is halo, (1-4C)haloalkyl, (1-4C)haloalkoxy, cyano, hydroxy, (1-4C)alkoxy, C(O)R$^{xa}$, COOR$^{xa}$, C(O)NR$^{xa}$R$^{xb}$ or NR$^{xa}$R$^{xb}$, wherein R$^{xa}$ and R$^{xb}$ are each independently selected from hydrogen or (1-4C)alkyl;

ii) a group of Formula B shown below:

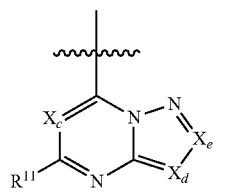

Formula B wherein:

denotes the point of attachment;
X$_c$, X$_d$ and X$_e$ are independently selected from N, CH, CF, CCl, C—CN or CCH$_3$;
R$^{11}$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y$_5$—Z$_5$ wherein:
Y$_5$ is absent or O, N(R$^w$), C(O), C(O)O, OC(O), C(O)N(R$^w$), N(R$^w$)C(O), N(R$^w$)C(O)N(R$^x$), N(R$^w$)C(O)O, OC(O)N(R$^w$), S(O)$_2$N(R$^w$), N(R$^w$)SO$_2$, wherein R$^w$ and R$^x$ are each independently selected from hydrogen or (1-4C)alkyl; and Z$_5$ is hydrogen, (1-6C)alkyl, aryl, (3-8C)cycloalkyl, (3-8C)cycloalkenyl, heteroaryl or heterocyclyl; wherein Z$_5$ is optionally further substituted by one or more substituent groups independently selected from (1-4C)alkyl, halo, (1-4C)haloalkyl, (1-4C)haloalkoxy, amino, cyano, hydroxy, amido, carboxy, carbamoyl, sulphamoyl, mercapto, NR$^y$R$^z$, OR$^y$, wherein R$^y$ and R$^z$ are each independently selected from hydrogen, (1-4C)alkyl or (3-6C)cycloalkyl;

iii) a group of Formula C shown below:

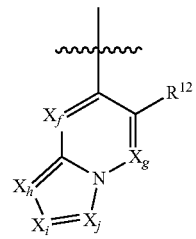

Formula C wherein:

denotes the point of attachment;
R$^{12}$ is selected from fluoro, chloro, bromo, (1-2C)alkyl, (1-2C)alkoxy, cyano, nitro, (2-4C)alkenyl, (2-4C)alkynyl, CH$_2$F, CF$_2$H or CF$_3$;
X$_f$ and X$_g$ are independently selected from N or CR$^{13}$, wherein R$^{13}$ is selected from hydrogen, fluoro, chloro, (1-2C)alkyl, (1-2C)haloalkyl or (1-2C)haloalkoxy;
X$_h$, X$_i$ and X$_j$ are independently selected from N or CR$^{14}$, wherein R$^{14}$ is selected from hydrogen, halo, (1-2C)alkyl, (1-2C)alkoxy, (1-2C)haloalkyl or (1-2C)haloalkoxy;
with the proviso that:
(i) when R$^3$ is a group of Formula B, no more than two of X$_c$, X$_d$ and X$_e$ are nitrogen; and
(ii) when R$^3$ is a group of Formula C, no more than three of X$_f$, X$_g$, X$_h$, X$_i$ and X$_j$ are nitrogen.

In another embodiment, the present invention relates to compounds, or pharmaceutically acceptable salts, hydrates or solvates thereof, having the structural formula (I), shown below:

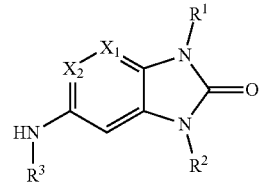

Formula (I)

wherein:
X$_1$ is selected from N or CR$^a$, wherein R$^a$ is selected from hydrogen, (1-2C)alkyl, halogen, hydroxy, (1-2C)

alkoxy, (1-2C)haloalkyl, (1-2C)haloalkoxy, (2-4C)alkenyl, (2-4C)alkynyl, nitro, cyano or NR$^b$R$^c$, wherein R$^b$ and R$^c$ are independently selected from hydrogen or (1-2C)alkyl;

X$_2$ is selected from N or CR$^d$, wherein R$^d$ is selected from hydrogen, (1-2C)alkyl, fluoro, chloro, bromo, hydroxy, (1-2C)alkoxy, (1-2C)haloalkyl or (1-2C)haloalkoxy;

R$^1$ is selected from hydrogen or a group of the formula:

-L-Y—Z wherein:
L is absent or (1-5C)alkylene optionally substituted by one or more substituents selected from (1-2C)alkyl or oxo;
Y is absent or O, S, SO, SO$_2$, N(R$^e$), C(O), C(O)O, OC(O), C(O)N(R$^e$), N(R$^e$)C(O), N(R$^e$)C(O)N(R$^f$), N(R$^e$)C(O)O, OC(O)N(R$^e$), S(O)$_2$N(R$^e$), or N(R$^e$)SO$_2$, wherein R$^e$ and R$^f$ are each independently selected from hydrogen or (1-4C)alkyl; and
Z is hydrogen, (1-6C)alkyl, (2-6C)alkenyl, (2-6C)alkynyl, aryl, (3-10C)cycloalkyl, (3-10C)cycloalkenyl, heteroaryl or heterocyclyl; wherein Z is optionally further substituted by one or more substituent groups independently selected from (1-4C)alkyl, halo, (1-4C)haloalkyl, (1-4C)haloalkoxy, amino, (1-4C)aminoalkyl, cyano, hydroxy, carboxy, carbamoyl, sulphamoyl, mercapto, ureido, NR$^g$R$^h$, OR$^g$, C(O)R$^g$, C(O)OR$^g$, OC(O)R$^g$, C(O)N(R$^g$)R$^h$, N(R$^g$)C(O)R$^h$, S(O)$_y$R$^g$ (where y is 0, 1 or 2), SO$_2$N(R$^g$)R$^h$, N(R$^g$)SO$_2$R$^g$, Si(R$^g$)(R$^h$)R$^i$ or (CH$_2$)$_z$NR$^g$R$^h$ (where z is 1, 2 or 3); wherein R$^{g'}$ R$^h$ and R$^i$ are each independently selected from hydrogen, (1-6C)alkyl or (3-6C)cycloalkyl; or R$^g$ and R$^h$ can be linked such that, together with the nitrogen atom to which they are attached, they form a 4-9 membered heterocyclic ring which is optionally substituted by one or more substituents selected from (1-4C)alkyl, halo, (1-4C)haloalkyl, (1-4C)haloalkoxy, (1-4C)alkoxy, (1-4C)alkylamino, amino, cyano or hydroxy;

R$^2$ is selected from:
(i) hydrogen or methyl;
(ii) a group of the formula:

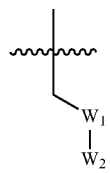

wherein:

denotes the point of attachment;
W$_1$ is selected from CR$^4$R$^5$ or C(O), wherein R$^4$ and R$^5$ are independently selected from hydrogen, (1-2C)alkyl, fluoro, hydroxy, cyano, nitro, (1-2C)alkoxy, (1-2C)haloalkyl, (1-2C)haloalkoxy or NR$^j$R$^k$, wherein R$^j$ and R$^k$ are independently selected from hydrogen or (1-2C)alkyl; or R$^4$ and R$^5$ can be linked such that, together with the carbon atom to which they are attached, they form a 3-6-membered carbocyclic ring or a 3-6-membered heterocyclic ring, which is optionally substituted by one or more substituents selected from (1-2C)alkyl, halo, (1-2C)haloalkyl, (1-2C)haloalkoxy, (1-2C)alkoxy, (1-2C)alkylamino, amino, cyano or hydroxy;

W$_2$ is selected from cyano, a 5- or 6-membered heteroaryl, phenyl, C(O)OCH$_3$, C(O)N(H)CH$_3$, CR$^6$R$^7$R$^8$ or NR$^l$R$^m$, wherein R$^l$ and R$^m$ are independently selected from hydrogen or (1-2C)alkyl, and wherein:

R$^6$ is selected from hydrogen, (1-2C)alkyl, fluoro, chloro, bromo, hydroxy, amino, cyano, nitro, (1-2C)alkoxy, (1-2C)haloalkyl or (1-2C)haloalkoxy;

R$^7$ is selected from hydrogen, (1-2C)alkyl, fluoro, chloro, bromo, hydroxy, cyano, nitro, (1-2C)alkoxy, (1-2C)haloalkyl, (1-2C)haloalkoxy or a group of the formula:

—Y$_2$-L$_2$-Z$_2$ wherein:
Y$_2$ is absent or selected from O, N(R″), S, SO, SO$_2$, C(O), C(O)O, OC(O), C(O)N(R″), N(R″)C(O), S(O)$_2$N(R″), or N(R″)SO$_2$, wherein R″ is selected from hydrogen or (1-2C)alkyl;
L$_2$ is absent or (1-2C)alkylene; and
Z$_2$ is hydrogen, (1-6C)alkyl, (2-4C)alkenyl, (2-4C)alkynyl, phenyl, (3-6C)cycloalkyl, 5-6 membered heteroaryl or a 4-6-membered heterocyclyl; wherein Z$_2$ is optionally substituted by one or more substituents selected from (1-4C)alkyl, halo, (1-4C)haloalkyl, (1-4C)haloalkoxy, (1-4C)alkoxy, (1-4C)alkylamino, amino, cyano, nitro, hydroxy, C(O)R$^o$, C(O)OR$^o$, OC(O)R$^o$, C(O)N(R$^o$)R$^p$, NR$^o$C(O)R$^p$, wherein R$^o$ and R$^p$ are independently selected from hydrogen or (1-4C)alkyl; and R$^8$ is selected from (1-2C)alkyl, —C(O)OR$^q$, OR$^q$, —C(O)NR$^q$, NR$^q$R$^r$, phenyl or a 5-membered heteroaryl, wherein R$^q$ and R$^r$ are independently selected from hydrogen or (1-2C)alkyl;

or R$^6$ and R$^7$ can be linked such that, together with the carbon atom to which they are attached, they form a 3-6-membered carbocyclic ring or a 3-6-membered heterocyclic ring, which is optionally substituted by one or more substituents selected from (1-2C)alkyl, halo, (1-2C)haloalkyl, (1-2C)haloalkoxy, (1-2C)alkoxy, (1-2C)alkylamino, amino, cyano or hydroxyl; or (iii) a group of the formula:

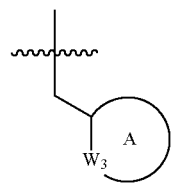

wherein:

denotes the point of attachment;
ring A is a 4 to 6 membered cycloalkyl or heterocyclyl ring;
$W_3$ is selected from $NR^{100}$ or $CR^{101}R^{102}$, wherein $R^{100}$ is selected from hydrogen, (1-2C)alkyl, —C(O)—CH$_3$ or —C(O)OR$^{ab}$, wherein R$^{ab}$ is (1-2C)alkyl, $R^{101}$ and $R^{102}$ are each independently selected from hydrogen, (1-2C)alkyl, fluoro, chloro, bromo, hydroxy, amino, cyano, nitro, (1-2C)alkoxy, (1-2C)haloalkyl, (1-2C)haloalkoxy, —C(O)OR$^{ac}$, —NR$^{ac}$R$^{ad}$ phenyl or a 5-membered heteroaryl, wherein R$^{ac}$ and R$^{ad}$ are independently selected from hydrogen or (1-2C)alkyl; and
$R^3$ is selected from:
i) a group of Formula A shown below:

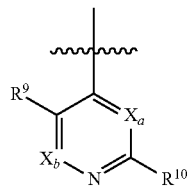

Formula A wherein:

denotes the point of attachment;
$X_a$ and $X_b$ are independently selected from N or $CR^{x1}$, wherein $R^{x1}$ is selected from hydrogen, fluoro, chloro, bromo, (1-2C)alkyl, (1-2C)alkoxy, cyano, nitro, acetylenyl, CH$_2$F, CF$_2$H or CF$_3$;
$R^9$ is selected from hydrogen, fluoro, chloro, bromo, (1-2C)alkyl, (1-2C)alkoxy, cyano, nitro, acetylenyl, CH$_2$F, CF$_2$H or CF$_3$;
$R^{10}$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y$_3$—Z$_3$ wherein:
Y$_3$ is absent or C(O), C(O)O, OC(O), C(O)N(R$^s$), N(R$^s$)C(O), N(R$^s$)C(O)N(R$^t$), N(R$^s$)C(O)O, OC(O)N(R$^s$), S(O)$_2$N(R$^s$), N(R$^s$)SO$_2$, wherein R$^s$ and R$^t$ are each independently selected from hydrogen or (1-4C)alkyl; and
Z$_3$ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or 5- or 6-membered heterocyclyl; wherein Z$_3$ is optionally further substituted by one or more substituent groups independently selected from (1-4C)alkyl, halo, (1-4C)haloalkyl, (1-4C)haloalkoxy, amino, cyano, hydroxy, amido, carboxy, carbamoyl, sulphamoyl, mercapto, NR$^u$R$^v$ or OR$^u$, wherein R$^u$ and R$^v$ are each independently selected from hydrogen, (1-4C)alkyl or (3-6C)cycloalkyl;

ii) a group of Formula B shown below:

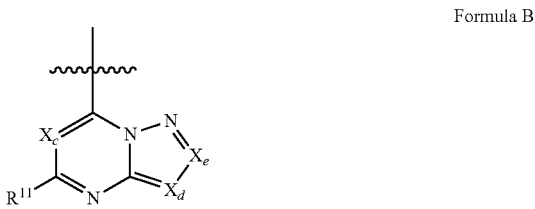

Formula B wherein:

denotes the point of attachment;
$X_c$, $X_d$ and $X_e$ are independently selected from N, CH, CF, CCl, C—CN or CCH$_3$;
$R^{11}$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y$_5$—Z$_5$ wherein:
Y$_5$ is absent or O, N(R$^w$), C(O), C(O)O, OC(O), C(O)N(R$^w$), N(R$^w$)C(O), N(R$^w$)C(O)N(R$^x$), N(R$^w$)C(O)O, OC(O)N(R$^w$), S(O)$_2$N(R$^w$), N(R$^w$)SO$_2$, wherein R$^w$ and R$^x$ are each independently selected from hydrogen or (1-4C)alkyl; and
Z$_5$ is hydrogen, (1-6C)alkyl, aryl, (3-8C)cycloalkyl, (3-8C)cycloalkenyl, heteroaryl or heterocyclyl; wherein Z$_5$ is optionally further substituted by one or more substituent groups independently selected from (1-4C)alkyl, halo, (1-4C)haloalkyl, (1-4C)haloalkoxy, amino, cyano, hydroxy, amido, carboxy, carbamoyl, sulphamoyl, mercapto, NR$^y$R$^z$, OR$^y$, wherein R$^y$ and R$^z$ are each independently selected from hydrogen, (1-4C)alkyl or (3-6C)cycloalkyl;

iii) a group of Formula C shown below:

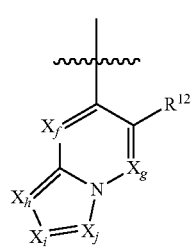

Formula C wherein:

denotes the point of attachment;
R$^{12}$ is selected from fluoro, chloro, bromo, (1-2C)alkyl, (1-2C)alkoxy, cyano, nitro, (2-4C)alkenyl, (2-4C)alkynyl, CH$_2$F, CF$_2$H or CF$_3$;
X$_f$ and X$_g$ are independently selected from N or CR$^{13}$, wherein R$^{13}$ is selected from hydrogen, fluoro, chloro, (1-2C)alkyl, (1-2C)haloalkyl or (1-2C)haloalkoxy;
X$_h$, X$_i$ and X$_j$ are independently selected from N or CR$^{14}$, wherein R$^{14}$ is selected from hydrogen, halo, (1-2C)alkyl, (1-2C)alkoxy, (1-2C)haloalkyl or (1-2C)haloalkoxy;
with the proviso that:
  (i) when R$^3$ is a group of Formula B, only one or two of X$_c$, X$_d$ and X$_e$ are nitrogen; and
  (ii) when R$^3$ is a group of Formula C, no more than three of X$_f$, X$_g$, X$_h$, X$_i$ and X$_j$ are nitrogen.

In a particular group of compounds of the present invention, when R$^3$ is a group of Formula B, no more than one of X$_c$, X$_d$ and X$_e$ is nitrogen.

In a particular group of compounds of the present invention, when R$^3$ is a group of Formula C, no more than two of X$_f$, X$_g$, X$_h$, X$_i$ and X$_j$ are nitrogen.

In a particular group of compounds of the present invention, when R$^3$ is a group of Formula C, no more than one of X$_f$, X$_g$, X$_h$, X$_i$ and X$_j$ is nitrogen.

In a particular group of compounds of the present invention, when R$^1$ is hydrogen, R$^2$ is not hydrogen.

Particular compounds of the invention include, for example, compounds of the Formula I, or pharmaceutically acceptable salts, hydrates and/or solvates thereof, wherein, unless otherwise stated, each of X$_1$, X$_2$, R$^1$, R$^2$, R$^3$ and any associated substituent groups has any of the meanings defined hereinbefore or in any of paragraphs (1) to (89) hereinafter:—

(1) X$_1$ is selected from N or CR$^a$, wherein R$^a$ is selected from hydrogen, (1-2C)alkyl, fluoro, chloro, hydroxy, (1-2C)alkoxy, CH$_2$F, CHF$_2$, CF$_3$, OCF$_3$, acetylenyl, nitro, cyano or NR$^b$R$^c$, wherein R$^b$ and R$^c$ are independently selected from hydrogen or (1-2C)alkyl;
(2) X$_1$ is selected from N or CR$^a$, wherein R$^a$ is selected from hydrogen, methyl, fluoro, chloro, hydroxy, OCH$_3$, CH$_2$F, CHF$_2$, CF$_3$, OCF$_3$, acetylenyl, cyano or NH$_2$;
(3) X$_1$ is selected from N or CR$^a$, wherein R$^a$ is selected from hydrogen, methyl, fluoro, chloro, hydroxy, OCH$_3$, CH$_2$F, CHF$_2$, acetylenyl, cyano or NH$_2$;
(4) X$_1$ is selected from N or CR$^a$, wherein R$^a$ is selected from hydrogen, methyl, fluoro, chloro, hydroxy, OCH$_3$, acetylenyl or cyano;
(5) X$_1$ is selected from N or CR$^a$, wherein R$^a$ is selected from hydrogen, methyl, fluoro, chloro, hydroxy, OCH$_3$ or cyano;
(6) X$_1$ is selected from N or CR$^a$, wherein R$^a$ is selected from hydrogen, methyl, fluoro or chloro;
(7) X$_1$ is selected from N or CH;
(8) X$_1$ is N;
(9) X$_1$ is CH;
(10) X$_2$ is selected from N, CH, CF or C—CH$_3$;
(11) X$_2$ is selected from N or CH;
(12) X$_2$ is N;
(13) X$_2$ is selected from CH, CF or C—CH$_3$;
(14) X$_2$ is CH;
(15) R$^1$ is selected from hydrogen or a group of the formula:

-L-Y—Z wherein:
  L is absent or (1-5C)alkylene optionally substituted by one or more substituents selected from (1-2C)alkyl or oxo;
  Y is absent or O, S, SO, SO$_2$, N(R$^e$), C(O), C(O)O, OC(O), C(O)N(R$^e$), N(R$^e$)(O), S(O)$_2$N(R$^e$), or N(R$^e$)SO$_2$, wherein R$^e$ is selected from hydrogen or (1-4C)alkyl; and
  Z is hydrogen, (1-6C)alkyl, (2-6C)alkenyl, (2-6C)alkynyl, aryl, (3-10C)cycloalkyl, (3-10C)cycloalkenyl, heteroaryl or heterocyclyl; wherein Z is optionally further substituted by one or more substituent groups independently selected from (1-4C)alkyl, halo, (1-4C)haloalkyl, (1-4C)haloalkoxy, amino, (1-4C)aminoalkyl, cyano, hydroxy, carboxy, carbamoyl, sulphamoyl, mercapto, ureido, NR$^g$R$^h$, OR$^g$, C(O)R$^g$, C(O)OR$^g$, OC(O)R$^g$, C(O)N(R$^g$)R$^h$, N(R$^g$)C(O)R$^h$, S(O)$_y$R$^g$ (where y is 0, 1 or 2), SO$_2$N(R$^g$)R$^h$, N(R$^g$)SO$_2$R$^g$, Si(R$^g$)(R$^h$)R$^i$ or (CH$_2$)$_z$NR$^g$R$^h$ (where z is 1, 2 or 3); wherein R$^{g'}$ R$^h$ and R$^i$ are each independently selected from hydrogen, (1-6C)alkyl or (3-6C)cycloalkyl; or R$^g$ and R$^h$ can be linked such that, together with the nitrogen atom to which they are attached, they form a 4-9 membered heterocyclic ring which is optionally substituted by one or more substituents selected from (1-4C)alkyl, halo, (1-4C)haloalkyl, (1-4C)haloalkoxy, (1-4C)alkoxy, (1-4C)alkylamino, amino, cyano or hydroxy;
(16) R$^1$ is selected from hydrogen or a group of the formula:

-L-Y—Z wherein:
  L is absent or (1-5C)alkylene optionally substituted by one or more substituents selected from (1-2C)alkyl;
  Y is absent or O, S, SO, SO$_2$, N(R$^e$), C(O), C(O)O, OC(O), C(O)N(R$^e$), N(R$^e$)C(O), S(O)$_2$N(R$^e$), or N(R$^e$)SO$_2$, wherein R$^e$ is selected from hydrogen or (1-4C)alkyl; and
  Z is hydrogen, (1-6C)alkyl, (2-6C)alkenyl, (2-6C)alkynyl, aryl, (3-10C)cycloalkyl, (3-10C)cycloalkenyl, heteroaryl or heterocyclyl; wherein Z is optionally further substituted by one or more substituent groups independently selected from (1-4C)alkyl, halo, (1-4C)haloalkyl, (1-4C)haloalkoxy, amino, (1-4C)aminoalkyl, cyano, hydroxy, carboxy, carbamoyl, sulphamoyl, mercapto, ureido, NR$^g$R$^h$, OR$^g$, C(O)R$^g$, C(O)OR$^g$, OC(O)R$^g$, C(O)N(R$^g$)R$^h$, N(R$^g$)C(O)R$^h$, S(O)$_y$R$^g$ (where y is 0, 1 or 2), SO$_2$N(R$^g$)R$^h$, N(R$^g$)SO$_2$R$^g$, Si(R$^g$)(R$^h$)R$^i$ or (CH$_2$)$_z$NR$^g$R$^h$ (where z is 1, 2 or 3); wherein R$^{g'}$ R$^h$ and R$^i$ are each independently selected from hydrogen, (1-6C)alkyl or (3-6C)cycloalkyl; or R$^g$ and R$^h$ can be linked such that, together with the nitrogen atom to which they are attached, they form a 4-9 membered heterocyclic ring;

(17) $R^1$ is selected from hydrogen or a group of the formula:

-L-Y—Z wherein:
L is absent or (1-5C)alkylene;
Y is absent or O, $SO_2$, $N(R^e)$, C(O), C(O)O, OC(O), $C(O)N(R^e)$, $N(R^e)C(O)$, $S(O)_2N(R^e)$, or $N(R^e)SO_2$, wherein $R^e$ is selected from hydrogen or (1-4C)alkyl; and
Z is hydrogen, (1-6C)alkyl, (2-6C)alkenyl, (2-6C)alkynyl, aryl, (3-10C)cycloalkyl, (3-10C)cycloalkenyl, heteroaryl or heterocyclyl; wherein Z is optionally further substituted by one or more substituent groups independently selected from (1-4C)alkyl, halo, (1-4C)haloalkyl, (1-4C)haloalkoxy, amino, (1-4C)aminoalkyl, cyano, hydroxy, carboxy, carbamoyl, sulphamoyl, mercapto, ureido, $NR^gR^h$, $OR^g$, $C(O)R^g$, $C(O)OR^g$, $OC(O)R^g$, $C(O)N(R^g)R^h$, $N(R^g)C(O)R^h$, $S(O)_yR^g$ (where y is 0, 1 or 2), $SO_2N(R^g)R^h$, $N(R^g)SO_2R^g$, $Si(R^g)(R^h)R^i$ or $(CH_2)_zNR^gR^h$ (where z is 1, 2 or 3); wherein $R^{g'}$ $R^h$ and $R^i$ are each independently selected from hydrogen, (1-6C)alkyl or (3-6C)cycloalkyl;

(18) $R^1$ is selected from hydrogen or a group of the formula:

-L-Y—Z wherein:
L is absent or (1-5C)alkylene;
Y is absent or O, $SO_2$, C(O), C(O)O, $C(O)N(R^e)$ or $S(O)_2N(R^e)$, wherein $R^e$ is selected from hydrogen or (1-4C)alkyl; and
Z is hydrogen, (1-6C)alkyl, (2-6C)alkenyl, (2-6C)alkynyl, aryl, (3-10C)cycloalkyl, (3-10C)cycloalkenyl, heteroaryl or heterocyclyl; wherein Z is optionally further substituted by one or more substituent groups independently selected from (1-2C)alkyl, halo, (1-2C)haloalkyl, (1-2C)haloalkoxy, amino, (1-2C)aminoalkyl, cyano, hydroxy, carboxy, carbamoyl, sulphamoyl, mercapto, ureido, $NR^gR^h$, $OR^g$, $C(O)R^g$, $C(O)OR^g$, $OC(O)R^g$, $C(O)N(R^g)R^h$, $N(R^g)C(O)R^h$, $S(O)_yR^g$ (where y is 0, 1 or 2), $SO_2N(R^g)R^h$, $N(R^g)SO_2R^g$, $Si(R^g)(R^h)R^i$ or $(CH_2)_zNR^gR^h$ (where z is 1, 2 or 3); wherein $R^{g'}$ $R^h$ and $R^i$ are each independently selected from hydrogen or (1-4C)alkyl;

(19) $R^1$ is selected from hydrogen or a group of the formula:

-L-Y—Z wherein:
L is absent or (1-5C)alkylene;
Y is absent or O, $SO_2$, C(O), C(O)O, $C(O)N(R^e)$ or $S(O)_2N(R^e)$, wherein $R^e$ is selected from hydrogen or (1-4C)alkyl; and
Z is hydrogen, (1-6C)alkyl, (2-6C)alkenyl, (2-6C)alkynyl, aryl, (3-10C)cycloalkyl, (3-10C)cycloalkenyl, heteroaryl or heterocyclyl; wherein Z is optionally further substituted by one or more substituent groups independently selected from (1-2C)alkyl, halo, (1-2C)haloalkyl, (1-2C)haloalkoxy, amino, (1-2C)aminoalkyl, cyano, hydroxy, carboxy, carbamoyl, sulphamoyl, mercapto, ureido, $NR^gR^h$ or $OR^g$; wherein $R^{g'}$ $R^h$ and $R^i$ are each independently selected from hydrogen or (1-4C)alkyl;

(20) $R^1$ is selected from hydrogen or a group of the formula:

-L-Y—Z wherein:
L is absent or (1-5C)alkylene;
Y is absent or O, $SO_2$, C(O), C(O)O, $C(O)N(R^e)$ or $S(O)_2N(R^e)$, wherein $R^e$ is selected from hydrogen or (1-4C)alkyl; and
Z is hydrogen, (1-6C)alkyl, (2-6C)alkenyl, (2-6C)alkynyl, aryl, (3-10C)cycloalkyl, (3-10C)cycloalkenyl, heteroaryl or heterocyclyl; wherein Z is optionally further substituted by one or more substituent groups independently selected from (1-2C)alkyl, halo, (1-2C)haloalkyl, (1-2C)haloalkoxy, amino, (1-2C)aminoalkyl, cyano, hydroxy, $NR^gR^h$ or $OR^g$; wherein $R^{g'}R^h$ and $R^i$ are each independently selected from hydrogen or (1-4C)alkyl;

(21) $R^1$ is selected from hydrogen or a group of the formula:

-L-Y—Z wherein:
L is absent or (1-3C)alkylene;
Y is absent or O, C(O), C(O)O or $C(O)N(R^e)$, wherein $R^e$ is selected from hydrogen or (1-4C)alkyl; and
Z is hydrogen, (1-6C)alkyl, (2-4C)alkenyl, (2-4C)alkynyl, aryl, (3-6C)cycloalkyl, (3-6C)cycloalkenyl, a 5 or 6 membered heteroaryl or a 4- to 7-membered heterocyclyl; wherein Z is optionally further substituted by one or more substituent groups independently selected from (1-2C)alkyl, halo, (1-2C)haloalkyl, (1-2C)haloalkoxy, amino, (1-2C)aminoalkyl, cyano, hydroxy, $NR^gR^h$ or $OR^g$; wherein $R^{g'}$ $R^h$ and $R^i$ are each independently selected from hydrogen or (1-4C)alkyl;

(22) $R^1$ is selected from hydrogen or a group of the formula:

-L-Y—Z wherein:
L is absent or (1-3C)alkylene;
Y is absent or O, C(O), C(O)O or $C(O)N(R^e)$, wherein $R^e$ is selected from hydrogen or (1-4C)alkyl; and
Z is hydrogen, (1-6C)alkyl, (2-4C)alkenyl, (2-4C)alkynyl, aryl, (3-6C)cycloalkyl, (3-6C)cycloalkenyl, 5 or 6 membered heteroaryl or 5 or 6 membered heterocyclyl; wherein Z is optionally further substituted by one or more substituent groups independently selected from (1-2C)alkyl, halo, (1-2C)haloalkyl, (1-2C)haloalkoxy, amino, (1-2C)aminoalkyl, cyano, hydroxy, $NR^gR^h$ or $OR^g$; wherein $R^{g'}$ $R^h$ and $R^i$ are each independently selected from hydrogen or (1-4C)alkyl;

(23) $R^1$ is selected from hydrogen or a group of the formula:

-L-Y—Z wherein:
L is absent or (1-3C)alkylene;
Y is absent or O, C(O), C(O)O or $C(O)N(R^e)$, wherein $R^e$ is selected from hydrogen or (1-4C)alkyl; and
Z is hydrogen, (1-6C)alkyl, aryl, (3-6C)cycloalkyl, (3-6C)cycloalkenyl, 5 or 6 membered heteroaryl or 4- to 7-membered heterocyclyl; wherein Z is optionally further substituted by one or more substituent groups independently selected from (1-2C)alkyl, halo, (1-2C)haloalkyl, (1-2C)haloalkoxy, amino, (1-2C)aminoalkyl, cyano, hydroxy or $NH_2$;

(24) $R^1$ is selected from hydrogen or a group of the formula:

-L-Y—Z wherein:
L is absent or (1-3C)alkylene;
Y is absent or O, C(O), C(O)O or C(O)N($R^e$), wherein $R^e$ is selected from hydrogen or (1-4C)alkyl; and
Z is hydrogen, (1-6C)alkyl, aryl, (3-6C)cycloalkyl, (3-6C)cycloalkenyl, 5 or 6 membered heteroaryl or 5 or 6 membered heterocyclyl; wherein Z is optionally further substituted by one or more substituent groups independently selected from (1-2C)alkyl, halo, (1-2C)haloalkyl, (1-2C)haloalkoxy, amino, (1-2C)aminoalkyl, cyano, hydroxy or $NH_2$;

(25) $R^1$ is selected from hydrogen or a group of the formula:

-L-Z wherein:
L is absent or (1-3C)alkylene; and
Z is (1-6C)alkyl, aryl, (3-6C)cycloalkyl, (3-6C)cycloalkenyl, 5 or 6 membered heteroaryl or 4 to 7 membered heterocyclyl; wherein Z is optionally further substituted by one or more substituent groups independently selected from oxo, (1-2C)alkyl, halo, (1-2C)haloalkyl, (1-2C)haloalkoxy, amino, (1-2C)aminoalkyl, cyano, hydroxy, $NR^gR^h$ or $OR^g$; wherein $R^g$ and $R^h$ are each independently selected from hydrogen or (1-2C)alkyl;

(26) $R^1$ is selected from hydrogen or a group of the formula:

-L-Z wherein:
L is absent or (1-2C)alkylene; and
Z is (1-6C)alkyl, (3-6C)cycloalkyl or 4 to 7 membered heterocyclyl; wherein Z is optionally further substituted by one or more substituent groups independently selected from oxo, (1-2C)alkyl, halo, (1-2C)haloalkyl, (1-2C)haloalkoxy, amino, (1-2C)aminoalkyl, cyano, hydroxy, $NR^gR^h$ or $OR^g$; wherein $R^g$ and $R^h$ are each independently selected from hydrogen or (1-2C)alkyl;

(27) $R^1$ is selected from hydrogen, (1-6C)alkyl or a group of the formula:

-L-Z wherein:
L is (1-2C)alkylene; and
Z is (3-6C)cycloalkyl or 4 to 7 membered heterocyclyl; wherein Z is optionally further substituted by one or more substituent groups independently selected from oxo, (1-2C)alkyl, halo, (1-2C)haloalkyl, (1-2C)haloalkoxy, amino, (1-2C)aminoalkyl, cyano, hydroxy, $NR^gR^h$ or $OR^g$; wherein $R^g$ and $R^h$ are each independently selected from hydrogen or methyl;

(28) $R^1$ is selected from hydrogen, (1-6C)alkyl or (3-6C)cycloalkyl; wherein each (1-6C)alkyl or (3-6C)cycloalkyl is optionally further substituted by one or more substituent groups independently selected from oxo, (1-2C)alkyl, halo, (1-2C)haloalkyl, (1-2C)haloalkoxy, amino, (1-2C)aminoalkyl, cyano, hydroxy or $NH_2$;

(29) $R^1$ is selected from hydrogen, (1-6C)alkyl or (3-6C)cycloalkyl;

(30) $R^1$ is selected from hydrogen or (1-4C)alkyl (e.g. methyl);

(31) $R^1$ is (1-4C)alkyl (e.g. methyl);

(32) $R^2$ is selected from:
(i) hydrogen or methyl;
(ii) a group of the formula:

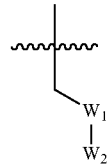

wherein:

denotes the point of attachment;
$W_1$ is selected from $CR^4R^5$ or C(O), wherein $R^4$ and $R^5$ are independently selected from hydrogen, (1-2C)alkyl, fluoro, hydroxy, cyano, nitro, (1-2C)alkoxy, (1-2C)haloalkyl, (1-2C)haloalkoxy or $NR^jR^k$, wherein $R^j$ and $R^k$ are independently selected from hydrogen or (1-2C)alkyl; or
$R^4$ and $R^5$ can be linked such that, together with the carbon atom to which they are attached, they form a 3-6-membered carbocyclic ring or a 3-6-membered heterocyclic ring, which is optionally substituted by one or more substituents selected from (1-2C)alkyl, halo, (1-2C)haloalkyl, (1-2C)haloalkoxy, (1-2C)alkoxy, (1-2C)alkylamino, amino, cyano or hydroxy;
$W_2$ is selected from cyano, a 5- or 6-membered heteroaryl, phenyl, $C(O)R^l$, $SO_2R^l$, C(O)OCH_3, C(O)N(H)CH_3, $CR^6R^7R^8$ or $NR^lR^m$, wherein $R^l$ and $R^m$ are independently selected from hydrogen or (1-4C)alkyl, and wherein:
$R^6$ is selected from hydrogen, (1-2C)alkyl, fluoro, chloro, bromo, hydroxy, amino, cyano, nitro, (1-2C)alkoxy, (1-2C)haloalkyl or (1-2C)haloalkoxy;
$R^7$ is selected from hydrogen, (1-2C)alkyl, fluoro, chloro, bromo, hydroxy, cyano, nitro, (1-2C)alkoxy, (1-2C)haloalkyl, (1-2C)haloalkoxy or a group of the formula:

—$Y_2$-$L_2$-$Z_2$ wherein:
$Y_2$ is absent or selected from O, N(R"), S, SO, $SO_2$, C(O), C(O)O, OC(O), C(O)N(R") or N(R")C(O), wherein R" is selected from hydrogen or (1-2C)alkyl;
$L_2$ is absent or (1-2C)alkylene; and
$Z_2$ is hydrogen, (1-6C)alkyl, (2-4C)alkenyl, (2-4C)alkynyl, phenyl, (3-6C)cycloalkyl, 5-6 membered heteroaryl or a 4-6-membered heterocyclyl; wherein $Z_2$ is optionally substituted by one or more substituents selected from (1-4C)alkyl, halo, (1-4C)haloalkyl, (1-4C)haloalkoxy, (1-4C)alkoxy, (1-4C)alkylamino, amino, cyano, nitro or hydroxy; and $R^8$ is selected from (1-2C)alkyl, —C(O)OR$^q$, OR$^q$, —C(O)NR$^q$, NR$^q$R$^r$, phenyl or a 5-membered heteroaryl, wherein R$^q$ and R$^r$ are independently selected from hydrogen or (1-2C) alkyl;

or R$^6$ and R$^7$ can be linked such that, together with the carbon atom to which they are attached, they form a 3-6-membered carbocyclic ring or a 3-6-membered heterocyclic ring, which is optionally substituted by one or more substituents selected from (1-2C)alkyl, fluoro, chloro, CH$_2$F, CF$_2$H or CF$_3$, (1-2C)alkoxy, amino, cyano or hydroxy; or (iii) a group of the formula:

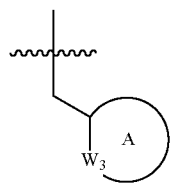

wherein:

denotes the point of attachment;

ring A is a 4 to 6 membered cycloalkyl or heterocyclyl ring, optionally substituted with one or more substituent groups selected from (1-2C)alkyl, halo, hydroxy, cyano or (1-2C)alkoxy;

$W_3$ is selected from NR$^{100}$ or CR$^{101}$R$^{102}$, wherein R$^{100}$ is selected from hydrogen, (1-2C)alkyl, (1-2C)haloalkyl, (1-2C)hydroxyalkyl, —C(O)—CH$_3$ or —C(O)OR$^{ab}$, wherein R$^{ab}$ is (1-4C)alkyl, R$^{101}$ and R$^{102}$ are each independently selected from hydrogen, (1-2C)alkyl, cyclopropyl, fluoro, chloro, bromo, hydroxy, amino, cyano, nitro, (1-2C)alkoxy, (1-2C)haloalkyl, (1-2C)haloalkoxy, —C(O)OR$^{ac}$, —NR$^{ac}$R$^{ad}$, phenyl or a 5-membered heteroaryl, wherein R$^{ac}$ and R$^{ad}$ are independently selected from hydrogen or (1-2C)alkyl;

(33) R$^2$ is selected from:

(i) hydrogen or methyl;

(ii) a group of the formula:

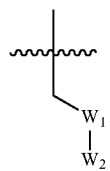

wherein:

denotes the point of attachment;

$W_1$ is selected from CR$^4$R$^5$ or C(O), wherein R$^4$ and R$^5$ are independently selected from hydrogen, (1-2C)alkyl, fluoro, hydroxy, cyano, nitro, (1-2C) alkoxy, (1-2C)haloalkyl, (1-2C)haloalkoxy or NR$^j$R$^k$, wherein R$^j$ and R$^k$ are independently selected from hydrogen or (1-2C)alkyl; or R$^4$ and R$^5$ can be linked such that, together with the carbon atom to which they are attached, they form a 3-6-membered carbocyclic ring or a 3-6-membered heterocyclic ring, which is optionally substituted by one or more substituents selected from (1-2C)alkyl, halo, (1-2C) haloalkyl, (1-2C)haloalkoxy, (1-2C)alkoxy, (1-2C)alkylamino, amino, cyano or hydroxy;

$W_2$ is selected from cyano, a 5- or 6-membered heteroaryl, phenyl, C(O)R$^l$, SO$_2$R$^l$, C(O)OCH$_3$, C(O)N(H)CH$_3$, CR$^6$R$^7$R$^8$ or NR$^l$R$^m$, wherein R$^l$ and R$^m$ are independently selected from hydrogen or (1-4C)alkyl, and wherein:

R$^6$ is selected from hydrogen, (1-2C)alkyl, fluoro, chloro, bromo, hydroxy, amino, cyano, nitro, (1-2C)alkoxy, (1-2C)haloalkyl or (1-2C)haloalkoxy;

R$^7$ is selected from hydrogen, (1-2C)alkyl, fluoro, chloro, bromo, hydroxy, cyano, nitro, (1-2C) alkoxy, (1-2C)haloalkyl, (1-2C)haloalkoxy or a group of the formula:

—Y$_2$-L$_2$-Z$_2$ wherein:

Y$_2$ is absent or selected from O, N(R″), S, SO, SO$_2$, C(O), C(O)O, OC(O), C(O)N(R″) or N(R″)C(O), wherein R″ is selected from hydrogen or (1-2C)alkyl;

L$_2$ is absent or (1-2C)alkylene; and

Z$_2$ is hydrogen, (1-6C)alkyl, (2-4C)alkenyl, (2-4C)alkynyl, phenyl, (3-6C)cycloalkyl, 5-6 membered heteroaryl or a 4-6-membered heterocyclyl; wherein Z$_2$ is optionally substituted by one or more substituents selected from (1-4C)alkyl, halo, (1-4C)haloalkyl, (1-4C)haloalkoxy, (1-4C)alkoxy, (1-4C)alkylamino, amino, cyano, nitro or hydroxy; and $R^8$ is selected from (1-2C)alkyl, —C(O)OR$^q$, OR$^q$, —C(O)NR$^q$, NR$^q$R$^r$, phenyl or a 5-membered heteroaryl, wherein R$^q$ and R$^r$ are independently selected from hydrogen or (1-2C) alkyl;

or R$^6$ and R$^7$ can be linked such that, together with the carbon atom to which they are attached, they form a 3-6-membered carbocyclic ring or a 3-6-membered heterocyclic ring, which is optionally substituted by one or more substituents selected from (1-2C)alkyl, fluoro, chloro, CH$_2$F, CF$_2$H or CF$_3$, (1-2C)alkoxy, amino, cyano or hydroxy; or (iii) a group of the formula:

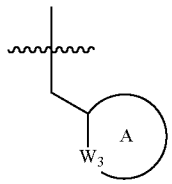

wherein:

denotes the point of attachment;
ring A is a 4 to 6 membered cycloalkyl or heterocyclyl ring, optionally substituted with one or more substituent groups selected from (1-2C)alkyl, halo, hydroxy, cyano or (1-2C)alkoxy;
$W_3$ is selected from $NR^{100}$ or $CR^{101}R^{102}$, wherein $R^{100}$ is selected from hydrogen, (1-2C)alkyl, (1-2C)haloalkyl, (1-2C)hydroxyalkyl, —C(O)—CH$_3$ or —C(O)OR$^{ab}$, wherein R$^{ab}$ is (1-2C)alkyl, $R^{101}$ and $R^{102}$ are each independently selected from hydrogen, (1-2C)alkyl, cyclopropyl, fluoro, chloro, bromo, hydroxy, amino, cyano, nitro, (1-2C)alkoxy, (1-2C)haloalkyl, (1-2C)haloalkoxy, —C(O)OR$^{ac}$, —NR$^{ac}$R$^{ad}$, phenyl or a 5-membered heteroaryl, wherein R$^{ac}$ and R$^{ad}$ are independently selected from hydrogen or (1-2C)alkyl;
(34) $R^2$ is selected from:
(i) hydrogen or methyl;
(ii) a group of the formula:

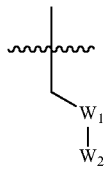

wherein:

denotes the point of attachment;
$W_1$ is selected from $CR^4R^5$ or C(O), wherein $R^4$ and $R^5$ are independently selected from hydrogen, (1-2C)alkyl, fluoro, hydroxy, cyano, nitro, (1-2C)alkoxy, (1-2C)haloalkyl, (1-2C)haloalkoxy or NR$^j$R$^k$, wherein R$^j$ and R$^k$ are independently selected from hydrogen or (1-2C)alkyl; or
$R^4$ and $R^5$ can be linked such that, together with the carbon atom to which they are attached, they form a 3-6-membered carbocyclic ring or a 3-6-membered heterocyclic ring, which is optionally substituted by one or more substituents selected from (1-2C)alkyl, halo, (1-2C)haloalkyl, (1-2C)haloalkoxy, (1-2C)alkoxy, amino, cyano or hydroxy;
$W_2$ is selected from cyano, a 5- or 6-membered heteroaryl, phenyl, C(O)R$^l$, SO$_2$R$^l$, C(O)OCH$_3$, C(O)N(H)CH$_3$, CR$^6$R$^7$R$^8$ or NR$^l$R$^m$, wherein R$^l$ and R$^m$ are independently selected from hydrogen or (1-4C)alkyl, and wherein:
$R^6$ is selected from hydrogen, (1-2C)alkyl, fluoro, chloro, bromo, hydroxy, amino, cyano, nitro, (1-2C)alkoxy, (1-2C)haloalkyl or (1-2C)haloalkoxy;
$R^7$ is selected from hydrogen, (1-2C)alkyl, fluoro, chloro, bromo, hydroxy, cyano, nitro, (1-2C)alkoxy, (1-2C)haloalkyl, (1-2C)haloalkoxy or a group of the formula:

—$Y_2$-$L_2$-$Z_2$ wherein:
$Y_2$ is absent or selected from O, N(R″), C(O), C(O)O, OC(O), C(O)N(R″) or N(R″)C(O), wherein R″ is selected from hydrogen or (1-2C)alkyl;
$L_2$ is absent or (1-2C)alkylene; and
$Z_2$ is hydrogen, (1-6C)alkyl, (2-4C)alkenyl, (2-4C)alkynyl, phenyl, (3-6C)cycloalkyl, 5-6 membered heteroaryl or a 4-6-membered heterocyclyl; wherein $Z_2$ is optionally substituted by one or more substituents selected from (1-4C)alkyl, halo, (1-4C)haloalkyl, (1-4C)haloalkoxy, (1-4C)alkoxy, (1-4C)alkylamino, amino, cyano, nitro or hydroxy; and
$R^3$ is selected from (1-2C)alkyl, —C(O)OR$^q$, OR$^q$, —C(O)NR$^q$, NR$^q$R$^r$, phenyl or a 5-membered heteroaryl, wherein R$^q$ and R$^r$ are independently selected from hydrogen or (1-2C) alkyl;
or $R^6$ and $R^7$ can be linked such that, together with the carbon atom to which they are attached, they form a 3-6-membered carbocyclic ring or a 3-6-membered heterocyclic ring, which is optionally substituted by one or more substituents selected from (1-2C)alkyl, fluoro, chloro, CH$_2$F, CF$_2$H or CF$_3$, (1-2C)alkoxy, amino, cyano or hydroxy; or
(iii) a group of the formula:

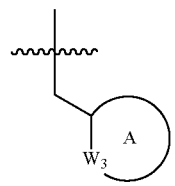

wherein:

denotes the point of attachment;
ring A is a 4 to 6 membered cycloalkyl or heterocyclyl ring, optionally substituted with one or more substituent groups selected from (1-2C)alkyl, halo, hydroxy, cyano or (1-2C)alkoxy;

W₃ is selected from NR¹⁰⁰ or CR¹⁰¹R¹⁰², wherein R¹⁰⁰ is selected from hydrogen, (1-2C)alkyl, (1-2C)haloalkyl, (1-2C)hydroxyalkyl, —C(O)—CH₃ or —C(O)OR$^{ab}$, wherein R$^{ab}$ is (1-2C)alkyl, R¹⁰¹ and R¹⁰² are each independently selected from hydrogen, (1-2C)alkyl, cyclopropyl, fluoro, chloro, bromo, hydroxy, amino, cyano, (1-2C)alkoxy, (1-2C)haloalkyl, (1-2C)haloalkoxy, —C(O)OR$^{ac}$, —NR$^{ac}$R$^{ad}$, phenyl or a 5-membered heteroaryl, wherein R$^{ac}$ and R$^{ad}$ are independently selected from hydrogen or methyl;

(35) R² is selected from:
(i) hydrogen or methyl;
(ii) a group of the formula:

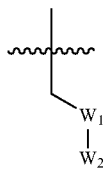

wherein:

denotes the point of attachment;
W₁ is selected from CR⁴R⁵ or C(O), wherein R⁴ and R⁵ are independently selected from hydrogen, (1-2C)alkyl, fluoro, hydroxy, cyano, (1-2C)alkoxy, (1-2C)haloalkyl, (1-2C)haloalkoxy or NR$^{j}$R$^{k}$, wherein R$^{j}$ and R$^{k}$ are independently selected from hydrogen or (1-2C)alkyl; or
R⁴ and R⁵ can be linked such that, together with the carbon atom to which they are attached, they form a 3-6-membered carbocyclic ring or a 3-6-membered heterocyclic ring, which is optionally substituted by one or more substituents selected from (1-2C)alkyl, halo, (1-2C)haloalkyl, (1-2C)alkoxy, amino, cyano or hydroxy;
W₂ is selected from cyano, a 5- or 6-membered heteroaryl, phenyl, C(O)R$^{l}$, SO₂R$^{l}$, C(O)OCH₃, C(O)N(H)CH₃, CR⁶R⁷R⁸ or NR$^{l}$R$^{m}$, wherein R$^{l}$ and R$^{m}$ are independently selected from hydrogen or (1-2C)alkyl, and wherein:
R⁶ is selected from hydrogen, (1-2C)alkyl, fluoro, chloro, bromo, hydroxy, amino, cyano, nitro, (1-2C)alkoxy, CH₂F, CF₂H or CF₃;
R⁷ is selected from hydrogen, (1-2C)alkyl, fluoro, chloro, bromo, hydroxy, cyano, nitro, (1-2C)alkoxy, (1-2C)haloalkyl, (1-2C)haloalkoxy or a group of the formula:

—Y₂-L₂-Z₂ wherein:
Y₂ is absent or selected from O, N(R″), C(O), C(O)O, OC(O), C(O)N(R″) or N(R″)C(O), wherein R″ is selected from hydrogen or (1-2C)alkyl;
L₂ is absent or (1-2C)alkylene; and
Z₂ is hydrogen, (1-6C)alkyl, (2-4C)alkenyl, (2-4C)alkynyl, phenyl, (3-6C)cycloalkyl, 5-6 membered heteroaryl or a 4-6-membered heterocyclyl; wherein Z₂ is optionally substituted by one or more substituents selected from (1-2C)alkyl, halo, (1-2C)haloalkyl, (1-2C)haloalkoxy, (1-2C)alkoxy, (1-2C)alkylamino, amino, cyano, nitro or hydroxy; and
R⁸ is selected from (1-2C)alkyl, —C(O)OR$^{q}$, OR$^{q}$, —C(O)NR$^{q}$, NR$^{q}$R$^{r}$, phenyl or a 5-membered heteroaryl, wherein R$^{q}$ and R$^{r}$ are independently selected from hydrogen or (1-2C)alkyl;
or R⁶ and R⁷ can be linked such that, together with the carbon atom to which they are attached, they form a 3-6-membered carbocyclic ring or a 3-6-membered heterocyclic ring; or
(iii) a group of the formula:

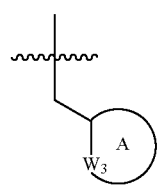

wherein:

denotes the point of attachment;
ring A is a 4 to 6 membered cycloalkyl or heterocyclyl ring, optionally substituted with one or more substituent groups selected from (1-2C)alkyl or halo;
W₃ is selected from NR¹⁰⁰ or CR¹⁰¹R¹⁰², wherein R¹⁰⁰ is selected from hydrogen, (1-2C)alkyl, (1-2C)haloalkyl, (1-2C)hydroxyalkyl, —C(O)—CH₃ or —C(O)OR$^{ab}$, wherein R$^{ab}$ is (1-2C)alkyl, R¹⁰¹ and R¹⁰² are each independently selected from (1-2C)alkyl, fluoro, chloro, hydroxy, (1-2C)alkoxy, CH₂F, CF₂H, CF₃, —C(O)OR$^{ac}$ or —NR$^{ac}$R$^{ad}$ wherein R$^{ac}$ and R$^{ad}$ are independently selected from hydrogen or methyl;

(36) R² is selected from:
(i) hydrogen or methyl;
(ii) a group of the formula:

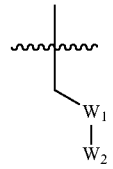

wherein:

denotes the point of attachment;

$W_1$ is selected from $CR^4R^5$ or $C(O)$, wherein $R^4$ and $R^5$ are independently selected from hydrogen, (1-2C)alkyl, fluoro, hydroxy, cyano, (1-2C)alkoxy, (1-2C)haloalkyl, (1-2C)haloalkoxy or $NR^jR^k$, wherein $R^j$ and $R^k$ are independently selected from hydrogen or (1-2C)alkyl; or $R^4$ and $R^5$ can be linked such that, together with the carbon atom to which they are attached, they form a 3-6-membered carbocyclic ring or a 3-6-membered heterocyclic ring;

$W_2$ is selected from cyano, a 5- or 6-membered heteroaryl, phenyl, $SO_2R^i$, $C(O)OCH_3$, $C(O)N(H)CH_3$, $CR^6R^7R^8$ or $NR^iR^m$, wherein $R^i$ and $R^m$ are independently selected from hydrogen or (1-2C)alkyl, and wherein:

$R^6$ is selected from hydrogen, (1-2C)alkyl, fluoro, chloro, bromo, hydroxy, amino, cyano, (1-2C)alkoxy, $CH_2F$, $CF_2H$ or $CF_3$;

$R^7$ is selected from hydrogen, (1-2C)alkyl, fluoro, chloro, bromo, hydroxy, cyano, (1-2C)alkoxy, (1-2C)haloalkyl, (1-2C)haloalkoxy or a group of the formula:

—$Y_2$-$L_2$-$Z_2$ wherein:
$Y_2$ is absent or selected from O, N(R''), C(O), C(O)O, OC(O), C(O)N(R'') or N(R'')C(O), wherein R'' is selected from hydrogen or (1-2C)alkyl;
$L_2$ is absent or (1-2C)alkylene; and
$Z_2$ is hydrogen, (1-6C)alkyl, (2-4C)alkenyl, phenyl, (3-6C)cycloalkyl, 5-6 membered heteroaryl or a 4-6-membered heterocyclyl; wherein $Z_2$ is optionally substituted by one or more substituents selected from (1-2C)alkyl, halo, (1-2C)haloalkyl, (1-2C)alkoxy, amino, cyano or hydroxy; and
$R^8$ is selected from (1-2C)alkyl, —$C(O)OR^q$, $OR^q$, —$C(O)NR^q$, $NR^qR^r$, phenyl or a 5-membered heteroaryl, wherein $R^q$ and $R^r$ are independently selected from hydrogen or (1-2C)alkyl;
or $R^6$ and $R^7$ can be linked such that, together with the carbon atom to which they are attached, they form a 3-6-membered carbocyclic ring or a 3-6-membered heterocyclic ring; or (iii) a group of the formula:

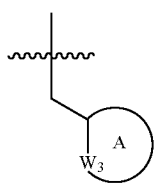

wherein:

denotes the point of attachment;
ring A is a 4 to 6 membered cycloalkyl or heterocyclyl ring;

$W_3$ is selected from $NR^{100}$ or $CR^{101}R^{102}$, wherein $R^{100}$ is selected from hydrogen, (1-2C)alkyl, (1-2C)haloalkyl, (1-2C)hydroxyalkyl, —C(O)—$CH_3$ or —$C(O)OR^{ab}$, wherein $R^{ab}$ is (1-2C)alkyl, $R^{101}$ and $R^{102}$ are each independently selected from (1-2C)alkyl, fluoro, chloro, hydroxy, (1-2C)alkoxy, $CH_2F$, $CF_2H$, $CF_3$, —$C(O)OR^{ac}$ or —$NR^{ac}R^{ad}$ wherein $R^{ac}$ and $R^{ad}$ are independently selected from hydrogen or methyl;

(37) $R^2$ is selected from:
(i) hydrogen or methyl;
(ii) a group of the formula:

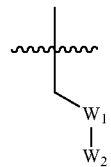

wherein:

denotes the point of attachment;

$W_1$ is selected from $CR^4R^5$ or $C(O)$, wherein $R^4$ and $R^5$ are independently selected from hydrogen, (1-2C)alkyl, fluoro, hydroxy, cyano, nitro, (1-2C)alkoxy, (1-2C)haloalkyl, (1-2C)haloalkoxy or $NR^jR^k$, wherein $R^j$ and $R^k$ are independently selected from hydrogen or (1-2C)alkyl; or $R^4$ and $R^5$ can be linked such that, together with the carbon atom to which they are attached, they form a 3-6-membered carbocyclic ring or a 3-6-membered heterocyclic ring, which is optionally substituted by one or more substituents selected from (1-2C)alkyl, halo, (1-2C)haloalkyl, (1-2C)haloalkoxy, (1-2C)alkoxy, (1-2C)alkylamino, amino, cyano or hydroxy;

$W_2$ is selected from cyano, a 5- or 6-membered heteroaryl, phenyl, $C(O)OCH_3$, $C(O)N(H)CH_3$, $CR^6R^7R^8$ or $NR^iR^m$, wherein $R^i$ and $R^m$ are independently selected from hydrogen or (1-2C)alkyl, and wherein:

$R^6$ is selected from hydrogen, (1-2C)alkyl, fluoro, chloro, bromo, hydroxy, amino, cyano, nitro, (1-2C)alkoxy, (1-2C)haloalkyl or (1-2C)haloalkoxy;

$R^7$ is selected from hydrogen, (1-2C)alkyl, fluoro, chloro, bromo, hydroxy, cyano, nitro, (1-2C)alkoxy, (1-2C)haloalkyl, (1-2C)haloalkoxy or a group of the formula:

—$Y_2$-$L_2$-$Z_2$ wherein:
$Y_2$ is absent or selected from O, N(R''), S, SO, $SO_2$, C(O), C(O)O, OC(O), C(O)N(R''), N(R'')C(O), $S(O)_2N(R'')$, or $N(R'')SO_2$, wherein R'' is selected from hydrogen or (1-2C)alkyl;
$L_2$ is absent or (1-2C)alkylene; and
$Z_2$ is hydrogen, (1-6C)alkyl, (2-4C)alkenyl, (2-4C)alkynyl, phenyl, (3-6C)cycloalkyl, 5-6 membered heteroaryl or a 4-6-membered heterocyclyl; wherein $Z_2$ is optionally substituted by one or more substituents selected from (1-4C)alkyl, halo, (1-4C)haloalkyl, (1-4C)haloalkoxy, (1-4C)alkoxy, (1-4C)alkylamino, amino, cyano, nitro, hydroxy, $C(O)R^o$, $C(O)OR^o$, $OC(O)R^o$, $C(O)N(R^o)R^p$, $NR^oC(O)R^p$, wherein $R^o$ and $R^p$ are independently selected from hydrogen or (1-4C)alkyl; and $R^8$ is selected from (1-2C)alkyl, —$C(O)OR^q$, $OR^q$, —$C(O)NR^q$, $NR^qR^r$, phenyl or a 5-membered heteroaryl, wherein $R^q$ and $R^r$ are independently selected from hydrogen or (1-2C)alkyl;

or $R^6$ and $R^7$ can be linked such that, together with the carbon atom to which they are attached, they form a 3-6-membered carbocyclic ring or a 3-6-membered heterocyclic ring, which is optionally substituted by one or more substituents selected from (1-2C)alkyl, halo, (1-2C)haloalkyl, (1-2C)haloalkoxy, (1-2C)alkoxy, (1-2C)alkylamino, amino, cyano or hydroxyl; or (iii) a group of the formula:

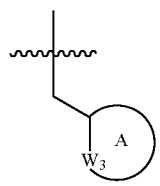

wherein:

denotes the point of attachment;
ring A is a 4 to 6 membered cycloalkyl or heterocyclyl ring;
$W_3$ is selected from $NR^{100}$ or $CR^{101}R^{102}$, wherein $R^{100}$ is selected from hydrogen, (1-2C)alkyl, —$C(O)$—$CH_3$ or —$C(O)OR^{ab}$, wherein $R^{ab}$ is (1-2C)alkyl, $R^{101}$ and $R^{102}$ are each independently selected from hydrogen, (1-2C)alkyl, fluoro, chloro, bromo, hydroxy, amino, cyano, nitro, (1-2C)alkoxy, (1-2C)haloalkyl, (1-2C)haloalkoxy, —$C(O)OR^{ac}$, —$NR^{ac}R^{ad}$ phenyl or a 5-membered heteroaryl, wherein $R^{ac}$ and $R^{ad}$ are independently selected from hydrogen or (1-2C)alkyl;

(38) $R^2$ is selected from:
(i) hydrogen or methyl;
(ii) a group of the formula:

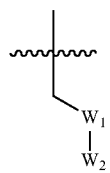

wherein:

denotes the point of attachment;
$W_1$ is selected from $CR^4R^5$ or $C(O)$, wherein $R^4$ and $R^5$ are independently selected from hydrogen, (1-2C)alkyl, fluoro, hydroxy, cyano, nitro, (1-2C)alkoxy, (1-2C)haloalkyl, (1-2C)haloalkoxy or $NR^jR^k$, wherein $R^j$ and $R^k$ are independently selected from hydrogen or (1-2C)alkyl; or $R^4$ and $R^5$ can be linked such that, together with the carbon atom to which they are attached, they form a 3-6-membered carbocyclic ring or a 3-6-membered heterocyclic ring, which is optionally substituted by one or more substituents selected from (1-2C)alkyl, halo, (1-2C)haloalkyl, (1-2C)haloalkoxy, (1-2C)alkoxy, (1-2C)alkylamino, amino, cyano or hydroxy;

$W_2$ is selected from cyano, a 5- or 6-membered heteroaryl, phenyl, $C(O)OCH_3$, $C(O)N(H)CH_3$, $CR^6R^7R^8$ or $NR^lR^m$, wherein $R^l$ and $R^m$ are independently selected from hydrogen or (1-2C)alkyl, and wherein:

$R^6$ is selected from hydrogen, (1-2C)alkyl, fluoro, chloro, bromo, hydroxy, amino, cyano, nitro, (1-2C)alkoxy, (1-2C)haloalkyl or (1-2C)haloalkoxy;

$R^7$ is selected from hydrogen, (1-2C)alkyl, fluoro, chloro, bromo, hydroxy, cyano, nitro, (1-2C)alkoxy, (1-2C)haloalkyl, (1-2C)haloalkoxy or a group of the formula:

—$Y_2$-$L_2$-$Z_2$ wherein:
$Y_2$ is absent or selected from O, $N(R'')$, S, SO, $SO_2$, $C(O)$, $C(O)O$, $OC(O)$, $C(O)N(R'')$, $N(R'')C(O)$, $S(O)_2N(R'')$, or $N(R'')SO_2$, wherein $R''$ is selected from hydrogen or (1-2C)alkyl;

$L_2$ is absent or (1-2C)alkylene; and $Z_2$ is hydrogen, (1-6C)alkyl, (2-4C)alkenyl, (2-4C)alkynyl, phenyl, (3-6C)cycloalkyl, 5-6 membered heteroaryl or a 4-6-membered heterocyclyl; wherein $Z_2$ is optionally substituted by one or more substituents selected from (1-4C)alkyl, halo, (1-4C)haloalkyl, (1-4C)haloalkoxy, (1-4C)alkoxy, (1-4C)alkylamino, amino, cyano, nitro or hydroxy; and $R^8$ is selected from (1-2C)alkyl, —$C(O)OR^q$, $OR^q$, $NR^qR^r$, phenyl or a 5-membered heteroaryl, wherein $R^q$ and $R^r$ are independently selected from hydrogen or (1-2C)alkyl;

or $R^6$ and $R^7$ can be linked such that, together with the carbon atom to which they are attached, they form a 4-6-membered carbocyclic ring or a 4-6-membered heterocyclic ring, which is optionally substituted by one or more substituents selected from (1-2C)alkyl, fluoro, chloro, $CH_2F$, $CF_2H$ or $CF_3$, (1-2C)alkoxy, amino, cyano or hydroxy; or

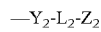

(iii) a group of the formula:

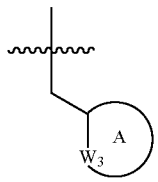

wherein:

denotes the point of attachment;
ring A is a 4 to 6 membered cycloalkyl or heterocyclyl ring;
$W_3$ is selected from $NR^{100}$ or $CR^{101}R^{102}$, wherein $R^{100}$ is selected from hydrogen, (1-2C)alkyl, —C(O)—$CH_3$ or —C(O)$OR^{ab}$, wherein $R^{ab}$ is (1-2C)alkyl, $R^{101}$ and $R^{102}$ are each independently selected from hydrogen, (1-2C)alkyl, fluoro, chloro, hydroxy, cyano, (1-2C)alkoxy, (1-2C)haloalkyl, (1-2C)haloalkoxy, —C(O)$OR^{ac}$, —$NR^{ac}R^{ad}$, phenyl or a 5-membered heteroaryl, and wherein $R^{ac}$ and $R^{ad}$ are independently selected from hydrogen or (1-2C)alkyl;

(39) $R^2$ is selected from:
(i) hydrogen or methyl;
(ii) a group of the formula:

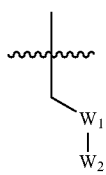

wherein:

denotes the point of attachment;
$W_1$ is selected from $CR^4R^5$ or C(O), wherein $R^4$ and $R^5$ are independently selected from hydrogen, (1-2C)alkyl, fluoro, hydroxy, cyano, nitro, (1-2C)alkoxy, (1-2C)haloalkyl, (1-2C)haloalkoxy or $NR^jR^k$, wherein $R^j$ and $R^k$ are independently selected from hydrogen or (1-2C)alkyl; or
$R^4$ and $R^5$ can be linked such that, together with the carbon atom to which they are attached, they form a 3-6-membered carbocyclic ring or a 3-6-membered heterocyclic ring, which is optionally substituted by one or more substituents selected from (1-2C)alkyl, fluoro, chloro, $CH_2F$, $CF_2H$, $CF_3$, (1-2C)alkoxy, amino, cyano or hydroxy;

$W_2$ is selected from cyano, a 5- or 6-membered heteroaryl, phenyl, C(O)$OCH_3$, C(O)N(H)$CH_3$, $CR^6R^7R^8$ or $NR^lR^m$, wherein $R^l$ and $R^m$ are independently selected from hydrogen or (1-2C)alkyl, and wherein:
$R^6$ is selected from hydrogen, (1-2C)alkyl, fluoro, chloro, bromo, hydroxy, amino, cyano, nitro, (1-2C)alkoxy, (1-2C)haloalkyl or (1-2C)haloalkoxy;
$R^7$ is selected from hydrogen, (1-2C)alkyl, fluoro, chloro, bromo, hydroxy, cyano, nitro, (1-2C)alkoxy, (1-2C)haloalkyl, (1-2C)haloalkoxy or a group of the formula:

—$Y_2$-$L_2$-$Z_2$ wherein:
$Y_2$ is absent or selected from O, N(R″), S, SO, $SO_2$, C(O), C(O)O, OC(O), C(O)N(R″), N(R″)C(O), S(O)$_2$N(R″), or N(R″)$SO_2$, wherein R″ is selected from hydrogen or (1-2C)alkyl;
$L_2$ is absent or (1-2C)alkylene; and
$Z_2$ is hydrogen, (1-6C)alkyl, (2-4C)alkenyl, (2-4C)alkynyl, phenyl, (3-6C)cycloalkyl, 5-6 membered heteroaryl or a 4-6-membered heterocyclyl; wherein $Z_2$ is optionally substituted by one or more substituents selected from (1-2C)alkyl, halo, (1-2C)haloalkyl, (1-2C)haloalkoxy, (1-2C)alkoxy, (1-2C)alkylamino, amino, cyano, nitro or hydroxy; and
$R^8$ is selected from (1-2C)alkyl, —C(O)$OR^q$, $OR^q$, $NR^qR^r$, phenyl or a 5-membered heteroaryl, wherein $R^q$ and $R^r$ are independently selected from hydrogen or (1-2C)alkyl;
or $R^6$ and $R^7$ can be linked such that, together with the carbon atom to which they are attached, they form a 4-6-membered carbocyclic ring or a 4-6-membered heterocyclic ring; or
(iii) a group of the formula:

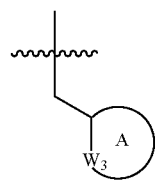

wherein:

denotes the point of attachment;
ring A is a 5-membered cycloalkyl or heterocyclyl ring;
$W_3$ is selected from $NR^{100}$ or $CR^{101}R^{102}$, wherein $R^{100}$ is selected from hydrogen, (1-2C)alkyl, —C(O)—$CH_3$ or —C(O)$OR^{ab}$, wherein $R^{ab}$ is (1-2C)alkyl, $R^{101}$ and $R^{102}$ are each independently selected from hydrogen, (1-2C)alkyl, fluoro, chloro, hydroxy, cyano, (1-2C)alkoxy, (1-2C)haloalkyl, (1-2C)haloalkoxy, —C(O)$OR^{ac}$, —$NR^{ac}R^{ad}$, phenyl or a 5-membered heteroaryl, and wherein $R^{ac}$ and $R^{ad}$ are independently selected from hydrogen or (1-2C)alkyl;

(40) $R^2$ is selected from:
 (i) hydrogen or methyl;
 (ii) a group of the formula:

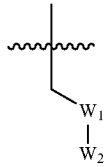

wherein:

denotes the point of attachment;
$W_1$ is selected from $CR^4R^5$ or $C(O)$, wherein $R^4$ and $R^5$ are independently selected from hydrogen, (1-2C)alkyl, fluoro, hydroxy, cyano, nitro, (1-2C)alkoxy, (1-2C)haloalkyl, (1-2C)haloalkoxy or $NR^jR^k$, wherein $R^j$ and $R^k$ are independently selected from hydrogen or (1-2C)alkyl; or
$R^4$ and $R^5$ can be linked such that, together with the carbon atom to which they are attached, they form a 3-6-membered carbocyclic ring or a 3-6-membered heterocyclic ring, which is optionally substituted by one or more substituents selected from (1-2C)alkyl, fluoro, chloro, $CH_2F$, $CF_2H$, $CF_3$, (1-2C)alkoxy, amino, cyano or hydroxy;
$W_2$ is selected from cyano, a 5- or 6-membered heteroaryl, phenyl, $C(O)OCH_3$, $C(O)N(H)CH_3$, $CR^6R^7R^8$ or $NR^lR^m$, wherein $R^l$ and $R^m$ are independently selected from hydrogen or (1-2C)alkyl, and wherein:
$R^6$ is selected from hydrogen, (1-2C)alkyl, fluoro, chloro, bromo, hydroxy, amino, cyano, nitro, (1-2C)alkoxy, $CH_2F$, $CF_2H$ or $CF_3$;
$R^7$ is selected from hydrogen, (1-2C)alkyl, fluoro, chloro, bromo, hydroxy, cyano, nitro, (1-2C)alkoxy, (1-2C)haloalkyl, (1-2C)haloalkoxy or a group of the formula:

—$Y_2$-$L_2$-$Z_2$ wherein:
 $Y_2$ is absent or selected from O, N(R″), C(O), C(O)O, OC(O), C(O)N(R″), N(R″)C(O), wherein R″ is selected from hydrogen or (1-2C)alkyl;
 $L_2$ is absent or (1-2C)alkylene; and
 $Z_2$ is hydrogen, (1-6C)alkyl, (2-4C)alkenyl, (2-4C)alkynyl, phenyl, (3-6C)cycloalkyl, 5-6 membered heteroaryl or a 4-6-membered heterocyclyl; wherein $Z_2$ is optionally substituted by one or more substituents selected from (1-2C)alkyl, halo, (1-2C)haloalkyl, (1-2C)haloalkoxy, (1-2C)alkoxy, (1-2C)alkylamino, amino, cyano, nitro or hydroxy; and
$R^8$ is selected from (1-2C)alkyl, —$C(O)OR^q$, $OR^q$, $NR^qR^r$, phenyl or a 5-membered heteroaryl, wherein $R^q$ and $R^r$ are independently selected from hydrogen or (1-2C)alkyl;

or $R^6$ and $R^7$ can be linked such that, together with the carbon atom to which they are attached, they form a 4-6-membered carbocyclic ring or a 4-6-membered heterocyclic ring; or
 (iii) a group of the formula:

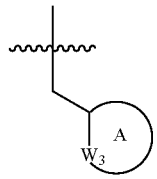

wherein:

denotes the point of attachment;
ring A is a 5-membered cycloalkyl or heterocyclyl ring;
$W_3$ is selected from $NR^{100}$ or $CR^{101}R^{102}$, wherein $R^{100}$ is selected from hydrogen, (1-2C)alkyl or —$C(O)OR^{ab}$, wherein $R^{ab}$ is (1-2C)alkyl, $R^{101}$ and $R^{102}$ are each independently selected from hydrogen, (1-2C)alkyl, fluoro, chloro, hydroxy, (1-2C)alkoxy, $CH_2F$, $CF_2H$, $CF_3$, —$C(O)OR^{ac}$ or —$NR^{ac}R^{ad}$, and wherein $R^{ac}$ and $R^{ad}$ are independently selected from hydrogen or (1-2C)alkyl;
(41) $R^2$ is selected from:
 (i) hydrogen or methyl;
 (ii) a group of the formula:

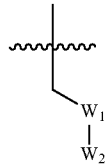

wherein:

denotes the point of attachment;
$W_1$ is selected from $CR^4R^5$ or $C(O)$, wherein $R^4$ and $R^5$ are independently selected from hydrogen, (1-2C)alkyl, fluoro, hydroxy, cyano, (1-2C)alkoxy, $CH_2F$, $CF_2H$, $CF_3$ or amino; or
$R^4$ and $R^5$ can be linked such that, together with the carbon atom to which they are attached, they form a 3-6-membered carbocyclic ring or a 3-6-membered heterocyclic ring, which is optionally substituted by one or more substituents selected from (1-2C)alkyl, fluoro, chloro, $CH_2F$, $CF_2H$, $CF_3$, (1-2C)alkoxy, amino, cyano or hydroxy;
$W_2$ is selected from cyano, a 5- or 6-membered heteroaryl, phenyl, $C(O)OCH_3$, $C(O)N(H)CH_3$, CR⁶R⁷R⁸ or NR^jR^m, wherein R^j and R^m are independently selected from hydrogen or (1-2C)alkyl, and wherein:
R⁶ is selected from hydrogen, (1-2C)alkyl, fluoro, chloro, hydroxy, amino, cyano, (1-2C)alkoxy, CH₂F or CF₂H;
R⁷ is selected from hydrogen, (1-2C)alkyl, fluoro, chloro, hydroxy, cyano, (1-2C)alkoxy, (1-2C)haloalkyl, (1-2C)haloalkoxy or a group of the formula:

—Y₂-L₂-Z₂ wherein:
Y₂ is absent or selected from O, N(R″), C(O), C(O)O, OC(O), C(O)N(R″), N(R″)C(O), wherein R″ is selected from hydrogen or (1-2C)alkyl;
L₂ is absent or (1-2C)alkylene; and
Z₂ is hydrogen, (1-6C)alkyl, (2-4C)alkenyl, (2-4C)alkynyl, phenyl, (3-6C)cycloalkyl, 5-6 membered heteroaryl or a 4-6-membered heterocyclyl; wherein Z₂ is optionally substituted by one or more substituents selected from (1-2C)alkyl, halo, (1-2C)haloalkyl, (1-2C)haloalkoxy, (1-2C)alkoxy, (1-2C)alkylamino, amino, cyano, nitro or hydroxy; and
R⁸ is selected from (1-2C)alkyl, —C(O)OR^q, OR^q, NR^qR^r, phenyl or a 5-membered heteroaryl, wherein R^q and R^r are independently selected from hydrogen or (1-2C)alkyl;
or R⁶ and R⁷ can be linked such that, together with the carbon atom to which they are attached, they form a 4-6-membered carbocyclic ring or a 4-6-membered heterocyclic ring; or
(iii) a group of the formula:

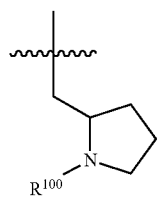

wherein:

denotes the point of attachment;
R¹⁰⁰ is selected from hydrogen, (1-2C)alkyl, —C(O)—CH₃ or —C(O)OR^{ab}, wherein R^{ab} is (1-2C)alkyl;
(42) R² is selected from:
(i) hydrogen or methyl;
(ii) a group of the formula:

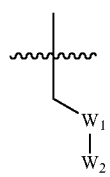

wherein:

denotes the point of attachment;
W₁ is selected from CR⁴R⁵ or C(O), wherein R⁴ and R⁵ are independently selected from hydrogen, (1-2C)alkyl, fluoro, hydroxy, cyano, (1-2C)alkoxy, CH₂F, CF₂H, CF₃ or amino; or
R⁴ and R⁵ can be linked such that, together with the carbon atom to which they are attached, they form a 3-6-membered carbocyclic ring or a 3-6-membered heterocyclic ring, which is optionally substituted by one or more substituents selected from (1-2C)alkyl, fluoro, chloro, CH₂F, CF₂H, CF₃, (1-2C)alkoxy, amino, cyano or hydroxy;
W₂ is selected from cyano, a 5- or 6-membered heteroaryl, phenyl, C(O)OCH₃, C(O)N(H)CH₃, CR⁶R⁷R⁸ or NR^jR^m, wherein R^j and R^m are independently selected from hydrogen or (1-2C)alkyl, and wherein:
R⁶ is selected from hydrogen, (1-2C)alkyl, fluoro, chloro, hydroxy, amino, cyano, (1-2C)alkoxy, CH₂F or CF₂H;
R⁷ is selected from hydrogen, (1-2C)alkyl, fluoro, chloro, hydroxy, cyano, (1-2C)alkoxy, (1-2C)haloalkyl, (1-2C)haloalkoxy or a group of the formula:

—Y₂-L₂-Z₂ wherein:
Y₂ is absent or selected from O, N(R″), C(O), C(O)O, OC(O), C(O)N(R″), N(R″)C(O), wherein R″ is selected from hydrogen or (1-2C)alkyl;
L₂ is absent or (1-2C)alkylene; and
Z₂ is hydrogen, (1-6C)alkyl, (2-4C)alkenyl, (2-4C)alkynyl, phenyl, (3-6C)cycloalkyl, 5-6 membered heteroaryl or a 4-6-membered heterocyclyl; wherein Z₂ is optionally substituted by one or more substituents selected from (1-2C)alkyl, halo, (1-2C)haloalkyl, (1-2C)haloalkoxy, (1-2C)alkoxy, (1-2C)alkylamino, amino, cyano, nitro or hydroxy; and
R⁸ is selected from (1-2C)alkyl, —C(O)OR^q, OR^q, NR^qR^r, phenyl or a 5-membered heteroaryl, wherein R^q and R^r are independently selected from hydrogen or (1-2C)alkyl;
or R⁶ and R⁷ can be linked such that, together with the carbon atom to which they are attached, they form a 4-6-membered carbocyclic ring or a 4-6-membered heterocyclic ring; or
(iii) a group of the formula:

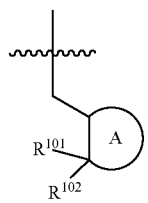

wherein:

denotes the point of attachment;
ring A is a 5-membered cycloalkyl or heterocyclyl ring;
$R^{101}$ and $R^{102}$ are each independently selected from hydrogen, (1-2C)alkyl, fluoro, chloro, hydroxy, cyano, (1-2C)alkoxy, (1-2C)haloalkyl, (1-2C)haloalkoxy, —C(O)OR$^{ac}$, —NR$^{ac}$R$^{ad}$, phenyl or a 5-membered heteroaryl, wherein R$^{ac}$ and R$^{ad}$ are independently selected from hydrogen or (1-2C)alkyl;

(43) $R^2$ is selected from:
(i) hydrogen or methyl;
(ii) a group of the formula:

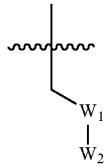

wherein:

denotes the point of attachment;
$W_1$ is selected from CR$^4$R$^5$ or C(O), wherein R$^4$ and R$^5$ are independently selected from hydrogen, (1-2C)alkyl, fluoro, hydroxy, cyano, (1-2C)alkoxy, CH$_2$F, CF$_2$H, CF$_3$ or amino; or
R$^4$ and R$^5$ can be linked such that, together with the carbon atom to which they are attached, they form a 3-6-membered carbocyclic ring or a 3-6-membered heterocyclic ring, which is optionally substituted by one or more substituents selected from (1-2C)alkyl, fluoro, chloro, CH$_2$F, CF$_2$H, CF$_3$, (1-2C)alkoxy, amino, cyano or hydroxy;
$W_2$ is selected from cyano, a 5- or 6-membered heteroaryl, phenyl, C(O)OCH$_3$, C(O)N(H)CH$_3$, CR$^6$R$^7$R$^8$ or NR$^l$R$^m$, wherein R$^l$ and R$^m$ are independently selected from hydrogen or (1-2C)alkyl, and wherein:
R$^6$ is selected from hydrogen, (1-2C)alkyl, fluoro, chloro, hydroxy, amino, cyano, (1-2C)alkoxy, CH$_2$F or CF$_2$H;
R$^7$ is selected from hydrogen, (1-2C)alkyl, fluoro, chloro, hydroxy, cyano, (1-2C)alkoxy, (1-2C)haloalkyl, (1-2C)haloalkoxy or a group of the formula:
—Y$_2$-L$_2$-Z$_2$
wherein:
Y$_2$ is absent or selected from O, N(R″), C(O), C(O)O, OC(O), C(O)N(R″), N(R″)C(O), wherein R″ is selected from hydrogen or (1-2C)alkyl;
L$_2$ is absent or (1-2C)alkylene; and
Z$_2$ is hydrogen, (1-6C)alkyl, (2-4C)alkenyl, (2-4C)alkynyl, phenyl, (3-6C)cycloalkyl, 5-6 membered heteroaryl or a 4-6-membered heterocyclyl; wherein Z$_2$ is optionally substituted by one or more substituents selected from (1-2C)alkyl, halo, (1-2C)haloalkyl, (1-2C)haloalkoxy, (1-2C)alkoxy, (1-2C)alkylamino, amino, cyano, nitro or hydroxy; and
R$^8$ is selected from (1-2C)alkyl, —C(O)OR$^q$, OR$^q$, NR$^q$R$^r$, phenyl or a 5-membered heteroaryl, wherein R$^q$ and R$^r$ are independently selected from hydrogen or (1-2C)alkyl;
or R$^6$ and R$^7$ can be linked such that, together with the carbon atom to which they are attached, they form a 4-6-membered carbocyclic ring or a 4-6-membered heterocyclic ring; or
(iii) a group of the formula:

wherein:

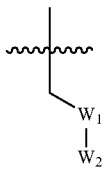

denotes the point of attachment;
ring A is a 5-membered cycloalkyl or heterocyclyl ring;
$R^{101}$ is selected from hydrogen or methyl; and
$R^{102}$ is selected from (1-2C)alkyl, fluoro, chloro, hydroxy, cyano, (1-2C)alkoxy, (1-2C)haloalkyl, (1-2C)haloalkoxy, —C(O)OR$^{ac}$, —NR$^{ac}$R$^{ad}$ phenyl or a 5-membered heteroaryl, wherein R$^{ac}$ and R$^{ad}$ are independently selected from hydrogen or (1-2C)alkyl;

(44) $R^2$ is selected from:
(i) hydrogen or methyl;
(ii) a group of the formula:

wherein:

denotes the point of attachment;

W₁ is selected from CR⁴R⁵ or C(O), wherein R⁴ and R⁵ are independently selected from hydrogen, (1-2C)alkyl, fluoro, hydroxy, cyano, (1-2C)alkoxy, CH₂F, CF₂H or amino; or R⁴ and R⁵ can be linked such that, together with the carbon atom to which they are attached, they form a 3-6-membered carbocyclic ring or a 3-6-membered heterocyclic ring, which is optionally substituted by one or more substituents selected from methyl, fluoro, chloro, OCH₃, amino, cyano or hydroxy;

W₂ is selected from cyano, a 5- or 6-membered heteroaryl, phenyl, C(O)OCH₃, C(O)N(H)CH₃, CR⁶R⁷R⁸ or NR^j R^m, wherein R^j and R^m are independently selected from hydrogen or (1-2C)alkyl, and wherein:

R⁶ is selected from hydrogen, (1-2C)alkyl, fluoro, chloro, hydroxy, amino, cyano or (1-2C)alkoxy;

R⁷ is selected from hydrogen, (1-2C)alkyl, fluoro, chloro, hydroxy, cyano, (1-2C)alkoxy, (1-2C)haloalkyl, (1-2C)haloalkoxy or a group of the formula:

—Y₂-L₂-Z₂ wherein:
Y₂ is absent or selected from O, C(O), C(O)O, OC(O), C(O)N(R″) or N(R″)C(O), wherein R″ is selected from hydrogen or (1-2C)alkyl;
L₂ is absent or (1-2C)alkylene; and
Z₂ is hydrogen, (1-6C)alkyl, (2-4C)alkenyl, (2-4C)alkynyl, phenyl, (3-6C)cycloalkyl, 5-6 membered heteroaryl or a 4-6-membered heterocyclyl; wherein Z₂ is optionally substituted by one or more substituents selected from (1-2C)alkyl, halo, (1-2C)haloalkyl, (1-2C)haloalkoxy, (1-2C)alkoxy, (1-2C)alkylamino, amino, cyano, nitro or hydroxy; and
R⁸ is selected from (1-2C)alkyl, —C(O)OR^q, OR^q, NR^qR^r, phenyl or a 5-membered heteroaryl, wherein R^q and R^r are independently selected from hydrogen or (1-2C)alkyl; or (iii) a group of the formula:

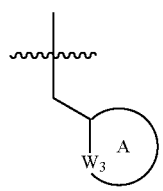

wherein:

denotes the point of attachment;
ring A is a 5-membered cycloalkyl or heterocyclyl ring;
W₃ is selected from NR¹⁰⁰ or CR¹⁰¹R¹⁰², wherein R¹⁰⁰ is selected from hydrogen, (1-2C)alkyl or —C(O)OR^{ab}, wherein R^{ab} is (1-2C)alkyl, R¹⁰¹ and R¹⁰² are each independently selected from hydrogen, (1-2C)alkyl, fluoro, chloro, hydroxy, (1-2C)alkoxy, CH₂F, CF₂H, CF₃, —C(O)OR^{ac} or —NR^{ac}R^{ad} and wherein R^{ac} and R^{ad} are independently selected from hydrogen or (1-2C)alkyl;

(45) R² is selected from:
(i) hydrogen or methyl;
(ii) a group of the formula:

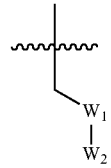

wherein:

denotes the point of attachment;
W₁ is selected from CR⁴R⁵ or C(O), wherein R⁴ and R⁵ are independently selected from hydrogen, (1-2C)alkyl, fluoro, hydroxy, cyano, (1-2C)alkoxy, CH₂F, CF₂H or amino; or R⁴ and R⁵ can be linked such that, together with the carbon atom to which they are attached, they form a 3-6-membered heterocyclic ring, which is optionally substituted by one or more substituents selected from methyl, fluoro, chloro, OCH₃, amino, cyano or hydroxy;

W₂ is selected from cyano, a 5- or 6-membered heteroaryl, phenyl, C(O)OCH₃, C(O)N(H)CH₃, CR⁶R⁷R⁸ or NR^j R^m, wherein R^j and R^m are independently selected from hydrogen or (1-2C)alkyl, and wherein:

R⁶ is selected from hydrogen, (1-2C)alkyl, fluoro, chloro, hydroxy, amino, cyano or (1-2C)alkoxy;

R⁷ is selected from hydrogen, (1-2C)alkyl, fluoro, chloro, hydroxy, cyano, (1-2C)alkoxy, (1-2C)haloalkyl, (1-2C)haloalkoxy or a group of the formula:

—Y₂-L₂-Z₂ wherein:
Y₂ is absent or selected from O, C(O), C(O)O, OC(O), C(O)N(R″) or N(R″)C(O), wherein R″ is selected from hydrogen or (1-2C)alkyl;
L₂ is absent or (1-2C)alkylene; and
Z₂ is hydrogen, (1-6C)alkyl, (2-4C)alkenyl, (2-4C)alkynyl, phenyl, (3-6C)cycloalkyl, 5-6 membered heteroaryl or a 4-6-membered heterocyclyl; wherein Z₂ is optionally substituted by one or more substituents selected from (1-2C)alkyl, halo, (1-2C)haloalkyl, (1-2C)haloalkoxy, (1-2C)alkoxy, (1-2C)alkylamino, amino, cyano, nitro or hydroxy; and
R⁸ is selected from (1-2C)alkyl, —C(O)OR^q, OR^q, NR^qR^r, phenyl or a 5-membered heteroaryl, wherein R^q and R^r are independently selected from hydrogen or (1-2C)alkyl; or

49

(iii) a group of the formula:

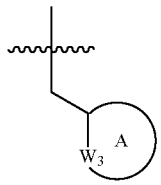

wherein:

denotes the point of attachment;
ring A is a 5-membered cycloalkyl or heterocyclyl ring;
$W_3$ is selected from $NR^{100}$ or $CR^{101}R^{102}$, wherein $R^{100}$ is selected from hydrogen, (1-2C)alkyl or —C(O)OR$^{ab}$, wherein R$^{ab}$ is (1-2C)alkyl, $R^{101}$ and $R^{102}$ are each independently selected from hydrogen, (1-2C)alkyl, fluoro, chloro, hydroxy, (1-2C)alkoxy, $CH_2F$, $CF_2H$, $CF_3$, —C(O)OR$^{ac}$ or —NR$^{ac}$R$^{ad}$, and wherein R$^{ac}$ and R$^{ad}$ are independently selected from hydrogen or (1-2C)alkyl;

(46) $R^2$ is selected from:
(i) hydrogen or methyl;
(ii) a group of the formula:

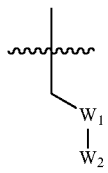

wherein:

denotes the point of attachment;
$W_1$ is selected from CHR$^4$ or C(O), wherein R$^4$ is selected from hydrogen, (1-2C)alkyl, fluoro, hydroxy, cyano, nitro, (1-2C)alkoxy, (1-2C)haloalkyl, (1-2C)haloalkoxy or NR$^j$R$^k$, wherein R$^j$ and R$^k$ are independently selected from hydrogen or (1-2C)alkyl;
$W_2$ is selected from cyano, a 5- or 6-membered heteroaryl, phenyl, C(O)OCH$_3$, C(O)N(H)CH$_3$, CR$^6$R$^7$R$^8$ or NR$^l$R$^m$, wherein R$^l$ and R$^m$ are independently selected from hydrogen or (1-2C)alkyl, and wherein:
  $R^6$ is selected from hydrogen, (1-2C)alkyl, fluoro, chloro, hydroxy, amino, cyano, (1-2C)alkoxy, $CH_2F$, $CF_2H$ or $CF_3$;
  $R^7$ is selected from hydrogen, (1-2C)alkyl, fluoro, chloro, hydroxy, cyano, (1-2C)alkoxy, (1-2C)haloalkyl, (1-2C)haloalkoxy or a group of the formula:
  —$Y_2$-$L_2$-$Z_2$

50 wherein:
  $Y_2$ is absent or selected from O, N(R″), SO$_2$, C(O), C(O)O, OC(O), C(O)N(R″), N(R″)C(O), S(O)$_2$N(R″), or N(R″)SO$_2$, wherein R″ is selected from hydrogen or (1-2C)alkyl;
  $L_2$ is absent or (1-2C)alkylene; and
  $Z_2$ is hydrogen, (1-6C)alkyl, (2-4C)alkenyl, (2-4C)alkynyl, phenyl, (3-6C)cycloalkyl, 5-6 membered heteroaryl or a 4-6-membered heterocyclyl; wherein $Z_2$ is optionally substituted by one or more substituents selected from (1-2C)alkyl, halo, (1-2C)haloalkyl, (1-2C)haloalkoxy, (1-2C)alkoxy, (1-2C)alkylamino, amino, cyano, nitro or hydroxy; and
  $R^8$ is selected from (1-2C)alkyl, —C(O)OR$^q$, OR$^q$, NR$^q$R$^r$, phenyl or a 5-membered heteroaryl, wherein R$^q$ and R$^r$ are independently selected from hydrogen or (1-2C)alkyl; or
  $R^6$ and $R^7$ can be linked such that, together with the carbon atoms to which they are attached, they form a 4-6 membered carbocyclic ring or a 4-6 membered heterocyclic ring, which is optionally substituted by one or more substituents selected from (1-2C)alkyl, fluoro, chloro, $CH_2F$, $CF_2H$ or $CF_3$, (1-2C)alkoxy, amino, cyano or hydroxy; or (iii) a group of the formula:

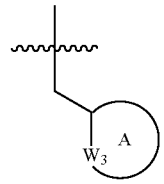

wherein:

denotes the point of attachment;
ring A is a 5-membered cycloalkyl or heterocyclyl ring;
$W_3$ is selected from $NR^{100}$ or $CR^{101}R^{102}$, wherein $R^{100}$ is selected from hydrogen, (1-2C)alkyl or —C(O)OR$^{ab}$, wherein R$^{ab}$ is (1-2C)alkyl, $R^{101}$ and $R^{102}$ are each independently selected from hydrogen, (1-2C)alkyl, fluoro, chloro, hydroxy, (1-2C)alkoxy, $CH_2F$, $CF_2H$, $CF_3$, —C(O)OR$^{ac}$ or —NR$^{ac}$R$^{ad}$, and wherein R$^{ac}$ and R$^{ad}$ are independently selected from hydrogen or (1-2C)alkyl;

(47) $R^2$ is selected from:
(i) hydrogen or methyl;
(ii) a group of the formula:

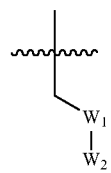

wherein:

denotes the point of attachment;
$W_1$ is selected from $CHR^4$ or $C(O)$, wherein $R^4$ is selected from hydrogen, (1-2C)alkyl, fluoro, hydroxy, cyano, (1-2C)alkoxy, $CH_2F$, $CF_2H$, $CF_3$ or amino;
$W_2$ is selected from cyano, a 5- or 6-membered heteroaryl, phenyl, $C(O)OCH_3$, $C(O)N(H)CH_3$, $CR^6R^7R^8$ or $NR^lR^m$, wherein $R^l$ and $R^m$ are independently selected from hydrogen or (1-2C)alkyl, and wherein:
$R^6$ is selected from hydrogen, (1-2C)alkyl, fluoro, chloro, hydroxy, amino, cyano, (1-2C)alkoxy, $CH_2F$, $CF_2H$ or $CF_3$;
$R^7$ is selected from hydrogen, (1-2C)alkyl, fluoro, chloro, hydroxy, cyano, (1-2C)alkoxy, (1-2C)haloalkyl, (1-2C)haloalkoxy or a group of the formula:

—$Y_2$-$L_2$-$Z_2$ wherein:
$Y_2$ is absent or selected from O, N(R″), $SO_2$, C(O), C(O)O, OC(O), C(O)N(R″) or N(R″)C(O), wherein R″ is selected from hydrogen or (1-2C)alkyl;
$L_2$ is absent or (1-2C)alkylene; and
$Z_2$ is hydrogen, (1-6C)alkyl, (2-4C)alkenyl, (2-4C)alkynyl, phenyl, (3-6C)cycloalkyl, 5-6 membered heteroaryl or a 4-6-membered heterocyclyl; wherein $Z_2$ is optionally substituted by one or more substituents selected from (1-2C)alkyl, halo, (1-2C)haloalkyl, (1-2C)haloalkoxy, (1-2C)alkoxy, (1-2C)alkylamino, amino, cyano, nitro or hydroxy; and
$R^8$ is selected from (1-2C)alkyl, —C(O)OR$^q$, OR$^q$, NR$^q$R$^r$, phenyl or a 5-membered heteroaryl, wherein R$^q$ and R$^r$ are independently selected from hydrogen or (1-2C)alkyl; or
$R^6$ and $R^7$ can be linked such that, together with the carbon atoms to which they are attached, they form a 4-6 membered carbocyclic ring or a 4-6 membered heterocyclic ring, which is optionally substituted by one or more substituents selected from (1-2C)alkyl, fluoro, chloro, $CH_2F$, $CF_2H$ or $CF_3$, (1-2C)alkoxy, amino, cyano or hydroxy; or
(iii) a group of the formula:

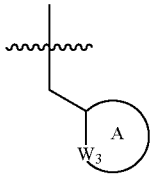

wherein:

denotes the point of attachment;
ring A is a 5-membered cycloalkyl or heterocyclyl ring;

$W_3$ is selected from $NR^{100}$ or $CR^{101}R^{102}$, wherein $R^{100}$ is selected from hydrogen, (1-2C)alkyl or —C(O)OR$^{ab}$, wherein R$^{ab}$ is (1-2C)alkyl, $R^{101}$ and $R^{102}$ are each independently selected from hydrogen, (1-2C)alkyl, fluoro, chloro, hydroxy, (1-2C)alkoxy, $CH_2F$, $CF_2H$, $CF_3$, —C(O)OR$^{ac}$ or —NR$^{ac}$R$^{ad}$, and wherein R$^{ac}$ and R$^{ad}$ are independently selected from hydrogen or (1-2C)alkyl;

(48) $R^2$ is selected from:
(i) hydrogen or methyl;
(ii) a group of the formula:

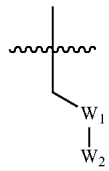

wherein:

denotes the point of attachment;
$W_1$ is selected from $CHR^4$ or $C(O)$, wherein $R^4$ is selected from hydrogen, (1-2C)alkyl, fluoro, hydroxy, cyano, (1-2C)alkoxy, $CH_2F$, $CF_2H$, $CF_3$ or amino;
$W_2$ is selected from cyano, a 5- or 6-membered heteroaryl, phenyl, $C(O)OCH_3$, $C(O)N(H)CH_3$, $CR^6R^7R^8$ or $NR^lR^m$, wherein $R^l$ and $R^m$ are independently selected from hydrogen or (1-2C)alkyl, and wherein:
$R^6$ is selected from hydrogen, (1-2C)alkyl, fluoro, chloro, hydroxy, amino, cyano, (1-2C)alkoxy, $CH_2F$, $CF_2H$ or $CF_3$;
$R^7$ is selected from hydrogen, (1-2C)alkyl, fluoro, chloro, hydroxy, cyano, (1-2C)alkoxy, (1-2C)haloalkyl, (1-2C)haloalkoxy or a group of the formula:

—$Y_2$-$L_2$-$Z_2$ wherein:
$Y_2$ is absent or selected from O, C(O)O, C(O)N(R″) or N(R″)C(O), wherein R″ is selected from hydrogen or (1-2C)alkyl;
$L_2$ is absent or (1-2C)alkylene; and
$Z_2$ is hydrogen, (1-6C)alkyl, (2-4C)alkenyl, (2-4C)alkynyl, phenyl, (3-6C)cycloalkyl, 5-6 membered heteroaryl or a 4-6-membered heterocyclyl; wherein $Z_2$ is optionally substituted by one or more substituents selected from (1-2C)alkyl, halo, (1-2C)haloalkyl, (1-2C)haloalkoxy, (1-2C)alkoxy, (1-2C)alkylamino, amino, cyano, nitro or hydroxy; and
$R^8$ is selected from (1-2C)alkyl, —C(O)OR$^q$, OR$^q$, NR$^q$R$^r$, phenyl or a 5-membered heteroaryl, wherein R$^q$ and R$^r$ are independently selected from hydrogen or (1-2C)alkyl; or $R^6$ and $R^7$ can be linked such that, together with the carbon atoms to which they are attached, they form a 4-6 membered carbocyclic ring or a 4-6 membered heterocyclic ring, which is optionally substituted by one or more substituents selected from (1-2C)alkyl, fluoro, chloro or hydroxy; or
(iii) a group of the formula:

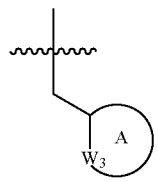

wherein:

denotes the point of attachment;
ring A is a 5-membered cycloalkyl or heterocyclyl ring;
$W_3$ is selected from $NR^{100}$ or $CR^{101}R^{102}$, wherein $R^{100}$ is selected from hydrogen, (1-2C)alkyl or —C(O)OR$^{ab}$, wherein R$^{ab}$ is (1-2C)alkyl, $R^{101}$ and $R^{102}$ are each independently selected from hydrogen, (1-2C)alkyl, hydroxy, (1-2C)alkoxy or —C(O)OR$^{ac}$, and wherein R$^{ac}$ is selected from hydrogen or (1-2C)alkyl;
(49) $R^2$ is selected from:
(i) hydrogen or methyl;
(ii) a group of the formula:

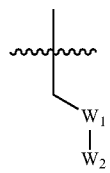

wherein:

denotes the point of attachment;
$W_1$ is selected from $CHR^4$ or $C(O)$, wherein $R^4$ is selected from hydrogen, (1-2C)alkyl, fluoro, hydroxy, cyano, (1-2C)alkoxy, $CH_2F$, $CF_2H$ or amino;
$W_2$ is selected from cyano, a 5- or 6-membered heteroaryl, phenyl, $C(O)OCH_3$, $C(O)N(H)CH_3$, $CR^6R^7R^8$ or $NR^lR^m$, wherein $R^l$ and $R^m$ are independently selected from hydrogen or (1-2C)alkyl, and wherein:
$R^6$ is selected from hydrogen, (1-2C)alkyl, fluoro, chloro, hydroxy, amino, cyano, (1-2C)alkoxy, $CH_2F$ or $CF_2H$;

$R^7$ is selected from hydrogen, (1-2C)alkyl, fluoro, chloro, hydroxy, cyano, (1-2C)alkoxy, (1-2C)haloalkyl, (1-2C)haloalkoxy or a group of the formula:
—$Y_2$-$L_2$-$Z_2$
wherein:
$Y_2$ is absent or selected from O, C(O)O, C(O)N(R″) or N(R″)C(O), wherein R″ is selected from hydrogen or (1-2C)alkyl;
$L_2$ is absent or (1-2C)alkylene; and
$Z_2$ is hydrogen, (1-6C)alkyl, (2-4C)alkenyl, (2-4C)alkynyl, phenyl, (3-6C)cycloalkyl, 5-6 membered heteroaryl or a 4-6-membered heterocyclyl; wherein $Z_2$ is optionally substituted by one or more substituents selected from (1-2C)alkyl, halo, (1-2C)haloalkyl, (1-2C)haloalkoxy, (1-2C)alkoxy, (1-2C)alkylamino, amino, cyano or hydroxy; and
$R^8$ is selected from (1-2C)alkyl, —C(O)OR$^q$, OR$^q$, NR$^q$R$^r$, phenyl or a 5-membered heteroaryl, wherein R$^q$ and R$^r$ are independently selected from hydrogen or (1-2C)alkyl; or
$R^6$ and $R^7$ can be linked such that, together with the carbon atoms to which they are attached, they form a 4-6 membered carbocyclic ring or a 4-6 membered heterocyclic ring; or
(iii) a group of the formula:

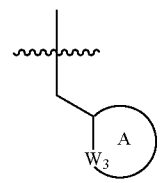

wherein:

denotes the point of attachment;
ring A is a 5-membered cycloalkyl or heterocyclyl ring;
$W_3$ is selected from $NR^{100}$ or $CR^{101}R^{102}$, wherein $R^{100}$ is selected from hydrogen, (1-2C)alkyl or —C(O)OR$^{ab}$, wherein R$^{ab}$ is (1-2C)alkyl, $R^{101}$ is selected from hydrogen or methyl and $R^{102}$ is selected from (1-2C)alkyl, hydroxy, (1-2C)alkoxy, C(O)OR$^{ac}$, or —NR$^{ac}$R$^{ad}$ and wherein R$^{ac}$ and R$^{ad}$ are independently selected from hydrogen or (1-2C)alkyl;
(50) $R^2$ is selected from:
(i) hydrogen or methyl;
(ii) a group of the formula:

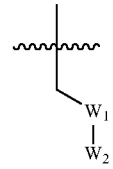

wherein:

denotes the point of attachment;
$W_1$ is selected from $CHR^4$ or $C(O)$, wherein $R^4$ is selected from hydrogen, (1-2C)alkyl, fluoro, hydroxy, cyano or (1-2C)alkoxy;
$W_2$ is selected from cyano, a 5- or 6-membered heteroaryl, phenyl, $C(O)OCH_3$, $C(O)N(H)CH_3$, $CR^6R^7R^8$ or $NR^lR^m$, wherein $R^l$ and $R^m$ are independently selected from hydrogen or (1-2C)alkyl, and wherein:
$R^6$ is selected from hydrogen, (1-2C)alkyl, fluoro, chloro, hydroxy, amino, cyano or (1-2C)alkoxy;
$R^7$ is selected from hydrogen, (1-2C)alkyl, fluoro, chloro, hydroxy, cyano, (1-2C)alkoxy, (1-2C)haloalkyl, (1-2C)haloalkoxy or a group of the formula:

wherein:
$Y_2$ is absent or selected from O, C(O)O, C(O)N(R'') or N(R'')C(O), wherein R'' is selected from hydrogen or (1-2C)alkyl;
$L_2$ is absent or (1-2C)alkylene; and
$Z_2$ is hydrogen, (1-6C)alkyl, (2-4C)alkenyl, (2-4C)alkynyl, phenyl, (3-6C)cycloalkyl, 5-6 membered heteroaryl or a 4-6-membered heterocyclyl; wherein $Z_2$ is optionally substituted by one or more substituents selected from (1-2C)alkyl, halo, (1-2C)haloalkyl, (1-2C)haloalkoxy, (1-2C)alkoxy, (1-2C)alkylamino, amino, cyano or hydroxy; and
$R^8$ is selected from (1-2C)alkyl, —$C(O)OR^q$, $OR^q$, $NR^qR^r$, phenyl or pyrazolyl, wherein $R^q$ and $R^r$ are independently selected from hydrogen or (1-2C)alkyl; or
(iii) a group of the formula:

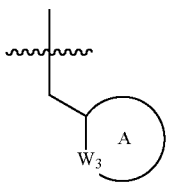

wherein:

denotes the point of attachment;
ring A is a 5-membered cycloalkyl or heterocyclyl ring;
$W_3$ is selected from $NR^{100}$ or $CR^{101}R^{102}$, wherein $R^{100}$ is selected from hydrogen, (1-2C)alkyl or —$C(O)OR^{ab}$, wherein $R^{ab}$ is (1-2C)alkyl, $R^{101}$ is selected from hydrogen or methyl and $R^{102}$ is selected from (1-2C)alkyl, hydroxy or $C(O)OR^{ac}$ wherein $R^{ac}$ is selected from hydrogen or (1-2C)alkyl;

(51) $R^2$ is selected from a group of the formula:

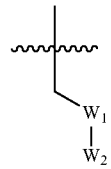

wherein:

denotes the point of attachment;
$W_1$ is selected from $CHR^4$, wherein $R^4$ is selected from hydrogen, (1-2C)alkyl, fluoro, hydroxy, cyano or (1-2C)alkoxy;
$W_2$ is $CR^6R^7R^8$, wherein:
$R^6$ is selected from hydrogen, (1-2C)alkyl, fluoro, chloro, hydroxy, amino, cyano or (1-2C)alkoxy;
$R^7$ is selected from hydrogen, (1-2C)alkyl, fluoro, chloro, hydroxy, cyano, (1-2C)alkoxy, (1-2C)haloalkyl, (1-2C)haloalkoxy; and
$R^8$ is selected from (1-2C)alkyl, —$C(O)OR^q$, $OR^q$, $NR^qR^r$, phenyl or pyrazolyl, wherein $R^q$ and $R^r$ are independently selected from hydrogen or (1-2C)alkyl;

(52) $R^2$ is selected from a group of the formula:

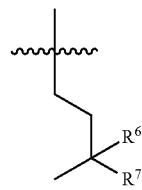

wherein:

denotes the point of attachment;
$W_2$ is $CR^6R^7R^8$, wherein:
$R^6$ is selected from (1-2C)alkyl, fluoro, chloro, hydroxy, amino, cyano or (1-2C)alkoxy; and
$R^7$ is selected from hydrogen, (1-2C)alkyl, fluoro, chloro, hydroxy, cyano, (1-2C)alkoxy, (1-2C)haloalkyl, (1-2C)haloalkoxy;

(53) $R^2$ is a group of the formula:

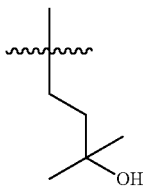 [SMILES: *CCC(C)(C)O]

wherein:

denotes the point of attachment;
(54) $R^3$ is selected from:
i) a group of Formula A shown below:

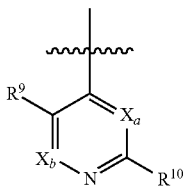

Formula A wherein:

denotes the point of attachment;
$X_a$ and $X_b$ are independently selected from N or $CR^{x1}$, wherein $R^{x1}$ is selected from hydrogen, fluoro, chloro, bromo, (1-2C)alkyl, (1-2C)alkoxy, cyano, nitro, acetylenyl, $CH_2F$, $CF_2H$ or $CF_3$;
$R^9$ is selected from hydrogen, fluoro, chloro, bromo, (1-2C)alkyl, (1-2C)alkoxy, cyano, nitro, acetylenyl, $CH_2F$, $CF_2H$ or $CF_3$;
$R^{10}$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—$Y_3$—$Z_3$ wherein:
$Y_3$ is absent or O, $N(R^s)(CR^sR^t)_{q1}$ (where $q_1$ is 0, 1 or 2), S, SO, $SO_2$, C(O), C(O)O, OC(O), C(O)N($R^s$), N($R^s$)C(O), S(O)$_2$N($R^s$) or N($R^s$)SO$_2$, wherein $R^s$ is selected from hydrogen or (1-4C)alkyl; and
$Z_3$ is hydrogen, (1-6C)alkyl, aryl, (3-6C)cycloalkyl, (2-4C)alkenyl, (2-4C)alkynyl, (3-6C)cycloalkenyl, heteroaryl or 4 to 11-membered heterocyclyl; wherein $Z_3$ is optionally further substituted by one substituent groups independently selected from oxo, (1-4C)alkyl, (3-6C)cycloalkyl, halo, (1-4C)haloalkyl, (1-4C)haloalkoxy, (1-4C)hydroxyalkyl, amino, cyano, hydroxy, amido, carboxy, carbamoyl, sulphamoyl, mercapto, C(O)$NR^uR^v$, $NR^uR^v$ or $OR^u$, wherein $R^u$ and $R^v$ are each independently selected from hydrogen, (1-4C)alkyl or (3-6C)cycloalkyl; and/or $Z^3$ is optionally further substituted by a group of the formula:

-$L_Z$-$W_Z$ wherein:
$L_Z$ is absent or a (1-5C)alkylene optionally substituted by one or more (1-2C)alkyl groups; and
$W_Z$ is aryl, 5- or 6-membered heteroaryl, 4- to 7-membered heterocyclyl, halo, (1-4C)haloalkyl, (1-4C)haloalkoxy, cyano, hydroxy, (1-4C)alkoxy, C(O)$R^{xa}$, COO$R^{xa}$, C(O)$NR^{xa}R^{xb}$ or $NR^{xa}R^{xb}$, wherein $R^{xa}$ and $R^{xb}$ are each independently selected from hydrogen or (1-4C)alkyl; and wherein each aryl, 5- or 6-membered heteroaryl or 4- to 7-membered heterocyclyl is optionally further substituted by one or more substituent groups independently selected from (1-2C)alkyl, halo, (1-2C)haloalkyl, amino, cyano or hydroxy;
ii) a group of Formula B shown below:

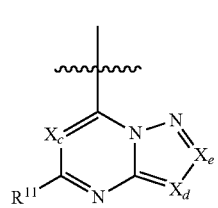

Formula B wherein:

denotes the point of attachment;
$X_c$, $X_d$ and $X_e$ are independently selected from N, CH, CF, CCl, C—CN or CCH$_3$;
$R^{11}$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—$Y_5$—$Z_5$ wherein:
$Y_5$ is absent or O, N($R^w$), C(O), C(O)O, OC(O), C(O)N($R^w$), N($R^w$)C(O), S(O)$_2$N($R^w$) or N($R^w$)SO$_2$, wherein $R^w$ is selected from hydrogen or (1-4C)alkyl; and
$Z_5$ is hydrogen, (1-6C)alkyl, aryl, (3-8C)cycloalkyl, (3-8C)cycloalkenyl, heteroaryl or heterocyclyl; wherein $Z_5$ is optionally further substituted by one or more substituent groups independently selected from (1-4C)alkyl, halo, (1-4C)haloalkyl, (1-4C)haloalkoxy, (1-4C)hydroxyalkyl, amino, cyano, hydroxy, amido, carboxy, carbamoyl, sulphamoyl, mercapto, NR$^y$R$^z$, OR$^y$, wherein R$^y$ and R$^z$ are each independently selected from hydrogen, (1-4C)alkyl or (3-6C)cycloalkyl;

iii) a group of Formula C shown below:

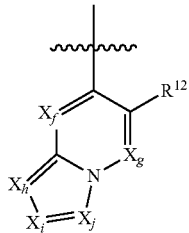

Formula C wherein:

denotes the point of attachment;

R$^{12}$ is selected from fluoro, chloro, bromo, (1-2C)alkyl, (1-2C)alkoxy, cyano, nitro, (2-4C)alkynyl, CH$_2$F, CF$_2$H or CF$_3$;

X$_f$ and X$_g$ are independently selected from N or CR$^{13}$, wherein R$^{13}$ is selected from hydrogen, fluoro, chloro, (1-2C)alkyl, (1-2C)haloalkyl or (1-2C)haloalkoxy;

X$_h$, X$_i$ and X$_j$ are independently selected from N or CR$^{14}$, wherein R$^{14}$ is selected from hydrogen, halo, (1-2C)alkyl, (1-2C)alkoxy, (1-2C)haloalkyl or (1-2C)haloalkoxy;

(55) R$^3$ is selected from:

i) a group of Formula A shown below:

Formula A

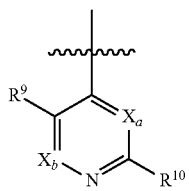

wherein:

denotes the point of attachment;

X$_a$ and X$_b$ are independently selected from N or CR$^{x1}$, wherein R$^1$ is selected from hydrogen, fluoro, chloro, bromo, (1-2C)alkyl, (1-2C)alkoxy, cyano, nitro, acetylenyl, CH$_2$F, CF$_2$H or CF$_3$;

R$^9$ is selected from hydrogen, fluoro, chloro, bromo, (1-2C)alkyl, (1-2C)alkoxy, cyano, nitro, acetylenyl, CH$_2$F, CF$_2$H or CF$_3$;

R$^{10}$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y$_3$—Z$_3$ wherein:

Y$_3$ is absent or O, N(R$^s$)(CR$^s$R$^t$)$_{q_1}$ (where q$_1$ is 0, 1 or 2), S, SO, SO$_2$, C(O), C(O)O, OC(O), C(O)N(R$^s$), N(R$^s$)C(O), S(O)$_2$N(R$^s$) or N(R$^s$)SO$_2$, wherein R$^s$ is selected from hydrogen or (1-4C)alkyl; and Z$_3$ is hydrogen, (1-6C)alkyl, aryl, (3-6C)cycloalkyl, (2-4C)alkenyl, (2-4C)alkynyl, (3-6C)cycloalkenyl, heteroaryl or 4 to 11-membered heterocyclyl; wherein Z$_3$ is optionally further substituted by one or more substituent groups independently selected from oxo, (1-4C)alkyl, (3-6C)cycloalkyl, halo, (1-4C)haloalkyl, (1-4C)haloalkoxy, (1-4C)hydroxyalkyl, amino, cyano, hydroxy, amido, carboxy, carbamoyl, sulphamoyl, mercapto, C(O)NR$^u$R$^v$, NR$^u$R$^v$ or OR$^u$, wherein R$^u$ and R$^v$ are each independently selected from hydrogen, (1-4C)alkyl or (3-6C)cycloalkyl; and/or Z$^3$ is optionally further substituted by a group of the formula:

-L$_Z$-W$_Z$

wherein:

L$_Z$ is absent or a (1-3C)alkylene optionally substituted by one or more (1-2C)alkyl groups; and W$_Z$ is aryl, 5- or 6-membered heteroaryl, 4- to 7-membered heterocyclyl, halo, (1-4C)haloalkyl, (1-4C)haloalkoxy, cyano, hydroxy, (1-4C)alkoxy, C(O)R$^{xa}$, COOR$^{xa}$, C(O)NR$^{xa}$R$^{xb}$ or NR$^{xa}$R$^{xb}$, wherein R$^{xa}$ and R$^{xb}$ are each independently selected from hydrogen or (1-4C)alkyl;

ii) a group of Formula B shown below:

Formula B

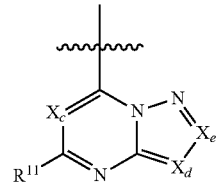

wherein:

denotes the point of attachment;

X$_c$, X$_d$ and X$_e$ are independently selected from N, CH, CF, CCl, C—CN or CCH$_3$;

R$^{11}$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y$_5$—Z$_5$

wherein:

Y₅ is absent or O, N(Rʷ), C(O), C(O)O, OC(O), C(O)N(Rʷ), N(Rʷ)C(O), S(O)₂N(Rʷ) or N(Rʷ)SO₂, wherein Rʷ is selected from hydrogen or (1-4C)alkyl; and Z₅ is hydrogen, (1-6C)alkyl, aryl, (3-8C)cycloalkyl, (3-8C)cycloalkenyl, heteroaryl or heterocyclyl; wherein Z₅ is optionally further substituted by one or more substituent groups independently selected from (1-4C)alkyl, halo, (1-4C)haloalkyl, (1-4C)haloalkoxy, (1-4C)hydroxyalkyl, amino, cyano, hydroxy, amido, carboxy, carbamoyl, sulphamoyl, mercapto, NRʸRᶻ, ORʸ, wherein Rʸ and Rᶻ are each independently selected from hydrogen, (1-4C)alkyl or (3-6C)cycloalkyl;

iii) a group of Formula C shown below:

Formula C

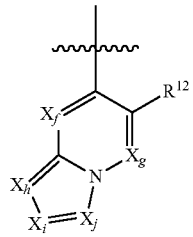

wherein:

denotes the point of attachment;

R¹² is selected from fluoro, chloro, bromo, (1-2C)alkyl, (1-2C)alkoxy, cyano, nitro, (2-4C)alkynyl, CH₂F, CF₂H or CF₃;

X_f and X_g are independently selected from N or CR¹³, wherein R¹³ is selected from hydrogen, fluoro, chloro, (1-2C)alkyl, (1-2C)haloalkyl or (1-2C)haloalkoxy;

X_h, X_i and X_j are independently selected from N or CR¹⁴, wherein R¹⁴ is selected from hydrogen, halo, (1-2C)alkyl, (1-2C)alkoxy, (1-2C)haloalkyl or (1-2C)haloalkoxy;

(56) R³ is selected from:

i) a group of Formula A shown below:

Formula A

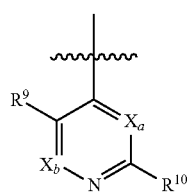

wherein:

denotes the point of attachment;

X_a and X_b are independently selected from N or CR^{x1}, wherein R^{x1} is selected from hydrogen, fluoro, chloro, bromo, (1-2C)alkyl, (1-2C)alkoxy, cyano, nitro, acetylenyl, CH₂F, CF₂H or CF₃;

R⁹ is selected from hydrogen, fluoro, chloro, bromo, (1-2C)alkyl, (1-2C)alkoxy, cyano, nitro, acetylenyl, CH₂F, CF₂H or CF₃;

R¹⁰ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y₃—Z₃ wherein:

Y₃ is absent or O, N(Rˢ)(CRˢRᵗ)_{q1} (where q₁ is 0, 1 or 2), S, SO, SO₂, C(O), C(O)O, OC(O), C(O)N(Rˢ), N(Rˢ)C(O), S(O)₂N(Rˢ) or N(Rˢ)SO₂, wherein Rˢ is selected from hydrogen or (1-4C)alkyl; and Z₃ is hydrogen, (1-6C)alkyl, aryl, (3-6C)cycloalkyl, (2-4C)alkenyl, (2-4C)alkynyl, (3-6C)cycloalkenyl, heteroaryl or 4 to 11-membered heterocyclyl; wherein Z₃ is optionally further substituted by one or more substituent groups independently selected from oxo, (1-4C)alkyl, (3-6C)cycloalkyl, halo, (1-4C)haloalkyl, (1-4C)haloalkoxy, amino, cyano, hydroxy, amido, carboxy, carbamoyl, sulphamoyl, mercapto, C(O)NRᵘRᵛ, NRᵘRᵛ or ORᵘ, wherein Rᵘ and Rᵛ are each independently selected from hydrogen, (1-4C)alkyl or (3-6C)cycloalkyl; or Z³ is optionally further substituted by a group of the formula:

-L_Z-W_Z wherein:

L_Z is a (1-5C)alkylene optionally substituted by one or more substituents selected from (1-2C)alkyl or oxo; and W_Z is halo, (1-4C)haloalkyl, (1-4C)haloalkoxy, cyano, hydroxy, (1-4C)alkoxy, C(O)R^{xa}, COOR^{xa}, C(O)NR^{xa}R^{xb} or NR^{xa}R^{xb}, wherein R^{xa} and R^{xb} are each independently selected from hydrogen or (1-4C)alkyl;

ii) a group of Formula B shown below:

Formula B

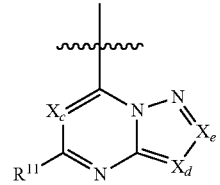

wherein:

denotes the point of attachment;

$X_c$, $X_d$ and $X_e$ are independently selected from N, CH, CF, CCl, C—CN or CCH$_3$;

$R^{11}$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—$Y_5$—$Z_5$ wherein:

$Y_5$ is absent or O, N(R$^w$), C(O), C(O)O, OC(O), C(O)N(R$^w$), N(R$^w$)C(O), S(O)$_2$N(R$^w$) or N(R$^w$)SO$_2$, wherein R$^w$ is selected from hydrogen or (1-4C)alkyl; and $Z_5$ is hydrogen, (1-6C)alkyl, aryl, (3-8C)cycloalkyl, (3-8C)cycloalkenyl, heteroaryl or heterocyclyl; wherein $Z_5$ is optionally further substituted by one or more substituent groups independently selected from (1-4C)alkyl, halo, (1-4C)haloalkyl, (1-4C)haloalkoxy, amino, cyano, hydroxy, amido, carboxy, carbamoyl, sulphamoyl, mercapto, NR$^y$R$^z$, OR$^y$, wherein R$^y$ and R$^z$ are each independently selected from hydrogen, (1-4C)alkyl or (3-6C)cycloalkyl;

iii) a group of Formula C shown below:

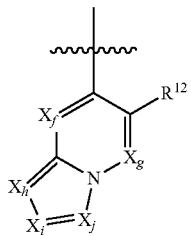

Formula C wherein:

denotes the point of attachment;

$R^{12}$ is selected from fluoro, chloro, bromo, (1-2C)alkyl, (1-2C)alkoxy, cyano, nitro, (2-4C)alkynyl, CH$_2$F, CF$_2$H or CF$_3$;

$X_f$ and $X_g$ are independently selected from N or CR$^{13}$, wherein R$^{13}$ is selected from hydrogen, fluoro, chloro, (1-2C)alkyl, (1-2C)haloalkyl or (1-2C)haloalkoxy;

$X_h$, $X_i$ and $X_j$ are independently selected from N or CR$^{14}$, wherein R$^{14}$ is selected from hydrogen, halo, (1-2C)alkyl, (1-2C)alkoxy, (1-2C)haloalkyl or (1-2C)haloalkoxy;

(57) $R^3$ is selected from:

i) a group of Formula A shown below:

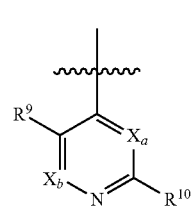

Formula A wherein:

denotes the point of attachment;

$X_a$ and $X_b$ are independently selected from N or CR$^{x1}$, wherein R$^{x1}$ is selected from hydrogen, fluoro, chloro, bromo, (1-2C)alkyl, (1-2C)alkoxy, cyano, nitro, acetylenyl, CH$_2$F, CF$_2$H or CF$_3$;

$R^9$ is selected from hydrogen, fluoro, chloro, bromo, (1-2C)alkyl, (1-2C)alkoxy, cyano, nitro, acetylenyl, CH$_2$F, CF$_2$H or CF$_3$;

$R^{10}$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—$Y_3$—$Z_3$ wherein:

$Y_3$ is absent or N(R$^s$)(CR$^s$R$^t$)$_{q1}$ (where $q_1$ is 0, 1 or 2), S, C(O), C(O)O, C(O)N(R$^s$), N(R$^s$)C(O), S(O)$_2$N(R$^s$) or N(R$^s$)SO$_2$, wherein R$^s$ is selected from hydrogen or (1-4C)alkyl; and $Z_3$ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or 4 to 11-membered heterocyclyl; wherein $Z_3$ is optionally further substituted by one or more substituent groups independently selected from oxo, (1-4C)alkyl, (3-6C)cycloalkyl, halo, (1-4C)haloalkyl, (1-4C)haloalkoxy, amino, cyano, hydroxy, amido, carboxy, carbamoyl, sulphamoyl, mercapto, C(O)NR$^u$R$^v$, NR$^u$R$^v$ or OR$^u$, wherein R$^u$ and R$^v$ are each independently selected from hydrogen, (1-4C)alkyl or (3-6C)cycloalkyl; and/or $Z^3$ is optionally further substituted by a group of the formula:

-L$_Z$-W$_Z$ wherein:

L$_Z$ is absent or a (1-3C)alkylene; and

W$_Z$ is phenyl, 5- or 6-membered heteroaryl, 6-membered heterocyclyl, halo, (1-4C)haloalkyl, (1-4C)haloalkoxy, cyano, hydroxy, (1-4C)alkoxy, C(O)R$^{xa}$, COOR$^{xa}$, C(O)NR$^{xa}$R$^{xb}$ or NR$^{xa}$R$^{xb}$, wherein R$^{xa}$ and R$^{xb}$ are each independently selected from hydrogen or (1-4C)alkyl;

ii) a group of Formula B shown below:

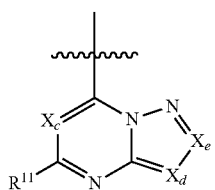

Formula B wherein:

denotes the point of attachment;
$X_c$, $X_d$ and $X_e$ are independently selected from N, CH, CF, CCl, C—CN or CCH$_3$;
$R^{11}$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—$Y_5$—$Z_5$ wherein:
$Y_5$ is absent or O, N($R^w$), C(O), C(O)O, C(O)N($R^w$) or S(O)$_2$N($R^w$), wherein $R^w$ is selected from hydrogen or (1-4C)alkyl; and
$Z_5$ is hydrogen, (1-6C)alkyl, aryl, (3-8C)cycloalkyl, (3-8C)cycloalkenyl, heteroaryl or heterocyclyl; wherein $Z_5$ is optionally further substituted by one or more substituent groups independently selected from (1-4C)alkyl, halo, (1-4C)haloalkyl, (1-4C)haloalkoxy, (1-4C)hydroxyalkyl, amino, cyano, hydroxy, amido, carboxy, carbamoyl, sulphamoyl, mercapto, $NR^yR^z$, $OR^y$, wherein $R^y$ and $R^z$ are each independently selected from hydrogen, (1-4C)alkyl or (3-6C)cycloalkyl;

iii) a group of Formula C shown below:

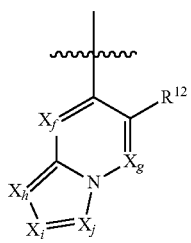

Formula C wherein:

denotes the point of attachment;
$R^{12}$ is selected from fluoro, chloro, bromo, (1-2C)alkyl, (1-2C)alkoxy, cyano, nitro, (2-4C)alkynyl, CH$_2$F, CF$_2$H or CF$_3$;

$X_f$ and $X_g$ are independently selected from N or CR$^{13}$, wherein R$^{13}$ is selected from hydrogen, fluoro, chloro, methyl, CH$_2$F, CF$_2$H or CF$_3$;
$X_h$, $X_i$ and $X_j$ are independently selected from N or CR$^{14}$, wherein R$^{14}$ is selected from hydrogen, halo, (1-2C)alkyl, (1-2C)alkoxy, (1-2C)haloalkyl or (1-2C)haloalkoxy;

(58) R$^3$ is selected from:
i) a group of Formula A shown below:

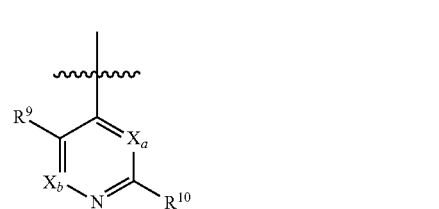

Formula A wherein:

denotes the point of attachment;
$X_a$ and $X_b$ are independently selected from N or CR$^{x1}$, wherein R$^{x1}$ is selected from hydrogen, fluoro, chloro, bromo, (1-2C)alkyl, (1-2C)alkoxy, cyano, nitro, acetylenyl, CH$_2$F, CF$_2$H or CF$_3$;
$R^9$ is selected from hydrogen, fluoro, chloro, bromo, (1-2C)alkyl, (1-2C)alkoxy, cyano, nitro, acetylenyl, CH$_2$F, CF$_2$H or CF$_3$;
$R^{10}$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—$Y_3$—$Z_3$ wherein:
$Y_3$ is absent or N($R^s$)(CR$^s$R$^t$)$_{q^1}$ (where q is 0, 1 or 2), S, C(O), C(O)O, C(O)N($R^s$), N($R^s$)C(O), S(O)$_2$N($R^s$) or N($R^s$)SO$_2$, wherein $R^s$ is selected from hydrogen or (1-4C)alkyl; and
$Z_3$ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or 4 to 11-membered heterocyclyl; wherein $Z_3$ is optionally further substituted by one or more substituent groups independently selected from oxo, (1-4C)alkyl, (3-6C)cycloalkyl, halo, (1-4C)haloalkyl, (1-4C)haloalkoxy, amino, cyano, hydroxy, amido, carboxy, carbamoyl, sulphamoyl, mercapto, C(O)NR$^u$R$^v$, NR$^u$R$^v$ or OR$^u$, wherein R$^u$ and R$^v$ are each independently selected from hydrogen, (1-4C)alkyl or (3-6C)cycloalkyl; or $Z^3$ is optionally further substituted by a group of the formula:

-$L_Z$-$W_Z$ wherein:
$L_Z$ is a (1-3C)alkylene; and
$W_Z$ is halo, (1-4C)haloalkyl, (1-4C)haloalkoxy, cyano, hydroxy, (1-4C)alkoxy, C(O)R$^{xa}$, COOR$^{xa}$, C(O)NR$^{xa}$R$^{xb}$ or NR$^{xa}$R$^{xb}$ wherein R$^{xa}$ and R$^{xb}$ are each independently selected from hydrogen or (1-4C)alkyl;

ii) a group of Formula B shown below:

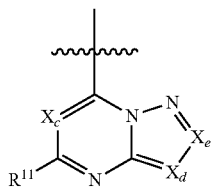

Formula B wherein:

denotes the point of attachment;

$X_c$, $X_d$ and $X_e$ are independently selected from N, CH, CF, CCl, C—CN or CCH$_3$;

R$^{11}$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y$_5$—Z$_5$ wherein:
Y$_5$ is absent or O, N(R$^w$), C(O), C(O)O, C(O)N(R$^w$) or S(O)$_2$N(R$^w$), wherein R$^w$ is selected from hydrogen or (1-4C)alkyl; and
Z$_5$ is hydrogen, (1-6C)alkyl, aryl, (3-8C)cycloalkyl, (3-8C)cycloalkenyl, heteroaryl or heterocyclyl; wherein Z$_5$ is optionally further substituted by one or more substituent groups independently selected from (1-4C)alkyl, halo, (1-4C)haloalkyl, (1-4C)haloalkoxy, amino, cyano, hydroxy, amido, carboxy, carbamoyl, sulphamoyl, mercapto, NR$^y$R$^z$, OR$^y$, wherein R$^y$ and R$^z$ are each independently selected from hydrogen, (1-4C)alkyl or (3-6C)cycloalkyl;

iii) a group of Formula C shown below:

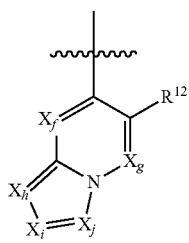

Formula C wherein:

denotes the point of attachment;

R$^{12}$ is selected from fluoro, chloro, bromo, (1-2C)alkyl, (1-2C)alkoxy, cyano, nitro, (2-4C)alkynyl, CH$_2$F, CF$_2$H or CF$_3$;

$X_f$ and $X_g$ are independently selected from N or CR$^{13}$, wherein R$^{13}$ is selected from hydrogen, fluoro, chloro, methyl, CH$_2$F, CF$_2$H or CF$_3$;

$X_h$, $X_i$ and $X_j$ are independently selected from N or CR$^{14}$, wherein R$^{14}$ is selected from hydrogen, halo, (1-2C)alkyl, (1-2C)alkoxy, (1-2C)haloalkyl or (1-2C)haloalkoxy;

(59) R$^3$ is selected from:
i) a group of Formula A shown below:

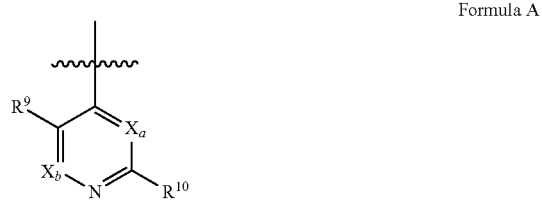

Formula A wherein:

denotes the point of attachment;

$X_a$ and $X_b$ are independently selected from N or CR$^{x1}$, wherein R$^{x1}$ is selected from hydrogen, fluoro, chloro, bromo, (1-2C)alkyl, (1-2C)alkoxy, cyano, nitro, acetylenyl, CH$_2$F, CF$_2$H or CF$_3$;

R$^9$ is selected from hydrogen, fluoro, chloro, bromo, (1-2C)alkyl, (1-2C)alkoxy, cyano, nitro, acetylenyl, CH$_2$F, CF$_2$H or CF$_3$;

R$^{10}$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y$_3$—Z$_3$ wherein:
Y$_3$ is absent or C(O), C(O)O, OC(O), C(O)N(R$^s$), N(R$^s$)C(O), N(R$^s$)C(O)N(R$^t$), N(R$^s$)C(O)O, OC(O)N(R$^s$), S(O)$_2$N(R$^s$), N(R$^s$)SO$_2$, wherein R$^s$ and R$^t$ are each independently selected from hydrogen or (1-4C)alkyl; and
Z$_3$ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or 5- or 6-membered heterocyclyl; wherein Z$_3$ is optionally further substituted by one or more substituent groups independently selected from (1-4C)alkyl, halo, (1-4C)haloalkyl, (1-4C)haloalkoxy, amino, cyano, hydroxy, amido, carboxy, carbamoyl, sulphamoyl, mercapto, NR$^u$R$^v$ or OR$^u$, wherein R$^u$ and R$^v$ are each independently selected from hydrogen, (1-4C)alkyl or (3-6C)cycloalkyl;

ii) a group of Formula B shown below:

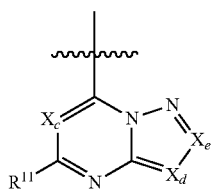

Formula B wherein:

denotes the point of attachment;
$X_c$, $X_d$ and $X_e$ are independently selected from N, CH, CF, CCl, C—CN or CCH$_3$;
$R^{11}$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y$_5$—Z$_5$ wherein:
$Y_5$ is absent or O, N(R$^w$), C(O), C(O)O, OC(O), C(O)N(R$^w$), N(R$^w$)C(O), N(R$^w$)C(O)N(R$^x$), N(R$^w$)C(O)O, OC(O)N(R$^w$), S(O)$_2$N(R$^w$), N(R$^w$)SO$_2$, wherein R$^w$ and R$^x$ are each independently selected from hydrogen or (1-4C)alkyl; and
$Z_5$ is hydrogen, (1-6C)alkyl, aryl, (3-8C)cycloalkyl, (3-8C)cycloalkenyl, heteroaryl or heterocyclyl; wherein $Z_5$ is optionally further substituted by one or more substituent groups independently selected from (1-4C)alkyl, halo, (1-4C)haloalkyl, (1-4C)haloalkoxy, amino, cyano, hydroxy, amido, carboxy, carbamoyl, sulphamoyl, mercapto, NR$^y$R$^z$, OR$^y$, wherein R$^y$ and R$^z$ are each independently selected from hydrogen, (1-4C)alkyl or (3-6C)cycloalkyl;
iii) a group of Formula C shown below:

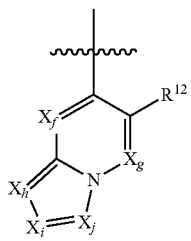

Formula C wherein:

denotes the point of attachment;

$R^{12}$ is selected from fluoro, chloro, bromo, (1-2C)alkyl, (1-2C)alkoxy, cyano, nitro, (2-4C)alkenyl, (2-4C)alkynyl, CH$_2$F, CF$_2$H or CF$_3$;
$X_f$ and $X_g$ are independently selected from N or CR$^{13}$, wherein R$^{13}$ is selected from hydrogen, fluoro, chloro, (1-2C)alkyl, (1-2C)haloalkyl or (1-2C)haloalkoxy;
$X_h$, $X_i$ and $X_j$ are independently selected from N or CR$^{14}$, wherein R$^{14}$ is selected from hydrogen, halo, (1-2C)alkyl, (1-2C)alkoxy, (1-2C)haloalkyl or (1-2C)haloalkoxy;
(60) R$^3$ is selected from:
i) a group of Formula A shown below:

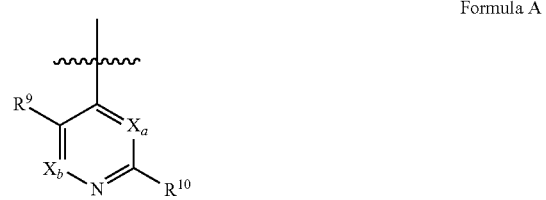

Formula A wherein:

denotes the point of attachment;
$X_a$ and $X_b$ are independently selected from N or CR$^{x1}$, wherein R$^{x1}$ is selected from hydrogen, fluoro, chloro, bromo, (1-2C)alkyl, (1-2C)alkoxy, cyano, nitro, acetylenyl, CH$_2$F, CF$_2$H or CF$_3$;
$R^9$ is selected from fluoro, chloro, bromo, (1-2C)alkyl, (1-2C)alkoxy, cyano, nitro, acetylenyl, CH$_2$F, CF$_2$H or CF$_3$;
$R^{10}$ is selected from hydrogen, halo, (1-2C)alkyl, (1-2C)alkoxy, (1-2C)haloalkyl, (1-2C)haloalkoxy, cyano, nitro, (2-4C)alkenyl, (2-4C)alkynyl or a group of the formula:

—Y$_3$—Z$_3$ wherein:
$Y_3$ is absent or C(O), C(O)O, OC(O), C(O)N(R$^s$), N(R$^s$)C(O), S(O)$_2$N(R$^s$), N(R$^s$)SO$_2$, wherein R$^s$ is selected from hydrogen or (1-4C)alkyl; and
$Z_3$ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or 5- or 6-membered heterocyclyl; wherein $Z_3$ is optionally further substituted by one or more substituent groups independently selected from (1-4C)alkyl, halo, (1-4C)haloalkyl, (1-4C)haloalkoxy, amino, cyano, hydroxy, amido, carboxy, carbamoyl, sulphamoyl, mercapto, NR$^u$R$^v$ or OR$^u$, wherein R$^u$ and R$^v$ are each independently selected from hydrogen, (1-4C)alkyl or (3-6C)cycloalkyl;

ii) a group of Formula B shown below:

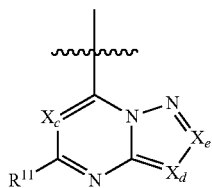

Formula B wherein:

denotes the point of attachment;

$X_c$, $X_d$ and $X_e$ are independently selected from N, CH, CF, CCl, C—CN or CCH$_3$;

$R^{11}$ is selected from hydrogen, halo, (1-2C)alkyl, (1-2C)alkoxy, (1-2C)haloalkyl, (1-2C)haloalkoxy, cyano, nitro, (2-4C)alkenyl, (2-4C)alkynyl or a group of the formula:

—Y$_5$—Z$_5$ wherein:

$Y_5$ is absent or O, N(R$^w$), C(O), C(O)O, OC(O), C(O)N(R$^w$), N(R$^w$)C(O), S(O)$_2$N(R$^w$), N(R$^w$)SO$_2$, wherein R$^w$ is selected from hydrogen or (1-4C)alkyl; and $Z_5$ is hydrogen, (1-6C)alkyl, aryl, (3-8C)cycloalkyl, (3-8C)cycloalkenyl, heteroaryl or heterocyclyl; wherein $Z_5$ is optionally further substituted by one or more substituent groups independently selected from (1-4C)alkyl, halo, (1-4C)haloalkyl, (1-4C)haloalkoxy, amino, cyano, hydroxy, amido, carboxy, carbamoyl, sulphamoyl, mercapto, NR$^y$R$^z$, OR$^y$, wherein R$^y$ and R$^z$ are each independently selected from hydrogen, (1-4C)alkyl or (3-6C)cycloalkyl; and iii) a group of Formula C shown below:

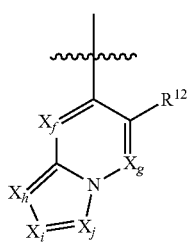

Formula C wherein:

denotes the point of attachment;

$R^{12}$ is selected from fluoro, chloro, bromo, (1-2C)alkyl, (1-2C)alkoxy, cyano, nitro, (2-4C)alkynyl, CH$_2$F, CF$_2$H or CF$_3$;

$X_f$ and $X_g$ are independently selected from N or CR$^{13}$, wherein R$^{13}$ is selected from hydrogen, fluoro, chloro, (1-2C)alkyl, (1-2C)haloalkyl or (1-2C)haloalkoxy;

$X_h$, $X_i$ and $X_j$ are independently selected from N or CR$^{14}$, wherein R$^{14}$ is selected from hydrogen, halo, (1-2C)alkyl, (1-2C)alkoxy, (1-2C)haloalkyl or (1-2C)haloalkoxy;

(61) $R^3$ is selected from:

i) a group of Formula A shown below:

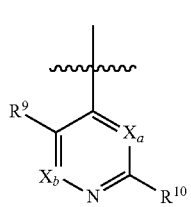

Formula A wherein:

denotes the point of attachment;

$X_a$ and $X_b$ are independently selected from N or CR$^{x1}$, wherein R$^{x1}$ is selected from hydrogen, fluoro, chloro, bromo, methyl, OCH$_3$, cyano, nitro, acetylenyl, CH$_2$F, CF$_2$H or CF$_3$;

$R^9$ is selected from fluoro, chloro, bromo, methyl, OCH$_3$, cyano, nitro, acetylenyl, CH$_2$F or CF$_2$H;

$R^{10}$ is selected from hydrogen, halo, (1-2C)alkyl, (1-2C)alkoxy, (1-2C)haloalkyl, (1-2C)haloalkoxy, cyano, nitro, (2-4C)alkenyl, (2-4C)alkynyl or a group of the formula:

—Y$_3$—Z$_3$ wherein:

$Y_3$ is absent or C(O), C(O)O, OC(O), C(O)N(R$^s$), N(R$^s$)C(O), S(O)$_2$N(R$^s$), N(R$^s$)SO$_2$, wherein R$^s$ is selected from hydrogen or (1-4C)alkyl; and $Z_3$ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or 5- or 6-membered heterocyclyl; wherein $Z_3$ is optionally further substituted by one or more substituent groups independently selected from (1-4C)alkyl, halo, (1-4C)haloalkyl, (1-4C)haloalkoxy, amino, cyano, hydroxy, amido, carboxy, NR$^u$R$^v$ or OR$^u$, wherein R$^u$ and R$^v$ are each independently selected from hydrogen or (1-4C)alkyl;

ii) a group of Formula B shown below:

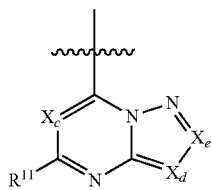

Formula B wherein:

denotes the point of attachment;

$X_c$, $X_d$ and $X_e$ are independently selected from N, CH, CF, CCl, C—CN or CCH$_3$;

$R^{11}$ is selected from hydrogen, halo, (1-2C)alkyl, (1-2C)alkoxy, (1-2C)haloalkyl, (1-2C)haloalkoxy, cyano, nitro, (2-4C)alkenyl, (2-4C)alkynyl or a group of the formula:

—Y$_5$—Z$_5$ wherein:

Y$_5$ is absent or O, N(R$^w$), C(O), C(O)O, OC(O), C(O)N(R$^w$), N(R$^w$)C(O), S(O)$_2$N(R$^w$), N(R$^w$)SO$_2$, wherein R$^w$ is selected from hydrogen or (1-4C)alkyl; and Z$_5$ is hydrogen, (1-6C)alkyl, aryl, (3-6C)cycloalkyl, (3-6C)cycloalkenyl, 5 or 6 membered heteroaryl or 5 or 6 membered heterocyclyl; wherein Z$_5$ is optionally further substituted by one or more substituent groups independently selected from (1-4C)alkyl, halo, (1-4C)haloalkyl, (1-4C)haloalkoxy, amino, cyano, hydroxy, amido, carboxy, NR$^y$R$^z$, OR$^y$, wherein R$^y$ and R$^z$ are each independently selected from hydrogen or (1-4C)alkyl; and iii) a group of Formula C shown below:

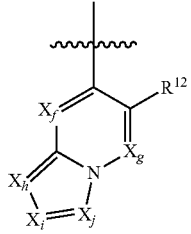

Formula C wherein:

denotes the point of attachment;

$R^{12}$ is selected from fluoro, chloro, bromo, methyl, OCH$_3$, cyano, nitro, acetylenyl, CH$_2$F CF$_2$H or CF$_3$;

$X_f$ and $X_g$ are independently selected from N or CR$^{13}$, wherein R$^{13}$ is selected from hydrogen, fluoro, chloro, (1-2C)alkyl, (1-2C)haloalkyl or (1-2C)haloalkoxy;

$X_h$, $X_i$ and $X_j$ are independently selected from N or CR$^{14}$, wherein R$^{14}$ is selected from hydrogen, halo, (1-2C)alkyl, (1-2C)alkoxy, (1-2C)haloalkyl or (1-2C)haloalkoxy;

(62) R$^3$ is selected from:

i) a group of Formula A shown below:

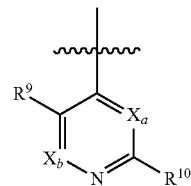

Formula A wherein:

denotes the point of attachment;

$X_a$ and $X_b$ are independently selected from N or CR$^{x1}$, wherein R$^{x1}$ is selected from hydrogen, fluoro, chloro, bromo, methyl, OCH$_3$, cyano, acetylenyl, CH$_2$F, CF$_2$H or CF$_3$;

R$^9$ is selected from fluoro, chloro, bromo, methyl, OCH$_3$, cyano, nitro or acetylenyl;

R$^{10}$ is selected from hydrogen, halo, (1-2C)alkyl, (1-2C)alkoxy, (1-2C)haloalkyl, (1-2C)haloalkoxy, cyano, nitro, (2-4C)alkenyl, (2-4C)alkynyl or a group of the formula:

—Y$_3$—Z$_3$ wherein:

Y$_3$ is absent or C(O), C(O)O, C(O)N(R$^s$) or S(O)$_2$N(R$^s$), wherein R$^s$ is selected from hydrogen or (1-4C)alkyl; and Z$_3$ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or 5- or 6-membered heterocyclyl; wherein Z$_3$ is optionally further substituted by one or more substituent groups independently selected from (1-2C)alkyl, halo, (1-2C)haloalkyl, (1-2C)haloalkoxy, amino, cyano, hydroxy, amido, carboxy, NR$^u$R$^v$ or OR$^u$, wherein R$^u$ and R$^v$ are each independently selected from hydrogen or (1-2C)alkyl;

ii) a group of Formula B shown below:

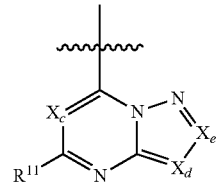

Formula B wherein:

denotes the point of attachment;

$X_c$, $X_d$ and $X_e$ are independently selected from N, CH, CF, CCl, C—CN or CCH$_3$;

$R^{11}$ is selected from hydrogen, halo, (1-2C)alkyl, (1-2C)alkoxy, (1-2C)haloalkyl, (1-2C)haloalkoxy, cyano, nitro, (2-4C)alkenyl, (2-4C)alkynyl or a group of the formula:

—Y$_5$—Z$_5$ wherein:

Y$_5$ is absent or O, N(R$^w$), C(O), C(O)O, C(O)N(R$^w$) or S(O)$_2$N(R$^w$), wherein R$^w$ is selected from hydrogen or (1-4C)alkyl; and Z$_5$ is hydrogen, (1-6C)alkyl, aryl, (3-6C)cycloalkyl, (3-6C)cycloalkenyl, 5 or 6 membered heteroaryl or 5 or 6 membered heterocyclyl; wherein Z$_5$ is optionally further substituted by one or more substituent groups independently selected from (1-2C)alkyl, halo, (1-2C)haloalkyl, (1-2C)haloalkoxy, amino, cyano, hydroxy, amido, carboxy, NR$^y$R$^z$, OR$^y$, wherein R$^y$ and R$^z$ are each independently selected from hydrogen or (1-2C)alkyl; and iii) a group of Formula C shown below:

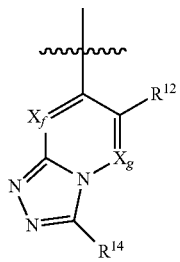

Formula C wherein:

denotes the point of attachment;

$R^9$ is selected from fluoro, chloro, bromo, methyl, OCH$_3$, cyano, acetylenyl, CH$_2$F, CF$_2$H or CF$_3$;

$X_f$ and $X_g$ are independently selected from N or CR$^{13}$, wherein R$^{13}$ is selected from hydrogen, fluoro, chloro, methyl, CH$_2$F, CF$_2$H or CF$_3$;

$R^{14}$ is selected from hydrogen, halo, (1-2C)alkyl, (1-2C)alkoxy, (1-2C)haloalkyl or (1-2C)haloalkoxy;

(63) R$^3$ is selected from:

i) a group of Formula A shown below:

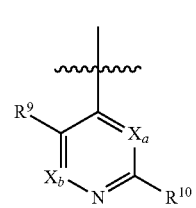

Formula A wherein:

denotes the point of attachment;

$X_a$ and $X_b$ are independently selected from N or CR$^{x1}$, wherein R$^{x1}$ is selected from hydrogen, fluoro, chloro, bromo, methyl, OCH$_3$, cyano, acetylenyl, CH$_2$F, CF$_2$H or CF$_3$;

$R^9$ is selected from fluoro, chloro, bromo, methyl, OCH$_3$, cyano, nitro or acetylenyl;

$R^{10}$ is selected from hydrogen, halo, (1-2C)alkyl, (1-2C)alkoxy, (1-2C)haloalkyl, (1-2C)haloalkoxy, cyano, nitro, (2-4C)alkenyl, (2-4C)alkynyl or a group of the formula:

—Y$_3$—Z$_3$ wherein:

Y$_3$ is absent or C(O), C(O)O, C(O)N(R$^s$) or S(O)$_2$N(R$^s$), wherein R$^s$ is selected from hydrogen or (1-4C)alkyl; and Z$_3$ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or 5- or 6-membered heterocyclyl; wherein Z$_3$ is optionally further substituted by one or more substituent groups independently selected from (1-2C)alkyl, halo, (1-2C)haloalkyl, (1-2C)haloalkoxy, amino, cyano, hydroxy, amido, carboxy, NR$^u$R$^v$ or OR$^u$, wherein R$^u$ and R$^v$ are each independently selected from hydrogen or (1-2C)alkyl;

ii) a group of Formula B shown below:

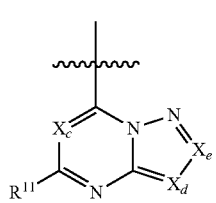

Formula B wherein:

denotes the point of attachment;

$X_c$, $X_d$ and $X_e$ are independently selected from N, CH, CF, CCl, C—CN or CCH$_3$;

R[11] is selected from hydrogen, halo, (1-2C)alkyl, (1-2C)alkoxy, (1-2C)haloalkyl, (1-2C)haloalkoxy, cyano, nitro, (2-4C)alkenyl, (2-4C)alkynyl or a group of the formula:

—Y$_5$—Z$_5$ wherein:

Y$_5$ is absent or O, N(R$^w$), C(O), C(O)O, C(O)N(R$^w$) or S(O)$_2$N(R$^w$), wherein R$^w$ is selected from hydrogen or (1-4C)alkyl; and Z$_5$ is hydrogen, (1-6C)alkyl, aryl, (3-6C)cycloalkyl, (3-6C)cycloalkenyl, 5 or 6 membered heteroaryl or 5 or 6 membered heterocyclyl; wherein Z$_5$ is optionally further substituted by one or more substituent groups independently selected from (1-2C)alkyl, halo, (1-2C)haloalkyl, (1-2C)haloalkoxy, amino, cyano, hydroxy, amido, carboxy, NR$^y$R$^z$, OR$^y$, wherein R$^y$ and R$^z$ are each independently selected from hydrogen or (1-2C)alkyl; and iii) a group of Formula C shown below:

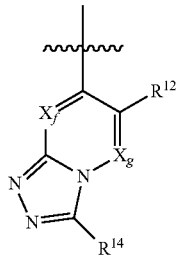

Formula C wherein:

denotes the point of attachment;

R[12] is selected from fluoro, chloro, bromo, methyl, OCH$_3$, cyano, acetylenyl, CH$_2$F, CF$_2$H or CF$_3$;

X$_f$ and X$_g$ are independently selected from N or CR[13], wherein R[13] is selected from hydrogen, fluoro, chloro or methyl;

R[14] is selected from hydrogen, halo, methyl, OCH$_3$, CH$_2$F, CF$_2$H or CF$_3$;

(64) R$^3$ is selected from:

i) a group of Formula A shown below:

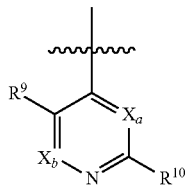

Formula A wherein:

denotes the point of attachment;

X$_a$ and X$_b$ are both CR$^{x1}$, wherein R$^{x1}$ is selected from hydrogen, fluoro, chloro, bromo, methyl, OCH$_3$, cyano or acetylenyl;

R$^9$ is selected from fluoro, chloro, bromo, methyl, OCH$_3$, cyano or acetylenyl;

R[10] is selected from hydrogen, halo, (1-2C)alkyl, (1-2C)alkoxy, (1-2C)haloalkyl, (1-2C)haloalkoxy, cyano, (2-4C)alkenyl, (2-4C)alkynyl or a group of the formula:

—Y$_3$—Z$_3$ wherein:

Y$_3$ is absent or C(O), C(O)O, C(O)N(R$^s$) or S(O)$_2$N(R$^s$), wherein R$^s$ is selected from hydrogen or (1-4C)alkyl; and Z$_3$ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or 5- or 6-membered heterocyclyl; wherein Z$_3$ is optionally further substituted by one or more substituent groups independently selected from (1-2C)alkyl, halo, (1-2C)haloalkyl, (1-2C)haloalkoxy, amino, cyano, hydroxy, amido, carboxy, NR$^u$R$^v$ or OR$^u$, wherein R$^u$ and R$^v$ are each independently selected from hydrogen or (1-2C)alkyl;

ii) a group of Formula B shown below:

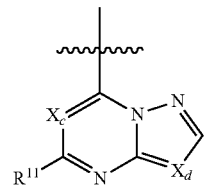

Formula B wherein:

denotes the point of attachment;

X$_c$ and X$_d$ are independently selected from N, CH, CF, CCl, C—CN or CCH$_3$;

R[11] is selected from hydrogen, halo, (1-2C)alkyl, (1-2C)alkoxy, (1-2C)haloalkyl, (1-2C)haloalkoxy, cyano, (2-4C)alkenyl, (2-4C)alkynyl or a group of the formula:

—Y$_5$—Z$_5$ wherein:

Y$_5$ is absent or O, N(R$^w$), C(O), C(O)O, C(O)N(R$^w$) or S(O)$_2$N(R$^w$), wherein R$^w$ is selected from hydrogen or (1-4C)alkyl; and Z$_5$ is hydrogen, (1-6C)alkyl, aryl, (3-6C)cycloalkyl, (3-6C)cycloalkenyl, 5 or 6 membered heteroaryl or 5 or 6 membered heterocyclyl;

wherein Z₅ is optionally further substituted by one or more substituent groups independently selected from (1-2C)alkyl, halo, (1-2C)haloalkyl, (1-2C)haloalkoxy, amino, cyano, hydroxy, amido, carboxy, NR$^y$R$^z$, OR$^y$, wherein R$^y$ and R$^z$ are each independently selected from hydrogen or (1-2C)alkyl; and iii) a group of Formula C shown below:

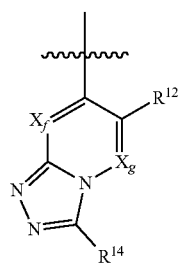

Formula C wherein:

denotes the point of attachment;
R$^{12}$ is selected from fluoro, chloro, bromo, methyl, OCH₃, cyano or acetylenyl;
X$_f$ and X$_g$ are independently selected from N or CR$^{13}$, wherein R$^{13}$ is selected from hydrogen, fluoro, chloro or methyl;
R$^{14}$ is selected from hydrogen, halo, methyl, OCH₃, CH₂F, CF₂H or CF₃;

(65) R³ is selected from:
i) a group of Formula A shown below:

Formula A

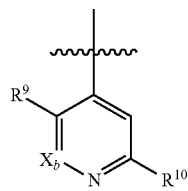

wherein:

denotes the point of attachment;
X$_b$ is CR$^{x1}$, wherein R$^{x1}$ is selected from hydrogen or chloro;
R⁹ is selected from fluoro, chloro, bromo, methyl, OCH₃, cyano or acetylenyl;
R¹⁰ is selected from hydrogen, halo, (1-2C)alkyl, (1-2C)alkoxy, (1-2C)haloalkyl, (1-2C)haloalkoxy, cyano, or a group of the formula:

—Y₃—Z₃ wherein:
Y₃ is absent or C(O), C(O)O, C(O)N(R$^s$) or S(O)₂N(R$^s$), wherein R$^s$ is selected from hydrogen or (1-4C)alkyl; and
Z₃ is hydrogen, (1-6C)alkyl, aryl, (2-4C)alkynyl, 5- or 6-membered heteroaryl or 5- or 6-membered heterocyclyl; wherein Z₃ is optionally further substituted by one or more substituent groups independently selected from (1-2C)alkyl, halo, (1-2C)haloalkyl, (1-2C)haloalkoxy, amino, cyano, hydroxy, amido, carboxy, NR$^u$R$^v$ or OR$^u$, wherein R$^u$ and R$^v$ are each independently selected from hydrogen or (1-2C)alkyl;

ii) a group of Formula B shown below:

Formula B

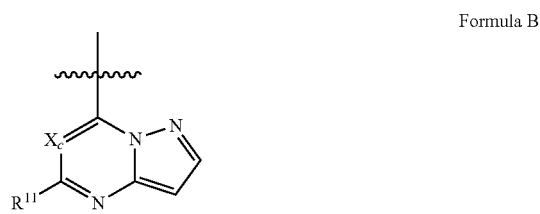

wherein:

denotes the point of attachment;
X$_c$ is selected from N, CH, CF, CCl, C—CN or CCH₃;
R¹¹ is selected from hydrogen, halo, (1-2C)alkyl, (1-2C)alkoxy, (1-2C)haloalkyl, (1-2C)haloalkoxy, cyano, (2-4C)alkenyl, (2-4C)alkynyl or a group of the formula:

—Y₅—Z₅ wherein:
Y₅ is absent or O, N(R$^w$), C(O), C(O)O, C(O)N(R$^w$) or S(O)₂N(R$^w$), wherein R$^w$ is selected from hydrogen or (1-4C)alkyl; and
Z₅ is hydrogen, (1-6C)alkyl, aryl, 5 or 6 membered heteroaryl or 5 or 6 membered heterocyclyl; wherein Z₅ is optionally further substituted by one or more substituent groups independently selected from (1-2C)alkyl, halo, (1-2C)haloalkyl, (1-2C)haloalkoxy, amino, cyano, hydroxy, amido, carboxy, NR$^y$R$^z$, OR$^y$, wherein R$^y$ and R$^z$ are each independently selected from hydrogen or (1-2C)alkyl; and iii) a group of Formula C shown below:

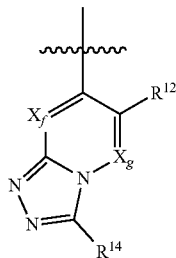

Formula C wherein:

denotes the point of attachment;
R$^{12}$ is selected from fluoro, chloro, bromo, methyl, OCH$_3$, cyano or acetylenyl;
X$_f$ and X$_g$ are independently selected from N or CR$^{13}$, wherein R$^{13}$ is selected from hydrogen, fluoro, chloro or methyl;
R$^{14}$ is selected from hydrogen, halo, methyl, OCH$_3$, CH$_2$F, CF$_2$H or CF$_3$;
(66) R$^3$ is selected from:
i) a group of Formula A shown below:

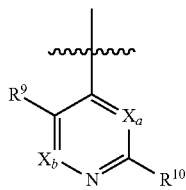

Formula A wherein:

denotes the point of attachment;
X$_a$ and X$_b$ are independently selected from N or CR$^{x1}$, wherein R$^{x1}$ is selected from hydrogen, fluoro, chloro, bromo, (1-2C)alkyl, (1-2C)alkoxy, cyano, nitro, acetylenyl, CH$_2$F, CF$_2$H or CF$_3$;
R$^9$ is selected from hydrogen, fluoro, chloro, bromo, (1-2C)alkyl, (1-2C)alkoxy, cyano, nitro, acetylenyl, CH$_2$F, CF$_2$H or CF$_3$;
R$^{10}$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:
—Y$_3$—Z$_3$
wherein:
Y$_3$ is absent or O, N(R$^s$)(CR$^sR^t$)$_{q1}$ (where q$_1$ is 0, 1 or 2), S, SO, SO$_2$, C(O), C(O)O, OC(O), C(O)N(R$^s$), N(R$^s$)C(O), N(R$^s$)C(O)N(R$^t$), N(R$^s$)C(O)O, OC(O)N(R$^s$), S(O)$_2$N(R$^s$), N(R$^s$)SO$_2$, wherein R$^s$ and R$^t$ are each independently selected from hydrogen or (1-4C)alkyl; and
Z$_3$ is hydrogen, (1-6C)alkyl, aryl, (3-6C)cycloalkyl, (2-4C)alkenyl, (2-4C)alkynyl, (3-6C)cycloalkenyl, heteroaryl or 4 to 11-membered heterocyclyl; wherein Z$_3$ is optionally further substituted by one or more substituent groups independently selected from oxo, (1-4C)alkyl, (3-6C)cycloalkyl, halo, (1-4C)haloalkyl, (1-4C)haloalkoxy, (1-4C)hydroxyalkyl, amino, cyano, hydroxy, amido, carboxy, carbamoyl, sulphamoyl, mercapto, C(O)NR$^u$R$^v$, NR$^u$R$^v$ or OR$^u$, wherein R$^u$ and R$^v$ are each independently selected from hydrogen, (1-4C)alkyl or (3-6C)cycloalkyl; and/or Z$^3$ is optionally further substituted by a group of the formula:

-L$_Z$-W$_Z$ wherein:
L$_Z$ is absent or a (1-5C)alkylene optionally substituted by one or more (1-2C)alkyl groups; and
W$_Z$ is aryl, 5- or 6-membered heteroaryl, 4- to 7-membered heterocyclyl, halo, (1-4C)haloalkyl, (1-4C)haloalkoxy, cyano, hydroxy, (1-4C)alkoxy, C(O)R$^{xa}$, COOR$^{xa}$, C(O)NR$^{xa}$R$^{xb}$ or NR$^{xa}$R$^{xb}$, wherein R$^{xa}$ and R$^{xb}$ are each independently selected from hydrogen or (1-4C)alkyl; and wherein each aryl, 5- or 6-membered heteroaryl or 4- to 7-membered heterocyclyl is optionally further substituted by one or more substituent groups independently selected from (1-2C)alkyl, halo, (1-2C)haloalkyl, amino, cyano or hydroxy;
ii) a group of Formula B shown below:

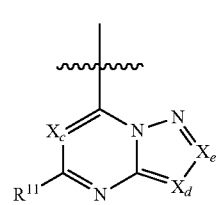

Formula B wherein:

denotes the point of attachment;
X$_c$, X$_d$ and X$_e$ are independently selected from N, CH, CF, CCl, C—CN or CCH$_3$;
R$^{11}$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:
—Y$_5$—Z$_5$
wherein:
Y$_5$ is absent or O, N(R$^w$), C(O), C(O)O, OC(O), C(O)N(R$^w$), N(R$^w$)C(O), N(R$^w$)C(O)N(R$^x$), N(R$^w$)C(O)O, OC(O)N(R$^w$), S(O)$_2$N(R$^w$), N(R$^w$)SO$_2$, wherein R$^w$ and R$^x$ are each independently selected from hydrogen or (1-4C) alkyl; and Z$_5$ is hydrogen, (1-6C)alkyl, aryl, (3-8C)cycloalkyl, (3-8C)cycloalkenyl, heteroaryl or heterocyclyl; wherein Z$_5$ is optionally further substituted by one or more substituent groups independently selected from (1-4C)alkyl, halo, (1-4C)haloalkyl, (1-4C)haloalkoxy, (1-4C)haloalkyl, amino, cyano, hydroxy, amido, carboxy, carbamoyl, sulphamoyl, mercapto, NR$^y$R$^z$, OR$^y$, wherein R$^y$ and R$^z$ are each independently selected from hydrogen, (1-4C)alkyl or (3-6C)cycloalkyl;

(67) R$^3$ is selected from:

i) a group of Formula A shown below:

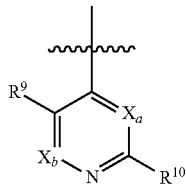

Formula A wherein:

denotes the point of attachment;

X$_a$ and X$_b$ are independently selected from N or CR$^{x1}$, wherein R$^{x1}$ is selected from hydrogen, fluoro, chloro, bromo, (1-2C)alkyl, (1-2C)alkoxy, cyano, nitro, acetylenyl, CH$_2$F, CF$_2$H or CF$_3$;

R$^9$ is selected from hydrogen, fluoro, chloro, bromo, (1-2C)alkyl, (1-2C)alkoxy, cyano, nitro, acetylenyl, CH$_2$F, CF$_2$H or CF$_3$;

R$^{10}$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y$_3$—Z$_3$ wherein:

Y$_3$ is absent or O, N(R$^s$)(CR$^s$R$^t$)$_{q_1}$ (where q$_1$ is 0, 1 or 2), S, SO, SO$_2$, C(O), C(O)O, OC(O), C(O)N(R$^s$), N(R$^s$)C(O), N(R$^s$)C(O)N(R$^t$), N(R$^s$)C(O)O, OC(O)N(R$^s$), S(O)$_2$N(R$^s$), N(R$^s$)SO$_2$, wherein R$^s$ and R$^t$ are each independently selected from hydrogen or (1-4C)alkyl; and Z$_3$ is hydrogen, (1-6C)alkyl, aryl, (3-6C)cycloalkyl, (2-4C)alkenyl, (2-4C)alkynyl, (3-6C)cycloalkenyl, heteroaryl or 4 to 11-membered heterocyclyl; wherein Z$_3$ is optionally further substituted by one or more substituent groups independently selected from oxo, (1-4C)alkyl, (3-6C)cycloalkyl, halo, (1-4C)haloalkyl, (1-4C)haloalkoxy, (1-4C)hydroxyalkyl, amino, cyano, hydroxy, amido, carboxy, carbamoyl, sulphamoyl, mercapto, C(O)NR$^u$R$^v$, NR$^u$R$^v$ or OR$^u$, wherein R$^u$ and R$^v$ are each independently selected from hydrogen, (1-4C)alkyl or (3-6C)cycloalkyl; and/or Z$^3$ is optionally further substituted by a group of the formula:

-L$_Z$-W$_Z$ wherein:

L$_Z$ is absent or a (1-5C)alkylene optionally substituted by one or more (1-2C)alkyl groups; and W$_Z$ is aryl, 5- or 6-membered heteroaryl, 4- to 7-membered heterocyclyl, halo, (1-4C)haloalkyl, (1-4C)haloalkoxy, cyano, hydroxy, (1-4C)alkoxy, C(O)R$^{xa}$, COOR$^{xa}$, C(O)NR$^{xa}$R$^{xb}$ or NR$^{xa}$R$^{xb}$, wherein R$^{xa}$ and R$^{xb}$ are each independently selected from hydrogen or (1-4C)alkyl;

ii) a group of Formula B shown below:

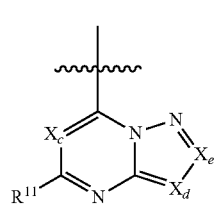

Formula B wherein:

denotes the point of attachment;

X$_c$, X$_d$ and X$_e$ are independently selected from N, CH, CF, CCl, C—CN or CCH$_3$;

R$^{11}$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y$_5$—Z$_5$ wherein:

Y$_5$ is absent or O, N(R$^w$), C(O), C(O)O, OC(O), C(O)N(R$^w$), N(R$^w$)C(O), N(R$^w$)C(O)N(R$^w$), N(R$^w$)C(O)O, OC(O)N(R$^w$), S(O)$_2$N(R$^w$), N(R$^w$)SO$_2$, wherein R$^w$ and R$^x$ are each independently selected from hydrogen or (1-4C)alkyl; and Z$_5$ is hydrogen, (1-6C)alkyl, aryl, (3-8C)cycloalkyl, (3-8C)cycloalkenyl, heteroaryl or heterocyclyl; wherein Z$_5$ is optionally further substituted by one or more substituent groups independently selected from (1-4C)alkyl, halo, (1-4C)haloalkyl, (1-4C)haloalkoxy, (1-4C)haloalkyl, amino, cyano, hydroxy, amido, carboxy, carbamoyl, sulphamoyl, mercapto, NR$^y$R$^z$, OR$^y$, wherein R$^y$ and R$^z$ are each independently selected from hydrogen, (1-4C)alkyl or (3-6C)cycloalkyl;

(68) $R^3$ is selected from:
i) a group of Formula A shown below:

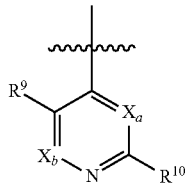

Formula A wherein:

denotes the point of attachment;
$X_a$ and $X_b$ are independently selected from N or $CR^{x1}$, wherein $R^{x1}$ is selected from hydrogen, fluoro, chloro, bromo, (1-2C)alkyl, (1-2C)alkoxy, cyano, nitro, acetylenyl, $CH_2F$, $CF_2H$ or $CF_3$;
$R^9$ is selected from hydrogen, fluoro, chloro, bromo, (1-2C)alkyl, (1-2C)alkoxy, cyano, nitro, acetylenyl, $CH_2F$, $CF_2H$ or $CF_3$;
$R^{10}$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—$Y_3$—$Z_3$ wherein:
$Y_3$ is absent or O, $N(R^s)(CR^sR^t)_{q_1}$ (where $q_1$ is 0, 1 or 2), S, SO, $SO_2$, C(O), C(O)O, OC(O), C(O)N($R^s$), N($R^s$)C(O), N($R^s$)C(O)N($R^t$), N($R^s$)C(O)O, OC(O)N($R^s$), S(O)$_2$N($R^s$), N($R^s$)SO$_2$, wherein $R^s$ and $R^t$ are each independently selected from hydrogen or (1-4C)alkyl; and
$Z_3$ is hydrogen, (1-6C)alkyl, aryl, (3-6C)cycloalkyl, (2-4C)alkenyl, (2-4C)alkynyl, (3-6C)cycloalkenyl, heteroaryl or 4 to 11-membered heterocyclyl; wherein $Z_3$ is optionally further substituted by one or more substituent groups independently selected from oxo, (1-4C)alkyl, (3-6C)cycloalkyl, halo, (1-4C)haloalkyl, (1-4C)haloalkoxy, amino, cyano, hydroxy, amido, carboxy, carbamoyl, sulphamoyl, mercapto, C(O)NR$^u$R$^v$, NR$^u$R$^v$ or OR$^u$, wherein R$^u$ and R$^v$ are each independently selected from hydrogen, (1-4C)alkyl or (3-6C)cycloalkyl; or $Z^3$ is optionally further substituted by a group of the formula:

-$L_Z$-$W_Z$ wherein:
$L_Z$ is a (1-5C)alkylene optionally substituted by one or more substituents selected from (1-2C)alkyl or oxo; and
$W_Z$ is halo, (1-4C)haloalkyl, (1-4C)haloalkoxy, cyano, hydroxy, (1-4C)alkoxy, C(O)R$^{xa}$, COOR$^{xa}$, C(O)NR$^{xa}$R$^{xb}$ or NR$^{xa}$R$^{xb}$, wherein R$^{xa}$ and R$^{xb}$ are each independently selected from hydrogen or (1-4C)alkyl;

ii) a group of Formula B shown below:

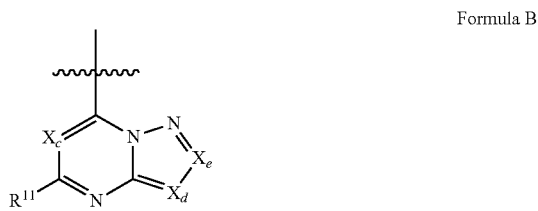

Formula B wherein:

denotes the point of attachment;
$X_c$, $X_d$ and $X_e$ are independently selected from N, CH, CF, CCl, C—CN or CCH$_3$;
$R^{11}$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—$Y_5$—$Z_5$ wherein:
$Y_5$ is absent or O, N($R^w$), C(O), C(O)O, OC(O), C(O)N($R^w$), N($R^w$)C(O), N($R^w$)C(O)N($R^x$), N($R^w$)C(O)O, OC(O)N($R^w$), S(O)$_2$N($R^w$), N($R^w$)SO$_2$, wherein $R^w$ and $R^x$ are each independently selected from hydrogen or (1-4C)alkyl; and
$Z_5$ is hydrogen, (1-6C)alkyl, aryl, (3-8C)cycloalkyl, (3-8C)cycloalkenyl, heteroaryl or heterocyclyl; wherein $Z_5$ is optionally further substituted by one or more substituent groups independently selected from (1-4C)alkyl, halo, (1-4C)haloalkyl, (1-4C)haloalkoxy, amino, cyano, hydroxy, amido, carboxy, carbamoyl, sulphamoyl, mercapto, NR$^y$R$^z$, OR$^y$, wherein R$^y$ and R$^z$ are each independently selected from hydrogen, (1-4C)alkyl or (3-6C)cycloalkyl;
(69) $R^3$ is selected from:
i) a group of Formula A shown below:

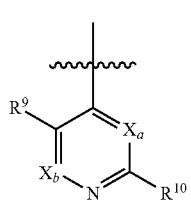

Formula A wherein:

denotes the point of attachment;
$X_a$ and $X_b$ are independently selected from N or $CR^{x1}$, wherein $R^{x1}$ is selected from hydrogen, fluoro, chloro, bromo, (1-2C)alkyl, (1-2C) alkoxy, cyano, nitro, acetylenyl, CH$_2$F, CF$_2$H or CF$_3$;

R$^9$ is selected from hydrogen, fluoro, chloro, bromo, (1-2C)alkyl, (1-2C)alkoxy, cyano, nitro, acetylenyl, CH$_2$F, CF$_2$H or CF$_3$;

R$^{10}$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y$_3$—Z$_3$ wherein:

Y$_3$ is absent or N(R$^s$)(CR$^s$R$^t$)$_{q^1}$ (where q$_1$ is 0, 1 or 2), S, C(O), C(O)O, C(O)N(R$^s$), N(R$^s$)C(O) or S(O)$_2$N(R$^s$), wherein R$^s$ is selected from hydrogen or (1-4C)alkyl; and Z$_3$ is hydrogen, (1-6C)alkyl, aryl, (3-6C)cycloalkyl, (2-4C)alkenyl, (2-4C)alkynyl, (3-6C)cycloalkenyl, heteroaryl or 4 to 11-membered heterocyclyl; wherein Z$_3$ is optionally further substituted by one or more substituent groups independently selected from oxo, (1-4C)alkyl, (3-6C)cycloalkyl, halo, (1-4C)haloalkyl, (1-4C)haloalkoxy, amino, cyano, hydroxy, amido, carboxy, carbamoyl, sulphamoyl, mercapto, C(O)NR$^u$R$^v$, NR$^u$R$^v$ or OR$^u$, wherein R$^u$ and R$^v$ are each independently selected from hydrogen, (1-4C)alkyl or (3-6C)cycloalkyl; and/or Z$^3$ is optionally further substituted by a group of the formula:

-L$_Z$-W$_Z$ wherein:

L$_Z$ is absent or a (1-3C)alkylene; and

W$_Z$ is phenyl, 5- or 6-membered heteroaryl, 6-membered heterocyclyl, halo, (1-4C)haloalkyl, (1-4C)haloalkoxy, cyano, hydroxy, (1-4C)alkoxy, C(O)R$^{xa}$, COOR$^{xa}$, C(O)NR$^{xa}$R$^{xb}$ or NR$^{xa}$R$^{xb}$, wherein R$^{xa}$ and R$^{xb}$ are each independently selected from hydrogen or (1-4C)alkyl;

ii) a group of Formula B shown below:

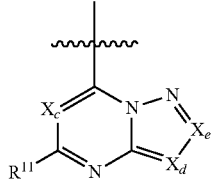

Formula B wherein:

denotes the point of attachment;

X$_c$, X$_d$ and X$_e$ are independently selected from N, CH, CF, CCl, C—CN or CCH$_3$;

R$^{11}$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y$_5$—Z$_5$ wherein:

Y$_5$ is absent or O, N(R$^w$), C(O), C(O)O, C(O)N(R$^w$) or S(O)$_2$N(R$^w$), wherein R$^w$ is selected from hydrogen or (1-4C)alkyl; and Z$_5$ is hydrogen, (1-6C)alkyl, aryl, (3-8C)cycloalkyl, (3-8C)cycloalkenyl, heteroaryl or heterocyclyl; wherein Z$_5$ is optionally further substituted by one or more substituent groups independently selected from (1-4C)alkyl, halo, (1-4C)haloalkyl, (1-4C)haloalkoxy, (1-4C)hydroxyalkyl, amino, cyano, hydroxy, amido, carboxy, carbamoyl, sulphamoyl, mercapto, NR$^y$R$^z$, OR$^y$, wherein R$^y$ and R$^z$ are each independently selected from hydrogen, (1-4C)alkyl or cyclopropyl;

(70) R$^3$ is selected from:

i) a group of Formula A shown below:

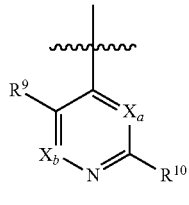

Formula A wherein:

denotes the point of attachment;

X$_a$ and X$_b$ are independently selected from N or CR$^{x1}$, wherein R$^{x1}$ is selected from hydrogen, fluoro, chloro, bromo, (1-2C)alkyl, (1-2C)alkoxy, cyano, nitro, acetylenyl, CH$_2$F, CF$_2$H or CF$_3$;

R$^9$ is selected from hydrogen, fluoro, chloro, bromo, (1-2C)alkyl, (1-2C)alkoxy, cyano, nitro, acetylenyl, CH$_2$F, CF$_2$H or CF$_3$;

R$^{10}$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y$_3$—Z$_3$ wherein:

Y$_3$ is absent or N(R$^s$)(CR$^s$R$^t$)$_{q^1}$ (where q is 0, 1 or 2), S, C(O), C(O)O, C(O)N(R$^s$), N(R$^s$)C(O) or S(O)$_2$N(R$^s$), wherein R$^s$ is selected from hydrogen or (1-4C)alkyl; and Z$_3$ is hydrogen, (1-6C)alkyl, aryl, (3-6C)cycloalkyl, (2-4C)alkenyl, (2-4C)alkynyl, (3-6C)cycloalkenyl, heteroaryl or 4 to 11-membered heterocyclyl; wherein Z$_3$ is optionally further substituted by one or more substituent groups independently selected from oxo, (1-4C)alkyl, (3-6C)cycloalkyl, halo, (1-4C)haloalkyl, (1-4C)haloalkoxy, amino, cyano, hydroxy, amido, carboxy, carbamoyl, sulphamoyl, mercapto, C(O)NR$^u$R$^v$, NR$^u$R$^v$ or OR$^u$, wherein R$^u$ and R$^v$ are each independently selected from hydrogen, (1-4C)alkyl or (3-6C)cycloalkyl; or Z$^3$ is optionally further substituted by a group of the formula:

-L$_Z$-W$_Z$ wherein:

L$_Z$ is a (1-5C)alkylene optionally substituted by one or more substituents selected from (1-2C)alkyl or oxo; and W$_Z$ is halo, (1-4C)haloalkyl, (1-4C)haloalkoxy, cyano, hydroxy, (1-4C)alkoxy, C(O)R$^{xa}$, COOR$^{xa}$, C(O)NR$^{xa}$R$^{xb}$ or NR$^{xa}$R$^{xb}$, wherein R$^{xa}$ and R$^{xb}$ are each independently selected from hydrogen or (1-4C)alkyl;

ii) a group of Formula B shown below:

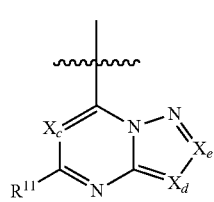

Formula B wherein:

denotes the point of attachment;

X$_c$, X$_d$ and X$_e$ are independently selected from N, CH, CF, CCl, C—CN or CCH$_3$;

R$^{11}$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y$_5$—Z$_5$ wherein:

Y$_5$ is absent or O, N(R$^w$), C(O), C(O)O, C(O)N(R$^w$) or S(O)$_2$N(R$^w$), wherein R$^w$ is selected from hydrogen or (1-4C)alkyl; and Z$_5$ is hydrogen, (1-6C)alkyl, aryl, (3-8C)cycloalkyl, (3-8C)cycloalkenyl, heteroaryl or heterocyclyl; wherein Z$_5$ is optionally further substituted by one or more substituent groups independently selected from (1-4C)alkyl, halo, (1-4C)haloalkyl, (1-4C)haloalkoxy, amino, cyano, hydroxy, amido, carboxy, carbamoyl, sulphamoyl, mercapto, NR$^y$R$^z$, OR$^y$, wherein R$^y$ and R$^z$ are each independently selected from hydrogen, (1-4C)alkyl or cyclopropyl;

(71) R$^3$ is selected from:

i) a group of Formula A shown below:

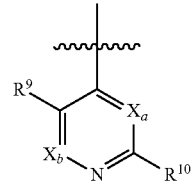

Formula A wherein:

denotes the point of attachment;

X$_a$ and X$_b$ are independently selected from N or CR$^{x1}$, wherein R$^{x1}$ is selected from hydrogen, fluoro, chloro, bromo, methyl, OCH$_3$, cyano or acetylenyl;

R$^9$ is selected from fluoro, chloro, bromo, methyl, OCH$_3$, cyano or acetylenyl;

R$^{10}$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y$_3$—Z$_3$ wherein:

Y$_3$ is absent or N(R$^s$)(CH$_2$)$_{q_1}$ (where q$_1$ is 0, 1 or 2), S, C(O), C(O)O, C(O)N(R$^s$), or S(O)$_2$N(R$^s$), wherein R$^s$ is selected from hydrogen or (1-4C)alkyl; and Z$_3$ is hydrogen, (1-6C)alkyl, aryl, (3-6C)cycloalkyl, (2-4C)alkenyl, (2-4C)alkynyl, (3-6C)cycloalkenyl, heteroaryl or 4 to 11-membered heterocyclyl; wherein Z$_3$ is optionally further substituted by one or more substituent groups independently selected from oxo, (1-4C)alkyl, (3-6C)cycloalkyl, halo, (1-4C)haloalkyl, (1-4C)haloalkoxy, amino, cyano, hydroxy, amido, carboxy, C(O)NR$^u$R$^v$, NR$^u$R$^v$ or OR$^u$, wherein R$^u$ and R$^v$ are each independently selected from hydrogen, (1-4C)alkyl or cyclopropyl; or Z$^3$ is optionally further substituted by a group of the formula:

-L$_Z$-W$_Z$ wherein:

L$_Z$ is a (1-3C)alkylene; and

W$_Z$ is halo, (1-2C)haloalkyl, (1-2C)haloalkoxy, cyano, hydroxy, (1-2C)alkoxy, C(O)R$^{xa}$, COOR$^{xa}$, C(O)NR$^{xa}$R$^{xb}$ or NR$^{xa}$R$^{xb}$, wherein R$^{xa}$ and R$^{xb}$ are each independently selected from hydrogen or (1-2C)alkyl;

ii) a group of Formula B shown below:

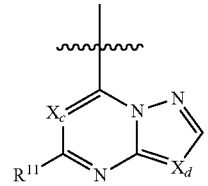

Formula B wherein:

denotes the point of attachment;
$X_c$ and $X_d$ are independently selected from N, CH, CF, CCl or CCH$_3$;
$R^{11}$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—$Y_5$—$Z_5$ wherein:
$Y_5$ is absent or O, N(R$^w$), C(O), C(O)O, C(O)N(R$^w$) or S(O)$_2$N(R$^w$), wherein R$^w$ is selected from hydrogen or (1-2C)alkyl; and
$Z_5$ is hydrogen, (1-6C)alkyl, aryl, (3-8C)cycloalkyl, 5 or 6 membered heteroaryl or 5 or 6 membered heterocyclyl; wherein $Z_5$ is optionally further substituted by one or more substituent groups independently selected from (1-2C)alkyl, halo, (1-2C)haloalkyl, (1-2C)haloalkoxy, amino, cyano, hydroxy, amido, carboxy, carbamoyl, sulphamoyl, mercapto, NR$^y$R$^z$, OR$^y$, wherein R$^y$ and R$^z$ are each independently selected from hydrogen or (1-2C)alkyl;

(72) $R^3$ is selected from:
i) a group of Formula A shown below:

Formula A

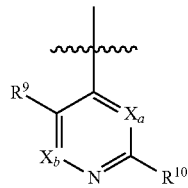

wherein:

denotes the point of attachment;
$X_a$ and $X_b$ are independently selected from N or CR$^{x1}$, wherein R$^{x1}$ is selected from hydrogen, fluoro, chloro, bromo, (1-2C)alkyl, (1-2C)alkoxy, cyano, nitro, acetylenyl, CH$_2$F or CF$_2$H;
$R^9$ is selected from fluoro, chloro, bromo, (1-2C)alkyl, (1-2C)alkoxy, cyano, nitro, acetylenyl, CH$_2$F, CF$_2$H or CF$_3$;
$R^{10}$ is selected from hydrogen, halo, (1-2C)alkyl, (1-2C)alkoxy, (1-2C)haloalkyl, (1-2C)haloalkoxy, cyano, nitro, (2-4C)alkenyl, (2-4C)alkynyl or a group of the formula:

—$Y_3$—$Z_3$ wherein:
$Y_3$ is absent or C(O), C(O)O, OC(O), C(O)N(R$^s$), N(R$^s$)C(O), S(O)$_2$N(R$^s$), N(R$^s$)SO$_2$, wherein R$^s$ is selected from hydrogen or (1-4C)alkyl; and
$Z_3$ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or 5- or 6-membered heterocyclyl; wherein $Z_3$ is optionally further substituted by one or more substituent groups independently selected from (1-4C)alkyl, halo, (1-4C)haloalkyl, (1-4C)haloalkoxy, amino, cyano, hydroxy, amido, carboxy, carbamoyl, sulphamoyl, mercapto, NR$^u$R$^v$ or OR$^u$, wherein R$^u$ and R$^v$ are each independently selected from hydrogen, (1-4C)alkyl or (3-6C)cycloalkyl;

ii) a group of Formula B shown below:

Formula B

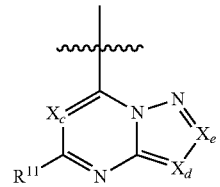

wherein:

denotes the point of attachment;
$X_c$, $X_d$ and $X_e$ are independently selected from N, CH, CF, CCl, C—CN or CCH$_3$;
$R^{11}$ is selected from hydrogen, halo, (1-2C)alkyl, (1-2C)alkoxy, (1-2C)haloalkyl, (1-2C)haloalkoxy, cyano, nitro, (2-4C)alkenyl, (2-4C)alkynyl or a group of the formula:

—$Y_5$—$Z_5$ wherein:
$Y_5$ is absent or O, N(R$^w$), C(O), C(O)O, OC(O), C(O)N(R$^w$), N(R$^w$)C(O), S(O)$_2$N(R$^w$), N(R$^w$)SO$_2$, wherein R$^w$ is selected from hydrogen or (1-4C)alkyl; and
$Z_5$ is hydrogen, (1-6C)alkyl, aryl, (3-8C)cycloalkyl, (3-8C)cycloalkenyl, heteroaryl or heterocyclyl; wherein $Z_5$ is optionally further substituted by one or more substituent groups independently selected from (1-4C)alkyl, halo, (1-4C)haloalkyl, (1-4C)haloalkoxy, amino, cyano, hydroxy, amido, carboxy, carbamoyl, sulphamoyl, mercapto, NR$^y$R$^z$, OR$^y$, wherein R$^y$ and R$^z$ are each independently selected from hydrogen, (1-4C)alkyl or (3-6C)cycloalkyl;

(73) $R^3$ is selected from:
i) a group of Formula A shown below:

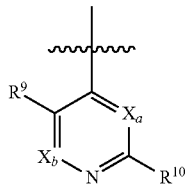

Formula A wherein:

denotes the point of attachment;
$X_a$ and $X_b$ are independently selected from N or $CR^{x1}$, wherein $R^{x1}$ is selected from hydrogen, fluoro, chloro, bromo, methyl, $OCH_3$, cyano or acetylenyl;
$R^9$ is selected from fluoro, chloro, bromo, methyl, $OCH_3$, cyano, nitro or acetylenyl;
$R^{10}$ is selected from hydrogen, halo, (1-2C)alkyl, (1-2C)alkoxy, (1-2C)haloalkyl, (1-2C)haloalkoxy, cyano, nitro, (2-4C)alkenyl, (2-4C)alkynyl or a group of the formula:

—$Y_3$—$Z_3$ wherein:
$Y_3$ is absent or C(O), C(O)O, C(O)N($R^s$) or S(O)$_2$N($R^s$), wherein $R^s$ is selected from hydrogen or (1-4C)alkyl; and
$Z_3$ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or 5- or 6-membered heterocyclyl; wherein $Z_3$ is optionally further substituted by one or more substituent groups independently selected from (1-2C)alkyl, halo, (1-2C)haloalkyl, (1-2C)haloalkoxy, amino, cyano, hydroxy, amido, carboxy, NR$^u$R$^v$ or OR$^u$, wherein R$^u$ and R$^v$ are each independently selected from hydrogen or (1-2C)alkyl;
ii) a group of Formula B shown below:

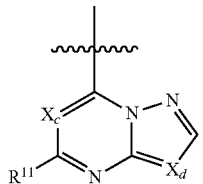

Formula B wherein:

denotes the point of attachment;
$X_c$ and $X_d$ are independently selected from N, CH, CF, CCl or CCH$_3$;

$R^{11}$ is selected from hydrogen, halo, (1-2C)alkyl, (1-2C)alkoxy, (1-2C)haloalkyl, (1-2C)haloalkoxy, cyano, nitro, (2-4C)alkenyl, (2-4C)alkynyl or a group of the formula:

—$Y_5$—$Z_5$ wherein:
$Y_5$ is absent or O, N(R$^w$), C(O), C(O)O, C(O)N (R$^w$) or S(O)$_2$N(R$^w$), wherein R$^w$ is selected from hydrogen or (1-4C)alkyl; and
$Z_5$ is hydrogen, (1-6C)alkyl, aryl, (3-6C)cycloalkyl, (3-6C)cycloalkenyl, 5 or 6 membered heteroaryl or 5 or 6 membered heterocyclyl; wherein $Z_5$ is optionally further substituted by one or more substituent groups independently selected from (1-2C)alkyl, halo, (1-2C)haloalkyl, (1-2C)haloalkoxy, amino, cyano, hydroxy, amido, carboxy, NR$^y$R$^z$, OR$^y$, wherein R$^y$ and R$^z$ are each independently selected from hydrogen or (1-2C)alkyl;

(74) $R^3$ is selected from:
i) a group of Formula A shown below:

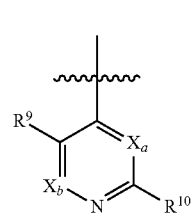

Formula A wherein:

denotes the point of attachment;
$X_a$ and $X_b$ are both CR$^{x1}$, wherein R$^{x1}$ is selected from hydrogen, fluoro, chloro, bromo or methyl;
$R^9$ is selected from fluoro, chloro, bromo, methyl, OCH$_3$, cyano or acetylenyl;
$R^{10}$ is selected from hydrogen, halo, (1-2C)alkyl, (1-2C)alkoxy, (1-2C)haloalkyl, (1-2C)haloalkoxy, cyano, (2-4C)alkenyl, (2-4C)alkynyl or a group of the formula:

—$Y_3$—$Z_3$ wherein:
$Y_3$ is absent or C(O), C(O)O, C(O)N(R$^s$) or S(O)$_2$N(R$^s$), wherein R$^s$ is selected from hydrogen or (1-4C)alkyl; and
$Z_3$ is hydrogen, (1-6C)alkyl, aryl, (3-6C)cycloalkyl, (2-4C)alkenyl, (2-4C)alkynyl, (3-6C) cycloalkenyl, 5- or 6-membered heteroaryl or 5- or 6-membered heterocyclyl; wherein $Z_3$ is optionally further substituted by one or more substituent groups independently selected from (1-2C)alkyl, halo, (1-2C)haloalkyl, (1-2C)haloalkoxy, amino, cyano, hydroxy, amido, carboxy, NR$^u$R$^v$ or OR$^u$, wherein R$^u$ and R$^v$ are each independently selected from hydrogen or (1-2C)alkyl;

ii) a group of Formula B shown below:

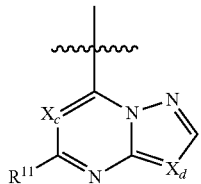

Formula B wherein:

denotes the point of attachment;
$X_c$ and $X_d$ are independently selected from N, CH, CF, CCl or CCH$_3$;
$R^{11}$ is selected from hydrogen, halo, (1-2C)alkyl, (1-2C)alkoxy, (1-2C)haloalkyl, (1-2C)haloalkoxy, cyano, (2-4C)alkenyl, (2-4C)alkynyl or a group of the formula:

—Y$_5$—Z$_5$ wherein:
$Y_5$ is absent or O, N(R$^w$), C(O), C(O)O, C(O)N(R$^w$) or S(O)$_2$N(R$^w$), wherein R$^w$ is selected from hydrogen or (1-4C)alkyl; and
$Z_5$ is hydrogen, (1-6C)alkyl, aryl, (3-6C)cycloalkyl, (3-6C)cycloalkenyl, 5 or 6 membered heteroaryl or 5 or 6 membered heterocyclyl; wherein $Z_5$ is optionally further substituted by one or more substituent groups independently selected from (1-2C)alkyl, halo, (1-2C)haloalkyl, (1-2C)haloalkoxy, amino, cyano, hydroxy, amido, carboxy, NR$^y$R$^z$, OR$^y$, wherein R$^y$ and R$^z$ are each independently selected from hydrogen or (1-2C)alkyl;

(75) R$^3$ is selected from:
i) a group of Formula A shown below:

Formula A

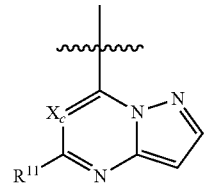

wherein:

denotes the point of attachment;
$X_b$ is CR$^{x1}$, wherein R$^{x1}$ is selected from hydrogen, fluoro, chloro, bromo or methyl;
$R^9$ is selected from fluoro, chloro, bromo, methyl, OCH$_3$, cyano or acetylenyl;

$R^{10}$ is selected from hydrogen, halo, (1-2C)alkyl, (1-2C)alkoxy, (1-2C)haloalkyl, (1-2C)haloalkoxy, cyano, (2-4C)alkenyl, (2-4C)alkynyl or a group of the formula:

—Y$_3$—Z$_3$ wherein:
$Y_3$ is absent or C(O), C(O)O, C(O)N(R$^s$) or S(O)$_2$N(R$^s$), wherein R$^s$ is selected from hydrogen or (1-4C)alkyl; and
$Z_3$ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or 5- or 6-membered heterocyclyl; wherein $Z_3$ is optionally further substituted by one or more substituent groups independently selected from (1-2C)alkyl, halo, (1-2C)haloalkyl, (1-2C)haloalkoxy, amino, cyano, hydroxy, amido, carboxy, NR$^u$R$^v$ or OR$^u$, wherein R$^u$ and R$^v$ are each independently selected from hydrogen or (1-2C)alkyl;

ii) a group of Formula B shown below:

Formula B

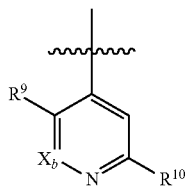

wherein:

denotes the point of attachment;
$X_c$ is selected from N, CH, CF, CCl or CCH$_3$;
$R^{11}$ is selected from hydrogen, halo, (1-2C)alkyl, (1-2C)alkoxy, (1-2C)haloalkyl, (1-2C)haloalkoxy, cyano, (2-4C)alkenyl, (2-4C)alkynyl or a group of the formula:

—Y$_5$—Z$_5$ wherein:
$Y_5$ is absent or O, N(R$^w$), C(O), C(O)O, C(O)N(R$^w$) or S(O)$_2$N(R$^w$), wherein R$^w$ is selected from hydrogen or (1-4C)alkyl; and
$Z_5$ is hydrogen, (1-6C)alkyl, aryl, (3-6C)cycloalkyl, (3-6C)cycloalkenyl, 5 or 6 membered heteroaryl or 5 or 6 membered heterocyclyl; wherein $Z_5$ is optionally further substituted by one or more substituent groups independently selected from (1-2C)alkyl, halo, (1-2C)haloalkyl, (1-2C)haloalkoxy, amino, cyano, hydroxy, amido, carboxy, NR$^y$R$^z$, OR$^y$, wherein R$^y$ and R$^z$ are each independently selected from hydrogen or (1-2C)alkyl;

(76) $R^3$ is selected from:
i) a group of Formula A shown below:

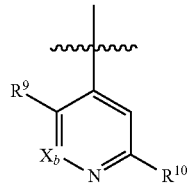

Formula A wherein:

denotes the point of attachment;
$X_b$ is $CR^{x1}$, wherein $R^{x1}$ is selected from hydrogen or chloro;
$R^9$ is selected from fluoro, chloro, bromo, methyl, $OCH_3$, cyano or acetylenyl;
$R^{10}$ is selected from hydrogen, halo, (1-2C)alkyl, (1-2C)alkoxy, (1-2C)haloalkyl, (1-2C)haloalkoxy, cyano, (2-4C)alkenyl, (2-4C)alkynyl or a group of the formula:

—$Y_3$—$Z_3$ wherein:
$Y_3$ is absent or C(O), C(O)O, C(O)N($R^s$) or S(O)$_2$N($R^s$), wherein $R^s$ is selected from hydrogen or (1-4C)alkyl; and
$Z_3$ is hydrogen, (1-6C)alkyl, aryl, (2-4C)alkynyl, 5- or 6-membered heteroaryl or 5- or 6-membered heterocyclyl; wherein $Z_3$ is optionally further substituted by one or more substituent groups independently selected from (1-2C)alkyl, halo, (1-2C)haloalkyl, (1-2C)haloalkoxy, amino, cyano, hydroxy, amido, carboxy, $NR^uR^v$ or $OR^u$, wherein $R^u$ and $R^v$ are each independently selected from hydrogen or (1-2C)alkyl;
ii) a group of Formula B shown below:

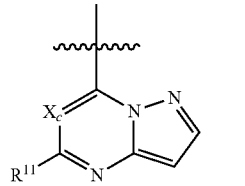

Formula B wherein:

denotes the point of attachment;
$X_c$ is selected from N, CH, CF, CCl or $CCH_3$;
$R^{11}$ is selected from hydrogen, halo, (1-2C)alkyl, (1-2C)alkoxy, (1-2C)haloalkyl, (1-2C)haloalkoxy, cyano, (2-4C)alkenyl, (2-4C)alkynyl or a group of the formula:

—$Y_5$—$Z_5$ wherein:
$Y_5$ is absent or O, N($R^w$), C(O), C(O)O, C(O)N($R^w$) or S(O)$_2$N($R^w$), wherein $R^w$ is selected from hydrogen or (1-4C)alkyl; and
$Z_5$ is hydrogen, (1-6C)alkyl, aryl, 5 or 6 membered heteroaryl or 5 or 6 membered heterocyclyl; wherein $Z_5$ is optionally further substituted by one or more substituent groups independently selected from (1-2C)alkyl, halo, (1-2C)haloalkyl, (1-2C)haloalkoxy, amino, cyano, hydroxy, amido, carboxy, $NR^yR^z$, $OR^y$, wherein $R^y$ and $R^z$ are each independently selected from hydrogen or (1-2C)alkyl;

(77) $R^3$ is a group of Formula A shown below:

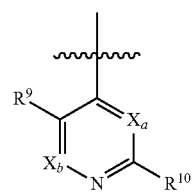

Formula A wherein:

denotes the point of attachment;
$X_a$ and $X_b$ are independently selected from N or $CR^{x1}$, wherein $R^{x1}$ is selected from hydrogen, fluoro, chloro, bromo, (1-2C)alkyl, (1-2C)alkoxy, cyano, nitro, acetylenyl, $CH_2F$, $CF_2H$ or $CF_3$;
$R^9$ is selected from hydrogen, fluoro, chloro, bromo, (1-2C)alkyl, (1-2C)alkoxy, cyano, nitro, acetylenyl, $CH_2F$, $CF_2H$ or $CF_3$;
$R^{10}$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—$Y_3$—$Z_3$ wherein:
$Y_3$ is absent or O, N($R^s$)($CR^sR^t$)$_{q1}$ (where $q_1$ is 0, 1 or 2), S, SO, SO$_2$, C(O), C(O)O, OC(O), C(O)N($R^s$), N($R^s$)C(O), N($R^s$)C(O)N($R^t$), N($R^s$)C(O)O, OC(O)N($R^s$), S(O)$_2$N($R^s$), N($R^s$)SO$_2$, wherein $R^s$ and $R^t$ are each independently selected from hydrogen or (1-4C)alkyl; and
$Z_3$ is hydrogen, (1-6C)alkyl, aryl, (3-6C)cycloalkyl, (2-4C)alkenyl, (2-4C)alkynyl, (3-6C)cycloalkenyl, heteroaryl or 4 to 11-membered heterocyclyl; wherein $Z_3$ is optionally further substituted by one or more substituent groups independently selected from oxo, (1-4C)alkyl, (3-6C)cycloalkyl, halo, (1-4C)haloalkyl, (1-4C)haloalkoxy, (1-4C)hydroxyalkyl, amino, cyano, hydroxy, amido, carboxy, carbamoyl, sulphamoyl, mercapto, C(O)$NR^uR^v$, $NR^uR^v$ or $OR^u$, wherein $R^u$ and $R^v$ are each independently selected from hydrogen, (1-4C)alkyl or (3-6C)

cycloalkyl; and/or $Z^3$ is optionally further substituted by a group of the formula:

-L$_Z$-W$_Z$ wherein:
L$_Z$ is absent or a (1-5C)alkylene optionally substituted by one or more (1-2C)alkyl groups; and
W$_Z$ is aryl, 5- or 6-membered heteroaryl, 4- to 7-membered heterocyclyl, halo, (1-4C)haloalkyl, (1-4C)haloalkoxy, cyano, hydroxy, (1-4C)alkoxy, C(O)R$^{xa}$, COOR$^{xa}$, C(O)NR$^{xa}$R$^{xb}$ or NR$^{xa}$R$^{xb}$, wherein R$^{xa}$ and R$^{xb}$ are each independently selected from hydrogen or (1-4C)alkyl; and wherein each aryl, 5- or 6-membered heteroaryl or 4- to 7-membered heterocyclyl is optionally further substituted by one or more substituent groups independently selected from (1-2C)alkyl, halo, (1-2C)haloalkyl, amino, cyano or hydroxy;

(78) $R^3$ is a group of Formula A shown below:

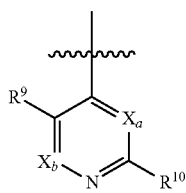

Formula A wherein:

denotes the point of attachment;
X$_a$ and X$_b$ are independently selected from N or CR$^{x1}$, wherein R$^{x1}$ is selected from hydrogen, fluoro, chloro, bromo, (1-2C)alkyl, (1-2C)alkoxy, cyano, nitro, acetylenyl, CH$_2$F, CF$_2$H or CF$_3$;
$R^9$ is selected from hydrogen, fluoro, chloro, bromo, (1-2C)alkyl, (1-2C)alkoxy, cyano, nitro, acetylenyl, CH$_2$F, CF$_2$H or CF$_3$;
$R^{10}$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y$_3$—Z$_3$ wherein:
Y$_3$ is absent or O, N(R$^s$)(CR$^s$R$^t$)$_{q1}$ (where q$_1$ is 0, 1 or 2), S, SO, SO$_2$, C(O), C(O)O, OC(O), C(O)N(R$^s$), N(R$^s$)C(O), N(R$^s$)C(O)N(R$^t$), N(R$^s$)C(O)O, OC(O)N(R$^s$), S(O)$_2$N(R$^s$), N(R$^s$)SO$_2$, wherein R$^s$ and R$^t$ are each independently selected from hydrogen or (1-4C)alkyl; and
Z$_3$ is hydrogen, (1-6C)alkyl, aryl, (3-6C)cycloalkyl, (2-4C)alkenyl, (2-4C)alkynyl, (3-6C)cycloalkenyl, heteroaryl or 4 to 11-membered heterocyclyl; wherein Z$_3$ is optionally further substituted by one or more substituent groups independently selected from oxo, (1-4C)alkyl, (3-6C)cycloalkyl, halo, (1-4C)haloalkyl, (1-4C)

haloalkoxy, amino, cyano, hydroxy, amido, carboxy, carbamoyl, sulphamoyl, mercapto, C(O)NR$^u$R$^v$, NR$^u$R$^v$ or OR$^u$, wherein R$^u$ and R$^v$ are each independently selected from hydrogen, (1-4C)alkyl or (3-6C)cycloalkyl; and/or $Z^3$ is optionally further substituted by a group of the formula:

-L$_Z$-W$_Z$ wherein:
L$_Z$ is absent or a (1-5C)alkylene optionally substituted by one or more (1-2C)alkyl groups; and
W$_Z$ is aryl, 5- or 6-membered heteroaryl, 4- to 7-membered heterocyclyl, halo, (1-4C)haloalkyl, (1-4C)haloalkoxy, cyano, hydroxy, (1-4C)alkoxy, C(O)R$^{xa}$, COOR$^{xa}$, C(O)NR$^{xa}$R$^{xb}$ or NR$^{xa}$R$^{xb}$, wherein R$^{xa}$ and R$^{xb}$ are each independently selected from hydrogen or (1-4C)alkyl;

(79) $R^3$ is a group of Formula A shown below:

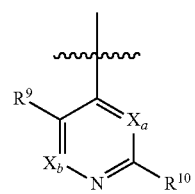

Formula A wherein:

denotes the point of attachment;
X$_a$ and X$_b$ are independently selected from N or CR$^{x1}$, wherein R$^{x1}$ is selected from hydrogen, fluoro, chloro, bromo, (1-2C)alkyl, (1-2C)alkoxy, cyano, nitro, acetylenyl, CH$_2$F, CF$_2$H or CF$_3$;
$R^9$ is selected from hydrogen, fluoro, chloro, bromo, (1-2C)alkyl, (1-2C)alkoxy, cyano, nitro, acetylenyl, CH$_2$F, CF$_2$H or CF$_3$;
$R^{10}$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y$_3$—Z$_3$ wherein:
Y$_3$ is absent or O, N(R$^s$)(CR$^s$R$^t$)$_{q1}$ (where q$_1$ is 0, 1 or 2), S, SO, SO$_2$, C(O), C(O)O, OC(O), C(O)N(R$^s$), N(R$^s$)C(O), N(R$^s$)C(O)N(R$^t$), N(R$^s$)C(O)O, OC(O)N(R$^s$), S(O)$_2$N(R$^s$), N(R$^s$)SO$_2$, wherein R$^s$ and R$^t$ are each independently selected from hydrogen or (1-4C)alkyl; and
Z$_3$ is hydrogen, (1-6C)alkyl, aryl, (3-6C)cycloalkyl, (2-4C)alkenyl, (2-4C)alkynyl, (3-6C)cycloalkenyl, heteroaryl or 4 to 11-membered heterocyclyl; wherein Z$_3$ is optionally further substituted by one or more substituent groups independently selected from oxo, (1-4C)alkyl, (3-6C)cycloalkyl, halo, (1-4C)haloalkyl, (1-4C)

haloalkoxy, amino, cyano, hydroxy, amido, carboxy, carbamoyl, sulphamoyl, mercapto, C(O)NR$^u$R$^v$, NR$^u$R$^v$ or OR$^u$, wherein R$^u$ and R$^v$ are each independently selected from hydrogen, (1-4C)alkyl or (3-6C)cycloalkyl; or Z$^3$ is optionally further substituted by a group of the formula:

-L$_Z$-W$_Z$ wherein:
L$_Z$ is a (1-5C)alkylene optionally substituted by one or more substituents selected from (1-2C)alkyl or oxo; and
W$_Z$ is halo, (1-4C)haloalkyl, (1-4C)haloalkoxy, cyano, hydroxy, (1-4C)alkoxy, C(O)R$^{xa}$, COOR$^{xa}$, C(O)NR$^{xa}$R$^{xb}$ or NR$^{xa}$R$^{xb}$, wherein R$^{xa}$ and R$^{xb}$ are each independently selected from hydrogen or (1-4C)alkyl;

(80) R$^3$ is a group of Formula A shown below:

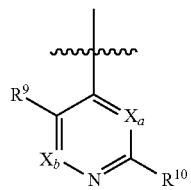

Formula A wherein:

denotes the point of attachment;
X$_a$ and X$_b$ are independently selected from N or CR$^{x1}$, wherein R$^{x1}$ is selected from hydrogen, fluoro, chloro, bromo, methyl, OCH$_3$, cyano or acetylenyl;
R$^9$ is selected from fluoro, chloro, bromo, methyl, OCH$_3$, cyano or acetylenyl;
R$^{10}$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y$_3$—Z$_3$ wherein:
Y$_3$ is absent or N(R$^s$)(CH$_2$)$_{q_1}$ (where q$_1$ is 0, 1 or 2), S, C(O), C(O)O, C(O)N(R$^s$), N(R$^s$)C(O), or S(O)$_2$N(R$^s$), wherein R$^s$ is selected from hydrogen or (1-4C)alkyl; and
Z$_3$ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or 4 to 11-membered heterocyclyl; wherein Z$_3$ is optionally further substituted by one or more substituent groups independently selected from oxo, (1-4C)alkyl, (3-6C)cycloalkyl, halo, (1-4C)haloalkyl, (1-4C)haloalkoxy, amino, cyano, hydroxy, amido, carboxy, C(O)NR$^u$R$^v$, NR$^u$R$^v$ or OR$^u$, wherein R$^u$ and R$^v$ are each independently selected from hydrogen, (1-4C) alkyl or cyclopropyl; or Z$^3$ is optionally further substituted by a group of the formula:

-L$_Z$-W$_Z$ wherein:
L$_Z$ is a (1-3C)alkylene; and
W$_Z$ is halo, (1-2C)haloalkyl, (1-2C)haloalkoxy, cyano, hydroxy, (1-2C)alkoxy, C(O)R$^{xa}$, COOR$^{xa}$, C(O)NR$^{xa}$R$^{xb}$ or NR$^{xa}$R$^{xb}$, wherein R$^{xa}$ and R$^{xb}$ are each independently selected from hydrogen or (1-2C)alkyl;

(81) R$^3$ is a group of Formula A shown below:

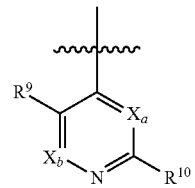

Formula A wherein:

denotes the point of attachment;
X$_a$ is CH or N;
X$_b$ is selected from CH, CCl, CF, CBr or CCH$_3$;
R$^9$ is selected from chloro or cyano;
R$^{10}$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y$_3$—Z$_3$ wherein:
Y$_3$ is absent or N(R$^s$)(CH$_2$)$_{q_1}$ (where q is 0, 1 or 2), S, C(O), C(O)O, C(O)N(R$^s$), N(R$^s$)C(O), or S(O)$_2$N(R$^s$), wherein R$^s$ is selected from hydrogen or (1-4C)alkyl; and
Z$_3$ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or 4 to 11-membered heterocyclyl; wherein Z$_3$ is optionally further substituted by one or more substituent groups independently selected from oxo, (1-4C)alkyl, (3-6C)cycloalkyl, halo, (1-4C)haloalkyl, (1-4C)haloalkoxy, amino, cyano, hydroxy, amido, carboxy, C(O)NR$^u$R$^v$, NR$^u$R$^v$ or OR$^u$, wherein R$^u$ and R$^v$ are each independently selected from hydrogen, (1-4C) alkyl or cyclopropyl; and/or Z$^3$ is optionally further substituted by a group of the formula:

-L$_Z$-W$_Z$ wherein:
L$_Z$ is absent or a (1-3C)alkylene; and
W$_Z$ is phenyl, 5- or 6-membered heteroaryl, 6-membered heterocyclyl, halo, (1-2C)haloalkyl, (1-2C)haloalkoxy, cyano, hydroxy, (1-2C)alkoxy, C(O)R$^{xa}$, COOR$^{xa}$, C(O)NR$^{xa}$R$^{xb}$ or NR$^{xa}$R$^{xb}$, wherein R$^{xa}$ and R$^{xb}$ are each independently selected from hydrogen or (1-2C) alkyl;

(82) R$^3$ is a group of Formula A shown below:

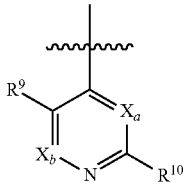

Formula A wherein:

denotes the point of attachment;
X$_a$ is CH or N;
X$_b$ is selected from N or CR$^{x1}$, wherein R$^{x1}$ is selected from hydrogen, fluoro, chloro, bromo, methyl, OCH$_3$, cyano or acetylenyl;
R$^9$ is selected from chloro or cyano;
R$^{10}$ is selected from hydrogen, halo, (1-4C)alkyl, (1-4C)alkoxy, (1-4C)haloalkyl, (1-4C)haloalkoxy, cyano or a group of the formula:

—Y$_3$—Z$_3$ wherein:
Y$_3$ is absent or N(R$^s$)(CH$_2$)$_{q^1}$ (where q$_1$ is 0 or 1), C(O), C(O)O or C(O)N(R$^s$), wherein R$^s$ is selected from hydrogen or methyl; and
Z$_3$ is hydrogen, (1-6C)alkyl, aryl, (3-6C)cycloalkyl, 5- or 6-membered heteroaryl or 4 to 9-membered heterocyclyl; wherein Z$_3$ is optionally further substituted by one or more substituent groups independently selected from oxo, (1-3C)alkyl, cyclopropyl, halo, (1-2C)haloalkyl, (1-2C)haloalkoxy, amino, cyano, hydroxy, amido, carboxy, C(O)NR$^u$R$^v$, NR$^u$R$^v$ or OR$^u$, wherein Ru and R$^v$ are each independently selected from hydrogen or methyl; or Z$^3$ is optionally further substituted by a group of the formula:

-L$_Z$-W$_Z$ wherein:
L$_Z$ is a (1-3C)alkylene; and
W$_Z$ is halo, (1-2C)haloalkyl, (1-2C)haloalkoxy, cyano, hydroxy, (1-2C)alkoxy, C(O)R$^{xa}$, COOR$^{xa}$, C(O)NR$^{xa}$R$^{xb}$ or NR$^{xa}$R$^{xb}$, wherein R$^{xa}$ and R$^{xb}$ are each independently selected from hydrogen or methyl;

(83) R$^3$ is a group of Formula A shown below:

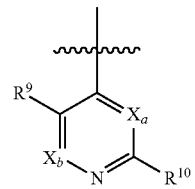

Formula A wherein:

denotes the point of attachment;
X$_a$ is CH or N;
X$_b$ is selected from N or CR$^{x1}$, wherein R$^{x1}$ is selected from hydrogen, fluoro, chloro, bromo, methyl, OCH$_3$, cyano or acetylenyl;
R$^9$ is selected from chloro or cyano;
R$^{10}$ is selected from hydrogen, halo, (1-4C)alkyl, (1-4C)alkoxy, (1-4C)haloalkyl, (1-4C)haloalkoxy, cyano or a group of the formula:

—Y$_3$—Z$_3$ wherein:
Y$_3$ is absent or N(R$^s$)(CH$_2$)$_{q^1}$ (where q$_1$ is 0 or 1), C(O), C(O)O or C(O)N(R$^s$), wherein R$^s$ is selected from hydrogen or methyl; and
Z$_3$ is hydrogen, (1-6C)alkyl, (3-6C)cycloalkyl, 5- or 6-membered heteroaryl or 4 to 9-membered heterocyclyl; wherein Z$_3$ is optionally further substituted by one or more substituent groups independently selected from oxo, (1-3C)alkyl, cyclopropyl, halo, (1-2C)haloalkyl, (1-2C)haloalkoxy, amino, cyano, hydroxy, amido, carboxy, C(O)NR$^u$R$^v$, NR$^u$R$^v$ or OR$^u$, wherein R and R$^v$ are each independently selected from hydrogen or methyl;

(84) R$^3$ is a group of Formula A shown below:

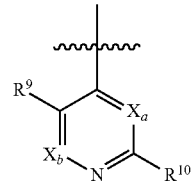

Formula A wherein:

denotes the point of attachment;
X$_a$ is CH or N;
X$_b$ is selected from N or CR$^{x1}$, wherein R$^{x1}$ is selected from hydrogen, fluoro, chloro, bromo, methyl, OCH$_3$, cyano or acetylenyl;

$R^9$ is selected from chloro or cyano;
$R^{10}$ is selected from hydrogen, halo, (1-4C)alkyl, (1-4C)alkoxy or a group of the formula:

wherein:
  $Y_3$ is absent or $C(O)N(R^s)$, wherein $R^s$ is selected from hydrogen or methyl; and
  $Z_3$ is (3-6C)cycloalkyl, 5- or 6-membered heteroaryl or 4 to 9-membered heterocyclyl; wherein $Z_3$ is optionally further substituted by one or more substituent groups independently selected from (1-2C)alkyl, halo, (1-2C)haloalkyl, cyano, hydroxy, $C(O)NR^uR^v$, $NR^uR^v$ or $OR^u$, wherein $R^u$ and $R^v$ are each independently selected from hydrogen or methyl;
(85) $R^3$ is a group of Formula A shown below:

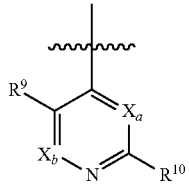

Formula A wherein:

denotes the point of attachment;
$X_a$ is CH or N;
$X_b$ is selected from CH, CCl, CF, CBr or CCH$_3$;
$R^9$ is selected from chloro or cyano;
$R^{10}$ is selected from a (3-6C)cycloalkyl, a 5- or 6-membered heteroaryl or a 4 to 9-membered heterocyclyl; wherein said (3-6C)cycloalkyl, 5- or 6-membered heteroaryl or 4 to 9-membered heterocyclyl is optionally further substituted by one or more substituent groups independently selected from (1-2C)alkyl, halo, (1-2C)haloalkyl, cyano, hydroxy, $C(O)NR^uR^v$, $NR^uR^v$ or $OR^u$, wherein $R^u$ and $R^v$ are each independently selected from hydrogen or methyl;
(86) $R^3$ is a group of Formula A shown below:

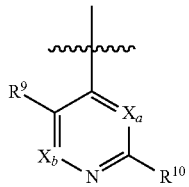

Formula A wherein:

denotes the point of attachment;
$X_a$ is CH or N;
$X_b$ is selected from CH, CCl, CF, CBr or CCH$_3$;
$R^9$ is selected from chloro or cyano;
$R^{10}$ is selected from a 5- or 6-membered heteroaryl or a 4 to 8-membered heterocyclyl; wherein said 5- or 6-membered heteroaryl or 4 to 8-membered heterocyclyl is optionally further substituted by one or more substituent groups independently (1-4C)alkyl, halo, (1-4C)haloalkyl, (1-4C)haloalkoxy, (1-4C)alkoxyalkyl, cyano or hydroxy;
(87) $R^3$ is a compound of Formula A as defined in any one of paragraphs 54 to 86 above;
(88) $R^3$ is a compound of Formula B as defined in any one of paragraphs 54 to 76 above;
(89) $R^3$ is a compound of Formula C as defined in any one of paragraphs 54 to 65 above.

Suitably, a heteroaryl is a 5- or 6-membered heteroaryl ring comprising one, two or three heteroatoms selected from N, O or S.

Suitably, a heterocyclyl group is a 4-, 5- or 6-membered heterocyclyl ring comprising one, two or three heteroatoms selected from N, O or S. Most suitably, a heterocyclyl group is a 5-, 6- or 7-membered ring comprising one, two or three heteroatoms selected from N, O or S [e.g. morpholinyl (e.g. 4-morpholinyl), pyridinyl, piperazinyl, homopiperazinyl or pyrrolidinonyl].

Suitably an aryl group is phenyl.

Suitably, $X_1$ is as defined in any one of paragraphs (1) to 9) above. Most suitably, X is as defined in paragraph (9) above.

Suitably, $X_2$ is as defined in any one of paragraphs (10) to (14) above. Most suitably, $X_2$ is as defined in paragraph (14) above.

Suitably, $R^1$ is as defined in any one of paragraphs (15) to (31) above. Most suitably, $R^1$ is as defined in paragraph (31) above.

Suitably, $R^2$ is as defined in any one of paragraphs (32) to (53) above. Most suitably, $R^2$ is as defined in any one of paragraphs (49) or (53) above.

Most suitably, $R^3$ is as defined in any one of paragraphs (54) to (86) above. Most suitably $R^3$ is as defined in paragraph (86) above.

In a particular group of compounds of the invention, $X_2$ is CH, i.e. the compounds have the structural formula Ia (a sub-definition of Formula (I)) shown below, or a pharmaceutically acceptable salt, hydrate and/or solvate thereof:

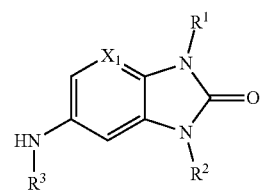

Formula Ia wherein each of $X_1$, $R^1$, $R^2$ and $R^3$ are as defined hereinabove.

In an embodiment of the compounds of Formula Ia:
  $X_1$ is as defined in any one of paragraphs (1) to (9) above;
  $R^1$ is as defined in any one of paragraphs (15) to (31) above;
  $R^2$ is as defined in any one of paragraphs (32) to (53) above; and $R^3$ is as defined in any one of paragraphs (54) to (86) above.

In another embodiment of the compounds of Formula Ia:
$X_1$ is as defined in paragraph (9) above;
$R^1$ is as defined in any one of paragraphs (28) to (31) above;
$R^2$ is as defined in any one of paragraphs (49) to (53) above; and
$R^3$ is as defined in paragraph (86) above.

In a particular group of compounds of the invention, $X_1$ and $X_2$ are CH, i.e. the compounds have the structural formula Ib (a sub-definition of Formula (I)) shown below, or a pharmaceutically acceptable salt, hydrate and/or solvate thereof:

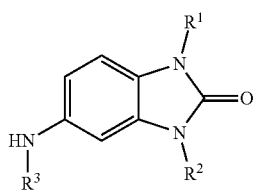

Formula Ib wherein each of $R^1$, $R^2$ and $R^3$ are as defined hereinabove.

In an embodiment of the compounds of Formula Ib:
$R^1$ is as defined in any one of paragraphs (15) to (31) above;
$R^2$ is as defined in any one of paragraphs (32) to (53) above; and
$R^3$ is as defined in any one of paragraphs (54) to (86) above.

In another embodiment of the compounds of Formula Ib:
$R^1$ is as defined in any one of paragraphs (28) to (31) above;
$R^2$ is as defined in any one of paragraphs (49) to (53) above; and
$R^3$ is as defined in paragraph (86) above.

In a particular group of compounds of the invention, $R^2$ is of the formula shown below, i.e. the compounds have the structural formula Ic (a sub-definition of Formula (I)) shown below, or a pharmaceutically acceptable salt, hydrate and/or solvate thereof:

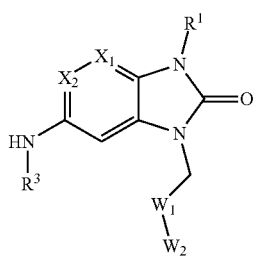

Formula Ic wherein each of $X_1$, $X_2$, $R^1$, $R^3$, $W^1$ and $W^2$ are as defined hereinabove.

In an embodiment of the compounds of Formula Ic:
$X_1$ is as defined in any one of paragraphs (1) to (9) above;
$X_2$ is as defined in any one of paragraphs (10) to (14) above;
$R^1$ is as defined in any one of paragraphs (15) to (31) above;
$W^1$ and $W^2$ are as defined in any one of paragraphs (32) to (51) above; and
$R^3$ is as defined in any one of paragraphs (54) to (86) above.

In another embodiment of the compounds of Formula Ic:
$X_1$ is as defined in paragraph (9) above;
$X_2$ is as defined in paragraph (14) above;
$R^1$ is as defined in any one of paragraphs (28) to (31) above;
$W^1$ and $W^2$ are as defined in paragraph (51) above; and
$R^3$ is as defined in paragraph (86) above.

In a particular group of compounds of the invention, $X_1$ and $X_2$ are CH and $R^2$ is of the formula shown below, i.e. the compounds have the structural formula Id (a sub-definition of Formula (I)) shown below, or a pharmaceutically acceptable salt, hydrate and/or solvate thereof:

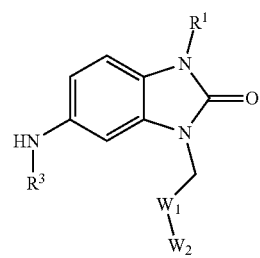

Formula Id wherein each of $R^1$, $R^3$, $W^1$ and $W^2$ are as defined hereinabove In an embodiment of the compounds of Formula Id:
$R^1$ is as defined in any one of paragraphs (15) to (31) above;
$W^1$ and $W^2$ are as defined in any one of paragraphs (32) to (51) above; and
$R^3$ is as defined in any one of paragraphs (54) to (86) above.

In another embodiment of the compounds of Formula Id:
$R^1$ is as defined in any one of paragraphs (28) to (31) above;
$W^1$ and $W^2$ are as defined in paragraph (51) above; and
$R^3$ is as defined in paragraph (86) above.

In a particular group of compounds of the invention, $X_1$ and $X_2$ are CH, $R^1$ is methyl and $R^2$ is of the formula shown below, i.e. the compounds have the structural formula Ie (a sub-definition of Formula (I)) shown below, or a pharmaceutically acceptable salt, hydrate and/or solvate thereof:

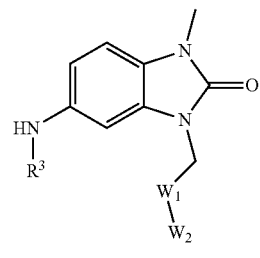

Formula Ie wherein each of $R^3$, $W^1$ and $W^2$ are as defined hereinabove.

In an embodiment of the compounds of Formula Ie:
$W^1$ and $W^2$ are as defined in any one of paragraphs (32) to (51) above; and R³ is as defined in any one of paragraphs (54) to (86) above.

In another embodiment of the compounds of Formula Ie:
W¹ and W² are as defined in paragraph (51) above; and
R³ is as defined in paragraph (86) above.

In a particular group of compounds of the invention, $X_1$ and $X_2$ are CH and R² is of the formula shown below, i.e. the compounds have the structural formula If (a sub-definition of Formula (I)) shown below, or a pharmaceutically acceptable salt, hydrate and/or solvate thereof:

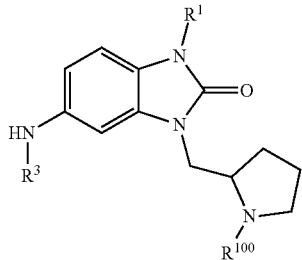

Formula If wherein each of $R^1$, $R^3$ and $R^{100}$ are as defined hereinabove.

In an embodiment of the compounds of Formula If:
$R^1$ is as defined in any one of paragraphs (15) to (31) above;
$R^3$ is as defined in any one of paragraphs (54) to (86) above; and
$R^{100}$ is as defined in any one of paragraphs (39) to (41), or (45) to (50) above.

In another embodiment of the compounds of Formula If:
$R^1$ is as defined in any one of paragraphs (28) to (31) above;
$R^3$ is as defined in paragraph (86) above; and
$R^{100}$ is —C(O)OR$^{ab}$, wherein R$^{ab}$ is selected from (1-2C) alkyl.

In a particular group of compounds of the invention, $X_1$ and $X_2$ are CH and R² is of the formula shown below, i.e. the compounds have the structural formula Ig (a sub-definition of Formula (I)) shown below, or a pharmaceutically acceptable salt, hydrate and/or solvate thereof:

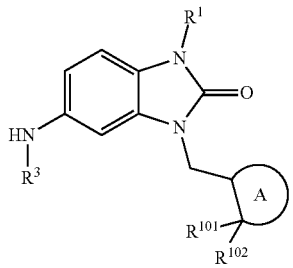

Formula Ig wherein each of $R^1$, $R^3$, $R^{101}$, $R^{102}$ and ring A are as defined hereinabove.

In an embodiment of the compounds of Formula Ig:
$R^1$ is as defined in any one of paragraphs (15) to (31) above;
$R^3$ is as defined in any one of paragraphs (54) to (86) above; and
$R^{101}$, $R^{102}$ and ring A are as defined in any one of paragraphs (39) to (41), or (43) to (50) above.

In another embodiment of the compounds of Formula Ig:
$R^1$ is as defined in any one of paragraphs (28) to (31) above;
$R^3$ is as defined in paragraph (86) above; and
$R^{101}$, $R^{102}$ and ring A are as defined in paragraphs (49) or (50) above.

In a particular group of compounds of the invention, the compounds have the structural formula Ih (a sub-definition of Formula (I)) shown below, or a pharmaceutically acceptable salt, hydrate and/or solvate thereof:

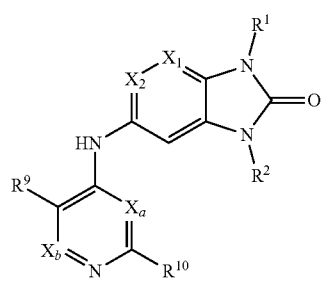

Formula Ih wherein each of $X_1$, $X_2$, $X_a$, $X_b$, $R^1$, $R^2$, $R^9$ and $R^{10}$ are as defined hereinabove.

In an embodiment of the compounds of Formula Ih:
$X_1$ is as defined in any one of paragraphs (1) to (9) above;
$X_2$ is as defined in any one of paragraphs (10) to (14) above;
$X_a$ and $X_b$ are as defined in any one of paragraphs (54) to (86) above;
$R^1$ is as defined in any one of paragraphs (15) to (31) above;
$R^2$ is as defined in any one of paragraphs (32) to (53) above;
$R^9$ is as defined in any one of paragraphs (54) to (86) above; and
$R^{10}$ is as defined in any one of paragraphs (54) to (86) above.

In another embodiment of the compounds of Formula Ih:
$X_1$ is as defined in paragraph (9) above;
$X_2$ is as defined in paragraph (14) above;
$X_a$ and $X_b$ are as defined in paragraph (83) above;
$R^1$ is as defined in any one of paragraphs (28) to (31) above;
$R^2$ is as defined in any one of paragraphs (51) to (53) above;
$R^9$ is as defined in paragraph (86) above; and
$R^{10}$ is as defined in paragraph (86) above.

In a particular group of compounds of the invention, the compounds have the structural formula Ij (a sub-definition of Formula (I)) shown below, or a pharmaceutically acceptable salt, hydrate and/or solvate thereof:

Formula Ij

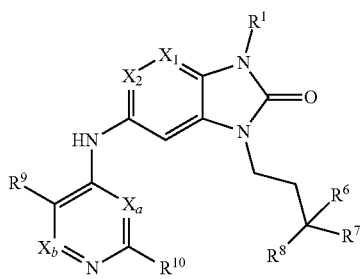

wherein each of $X_1$, $X_2$, $X_a$, $X_b$, $R^1$, $R^6$, $R^1$, $R^8$, $R^9$ and $R^{10}$ are as defined hereinabove.

In an embodiment of the compounds of Formula Ij:
$X_1$ is as defined in any one of paragraphs (1) to (9) above;
$X_2$ is as defined in any one of paragraphs (10) to (14) above;
$X_a$ and $X_b$ are as defined in any one of paragraphs (54) to (86) above;
$R^1$ is as defined in any one of paragraphs (15) to (31) above;
$R^6$, $R^7$ and $R^8$ are each as defined in any one of paragraphs (50) to (51) above;
$R^9$ is as defined in any one of paragraphs (54) to (86) above; and
$R^{10}$ is as defined in any one of paragraphs (54) to (86) above.

In another embodiment of the compounds of Formula Ij:
$X_1$ is as defined in paragraph (9) above;
$X_2$ is as defined in paragraph (14) above;
$X_a$ and $X_b$ are as defined in paragraph (86) above;
$R^1$ is as defined in any one of paragraphs (28) to (31) above;
$R^6$ is OH;
$R^7$ and $R^3$ are $CH_3$;
$R^9$ is as defined in paragraph (86) above; and
$R^{10}$ is as defined in paragraph (86) above.

Particular compounds of the present invention include any of the compounds exemplified in the present application, or a pharmaceutically acceptable salt or solvate thereof, and, in particular, any of the following:

6-Chloro-5-cyano-4-[[3-(3-hydroxy-3-methyl-butyl)-1-methyl-2-oxo-benzimidazol-5-yl]amino]-N-methyl-pyridine-2-carboxamide;
2-chloro-4-[[3-(3-hydroxy-3-methyl-butyl)-1-methyl-2-oxo-benzimidazol-5-yl]amino]-6-methyl-pyridine-3-carbonitrile;
6-chloro-5-cyano-4-[(1,3-dimethyl-2-oxo-benzimidazol-5-yl)amino]pyridine-2-carboxylic acid;
6-chloro-5-cyano-N-methyl-4-[[1-methyl-2-oxo-3-[(3S)-3-pyrazol-1-ylbutyl]benzimidazol-5-yl]amino]pyridine-2-carboxamide;
6-chloro-5-cyano-4-[[3-[(3R)-3-hydroxybutyl]-1-methyl-2-oxo-benzimidazol-5-yl]amino]pyridine-2-carboxylic acid;
6-chloro-5-cyano-N-methyl-4-[(1-methyl-2-oxo-3H-benzimidazol-5-yl)amino]pyridine-2-carboxamide;
6-chloro-5-cyano-4-[[3-(3-hydroxy-3-methyl-butyl)-2-oxo-1-(tetrahydropyran-4-ylmethyl)benzimidazol-5-yl]amino]-N-methyl-pyridine-2-carboxamide;
Ethyl 7-[[3-(3-hydroxy-3-methyl-butyl)-1-methyl-2-oxo-benzimidazol-5-yl]amino]pyrazolo[1,5-a]pyrimidine-5-carboxylate;
2-chloro-4-[[3-(3-hydroxy-3-methyl-butyl)-1-methyl-2-oxo-benzimidazol-5-yl]amino]pyridine-3-carbonitrile;
Methyl 4-[6-[(2-chloro-3-cyano-4-pyridyl)amino]-3-methyl-2-oxo-benzimidazol-1-yl]-2-methyl-butanoate;
2-bromo-4-[[3-(3-hydroxy-3-methyl-butyl)-1-methyl-2-oxo-benzimidazol-5-yl]amino]pyridine-3-carbonitrile;
2-chloro-4-[[3-[(3R)-3-hydroxybutyl]-1-methyl-2-oxo-benzimidazol-5-yl]amino]-6-methyl-pyridine-3-carbonitrile;
5-[(2,5-dichloro-4-pyridyl)amino]-3-[(3R)-3-hydroxybutyl]-1-methyl-benzimidazol-2-one;
5-[(2,5-dichloropyrimidin-4-yl)amino]-3-(3-hydroxy-3-methyl-butyl)-1-methyl-benzimidazol-2-one;
Ethyl 7-[[3-[(3R)-3-hydroxybutyl]-1-methyl-2-oxo-benzimidazol-5-yl]amino]pyrazolo[1,5-a]pyrimidine-5-carboxylate;
4-chloro-6-[[3-(3-hydroxy-3-methyl-butyl)-1-methyl-2-oxo-benzimidazol-5-yl]amino]pyrimidine-5-carbonitrile;
5-[(2,3-dichloro-4-pyridyl)amino]-3-[(3R)-3-hydroxybutyl]-1-methyl-benzimidazol-2-one;
Ethyl 3-fluoro-7-((3-(2-hydroxybutyl)-1-methyl-2-oxo-2,3-dihydro-1H-benzo[d]imidazol-5-yl)amino)pyrazolo[1,5-a]pyrimidine-5-carboxylate;
Methyl 6-chloro-5-cyano-4-[[3-(4-methoxy-3-methyl-4-oxo-butyl)-1-methyl-2-oxo-benzimidazol-5-yl]amino]pyridine-2-carboxylate;
Ethyl 6-chloro-5-cyano-4-[[3-(4-methoxy-3-methyl-4-oxo-butyl)-1-methyl-2-oxo-benzimidazol-5-yl]amino]pyridine-2-carboxylate;
Isopropyl 6-chloro-5-cyano-4-[[3-(4-methoxy-3-methyl-4-oxo-butyl)-1-methyl-2-oxo-benzimidazol-5-yl]amino]pyridine-2-carboxylate;
Ethyl 6-chloro-5-cyano-4-[[3-[(3R)-3-hydroxybutyl]-1-methyl-2-oxo-benzimidazol-5-yl]amino]pyridine-2-carboxylate;
6-Chloro-5-cyano-4-[[3-(4-methoxy-3-methyl-4-oxo-butyl)-1-methyl-2-oxo-benzimidazol-5-yl]amino]pyridine-2-carboxylic acid;
Methyl 3-[6-[(2-chloro-3-cyano-4-pyridyl)amino]-3-methyl-2-oxo-benzimidazol-1-yl]-2-methyl-propanoate;
Methyl 4-[6-[(5-chloro-2-methyl-pyrimidin-4-yl)amino]-3-methyl-2-oxo-benzimidazol-1-yl]-2-methyl-butanoate;
6-Chloro-5-cyano-4-[[3-[(3R)-3-hydroxybutyl]-1-methyl-2-oxo-benzimidazol-5-yl]amino]-N-methyl-pyridine-2-carboxamide;
Methyl 4-[6-[[2-chloro-3-cyano-6-(3-methyl-1,2,4-oxadiazol-5-yl)-4-pyridyl]amino]-3-methyl-2-oxo-benzimidazol-1-yl]-2-methyl-butanoate;
Methyl (2S)-2-amino-4-[6-[(2-chloro-3-cyano-4-pyridyl)amino]-3-methyl-2-oxo-benzimidazol-1-yl]butanoate;
Methyl 4-[6-[[2-chloro-3-cyano-6-(methylcarbamoyl)-4-pyridyl]amino]-3-methyl-2-oxo-benzimidazol-1-yl]-2-methyl-butanoate;
Methyl 4-[6-[[6-(but-3-ynylcarbamoyl)-2-chloro-3-cyano-4-pyridyl]amino]-3-methyl-2-oxo-benzimidazol-1-yl]-2-methyl-butanoate;
Methyl 4-[6-[[2-chloro-3-cyano-6-(dimethylcarbamoyl)-4-pyridyl]amino]-3-methyl-2-oxo-benzimidazol-1-yl]-2-methyl-butanoate;
6-Chloro-5-cyano-N-[2-(dimethylamino)ethyl]-4-[(1,3-dimethyl-2-oxo-benzimidazol-5-yl)amino]pyridine-2-carboxamide;
Ethyl 7-[[3-(4-methoxy-3-methyl-4-oxo-butyl)-1-methyl-2-oxo-benzimidazol-5-yl]amino]pyrazolo[1,5-a]pyrimidine-5-carboxylate;
Methyl 4-[6-[(2-chloro-3-cyano-4-pyridyl)amino]-3-methyl-2-oxo-benzimidazol-1-yl]-2-hydroxy-butanoate;

2-Chloro-4-[[3-(2,3-dihydroxy-3-methyl-butyl)-1-methyl-2-oxo-benzimidazol-5-yl]amino]pyridine-3-carbonitrile;
Methyl 4-[6-[(2-chloro-3-cyano-4-pyridyl)amino]-3-methyl-2-oxo-benzimidazol-1-yl]-2-methoxy-butanoate;
Methyl 4-[6-[(2-chloro-3-cyano-4-pyridyl)amino]-3-methyl-2-oxo-benzimidazol-1-yl]-2-ethoxy-butanoate;
Methyl 4-[6-[(2-chloro-3-cyano-4-pyridyl)amino]-3-methyl-2-oxo-benzimidazol-1-yl]butanoate;
methyl 4-[6-[(2-chloro-3-cyano-4-pyridyl)amino]-3-methyl-2-oxo-benzimidazol-1-yl]-2-(cyclopropylmethoxy)butanoate;
2-chloro-4-[[3-(2-hydroxy-3-pyrazol-1-yl-propyl)-1-methyl-2-oxo-benzimidazol-5-yl]amino]pyridine-3-carbonitrile;
2-chloro-4-[[3-(2-cyanobutyl)-1-methyl-2-oxo-benzimidazol-5-yl]amino]pyridine-3-carbonitrile;
2-chloro-4-[[3-[(3S)-3-hydroxybutyl]-1-methyl-2-oxo-benzimidazol-5-yl]amino]pyridine-3-carbonitrile;
Methyl 2-[[6-[(2-chloro-3-cyano-4-pyridyl)amino]-3-methyl-2-oxo-benzimidazol-1-yl]methyl]cyclopentanecarboxylate;
Methyl (2R)-2-amino-4-[6-[(2-chloro-3-cyano-4-pyridyl)amino]-3-methyl-2-oxo-benzimidazol-1-yl]butanoate;
N-[3-[6-[(2-Chloro-3-cyano-4-pyridyl)amino]-3-methyl-2-oxo-benzimidazol-1-yl]-1-methyl-propyl]acetamide;
5-Chloro-N-ethyl-4-[[3-(3-hydroxy-3-methyl-butyl)-1-methyl-2-oxo-benzimidazol-5-yl]amino]pyridine-2-carboxamide;
5-[[5-Chloro-2-(3,5-dimethylpyrazol-1-yl)pyrimidin-4-yl]amino]-3-(3-hydroxy-3-methyl-butyl)-1-methyl-benzimidazol-2-one;
5-((5-chloro-2-((3R,5S)-4,4-difluoro-3,5-dimethylpiperidin-1-yl)pyrimidin-4-yl)amino)-3-(3-hydroxy-3-methylbutyl)-1-methyl-1,3-dihydro-2H-benzo[d]imidazol-2-one;
ethyl 1-(5-chloro-4-((3-(3-hydroxy-3-methylbutyl)-1-methyl-2-oxo-2,3-dihydro-1H-benzo[d]imidazol-5-yl)amino)pyrimidin-2-yl)-1H-pyrazole-4-carboxylate;
ethyl 1-(5-chloro-4-((3-(3-hydroxy-3-methylbutyl)-1-methyl-2-oxo-2,3-dihydro-1H-benzo[d]imidazol-5-yl)amino)pyrimidin-2-yl)-3,5-dimethyl-1H-pyrazole-4-carboxylate;
5-((5-chloro-2-(3-(trifluoromethyl)-1H-pyrazol-1-yl)pyrimidin-4-yl)amino)-3-(3-hydroxy-3-methylbutyl)-1-methyl-1,3-dihydro-2H-benzo[d]imidazol-2-one;
5-((5-chloro-2-(3,5-dimethyl-1H-pyrazol-1-yl)pyrimidin-4-yl)amino)-3-(3,5-dihydroxy-3-methylpentyl)-1-methyl-1,3-dihydro-2H-benzo[d]imidazol-2-one;
5-((5-chloro-2-(3,5-dimethyl-1H-pyrazol-1-yl)pyrimidin-4-yl)amino)-3-(3-hydroxy-3-methylpentyl)-1-methyl-1,3-dihydro-2H-benzo[d]imidazol-2-one;
5-((5-chloro-2-(dimethylamino)pyrimidin-4-yl)amino)-3-(3-hydroxy-3-methylbutyl)-1-methyl-1,3-dihydro-2H-benzo[d]imidazol-2-one;
5-((5-chloro-2-(3,5-dimethyl-1H-pyrazol-1-yl)pyrimidin-4-yl)amino)-1-methyl-1,3-dihydro-2H-benzo[d]imidazol-2-one;
1-(5-chloro-4-((3-(3-hydroxy-4-methoxy-3-methylbutyl)-1-methyl-2-oxo-2,3-dihydro-1H-benzo[d]imidazol-5-yl)amino)pyrimidin-2-yl)-N, N-dimethylpiperidine-4-carboxamide;
5-((5-chloro-2-(3,5-dimethyl-1H-pyrazol-1-yl)pyrimidin-4-yl)amino)-3-(3-hydroxy-4-methoxy-3-methylbutyl)-1-methyl-1,3-dihydro-2H-benzo[d]imidazol-2-one;
1-(5-chloro-4-((3-(3,5-dihydroxy-3-methylpentyl)-1-methyl-2-oxo-2,3-dihydro-1H-benzo[d]imidazol-5-yl)amino)pyrimidin-2-yl)-N, N-dimethylpiperidine-4-carboxamide;
1-(5-chloro-4-((3-(3-hydroxy-3-methylpentyl)-1-methyl-2-oxo-2,3-dihydro-1H-benzo[d]imidazol-5-yl)amino)pyrimidin-2-yl)-N, N-dimethylpiperidine-4-carboxamide;
5-((5-chloro-2-(1H-pyrazol-1-yl)pyrimidin-4-yl)amino)-3-(3-hydroxy-3-methylbutyl)-1-methyl-1,3-dihydro-2H-benzo[d]imidazol-2-one;
5-((5-chloro-2-(4-chloro-3,5-dimethyl-1H-pyrazol-1-yl)pyrimidin-4-yl)amino)-3-(3-hydroxy-3-methylbutyl)-1-methyl-1,3-dihydro-2H-benzo[d]imidazol-2-one;
6-(3,5-dimethyl-1H-pyrazol-1-yl)-4-((3-(3-hydroxy-3-methylbutyl)-1-methyl-2-oxo-2,3-dihydro-1H-benzo[d]imidazol-5-yl)amino)nicotinonitrile;
5-((5-chloro-2-(3,5-dimethyl-1H-pyrazol-1-yl)-6-methylpyrimidin-4-yl)amino)-3-(3-hydroxy-3-methylbutyl)-1-methyl-1,3-dihydro-2H-benzo[d]imidazol-2-one;
5-((5-bromo-2-(3,5-dimethyl-1H-pyrazol-1-yl)pyrimidin-4-yl)amino)-3-(3-hydroxy-3-methylbutyl)-1-methyl-1,3-dihydro-2H-benzo[d]imidazol-2-one;
5-((5-chloro-2-(3-methyl-1H-pyrazol-1-yl)pyrimidin-4-yl)amino)-3-(3-hydroxy-3-methylbutyl)-1-methyl-1,3-dihydro-2H-benzo[d]imidazol-2-one;
5-((5-chloro-2-(5-methyl-1H-pyrazol-1-yl)pyrimidin-4-yl)amino)-3-(3-hydroxy-3-methylbutyl)-1-methyl-1,3-dihydro-2H-benzo[d]imidazol-2-one;
5-((5-chloro-2-(1H-indazol-3-yl)pyrimidin-4-yl)amino)-3-(3-hydroxy-3-methylbutyl)-1-methyl-1,3-dihydro-2H-benzo[d]imidazol-2-one;
5-((5-chloro-2-(1H-indazol-1-yl)pyrimidin-4-yl)amino)-3-(3-hydroxy-3-methylbutyl)-1-methyl-1,3-dihydro-2H-benzo[d]imidazol-2-one;
2-chloro-4-((3-(2-(1-hydroxycyclobutyl)ethyl)-1-methyl-2-oxo-2,3-dihydro-1H-benzo[d]imidazol-5-yl)amino)nicotinonitrile;
2-chloro-4-((1-methyl-3-(2-(methylsulfonyl)ethyl)-2-oxo-2,3-dihydro-1H-benzo[d]imidazol-5-yl)amino)nicotinonitrile;
2-chloro-4-((1-methyl-2-oxo-3-(3-oxopentyl)-2,3-dihydro-1H-benzo[d]imidazol-5-yl)amino)nicotinonitrile;
2-chloro-4-((1-methyl-3-((2-methyltetrahydrofuran-3-yl)methyl)-2-oxo-2,3-dihydro-1H-benzo[d]imidazol-5-yl)amino)nicotinonitrile;
2-chloro-4-((1-methyl-3-(2-(2-methyl-1,3-dioxolan-2-yl)ethyl)-2-oxo-2,3-dihydro-1H-benzo[d]imidazol-5-yl)amino)nicotinonitrile;
tert-butyl 2-((6-((2-chloro-3-cyanopyridin-4-yl)amino)-3-methyl-2-oxo-2,3-dihydro-1H-benzo[d]imidazol-1-yl)methyl)azetidine-1-carboxylate;
5-((6-((5-chloro-2-(2,2,6,6-tetramethylmorpholino)pyrimidin-4-yl)amino)-3-methyl-2-oxo-2,3-dihydro-1H-benzo[d]imidazol-1-yl)methyl)-5-(2-hydroxypropan-2-yl)-3-methyloxazolidin-2-one;
1-(5-chloro-4-((3-(3-hydroxy-3-methylbutyl)-1-methyl-2-oxo-2,3-dihydro-1H-benzo[d]imidazol-5-yl)amino)pyrimidin-2-yl)-N, N-dimethylpiperidine-4-carboxamide;
5-((5-chloro-2-(piperidin-1-yl)pyrimidin-4-yl)amino)-3-(3-hydroxy-3-methylbutyl)-1-methyl-1,3-dihydro-2H-benzo[d]imidazol-2-one;
5-((5-chloro-2-((3S,5R)-3,5-dimethylpiperidin-1-yl)pyrimidin-4-yl)amino)-3-(3-hydroxy-3-methylbutyl)-1-methyl-1,3-dihydro-2H-benzo[d]imidazol-2-one;
5-((5-chloro-2-(isopropylamino)pyrimidin-4-yl)amino)-3-(3-hydroxy-3-methylbutyl)-1-methyl-1,3-dihydro-2H-benzo[d]imidazol-2-one;

5-((5-chloro-2-(3-methylpiperidin-1-yl)pyrimidin-4-yl) amino)-3-(3-hydroxy-3-methylbutyl)-1-methyl-1,3-dihydro-2H-benzo[d]imidazol-2-one;

5-((5-chloro-2-(3-(trifluoromethyl) piperidin-1-yl)pyrimidin-4-yl)amino)-3-(3-hydroxy-3-methylbutyl)-1-methyl-1,3-dihydro-2H-benzo[d]imidazol-2-one;

5-((5-chloro-2-(ethyl(methyl)amino)pyrimidin-4-yl) amino)-3-(3-hydroxy-3-methylbutyl)-1-methyl-1,3-dihydro-2H-benzo[d]imidazol-2-one;

5-((5-chloro-2-((2R,6S)-2,6-dimethylmorpholino)pyrimidin-4-yl)amino)-3-(3-hydroxy-3-methylbutyl)-1-methyl-1,3-dihydro-2H-benzo[d]imidazol-2-one;

5-((5-chloro-2-(2,2-dimethyl-6-(trifluoromethyl)morpholino)pyrimidin-4-yl)amino)-3-(3-hydroxy-3-methylbutyl)-1-methyl-1,3-dihydro-2H-benzo[d]imidazol-2-one;

5-((6-((5-chloro-2-((2R,6S)-2,6-dimethylmorpholino)pyrimidin-4-yl)amino)-3-methyl-2-oxo-2,3-dihydro-1H-benzo[d]imidazol-1-yl)methyl)-5-ethyl-3-methyloxazolidin-2-one;

5-((6-((5-chloro-2-(3-(trifluoromethyl)-1H-pyrazol-1-yl)pyrimidin-4-yl)amino)-3-methyl-2-oxo-2,3-dihydro-1H-benzo[d]imidazol-1-yl)methyl)-5-ethyl-3-methyloxazolidin-2-one;

5-((6-((5-chloro-2-((2R,6S)-2,6-dimethylmorpholino)pyrimidin-4-yl)amino)-3-methyl-2-oxo-2,3-dihydro-1H-benzo[d]imidazol-1-yl)methyl)-5-ethyloxazolidin-2-one;

5-((6-((5-chloro-2-(3-(trifluoromethyl)-1H-pyrazol-1-yl)pyrimidin-4-yl)amino)-3-methyl-2-oxo-2,3-dihydro-1H-benzo[d]imidazol-1-yl)methyl)-5-ethyloxazolidin-2-one;

5-((5-chloro-2-((2R,6S)-2,6-dimethylmorpholino) pyrimidin-4-yl)amino)-6-fluoro-3-(3-hydroxy-3-methylbutyl)-1-methyl-1,3-dihydro-2H-benzo[d]imidazol-2-one;

5-((5-chloro-2-((3S,5R)-3,5-dimethylpiperidin-1-yl)pyrimidin-4-yl)amino)-6-fluoro-3-(3-hydroxy-3-methylbutyl)-1-methyl-1,3-dihydro-2H-benzo[d]imidazol-2-one;

5-((5-chloro-2-(3-(trifluoromethyl)-1H-pyrazol-1-yl)pyrimidin-4-yl)amino)-6-fluoro-3-(3-hydroxy-3-methylbutyl)-1-methyl-1,3-dihydro-2H-benzo[d]imidazol-2-one;

5-((5-chloro-2-(4-(trifluoromethyl)-1H-pyrazol-1-yl)pyrimidin-4-yl)amino)-3-(3-hydroxy-3-methylbutyl)-1-methyl-1,3-dihydro-2H-benzo[d]imidazol-2-one;

5-((5-chloro-2-morpholinopyrimidin-4-yl)amino)-3-(3-hydroxy-3-methylbutyl)-1-methyl-1,3-dihydro-2H-benzo[d]imidazol-2-one;

5-((5-chloro-2-((2S,6R)-2-cyclopropyl-6-methylmorpholino)pyrimidin-4-yl)amino)-3-(3-hydroxy-3-methylbutyl)-1-methyl-1,3-dihydro-2H-benzo[d]imidazol-2-one;

5-((5-chloro-2-((2R,6R)-2-cyclopropyl-6-methylmorpholino)pyrimidin-4-yl)amino)-3-(3-hydroxy-3-methylbutyl)-1-methyl-1,3-dihydro-2H-benzo[d]imidazol-2-one;

5-((5-chloro-2-(methylthio)pyrimidin-4-yl)amino)-3-(3-hydroxy-3-methylbutyl)-1-methyl-1,3-dihydro-2H-benzo[d]imidazol-2-one;

5-((2-bromo-5-chloropyridin-4-yl)amino)-3-(3-hydroxy-3-methylbutyl)-1-methyl-1,3-dihydro-2H-benzo[d]imidazol-2-one;

2-chloro-4-((3-((5-ethyl-2-oxooxazolidin-5-yl)methyl)-1-methyl-2-oxo-2,3-dihydro-1H-benzo[d]imidazol-5-yl) amino)nicotinonitrile;

4-chloro-6-((6-fluoro-3-(3-hydroxy-3-methylbutyl)-1-methyl-2-oxo-2,3-dihydro-1H-benzo[d]imidazol-5-yl) amino)pyrimidine-5-carbonitrile;

2-chloro-4-((3-((5-ethyl-3-methyl-2-oxooxazolidin-5-yl) methyl)-1-methyl-2-oxo-2,3-dihydro-1H-benzo[d]imidazol-5-yl)amino)nicotinonitrile;

2-chloro-4-((6-fluoro-3-(3-hydroxy-3-methylbutyl)-1-methyl-2-oxo-2,3-dihydro-1H-benzo[d]imidazol-5-yl) amino)nicotinonitrile;

5-((2,5-dichloropyrimidin-4-yl)amino)-3-(3-hydroxy-3-methylpentyl)-1-methyl-1,3-dihydro-2H-benzo[d]imidazol-2-one;

5-((5-chloropyrazolo[1,5-a]pyrimidin-7-yl)amino)-3-(3-hydroxy-3-methylbutyl)-1-methyl-1,3-dihydro-2H-benzo[d]imidazol-2-one;

3-(3-hydroxy-3-methylbutyl)-1-methyl-5-((2,5,6-trichloropyrimidin-4-yl)amino)-1,3-dihydro-2H-benzo[d]imidazol-2-one;

(R)-6-chloro-5-cyano-4-((3-(3-methoxybutyl)-1-methyl-2-oxo-2,3-dihydro-1H-benzo[d]imidazol-5-yl)amino)-N-methylpicolinamide;

4-((3-(3-acetamido-3-methylbutyl)-1-methyl-2-oxo-2,3-dihydro-1H-benzo[d]imidazol-5-yl)amino)-6-chloro-5-cyano-N-methylpicolinamide;

5-((5,6-dichloropyrimidin-4-yl)amino)-3-(3-hydroxy-3-methylbutyl)-1-methyl-1,3-dihydro-2H-benzo[d]imidazol-2-one;

2-chloro-4-((3-(((1S,2S)-2-ethyl-2-hydroxycyclopentyl) methyl)-1-methyl-2-oxo-2,3-dihydro-1H-benzo[d]imidazol-5-yl)amino)nicotinonitrile;

2-chloro-4-((3-(((1S,2S)-2-hydroxy-2-methylcyclopentyl) methyl)-1-methyl-2-oxo-2,3-dihydro-1H-benzo[d]imidazol-5-yl)amino)nicotinonitrile;

5-((5-chloro-2-(1-methyl-1H-pyrazol-3-yl)pyrimidin-4-yl) amino)-3-(3-hydroxy-3-methylbutyl)-1-methyl-1,3-dihydro-2H-benzo[d]imidazol-2-one;

5-((5-chloro-2-(1,3-dimethyl-1H-pyrazol-5-yl)pyrimidin-4-yl)amino)-3-(3-hydroxy-3-methylbutyl)-1-methyl-1,3-dihydro-2H-benzo[d]imidazol-2-one;

5-((5-chloro-2-(2,4-dimethylthiazol-5-yl)pyrimidin-4-yl) amino)-3-(3-hydroxy-3-methylbutyl)-1-methyl-1,3-dihydro-2H-benzo[d]imidazol-2-one;

5-((5-chloro-2-(thiophen-2-yl)pyrimidin-4-yl)amino)-3-(3-hydroxy-3-methylbutyl)-1-methyl-1,3-dihydro-2H-benzo[d]imidazol-2-one;

5-((5-chloro-2-(1-methyl-1H-imidazol-2-yl)pyrimidin-4-yl) amino)-3-(3-hydroxy-3-methylbutyl)-1-methyl-1,3-dihydro-2H-benzo[d]imidazol-2-one;

2-chloro-4-((1-methyl-2-oxo-3-((4-(2,2,2-trifluoroethyl) morpholin-3-yl)methyl)-2,3-dihydro-1H-benzo[d]imidazol-5-yl)amino)nicotinonitrile;

2-chloro-4-((3-(2-(dimethylamino)butyl)-1-methyl-2-oxo-2,3-dihydro-1H-benzo[d]imidazol-5-yl)amino)nicotinonitrile;

(S)-2-chloro-4-((3-((1-ethylpyrrolidin-2-yl)methyl)-1-methyl-2-oxo-2,3-dihydro-1H-benzo[d]imidazol-5-yl) amino)nicotinonitrile;

2-chloro-4-((1-methyl-2-oxo-3-((1-(2,2,2-trifluoroethyl)piperidin-2-yl)methyl)-2,3-dihydro-1H-benzo[d]imidazol-5-yl)amino)nicotinonitrile;

(S)-2-chloro-4-((3-((1-(2-fluoroethyl)pyrrolidin-2-yl) methyl)-1-methyl-2-oxo-2,3-dihydro-1H-benzo[d]imidazol-5-yl)amino)nicotinonitrile;

(S)-2-chloro-4-((3-((1-(2-hydroxyethyl)pyrrolidin-2-yl) methyl)-1-methyl-2-oxo-2,3-dihydro-1H-benzo[d]imidazol-5-yl)amino)nicotinonitrile;

2-chloro-4-((3-(((2R,4S)-4-fluoro-1-(2,2,2-trifluoroethyl) pyrrolidin-2-yl)methyl)-1-methyl-2-oxo-2,3-dihydro-1H-benzo[d]imidazol-5-yl)amino)nicotinonitrile;

2-chloro-4-((3-(3-(ethylamino)butyl)-1-methyl-2-oxo-2,3-dihydro-1H-benzo[d]imidazol-5-yl)amino)nicotinonitrile;

2-chloro-4-((3-(3-hydroxy-3-methylhex-5-yn-1-yl)-1-methyl-2-oxo-2,3-dihydro-1H-benzo[d]imidazol-5-yl)amino)nicotinonitrile;

2-chloro-4-((3-(3-hydroxy-4-methoxy-3-methylbutyl)-1-methyl-2-oxo-2,3-dihydro-1H-benzo[d]imidazol-5-yl)amino)nicotinonitrile;

2-chloro-4-((3-(3-hydroxy-3-methylpentyl)-1-methyl-2-oxo-2,3-dihydro-1H-benzo[d]imidazol-5-yl)amino)nicotinonitrile;

2-chloro-4-((1-methyl-2-oxo-3-(4,4,4-trifluoro-3-hydroxy-3-methylbutyl)-2,3-dihydro-1H-benzo[d]imidazol-5-yl)amino)nicotinonitrile;

2-chloro-4-((3-(3-hydroxy-2,3-dimethylbutyl)-1-methyl-2-oxo-2,3-dihydro-1H-benzo[d]imidazol-5-yl)amino)nicotinonitrile;

2-chloro-4-((3-(3-hydroxy-3,4-dimethylpentyl)-1-methyl-2-oxo-2,3-dihydro-1H-benzo[d]imidazol-5-yl)amino)nicotinonitrile;

5-((5-chloro-2-(2,2,6,6-tetramethylmorpholino)pyrimidin-4-yl)amino)-3-(3-hydroxy-3-methylbutyl)-1-methyl-1,3-dihydro-2H-benzo[d]imidazol-2-one;

5-((5-chloro-2-(2-(trifluoromethyl)morpholino)pyrimidin-4-yl)amino)-3-(3-hydroxy-3-methylbutyl)-1-methyl-1,3-dihydro-2H-benzo[d]imidazol-2-one;

5-((3-chloro-2-fluoropyridin-4-yl)amino)-3-(3-hydroxy-3-methylbutyl)-1-methyl-1,3-dihydro-2H-benzo[d]imidazol-2-one;

5-((2,3-dichloropyridin-4-yl)amino)-3-(3-hydroxy-3-methylbutyl)-1-methyl-1,3-dihydro-2H-benzo[d]imidazol-2-one;

5-((3-bromopyridin-4-yl)amino)-3-(3-hydroxy-3-methylbutyl)-1-methyl-1,3-dihydro-2H-benzo[d]imidazol-2-one;

5-((5-chloro-2-(trifluoromethyl)pyridin-4-yl)amino)-3-(3-hydroxy-3-methylbutyl)-1-methyl-1,3-dihydro-2H-benzo[d]imidazol-2-one;

5-((3-chloropyridin-4-yl)amino)-3-(3-hydroxy-3-methylbutyl)-1-methyl-1,3-dihydro-2H-benzo[d]imidazol-2-one;

5-((5-chloro-2-(3,5-dimethyl-1H-pyrazol-1-yl)pyridin-4-yl)amino)-3-(3-hydroxy-3-methylbutyl)-1-methyl-1,3-dihydro-2H-benzo[d]imidazol-2-one;

5-((5-chloro-2-(2-oxopyrrolidin-1-yl)pyrimidin-4-yl)amino)-3-(3-hydroxy-3-methylbutyl)-1-methyl-1,3-dihydro-2H-benzo[d]imidazol-2-one;

(S)-5-((5-chloro-2-(2-(hydroxymethyl)pyrrolidin-1-yl)pyrimidin-4-yl)amino)-3-(3-hydroxy-3-methylbutyl)-1-methyl-1,3-dihydro-2H-benzo[d]imidazol-2-one;

(S)-7-((3-(3-hydroxy-3-methylbutyl)-1-methyl-2-oxo-2,3-dihydro-1H-benzo[d]imidazol-5-yl)amino)-5-(2-(hydroxymethyl)pyrrolidin-1-yl)pyrazolo[1,5-a]pyrimidine-3-carbonitrile;

2-chloro-4-((1-methyl-3-(2-(2-methyloxiran-2-yl)ethyl)-2-oxo-2,3-dihydro-1H-benzo[d]imidazol-5-yl)amino)nicotinonitrile;

2-chloro-4-((3-(2-(3,5-dimethyl-2-oxooxazolidin-5-yl)ethyl)-1-methyl-2-oxo-2,3-dihydro-1H-benzo[d]imidazol-5-yl)amino)nicotinonitrile;

2-chloro-4-((1-methyl-3-((5-methyl-2-oxooxazolidin-4-yl)methyl)-2-oxo-2,3-dihydro-1H-benzo[d]imidazol-5-yl)amino)nicotinonitrile;

(S)-5-((5-chloro-2-(2,2,6,6-tetramethylmorpholino)pyrimidin-4-yl)amino)-1-methyl-3-((1-(2,2,2-trifluoroethyl)pyrrolidin-2-yl)methyl)-1,3-dihydro-2H-benzo[d]imidazol-2-one;

5-((5-chloro-2-((3R,5S)-4,4-difluoro-3,5-dimethylpiperidin-1-yl)pyrimidin-4-yl)amino)-1,3-bis(3-hydroxy-3-methylbutyl)-1,3-dihydro-2H-benzo[d]imidazol-2-one;

5-((5-chloro-2-(2,2,6,6-tetramethylmorpholino)pyrimidin-4-yl)amino)-1,3-bis(3-hydroxy-3-methylbutyl)-1,3-dihydro-2H-benzo[d]imidazol-2-one;

5-((5-chloro-2-(4,4-difluoropiperidin-1-yl)pyrimidin-4-yl)amino)-3-(3-hydroxy-3-methylbutyl)-1-methyl-1,3-dihydro-2H-benzo[d]imidazol-2-one;

5-((5-chloro-2-(3,3-difluoro-8-azabicyclo[3.2.1]octan-8-yl)pyrimidin-4-yl)amino)-3-(3-hydroxy-3-methylbutyl)-1-methyl-1,3-dihydro-2H-benzo[d]imidazol-2-one;

5-((5-chloro-2-(2,2-difluoro-7-azaspiro[3.5]nonan-7-yl)pyrimidin-4-yl)amino)-3-(3-hydroxy-3-methylbutyl)-1-methyl-1,3-dihydro-2H-benzo[d]imidazol-2-one;

5-((5-chloro-2-(4-(trifluoromethyl)piperidin-1-yl)pyrimidin-4-yl)amino)-3-(3-hydroxy-3-methylbutyl)-1-methyl-1,3-dihydro-2H-benzo[d]imidazol-2-one;

5-((5-chloro-2-(4,4-difluoropiperidin-1-yl)pyridin-4-yl)amino)-3-(3-hydroxy-3-methylbutyl)-1-methyl-1,3-dihydro-2H-benzo[d]imidazol-2-one;

5-((5-chloro-2-((2R,6S)-2,6-dimethylmorpholino)pyridin-4-yl)amino)-3-(3-hydroxy-3-methylbutyl)-1-methyl-1,3-dihydro-2H-benzo[d]imidazol-2-one;

1-(5-chloro-4-((3-(3-hydroxy-3-methylbutyl)-1-methyl-2-oxo-2,3-dihydro-1H-benzo[d]imidazol-5-yl)amino)pyridin-2-yl)-N,N-dimethylpiperidine-4-carboxamide;

(R)-2-chloro-4-((3-(3-hydroxybutyl)-1-methyl-2-oxo-2,3-dihydro-1H-benzo[d]imidazol-5-yl)amino)nicotinonitrile;

(S)-2-chloro-4-((3-((1-(2,2-difluoroethyl)pyrrolidin-2-yl)methyl)-1-methyl-2-oxo-2,3-dihydro-1H-benzo[d]imidazol-5-yl)amino)nicotinonitrile;

5-((5-chloro-2-(4,4-difluoro-3-(hydroxymethyl)piperidin-1-yl)pyrimidin-4-yl)amino)-3-(3-hydroxy-3-methylbutyl)-1-methyl-1,3-dihydro-2H-benzo[d]imidazol-2-one;

5-((5-chloro-2-(4,4-difluoro-3-(methoxymethyl) piperidin-1-yl)pyrimidin-4-yl)amino)-3-(3-hydroxy-3-methylbutyl)-1-methyl-1,3-dihydro-2H-benzo[d]imidazol-2-one;

5-((5-chloro-2-(4,4-difluoro-3-methylpiperidin-1-yl)pyrimidin-4-yl)amino)-3-(3-hydroxy-3-methylbutyl)-1-methyl-1,3-dihydro-2H-benzo[d]imidazol-2-one;

5-((5-chloro-2-((3R,4S)-3,4-difluoropyrrolidin-1-yl)pyrimidin-4-yl)amino)-3-(3-hydroxy-3-methylbutyl)-1-methyl-1,3-dihydro-2H-benzo[d]imidazol-2-one;

5-((5-chloro-2-((3S,5R)-3,4,5-trimethylpiperazin-1-yl)pyrimidin-4-yl)amino)-3-(3-hydroxy-3-methylbutyl)-1-methyl-1,3-dihydro-2H-benzo[d]imidazol-2-one;

5-((2-((1R,5S)-8-azabicyclo[3.2.1]octan-8-yl)-5-chloropyrimidin-4-yl)amino)-3-(3-hydroxy-3-methylbutyl)-1-methyl-1,3-dihydro-2H-benzo[d]imidazol-2-one;

5-((2-((1R,5S)-3-azabicyclo[3.2.1]octan-3-yl)-5-chloropyrimidin-4-yl)amino)-3-(3-hydroxy-3-methylbutyl)-1-methyl-1,3-dihydro-2H-benzo[d]imidazol-2-one;

5-((5-chloro-2-((3aR,7aS)-octahydro-2H-isoindol-2-yl)pyrimidin-4-yl)amino)-3-(3-hydroxy-3-methylbutyl)-1-methyl-1,3-dihydro-2H-benzo[d]imidazol-2-one;

5-((5-chloro-2-((3R,4S)-3,4-dimethylpyrrolidin-1-yl)pyrimidin-4-yl)amino)-3-(3-hydroxy-3-methylbutyl)-1-methyl-1,3-dihydro-2H-benzo[d]imidazol-2-one;

6-((5-chloro-2-(2,2,6,6-tetramethylmorpholino)pyrimidin-4-yl)amino)-1,3-bis(3-hydroxy-3-methylbutyl)-1,3-dihydro-2H-imidazo[4,5-b]pyridin-2-one;

6-((5-chloro-2-((3R,5S)-4,4-difluoro-3,5-dimethylpiperidin-1-yl)pyrimidin-4-yl)amino)-1,3-bis(3-hydroxy-3-methylbutyl)-1,3-dihydro-2H-imidazo[4,5-b]pyridin-2-one;

5-((5-chloro-2-(8,8-difluoro-3-azabicyclo[3.2.1]octan-3-yl)pyrimidin-4-yl)amino)-3-(3-hydroxy-3-methylbutyl)-1-methyl-1,3-dihydro-2H-benzo[d]imidazol-2-one;

5-((2-((1r,3r,5r,7r)-2-azaadamantan-2-yl)-5-chloropyrimidin-4-yl)amino)-3-(3-hydroxy-3-methylbutyl)-1-methyl-1,3-dihydro-2H-benzo[d]imidazol-2-one;

4-chloro-6-((5-chloro-2-(2,2,6,6-tetramethylmorpholino)pyrimidin-4-yl)amino)-1,3-bis(3-hydroxy-3-methylbutyl)-1,3-dihydro-2H-benzo[d]imidazol-2-one;

5-((5-chloro-2-(3-(methoxymethyl) piperidin-1-yl)pyrimidin-4-yl)amino)-3-(3-hydroxy-3-methylbutyl)-1-methyl-1,3-dihydro-2H-benzo[d]imidazol-2-one;

5-((5-chloro-2-(6,6-difluoro-3-azabicyclo[3.1.1]heptan-3-yl)pyrimidin-4-yl)amino)-3-(3-hydroxy-3-methylbutyl)-1-methyl-1,3-dihydro-2H-benzo[d]imidazol-2-one;

5-((5-chloro-2-((3S,5R)-3-hydroxy-5-methylpiperidin-1-yl)pyrimidin-4-yl)amino)-3-(3-hydroxy-3-methylbutyl)-1-methyl-1,3-dihydro-2H-benzo[d]imidazol-2-one;

5-((5-chloro-2-((3R,5S)-3,5-dimethylazepan-1-yl)pyrimidin-4-yl)amino)-3-(3-hydroxy-3-methylbutyl)-1-methyl-1,3-dihydro-2H-benzo[d]imidazol-2-one;

5-((5-chloro-2-(3-phenylpiperidin-1-yl)pyrimidin-4-yl)amino)-3-(3-hydroxy-3-methylbutyl)-1-methyl-1,3-dihydro-2H-benzo[d]imidazol-2-one;

5-((2-(4-((1H-pyrazol-1-yl)methyl)piperidin-1-yl)-5-chloropyrimidin-4-yl)amino)-3-(3-hydroxy-3-methylbutyl)-1-methyl-1,3-dihydro-2H-benzo[d]imidazol-2-one;

5-((5-chloro-2-((3S,5R)-3,5-dimethylpiperidin-1-yl)pyridin-4-yl)amino)-3-(3-hydroxy-3-methylbutyl)-1-methyl-1,3-dihydro-2H-benzo[d]imidazol-2-one;

5-((5-chloro-2-((3R,5S)-3,5-dimethylpiperidine-1-carbonyl)pyridin-4-yl)amino)-3-(3-hydroxy-3-methylbutyl)-1-methyl-1,3-dihydro-2H-benzo[d]imidazol-2-one;

5-((5-chloro-2-((3S,5R)-4,4-difluoro-3,5-dimethylpiperidine-1-carbonyl)pyridin-4-yl)amino)-3-(3-hydroxy-3-methylbutyl)-1-methyl-1,3-dihydro-2H-benzo[d]imidazol-2-one;

5-((5-chloro-2-((3S,5R)-4,4-difluoro-3,5-dimethylpiperidin-1-yl)pyrimidin-4-yl)amino)-1-(2-(dimethylamino)ethyl)-3-(3-hydroxy-3-methylbutyl)-1,3-dihydro-2H-benzo[d]imidazol-2-one;

5-((5-chloro-2-((3S,5R)-4,4-difluoro-3,5-dimethylpiperidin-1-yl)pyrimidin-4-yl)amino)-3-(3-hydroxy-3-methylbutyl)-1-(2-morpholinoethyl)-1,3-dihydro-2H-benzo[d]imidazol-2-one;

ethyl (E)-4-(5-((5-chloro-2-((3S,5R)-4,4-difluoro-3,5-dimethylpiperidin-1-yl)pyrimidin-4-yl)amino)-3-(3-hydroxy-3-methylbutyl)-2-oxo-2,3-dihydro-1H-benzo[d]imidazol-1-yl)but-2-enoate;

5-((5-Chloro-2-(2,2,2-trifluoroethoxy)pyrimidin-4-yl)amino)-3-(3-hydroxy-3-methylbutyl)-1-methyl-1,3-dihydro-2H-benzo[d]imidazol-2-one;

5-[[5-chloro-2-[(3S,5R)-4,4-difluoro-3,5-dimethyl-1-piperidyl]pyrimidin-4-yl]amino]-1-(2-hydroxyethyl)-3-(3-hydroxy-3-methyl-butyl)benzimidazol-2-one;

5-((5-chloro-2-((3S,5R)-4,4-difluoro-3,5-dimethylpiperidin-1-yl)pyrimidin-4-yl)amino)-1-(2,2-dimethoxyethyl)-3-(3-hydroxy-3-methylbutyl)-1,3-dihydro-2H-benzo[d]imidazol-2-one;

1-(5-chloro-4-((3-(3-hydroxy-3-methylbutyl)-1-methyl-2-oxo-2,3-dihydro-1H-benzo[d]imidazol-5-yl)amino)pyrimidin-2-yl)piperidine-4-carbonitrile;

1-(5-chloro-4-((3-(3-hydroxy-3-methylbutyl)-1-methyl-2-oxo-2,3-dihydro-1H-benzo[d]imidazol-5-yl)amino)pyrimidin-2-yl)piperidine-3-carbonitrile;

5-((5-chloro-2-(4-(morpholinomethyl)piperidin-1-yl)pyrimidin-4-yl)amino)-3-(3-hydroxy-3-methylbutyl)-1-methyl-1,3-dihydro-2H-benzo[d]imidazol-2-one;

5-((5-chloro-2-(3-(morpholinomethyl)piperidin-1-yl)pyrimidin-4-yl)amino)-3-(3-hydroxy-3-methylbutyl)-1-methyl-1,3-dihydro-2H-benzo[d]imidazol-2-one;

5-((5-chloro-2-(2-methyl-2,4,5,7-tetrahydro-6H-pyrazolo[3,4-c]pyridin-6-yl)pyrimidin-4-yl)amino)-3-(3-hydroxy-3-methylbutyl)-1-methyl-1,3-dihydro-2H-benzo[d]imidazol-2-one;

5-((5-chloro-2-(1-methyl-1,4,5,7-tetrahydro-6H-pyrazolo[3,4-c]pyridin-6-yl)pyrimidin-4-yl)amino)-3-(3-hydroxy-3-methylbutyl)-1-methyl-1,3-dihydro-2H-benzo[d]imidazol-2-one;

5-((5-chloro-2-(3-(hydroxymethyl)piperidin-1-yl)pyrimidin-4-yl)amino)-3-(3-hydroxy-3-methylbutyl)-1-methyl-1,3-dihydro-2H-benzo[d]imidazol-2-one;

5-((5-chloro-2-(4-morpholinopiperidin-1-yl)pyrimidin-4-yl)amino)-3-(3-hydroxy-3-methylbutyl)-1-methyl-1,3-dihydro-2H-benzo[d]imidazol-2-one;

5-((2-(4-(1H-pyrazol-1-yl)piperidin-1-yl)-5-chloropyrimidin-4-yl)amino)-3-(3-hydroxy-3-methylbutyl)-1-methyl-1,3-dihydro-2H-benzo[d]imidazol-2-one; or 5-((5-chloro-2-(2-(hydroxymethyl)morpholino)pyrimidin-4-yl)amino)-3-(3-hydroxy-3-methylbutyl)-1-methyl-1,3-dihydro-2H-benzo[d]imidazol-2-one.

Particular compounds of the present invention include any of the compounds exemplified in the present application, or a pharmaceutically acceptable salt or solvate thereof, and, in particular, any of the following:

6-Chloro-5-cyano-4-[[3-(3-hydroxy-3-methyl-butyl)-1-methyl-2-oxo-benzimidazol-5-yl]amino]-N-methyl-pyridine-2-carboxamide;

2-chloro-4-[[3-(3-hydroxy-3-methyl-butyl)-1-methyl-2-oxo-benzimidazol-5-yl]amino]-6-methyl-pyridine-3-carbonitrile;

6-chloro-5-cyano-4-[(1,3-dimethyl-2-oxo-benzimidazol-5-yl)amino]pyridine-2-carboxylic acid;

6-chloro-5-cyano-N-methyl-4-[[1-methyl-2-oxo-3-[(3S)-3-pyrazol-1-ylbutyl]benzimidazol-5-yl]amino]pyridine-2-carboxamide;

6-chloro-5-cyano-4-[[3-[(3R)-3-hydroxybutyl]-1-methyl-2-oxo-benzimidazol-5-yl]amino]pyridine-2-carboxylic acid;

6-chloro-5-cyano-N-methyl-4-[(1-methyl-2-oxo-3H-benzimidazol-5-yl)amino]pyridine-2-carboxamide;

6-chloro-5-cyano-4-[[3-(3-hydroxy-3-methyl-butyl)-2-oxo-1-(tetrahydropyran-4-ylmethyl)benzimidazol-5-yl]amino]-N-methyl-pyridine-2-carboxamide:

Ethyl 7-[[3-(3-hydroxy-3-methyl-butyl)-1-methyl-2-oxo-benzimidazol-5-yl]amino]-pyrazolo[1,5-a]pyrimidine-5-carboxylate;

2-chloro-4-[[3-(3-hydroxy-3-methyl-butyl)-1-methyl-2-oxo-benzimidazol-5-yl]amino]pyridine-3-carbonitrile;

Methyl 4-[6-[(2-chloro-3-cyano-4-pyridyl)amino]-3-methyl-2-oxo-benzimidazol-1-yl]-2-methyl-butanoate;

2-bromo-4-[[3-(3-hydroxy-3-methyl-butyl)-1-methyl-2-oxo-benzimidazol-5-yl]amino]pyridine-3-carbonitrile;

2-chloro-4-[[3-[(3R)-3-hydroxybutyl]-1-methyl-2-oxo-benzimidazol-5-yl]amino]-6-methyl-pyridine-3-carbonitrile;

5-[(2,5-dichloro-4-pyridyl)amino]-3-[(3R)-3-hydroxybutyl]-1-methyl-benzimidazol-2-one;
5-[(2,5-dichloropyrimidin-4-yl)amino]-3-(3-hydroxy-3-methyl-butyl)-1-methyl-benzimidazol-2-one;
Ethyl 7-[[3-[(3R)-3-hydroxybutyl]-1-methyl-2-oxo-benzimidazol-5-yl]amino]pyrazolo-[1,5-a]pyrimidine-5-carboxylate;
4-chloro-6-[[3-(3-hydroxy-3-methyl-butyl)-1-methyl-2-oxo-benzimidazol-5-yl]amino]pyrimidine-5-carbonitrile;
5-[(2,3-dichloro-4-pyridyl)amino]-3-[(3R)-3-hydroxybutyl]-1-methyl-benzimidazol-2-one;
Ethyl 3-fluoro-7-((3-(2-hydroxybutyl)-1-methyl-2-oxo-2,3-dihydro-1H-benzo[d]-imidazol-5-yl)amino)pyrazolo[1,5-a]pyrimidine-5-carboxylate;
Methyl 6-chloro-5-cyano-4-[[3-(4-methoxy-3-methyl-4-oxo-butyl)-1-methyl-2-oxo-benzimidazol-5-yl]amino]pyridine-2-carboxylate;
Ethyl 6-chloro-5-cyano-4-[[3-(4-methoxy-3-methyl-4-oxo-butyl)-1-methyl-2-oxo-benzimidazol-5-yl]amino]pyridine-2-carboxylate;
Isopropyl 6-chloro-5-cyano-4-[[3-(4-methoxy-3-methyl-4-oxo-butyl)-1-methyl-2-oxo-benzimidazol-5-yl]amino]pyridine-2-carboxylate;
Ethyl 6-chloro-5-cyano-4-[[3-[(3R)-3-hydroxybutyl]-1-methyl-2-oxo-benzimidazol-5-yl]amino]pyridine-2-carboxylate;
6-Chloro-5-cyano-4-[[3-(4-methoxy-3-methyl-4-oxo-butyl)-1-methyl-2-oxo-benzimidazol-5-yl]amino]pyridine-2-carboxylic acid;
Methyl 3-[6-[(2-chloro-3-cyano-4-pyridyl)amino]-3-methyl-2-oxo-benzimidazol-1-yl]-2-methyl-propanoate;
Methyl 4-[6-[(5-chloro-2-methyl-pyrimidin-4-yl)amino]-3-methyl-2-oxo-benzimidazol-1-yl]-2-methyl-butanoate;
6-Chloro-5-cyano-4-[[3-[(3R)-3-hydroxybutyl]-1-methyl-2-oxo-benzimidazol-5-yl]amino]-N-methyl-pyridine-2-carboxamide;
Methyl 4-[6-[[2-chloro-3-cyano-6-(3-methyl-1,2,4-oxadiazol-5-yl)-4-pyridyl]amino]-3-methyl-2-oxo-benzimidazol-1-yl]-2-methyl-butanoate;
Methyl (2S)-2-amino-4-[6-[(2-chloro-3-cyano-4-pyridyl)amino]-3-methyl-2-oxo-benzimidazol-1-yl]butanoate;
Methyl 4-[6-[[2-chloro-3-cyano-6-(methylcarbamoyl)-4-pyridyl]amino]-3-methyl-2-oxo-benzimidazol-1-yl]-2-methyl-butanoate;
Methyl 4-[6-[[6-(but-2-ynylcarbamoyl)-2-chloro-3-cyano-4-pyridyl]amino]-3-methyl-2-oxo-benzimidazol-1-yl]-2-methyl-butanoate;
Methyl 4-[6-[[2-chloro-3-cyano-6-(dimethylcarbamoyl)-4-pyridyl]amino]-3-methyl-2-oxo-benzimidazol-1-yl]-2-methyl-butanoate;
6-Chloro-5-cyano-N-[2-(dimethylamino)ethyl]-4-[(1,3-dimethyl-2-oxo-benzimidazol-5-yl)amino]pyridine-2-carboxamide;
Ethyl 7-[[3-(4-methoxy-3-methyl-4-oxo-butyl)-1-methyl-2-oxo-benzimidazol-5-yl]amino]pyrazolo[1,5-a]pyrimidine-5-carboxylate;
Methyl 4-[6-[(2-chloro-3-cyano-4-pyridyl)amino]-3-methyl-2-oxo-benzimidazol-1-yl]-2-hydroxy-butanoate;
2-Chloro-4-[[3-(2,3-dihydroxy-3-methyl-butyl)-1-methyl-2-oxo-benzimidazol-5-yl]amino]pyridine-3-carbonitrile;
Methyl 4-[6-[(2-chloro-3-cyano-4-pyridyl)amino]-3-methyl-2-oxo-benzimidazol-1-yl]-2-methoxy-butanoate;
Methyl 4-[6-[(2-chloro-3-cyano-4-pyridyl)amino]-3-methyl-2-oxo-benzimidazol-1-yl]-2-ethoxy-butanoate;
Methyl 4-[6-[(2-chloro-3-cyano-4-pyridyl)amino]-3-methyl-2-oxo-benzimidazol-1-yl]butanoate;
methyl 4-[6-[(2-chloro-3-cyano-4-pyridyl)amino]-3-methyl-2-oxo-benzimidazol-1-yl]-2-(cyclopropylmethoxy)butanoate;
2-chloro-4-[[3-(2-hydroxy-3-pyrazol-1-yl-propyl)-1-methyl-2-oxo-benzimidazol-5-yl]amino]pyridine-3-carbonitrile;
2-chloro-4-[[3-(2-cyanobutyl)-1-methyl-2-oxo-benzimidazol-5-yl]amino]pyridine-3-carbonitrile;
2-chloro-4-[[3-[(3S)-3-hydroxybutyl]-1-methyl-2-oxo-benzimidazol-5-yl]amino]pyridine-3-carbonitrile;
Methyl 2-[[6-[(2-chloro-3-cyano-4-pyridyl)amino]-3-methyl-2-oxo-benzimidazol-1-yl]methyl]cyclopentanecarboxylate;
Methyl (2R)-2-amino-4-[6-[(2-chloro-3-cyano-4-pyridyl)amino]-3-methyl-2-oxo-benzimidazol-1-yl]butanoate;
N-[3-[6-[(2-Chloro-3-cyano-4-pyridyl)amino]-3-methyl-2-oxo-benzimidazol-1-yl]-1-methyl-propyl]acetamide;
5-Chloro-N-ethyl-4-[[3-(3-hydroxy-3-methyl-butyl)-1-methyl-2-oxo-benzimidazol-5-yl]amino]pyridine-2-carboxamide;
5-[[5-Chloro-2-(3,5-dimethylpyrazol-1-yl)pyrimidin-4-yl]amino]-3-(3-hydroxy-3-methyl-butyl)-1-methyl-benzimidazol-2-one;
5-((5-chloro-2-((3R,5S)-4,4-difluoro-3,5-dimethylpiperidin-1-yl)pyrimidin-4-yl)amino)-3-(3-hydroxy-3-methyl-butyl)-1-methyl-1,3-dihydro-2H-benzo[d]imidazol-2-one;
ethyl 1-(5-chloro-4-((3-(3-hydroxy-3-methylbutyl)-1-methyl-2-oxo-2,3-dihydro-1H-benzo[d]imidazol-5-yl)amino)pyrimidin-2-yl)-1H-pyrazole-4-carboxylate;
ethyl 1-(5-chloro-4-((3-(3-hydroxy-3-methylbutyl)-1-methyl-2-oxo-2,3-dihydro-1H-benzo[d]imidazol-5-yl)amino)pyrimidin-2-yl)-3,5-dimethyl-1H-pyrazole-4-carboxylate;
5-((5-chloro-2-(3-(trifluoromethyl)-1H-pyrazol-1-yl)pyrimidin-4-yl)amino)-3-(3-hydroxy-3-methylbutyl)-1-methyl-1,3-dihydro-2H-benzo[d]imidazol-2-one;
5-((5-chloro-2-(3,5-dimethyl-1H-pyrazol-1-yl)pyrimidin-4-yl)amino)-3-(3,5-dihydroxy-3-methylpentyl)-1-methyl-1,3-dihydro-2H-benzo[d]imidazol-2-one;
5-((5-chloro-2-(3,5-dimethyl-1H-pyrazol-1-yl)pyrimidin-4-yl)amino)-3-(3-hydroxy-3-methylpentyl)-1-methyl-1,3-dihydro-2H-benzo[d]imidazol-2-one;
5-((5-chloro-2-(dimethylamino)pyrimidin-4-yl)amino)-3-(3-hydroxy-3-methylbutyl)-1-methyl-1,3-dihydro-2H-benzo[d]imidazol-2-one;
5-((5-chloro-2-(3,5-dimethyl-1H-pyrazol-1-yl)pyrimidin-4-yl)amino)-1-methyl-1,3-dihydro-2H-benzo[d]imidazol-2-one;
1-(5-chloro-4-((3-(3-hydroxy-4-methoxy-3-methylbutyl)-1-methyl-2-oxo-2,3-dihydro-1H-benzo[d]imidazol-5-yl)amino)pyrimidin-2-yl)-N,N-dimethylpiperidine-4-carboxamide;
5-((5-chloro-2-(3,5-dimethyl-1H-pyrazol-1-yl)pyrimidin-4-yl)amino)-3-(3-hydroxy-4-methoxy-3-methylbutyl)-1-methyl-1,3-dihydro-2H-benzo[d]imidazol-2-one;
1-(5-chloro-4-((3-(3,5-dihydroxy-3-methylpentyl)-1-methyl-2-oxo-2,3-dihydro-1H-benzo[d]imidazol-5-yl)amino)pyrimidin-2-yl)-N,N-dimethylpiperidine-4-carboxamide;
1-(5-chloro-4-((3-(3-hydroxy-3-methylpentyl)-1-methyl-2-oxo-2,3-dihydro-1H-benzo[d]imidazol-5-yl)amino)pyrimidin-2-yl)-N,N-dimethylpiperidine-4-carboxamide;
5-((5-chloro-2-(1H-pyrazol-1-yl)pyrimidin-4-yl)amino)-3-(3-hydroxy-3-methylbutyl)-1-methyl-1,3-dihydro-2H-benzo[d]imidazol-2-one;

5-((5-chloro-2-(4-chloro-3,5-dimethyl-1H-pyrazol-1-yl)pyrimidin-4-yl)amino)-3-(3-hydroxy-3-methylbutyl)-1-methyl-1,3-dihydro-2H-benzo[d]imidazol-2-one;

6-(3,5-dimethyl-1H-pyrazol-1-yl)-4-((3-(3-hydroxy-3-methylbutyl)-1-methyl-2-oxo-2,3-dihydro-1H-benzo[d]imidazol-5-yl)amino)nicotinonitrile;

5-((5-chloro-2-(3,5-dimethyl-1H-pyrazol-1-yl)-6-methylpyrimidin-4-yl)amino)-3-(3-hydroxy-3-methylbutyl)-1-methyl-1,3-dihydro-2H-benzo[d]imidazol-2-one;

5-((5-bromo-2-(3,5-dimethyl-1H-pyrazol-1-yl)pyrimidin-4-yl)amino)-3-(3-hydroxy-3-methylbutyl)-1-methyl-1,3-dihydro-2H-benzo[d]imidazol-2-one;

5-((5-chloro-2-(3-methyl-1H-pyrazol-1-yl)pyrimidin-4-yl)amino)-3-(3-hydroxy-3-methylbutyl)-1-methyl-1,3-dihydro-2H-benzo[d]imidazol-2-one;

5-((5-chloro-2-(5-methyl-1H-pyrazol-1-yl)pyrimidin-4-yl)amino)-3-(3-hydroxy-3-methylbutyl)-1-methyl-1,3-dihydro-2H-benzo[d]imidazol-2-one;

5-((5-chloro-2-(1H-indazol-3-yl)pyrimidin-4-yl)amino)-3-(3-hydroxy-3-methylbutyl)-1-methyl-1,3-dihydro-2H-benzo[d]imidazol-2-one;

5-((5-chloro-2-(1H-indazol-1-yl)pyrimidin-4-yl)amino)-3-(3-hydroxy-3-methylbutyl)-1-methyl-1,3-dihydro-2H-benzo[d]imidazol-2-one;

2-chloro-4-((3-(2-(1-hydroxycyclobutyl)ethyl)-1-methyl-2-oxo-2,3-dihydro-1H-benzo[d]imidazol-5-yl)amino)nicotinonitrile;

2-chloro-4-((1-methyl-3-(2-(methylsulfonyl)ethyl)-2-oxo-2,3-dihydro-1H-benzo[d]imidazol-5-yl)amino)nicotinonitrile;

2-chloro-4-((1-methyl-2-oxo-3-(3-oxopentyl)-2,3-dihydro-1H-benzo[d]imidazol-5-yl)amino)nicotinonitrile;

2-chloro-4-((1-methyl-3-((2-methyltetrahydrofuran-3-yl)methyl)-2-oxo-2,3-dihydro-1H-benzo[d]imidazol-5-yl)amino)nicotinonitrile;

2-chloro-4-((1-methyl-3-(2-(2-methyl-1,3-dioxolan-2-yl)ethyl)-2-oxo-2,3-dihydro-1H-benzo[d]imidazol-5-yl)amino)nicotinonitrile;

tert-butyl 2-((6-((2-chloro-3-cyanopyridin-4-yl)amino)-3-methyl-2-oxo-2,3-dihydro-1H-benzo[d]imidazol-1-yl)methyl)azetidine-1-carboxylate;

5-((6-((5-chloro-2-(2,2,6,6-tetramethylmorpholino)pyrimidin-4-yl)amino)-3-methyl-2-oxo-2,3-dihydro-1H-benzo[d]imidazol-1-yl)methyl)-5-(2-hydroxypropan-2-yl)-3-methyloxazolidin-2-one;

1-(5-chloro-4-((3-(3-hydroxy-3-methylbutyl)-1-methyl-2-oxo-2,3-dihydro-1H-benzo[d]imidazol-5-yl)amino)pyrimidin-2-yl)-N,N-dimethylpiperidine-4-carboxamide;

5-((5-chloro-2-(piperidin-1-yl)pyrimidin-4-yl)amino)-3-(3-hydroxy-3-methylbutyl)-1-methyl-1,3-dihydro-2H-benzo[d]imidazol-2-one;

5-((5-chloro-2-((3S,5R)-3,5-dimethylpiperidin-1-yl)pyrimidin-4-yl)amino)-3-(3-hydroxy-3-methylbutyl)-1-methyl-1,3-dihydro-2H-benzo[d]imidazol-2-one;

5-((5-chloro-2-(isopropylamino)pyrimidin-4-yl)amino)-3-(3-hydroxy-3-methylbutyl)-1-methyl-1,3-dihydro-2H-benzo[d]imidazol-2-one;

5-((5-chloro-2-(3-methylpiperidin-1-yl)pyrimidin-4-yl)amino)-3-(3-hydroxy-3-methylbutyl)-1-methyl-1,3-dihydro-2H-benzo[d]imidazol-2-one;

5-((5-chloro-2-(3-(trifluoromethyl)piperidin-1-yl)pyrimidin-4-yl)amino)-3-(3-hydroxy-3-methylbutyl)-1-methyl-1,3-dihydro-2H-benzo[d]imidazol-2-one;

5-((5-chloro-2-(ethyl(methyl)amino)pyrimidin-4-yl)amino)-3-(3-hydroxy-3-methylbutyl)-1-methyl-1,3-dihydro-2H-benzo[d]imidazol-2-one;

5-((5-chloro-2-((2R,6S)-2,6-dimethylmorpholino)pyrimidin-4-yl)amino)-3-(3-hydroxy-3-methylbutyl)-1-methyl-1,3-dihydro-2H-benzo[d]imidazol-2-one;

5-((5-chloro-2-(2,2-dimethyl-6-(trifluoromethyl)morpholino)pyrimidin-4-yl)amino)-3-(3-hydroxy-3-methylbutyl)-1-methyl-1,3-dihydro-2H-benzo[d]imidazol-2-one;

5-((6-((5-chloro-2-((2R,6S)-2,6-dimethylmorpholino)pyrimidin-4-yl)amino)-3-methyl-2-oxo-2,3-dihydro-1H-benzo[d]imidazol-1-yl)methyl)-5-ethyl-3-methyloxazolidin-2-one;

5-((6-((5-chloro-2-(3-(trifluoromethyl)-1H-pyrazol-1-yl)pyrimidin-4-yl)amino)-3-methyl-2-oxo-2,3-dihydro-1H-benzo[d]imidazol-1-yl)methyl)-5-ethyl-3-methyloxazolidin-2-one;

5-((6-((5-chloro-2-((2R,6S)-2,6-dimethylmorpholino)pyrimidin-4-yl)amino)-3-methyl-2-oxo-2,3-dihydro-1H-benzo[d]imidazol-1-yl)methyl)-5-ethyloxazolidin-2-one;

5-((6-((5-chloro-2-(3-(trifluoromethyl)-1H-pyrazol-1-yl)pyrimidin-4-yl)amino)-3-methyl-2-oxo-2,3-dihydro-1H-benzo[d]imidazol-1-yl)methyl)-5-ethyloxazolidin-2-one;

5-((5-chloro-2-((2R,6S)-2,6-dimethylmorpholino)pyrimidin-4-yl)amino)-6-fluoro-3-(3-hydroxy-3-methylbutyl)-1-methyl-1,3-dihydro-2H-benzo[d]imidazol-2-one;

5-((5-chloro-2-((3S,5R)-3,5-dimethylpiperidin-1-yl)pyrimidin-4-yl)amino)-6-fluoro-3-(3-hydroxy-3-methylbutyl)-1-methyl-1,3-dihydro-2H-benzo[d]imidazol-2-one;

5-((5-chloro-2-(3-(trifluoromethyl)-1H-pyrazol-1-yl)pyrimidin-4-yl)amino)-6-fluoro-3-(3-hydroxy-3-methylbutyl)-1-methyl-1,3-dihydro-2H-benzo[d]imidazol-2-one;

5-((5-chloro-2-(4-(trifluoromethyl)-1H-pyrazol-1-yl)pyrimidin-4-yl)amino)-3-(3-hydroxy-3-methylbutyl)-1-methyl-1,3-dihydro-2H-benzo[d]imidazol-2-one;

5-((5-chloro-2-morpholinopyrimidin-4-yl)amino)-3-(3-hydroxy-3-methylbutyl)-1-methyl-1,3-dihydro-2H-benzo[d]imidazol-2-one;

5-((5-chloro-2-((2S,6R)-2-cyclopropyl-6-methylmorpholino)pyrimidin-4-yl)amino)-3-(3-hydroxy-3-methylbutyl)-1-methyl-1,3-dihydro-2H-benzo[d]imidazol-2-one;

5-((5-chloro-2-((2R,6R)-2-cyclopropyl-6-methylmorpholino)pyrimidin-4-yl)amino)-3-(3-hydroxy-3-methylbutyl)-1-methyl-1,3-dihydro-2H-benzo[d]imidazol-2-one;

5-((5-chloro-2-(methylthio)pyrimidin-4-yl)amino)-3-(3-hydroxy-3-methylbutyl)-1-methyl-1,3-dihydro-2H-benzo[d]imidazol-2-one;

5-((2-bromo-5-chloropyridin-4-yl)amino)-3-(3-hydroxy-3-methylbutyl)-1-methyl-1,3-dihydro-2H-benzo[d]imidazol-2-one;

2-chloro-4-((3-((5-ethyl-2-oxooxazolidin-5-yl)methyl)-1-methyl-2-oxo-2,3-dihydro-1H-benzo[d]imidazol-5-yl)amino)nicotinonitrile;

4-chloro-6-((6-fluoro-3-(3-hydroxy-3-methylbutyl)-1-methyl-2-oxo-2,3-dihydro-1H-benzo[d]imidazol-5-yl)amino)pyrimidine-5-carbonitrile;

2-chloro-4-((3-((5-ethyl-3-methyl-2-oxooxazolidin-5-yl)methyl)-1-methyl-2-oxo-2,3-dihydro-1H-benzo[d]imidazol-5-yl)amino)nicotinonitrile;

2-chloro-4-((6-fluoro-3-(3-hydroxy-3-methylbutyl)-1-methyl-2-oxo-2,3-dihydro-1H-benzo[d]imidazol-5-yl)amino)nicotinonitrile;

5-((2,5-dichloropyrimidin-4-yl)amino)-3-(3-hydroxy-3-methylpentyl)-1-methyl-1,3-dihydro-2H-benzo[d]imidazol-2-one;

5-((5-chloropyrazolo[1,5-a]pyrimidin-7-yl)amino)-3-(3-hydroxy-3-methylbutyl)-1-methyl-1,3-dihydro-2H-benzo[d]imidazol-2-one;

3-(3-hydroxy-3-methylbutyl)-1-methyl-5-((2,5,6-trichloropyrimidin-4-yl)amino)-1,3-dihydro-2H-benzo[d]imidazol-2-one;

(R)-6-chloro-5-cyano-4-((3-(3-methoxybutyl)-1-methyl-2-oxo-2,3-dihydro-1H-benzo[d]imidazol-5-yl)amino)-N-methylpicolinamide;

4-((3-(3-acetamido-3-methylbutyl)-1-methyl-2-oxo-2,3-dihydro-1H-benzo[d]imidazol-5-yl)amino)-6-chloro-5-cyano-N-methylpicolinamide;

5-((5,6-dichloropyrimidin-4-yl)amino)-3-(3-hydroxy-3-methylbutyl)-1-methyl-1,3-dihydro-2H-benzo[d]imidazol-2-one;

2-chloro-4-((3-(((1S,2S)-2-ethyl-2-hydroxycyclopentyl)methyl)-1-methyl-2-oxo-2,3-dihydro-1H-benzo[d]imidazol-5-yl)amino)nicotinonitrile;

2-chloro-4-((3-(((1S,2S)-2-hydroxy-2-methylcyclopentyl)methyl)-1-methyl-2-oxo-2,3-dihydro-1H-benzo[d]imidazol-5-yl)amino)nicotinonitrile;

5-((5-chloro-2-(1-methyl-1H-pyrazol-3-yl)pyrimidin-4-yl)amino)-3-(3-hydroxy-3-methylbutyl)-1-methyl-1,3-dihydro-2H-benzo[d]imidazol-2-one;

5-((5-chloro-2-(1,3-dimethyl-1H-pyrazol-5-yl)pyrimidin-4-yl)amino)-3-(3-hydroxy-3-methylbutyl)-1-methyl-1,3-dihydro-2H-benzo[d]imidazol-2-one;

5-((5-chloro-2-(2,4-dimethylthiazol-5-yl)pyrimidin-4-yl)amino)-3-(3-hydroxy-3-methylbutyl)-1-methyl-1,3-dihydro-2H-benzo[d]imidazol-2-one;

5-((5-chloro-2-(thiophen-2-yl)pyrimidin-4-yl)amino)-3-(3-hydroxy-3-methylbutyl)-1-methyl-1,3-dihydro-2H-benzo[d]imidazol-2-one;

5-((5-chloro-2-(1-methyl-1H-imidazol-2-yl)pyrimidin-4-yl)amino)-3-(3-hydroxy-3-methylbutyl)-1-methyl-1,3-dihydro-2H-benzo[d]imidazol-2-one;

2-chloro-4-((1-methyl-2-oxo-3-((4-(2,2,2-trifluoroethyl)morpholin-3-yl)methyl)-2,3-dihydro-1H-benzo[d]imidazol-5-yl)amino)nicotinonitrile;

2-chloro-4-((3-(2-(dimethylamino)butyl)-1-methyl-2-oxo-2,3-dihydro-1H-benzo[d]imidazol-5-yl)amino)nicotinonitrile;

(S)-2-chloro-4-((3-((1-ethylpyrrolidin-2-yl)methyl)-1-methyl-2-oxo-2,3-dihydro-1H-benzo[d]imidazol-5-yl)amino)nicotinonitrile;

2-chloro-4-((1-methyl-2-oxo-3-((1-(2,2,2-trifluoroethyl)piperidin-2-yl)methyl)-2,3-dihydro-1H-benzo[d]imidazol-5-yl)amino)nicotinonitrile;

(S)-2-chloro-4-((3-((1-(2-fluoroethyl)pyrrolidin-2-yl)methyl)-1-methyl-2-oxo-2,3-dihydro-1H-benzo[d]imidazol-5-yl)amino)nicotinonitrile;

(S)-2-chloro-4-((3-((1-(2-hydroxyethyl)pyrrolidin-2-yl)methyl)-1-methyl-2-oxo-2,3-dihydro-1H-benzo[d]imidazol-5-yl)amino)nicotinonitrile;

2-chloro-4-((3-(((2R,4S)-4-fluoro-1-(2,2,2-trifluoroethyl)pyrrolidin-2-yl)methyl)-1-methyl-2-oxo-2,3-dihydro-1H-benzo[d]imidazol-5-yl)amino)nicotinonitrile;

2-chloro-4-((3-(3-(ethylamino)butyl)-1-methyl-2-oxo-2,3-dihydro-1H-benzo[d]imidazol-5-yl)amino)nicotinonitrile;

2-chloro-4-((3-(3-hydroxy-3-methylhex-5-yn-1-yl)-1-methyl-2-oxo-2,3-dihydro-1H-benzo[d]imidazol-5-yl)amino)nicotinonitrile;

2-chloro-4-((3-(3-hydroxy-4-methoxy-3-methylbutyl)-1-methyl-2-oxo-2,3-dihydro-1H-benzo[d]imidazol-5-yl)amino)nicotinonitrile;

2-chloro-4-((3-(3-hydroxy-3-methylpentyl)-1-methyl-2-oxo-2,3-dihydro-1H-benzo[d]imidazol-5-yl)amino)nicotinonitrile;

2-chloro-4-((1-methyl-2-oxo-3-(4,4,4-trifluoro-3-hydroxy-3-methylbutyl)-2,3-dihydro-1H-benzo[d]imidazol-5-yl)amino)nicotinonitrile;

2-chloro-4-((3-(3-hydroxy-2,3-dimethylbutyl)-1-methyl-2-oxo-2,3-dihydro-1H-benzo[d]imidazol-5-yl)amino)nicotinonitrile;

2-chloro-4-((3-(3-hydroxy-3,4-dimethylpentyl)-1-methyl-2-oxo-2,3-dihydro-1H-benzo[d]imidazol-5-yl)amino)nicotinonitrile;

5-((5-chloro-2-(2,2,6,6-tetramethylmorpholino)pyrimidin-4-yl)amino)-3-(3-hydroxy-3-methylbutyl)-1-methyl-1,3-dihydro-2H-benzo[d]imidazol-2-one;

5-((5-chloro-2-(2-(trifluoromethyl)morpholino)pyrimidin-4-yl)amino)-3-(3-hydroxy-3-methylbutyl)-1-methyl-1,3-dihydro-2H-benzo[d]imidazol-2-one;

5-((3-chloro-2-fluoropyridin-4-yl)amino)-3-(3-hydroxy-3-methylbutyl)-1-methyl-1,3-dihydro-2H-benzo[d]imidazol-2-one;

5-((2,3-dichloropyridin-4-yl)amino)-3-(3-hydroxy-3-methylbutyl)-1-methyl-1,3-dihydro-2H-benzo[d]imidazol-2-one;

5-((3-bromopyridin-4-yl)amino)-3-(3-hydroxy-3-methylbutyl)-1-methyl-1,3-dihydro-2H-benzo[d]imidazol-2-one;

5-((5-chloro-2-(trifluoromethyl)pyridin-4-yl)amino)-3-(3-hydroxy-3-methylbutyl)-1-methyl-1,3-dihydro-2H-benzo[d]imidazol-2-one;

5-((3-chloropyridin-4-yl)amino)-3-(3-hydroxy-3-methylbutyl)-1-methyl-1,3-dihydro-2H-benzo[d]imidazol-2-one;

5-((5-chloro-2-(3,5-dimethyl-1H-pyrazol-1-yl)pyridin-4-yl)amino)-3-(3-hydroxy-3-methylbutyl)-1-methyl-1,3-dihydro-2H-benzo[d]imidazol-2-one;

5-((5-chloro-2-(2-oxopyrrolidin-1-yl)pyrimidin-4-yl)amino)-3-(3-hydroxy-3-methylbutyl)-1-methyl-1,3-dihydro-2H-benzo[d]imidazol-2-one;

(S)-5-((5-chloro-2-(2-(hydroxymethyl)pyrrolidin-1-yl)pyrimidin-4-yl)amino)-3-(3-hydroxy-3-methylbutyl)-1-methyl-1,3-dihydro-2H-benzo[d]imidazol-2-one;

(S)-7-((3-(3-hydroxy-3-methylbutyl)-1-methyl-2-oxo-2,3-dihydro-1H-benzo[d]imidazol-5-yl)amino)-5-(2-(hydroxymethyl)pyrrolidin-1-yl)pyrazolo[1,5-a]pyrimidine-3-carbonitrile;

2-chloro-4-((1-methyl-3-(2-(2-methyloxiran-2-yl)ethyl)-2-oxo-2,3-dihydro-1H-benzo[d]imidazol-5-yl)amino)nicotinonitrile;

2-chloro-4-((3-(2-(3,5-dimethyl-2-oxooxazolidin-5-yl)ethyl)-1-methyl-2-oxo-2,3-dihydro-1H-benzo[d]imidazol-5-yl)amino)nicotinonitrile;

2-chloro-4-((1-methyl-3-((5-methyl-2-oxooxazolidin-4-yl)methyl)-2-oxo-2,3-dihydro-1H-benzo[d]imidazol-5-yl)amino)nicotinonitrile;

(S)-5-((5-chloro-2-(2,2,6,6-tetramethylmorpholino)pyrimidin-4-yl)amino)-1-methyl-3-((1-(2,2,2-trifluoroethyl)pyrrolidin-2-yl)methyl)-1,3-dihydro-2H-benzo[d]imidazol-2-one;

5-((5-chloro-2-((3R,5S)-4,4-difluoro-3,5-dimethylpiperidin-1-yl)pyrimidin-4-yl)amino)-1,3-bis(3-hydroxy-3-methylbutyl)-1,3-dihydro-2H-benzo[d]imidazol-2-one;

5-((5-chloro-2-(2,2,6,6-tetramethylmorpholino)pyrimidin-4-yl)amino)-1,3-bis(3-hydroxy-3-methylbutyl)-1,3-dihydro-2H-benzo[d]imidazol-2-one;

5-((5-chloro-2-(4,4-difluoropiperidin-1-yl)pyrimidin-4-yl) amino)-3-(3-hydroxy-3-methylbutyl)-1-methyl-1,3-dihydro-2H-benzo[d]imidazol-2-one;

5-((5-chloro-2-(3,3-difluoro-8-azabicyclo[3.2.1]octan-8-yl) pyrimidin-4-yl)amino)-3-(3-hydroxy-3-methylbutyl)-1-methyl-1,3-dihydro-2H-benzo[d]imidazol-2-one;

5-((5-chloro-2-(2,2-difluoro-7-azaspiro[3.5]nonan-7-yl)pyrimidin-4-yl)amino)-3-(3-hydroxy-3-methylbutyl)-1-methyl-1,3-dihydro-2H-benzo[d]imidazol-2-one;

5-((5-chloro-2-(4-(trifluoromethyl)piperidin-1-yl)pyrimidin-4-yl)amino)-3-(3-hydroxy-3-methylbutyl)-1-methyl-1,3-dihydro-2H-benzo[d]imidazol-2-one;

5-((5-chloro-2-(4,4-difluoropiperidin-1-yl)pyridin-4-yl) amino)-3-(3-hydroxy-3-methylbutyl)-1-methyl-1,3-dihydro-2H-benzo[d]imidazol-2-one;

5-((5-chloro-2-((2R,6S)-2,6-dimethylmorpholino)pyridin-4-yl)amino)-3-(3-hydroxy-3-methylbutyl)-1-methyl-1,3-dihydro-2H-benzo[d]imidazol-2-one; or 1-(5-chloro-4-((3-(3-hydroxy-3-methylbutyl)-1-methyl-2-oxo-2,3-dihydro-1H-benzo[d]imidazol-5-yl)amino)pyridin-2-yl)-N,N-dimethylpiperidine-4-carboxamide.

Particular compounds of the present invention include any of the compounds exemplified in the present application, or a pharmaceutically acceptable salt or solvate thereof, and, in particular, any of the following:

6-Chloro-5-cyano-4-[[3-(3-hydroxy-3-methyl-butyl)-1-methyl-2-oxo-benzimidazol-5-yl]amino]-N-methyl-pyridine-2-carboxamide;

2-chloro-4-[[3-(3-hydroxy-3-methyl-butyl)-1-methyl-2-oxo-benzimidazol-5-yl]amino]-6-methyl-pyridine-3-carbonitrile;

6-chloro-5-cyano-4-[(1,3-dimethyl-2-oxo-benzimidazol-5-yl)amino]pyridine-2-carboxylic acid;

6-chloro-5-cyano-N-methyl-4-[[1-methyl-2-oxo-3-[(3S)-3-pyrazol-1-ylbutyl]benzimidazol-5-yl]amino]pyridine-2-carboxamide;

6-chloro-5-cyano-4-[[3-[(3R)-3-hydroxybutyl]-1-methyl-2-oxo-benzimidazol-5-yl]amino]pyridine-2-carboxylic acid;

6-chloro-5-cyano-N-methyl-4-[(1-methyl-2-oxo-3H-benzimidazol-5-yl)amino]pyridine-2-carboxamide;

6-chloro-5-cyano-4-[[3-(3-hydroxy-3-methyl-butyl)-2-oxo-1-(tetrahydropyran-4-ylmethyl)benzimidazol-5-yl]amino]-N-methyl-pyridine-2-carboxamide;

Ethyl 7-[[3-(3-hydroxy-3-methyl-butyl)-1-methyl-2-oxo-benzimidazol-5-yl]amino]-pyrazolo[1,5-a]pyrimidine-5-carboxylate;

2-chloro-4-[[3-(3-hydroxy-3-methyl-butyl)-1-methyl-2-oxo-benzimidazol-5-yl]amino]pyridine-3-carbonitrile;

Methyl 4-[6-[(2-chloro-3-cyano-4-pyridyl)amino]-3-methyl-2-oxo-benzimidazol-1-yl]-2-methyl-butanoate;

2-bromo-4-[[3-(3-hydroxy-3-methyl-butyl)-1-methyl-2-oxo-benzimidazol-5-yl]amino]pyridine-3-carbonitrile;

2-chloro-4-[[3-[(3R)-3-hydroxybutyl]-1-methyl-2-oxo-benzimidazol-5-yl]amino]-6-methyl-pyridine-3-carbonitrile;

5-[(2,5-dichloro-4-pyridyl)amino]-3-[(3R)-3-hydroxybutyl]-1-methyl-benzimidazol-2-one;

5-[(2,5-dichloropyrimidin-4-yl)amino]-3-(3-hydroxy-3-methyl-butyl)-1-methyl-benzimidazol-2-one;

Ethyl 7-[[3-[(3R)-3-hydroxybutyl]-1-methyl-2-oxo-benzimidazol-5-yl]amino]pyrazolo-[1,5-a]pyrimidine-5-carboxylate;

4-chloro-6-[[3-(3-hydroxy-3-methyl-butyl)-1-methyl-2-oxo-benzimidazol-5-yl]amino]pyrimidine-5-carbonitrile;

5-[(2,3-dichloro-4-pyridyl)amino]-3-[(3R)-3-hydroxybutyl]-1-methyl-benzimidazol-2-one;

Ethyl 3-fluoro-7-((3-(2-hydroxybutyl)-1-methyl-2-oxo-2,3-dihydro-1H-benzo[d]-imidazol-5-yl)amino)pyrazolo[1,5-a]pyrimidine-5-carboxylate;

Methyl 6-chloro-5-cyano-4-[[3-(4-methoxy-3-methyl-4-oxo-butyl)-1-methyl-2-oxo-benzimidazol-5-yl]amino] pyridine-2-carboxylate;

Ethyl 6-chloro-5-cyano-4-[[3-(4-methoxy-3-methyl-4-oxo-butyl)-1-methyl-2-oxo-benzimidazol-5-yl]amino]pyridine-2-carboxylate;

Isopropyl 6-chloro-5-cyano-4-[[3-(4-methoxy-3-methyl-4-oxo-butyl)-1-methyl-2-oxo-benzimidazol-5-yl]amino] pyridine-2-carboxylate;

Ethyl 6-chloro-5-cyano-4-[[3-[(3R)-3-hydroxybutyl]-1-methyl-2-oxo-benzimidazol-5-yl]amino]pyridine-2-carboxylate;

6-Chloro-5-cyano-4-[[3-(4-methoxy-3-methyl-4-oxo-butyl)-1-methyl-2-oxo-benzimidazol-5-yl]amino]pyridine-2-carboxylic acid;

Methyl 3-[6-[(2-chloro-3-cyano-4-pyridyl)amino]-3-methyl-2-oxo-benzimidazol-1-yl]-2-methyl-propanoate;

Methyl 4-[6-[(5-chloro-2-methyl-pyrimidin-4-yl)amino]-3-methyl-2-oxo-benzimidazol-1-yl]-2-methyl-butanoate;

6-Chloro-5-cyano-4-[[3-[(3R)-3-hydroxybutyl]-1-methyl-2-oxo-benzimidazol-5-yl]amino]-N-methyl-pyridine-2-carboxamide;

Methyl 4-[6-[[2-chloro-3-cyano-6-(3-methyl-1,2,4-oxadiazol-5-yl)-4-pyridyl]amino]-3-methyl-2-oxo-benzimidazol-1-yl]-2-methyl-butanoate;

Methyl (2S)-2-amino-4-[6-[(2-chloro-3-cyano-4-pyridyl) amino]-3-methyl-2-oxo-benzimidazol-1-yl]butanoate;

Methyl 4-[6-[[2-chloro-3-cyano-6-(methylcarbamoyl)-4-pyridyl]amino]-3-methyl-2-oxo-benzimidazol-1-yl]-2-methyl-butanoate;

Methyl 4-[6-[[6-(but-3-ynylcarbamoyl)-2-chloro-3-cyano-4-pyridyl]amino]-3-methyl-2-oxo-benzimidazol-1-yl]-2-methyl-butanoate;

Methyl 4-[6-[[2-chloro-3-cyano-6-(dimethylcarbamoyl)-4-pyridyl]amino]-3-methyl-2-oxo-benzimidazol-1-yl]-2-methyl-butanoate;

6-Chloro-5-cyano-N-[2-(dimethylamino)ethyl]-4-[(1,3-dimethyl-2-oxo-benzimidazol-5-yl)amino]pyridine-2-carboxamide;

Ethyl 7-[[3-(4-methoxy-3-methyl-4-oxo-butyl)-1-methyl-2-oxo-benzimidazol-5-yl]amino]pyrazolo[1,5-a]pyrimidine-5-carboxylate;

Methyl 4-[6-[(2-chloro-3-cyano-4-pyridyl)amino]-3-methyl-2-oxo-benzimidazol-1-yl]-2-hydroxy-butanoate;

2-Chloro-4-[[3-(2,3-dihydroxy-3-methyl-butyl)-1-methyl-2-oxo-benzimidazol-5-yl]amino]pyridine-3-carbonitrile;

Methyl 4-[6-[(2-chloro-3-cyano-4-pyridyl)amino]-3-methyl-2-oxo-benzimidazol-1-yl]-2-methoxy-butanoate;

Methyl 4-[6-[(2-chloro-3-cyano-4-pyridyl)amino]-3-methyl-2-oxo-benzimidazol-1-yl]-2-ethoxy-butanoate;

Methyl 4-[6-[(2-chloro-3-cyano-4-pyridyl)amino]-3-methyl-2-oxo-benzimidazol-1-yl]butanoate;

methyl 4-[6-[(2-chloro-3-cyano-4-pyridyl)amino]-3-methyl-2-oxo-benzimidazol-1-yl]-2-(cyclopropylmethoxy)butanoate;

2-chloro-4-[[3-(2-hydroxy-pyrazol-1-yl-propyl)-1-methyl-2-oxo-benzimidazol-5-yl]amino]pyridine-3-carbonitrile;

2-chloro-4-[[3-(2-cyanobutyl)-1-methyl-2-oxo-benzimidazol-5-yl]amino]pyridine-3-carbonitrile;

2-chloro-4-[[3-[(3S)-3-hydroxybutyl]-1-methyl-2-oxo-benzimidazol-5-yl]amino]pyridine-3-carbonitrile;

Methyl 2-[[6-[(2-chloro-3-cyano-4-pyridyl)amino]-3-methyl-2-oxo-benzimidazol-1-yl]methyl]cyclopentanecarboxylate;

Methyl (2R)-2-amino-4-[6-[(2-chloro-3-cyano-4-pyridyl)amino]-3-methyl-2-oxo-benzimidazol-1-yl]butanoate;

N-[3-[6-[(2-Chloro-3-cyano-4-pyridyl)amino]-3-methyl-2-oxo-benzimidazol-1-yl]-1-methyl-propyl]acetamide;

5-Chloro-N-ethyl-4-[[3-(3-hydroxy-3-methyl-butyl)-1-methyl-2-oxo-benzimidazol-5-yl]amino]pyridine-2-carboxamide; or 5-[[5-Chloro-2-(3,5-dimethylpyrazol-1-yl)pyrimidin-4-yl]amino]-3-(3-hydroxy-3-methyl-butyl)-1-methyl-benzimidazol-2-one.

The various functional groups and substituents making up the compounds of the Formula (I), or sub-formulae Ia to Ij, are typically chosen such that the molecular weight of the compound of the formula (I) does not exceed 1000. More usually, the molecular weight of the compound will be less than 900, for example less than 800, or less than 750, or less than 700, or less than 650. More preferably, the molecular weight is less than 600 and, for example, is 550 or less.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric, methane sulfonate or maleic acid. In addition, a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, trimethylamine, piperidine, morpholine or tris-(2-hydroxyethyl)amine.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that possess antiproliferative activity.

The present invention also encompasses compounds of the invention as defined herein which comprise one or more isotopic substitutions. For example, H may be in any isotopic form, including 1H, 2H(D), and 3H (T); C may be in any isotopic form, including 12C, 13C, and 14C; and O may be in any isotopic form, including 16O and 18O; and the like.

It is also to be understood that certain compounds of the Formula (I), or sub-formulae Ia to Ij, may exist in solvated as well as unsolvated forms such as, for example, hydrated forms. It is to be understood that the invention encompasses all such solvated forms that possess antiproliferative activity.

It is also to be understood that certain compounds of the Formula I, or sub-formulae Ia to Ij, may exhibit polymorphism, and that the invention encompasses all such forms that possess antiproliferative activity.

Compounds of the Formula I, or sub-formulae Ia to Ij, may exist in a number of different tautomeric forms and references to compounds of the Formula I, or sub-formulae Ia to Ij, include all such forms. For the avoidance of doubt, where a compound can exist in one of several tautomeric forms, and only one is specifically described or shown, all others are nevertheless embraced by Formula I, or sub-formulae Ia to Ij. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

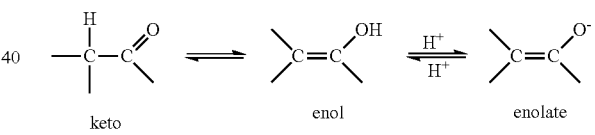

keto   enol   enolate

Compounds of the Formula I, or sub-formulae Ia to Ij, containing an amine function may also form N-oxides. A reference herein to a compound of the Formula I, or sub-formulae Ia to Ij, that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example Advanced Organic Chemistry, by Jerry March, 4th Edition, Wiley Interscience, pages. More particularly, N-oxides can be made by the procedure of L. W. Deady (Syn. Comm. 1977, 7, 509-514) in which the amine compound is reacted with m-chloroperoxybenzoic acid (mCPBA), for example, in an inert solvent such as dichloromethane.

The compounds of Formula (I), or sub-formulae Ia to Ij, may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the Formula (I), or sub-formulae Ia to Ij, and in-vivo cleavable amide derivatives that may be formed at a carboxy group or an amino group in a compound of the Formula (I), or sub-formulae Ia to Ij.

Accordingly, the present invention includes those compounds of the Formula (I), or sub-formulae Ia to Ij, as defined hereinbefore, when made available by organic synthesis and when made available within the human or animal body by way of cleavage of a pro-drug thereof. Accordingly, the present invention includes those compounds of the Formula I, or sub-formulae Ia to Ij, that are produced by organic synthetic means and also such compounds that are produced in the human or animal body by way of metabolism of a precursor compound, that is a compound of the Formula (I), or sub-formulae Ia to Ij, may be a synthetically-produced compound or a metabolically-produced compound.

A suitable pharmaceutically acceptable pro-drug of a compound of the Formula (I), or sub-formulae Ia to Ij, is one that is based on reasonable medical judgement as being suitable for administration to the human or animal body without undesirable pharmacological activities and without undue toxicity.

Various forms of pro-drug have been described, for example in the following documents:—
a) Methods in Enzymology, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, Advanced Drug Delivery Reviews, 8, 1-38 (1992);
e) H. Bundgaard, et al., Journal of Pharmaceutical Sciences, 77, 285 (1988);
f) N. Kakeya, et al., Chem. Pharm. Bull., 32, 692 (1984);
g) J. Rautio, et al. Nature Reviews Drug Discover (2018);
h) T. Higuchi and V. Stella, "Pro-Drugs as Novel Delivery Systems", A.C.S. Symposium Series, Volume 14; and
i) E. Roche (editor), "Bioreversible Carriers in Drug Design", Pergamon Press, 1987.

A suitable pharmaceutically acceptable pro-drug of a compound of the Formula I, or sub-formulae Ia to Ij, that possesses a carboxy group is, for example, an in vivo cleavable ester thereof. An in vivo cleavable ester of a compound of the Formula I, or sub-formulae Ia to Ij, containing a carboxy group is, for example, a pharmaceutically acceptable ester which is cleaved in the human or animal body to produce the parent acid. Suitable pharmaceutically acceptable esters for carboxy include C1-6alkyl esters such as methyl, ethyl and tert-butyl, C1-6alkoxymethyl esters such as methoxymethyl esters, C1-6alkanoyloxymethyl esters such as pivaloyloxymethyl esters, 3-phthalidyl esters, C3-8cycloalkylcarbonyloxy-C1-6alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and C1-6alkoxycarbonyloxy-C1-6alkyl esters such as methoxycarbonyloxymethyl and 1-methoxycarbonyloxyethyl esters.

A suitable pharmaceutically acceptable pro-drug of a compound of the Formula (I), or sub-formulae Ia to Ij, that possesses a hydroxy group is, for example, an in vivo cleavable ester or ether thereof. An in vivo cleavable ester or ether of a compound of the Formula I, or sub-formulae Ia to Ij, containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include C1-10alkanoyl groups such as acetyl, benzoyl, phenylacetyl and substituted benzoyl and phenylacetyl groups, C1-10alkoxycarbonyl groups such as ethoxycarbonyl, N,N-(C1-6)2carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-(C1-4alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable pro-drug of a compound of the Formula (I), or sub-formulae Ia to Ij, that possesses a carboxy group is, for example, an in vivo cleavable amide thereof, for example an amide formed with an amine such as ammonia, a C1-4alkylamine such as methylamine, a (C1-4alkyl)2amine such as dimethylamine, N-ethyl-N-methylamine or diethylamine, a C1-4alkoxy-C2-4alkylamine such as 2-methoxyethylamine, a phenyl-C1-4alkylamine such as benzylamine and amino acids such as glycine or an ester thereof.

A suitable pharmaceutically acceptable pro-drug of a compound of the Formula I, or sub-formulae Ia to Ij, that possesses an amino group is, for example, an in vivo cleavable amide derivative thereof. Suitable pharmaceutically acceptable amides from an amino group include, for example an amide formed with C1-10alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-(C1-4alkyl)piperazin-1-ylmethyl.

The in vivo effects of a compound of the Formula (I), or sub-formulae Ia to Ij, may be exerted in part by one or more metabolites that are formed within the human or animal body after administration of a compound of the Formula (I), or sub-formulae Ia to Ij. As stated hereinbefore, the in vivo effects of a compound of the Formula (I), or sub-formulae Ia to Ij, may also be exerted by way of metabolism of a precursor compound (a pro-drug).

Though the present invention may relate to any compound or particular group of compounds defined herein by way of optional, preferred or suitable features or otherwise in terms of particular embodiments, the present invention may also relate to any compound or particular group of compounds that specifically excludes said optional, preferred or suitable features or particular embodiments.

Suitably, the present invention excludes any individual compounds not possessing the biological activity defined herein.

Synthesis

The compounds of the present invention can be prepared by any suitable technique known in the art. Particular processes for the preparation of these compounds are described further in the accompanying examples.

In the description of the synthetic methods described herein and in any referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

It will be appreciated that during the synthesis of the compounds of the invention in the processes defined herein, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively, an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively, an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

The methodology employed to synthesise a compound of Formula (I), or sub-formulae Ia to Ij, will vary depending on the nature of $X_1$, $X_2$, $R^1$, $R^2$, $R^3$ and any substituent groups associated therewith. Suitable processes for their preparation are described further in the accompanying Examples.

Once a compound of Formula (I), or sub-formulae Ia to Ij, has been synthesised by any one of the processes defined herein, the processes may then further comprise the additional steps of:

(i) removing any protecting groups present;
(ii) converting the compound Formula (I) into another compound of Formula (I);
(iii) forming a pharmaceutically acceptable salt, hydrate or solvate thereof; and/or
(iv) forming a prodrug thereof.

An example of (ii) above is when a compound of Formula (I) is synthesised and then one or more of the groups of $X_1$, $X_2$, $R^1$, $R^2$, $R^3$ may be further reacted to change the nature of the group and provide an alternative compound of Formula (I). For example, the compound can be reacted to convert any R group into a substituent group other than hydrogen.

The resultant compounds of Formula (I), or sub-formulae Ia to Ij, can be isolated and purified using techniques well known in the art.

The compounds of Formula (I) may be synthesised by the general synthetic routes (e.g. Schemes 1 to 7) below, specific examples of which are described in more detail in the Examples.

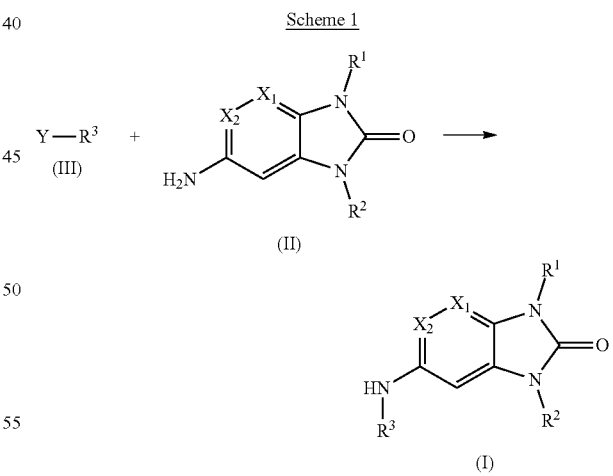

wherein, Y is a halogen such as Cl, Br, I or a suitable alternative such as OTf, and $R^1$, $R^2$, $R^3$, $X_1$, $X_2$ are appropriate groups chosen from those defined previously.

The reaction between aromatic amines (II) and aryl halides or appropriate equivalent reagents (III) to form compounds of formula (I) as shown in Scheme 1 may be carried out at elevated temperature (e.g. 60-180° C.), using conventional or microwave heating, in a suitable solvent or solvent mixture, such as NMP, DMA, DMF, dioxane or acetonitrile. The reaction is carried out in the presence of a base (such as triethylamine or DIPEA) or with no base. Alternative reaction conditions include the use of a transition metal catalyst such as Pd$_2$(dba)$_3$ combined with a suitable ligand such as Xantphos, in the presence of a base such as cesium carbonate at elevated temperature (such as 140° C.), using a suitable solvent or solvent mixture, such as toluene or mixtures of toluene and DMF or NMP.

A compound of formula (I) may be converted to another compound of formula (I) by methods generally known to those skilled in the art.

Compounds of formula (II) may be obtained from commercial suppliers, prepared as described in Scheme 2 or by other methods known in the art. Compounds (III) may be obtained from commercial suppliers or prepared by reported methods.

the presence of a metal catalyst such as palladium, typically on carbon support, in an appropriate solvent or mixture of solvents such as ethanol, methanol, ethyl acetate or ethanol/NMP at ambient or elevated temperature (such as 60-75° C.) using conventional or microwave heating. These reactions are carried out under a hydrogen atmosphere, or alternatively by "transfer hydrogenation" using a reagent such as ammonium formate or triethylsilane. Other approaches are known in the art including the use of tin chloride, iron or zinc metal mediated reductions. Compounds of formula (IV) may be obtained from commercial suppliers, prepared by methods shown in Scheme 3 or by other methods known in the art.

Scheme 3

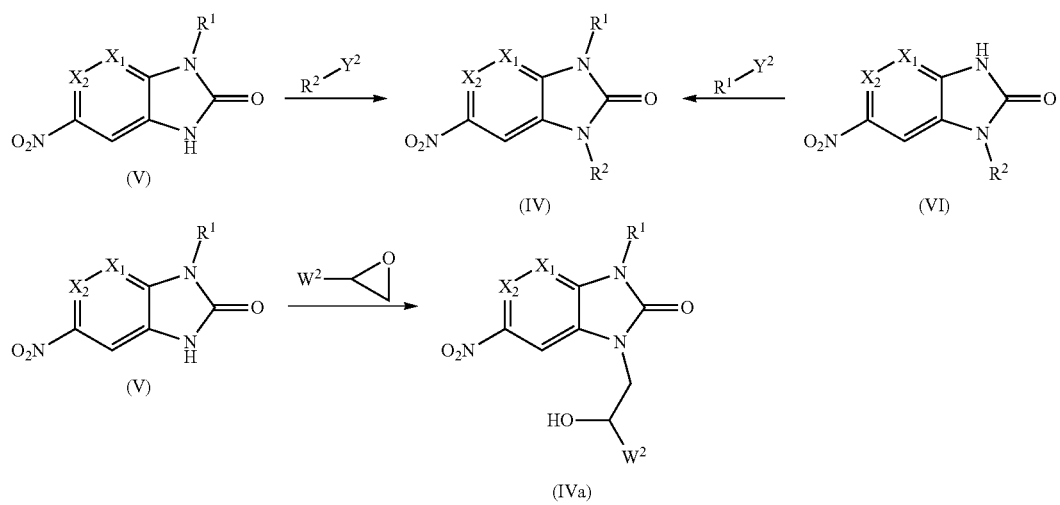

wherein, Y$^2$ is a halogen such as Cl, Br, I or a suitable alternative such as OTs, OMs and R$^1$, R$^2$, W$^2$, X$_1$, X$_2$ are appropriate groups chosen from those defined previously.

Introduction of R$^2$ group onto compounds (V) may be carried out by alkylation to form compounds (IV). Alkylation conditions are well known in the art, and include the use of an alkyl halide, tosylate or equivalent (Y$^2$—R$^2$, such as iodomethane or 3-hydroxy-3-methyl-butyl 4-methylbenzenesulfonate) in an appropriate solvent such as acetonitrile or DMF, in the presence of a base such as cesium carbonate, at ambient or elevated temperature (e.g. 60-100° C.). Where Y$^2$ is not iodide, potassium iodide may be added to the reaction conditions to increase the rate of reaction. Alternative alkylating agents such as epoxides may be used for form compounds of formula (IV), specifically those with structure (IVa). Similarly, compounds (IV) may be formed by alkylation of compounds (VI) with alkylating agent Y$^2$—R$^1$, or with epoxides or with other appropriate reagents. Particularly where R$^1$=R$^2$, compounds (IV) can be formed by successive alkylations starting from compounds where R$^1$=R$^2$=H. Where R$^1$ and R2 are different, this approach may lead to mixtures of compounds which could be separated using known methods. Alternatively, the well-known Mitsunobu reaction may be applied to convert compounds (V) or (VI) into (IV) using an appropriate alcohol R$^2$—OH. Further manipulation of compounds (IV) by known methods can be used to modify R$^1$, R$^2$. For example, ring expansion of an epoxide group to an oxazolidinone group by known methods including ring opening with ammonia or an amine, Scheme 2

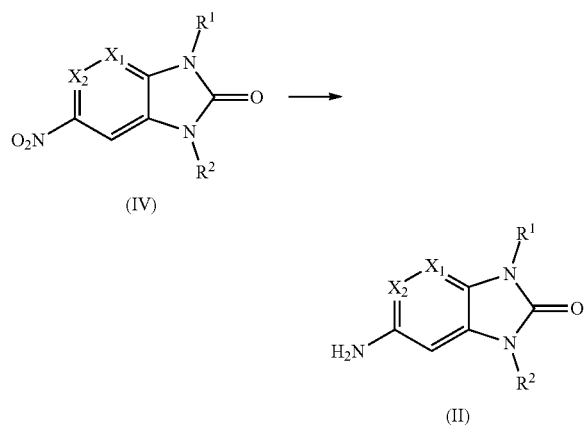

wherein, R$^1$, R$^2$, R$^3$, X$_1$, X$_2$ are appropriate groups chosen from those defined previously.

The reduction of nitro compounds (IV) to aromatic amines (II) may be carried out by numerous methods which are well known in the art. Hydrogenation can be carried out in followed by cyclisation with a phosgene equivalent such as triphosgene or disuccinimidyl carbonate. Certain compounds of formula (V) and (VI) are commercially available, or may be prepared using known methods. Nitro compounds such as (IV) (V) and (V), particularly where $X_2$=F, halo, alkyl, may also be prepared by nitration using known methods. Compounds (V) may also be prepared as described in Scheme 4. Alkylating agents $Y^2$—$R^1$, $Y^2$—$R^2$ are commercially available, or prepared as described in Scheme 6 or by known methods such as tosylation or mesylation of an alcohol, or conversion of an alcohol into a halide. Epoxides may be obtained from commercial suppliers or prepared by known methods such as oxidation of alkenes with m-CPBA.

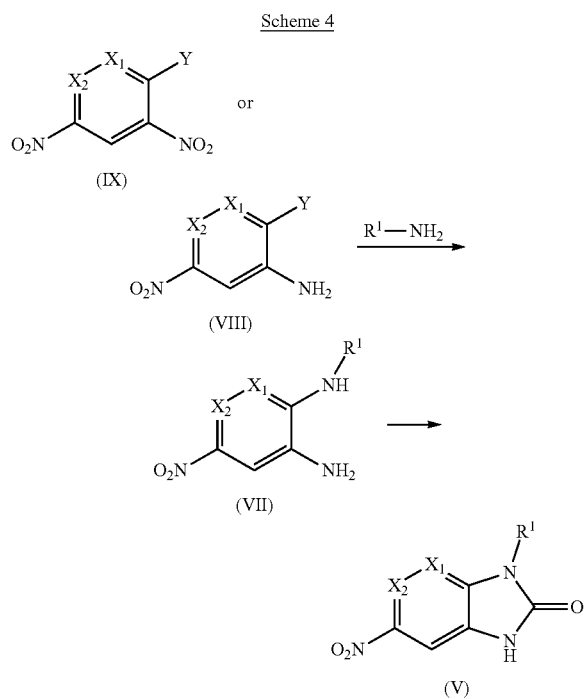

wherein Y is a halogen such as Cl, Br, I or a suitable alternative such as OTs, OTf, and $R^1$, $X_1$, $X_2$ are appropriate groups chosen from those defined previously.

Compounds (V) may be formed by cyclisation of diamino compounds (VII). Possible conditions include the use of bis(2,5-dioxopyrrolidin-1-yl) carbonate in acetonitrile at ambient temperature, but alternative conditions for these cyclisations are well known in the art using reagents such as carbonyl diimidazole, triphosgene and urea. Compounds (VII) may be formed by reaction of compounds (VIII) with an appropriate amine $R^1$—$NH_2$. Suitable conditions for these transformations include the use of a base (such as DIPEA) in an appropriate solvent (such as NMP) at elevated temperature (such as 180° C.), although many alternative conditions are known by those skilled in the art for this class of transformation including metal-catalysed couplings. Alternatively, the more reactive di-nitro compounds (IX) can be used to prepare (VII) by halogen displacement followed by nitro reduction as described in the literature, for example Freitag et al, *Bioorg. Med. Chem.* 2011 p 3669-3677. Amines $R^1$—$NH_2$. and nitro-compounds (IX) and (VIII) may be prepared by known methods or obtained from commercial suppliers.

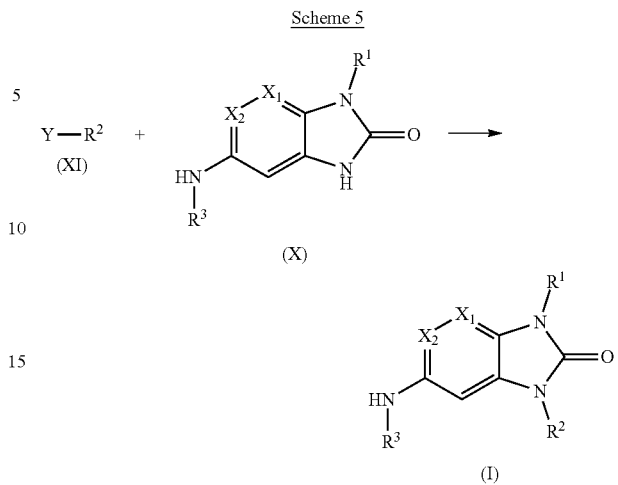

wherein, Y is a halogen such as Cl, Br, I or a suitable alternative such as OTf, OTs, and $R^1$, $R^2$, $R^3$, $X_1$, $X_2$ are appropriate groups chosen from those defined previously.

Introduction of $R^2$ group onto compounds (X) may be carried out by alkylation using compounds (XI) to form compounds (I), using conditions such as those described in Scheme 3 or others known in the art. Similar reagents such as epoxides may also be used to form compounds (I) from (X). The Mitsunobu reaction as described in Scheme 3 may also be used to form certain compounds (I) from (X) using an alcohol $R^2$—OH. In particular, the use of the Mitsunobu reagent CMBP (available from TCI Chemicals) as described in, *Pure Appl. Chem.* 1999, (71), 6, 1053-1057 can enable this reaction to work effectively, despite the relatively weak acidity of compounds (X). Typically, this reaction is carried out at elevated temperature (such as 60-100° C.) in an appropriate solvent or solvent mixture such as DMF and THF.

Alkylation may occur on the desired or other positions, appropriate choice of reaction conditions may modify selectivity and regioisomers formed may be separable by appropriate use of known purification techniques such as HPLC, flash chromatography and crystallisation. Compounds (X) may be prepared by methods including those described in Scheme 1. Compounds (XI) may be commercially available, prepared as described in Scheme 6 or by known methods such as tosylation or mesylation of an alcohol, or conversion of an alcohol into a halide. Epoxides may be obtained from commercial suppliers or prepared by known methods. Functionality on R2 may be masked in compound (XI) by the use of protecting groups, which can be removed at a later stage in the synthesis. The application of protecting groups is well known in the art. For example, the Schollkopf auxiliary may be used as a protected form of amino acid derivatives as described in Ma et al *J. Org. Chem.*, 2001, pp 4525-4542.

Scheme 6

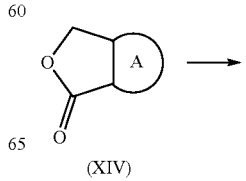

-continued

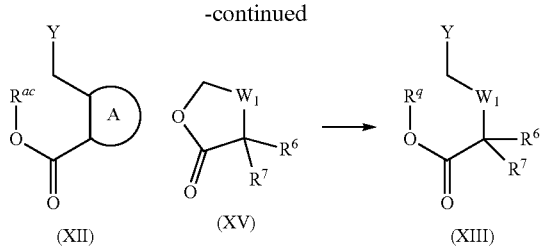

wherein, Y is a halogen such as Br, I and $W^1$, $R^6$, $R^7$, $R^q$, $R^{ac}$ and A are appropriate groups chosen from those defined previously.

Alkylating agents of the general formula (XII) or (XII) [equivalent to compounds (XI) for specific $R^2$ groups) where Y=iodo may be prepared using conditions analogous to those reported in Bartrum et al, Synlett 2009 p 2257-2260, via iodotrimethylsilane-mediated ring opening of the lactone (XIV) or (XV) and quenching of the resultant silyl ester with an alcohol Rq-OH or Rac-OH. Alternatively, ring opening of (XIV) or (XV) with an alcohol such as methanol may be employed to form esters analogous to (XII) and (XIII) except where Y=OH, which can then be further converted into alkylating agents by known methods. This route is exemplified in WO 2009/097578 A1, 2009, p. 244-245. (XIV) and (XV) may be obtained from commercial suppliers or prepared by methods known in the art.

reaction, or with other organometallic compounds (such as organotin species) in similar reactions (including the Stille reaction). Acids (Ic) may be converted into compounds of formula (Ia) using known methods such as amide or ester formation. Heteroaryls may also be prepared from these compounds (for example, the formation of $R^{10}$=oxadiazole by condensation of (1c) with amidoximes in the presence of a coupling or dehydrating reagent such as T3P). Similar procedures to those described in this scheme may also be used for modifying other positions of molecules of formula (I) such as the $R^{11}$ group in compounds containing the Formula B substructure as described in the embodiments.

Biological Activity

The biological assays described in the Examples section herein may be used to measure the pharmacological effects of the compounds of the present invention.

Although the pharmacological properties of the compounds of Formula I vary with structural change, as expected, the compounds of the invention were found to be active in the HTRF in vitro assay described in the Examples section.

In general, as illustrated by the Example compound data in Table 1a or Table 1b, in the HTRF assay described in the Examples section, the compounds of the invention demonstrate an $IC_{50}$ of 5 µM or less, which corresponds to a $pIC_{50}$ of 5.3 or more, with preferred compounds of the invention demonstrating an $IC_{50}$ of 1 µM or less, which corresponds to a $pIC_{50}$ of 6.0 or more.

Scheme 7

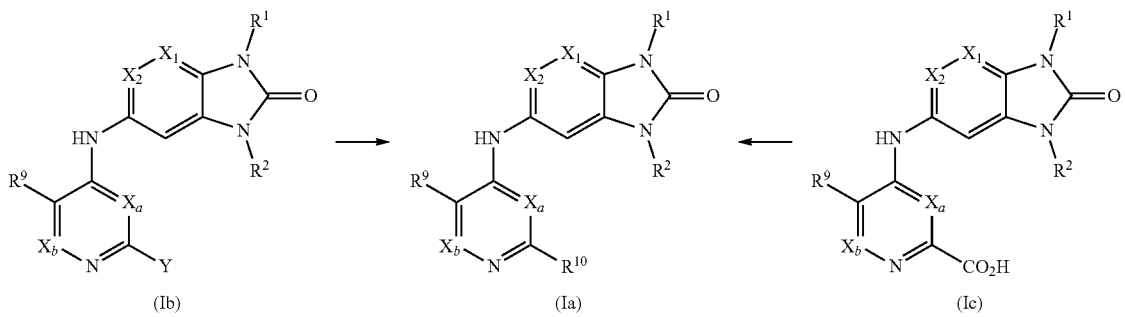

wherein, Y is a halogen such as Cl, Br, I or a suitable alternative such as OTf, OTs, and $R^1$, $R^2$, $R^3$, $R^9$, $R^{10}$, $X_1$, $X_2$, $X_a$, $X_b$ are appropriate groups chosen from those defined previously.

A compound of formula (I) may be converted to another compound of formula (I) by methods generally known to those skilled in the art. Some examples of this are represented in this scheme. A subset of compounds of formula (I) represented by formula (Ia) may be formed from compounds of formula (Ib) by known methods, including aromatic nucleophilic substitution with an appropriate amine, or with a heterocycle containing an NH (such as a piperidine or morpholine), or with a heteroaryl containing an NH (such as a pyrazole), or with an alcohol. These reactions are typically carried out at elevated temperature, in an appropriate solvent (such as DMF, NMP, ethanol or acetonitrile) and may benefit from the addition of a base (such as cesium or other metal carbonates, DIPEA, triethylamine or sodium hydride), and in some cases by addition of an appropriate metal catalyst and ligand. Metal catalysis may also be used for reactions of (Ib) with boronic acids or esters via the well-known Suzuki In the NanoBRET cell assay described herein in the Examples section, as illustrated by the Example compound data in Table 2a or Table 2b, the compounds of Formula I typically demonstrate a $pIC_{50}$ of 5.0 or more.

In the immunofluorescence assay described herein in the Examples section, certain compounds of the invention have been shown to enable degradation of BCL6. This is illustrated by the Example compound data shown in Table 2c.

In general, as illustrated by the Example compound data in Table 2d, compounds of the invention show inhibition of cell proliferation when tested in the assay described herein in the Examples section.

The following data were generated for the Examples:

TABLE 1a

Initially Generated Data from the HTRF in vitro Assay

| Example | HTRF $pIC_{50}$ |
|---|---|
| 1a | 6.48 |
| 1b | 6.09 |

TABLE 1a-continued

Initially Generated Data from the HTRF in vitro Assay

| Example | HTRF pIC$_{50}$ |
|---|---|
| 1c | 6.05 |
| 1d | 6.04 |
| 1e | 6.01 |
| 1f | 5.84 |
| 1g | 5.82 |
| 1h | 5.79 |
| 1i | 5.77 |
| 1j | 5.67 |
| 1k | 5.63 |
| 1l | 5.62 |
| 1m | 5.62 |
| 1n | 5.61 |
| 1o | 5.58 |
| 1p | 5.41 |
| 1q | 5.49 |
| 1r | 5.39 |
| 2a | 6.41 |
| 2b | 6.19 |
| 2c | 6.10 |
| 2d | 6.17 |
| 3a | 6.21 |
| 3b | 5.39 |
| 3c | 5.37 |
| 4 | 5.99 |
| 5 | 5.99 |
| 6 | 5.97 |
| 7a | 5.97 |
| 7b | 5.84 |
| 7c | 5.57 |
| 7d | 5.50 |
| 8 | 5.83 |
| 9 | 5.83 |
| 10a | 5.81 |
| 10b | 5.71 |
| 10c | 5.65 |
| 10d | 5.55 |
| 10e | 5.52 |
| 10f | 5.49 |
| 10g | 5.38 |
| 10h | 5.33 |
| 11 | 5.71 |
| 12 | 5.79 |
| 13 | 5.75 |
| 14 | 6.05 |
| 15a | 6.56 |
| 20a | 6.62 |

TABLE 1b

Further Generated Data from the HTRF in vitro Assay

| Example | HTRF pIC$_{50}$ |
|---|---|
| 1a | 6.22 |
| 1c | 6.08 |
| 1f | 5.59 |
| 1g | 5.95 |
| 1h | 5.94 |
| 1i | 6.08 |
| 1j | 5.78 |
| 1k | 5.82 |
| 1l | 5.53 |
| 1m | 5.47 |
| 1n | 5.82 |
| 1o | 5.48 |
| 1p | 5.56 |
| 1q | 5.45 |
| 1r | 5.91 |
| 2a | 6.18 |
| 2b | 6.10 |
| 2d | 5.87 |
| 3a | 5.93 |

TABLE 1b-continued

Further Generated Data from the HTRF in vitro Assay

| Example | HTRF pIC$_{50}$ |
|---|---|
| 3b | 5.35 |
| 3c | 5.37 |
| 4 | 5.79 |
| 5 | 6.19 |
| 6 | 6.00 |
| 7a | 6.09 |
| 8 | 6.01 |
| 9 | 5.97 |
| 10a | 5.93 |
| 10b | 5.57 |
| 10c | 5.69 |
| 10d | 5.29 |
| 10e | 5.38 |
| 10f | 5.48 |
| 10g | 5.45 |
| 10h | 5.32 |
| 10i | 5.81 |
| 11 | 5.72 |
| 12 | 5.68 |
| 14 | 6.29 |
| 15a | 6.61 |
| 15b | 5.96 |
| 15c | 6.22 |
| 15d | 6.41 |
| 15e | 6.02 |
| 15f | 6.00 |
| 15g | 5.89 |
| 15h | 5.86 |
| 15i | 6.75 |
| 15j | 5.76 |
| 15k | 6.27 |
| 15l | 6.63 |
| 15m | 6.08 |
| 15n | 6.35 |
| 15o | 5.88 |
| 15p | 5.82 |
| 15q | 6.09 |
| 16a | 6.38 |
| 16b | 6.31 |
| 17a | 6.27 |
| 17b | 6.21 |
| 18a | 5.90 |
| 18b | 5.31 |
| 19a | 5.83 |
| 19b | 5.55 |
| 19c | 5.45 |
| 19d | 5.44 |
| 20a | 6.46 |
| 20b | 6.01 |
| 20c | 6.60 |
| 20d | 5.92 |
| 20e | 6.09 |
| 20f | 5.99 |
| 20g | 6.07 |
| 20h | 6.49 |
| 20i | 6.17 |
| 20j | 6.80 |
| 20k | 6.11 |
| 20l | 6.39 |
| 20m | 5.97 |
| 20n | 6.42 |
| 20o | 6.22 |
| 20p | 6.44 |
| 20q | 5.87 |
| 20r | 6.53 |
| 20s | 6.26 |
| 20t | 6.51 |
| 21a | 7.00 |
| 21b | 7.01 |
| 22a | 6.19 |
| 22b | 5.65 |
| 22c | 5.76 |
| 22d | 5.45 |
| 22e | 5.88 |
| 22f | 5.75 |

TABLE 1b-continued

Further Generated Data from the HTRF in vitro Assay

| Example | HTRF pIC$_{50}$ |
| --- | --- |
| 22g | 5.27 |
| 22h | 5.47 |
| 22i | 5.54 |
| 22l | 5.64 |
| 22m | 5.52 |
| 22n | 5.90 |
| 23a | 6.35 |
| 23b | 6.05 |
| 23c | 5.99 |
| 23d | 5.62 |
| 24a | 6.33 |
| 25a | 5.58 |
| 25b | 5.34 |
| 25c | 5.34 |
| 25e | 5.37 |
| 25f | 5.73 |
| 25g | 5.34 |
| 25h | 5.55 |
| 25i | 5.71 |
| 26a | 5.41 |
| 27a | 5.86 |
| 27b | 6.14 |
| 27c | 5.93 |
| 27d | 5.70 |
| 27e | 5.55 |
| 27f | 5.40 |
| 28a | 7.06 |
| 28b | 6.55 |
| 29a | 6.21 |
| 29b | 5.88 |
| 29c | 5.38 |
| 29d | 5.48 |
| 29e | 5.93 |
| 30a | 6.09 |
| 30b | 5.99 |
| 31a | 6.46 |
| 31b | 5.73 |
| 32 | 5.44 |
| 33 | 5.43 |
| 34 | 5.31 |
| 35a | 7.15 |
| 35b | 6.70 |
| 35c | 6.53 |
| 35d | 6.48 |
| 35e | 6.71 |
| 35f | 6.05 |
| 35g | 6.12 |
| 35h | 6.36 |
| 35i | 6.01 |
| 35j | 5.76 |
| 35k | 6.56 |
| 35l | 6.76 |
| 35m | 6.81 |
| 35n | 6.05 |
| 35o | 6.04 |
| 35p | 6.15 |
| 35q | 6.63 |
| 35r | 5.98 |
| 35s | 6.16 |
| 35t | 6.46 |
| 35u | 5.74 |
| 35v | 6.70 |
| 35w | 5.74 |
| 35x | 7.01 |
| 35y | 5.70 |
| 35za | 6.00 |
| 35zb | 6.49 |
| 36a | 6.09 |
| 36b | 5.99 |
| 36c | 5.88 |
| 36d | 5.48 |
| 36e | 6.22 |
| 36f | 6.07 |
| 37a | 6.53 |
| 37b | 6.47 |
| 38a | 5.53 |
| 39a | 6.09 |
| 40a | 6.49 |
| 41a | 6.06 |
| 42a | 6.60 |
| 42b | 6.46 |
| 42c | 6.56 |
| 42d | 6.54 |
| 42e | 6.68 |
| 42f | 6.58 |
| 42g | 6.92 |
| 42h | 6.88 |
| 42i | 6.85 |
| 42j | 6.81 |

TABLE 2a

Initially Generated Data from the NanoBRET cell assay

| Example | NanoBRET cell pIC$_{50}$ |
| --- | --- |
| 1a | 5.45 |
| 1b | 5.28 |
| 4 | 5.20 |
| 15a | 5.69 |

TABLE 2b

Further Generated Data from the NanoBRET cell assay

| Example | NanoBRET cell pIC$_{50}$ |
| --- | --- |
| 1a | 5.45 |
| 1b | 5.28 |
| 4 | 5.20 |
| 15a | 5.75 |
| 15c | 5.69 |
| 15d | 5.89 |
| 15i | 5.66 |
| 15l | 5.88 |
| 15n | 5.74 |
| 17a | 5.94 |
| 17b | 5.72 |
| 20c | 5.67 |
| 20j | 5.75 |
| 21a | 5.87 |
| 21b | 5.86 |
| 28a | 6.25 |
| 28b | 5.66 |
| 30a | 5.51 |
| 35e | 5.88 |
| 35g | 5.65 |
| 35k | 5.83 |
| 35l | 5.82 |
| 35m | 6.13 |
| 35q | 5.77 |
| 35t | 5.63 |
| 35v | 5.63 |
| 35x | 5.50 |

TABLE 2c

Data Generated from the Immunofluorescence Assay

| Example | Degradation assay in SU-DHL4 cells (pDC50) |
|---|---|
| 20a | 7.11 |
| 20e | 6.49 |
| 20g | 6.29 |
| 20h | 6.30 |
| 35a | 6.92 |
| 35b | 6.35 |
| 35c | 6.75 |
| 35d | 6.59 |
| 35j | 6.43 |
| 36a | 6.35 |

TABLE 2d

Data Generated from the Cell Viability Assay

| Example | Cell proliferation assay in SU-DHL4 cells (GI$_{50}$) (µM) |
|---|---|
| 20a | 0.07 |
| 20e | 0.35 |
| 20g | 0.75 |
| 35a | 1.14 |
| 35b | 1.84 |
| 35c | 0.44 |
| 35d | 1.13 |
| 35j | 0.76 |

The following compounds were tested but did not exhibit the desired activity in the HTRF assay described in the Examples section:

1,3-dimethyl-5-((3-(trifluoromethyl)pyridin-4-yl)amino)-1,3-dihydro-2H-benzo[d]imidazol-2-one
1,3-dimethyl-5-((5-methylpyrimidin-4-yl)amino)-1,3-dihydro-2H-benzo[d]imidazol-2-one
5-((6-chloro-5-methoxypyrimidin-4-yl)amino)-1,3-dimethyl-1,3-dihydro-2H-benzo[d]imidazol-2-one
4-((1,3-dimethyl-2-oxo-2,3-dihydro-1H-benzo[d]imidazol-5-yl)amino)pyrimidine-5-carbonitrile
2-chloro-4-((1-methyl-3-(2-morpholinoethyl)-2-oxo-2,3-dihydro-1H-benzo[d]imidazol-5-yl)amino)nicotinonitrile
2-chloro-4-((3-(2-(diethylamino)ethyl)-1-methyl-2-oxo-2,3-dihydro-1H-benzo[d]imidazol-5-yl)amino)nicotinonitrile
1-methyl-3-phenethyl-5-(pyrazolo[1,5-a]pyrimidin-7-ylamino)-1,3-dihydro-2H-benzo[d]imidazol-2-one
4-((1,3-dimethyl-2-oxo-2,3-dihydro-1H-benzo[d]imidazol-5-yl)amino)-2-methylnicotinonitrile
2-chloro-4-((1-methyl-2-oxo-3-((tetrahydro-2H-pyran-4-yl)methyl)-2,3-dihydro-1H-benzo[d]imidazol-5-yl)amino)nicotinonitrile
2-chloro-4-((1-methyl-2-oxo-3-(piperidin-4-ylmethyl)-2,3-dihydro-1H-benzo[d]imidazol-5-yl)amino)nicotinonitrile
2-chloro-4-((3-(2-hydroxy-3,3-dimethylbutyl)-1-methyl-2-oxo-2,3-dihydro-1H-benzo[d]imidazol-5-yl)amino)nicotinonitrile
1,3-dimethyl-5-((5-(trifluoromethyl)-[1,2,4]triazolo[1,5-a]pyrimidin-7-yl)amino)-1,3-dihydro-2H-benzo[d]imidazol-2-one
4-((1,3-dimethyl-2-oxo-2,3-dihydro-1H-benzo[d]imidazol-5-yl)amino)-2-(trifluoromethyl)nicotinonitrile
5-((5-((2-methoxyethyl)amino)pyrazolo[1,5-a]pyrimidin-7-yl)amino)-1,3-dimethyl-1,3-dihydro-2H-benzo[d]imidazol-2-one
2-chloro-4-((3-(2-hydroxy-2-methylbutyl)-1-methyl-2-oxo-2,3-dihydro-1H-benzo[d]imidazol-5-yl)amino)nicotinonitrile
5-((2-chloro-5-(difluoromethyl)pyridin-4-yl)amino)-3-(3-hydroxy-3-methylbutyl)-1-methyl-1,3-dihydro-2H-benzo[d]imidazol-2-one
5-((2-chloro-3-(trifluoromethyl)pyridin-4-yl)amino)-3-(3-hydroxy-3-methylbutyl)-1-methyl-1,3-dihydro-2H-benzo[d]imidazol-2-one
5-((2-chloro-3-(difluoromethyl)pyridin-4-yl)amino)-3-(3-hydroxy-3-methylbutyl)-1-methyl-1,3-dihydro-2H-benzo[d]imidazol-2-one
6-((5-chloro-2-(4,4-difluoropiperidin-1-yl)pyrimidin-4-yl)amino)-1-(3-hydroxy-3-methylbutyl)-3-methyl-1,3-dihydro-2H-imidazo[4,5-c]pyridin-2-one
6-((5-chloro-2-(3-(trifluoromethyl)-1H-pyrazol-1-yl)pyridin-4-yl)amino)-1-(3-hydroxy-3-methylbutyl)-3-methyl-1,3-dihydro-2H-imidazo[4,5-c]pyridin-2-one
6-((5-chloro-2-(3-(trifluoromethyl)-1H-pyrazol-1-yl)pyrimidin-4-yl)amino)-1-(3-hydroxy-3-methylbutyl)-3-methyl-1,3-dihydro-2H-imidazo[4,5-c]pyridin-2-one
6-((2,5-dichloropyrimidin-4-yl)amino)-1-(3-hydroxy-3-methylbutyl)-3-methyl-1,3-dihydro-2H-imidazo[4,5-c]pyridin-2-one
6-((3-chloropyridin-4-yl)amino)-1-(3-hydroxy-3-methylbutyl)-3-methyl-1,3-dihydro-2H-imidazo[4,5-c]pyridin-2-one
6-((5-chloro-2-(4,4-difluoropiperidin-1-yl)pyridin-4-yl)amino)-1-(3-hydroxy-3-methylbutyl)-3-methyl-1,3-dihydro-2H-imidazo[4,5-c]pyridin-2-one
(R)-2-chloro-4-((1-methyl-3-((1-methylpyrrolidin-2-yl)methyl)-2-oxo-2,3-dihydro-1H-benzo[d]imidazol-5-yl)amino)nicotinonitrile
5-((3,5-dichloropyridin-4-yl)amino)-3-(3-hydroxy-3-methylbutyl)-1-methyl-1,3-dihydro-2H-benzo[d]imidazol-2-one
5-((6-chloroimidazo[1,2-a]pyridin-7-yl)amino)-3-(3-hydroxy-3-methylbutyl)-1-methyl-1,3-dihydro-2H-benzo[d]imidazol-2-one
2-chloro-4-((3-((3-(hydroxymethyl)oxetan-3-yl)methyl)-1-methyl-2-oxo-2,3-dihydro-1H-benzo[d]imidazol-5-yl)amino)nicotinonitrile
2-chloro-4-((3-((4-cyanotetrahydro-2H-pyran-4-yl)methyl)-1-methyl-2-oxo-2,3-dihydro-1H-benzo[d]imidazol-5-yl)amino)nicotinonitrile
2-chloro-4-((1-methyl-2-oxo-3-(piperidin-3-ylmethyl)-2,3-dihydro-1H-benzo[d]imidazol-5-yl)amino)nicotinonitrile
4-((3-(azetidin-2-ylmethyl)-1-methyl-2-oxo-2,3-dihydro-1H-benzo[d]imidazol-5-yl)amino)-2-chloronicotinonitrile
2-chloro-4-((3-((3,3-dimethylcyclobutyl)methyl)-1-methyl-2-oxo-2,3-dihydro-1H-benzo[d]imidazol-5-yl)amino)nicotinonitrile
5-((2,5-dichloropyrimidin-4-yl)amino)-3-(3,5-dihydroxy-3-methylpentyl)-1-methyl-1,3-dihydro-2H-benzo[d]imidazol-2-one
tert-butyl 3-((6-((2-chloro-3-cyanopyridin-4-yl)amino)-3-methyl-2-oxo-2,3-dihydro-1H-benzo[d]imidazol-1-yl)methyl)piperidine-1-carboxylate
(S)-2-chloro-4-((3-((1-(cyclopropylmethyl)pyrrolidin-2-yl)methyl)-1-methyl-2-oxo-2,3-dihydro-1H-benzo[d]imidazol-5-yl)amino)nicotinonitrile
2-chloro-4-((3-((2,2-dimethyltetrahydrofuran-3-yl)methyl)-1-methyl-2-oxo-2,3-dihydro-1H-benzo[d]imidazol-5-yl)amino)nicotinonitrile In an embodiment, the compounds of the invention are compounds of formula I as defined hereinbefore, with the proviso that the compound is not one of the compounds listed in the preceding paragraph.

Pharmaceutical Compositions

According to a further aspect of the invention there is provided a pharmaceutical composition which comprises a compound of the invention as defined hereinbefore, or a pharmaceutically acceptable salt, hydrate or solvate thereof, in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy is an amount sufficient to treat or prevent a proliferative condition referred to herein, slow its progression and/or reduce the symptoms associated with the condition.

The amount of active ingredient that is combined with one or more excipients to produce a single dosage form will necessarily vary depending upon the individual treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the formula I will naturally vary according to the nature and severity of the conditions, the age and sex of the animal or patient and the route of administration, according to well-known principles of medicine.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

The present invention provides compounds that function as inhibitors of BCL6.

The present invention therefore provides a method of inhibiting BCL6 activity in vitro or in vivo, said method comprising contacting a cell with an effective amount of a compound, or a pharmaceutically acceptable salt, hydrate or solvate thereof, as defined herein.

The present invention also provides a method of treating a disease or disorder in which BCL6 activity is implicated in a patient in need of such treatment, said method comprising administering to said patient a therapeutically effective amount of a compound, or a pharmaceutically acceptable salt, hydrate or solvate thereof, or a pharmaceutical composition as defined herein.

The present invention provides a method of inhibiting cell proliferation, in vitro or in vivo, said method comprising contacting a cell with an effective amount of a compound, or a pharmaceutically acceptable salt, hydrate or solvate thereof, as defined herein.

The present invention provides a method of treating a proliferative disorder in a patient in need of such treatment, said method comprising administering to said patient a therapeutically effective amount of a compound, or a pharmaceutically acceptable salt, hydrate or solvate thereof, or a pharmaceutical composition as defined herein.

The present invention provides a method of treating cancer in a patient in need of such treatment, said method comprising administering to said patient a therapeutically effective amount of a compound, or a pharmaceutically acceptable salt, hydrate or solvate thereof, or a pharmaceutical composition as defined herein.

The present invention provides a compound, or a pharmaceutically acceptable salt, hydrate or solvate thereof, or a pharmaceutical composition as defined herein for use in therapy.

The present invention provides a compound, or a pharmaceutically acceptable salt, hydrate or solvate thereof, or a pharmaceutical composition as defined herein for use in the treatment of a proliferative condition.

The present invention provides a compound, or a pharmaceutically acceptable salt, hydrate or solvate thereof, or a pharmaceutical composition as defined herein for use in the treatment of cancer. In a particular embodiment, the cancer is human cancer.

The present invention provides a compound, or a pharmaceutically acceptable salt, hydrate or solvate thereof, as defined herein for use in the inhibition of BCL6 activity (i.e. in the inhibition of BCL6 transcriptional repression and/or co-repressor binding).

Certain compounds of the present invention have been found to bind to BCL6 and initiated the degradation of BCL6. Thus, the present invention also provides a compound, or a pharmaceutically acceptable salt, hydrate or solvate thereof, as defined herein for use in the degradation of BCL6.

The present invention provides a compound, or a pharmaceutically acceptable salt, hydrate or solvate thereof, as defined herein for use in the treatment of a disease or disorder in which BCL6 activity is implicated.

The present invention provides a use of a compound, or a pharmaceutically acceptable salt, hydrate or solvate thereof, as defined herein in the manufacture of a medicament for the treatment of a proliferative condition.

The present invention provides a use of a compound, or a pharmaceutically acceptable salt, hydrate or solvate thereof, as defined herein in the manufacture of a medicament for the treatment of cancer. Suitably, the medicament is for use in the treatment of human cancers.

The present invention provides a use of a compound, or a pharmaceutically acceptable salt, hydrate or solvate thereof, as defined herein in the manufacture of a medicament for the inhibition of BCL6 activity (i.e. in the inhibition of BCL6 transcriptional repression and/or co-repressor binding).

The present invention provides a use of a compound, or a pharmaceutically acceptable salt, hydrate or solvate thereof, as defined herein in the manufacture of a medicament for the degradation BCL6.

The present invention provides a use of a compound, or a pharmaceutically acceptable salt, hydrate or solvate thereof, as defined herein in the manufacture of a medicament for the treatment of a disease or disorder in which BCL6 activity is implicated.

The term "proliferative disorder" and "proliferative condition" are used interchangeably herein and pertain to an unwanted or uncontrolled cellular proliferation of excessive or abnormal cells which is undesired, such as, neoplastic or hyperplastic growth, whether in vitro or in vivo. Examples of proliferative conditions include, but are not limited to, pre-malignant and malignant cellular proliferation, including but not limited to, malignant neoplasms and tumours, cancers (including breast cancer, non-small cell lung cancer (NSCLC) and squamous cell carcinomas (SCC) (including SCC of the head and neck, oesophagus, lung and ovary), leukemias (including acute lymphoblastic leukaemia (ALL) and chronic myeloid leukaemia (CML)), lymphomas (including acute lymphoblastic leukaemia (ALL) and chronic myeloid leukaemia (CML)), psoriasis, bone diseases, fibroproliferative disorders (e.g., of connective tissues), and atherosclerosis. Any type of cell may be treated, including but not limited to, lymphatic, blood, lung, colon, breast, ovarian, prostate, liver, pancreas, brain, and skin.

The anti-cancer effect may arise through one or more mechanisms, including but not limited to, the regulation of cell proliferation, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death).

The compound of Formula (I), or a pharmaceutically acceptable salt thereof, being an inhibitor of BCL6, has potential therapeutic uses in a variety of BCL6-mediated disease states. BCL6 expression has been linked to a variety of lymphomas (Wagner et al., *British J Haematology*, 2010, 152, 3-12). BCL6 is involved in chromosomal translocations in diffuse large B-cell lymphoma (DLBCL) and inhibitors of BCL6 have been reported to kill DLBCL cells (Cerchietti et al., *Cancer Cell*, 2010, 17, 400-411), primary low grade follicular lymphoma cells (Cardenas et al., *Clin Cancer Res*, 2017, 23(4), 885-893) and Burkitt lymphoma cells (Polo et al., *Nat Med*, 2004, 10, 1329-1335). BCL6 is required for the formation of follicular helper T cells (Hatzi et al., *J Exp Med*, 2015, 212(4), 539-553), which raises the possibility that BCL6 inhibitors may be used to treat angioimmunoblastic T-cell lymphoma (AITL), in which BCL6 is strongly expressed (Cortes & Palomero, *Curr Opin Hematol*, 2016, 23, 434-443).

BCL6 has also been implicated in leukaemia cells which have acquired resistance to tyrosine kinase inhibitors (TKIs). TKIs typically fail to eradicate leukaemia-initiating cells, which may often cause recurrence of leukaemia after initial treatment. BCL6 has been identified as an important component of the TKI drug-resistance pathway in both Ph+ acute lymphoblastic leukaemia (ALL) (Duy et al., *Nature*, 2011, 473, 384-388) and Ph+ chronic myeloid leukaemia (CML) (Hurtz et al., *J Exp Med*, 2011, 208(11), 2163-2174). Inhibitors of BCL6 may therefore be used to treat ALL and CML in combination with a TKI.

Further non-haematological, solid tumours may be treated with an inhibitor of BCL6. BCL6 is amplified in approximately 50% of breast tumours and is expressed in many breast cancer cell lines, including triple negative breast cancer cell lines (Walker et al., *Oncogene*, 2015, 34, 1073-1082). BCL6 is also important for the survival and proliferation of non-small cell lung cancer (NSCLC) cells, primarily due to repression of genes involved in DNA damage repair (Marullo et al., *Proc 107th Annual Meeting AACR*, 2016, Abstract nr 1271 and Deb et al., Cancer Res., 2017, Apr. 4, doi: 10.1158/0008-5472.CAN-15-3052). BCL6 amplification may also be prevalent in squamous cell carcinomas (SCC) (including SCC of the head & neck, oesophagus, lung and ovary). Furthermore, inhibition of BCL6 has recently been reported to be a suitable therapeutic target for glioma and glioblatoma (Xu et al., *Proc. Natl. Acad. Sci. U.S. Pat. No.* 2,017,114(15), 3981-3986).

According to a further aspect of the specification there is provided a compound of Formula (I), or a pharmaceutically acceptable salt thereof, as defined hereinbefore for use in the treatment of haematological cancers such as lymphomas (including diffuse large B-cell lymphoma (DLBCL), follicular lymphoma (FL), Burkitt lymphoma (BL) and angioimmunoblastic T-cell lymphoma (AITL)), leukaemias (including acute lymphoblastic leukaemia (ALL) and chronic myeloid leukaemia (CML)) and multiple myeloma, and of solid tumours (including glioma, breast cancer, non-small cell lung cancer (NSCLC) and squamous cell carcinomas (SCC) (including SCC of the head and neck, oesophagus, lung and ovary)).

According to a further feature of this aspect of the specification there is provided a compound of Formula (I), or a pharmaceutically acceptable salt thereof, as defined hereinbefore for use in the treatment of lymphomas, including DLBCL, FL, BL and AITL.

According to a further feature of this aspect of the specification there is provided a compound of Formula (I), or a pharmaceutically acceptable salt thereof, as defined hereinbefore for use in the treatment of DLBCL and FL.

According to a further feature of this aspect of the specification there is provided a compound of Formula (I), or a pharmaceutically acceptable salt thereof, as defined hereinbefore for use in the treatment of leukaemias, including ALL and CML.

According to a further feature of this aspect of the specification there is provided a compound of Formula (I), or a pharmaceutically acceptable salt thereof, as defined hereinbefore for use in the treatment of solid tumours, including glioma, breast cancer, NSCLC and SCC.

According to a further feature of this aspect of the specification there is provided a method for treating haematological cancers such as lymphomas (including DLBCL, FL, BL and AITL), leukaemias (including ALL and CML) and multiple myeloma, and of solid tumours (including glioma, breast cancer, NSCLC and SCC (including SCC of the head and neck, oesophagus, lung and ovary)) in a warm-blooded animal such as man that is in need of such treatment, which comprises administering an effective amount of a compound of Formula (I), or a pharmaceutically acceptable salt thereof, as defined hereinbefore.

According to a further feature of this aspect of the specification there is provided a method for treating lymphomas, including DLBCL, FL, BL and AITL, in a warm-blooded animal such as man that is in need of such treatment, which comprises administering an effective amount of a compound of Formula (I), or a pharmaceutically acceptable salt thereof, as defined hereinbefore.

According to a further feature of this aspect of the specification there is provided a method for treating DLBCL and FL, in a warm-blooded animal such as man that is in need of such treatment, which comprises administering an effective amount of a compound of Formula (I), or a pharmaceutically acceptable salt thereof, as defined hereinbefore.

According to a further feature of this aspect of the specification there is provided a method for treating leukaemias, including ALL and CML, in a warm-blooded animal such as man that is in need of such treatment, which comprises administering an effective amount of a compound of Formula (I), or a pharmaceutically acceptable salt thereof, as defined hereinbefore.

According to a further feature of this aspect of the specification there is provided a method for treating solid tumours (including glioma, breast cancer, NSCLC and SCC (including SCC of the head and neck, oesophagus, lung and ovary)), in a warm-blooded animal such as man that is in need of such treatment, which comprises administering an effective amount of a compound of Formula (I), or a pharmaceutically acceptable salt thereof, as defined hereinbefore.

According to a further feature of this aspect of the specification there is provided the use of a compound of Formula (I), or a pharmaceutically acceptable salt thereof, as defined hereinbefore in the manufacture of a medicament for use in the treatment of haematological cancers such as lymphomas (including DLBCL, FL, BL and AITL), leukaemias (including ALL and CML) and multiple myeloma, and of solid tumours (including glioma, breast cancer, NSCLC and SCC (including SCC of the head and neck, oesophagus, lung and ovary)).

According to a further feature of this aspect of the specification there is provided the use of a compound of Formula (I), or a pharmaceutically acceptable salt thereof, as defined hereinbefore in the manufacture of a medicament for use in the treatment of lymphomas, including DLBCL, FL, BL and AITL.

According to a further feature of this aspect of the specification there is provided the use of a compound of Formula (I), or a pharmaceutically acceptable salt thereof, as defined hereinbefore in the manufacture of a medicament for use in the treatment of DLBCL and FL.

According to a further feature of this aspect of the specification there is provided the use of a compound of Formula (I), or a pharmaceutically acceptable salt thereof, as defined hereinbefore in the manufacture of a medicament for use in the treatment of leukaemias, including ALL and CML.

According to a further feature of this aspect of the specification there is provided the use of a compound of Formula (I), or a pharmaceutically acceptable salt thereof, as defined hereinbefore in the manufacture of a medicament for use in the treatment of solid tumours (including glioma, breast cancer, NSCLC and SCC (including SCC of the head and neck, oesophagus, lung and ovary)).

It will be appreciated that the provisos recited in respect of the compounds of Formula I, as defined hereinabove, exclude certain compounds per se, but the use of these compounds in any of the therapeutic applications, methods and/or combination therapies defined herein is still encompassed by the present invention.

Routes of Administration

The compounds of the invention or pharmaceutical compositions comprising these compounds may be administered to a subject by any convenient route of administration, whether systemically, peripherally or topically (i.e., at the site of desired action).

Routes of administration include, but are not limited to, oral (e.g, by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Combination Therapies

The antiproliferative treatment defined hereinbefore may be applied as a sole therapy or may involve, in addition to the compound of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), steroid hormones, including progestogens (for example megestrol acetate) and corticosteroids (for example dexamethasone, prednisone and prednisolone), aromatase inhibitors (for example as anastrozole, letrozole, vorazole and exemestane) and inhibitors of 5α-reductase such as finasteride;

(iii) anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; *J. Med. Chem.*, 2004, 47, 6658-6661) and bosutinib (SKI-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. (Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (Cl 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifarnib (R115777) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy)quinazoline (AZD2171; Example 240 within WO 00/47212), compounds such as those disclosed in International Patent Applications WO97/22596, WO 97/30035, WO 97/32856 and WO 98/13354 and compounds that work by other mechanisms (for example linomide, inhibitors of integrin avp3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) an endothelin receptor antagonist, for example zibotentan (ZD4054) or atrasentan;

(viii) antisense therapies, for example those which are directed to the targets listed above, such as ISIS 2503, an anti-ras antisense;

(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (x) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In a particular embodiment, the antiproliferative treatment defined hereinbefore may involve, in addition to the compound of the invention, conventional surgery or radiotherapy or chemotherapy, wherein the chemotherapy may include one or more anti-tumour agents selected from procarbazine, carmustine, lomustine, irinotecan, temozolomide, cisplatin, carboplatin, methotrexate, etoposide, cyclophosphamide, ifosfamide, and vincristine.

In another particular embodiment, the antiproliferative treatment defined hereinbefore may involve, in addition to the compound of the invention, conventional surgery or radiotherapy or chemotherapy, wherein the chemotherapy may include one or more chemotherapeutic agents selected from a BCL-2 family inhibitor (e.g. Venetoclax and/or navitoclax), a BTK inhibitor (e.g. Ibrutinib, Acalabrutinib, Tirabrutinib (ONO/GS-4059), BGB-3111 or Spebrutinib (CC-292) or a TNF inhibitor (e.g. Lenalidomide).

Such conjoint treatment may be achieved byway of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a combination for use in the treatment of a cancer (for example a cancer involving a solid tumour) comprising a compound of the invention as defined hereinbefore, or a pharmaceutically acceptable salt, hydrate or solvate thereof, and another anti-tumour agent.

According to this aspect of the invention there is provided a combination for use in the treatment of a proliferative condition, such as cancer (for example a cancer involving a solid tumour), comprising a compound of the invention as defined hereinbefore, or a pharmaceutically acceptable salt, hydrate or solvate thereof, and any one of the anti-tumour agents listed herein above.

According to this aspect of the invention there is provided a combination for use in the treatment of a cancer comprising a compound of the invention as defined hereinbefore, or a pharmaceutically acceptable salt, hydrate or solvate thereof, and a tyrosine kinase inhibitor.

According to this aspect of the invention there is provided a combination for use in the treatment of leukaemia (such as ALL or CML) comprising a compound of the invention as defined hereinbefore, or a pharmaceutically acceptable salt, hydrate or solvate thereof, and a tyrosine kinase inhibitor.

In a further aspect of the invention there is provided a compound of the invention or a pharmaceutically acceptable salt, hydrate or solvate thereof, for use in the treatment of cancer in combination with another anti-tumour agent, optionally selected from one listed herein above.

In a further aspect of the invention there is provided a compound of the invention or a pharmaceutically acceptable salt, hydrate or solvate thereof, for use in the treatment of cancer in combination with a tyrosine kinase inhibitor, optionally selected from one listed herein above.

In a further aspect of the invention there is provided a compound of the invention or a pharmaceutically acceptable salt, hydrate or solvate thereof, for use in the treatment of leukaemia (such as ALL or CML) in combination with a tyrosine kinase inhibitor, optionally selected from one listed herein above.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

According to a further aspect of the invention there is provided a pharmaceutical composition which comprises a compound of the invention, or a pharmaceutically acceptable salt, hydrate or solvate thereof, in combination with an anti-tumour agent (optionally selected from one listed herein above), in association with a pharmaceutically acceptable diluent or carrier.

EXAMPLES

Abbreviations

APCI Atmospheric pressure chemical ionization
AcOH acetic acid
aq. Aqueous
br broad (in NMR spectrum)
n-BuLi n-butyl lithium
conc. concentrated
d doublet (in NMR spectrum)
dba dibenzylideneacetone
DCM dichloromethane
DIPEA diisopropylethylamine
DMA dimethylacetamide
DME 1,2-dimethoxyethane
DMF N,N-dimethylformamide
DMSO dimethylsulfoxide
ESI electrospray ionisation
Et2O diethyl ether
EtOAc ethyl acetate
EtOH ethanol
h hour(s)
HATU N-[(Dimethylamino)-1H-1,2,3-triazolo-[4,5-b]pyridin-1-ylmethylene]-N-methylmethanaminium hexafluorophosphate N-oxide
Hex hexane
HPLC High Performance Liquid Chromatography
HRMS high resolution mass spectrometry
IPA iso-propyl alcohol
KOAc Potassium acetate
KP-Sil Biotage KP-Sil (50 uM irregular silica)
LCMS liquid chromatography and mass spectrometry
m-CPBA 3-chloroperbenzoic acid
MeOH methanol
MeCN acetonitrile
MS mass spectrometry
Ms mesyl (methanesulfonyl)
m multiplet (in NMR spectrum)
MHz megahertz
min minute(s)
mins minute(s)
mL milliliter(s)
MP macroporous polystyrene (solid support for polymer-bound reagents, such as Biotage MP-carbonate)
m/z mass to charge ratio
NMP N-methylpyrrolidinone
NMR nuclear magnetic resonance
NOESY nuclear Overhauser effect spectroscopy
Pd/C palladium on activated charcoal
PL-HCO3 polystyrene supported hydrogen carbonate (solid supported reagent)
ppm parts per million
q quartet (in NMR spectrum)
quin. quintet (in NMR spectrum)
Rt retention time (in LCMS)
rt room temperature
s singlet (in NMR spectrum)
sat. saturated
SCX-2 strong cation exchange (e.g. Isolute® SCX-2 columns)
sex. sextet (in NMR spectrum)
Si-DMT silica bound equivalent of 2,4,6-trimercaptotriazine, commercially available e.g. from Silicycle or Biotage. Also known as Si-TMT
t triplet (in NMR spectrum)
TBAF tetrabutylammonium fluoride
TEA triethylamine
Tf triflate (trifluoromethane sulfonate)
TFA trifluoroacetic acid
TFE 2,2,2-trifluoroethanol
THF tetrahydrofuran
T3P propylphosphonic anhydride
Ts tosyl (4-toluenesulfonyl)
uL microlitres
Xantphos 4,5-Bis(diphenylphosphino)-9,9-dimethylxanthene Analytical methods: LCMS
Method T2

LC/MS and HRMS analysis was performed on an Agilent 1200 series HPLC and diode array detector coupled to a 6210 time of flight mass spectrometer with dual multimode APCI/ESI source. Analytical separation was carried out at 40° C. on a Merck Chromolith Flash column (RP-18e, 25×2 mm) using a flow rate of 1.5 mL/min in a 2 minute gradient elution with detection at 254 nm. The mobile phase was a mixture of methanol (solvent A) and water (solvent B), both containing formic acid at 0.1%. Gradient elution was as follows: 5:95 (A/B) to 100:0 (A/B) over 1.25 min, 100:0 (A/B) for 0.5 min, and then reversion back to 5:95 (A/B) over 0.05 min, finally 5:95 (A/B) for 0.2 min Method T4

As for method T2 except at 30° C., using a flow rate of 0.75 mL/min in a 4 minute gradient elution as follows: 5:95 (A/B) to 100:0 (A/B) over 2.5 min, 100:0 (A/B) for 1 min, and then reversion back to 5:95 (A/B) over 0.1 min, finally 5:95 (A/B) for 0.4 min.

Method X2

LC/MS and HRMS analysis was performed on a Waters Acquity UPLC and diode array detector coupled to a Waters G2 QToF mass spectrometer fitted with a multimode ESI/APCI source. Analytical separation was carried out at 30° C. on a Phenomenex Kinetex C18 column (30×2.1 mm, 2.6 u, 100 A) using a flow rate of 0.5 mL/min in a 2 minute gradient elution with detection at 254 nm. The mobile phase was a mixture of methanol (solvent A) and water (solvent B), both containing formic acid at 0.1%. Gradient elution was as follows: 10:90 (A/B) to 90:10 (A/B) over 1.25 min, 90:10 (A/B) for 0.5 min, and then reversion back to 10:90 (A/B) over 0.15 min, finally 10:90 (A/B) for 0.1 min.

Method X4

As for method X2, except using a flow rate of 0.3 mL/min in a 4 minute gradient elution as follows: 10:90 (A/B) to 90:10 (A/B) over 3 min, 90:10 (A/B) for 0.5 min, and then reversion back to 10:90 (A/B) over 0.3 min, finally 10:90 (A/B) for 0.2 min.

Analytical Methods: NMR

NMR data was collected on a Bruker Avance 500 spectrometer equipped with a 5 mm BBO/QNP probe or on a Bruker Avance Neo 600 spectrometer equipped with a 5 mm TCI Cryo-Probe. The $^1$H and $^{13}$C spectra were referenced to the internal deuterated solvent. All NMR data were acquired at the temperature of 298 K. All data were acquired and processed using Bruker Topspin 2.1 or Bruker Topspin 4.

The $^1$H-NMR spectrum was acquired using a Bruker standard 1D zg30 pulse sequence with 16 scans. The sweep width was 20.5 ppm, and the FID contained 64k time-domain data points.

As is well known in the art, in certain cases exchangeable (OH, NH) protons are not observed in the NMR spectrum due to exchange with deuterium (for example in methanol-d4) or are very broad and not clearly observed due to rapid exchange (for example with residual water in chloroform-d). In certain solvents, such as acetone-$d_6$, slower exchange may occur, resulting in reduced integrals for these protons.

Purification Methods

Unless otherwise described in the text, HPLC purification was carried out on an Agilent 6120 MS-Prep LC using an ACE 5 C18-PFP 250×21.2 mm column using a 15 min gradient of water:methanol (both modified with 0.1% formic acid)—for example 10-100%, 40-100%, 60-100% or 55-80%, at a flow rate of 20 mL per minute. Alternative column sizes and flow rates were used dependent on the scale of the purification, chosen from ACE 5 C18-PFP 250×10 mm (flow rate 5 mL per minute) or ACE 5 C18-PFP 250×30 mm (flow rate 40 mL per minute).

Flash column chromatography was carried out using prepacked Biotage™ SNAP KP-Sil columns. Reverse phase chromatography was carried out using a Biotage™ SNAP Ultra C18 12 g or 30 g column, using a gradient of water:methanol (both modified with 0.1% formic acid).

Example Compounds

Example 1a: 6-Chloro-5-cyano-4-[[3-(3-hydroxy-3-methyl-butyl)-1-methyl-2-oxo-benzimidazol-5-yl]amino]-N-methyl-pyridine-2-carboxamide

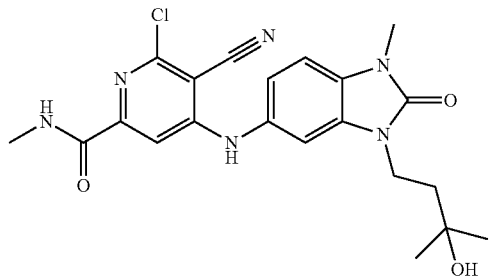 [SMILES: CNC(=O)c1cc(Nc2ccc3c(c2)n(CCC(C)(C)O)c(=O)n3C)c(C#N)c(Cl)n1]

A mixture of 4,6-dichloro-5-cyano-N-methyl-pyridine-2-carboxamide (Intermediate E1, 9 mg, 0.039 mmol), 5-amino-3-(3-hydroxy-3-methyl-butyl)-1-methyl-benzimidazol-2-one (Intermediate A1, 10 mg, 0.04 mmol) and N-ethyl-N-isopropyl-propan-2-amine (10 uL, 0.057 mmol) in NMP (0.5 mL) was heated in the microwave to 80° C. for 30 minutes. Diluted with 2:1 DMSO:MeCN (0.5 mL) and purified by preparative HPLC (ACE 5 C18-PFP column (5μ, 250×30 mm), 15 minute gradient elution from 60:40 to 0:100 water:methanol (both modified with 0.1% formic acid) at a flow rate of 40 mL/min) to give the title compound (10 mg) as a yellow solid. LCMS (Method X4) Rt 2.49 min; m/z 465.1416 expected 465.1418 for $C_{21}H_{23}ClN_6O_3Na$ [M+Na]$^+$. $^1$H NMR (500 MHz, chloroform-d) δ 7.82 (brq, J=5.0 Hz, 1H), 7.75 (s, 1H), 7.12 (s, 1H), 7.10 (d, J=1.9 Hz, 1H), 7.01 (d, J=8.2 Hz, 1H), 6.93 (dd, J=1.9, 8.2 Hz, 1H), 4.04 (t, J=7.3 Hz, 2H), 3.46 (s, 3H), 2.99 (d, J=5.4 Hz, 3H), 1.94 (t, J=7.3 Hz, 2H), 1.61 (br s, 1H,), 1.29 (s, 6H).

The following tabulated examples were prepared by a method analogous to that used for the preparation of example 1a, starting from the intermediate shown in Table 3. For examples 1b, 1e, 1i, 1j, 1k, 1n and 1o, a temperature of 120° C. was used. For example 11a temperature of 140° C. was used. For examples 1m and 1q, a temperature of 180° C. was used.

TABLE 3

Compounds prepared by a method analogous to that used for the preparation of Example 1a

| Example | Data and comments | Intermediate |
|---|---|---|
| Example 1b: 2-chloro-4-[[3-(3-hydroxy-3-methyl-butyl)-1-methyl-2-oxo-benzimidazol-5-yl]amino]-6-methyl-pyridine-3-carbonitrile | $^1$H NMR (500 MHz, chloroform-d) δ 7.04 (d, J = 8.2 Hz, 1H), 7.00 (dd, J = 8.3, 2.0 Hz, 1H), 6.93 (d, J = 2.0 Hz, 1H), 6.82 (s, 1H), 6.44 (s, 1H), 4.10-4.02 (m, 2H), 3.47 (s, 3H), 2.37 (s, 3H), 2.13 (br, 1H), 1.93-1.86 (m, 2H), 1.32 (s, 6H). LCMS (Method X4) Rt 2.54 min; m/z 400.1546 expected 400.1540 for $C_{20}H_{23}ClN_5O_2$ [M + H]$^+$. | 2,4-dichloro-6-methyl-pyridine-3-carbonitrile and 5-amino-3-(3-hydroxy-3-methyl-butyl)-1-methyl-benzimidazol-2-one (Intermediate A1) |

TABLE 3-continued

Compounds prepared by a method analogous to that used for the preparation of Example 1a

| Example | Data and comments | Intermediate |
|---|---|---|
| 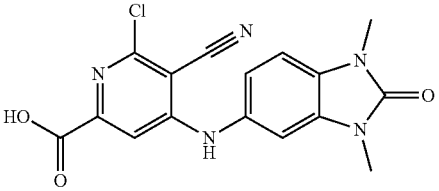 [SMILES: Cn1c(=O)n(C)c2cc(Nc3cc(C(=O)O)nc(Cl)c3C#N)ccc21]<br>Example 1c: 6-chloro-5-cyano-4-[(1,3-dimethyl-2-oxo-benzimidazol-5-yl)amino]pyridine-2-carboxylic acid | $^1$H NMR (500 MHz, DMSO-d6) δ 13.7 (br, 1H), 9.76 (br s, 1H), 7.23 (d, J = 8.2 Hz, 1H), 7.19 (s, 1H), 7.17 (d, J = 1.9 Hz, 1H), 7.03 (dd, J = 1.9, 8.2 Hz, 1H), 3.36 (s, 3H), 3.31 (s, 3H). LCMS (Method X4) Rt 2.04 min; m.z 358.0709 expected 358.0707 for $C_{16}H_{13}ClN_5O_3$ [M + H]+ | 5-amino-1,3-dimethyl-benzimidazol-2-one and 4,6-dichloro-5-cyano-pyridine-2-carboxylic acid. |
| 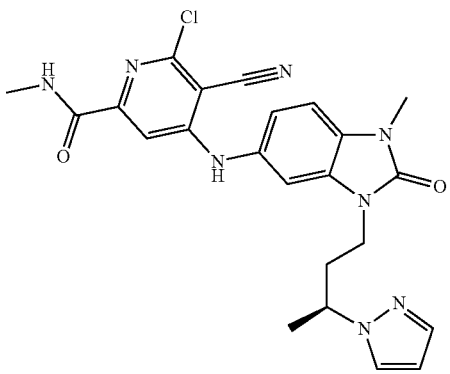 [SMILES: CNC(=O)c1cc(Nc2ccc3c(c2)n(CC[C@H](C)n2cccn2)c(=O)n3C)c(C#N)c(Cl)n1]<br>Example 1d: 6-chloro-5-cyano-N-methyl-4-[[1-methyl-2-oxo-3-[(3S)-3-pyrazol-1-ylbutyl]benzimidazol-5-yl]amino]pyridine-2-carboxamide | $^1$H NMR (500 MHz, chloroform-d) δ 7.78 (br q, J = 5.2 Hz, 1H), 7.50 (d, J = 1.8 Hz, 1H), 7.49 (d, J = 2 Hz, 1H), 7.48 (s, 1H), 7.03 (s, 1H), 7.00 (d, J = 8.2 Hz, 1H), 6.97 (dd, J = 8.2, 1.8 Hz, 1H), 6.66 (d, J = 2 Hz, 1H), 6.20 (t, J = 2 Hz, 1H), 4.42 (m, 1H), 3.89 (m, 1H), 3.60 (m, 1H), 3.46 (s, 3H), 2.98 (d, J = 5.2 Hz, 3H), 2.49-2.39 (m, 1H), 2.28-2.17 (m, 1H), 1.54 (d, J = 6.7 Hz, 3H). LCMS (Method X2) Rt 1.23 min; m/z 479.1713 expected 479.1711 for $C_{23}H_{24}N_8O_2Cl$ [M + H]$^+$. | 4,6-dichloro-5-cyano-N-methyl-pyridine-2-carboxamide (Intermediate E1) and Intermediate A2 5-amino-1-methyl-3-[(3S)-3-pyrazol-1-ylbutyl]benzimidazol-2-one |
| 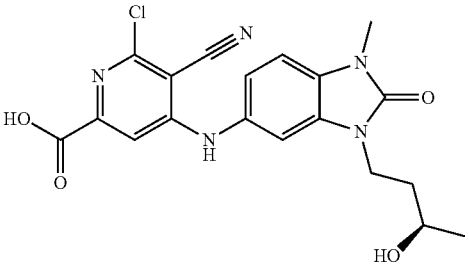 [SMILES: C[C@@H](O)CCn1c(=O)n(C)c2ccc(Nc3cc(C(=O)O)nc(Cl)c3C#N)cc21]<br>Example 1e: 6-chloro-5-cyano-4-[[3-[(3R)-3-hydroxybutyl]-1-methyl-2-oxo-benzimidazol-5-yl]amino]pyridine-2-carboxylic acid | $^1$H NMR (500 MHz, Methanol-d$_4$) δ 7.41 (s, 1H), 7.27 (d, J = 8.2 Hz, 1H) overlapping with 7.27 (d, J = 2.0 Hz, 1H), 7.13 (dd, J = 8.2, 2 Hz, 1H), 4.04 (m, 2H), 3.77 (m, 1H), 3.49 (s, 3H), 1.89 (m, 1H), 1.77 (m, 1H), 1.20 (m, 3H). LCMS (Method X4) Rt 2.15 min; m/z 416.1138 expected 416.1125 for $C_{19}H_{19}ClN_5O_4$ [M + H]$^+$. | 4,6-dichloro-5-cyano-pyridine-2-carboxylic acid and Intermediate A3c: 5-amino-3-[(3R)-3-hydroxybutyl]-1-methyl-benzimidazol-2-one |
| 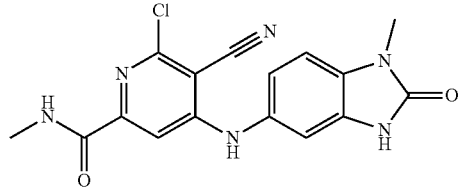 [SMILES: CNC(=O)c1cc(Nc2ccc3c(c2)[nH]c(=O)n3C)c(C#N)c(Cl)n1]<br>Example 1f: 6-chloro-5-cyano-N-methyl-4-[(1-methyl-2-oxo-3H-benzimidazol-5-yl)amino]pyridine-2-carboxamide | $^1$H NMR (500 MHz, DMSO-d$_6$) δ 10.99 (s, 1H), 9.69 (s, 1H), 8.62 (q, J = 4.8 Hz, 1H), 7.22 (s, 1H), 7.16 (d, J = 8.2 Hz, 1H), 6.97 (dd, J = 8.2, 2.0 Hz, 1H), 6.93 (d, J = 2 Hz, 1H), 3.31 (3H, s), 2.73 (d, J = 4.8 Hz, 3H). LCMS (Method X4) Rt 2.23 min; m/z 357.0868 expected 357.0867 [M + H]$^+$ for $C_{16}H_{14}ClN_6O_2$. | 4,6-dichloro-5-cyano-N-methyl-pyridine-2-carboxamide (Intermediate E1) and 6-amino-3-methyl-1H-benzimidazol-2-one. |

TABLE 3-continued

Compounds prepared by a method analogous to that used for the preparation of Example 1a

| Example | Data and comments | Intermediate |
| --- | --- | --- |
| Example 1g: 6-chloro-5-cyano-4-[[3-(3-hydroxy-3-methyl-butyl)-2-oxo-1-(tetrahydropyran-4-ylmethyl)benzimidazol-5-yl]amino]-N-methyl-pyridine-2-carboxamide | $^1$H NMR (500 MHz, DMSO-d6) δ 9.77 (s, 1H), 8.63 (q, J = 4.8 Hz, 1H), 7.31 (d, J = 8.4 Hz, 1H), 7.29 (s, 1H), 7.13 (d, J = 2.0 Hz, 1H), 7.01 (dd, J = 8.3, 2.0 Hz, 1H), 4.41 (s, 1H), 3.92-3.85 (m, 2H), 3.86-3.79 (m, 2H), 3.75 (d, J = 7.2 Hz, 2H), 3.23 (m, 2H), 2.73 (d, J = 4.8 Hz, 3H), 2.04 (m, 1H), 1.74-1.66 (m, 2H), 1.49 (m, 2H), 1.36-1.20 (m, 2H), 1.14 (s, 6H, 2 × Me). LCMS (Method X4) Rt 2.68 min; m/z 527.2175 expected 527.2174 for $C_{26}H_{32}ClN_6O_4$ [M + H]$^+$. | 4,6-dichloro-5-cyano-N-methyl-pyridine-2-carboxamide (Intermediate E1) and 5-amino-3-(3-hydroxy-3-methyl-butyl)-1-(tetrahydropyran-4-ylmethyl)benzimidazol-2-one (Intermediate A4A) |
| Example 1h: Ethyl 7-[[3-(3-hydroxy-3-methyl-butyl)-1-methyl-2-oxo-benzimidazol-5-yl]amino]pyrazolo[1,5-a]pyrimidine-5-carboxylate | $^1$H NMR (500 MHz, chloroform-d) δ 8.33 (s, 1H), 8.18 (d, J = 2.4 Hz, 1H), 7.22 (d, J = 1.9 Hz, 1H), 7.13 (dd, J = 8.2, 2.0 Hz, 1H), 7.11 (s, 1H), 7.07 (d, J = 8.2 Hz, 1H), 6.84 (d, J = 2.4 Hz, 1H), 4.49 (q, J = 7.1 Hz, 2H), 4.13-4.06 (m, 2H), 3.49 (s, 3H), 1.98-1.91 (m, 2H), 1.44 (t, J = 7.1 Hz, 3H), 1.32 (s, 6H). OH not clearly observed. LCMS (Method X4) Rt 2.53 min; m/z 439.2086 expected 439.2094 for $C_{22}H_{27}N_6O_4$ [M + H]$^+$. | 5-amino-3-(3-hydroxy-3-methyl-butyl)-1-methyl-benzimidazol-2-one (Intermediate A1) and ethyl 7-chloropyrazolo[1,5-a]pyrimidine-5-carboxylate |
| Example 1i: 2-chloro-4-[[3-(3-hydroxy-3-methyl-butyl)-1-methyl-2-oxo-benzimidazol-5-yl]amino]pyridine-3-carbonitrile | $^1$H NMR (500 MHz, DMSO-d$_6$) δ 9.46 (s, 1H), 8.00 (d, J = 6.1 Hz, 1H), 7.20 (d, J = 8.3 Hz, 1H), 7.11 (d, J = 1.9 Hz, 1H), 7.00 (dd, J = 8.3, 2.0 Hz, 1H), 6.68 (d, J = 6.2 Hz, 1H), 4.44 (s, 1H), 3.92-3.85 (m, 2H), 3.34 (s, 3H), 1.73-1.66 (m, 2H), 1.15 (s, 6H). LCMS (Method X4) Rt 2.40 min; m/z 386.1388 expected 386.1384 for $C_{19}H_{21}ClN_5O_2$ [M + H]$^+$. | 5-amino-3-(3-hydroxy-3-methyl-butyl)-1-methyl-benzimidazol-2-one (Intermediate A1) and 2,4-dichloropyridine-3-carbonitrile |

TABLE 3-continued

Compounds prepared by a method analogous to that used for the preparation of Example 1a

| Example | Data and comments | Intermediate |
|---|---|---|
| 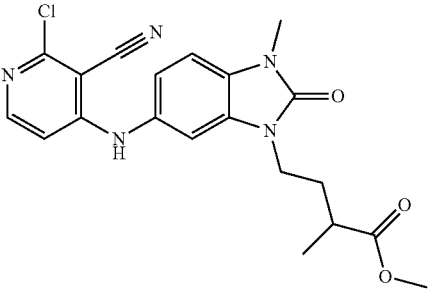<br>Example 1j: Methyl 4-[6-[(2-chloro-3-cyano-4-pyridyl)amino]-3-methyl-2-oxo-benzimidazol-1-yl]-2-methyl-butanoate | $^1$H NMR (500 MHz, methanol-$d_4$) δ 7.95 (d, J = 6.3 Hz, 1 H), 7.22 (d, J = 8.3 Hz, 1 H), 7.16 (d, J = 1.9 Hz, 1 H), 7.08 (dd, J = 8.3, 1.9 Hz, 1 H), 6.72 (d, J = 6.3 Hz, 1 H), 3.95 (t, J = 7.2 Hz, 2 H), 3.54 (s, 3 H), 3.45 (s, 3 H), 2.57-2.49 (m, 1 H), 2.19-2.10 (m, 1 H), 1.88-1.79 (m, 1 H), 1.21 (d, J = 7.1 Hz, 3 H). LCMS (Method T4) Rt 2.68 min; m/z 414.1306, expected 414.1327 for $C_{20}H_{21}ClN_5O_3^+$ [M + H]$^+$. | 2,4-dichloropyridine-3-carbonitrile and methyl 4-(6-amino-3-methyl-2-oxo-benzimidazol-1-yl)-2-methyl-butanoate (Intermediate A3a) |
| 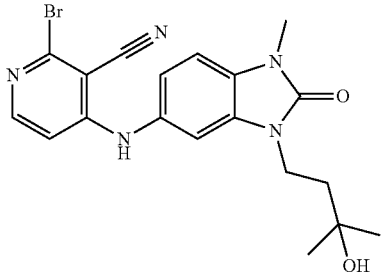<br>Example 1k: 2-bromo-4-[[3-(3-hydroxy-3-methyl-butyl)-1-methyl-2-oxo-benzimidazol-5-yl]amino]pyridine-3-carbonitrile | $^1$H NMR (500 MHz, DMSO-$d_6$) δ 9.43 (s, 1H), 7.96 (d, J = 6.2 Hz, 1H), 7.19 (d, J = 8.3 Hz, 1H), 7.10 (d, J = 2.0 Hz, 1H), 6.99 (dd, J = 8.2, 1.9 Hz, 1H), 6.69 (d, J = 6.1 Hz, 1H), 4.44 (s, 1H), 3.92-3.84 (m, 2H), 3.34 (s, 3H), 1.73-1.65 (m, 2H), 1.15 (s, 6H). LCMS (Method X4) Rt 2.43 min; m/z 430.0874 expected 430.0879 for $C_{19}H_{21}BrN_5O_2$ [M + H]$^+$. | 5-amino-3-(3-hydroxy-3-methyl-butyl)-1-methyl-benzimidazol-2-one (Intermediate A1) and 2,4-dibromopyridine-3-carbonitrile |
| 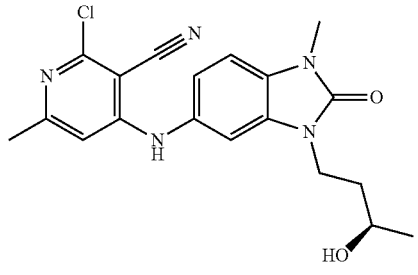 [SMILES: Cc1cc(Nc2ccc3c(c2)n(CC[C@@H](C)O)c(=O)n3C)c(C#N)c(Cl)n1]<br>Example 1l: 2-chloro-4-[[3-[(3R)-3-hydroxybutyl]-1-methyl-2-oxo-benzimidazol-5-yl]amino]-6-methyl-pyridine-3-carbonitrile | $^1$H NMR (500 MHz, chloroform-d) δ 7.07 (d, J = 8.2 Hz, 1H), 7.02 (dd, J = 8.3, 2.0 Hz, 1H), 6.95 (d, J = 1.9 Hz, 1H), 6.80 (s, 1H), 6.45 (s, 1H), 4.25 (ddd, J = 15, 11.0, 4.5 Hz, 1H), 3.89 (ddd, J = 15, 5.5, 4 Hz, 1H), 3.72 (dqd, J = 10.3, 6.3, 2.7 Hz, 1H), 3.49 (s, 3H), 3.3 (br, 1H, OH), 2.37 (s, 3H), 1.89 (dddd, J = 14, 11, 5.5, 2.7 Hz, 1H), 1.71 (ddt, J = 14, 10.3, 4 Hz, 1H), 1.23 (d, J = 6.3 Hz, 3H). LCMS (Method X2) Rt 1.19 min; m/z 386.1367 expected 386.1384 for $C_{19}H_{21}ClN_5O_2$ [M + H]$^+$. | 2,4-dichloro-6-methyl-pyridine-3-carbonitrile and Intermediate A3c: 5-amino-3-[(3R)-3-hydroxybutyl]-1-methyl-benzimidazol-2-one |
| 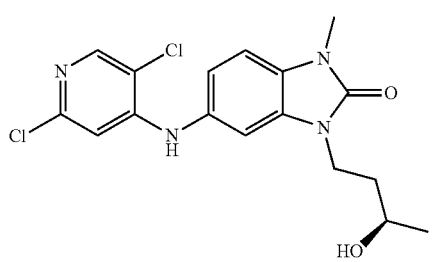 [SMILES: C[C@@H](O)CCn1c(=O)n(C)c2ccc(Nc3cc(Cl)ncc3Cl)cc21]<br>Example 1m: 5-[(2,5-dichloro-4-pyridyl)amino]-3-[(3R)-3-hydroxybutyl]-1-methyl-benzimidazol-2-one | $^1$H NMR (500 MHz, chloroform-d) δ 8.16 (s, 1H), 7.08 (d, J = 8.2 Hz, 1H), 7.04 (dd, J = 8.2, 1.9 Hz, 1H), 6.99 (d, J = 1.9 Hz, 1H), 6.71 (s, 1H), 6.58 (s, 1H), 4.27 (ddd, J = 14.8, 11.2, 4.4 Hz, 1H), 3.89 (ddd, J = 14.8, 5.4, 3.7 Hz, 1H), 3.73 (dqd, J = 10.3, 6.2, 2.7 Hz, 1H), 3.50 (s, 3H), 3.20 (br, 1H), 1.90 (dddd, J = 14, 11.2, 5.4, 2.7 Hz, 1H), 1.72 (dddd, J = 14, 10.3, 4.4, 3.7 Hz, 1H), 1.24 (d, J = 6.2 Hz, 3H). LCMS (Method X4) Rt 2.58 min; m/z 381.0888 expected 381.0885 for $C_{17}H_{19}Cl_2N_4O_2$ [M + H]$^+$. | 2,4,5-trichloropyridine and Intermediate A3c: 5-amino-3-[(3R)-3-hydroxybutyl]-1-methyl-benzimidazol-2-one |

TABLE 3-continued

Compounds prepared by a method analogous to that used for the preparation of Example 1a

| Example | Data and comments | Intermediate |
|---|---|---|
| Example 1n: 5-[(2,5-dichloropyrimidin-4-yl)amino]-3-(3-hydroxy-3-methyl-butyl)-1-methyl-benzimidazol-2-one | $^1$H NMR (500 MHz, DMSO-d6) δ 9.57 (s, 1H), 8.34 (s, 1H), 7.36 (d, J = 1.9 Hz, 1H), 7.20 (dd, J = 8.3, 1.9 Hz, 1H), 7.15 (d, J = 8.4 Hz, 1H), 4.44 (s, 1H), 3.92-3.85 (m, 2H), 3.33 (s, 3H), 1.76-1.69 (m, 2H), 1.17 (s, 6H). LCMS (Method X4) Rt 2.56 min; m/z 396.1003 expected 396.0994 for $C_{17}H_{20}Cl_2N_5O_2$ [M + H]$^+$. | 5-amino-3-(3-hydroxy-3-methyl-butyl)-1-methyl-benzimidazol-2-one (Intermediate A1) and 2,4,5-trichloropyrimidine |
| Example 1o: Ethyl 7-[[3-[(3R)-3-hydroxybutyl]-1-methyl-2-oxo-benzimidazol-5-yl]amino]pyrazolo[1,5-a]pyrimidine-5-carboxylate | $^1$H NMR (500 MHz, chloroform-d) δ 8.34 (s, 1H), 8.16 (d, J = 2.4 Hz, 1H), 7.30 (d, J = 2.0 Hz, 1H), 7.12 (dd, J = 8.3, 2.0 Hz, 1H), 7.10 (s, 1H), 7.07 (d, J = 8.2 Hz, 1H), 6.82 (d, J = 2.4 Hz, 1H), 4.49 (q, J = 7.1 Hz, 2H), 4.21 (ddd, J = 15, 11.5, 4 Hz, 1H), 3.95 (ddd, J = 15, 5, 4 Hz, 1H), 3.77 (dqd, J = 10.5, 6, 2.5 Hz, 1H), 3.49 (s, 3H), 1.96 (dddd, J = 14, 11.5, 5, 2.5 Hz, 1H), 1.73 (ddt, J = 14, 10.5, 4 Hz, 1H), 1.44 (t, J = 7.1 Hz, 3H), 1.25 (d, J = 6.2 Hz, 3H). OH not clearly observed. LCMS (Method X4) Rt 2.51 min; m/z 425.1918 expected 425.1937 for $C_{21}H_{25}N_6O_4$ [M + H]$^+$. | ethyl 7-chloropyrazolo[1,5-a]pyrimidine-5-carboxylate and Intermediate A3c: 5-amino-3-[(3R)-3-hydroxybutyl]-1-methyl-benzimidazol-2-one |
| Example 1p: 4-chloro-6-[[3-(3-hydroxy-3-methyl-butyl)-1-methyl-2-oxo-benzimidazol-5-yl]amino]-pyrimidine-5-carbonitrile | LCMS (Method X4) Rt 2.34 min observed 387.1340 expected 387.1336 for $C_{18}H_{20}ClN_6O_2$ [M + H]$^+$. $^1$H NMR (500 MHz, DMSO-d$_6$) δ 10.25 (br s, 1H), 8.49 (s, 1H), 7.23 (s, 1H), 7.14 (s, 2H), 4.45 (br s, 1H), 3.93-3.81 (m, 2H), 3.33 (s, 3H), 1.75-1.64 (m, 2H), 1.16 (m, 6H). | 5-amino-3-(3-hydroxy-3-methyl-butyl)-1-methyl-benzimidazol-2-one (Intermediate A1) and 4,6-dichloropyrimidine-5-carbonitrile. |

TABLE 3-continued

Compounds prepared by a method analogous to that used for the preparation of Example 1a

| Example | Data and comments | Intermediate |
|---|---|---|
| 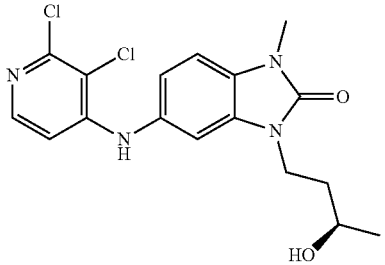 [SMILES: C[C@@H](O)CCn1c(=O)n(C)c2ccc(Nc3ccnc(Cl)c3Cl)cc21]<br>Example 1q: 5-[(2,3-dichloro-4-pyridyl)amino]-3-[(3R)-3-hydroxybutyl]-1-methyl-benzimidazol-2-one | $^1$H NMR (500 MHz, chloroform-d) δ 7.92 (d, J = 5.7 Hz, 1H), 7.06 (d, J = 8 Hz, 1H), 7.04 (dd, J = 8, 1.8 Hz, 1H), 6.97 (d, J = 1.8 Hz, 1H), 6.68 (br s, 1H), 6.66 (d, J = 5.7 Hz, 1H), 4.27 (m, 1H), 3.87 (m, 1H), 3.73 (m, 1H), 3.50 (s, 3H), 1.89 (m, 1H), 1.71 (m, 1H), 1.23 (d, J = 6.3 Hz, 3H). OH not clearly observed. NOE observed between benzimidazolone 4-position and pyridine 5-position supporting regiochemical assignment. LCMS (Method X2) Rt 1.23 min; m/z 381.0875 expected 381.0885 for $C_{17}H_{19}N_4O_2Cl_2$ [M + H]$^+$. | 2,3,4-trichloropyridine and Intermediate A3c: 5-amino-3-[(3R)-3-hydroxybutyl]-1-methyl-benzimidazol-2-one |

Example 1r: Ethyl 3-fluoro-7-((3-(2-hydroxybutyl)-1-methyl-2-oxo-2,3-dihydro-1H-benzo[d]imidazol-5-yl)amino)pyrazolo[1,5-a]pyrimidine-5-carboxylate

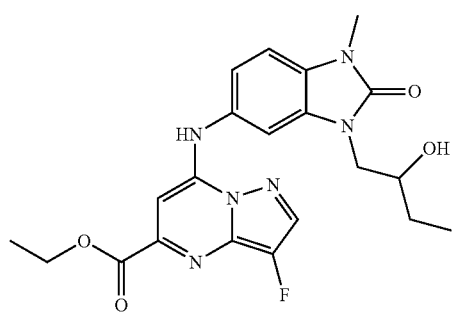 [SMILES: CCOC(=O)c1cc(Nc2ccc3c(c2)n(CC(O)CC)c(=O)n3C)n2ncc(F)c2n1]

Step 1: Ethyl 7-chloro-3-fluoropyrazolo[1,5-a]pyrimidine-5-carboxylate

To a suspension of ethyl 7-chloropyrazolo[1,5-a]pyrimidine-5-carboxylate (0.09 g, 0.4 mmol) in water (9 mL) was added Selectfluor (0.124 g, 0.35 mmol) and the resulting mixture heated to 50° C. for 24 h, then 60° C. for 18 h. Added acetonitrile (6 mL) until all in solution. Added further Selectfluor (0.124 g, 0.35 mmol) and heated to 67° C. overnight. Allowed to cool to room temperature, then added saturated sodium bicarbonate (6 mL) and extracted with DCM. Combined organics were passed through a phase separator cartridge and evaporated under reduced pressure, then purified by flash column chromatography (10 g KP-SIL, 5-15% ethyl acetate in cyclohexane) to give a yellow gummy solid (20 mg) containing both the desired ethyl 7-chloro-3-fluoropyrazolo[1,5-a]pyrimidine-5-carboxylate and also ethyl 3,7-dichloropyrazolo[1,5-a]pyrimidine-5-carboxylate.

Step 2: Ethyl 3-fluoro-7-((3-(2-hydroxybutyl)-1-methyl-2-oxo-2,3-dihydro-1H-benzo[d]imidazol-5-yl)amino)pyrazolo[1,5-a]pyrimidine-5-carboxylate The mixture from Step 1 was used to prepare the title compound using a method analogous to that used for the preparation of Example 1a, with heating at 120° C., using Intermediate A5: 5-amino-3-(2-hydroxybutyl)-1-methyl-1H-benzo[d]imidazol-2(3H)-one. LCMS (Method T4) Rt 2.71 min; m/z 443.1805 expected 443.1838 for $C_{21}H_{24}FN_6O_4$ [M+H]$^+$. $^1$H NMR (500 MHz, chloroform-d) δ 8.19 (s, 1H), 8.09 (d, J=3.6 Hz, 1H), 7.33 (d, J=1.9 Hz, 1H), 7.13 (dd, J=8, 1.9 Hz, 1H), 7.08 (d, J=8.0 Hz, 1H) overlapping with 7.07 (s, 1H), 4.48 (q, J=7.1 Hz, 2H), 4.06 (dd, J=2.5, 14.3 Hz, 1H), 3.98 (br m, 1H), 3.90 (dd, J=14.3, 7.3 Hz, 1H), 3.51 (s, 3H), 2.79 (br s, 1H), 1.72-1.53 (m, 2H), 1.46 (t, J=7.2 Hz, 3H), 1.07 (t, J=7.4 Hz, 3H). $^{19}$F NMR (471 MHz, chloroform-d) δ −179.0 (d, J=3.5 Hz).

Example 2a: Methyl 6-chloro-5-cyano-4-[[3-(4-methoxy-3-methyl-4-oxo-butyl)-1-methyl-2-oxo-benzimidazol-5-yl]amino]pyridine-2-carboxylate

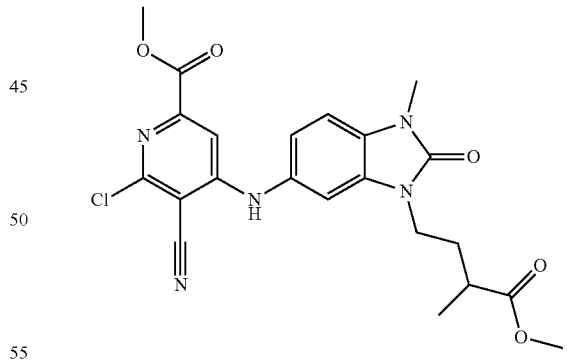

Sulfuric acid (1 drop) was added to a stirred solution of 6-chloro-5-cyano-4-[[3-(4-methoxy-3-methyl-4-oxo-butyl)-1-methyl-2-oxo-benzimidazol-5-yl]amino]pyridine-2-carboxylic acid (Example 3a, 12 mg, 0.025 mmol) in dry methanol (1 mL). The reaction mixture was stirred at rt for 21 h, during which a white precipitate formed. The precipitate was filtered, washed with diethyl ether (6 mL) and allowed to air dry overnight, affording the title compound as an off-white solid (6 mg). LCMS (Method T4) Rt 2.71 min; m/z 472.1372, expected 472.1382 for $C_{22}H_{23}ClN_5O_5^+$ [M+H]$^+$; $^1$H NMR (500 MHz, DMSO-d$_6$) δ 9.91 (br s, 1H), 7.29 (s, 1H), 7.23 (d, J=8.3 Hz, 1H), 7.21 (d, J=1.8 Hz, 1H), 7.04 (dd, J=8.3, 1.8 Hz, 1H), 3.84 (t, J=7.0 Hz, 2H), 3.79 (s, 3H), 3.50 (s, 3H), 3.35 (s, 3H), 2.49-2.45 (m, 1H), 2.03-1.94 (m, 1H), 1.74-1.65 (m, 1H), 1.13 (d, J=7.1 Hz, 3H).

Example 2b: Ethyl 6-chloro-5-cyano-4-[[3-(4-methoxy-3-methyl-4-oxo-butyl)-1-methyl-2-oxo-benzimidazol-5-yl]amino]pyridine-2-carboxylate

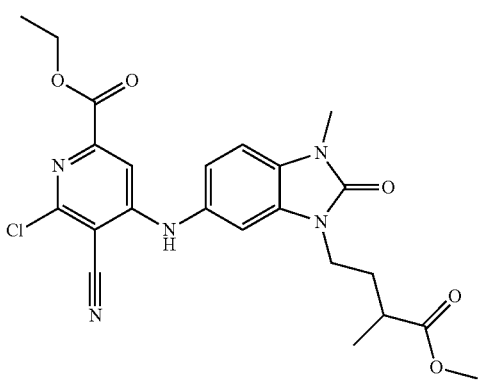 [SMILES: CCOC(=O)c1cc(Nc2ccc3c(c2)n(CCC(C)C(=O)OC)c(=O)n3C)c(C#N)c(Cl)n1]

Prepared by a method analogous to that used for the preparation of Example 2a. LCMS (Method T4) Rt 2.82 min; m/z 486.1530, expected 486.1539 for $C_{23}H_{25}ClN_5O_5^+$ [M+H]$^+$; $^1$H NMR (500 MHz, chloroform-d) δ 7.44 (s, 1H), 7.06 (br s, 1H), 7.05-7.03 (m, 1H), 7.01-6.99 (m, 2H), 4.40 (q, J=7.1 Hz, 2H), 4.00-3.93 (m, 1H), 3.91-3.85 (m, 1H), 3.66 (s, 3H), 3.47 (s, 3H), 2.58-2.50 (m, 1H), 2.18-2.10 (m, 1H), 1.88-1.81 (m, 1H), 1.37 (t, J=7.1 Hz, 3H), 1.26 (d, J=7.1 Hz, 3H).

Example 2c: Isopropyl 6-chloro-5-cyano-4-[[3-(4-methoxy-3-methyl-4-oxo-butyl)-1-methyl-2-oxo-benzimidazol-5-yl]amino]pyridine-2-carboxylate

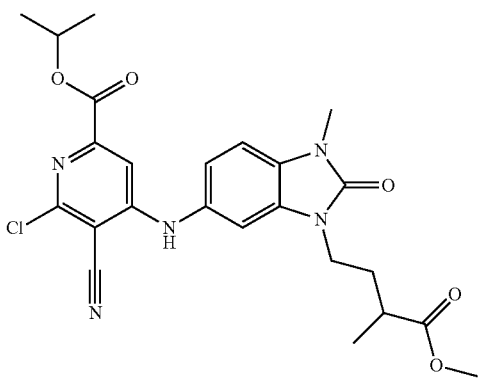 [SMILES: COC(=O)C(C)CCn1c(=O)n(C)c2ccc(Nc3cc(C(=O)OC(C)C)nc(Cl)c3C#N)cc21]

Prepared by a method analogous to that used for the preparation of Example 2a. Purification by HPLC (ACE 5 C18-PFP 250×21.2 mm column; 15 min gradient of 60:40 to 0:100 water:methanol (both modified with 0.1% formic acid); flow rate 20 mLmin$^{-1}$; Agilent 6120 MS-Prep LC) afforded the title compound. LCMS (Method T4) Rt 2.97 min; m/z 500.1687, expected 500.1695 for $C_{24}H_{27}ClN_5O_5^+$ [M+H]$^+$; $^1$H NMR (500 MHz, chloroform-d) δ 7.43 (s, 1H), 7.06-7.02 (m, 2H), 7.01-6.98 (m, 2H), 5.19 (pent, J=6.3 Hz, 1H), 4.00-3.92 (m, 1H), 3.91-3.84 (m, 1H), 3.66 (s, 3H), 3.47 (s, 3H), 2.59-2.51 (m, 1H), 2.18-2.09 (m, 1H), 1.89-1.81 (m, 1H), 1.36 (d, J=6.3 Hz, 6H), 1.26 (d, J=7.1 Hz, 3H).

Example 2d: Ethyl 6-chloro-5-cyano-4-[[3-[(3R)-3-hydroxybutyl]-1-methyl-2-oxo-benzimidazol-5-yl]amino]pyridine-2-carboxylate

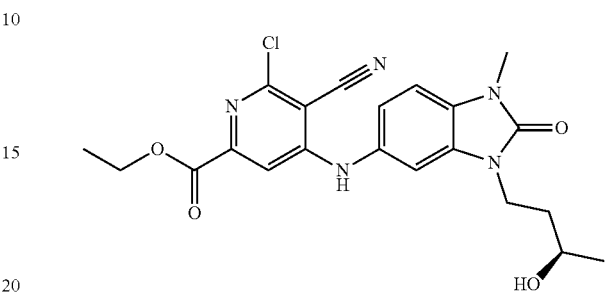

Prepared by a method analogous to that used for the preparation of Example 2a, starting from 6-chloro-5-cyano-4-[[3-[(3R)-3-hydroxybutyl]-1-methyl-2-oxo-benzimidazol-5-yl]amino]pyridine-2-carboxylic acid (Example 1e). LCMS (Method X4) Rt 2.55 min; m/z 444.1437 expected 444.1438 for $C_{21}H_{23}ClN_5O_4$ [M+H]$^+$. $^1$H NMR (500 MHz, chloroform-d) δ 7.53 (s, 1H), 7.15 (s, 1H), 7.10-7.04 (m, 2H), 7.00 (dd, J=8.3, 2.0 Hz, 1H), 4.43 (q, J=7.1 Hz, 2H), 4.20 (ddd, J=15, 11.3, 4 Hz, 1H), 3.92 (ddd, J=15, 5.3, 4 Hz, 1H), 3.72 (dqd, J=10.4, 6.2, 2.7 Hz, 1H), 3.49 (s, 3H), 3.45-3.25 (br, 1H, OH), 1.95 (dddd, J=14.0, 11.3, 5.3, 2.7 Hz, 1H), 1.71 (ddt, J=14, 10.4, 4 Hz, 1H), 1.39 (t, J=7.1 Hz, 3H), 1.24 (d, J=6.2 Hz, 3H).

Example 3a: 6-Chloro-5-cyano-4-[[3-(4-methoxy-3-methyl-4-oxo-butyl)-1-methyl-2-oxo-benzimidazol-5-yl]amino]pyridine-2-carboxylic acid

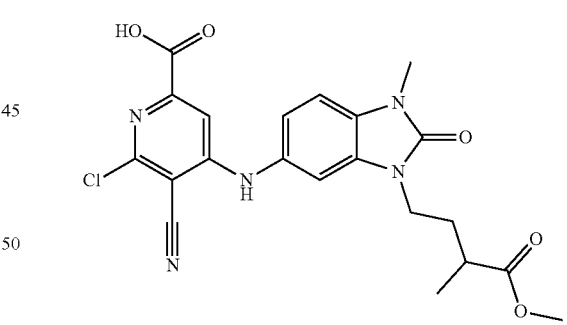

A microwave vial (0.5-2.0 mL volume) was charged with Intermediate A3a methyl 4-(6-amino-3-methyl-2-oxo-benzimidazol-1-yl)-2-methyl-butanoate (34 mg, 0.12 mmol) and 4,6-dichloro-5-cyano-pyridine-2-carboxylic acid (25 mg, 0.11 mmol). The reaction vial was flushed with Ar, sealed with a cap and then further flushed with Ar. Anhydrous DMF (1.1 mL) was added followed by DIPEA (43.00 uL, 0.25 mmol). The reaction mixture was heated at 80° C. under microwave irradiation for 90 min. The reaction mixture was allowed to cool to rt. The reaction mixture was diluted with a 1:1 mixture of DMSO:MeCN (0.3 mL) and purification by HPLC (ACE 5 C18-PFP 250×30 mm column; 15 min gradient of 60:40 to 0:100 water:methanol (both modified with 0.1% formic acid); flow rate 40 mL min⁻¹; Agilent 6120 MS-Prep LC) affording the title compound as a yellow solid (13 mg, 25%). LCMS (Method T4) Rt 2.58 min; m/z 458.1216, expected 458.1226 for $C_{21}H_{21}ClN_5O_5^+$ [M+H]⁺; ¹H NMR (500 MHz, methanol-$d_4$) δ 7.39 (s, 1H), 7.24 (d, J=8.3 Hz, 1H), 7.21 (d, J=1.9 Hz, 1H), 7.11 (dd, J=8.3, 1.9 Hz, 1H), 4.00-3.92 (m, 2H), 3.54 (s, 3H), 3.46 (s, 3H), 2.57-2.49 (m, 1H), 2.19-2.10 (m, 1H), 1.87-1.80 (m, 1H), 1.20 (d, J=7.1 Hz, 3H).

Example 3b: Methyl 3-[6-[(2-chloro-3-cyano-4-pyridyl)amino]-3-methyl-2-oxo-benzimidazol-1-yl]-2-methyl-propanoate

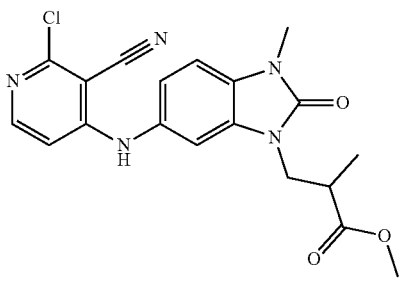 [SMILES: COC(=O)C(C)Cn1c(=O)n(C)c2ccc(Nc3ccnc(Cl)c3C#N)cc21]

Prepared by a method analogous to that used for the preparation of Example 3a, with heating at 120° C., starting from 2,4-dichloropyridine-3-carbonitrile and methyl 3-(6-amino-3-methyl-2-oxo-benzimidazol-1-yl)-2-methyl-propanoate (Intermediate A3b). LCMS (Method T4) Rt 2.62 min; m/z 400.1162, expected 400.1171 for $C_{19}H_{19}ClN_5O_3^+$ [M+H]⁺; ¹H NMR (500 MHz, chloroform-d) δ 8.04 (d, J=6.1 Hz, 1H), 7.03-6.95 (m, 3H), 6.94 (br s, 1H), 6.64 (d, J=6.1 Hz, 1H), 4.09 (dd, J=14.3, 8.1 Hz, 1H), 3.95 (dd, J=14.3, 6.4 Hz, 1H), 3.62 (s, 3H), 3.45 (s, 3H), 3.13-3.05 (m, 1H), 1.26 (d, J=7.1 Hz, 3H).

Example 3c: Methyl 4-[6-[(5-chloro-2-methyl-pyrimidin-4-yl)amino]-3-methyl-2-oxo-benzimidazol-1-yl]-2-methyl-butanoate

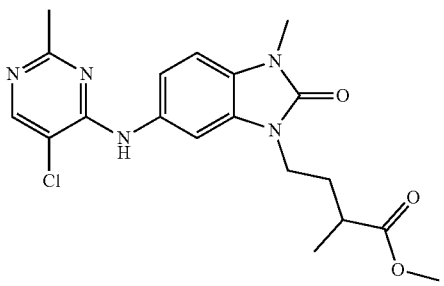 [SMILES: COC(=O)C(C)CCn1c(=O)n(C)c2ccc(Nc3nc(C)ncc3Cl)cc21]

Prepared by a method analogous to that used for the preparation of Example 3a, with heating at 120° C., using 4,5-dichloro-2-methyl-pyrimidine. LCMS (Method T4) Rt 2.31 min; m/z 404.1454, expected 404.1484 for $C_{19}H_{23}ClN_3O_3^+$ [M+H]⁺; ¹H NMR (500 MHz, chloroform-d) δ 8.25 (s, 1H), 7.66 (d, J=1.8 Hz, 1H), 7.15 (dd, J=8.3, 1.8 Hz, 1H), 7.13 (br s, 1H), 6.95 (d, J=8.3 Hz, 1H), 4.01-3.89 (m, 2H), 3.66 (s, 3H). 3.43 (s, 3H), 2.62-2.53 (m, 4H), 2.26-2.17 (m, 1H), 1.91-1.83 (m, 1H), 1.28 (d, J=7.1 Hz, 3H).

Example 4: 6-Chloro-5-cyano-4-[[3-[(3R)-3-hydroxybutyl]-1-methyl-2-oxo-benzimidazol-5-yl]amino]-N-methyl-pyridine-2-carboxamide

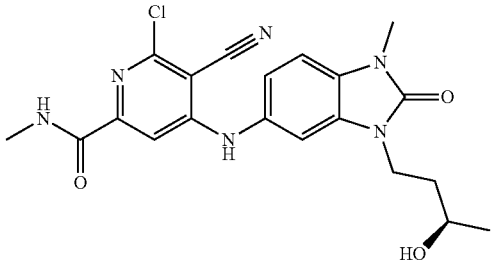 [SMILES: CNC(=O)c1cc(Nc2ccc3c(c2)n(CC[C@@H](C)O)c(=O)n3C)c(C#N)c(Cl)n1]

Ethyl 6-chloro-5-cyano-4-[[3-[(3R)-3-hydroxybutyl]-1-methyl-2-oxo-benzimidazol-5-yl]amino]pyridine-2-carboxylate (Example 2d, 3 mg, 0.0068 mmol) was dissolved in methanamine 2M in THF (0.50 mL, 1 mmol) and the resulting mixture stirred at room temperature in a sealed vessel overnight, then evaporated under reduced pressure and triturated with diethyl ether to give the title compound (2.5 mg) as yellow solid. ¹H NMR (500 MHz, chloroform-d) δ 7.86 (br q, J=5.4 Hz, 1H), 7.74 (s, 1H), 7.23 (d, J=2.1 Hz, 1H), 7.16 (s, 1H), 7.02 (d, J=8.2 Hz, 1H), 6.92 (dd, J=8.2, 2.1 Hz, 1H), 4.12 (ddd, J=14.8, 11.7, 3.6 Hz, 1H), 3.96 (ddd, J=14.8, 5, 3.6 Hz, 1H), 3.71 (dqd, J=10.6, 6.0, 2.7 Hz, 1H), 3.48 (s, 3H), 3.00 (d, J=5.2 Hz, 3H), 2.02 (dddd, J=14.2, 11.7, 5.0, 2.7 Hz, 1H), 1.70 (ddt, J=14.2, 10.6, 3.6 Hz, 1H), 1.27 (d, J=6.0 Hz, 3H). OH not clearly observed. LCMS (Method X4) Rt 2.42 min; m.z 451.1263 expected 451.1262 for $C_{20}H_{21}ClN_6O_3Na$ [M+Na]⁺

Example 5: Methyl 4-[6-[[2-chloro-3-cyano-6-(3-methyl-1,2,4-oxadiazol-5-yl)-4-pyridyl]amino]-3-methyl-2-oxo-benzimidazol-1-yl]-2-methyl-butanoate

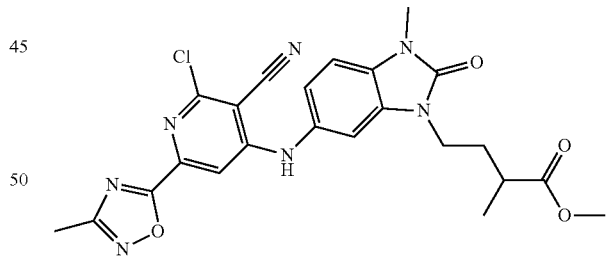

A microwave vial (0.5-2.0 mL volume) was charged with 6-chloro-5-cyano-4-[[3-(4-methoxy-3-methyl-4-oxo-butyl)-1-methyl-2-oxo-benzimidazol-5-yl]amino]pyridine-2-carboxylic acid (Example 3a, 7 mg, 0.014 mmol). The reaction vial was flushed with argon. THF (0.13 mL) was added followed by T3P (50 wt % in EtOAc; 11 uL, 0.019 mmol), DIPEA (7.00 uL, 0.040 mmol) and acetamide oxime (1.60 mg, 0.022 mmol). The reaction mixture was stirred under argon at rt for 3 h then heated to 75° C. for 17 h. The reaction mixture was allowed to cool to rt. Water (5 mL) was added and the reaction mixture was stirred for 5 min. The resulting precipitate was filtered and washed with water (2×5 mL). The precipitate was dissolved with methanol (10 mL) and concentrated in vacuo, affording the title compound as a yellow solid (1.7 mg). $^1$H NMR (500 MHz, chloroform-d) δ 7.49 (s, 1H), 7.18 (br s, 1H), 7.09-7.06 (m, 1H), 7.05-7.01 (m, 2H), 4.01-3.93 (m, 1H), 3.91-3.85 (m, 1H), 3.63 (s, 3H), 3.48 (s, 3H), 2.59-2.52 (m, 1H), 2.45 (s, 3H), 2.19-2.10 (m, 1H), 1.89-1.81 (m, 1H), 1.25 (d, J=7.1 Hz, 3H). LCMS (Method T4) Rt 2.86 min; m/z 496.1490, expected 496.1495 for $C_{23}H_{23}ClN_7O_4^+$ [M+H]$^+$.

Example 6: Methyl (2S)-2-amino-4-[6-[(2-chloro-3-cyano-4-pyridyl)amino]-3-methyl-2-oxo-benzimidazol-1-yl]butanoate

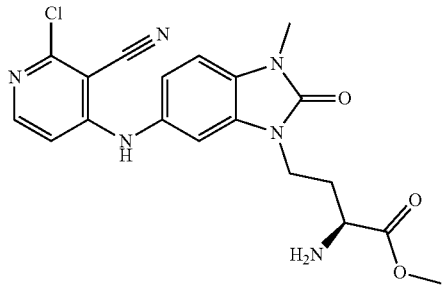 [SMILES: COC(=O)[C@@H](N)CCn1c(=O)n(C)c2ccc(Nc3ccnc(Cl)c3C#N)cc21]

Step 1: Methyl (2S)-2-(tert-butoxycarbonylamino)-4-[6-[(2-chloro-3-cyano-4-pyridyl)amino]-3-methyl-2-oxo-benzimidazol-1-yl]butanoate An oven-dried microwave vial (0.5-2.0 mL volume) was charged with 2-chloro-4-[(1-methyl-2-oxo-3H-benzimidazol-5-yl)amino]pyridine-3-carbonitrile (Intermediate D1, 30 mg, 0.10 mmol), methyl (2S)-4-bromo-2-(tert-butoxycarbonylamino)-butanoate (31 mg, 0.11 mmol) and cesium carbonate (39 mg, 0.12 mmol). The reaction vial was flushed with argon, sealed with a cap and then further flushed with argon. DMF (1.00 mL) was added. The reaction mixture was heated at 140° C. under microwave irradiation for 1 h. The reaction mixture was allowed to cool to rt. Water (10 mL) was added. The aqueous mixture was acidified to pH 5 with 1 M HCl. The aqueous mixture was extracted with EtOAc (4×10 mL). The organic extracts were combined, dried (sodium sulfate) and concentrated in vacuo. Purification by HPLC (2 injections; ACE 5 C18-PFP 250×21.2 mm column; 15 min gradient of 45:55 to 20:80 Water:methanol (both modified with 0.1% formic acid); flow rate 20 mL min-; Agilent 6120 MS-Prep LC) afforded methyl (2S)-2-(tert-butoxycarbonylamino)-4-[6-[(2-chloro-3-cyano-4-pyridyl)amino]-3-methyl-2-oxo-benzimidazol-1-yl]butanoate (15 mg) as an off-white solid. LCMS (Method T2) Rt 1.27 min; m/z 415.08 [M-Boc+H]$^+$; $^1$H NMR (500 MHz, chloroform-d) δ 8.06 (d, J=6.1 Hz, 1H), 7.03 (d, J=8.2 Hz, 1H), 6.99 (dd, J=8.2, 1.9 Hz, 1H), 6.95-6.92 (m, 1H), 6.86 (br s, 1H), 6.63 (d, J=6.1 Hz, 1H), 5.54-5.49 (m, 1H), 4.43-4.37 (m, 1H), 4.12-4.05 (m, 1H), 3.95-3.88 (m, 1H), 3.54 (s, 3H), 3.46 (s, 3H), 2.34-2.27 (m, 1H), 2.26-2.18 (m, 1H), 1.43 (s, 9H).

Step 2: Methyl (2S)-2-amino-4-[6-[(2-chloro-3-cyano-4-pyridyl)amino]-3-methyl-2-oxo-benzimidazol-1-yl]butanoate TFA (0.25 mL, 3.3 mmol) was added dropwise to a solution of methyl (2S)-2-(tert-butoxycarbonylamino)-4-[6-[(2-chloro-3-cyano-4-pyridyl)amino]-3-methyl-2-oxo-benzimidazol-1-yl]butanoate (13 mg, 0.025 mmol, from step 1) in DCM (2 mL) at 0° C. The reaction mixture was allowed to warm to rt over 90 min. The reaction mixture was concentrated in vacuo and the resulting residue was diluted with DCM (5 mL) and further concentrated in vacuo. The residue was dissolved in methanol and purified using an SCX-2 cartridge (2 g), eluting with methanol (20 mL) followed by 2N methanolic ammonia (20 mL). The methanolic ammonia fraction was collected and concentrated in vacuo affording the title compound as a yellow solid (10 mg, 93%). LCMS (Method T4) Rt 1.96 min; m/z 415.1269, expected 415.1280 for $C_{19}H_{20}ClN_6O_3^+$ [M+H]$^+$; $^1$H NMR (500 MHz, chloroform-d) δ 8.05 (d, J=6.1 Hz, 1H), 7.05-7.02 (m, 2H), 6.99 (dd, J=8.4, 1.7 Hz, 1H), 6.88 (br s, 1H), 6.63 (d, J=6.1 Hz, 1H), 5.7-5.0 (v br, 2H), 4.16-4.03 (m, 2H), 3.64 (s, 3H), 3.49-3.42 (m, 4H), 2.31-2.23 (m, 1H), 1.96-1.87 (m, 1H).

Example 7a: Methyl 4-[6-[[2-chloro-3-cyano-6-(methylcarbamoyl)-4-pyridyl]amino]-3-methyl-2-oxo-benzimidazol-1-yl]-2-methyl-butanoate

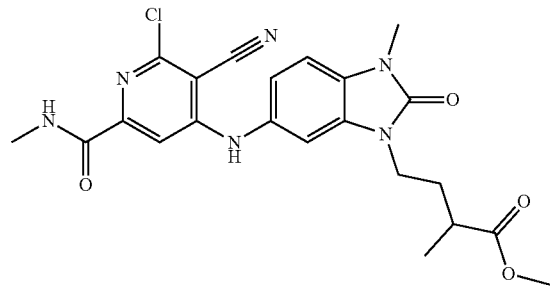

An oven-dried microwave vial (0.5-2.0 mL volume) was charged with 6-chloro-5-cyano-4-[[3-(4-methoxy-3-methyl-4-oxo-butyl)-1-methyl-2-oxo-benzimidazol-5-yl]amino]pyridine-2-carboxylic acid (Example 3a, 6 mg, 0.013 mmol). The reaction vial was flushed with argon, sealed with a cap and then further flushed with argon. THF (0.13 mL) was added followed by T3P (50 wt % in EtOAc; 10 uL, 0.017 mmol), DIPEA (6 uL, 0.034 mmol) and methylamine (2M in THF; 10 uL, 0.020 mmol). The reaction mixture was stirred at rt for 4 h. Water (3 mL) was added to the reaction mixture and the resulting yellow precipitate was filtered, washed with water (2×5 mL) and air dried overnight. The precipitate was dissolved in methanol, and then concentrated in vacuo affording the title compound as a yellow solid (2 mg). LCMS (Method T4) Rt 2.73 min; m/z 471.1542, expected 471.1542 for $C_{22}H_{24}ClN_6O_4^+$ [M+H]$^+$; $^1$H NMR (500 MHz, chloroform-d) δ 7.76 (br q, J=5.2 Hz, 1H), 7.49 (s, 1H), 7.07 (br s, 1H), 7.02 (d, J=8.2 Hz, 1H), 6.99 (dd, J=8.2, 1.8 Hz, 1H), 6.96 (d, J=1.8 Hz, 1H), 3.99-3.92 (m, 1H), 3.90-3.83 (m, 1H), 3.66 (s, 3H), 3.46 (s, 3H), 2.97 (d, J=5.2 Hz, 3H), 2.59-2.51 (m, 1H), 2.18-2.09 (m, 1H), 1.88-1.79 (m, 1H), 1.26 (d, J=7.1 Hz, 3H).

Example 7b: Methyl 4-[6-[[6-(but-3-ynylcarbamoyl)-2-chloro-3-cyano-4-pyridyl]amino]-3-methyl-2-oxo-benzimidazol-1-yl]-2-methyl-butanoate

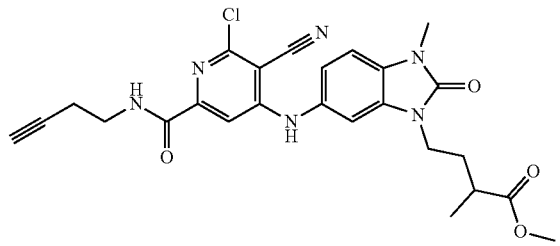 [SMILES: C#CCCNC(=O)c1cc(Nc2ccc3c(c2)n(CCC(C)C(=O)OC)c(=O)n3C)c(C#N)c(Cl)n1]

Prepared by a method analogous to that used for the preparation of Example 7a. LCMS (Method T4) Rt 2.86 min; m/z 509.1709, expected 509.1699 for $C_{25}H_{26}ClN_6O_4^+$ [M+H]$^+$; $^1$H NMR (500 MHz, chloroform-d) δ 8.05 (br t, J=6.2 Hz, 1H), 7.49 (s, 1H), 7.07 (br s, 1H), 7.02 (d, J=8.2 Hz, 1H), 6.99 (dd, J=8.2, 1.8 Hz, 1H), 6.96 (d, J=1.8 Hz, 1H), 3.99-3.92 (m, 1H), 3.90-3.84 (m, 1H), 3.66 (s, 3H), 3.58 (d, J=6.6 Hz, 1H), 3.55 (d, J=6.6 Hz, 1H), 3.46 (s, 3H), 2.58-2.52 (m, 1H), 2.49 (dt, J=6.6, 2.7 Hz, 2H), 2.17-2.09 (m, 1H), 2.05 (t, J=2.7 Hz, 1H), 1.87-1.82 (m, 1H), 1.26 (d, J=7.1 Hz, 3H).

Example 7c: Methyl 4-[6-[[2-chloro-3-cyano-6-(dimethylcarbamoyl)-4-pyridyl]amino]-3-methyl-2-oxo-benzimidazol-1-yl]-2-methyl-butanoate

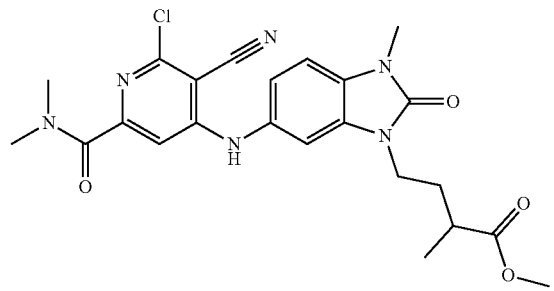

Prepared by a method analogous to that used for the preparation of Example 7a. LCMS (Method T4) Rt 2.59 min; m/z 485.1695, expected 485.1699 for $C_{23}H_{26}ClN_6O_4^+$ [M+H]$^+$; $^1$H NMR (500 MHz, chloroform-d) δ 7.02-6.98 (mi 3H), 6.95 (br s, 1H), 6.90 (s, 1H), 3.99-3.91 (m, 1H), 3.90-3.83 (m, 1H), 3.67 (s, 3H), 3.45 (s, 3H), 3.05 (s, 3H), 3.03 (s, 3H), 2.59-2.51 (m, 1H), 2.17-2.09 (m, 1H), 1.87-1.79 (m, 1H), 1.26 (d, J=7.1 Hz, 3H).

Example 7d: 6-Chloro-5-cyano-N-[2-(dimethylamino)ethyl]-4-[(1,3-dimethyl-2-oxo-benzimidazol-5-yl)amino]pyridine-2-carboxamide:formic acid (1:1)

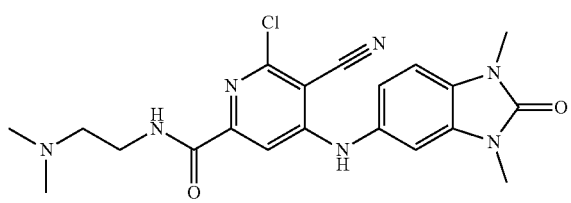 [SMILES: CN(C)CCNC(=O)c1cc(Nc2ccc3c(c2)n(C)c(=O)n3C)c(C#N)c(Cl)n1]

Prepared by a method analogous to that used for the preparation of Example 7a, starting from 6-chloro-5-cyano-4-[(1,3-dimethyl-2-oxo-benzimidazol-5-yl)amino]pyridine-2-carboxylic acid (Example 1c). LCMS (Method X2) Rt 0.84 min; m/z 428.1592 expected 428.1602 for $C_{20}H_{23}ClN_7O_2$ [M+H]$^+$; $^1$H NMR (500 MHz, chloroform-d) δ 8.48 (t, J=5.7 Hz, 1H), 8.35 (1H, s), 7.42 (s, 1H), 7.14 (s, 1H), 7.03 (d, J=8.2 Hz, 1H), 7.00 (dd, J=8.2, 2 Hz, 1H), 6.89 (d, J=2 Hz, 1H), 3.69 (q, J=6.0 Hz, 2H), 3.48 (s, 3H), 3.44 (s, 3H), 2.93 (t, J=6.0 Hz, 2H), 2.57 (s, 6H).

Example 8: Ethyl 7-[[3-(4-methoxy-3-methyl-4-oxo-butyl)-1-methyl-2-oxo-benzimidazol-5-yl]amino]pyrazolo[1,5-a]pyrimidine-5-carboxylate

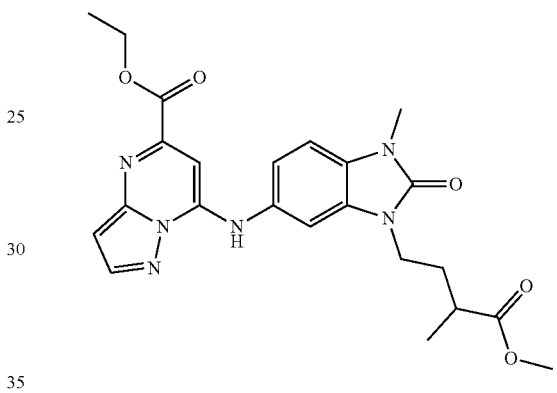

An oven dried microwave vial (0.5-2.0 mL volume) was charged with methyl 4-(6-amino-3-methyl-2-oxo-benzimidazol-1-yl)-2-methyl-butanoate (Intermediate A3a, 22 mg, 0.08 mmol) and ethyl 7-chloropyrazolo[1,5-a]pyrimidine-5-carboxylate (14 mg, 0.06 mmol). The reaction vial was flushed with argon, sealed with a cap and then further flushed with argon. Anhydrous 1,4-dioxane (0.6 mL) was added followed by triethylamine (22 uL, 0.16 mmol). The reaction mixture was heated at 120° C. under microwave irradiation for 7 h. The reaction mixture was allowed to cool to rt. Water (5 mL) was added. The aqueous mixture was acidified with 1 M HCl and extracted with EtOAc (4×5 mL). The organic extracts were combined, dried (sodium sulfate) and concentrated in vacuo. Purification by flash chromatography (10 g KP-SIL; 20% to 90% EtOAc in cyclohexane) afforded the title compound as a yellow solid (21 mg, 73%). LCMS (Method T4) Rt 2.77 min; m/z 467.2012, expected 467.2037 for $C_{23}H_{27}N_6O_5^+$ [M+H]$^+$; $^1$H NMR (500 MHz, chloroform-d) δ 8.26 (br s, 1H), 8.15 (s, 1H), 7.16 (d, J=8.2 Hz, 1H), 7.12 (s, 1H), 7.05 (d, J=8.2 Hz, 1H), 6.98 (s, 1H), 6.81 (s, 1H), 4.46 (q, J=7.1 Hz, 2H), 4.01-3.93 (m, 1H), 3.93-3.86 (m, 1H), 3.63 (s, 3H), 3.47 (s, 3H), 2.60-2.50 (m, 1H), 2.21-2.10 (m, 1H), 1.90-1.81 (m, 1H), 1.41 (t, J=7.1 Hz, 3H), 1.25 (d, J=7.0 Hz, 3H).

Example 9: Methyl 4-[6-[(2-chloro-3-cyano-4-pyridyl)amino]-3-methyl-2-oxo-benzimidazol-1-yl]-2-hydroxy-butanoate

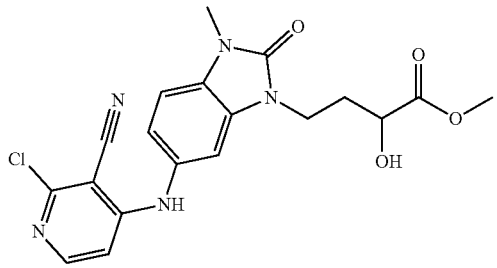 [SMILES: COC(=O)C(O)CCn1c(=O)n(C)c2ccc(Nc3ccnc(Cl)c3C#N)cc21]

Step 1: 3-[tert-butyl(dimethyl)silyl]oxytetrahydrofuran-2-one tert-Butyldimethylsilyl chloride (508 mg, 3.4 mmol) was added portionwise to a stirred mixture of 3-hydroxytetrahydrofuran-2-one (0.2 mL, 2.6 mmol) and imidazole (357 mg, 5.2 mmol) in DMF (4 mL) at 0° C. under argon. The reaction mixture was allowed to warm to rt and stirred at that temperature for 3 h. Saturated aq. ammonium chloride (10 mL) was added. The aqueous mixture was extracted with DCM (3×10 mL). The organic extracts were combined, dried over sodium sulfate and concentrated in vacuo. Purification by flash chromatography (50 g KP-SIL, 0% to 30% EtOAc in cyclohexane afforded 3-[tert-butyl(dimethyl)silyl]oxytetrahydrofuran-2-one (527 mg, 95%) as a colourless oil. $^1$H NMR (500 MHz, chloroform-d) δ 4.44-4.37 (m, 2H), 4.23-4.18 (m, 1H), 2.50-2.43 (m, 1H), 2.28-2.19 (m, 1H), 0.93 (s, 9H), 0.18 (s, 3H), 0.16 (s, 3H).

Step 2: Methyl 2-[tert-butyl(dimethyl)silyl]oxy-4-hydroxy-butanoate

A mixture of 3-[tert-butyl(dimethyl)silyl]oxytetrahydrofuran-2-one (101 mg, 0.47 mmol, from step 1) and potassium carbonate (15 mg, 0.11 mmol) in methanol (1 mL) was heated at 60° C. for 20 h under argon. The reaction mixture was allowed to cool to rt, diluted with methanol (10 mL) and directly dry-loaded onto silica gel. Purification by flash chromatography (25 g KP-SIL; 10% to 50% EtOAc in cyclohexane) afforded methyl 2-[tert-butyl(dimethyl)silyl]oxy-4-hydroxy-butanoate (38 mg) as a colourless oil. $^1$H NMR (500 MHz, chloroform-d) δ 4.46 (dd, J=6.7, 4.7 Hz, 1H), 3.83-3.76 (m, 2H), 3.75 (s, 3H), 2.07-1.94 (m, 3H), 0.93 (s, 9H), 0.12 (s, 3H), 0.09 (s, 3H).

Step 3: Methyl 2-[tert-butyl(dimethyl)silyl]oxy-4-(p-tolylsulfonyloxy)butanoate Triethylamine (30 uL, 0.22 mmol), pyridine (5 uL, 0.06 mmol) and tosyl chloride (33 mg, 0.17 mmol) were added sequentially to a stirred solution of methyl 2-[tert-butyl(dimethyl)silyl]oxy-4-hydroxy-butanoate (36 mg, 0.14 mmol from step 2) in DCM (1.5 mL) under Ar. The reaction mixture was stirred at 30° C. for 6 h. Water (10 mL) was added to the reaction mixture. The layers were separated and the aqueous layer was further extracted with DCM (2×10 mL). The organic extracts were combined, dried (sodium sulfate) and concentrated in vacuo. Purification by flash chromatography (10 g KP-SIL; 0% to 40% EtOAc in cyclohexane) afforded methyl 2-[tert-butyl(dimethyl)silyl]oxy-4-(p-tolylsulfonyloxy)butanoate (33.2 mg) as a pale yellow oil. $^1$H NMR (500 MHz, chloroform-d) δ 7.82-7.78 (m, 2H), 7.38-7.34 (m, 2H), 4.31 (dd, J=7.9, 4.2 Hz, 1H), 4.21-4.12 (m, 2H), 3.71 (s, 3H), 2.46 (s, 3H), 2.15-2.07 (m, 1H), 2.06-1.98 (m, 1H), 0.85 (s, 9H), 0.06 (s, 3H), 0.01 (s, 3H).

Step 4: Methyl 2-[tert-butyl(dimethyl)silyl]oxy-4-[6-[(2-chloro-3-cyano-4-pyridyl)amino]-3-methyl-2-oxo-benzimidazol-1-yl]butanoate A microwave vial (0.5-2.0 mL volume) was charged with methyl 2-[tert-butyl(dimethyl)silyl]oxy-4-(p-tolylsulfonyloxy)butanoate (31 mg, 0.08 mmol, from step 3), 2-chloro-4-[(1-methyl-2-oxo-3H-benzimidazol-5-yl)amino]pyridine-3-carbonitrile (Intermediate D1, 20 mg, 0.07 mmol) and cesium carbonate (36 mg, 0.11 mmol). The reaction vial was flushed with argon, sealed with a cap and then further flushed with argon. DMF (0.66 mL) was added, and the reaction mixture was heated at 120° C. under microwave irradiation for 1 h. The reaction mixture was allowed to cool to rt. Water (10 mL) was added. The aqueous mixture was acidified to pH 4 with 1 M HCl. The aqueous mixture was extracted with EtOAc (4×10 mL). The organic extracts were combined, dried (sodium sulfate) and concentrated in vacuo. Purification by HPLC (ACE 5 C18-PFP 250×21.2 mm column; 15 min gradient of 45:55 to 20:80 Water:methanol (both modified with 0.1% formic acid); flow rate 20 mLmin$^{-1}$; Agilent 6120 MS-Prep LC) afforded methyl 2-[tert-butyl(dimethyl)silyl]oxy-4-[6-[(2-chloro-3-cyano-4-pyridyl)amino]-3-methyl-2-oxo-benzimidazol-1-yl]butanoate (23 mg) as a sticky dark yellow solid. LCMS (Method T2) Rt 1.64 min; m/z 530.1958 [M+H]$^+$; $^1$H NMR (500 MHz, chloroform-d) δ 8.04 (d, J=6.1 Hz, 1H), 7.01 (d, J=8.2 Hz, 1H), 6.97 (dd, J=8.2, 1.9 Hz, 1H), 6.93 (d, J=1.9 Hz, 1H), 6.86 (br s, 1H), 6.64 (d, J=6.1 Hz, 1H), 4.36 (dd, J=6.4, 4.7 Hz, 1H), 4.08-4.01 (m, 1H), 3.98-3.91 (m, 1H), 3.66 (s, 3H), 3.45 (s, 3H), 2.26-2.14 (m, 2H), 0.90 (s, 9H), 0.07 (s, 3H), 0.07 (s, 3H).

Step 5: Methyl 4-[6-[(2-chloro-3-cyano-4-pyridyl)amino]-3-methyl-2-oxo-benzimidazol-1-yl]-2-hydroxy-butanoate TBAF (1 M in THF) (60 uL, 0.06 mmol) was added to a stirred solution of methyl 2-[tert-butyl(dimethyl)silyl]oxy-4-[6-[(2-chloro-3-cyano-4-pyridyl)amino]-3-methyl-2-oxo-benzimidazol-1-yl]butanoate (21 mg, 0.04 mmol, from step 4) in THF (0.6 mL) at 0° C. under argon. The reaction mixture was warmed to rt and stirred for 2.5 h. Saturated aq. NH$_4$Cl (5 mL) was added and the aqueous mixture was extracted with EtOAc (4×10 mL). The organic extracts were combined, dried (sodium sulfate) and concentrated in vacuo. Purification by HPLC (ACE 5 C18-PFP 250×21.2 mm column; 15 min gradient of 45:55 to 20:80 Water:methanol (both modified with 0.1% formic acid); flow rate 20 mL-min$^{-1}$; Agilent 6120 MS-Prep LC) afforded the title compound as a pale yellow solid (8 mg, 45%). LCMS (Method T4) Rt 2.48 min; m/z 416.1097, expected 416.1120 for $C_{19}H_{19}ClN_5O_4^+$ [M+H]$^+$; $^1$H NMR (500 MHz, chloroform-d) δ 8.03 (d, J=6.1 Hz, 1H), 7.04 (d, J=8.1 Hz, 1H), 7.02-6.97 (m, 3H), 6.64 (d, J=6.1 Hz, 1H), 4.19 (dd, J=8.9, 3.6 Hz, 1H), 4.11-4.06 (m, 2H), 3.67 (s, 3H), 3.47 (s, 3H), 2.36-2.25 (m, 1H), 2.11-2.02 (m, 1H), 1.70 (br s, 1H).

Example 10a: 2-Chloro-4-[[3-(2,3-dihydroxy-3-methyl-butyl)-1-methyl-2-oxo-benzimidazol-5-yl]amino]pyridine-3-carbonitrile

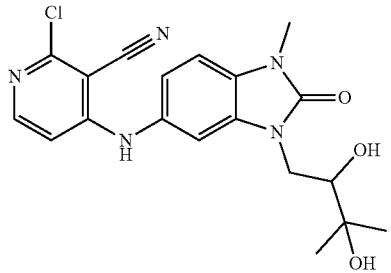 [SMILES: Cn1c(=O)n(CC(O)C(C)(C)O)c2cc(Nc3ccnc(Cl)c3C#N)ccc21]

To a mixture of 2-chloro-4-[(1-methyl-2-oxo-3H-benzimidazol-5-yl)amino]pyridine-3-carbonitrile (Intermediate D1, 30 mg, 0.10 mmol) and cesium carbonate (45 mg, 0.14 mmol) in DMF (0.60 mL) was added 2-(oxiran-2-yl)propan-2-ol (Intermediate F1, ~1:1 w/w mixture with DCM, 30 mg, 0.15 mmol) and the resulting mixture was heated in the microwave to 120° C. for 1 h, then diluted with DCM (3 mL) and water (2 mL). The biphasic mixture was acidified to pH5 with 10% citric acid and mixed thoroughly, then extracted with DCM and combined organics passed through a phase separator and evaporated under reduced pressure. The resulting crude mixture was purified by preparative HPLC (2 injections, ACE 5 C18-PFP column (5μ, 250×21.2 mm), 15 minute gradient elution from 45:55 to 20:80 water:methanol (both modified with 0.1% formic acid) at a flow rate of 2 mL/min) to give 2-chloro-4-[[3-(2,3-dihydroxy-3-methyl-butyl)-1-methyl-2-oxo-benzimidazol-5-yl]amino]pyridine-3-carbonitrile (8 mg) as off-white solid. LCMS (Method X4) Rt 2.25 min; m/z 402.1329 expected 402.1333 for $C_{19}H_{21}ClN_5O_3[M+H]^+$. $^1H$ NMR (500 MHz, Methanol-$d_4$)- 7.94 (d, J=6.3 Hz, 1H), 7.24 (d, J=2.0 Hz, 1H), 7.22 (d, J=8.3 Hz H, 7.07 (dd, J=8.3, 2.0 Hz, 1H), 6.71 (d, J=6.3 Hz, 1H), 4.18 (dd, J=14.4, 2.4 Hz, 1H), 3.91 (dd, J=14.4, 10.0 Hz, 1H), 3.70 (dd, J=10.0, 2.3 Hz, 1H), 3.47 (s, 3H), 1.29 (s, 3H), 1.27 (s, 3H).

The following tabulated examples were prepared by method analogous to that used for the preparation of example 10a, using the intermediate shown in Table 4. For example 10d, the reaction was heated at 140° C. for 1 instead of 120° C. For example 10g, the reaction was heated to 60° C. for 3 days instead of using microwave heating.

TABLE 4

Compounds prepared by a method analogous to that used for the preparation of Example 10a

| Example | Data and comments | Intermediate |
|---|---|---|
| Example 10b: Methyl 4-[6-[(2-chloro-3-cyano-4-pyridyl)amino]-3-methyl-2-oxo-benzimidazol-1-yl]-2-methoxy-butanoate | LCMS (Method T4) Rt 2.58 min; m/z 430.1268, expected 430.1277 for $C_{20}H_{21}ClN_5O_4^+$ [M + H]$^+$; $^1H$ NMR (500 MHz, chloroform-d) δ 8.03 (d, J = 6.1 Hz, 1H), 7.02 (d, J = 8.2 Hz, 1H), 6.98 (dd, J = 8.2, 1.7 Hz, 1H), 6.92 (d, J = 1.7 Hz, 1H), 6.90 (brs, 1H), 6.62 (d, J = 6.1 Hz, 1H), 4.14-4.05 (m, 1H), 3.99-3.91 (m, 1H), 3.80 (dd, J = 9.0, 3.6 Hz, 1H), 3.72 (s, 3H), 3.46 (s, 3H), 3.40 (s, 3H), 2.26-2.18 (m, 1H), 2.15-2.06 (m, 1H). | methyl 2-methoxy-4-(p-tolylsulfonyloxy)butanoate (Intermediate C4a). |
| Example 10c: Methyl 4-[6-[(2-chloro-3-cyano-4-pyridyl)amino]-3-methyl-2-oxo-benzimidazol-1-yl]-2-ethoxy-butanoate | LCMS (Method T4) Rt 2.67 min; m/z 444.1430, expected 444.1433 for $C_{21}H_{23}ClN_5O_4^+$ [M + H]$^+$; $^1H$ NMR (500 MHz, chloroform-d) δ 8.04 (d, J = 6.1 Hz, 1H), 7.02 (d, J = 8.2 Hz, 1H), 6.98 (dd, J = 8.2, 1.8 Hz, 1H), 6.94 (d, J = 1.8 Hz, 1H), 6.88 (br s, 1H), 6.62 (d, J = 6.1 Hz, 1H), 4.15-4.07 (m, 1H), 4.00-3.93 (m, 1H), 3.89 (dd, J = 9.0, 3.6 Hz, 1H), 3.71 (s, 3H), 3.69-3.62 (m, 1H), 3.46 (s, 3H), 3.43-3.36 (m, 1H), 2.25-2.17 (m, 1H), 2.16-2.07 (m, 1H), 1.20 (t, J = 7.0 Hz, 3H). | methyl 2-methoxy-4-(p-tolylsulfonyloxy)butanoate (Intermediate C4b) |

TABLE 4-continued

Compounds prepared by a method analogous to that used for the preparation of Example 10a

| Example | Data and comments | Intermediate |
|---|---|---|
| 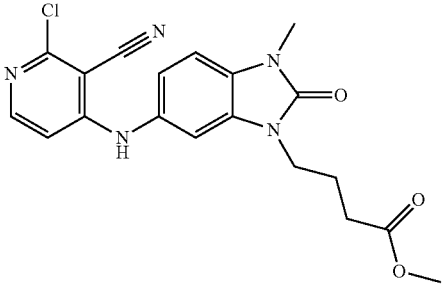<br>Example 10d: Methyl 4-[6-[(2-chloro-3-cyano-4-pyridyl)amino]-3-methyl-2-oxo-benzimidazol-1-yl]butanoate | LCMS (Method T4) Rt 2.59 min; m/z 400.1158, expected 400.1171 for $C_{19}H_{19}ClN_5O_3^+$ [M + H]$^+$; $^1$H NMR (500 MHz, chloroform-d) δ 8.03 (d, J = 6.1 Hz, 1H), 7.02 (d, J = 8.1 Hz, 1H), 7.00-6.96 (m, 3H), 6.63 (d, J = 6.1 Hz, 1H), 3.94 (t, J = 7.1 Hz, 2H), 3.65 (s, 3H), 3.45 (s, 3H), 2.42 (t, J = 7.1 Hz, 2H), 2.07 (pent, J = 7.1 Hz, 2H). | methyl 4-bromobutanoate |
| 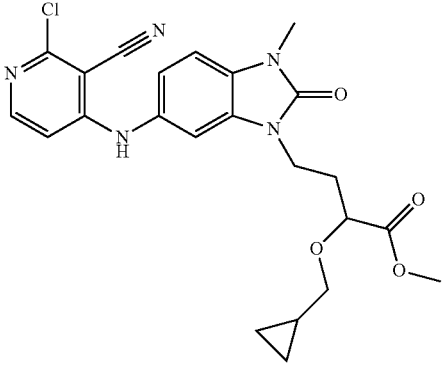<br>Example 10e: Methyl 4-[6-[(2-chloro-3-cyano-4-pyridyl)amino]-3-methyl-2-oxo-benzimidazol-1-yl]-2-(cyclopropylmethoxy)butanoate | LCMS (Method T4) Rt 2.78 min; m/z 470.1575, expected 470.1590 for $C_{23}H_{25}ClN_5O_4^+$ [M + H]$^+$; $^1$H NMR (500 MHz, chloroform-d) δ 8.04 (d, J = 6.1 Hz, 1H), 7.03 (d, J = 8.2 Hz, 1H), 6.99 (dd, J = 8.2, 1.9 Hz, 1H), 6.96 (d, J = 1.9 Hz, 1H), 6.87 (br s, 1H), 6.62 (d, J = 6.1 Hz, 1H), 4.18-4.10 (m, 1H), 4.00-3.94 (m, 1H), 3.92 (dd, J = 9.2, 3.6 Hz, 1H), 3.70 (s, 3H), 3.46 (s, 3H), 3.37-3.29 (m, 2H), 2.26-2.18 (m, 1H), 2.18-2.10 (m, 1H), 1.10-1.00 (m, 1H), 0.56-0.48 (m, 2H), 0.25-0.16 (m, 2H). | methyl 2-(cyclopropyl-methoxy)-4-(p-tolylsulfonyloxy) butanoate (Intermediate C4c) |
| 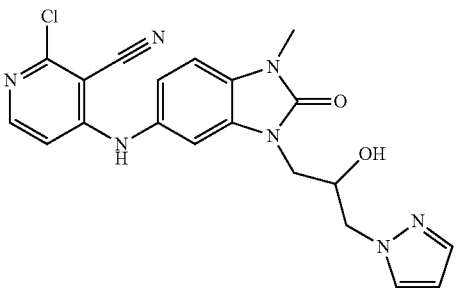<br>Example 10f: 2-chloro-4-[[3-(2-hydroxy-3-pyrazol-1-yl-propyl)-1-methyl-2-oxo-benzimidazol-5-yl]amino]pyridine-3-carbonitrile | LCMS (Method X2) Rt 1.11 min; m/z 424.1278 expected 424.1289 for $C_{20}H_{19}ClN_7O_2$ [M + H]$^+$. $^1$H NMR (500 MHz, chloroform-d) δ 8.04 (d, J = 6.1 Hz, 1H), 7.52 (d, J = 1.9 Hz, 1H), 7.50 (d, J = 2.3 Hz, 1H), 7.10 (d, J = 1.9 Hz, 1H), 7.03 (d, J = 8.3 Hz, 1H), 7.00 (dd, J = 8.2, 1.9 Hz, 1H), 6.94 (s, 1H), 6.66 (d, J = 6.1 Hz, 1H), 6.29 (t, J = 2.1 Hz, 1H), 4.43-4.35 (m, 2H), 4.24-4.15 (m, 1H), 4.08 (dd, J = 14.8, 3.7 Hz, 1H), 3.98 (dd, J = 1.8, 5.5 Hz, 1H), 3.48 (s, 3H). | 1-(oxiran-2-ylmethyl) pyrazole |

TABLE 4-continued

Compounds prepared by a method analogous to that used for the preparation of Example 10a

| Example | Data and comments | Intermediate |
|---|---|---|
| 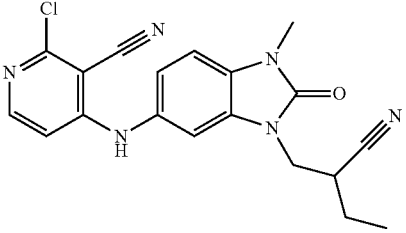<br>Example 10g: 2-chloro-4-[[3-(2-cyanobutyl)-1-methyl-2-oxo-benzimidazol-5-yl]amino]pyridine-3-carbonitrile | LCMS (Method T4) Rt 2.60 min; m/z 381.1209 expected 381.1225 for $C_{19}H_{18}ClN_6O$ [M + H]$^+$. $^1$H NMR (500 MHz, chloroform-d) δ 8.04 (d, J = 6.1 Hz, 1H), 7.08 (d, J = 1.9 Hz, 1H), 7.07 (d, J = 8.2 Hz, 1H), 7.02 (dd, J = 8.2, 1.0 Hz, 1H), 6.96 (s, 1H), 6.71 (d, J = 6.1 Hz, 1H), 4.11 (dd, J = 14.4, 5.7 Hz, 1H), 4.04 (dd, J = 14.5, 8.8 Hz, 1H), 3.48 (s, 3H), 3.11 (tt, J = 9.1, 5.4 Hz, 1H), 1.89-1.69 (m, 2H), 1.19 (t, J = 7.4 Hz, 3H). | 2-(bromomethyl)butanenitrile |
| 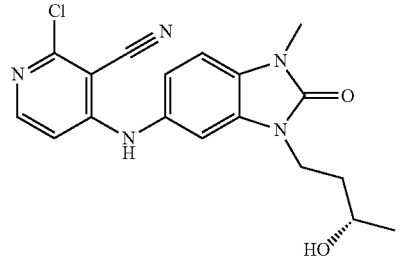<br>Example 10h: 2-chloro-4-[[3-[(3S)-3-hydroxybutyl]-1-methyl-2-oxo-benzimidazol-5-yl]amino]pyridine-3-carbonitrile | LCMS (Method X4): Rt 2.47 min; m/z 372.1219 expected 372.1227 for $C_{18}H_{19}ClN_5O_2$ [M + H]$^+$; $^1$H NMR (500 MHz, DMSO-d6) δ 9.48 (s, 1H), 8.00 (d, J = 6.0 Hz, 1H), 7.20 (d, J = 8.2 Hz, 1H), 7.17 (d, J = 1.9 Hz, 1H), 7.00 (dd, J = 1.9, 8.2 Hz, 1H), 6.68 (d, J = 6.0 Hz, 1H), 4.58 (d, J = 4.7 Hz, 1H), 3.94-3.79 (m, 2H), 3.65-3.58 (m, 1H), 3.34 (s, 3H), 1.72-1.58 (m, 2H), 1.08 (d, J = 6.3 Hz, 3H). | [(3S)-3-hydroxybutyl] 4-methylbenzene-sulfonate (which was prepared by analogy to its enantiomer, Intermediate C2) |
| 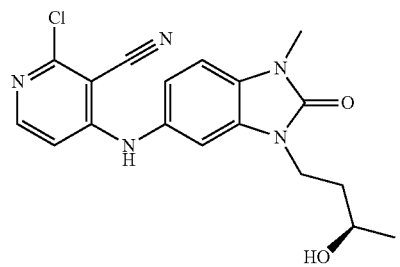<br>Example 10i: (R)-2-chloro-4-((3-(3-hydroxybutyl)-1-methyl-2-oxo-2,3-dihydro-1H-benzo[d]imidazol-5-yl)amino)nicotinonitrile | LCMS (Method X4): Rt 2.51 min; m/z 372.1228 expected 372.1227 for $C_{18}H_{19}ClN_5O_2$ [M + H]$^+$; $^1$H NMR (500 MHz, chloroform-d) δ 8.05 (d, J = 6.2 Hz, 1H), 7.07 (d, J = 8.2 Hz, 1H), 7.03 (dd, J = 2.0, 8.2 Hz, 1H), 6.97 (d, J = 1.9 Hz, 1H), 6.94 (s, 1H, NH), 6.63 (d, J = 6.1 Hz, 1H), 4.25 (m, 1H), 3.88 (m, 1H), 3.72 (dqd, J = 10.2, 6.2, 2.8 Hz, 1H), 3.49 (s, 3H), 1.88 (m, 1H), 1.71 (m, 1H), 1.22 (d, J = 6.2 Hz, 3H). OH not clearly observed. | Intermediate C2: [(3R)-3-hydroxybutyl] 4-methylbenzene-sulfonate |

Example 11: Methyl 2-[[6-[(2-chloro-3-cyano-4-pyridyl)amino]-3-methyl-2-oxo-benzimidazol-1-yl]methyl]cyclopentanecarboxylate (as a 2:1 mixture of diastereoisomers)

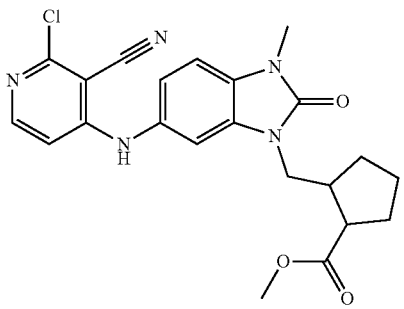 [SMILES: COC(=O)C1CCCC1Cn1c(=O)n(C)c2ccc(Nc3ccnc(Cl)c3C#N)cc21]

Step 1: Methyl 2-(iodomethyl)cyclopentanecarboxylate

Trimethylsilyl iodide (0.14 mL, 0.98 mmol) was added dropwise to a stirred solution of hexahydro-1H-cyclopenta[c]furan-1-one (42 mg, 0.33 mmol) and methanol (70 uL, 1.73 mmol) in DCM (1.6 mL) at 0° C. under argon. The reaction mixture was warmed to rt and stirred for 20 h. Water (5 mL) was added. The aqueous mixture was extracted with DCM (3×10 mL). The organic extracts were combined, dried (sodium sulfate) and concentrated in vacuo. Purification by flash chromatography (10 g KP-SIL; 0% to 30% EtOAc in cyclohexane) afforded methyl 2-(iodomethyl)cyclopentanecarboxylate (31 mg, 35%) as a pale yellow oil. $^1$H NMR (500 MHz, chloroform-d) δ 3.69 (s, 3H), 3.30 (dd, J=9.6, 6.6 Hz, 1H), 3.11 (t, J=9.3 Hz, 1H), 2.99-2.92 (m, 1H), 2.60-2.51 (m, 1H), 2.05-1.85 (m, 4H), 1.71-1.57 (m, 2H).

Step 2: 2-[[6-[(2-chloro-3-cyano-4-pyridyl)amino]-3-methyl-2-oxo-benzimidazol-1-yl]methyl]cycopentanecarboxylic acid A microwave vial (0.5-2.0 mL volume) was charged with methyl 2-(iodomethyl)cyclopentanecarboxylate (31 mg, 0.12 mmol, from step 1), 2-chloro-4-[(1-methyl-2-oxo-3H-benzimidazol-5-yl)amino]pyridine-3-carbonitrile (Intermediate D1, 30 mg, 0.10 mmol) and cesium carbonate (58 mg, 0.18 mmol). argon reaction vial was flushed with argon, sealed with a cap and then further flushed with Ar. DMF (1.0 mL) was added and the reaction mixture was heated at 120° C. under microwave irradiation for 1 h, followed by 160° C. under microwave irradation for a further 6 h. The crude reaction mixture was diluted with a 1:1 mixture of MeCN: DMSO (1.2 mL) and directly purified by HPLC (2 injections; ACE 5 C18-PFP 250×21.2 mm column; 15 min gradient of 60:40 to 0:100 Water:methanol (both modified with 0.1% formic acid); flow rate 20 mLmin−1; Agilent 6120 MS-Prep LC) affording the title compound (7 mg) as an off-white solid. LCMS (Method T2) Rt 1.43 min; m/z 426.1318 [M+H]$^+$; $^1$H NMR (500 MHz, methanol-d$_4$) δ 7.95 (d, J=6.2 Hz, 1H), 7.23 (d, J=8.3 Hz, 1H), 7.15 (d, J=1.9 Hz, 1H), 7.09 (dd, J=8.3, 1.9 Hz, 1H), 6.70 (d, J=6.2 Hz, 1H), 3.98-3.92 (m, 2H), 3.46 (s, 3H), 2.96-2.89 (m, 1H), 2.77-2.69 (m, 1H), 2.04-1.96 (m, 1H), 1.96-1.87 (m, 2H), 1.68-1.58 (m, 3H).

Step 3: Methyl 2-[[6-[(2-chloro-3-cyano-4-pyridyl)amino]-3-methyl-2-oxo-benzimidazol-1-yl]methyl] cyclopentanecarboxylate Sulfuric acid (1 drop) was added to a stirred mixture of 2-[[6-[(2-chloro-3-cyano-4-pyridyl)amino]-3-methyl-2-oxo-benzimidazol-1-yl]methyl]cyclopentanecarboxylic acid (7 mg, 0.02 mmol, from step 2) in dry methanol (3.0 mL). The reaction mixture was stirred at rt for 3 d. The reaction mixture was concentrated in vacuo. The resulting residue was washed with diethyl ether (6 mL) and dried, affording the title compound methyl 2-[[6-[(2-chloro-3-cyano-4-pyridyl)amino]-3-methyl-2-oxo-benzimidazo-1-yl]methyl] cyclopentanecarboxylate (5 mg, 2:1 mixture of diastereoisomers) as a yellow solid. LCMS (Method T4) Rt 2.80 min; m/z 440.1489, expected 440.1484 for $C_{22}H_{23}ClN_5O_3^+$ [M+H]$^+$; Major diastereoisomer: $^1$H NMR (500 MHz, methanol-d$_4$) δ 8.13 (d, J=7.3 Hz, 1H), 7.31 (d, J=8.3 Hz, 1H), 7.24-7.22 (m, 1H), 7.19-7.15 (m, 1H), 6.97 (d, J=7.3 Hz, 1H), 3.96 (dd, J=14.9, 6.0 Hz, 2H), 3.69 (s, 3H), 3.46 (s, 3H), 2.98-2.91 (m, 1H), 2.84-2.71 (m, 1H), 2.05-1.86 (m, 3H), 1.72-1.60 (m, 3H); Minor diastereoisomer: $^1$H NMR (500 MHz, methanol-d$_4$) δ 8.12 (d, J=7.3 Hz, 1H), 7.31 (d, J=8.3 Hz, 1H), 7.24-7.22 (m, 1H), 7.19-7.15 (m, 1H), 6.96 (d, J=7.3 Hz, 1H), 3.86 (dd, J=14.3, 9.7 Hz, 2H), 3.62 (s, 3H), 3.47 (s, 3H), 2.98-2.91 (m, 1H), 2.84-2.71 (m, 1H), 2.05-1.86 (m, 3H), 1.72-1.60 (m, 3H).

Example 12: Methyl (2R)-2-amino-4-[6-[(2-chloro-3-cyano-4-pyridyl)amino]-3-methyl-2-oxo-benzimidazol-1-yl]butanoate

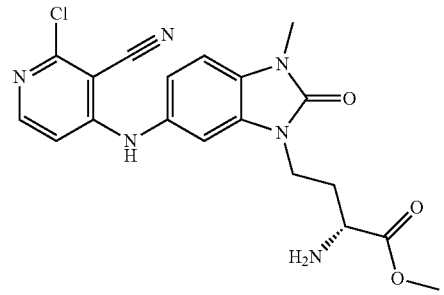 [SMILES: COC(=O)[C@H](N)CCn1c(=O)n(C)c2ccc(Nc3ccnc(Cl)c3C#N)cc21]

Step 1: 2-[(2R,5S)-5-isopropyl-3,6-dimethoxy-2,5-dihydropyrazin-2-yl]ethyl 4-methylbenzenesulfonate An oven-dried microwave vial (2.0-5.0 mL volume) was charged with (2S)-2-isopropyl-3,6-dimethoxy-2,5-dihydropyrazine (100 uL, 0.56 mmol). The reaction vial was flushed with argon, sealed with a cap and then further flushed with argon. Dry THF (2 mL) was added. The reaction vessel was cooled to −78° C. and n-BuLi (1.59M in hexanes; 0.74 mL, 1.18 mmol) was added dropwise. The reaction mixture was stirred at −78° C. for 30 min. 2-Bromoethanol (40 uL, 0.56 mmol) was added dropwise and the reaction mixture was allowed to warm to rt and stirred for 4 h. The reaction mixture was cooled to 0° C. and a solution of 4-methylbenzenesulfonyl chloride (106 mg, 0.56 mmol) in THF (1 mL) was added. The reaction mixture was allowed to warm to rt and stirred for 2 h. The reaction mixture was quenched with saturated aq. NH$_4$Cl (5 mL) and the aqueous mixture was extracted with DCM (3×10 mL). The organic extracts were combined, dried (Na₂SO₄) and concentrated in vacuo. Purification by flash chromatography (25 g KP-SIL; 0% to 40% EtOAc in cyclohexane) afforded 2-[(2R,5S)-5-isopropyl-3,6-dimethoxy-2,5-dihydropyrazin-2-yl]ethyl 4-methylbenzenesulfonate (d.r.>20:1, 107 mg) as a viscous yellow oil. LCMS (Method T2) Rt 1.60 min; m/z 383.1639 [M+H]⁺

Step 2: 2-chloro-4-[[3-[2-[(2R,5S)-5-isopropyl-3,6-dimethoxy-2,5-dihydropyrazin-2-yl]ethyl]-1-methyl-2-oxo-benzimidazol-5-yl]amino]pyridine-3-carbonitrile An oven-dried microwave vial (0.5-2.0 mL volume) was charged with 2-chloro-4-[(1-methyl-2-oxo-3H-benzimidazol-5-yl)amino]pyridine-3-carbonitrile (Intermediate D1, 30 mg, 0.1 mmol), 2-[(2R,5S)-5-isopropyl-3,6-dimethoxy-2,5-dihydropyrazin-2-yl]ethyl 4-methylbenzenesulfonate (41 mg, 0.11 mmol, from step 1) and cesium carbonate (39 mg, 0.12 mmol). The reaction vial was flushed with argon, sealed with a cap and then further flushed with argon. DMF (1 mL) was added and the reaction mixture was stirred at 140° C. under microwave irradiation for 2 h. The reaction mixture was allowed to cool to rt. Water (10 mL) was added. The aqueous mixture was acidified with 1 M HCl. The aqueous mixture was extracted with EtOAc (5×10 mL). The organic extracts were combined, dried (sodium sulfate) and concentrated in vacuo. Purification by HPLC (ACE 5 C18-PFP 250×30 mm column; 15 min gradient of 40:60 to 0:100 Water:methanol (both modified with 0.1% formic acid); flow rate 40 mLmin⁻¹; Agilent 6120 MS-Prep LC) afforded 2-chloro-4-[[3-[2-[(2R,5S)-5-isopropyl-3,6-dimethoxy-2,5-dihydropyrazin-2-yl]ethyl]-1-methyl-2-oxo-benzimidazo-5-yl]amino]pyridine-3-carbonitrile (14 mg, 28%) as a pale yellow solid. LCMS (Method T2) Rt 1.57 min; m/z 510.2028 [M+H]⁺.

Step 3: Methyl (2R)-2-amino-4-[6-[(2-chloro-3-cyano-4-pyridyl)amino]-3-methyl-2-oxo-benzimidazol-1-yl]butanoate TFA (0.16 mL, 2.1 mmol) in water (1 mL) was added dropwise to a solution of 2-chloro-4-[[3-[2-[(2R,5S)-5-isopropyl-3,6-dimethoxy-2,5-dihydropyrazin-2-yl]ethyl]-1-methyl-2-oxo-benzimidazol-5-yl]amino]pyridine-3-carbonitrile (14 mg, 0.03 mmol, from step 2) in acetonitrile (2 mL) at rt. The reaction mixture was stirred at rt for 3 h. The reaction mixture was concentrated in vacuo and the resulting residue was diluted with DCM (5 mL) and further concentrated in vacuo. Purification by HPLC (ACE 5 C18-PFP 250×21.2 mm column; 15 min gradient of 60:40 to 0:100 water:methanol (both modified with 0.1% formic acid); flow rate 20 mLmin⁻¹; Agilent 6120 MS-Prep LC) afforded the title compound methyl (2R)-2-amino-4-[6-[(2-chloro-3-cyano-4-pyridyl)amino]-3-methyl-2-oxo-benzimidazol-1-yl]butanoate (5 mg, 46%) as a pale yellow solid. LCMS (Method T4) Rt 2.06 min; m/z 415.1271, expected 415.1280 for C₁₉H₂₀ClN₆O₃⁺ [M+H]⁺; ¹H NMR (500 MHz, chloroform-d) δ 8.04 (d, J=6.1 Hz, 1H), 7.05-7.02 (m, 2H), 7.02-6.96 (m, 2H), 6.63 (d, J=6.1 Hz, 1H), 4.15-4.04 (m, 2H), 3.62 (s, 3H), 3.57-3.51 (m, 1H), 3.46 (s, 3H), 2.34-2.24 (m, 1H), 2.06-1.96 (m, 1H).

Example 13: N-[3-[6-[(2-Chloro-3-cyano-4-pyridyl)amino]-3-methyl-2-oxo-benzimidazol-1-yl]-1-methyl-propyl]acetamide

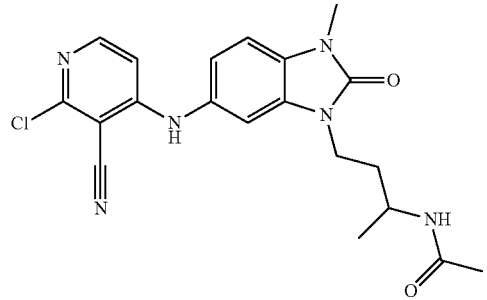 [SMILES: CC(=O)NC(C)CCn1c(=O)n(C)c2ccc(Nc3ccnc(Cl)c3C#N)cc21]

Step 1: 3-(tert-butoxycarbonylamino)butyl methanesulfonate

An oven-dried microwave vial (2.0-5.0 mL volume) was charged with tert-butyl N-(3-hydroxy-1-methyl-propyl)carbamate (100 mg, 0.53 mmol). The reaction vial was flushed with argon, sealed with a cap and then further flushed with argon. THF (1.5 mL) was added followed by triethylamine (0.15 mL, 1.08 mmol). Methanesulfonyl chloride (50 uL, 0.65 mmol) was added dropwise to the reaction mixture. The reaction mixture was stirred at rt for 1 h. The reaction mixture was quenched with saturated aq. NaHCO₃ (3 mL). The aqueous mixture was extracted with ethyl acetate (4×5 mL). The organic extracts were combined, dried (sodium sulfate) and concentrated in vacuo. The crude product was used in the next step without further purification.

Step 2: tert-Butyl N-[3-[6-[(2-choro-3-cyano-4-pyridyl)amino]-3-methyl-2-oxo-benzimidazol-1-yl]-1-methyl-propyl]carbamate A microwave vial (2.0-5.0 mL volume) was charged with crude 3-(tert-butoxycarbonylamino)butyl methanesulfonate (141 mg, from step 1), 2-chloro-4-[(1-methyl-2-oxo-3H-benzimidazol-5-yl)amino]pyridine-3-carbonitrile (Intermediate D1, 131 mg, 0.44 mmol) and cesium carbonate (171 mg, 0.53 mmol). The reaction vial was flushed with argon, sealed with a cap and then further flushed with argon. DMF (4 mL) was added and the reaction mixture was stirred at 140° C. under microwave irradiation for 1 h. The reaction mixture was allowed to cool to rt. Water (20 mL) was added. The aqueous mixture was acidified to pH 6 with 1 M HCl. The aqueous mixture was extracted with EtOAc (4×20 mL). The organic extracts were combined, dried (Na₂SO₄) and concentrated in vacuo. Purification by HPLC (3 injections; ACE 5 C18-PFP 250×30 mm column; 15 min gradient of 45:55 to 20:80 water:methanol (both modified with 0.1% formic acid); flow rate 40 mLmin⁻¹; Agilent 6120 MS-Prep LC) afforded tert-butyl N-[3-[6-[(2-chloro-3-cyano-4-pyridyl)amino]-3-methyl-2-oxo-benzimidazol-1-yl]-1-methyl-propyl]carbamate (62 mg, 30% over 2 steps) as a yellow solid. LCMS (Method T2) Rt 1.31 min; m/z 371.1391 [M-Boc+H]⁺; ¹H NMR (500 MHz, chloroform-d) δ 8.04 (dd, J=6.1, 0.7 Hz, 1H), 7.02 (d, J=8.2 Hz, 1H), 6.98 (dd, J=8.2, 1.7 Hz, 1H), 6.92 (br s, 1H), 6.87 (br s, 1H), 6.62 (d, J=6.1 Hz, 1H), 4.52 (br s, 1H), 4.01-3.89 (m, 2H), 3.78-3.66 (m, 1H), 3.46 (s, 3H), 1.98-1.89 (m, 1H), 1.89-1.81 (m, 1H), 1.39 (s, 9H), 1.21 (d, J=6.7 Hz, 3H).

Step 3: 4-[[3-(3-aminobutyl)-1-methyl-2-oxo-benzimidazol-5-yl]amino]-2-chloro-pyridine-3-carbonitrile TFA (1.20 mL, 15.67 mmol) was added dropwise to a solution of tert-butyl N-[3-[6-[(2-chloro-3-cyano-4-pyridyl)amino]-3-methyl-2-oxo-benzimidazol-1-yl]-1-methyl-propyl]carbamate (60 mg, 0.13 mmol, from step 2) in DCM (8 mL) at 0° C. The reaction mixture was allowed to warm to rt over 90 min. The reaction mixture was concentrated in vacuo and the resulting residue was diluted with DCM (10 mL) and further concentrated in vacuo. The residue was dissolved in methanol and purified using an SCX-2 cartridge (2 g), eluting with methanol (2×20 mL) followed by 2N methanolic ammonia (2×20 mL). The methanolic ammonia fractions were collected and concentrated in vacuo affording 4-[[3-(3-aminobutyl)-1-methyl-2-oxo-benzimidazol-5-yl]amino]-2-chloro-pyridine-3-carbonitrile (39 mg) as a yellow solid. LCMS (Method T4) Rt 1.99 min; m/z 371.1363, expected 371.1382 for $C_{18}H_{20}ClN_6O^+$ [M+H]$^+$; $^1$H NMR (500 MHz, chloroform-d) δ 8.01 (d, J=6.1 Hz, 1H), 7.14 (br s, 1H), 7.02 (d, J=8.2 Hz, 1H), 6.99 (dd, J=8.2, 1.7 Hz, 1H), 6.96 (d, J=1.7 Hz, 1H), 6.60 (d, J=6.1 Hz, 1H), 4.13-4.02 (m, 1H), 3.95-3.86 (m, 1H), 3.45 (s, 3H), 2.94-2.86 (m, 1H), 1.88-1.77 (m, 1H), 1.67-1.58 (m, 1H), 1.12 (d, J=6.3 Hz, 3H).

Step 4: N-[3-[6-[(2-chloro-3-cyano-4-pyridyl)amino]-3-methyl-2-oxo-benzimidazol-1-yl]-1-methyl-propyl]acetamide Acetyl chloride (4 uL, 0.056 mmol) was added to a stirred solution of 4-[[3-(3-aminobutyl)-1-methyl-2-oxo-benzimidazol-5-yl]amino]-2-chloro-pyridine-3-carbonitrile (18 mg, 0.048 mmol, from step 3) and trimethylamine (14 uL, 0.100 mmol) in DCM (0.25 mL) at 0° C. The reaction mixture was stirred vigorously at 0° C. for 1 h. The reaction mixture was diluted with DCM and concentrated in vacuo. The crude reaction mixture was diluted with DCM (8 mL) and washed with water (3 mL), saturated aq. NH$_4$Cl (3 mL) and brine (3 mL). The organic layer was dried (sodium sulfate) and concentrated in vacuo affording the title compound (9 mg, 46%) as a yellow solid. LCMS (Method T4) Rt 2.50 min; m/z 413.1466, expected 413.1487 for $C_{20}H_{22}ClN_6O_2^+$ [M+H]$^+$; $^1$H NMR (500 MHz, chloroform-d) δ 8.04 (d, J=6.1 Hz, 1H), 7.14 (br s, 1H), 7.03 (d, J=8.2 Hz, 1H), 7.00 (dd, J=8.2, 1.6 Hz, 1H), 6.91 (d, J=1.6 Hz, 1H), 6.65 (d, J=6.1 Hz, 1H), 5.82 (d, J=8.2 Hz, 1H), 4.09-4.00 (m, 1H), 3.97-3.89 (m, 2H), 3.45 (s, 3H), 1.95-1.89 (m, 2H), 1.93 (s, 3H), 1.20 (d, J=6.8 Hz, 3H).

Example 14: 5-Chloro-N-ethyl-4-[[3-(3-hydroxy-3-methyl-butyl)-1-methyl-2-oxo-benzimidazol-5-yl]amino]pyridine-2-carboxamide

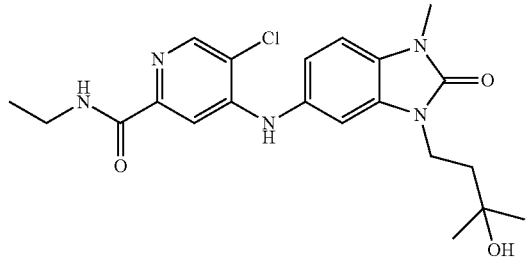 [SMILES: CCNC(=O)c1cc(Nc2ccc3c(c2)n(CCC(C)(C)O)c(=O)n3C)c(Cl)cn1]

4,5-dichloro-N-ethyl-pyridine-2-carboxamide (Intermediate E2, 9 mg, 0.041 mmol), 5-amino-3-(3-hydroxy-3-methyl-butyl)-1-methyl-benzimidazol-2-one (Intermediate A1, 9 mg, 0.036 mmol), Xantphos (10 mg, 0.0173 mmol), Pd$_2$(dba)$_3$ (2 mg, 0.0035 mmol), cesium carbonate (30 mg, 0.092 mmol) in NMP (0.3 mL) and toluene (0.3 mL) was degassed and heated in the microwave under a nitrogen atmosphere to 140° C. for 1 h. Added further 5-amino-3-(3-hydroxy-3-methyl-butyl)-1-methyl-benzimidazol-2-one (9 mg, 0.036 mmol) in NMP (0.3 mL), heated in the microwave under a nitrogen atmosphere to 140° C. for 1 h. Partitioned between DCM and water, acidified aqueous layer to pH5 with 10% citric acid. Organic layer was collected and passed through a Si-DMT column, then evaporated under reduced pressure and purified by preparative HPLC (ACE 5 C18-PFP column (5μ, 250×21.2 mm), 15 minute gradient elution from 45:55 to 20:80 water:methanol (both modified with 0.1% formic acid) at a flow rate of 20 mL/min) to give the title compound (4 mg) as a white solid. LCMS (Method T4) Rt 2.70 min; m/z 432.1788 expected 432.1797 for $C_{21}H_{27}ClN_5O_3$ [M+H]$^+$. $^1$H NMR (500 MHz, chloroform-d) δ 8.28 (s, 1H), 7.97 (t, J=6.2 Hz, 1H), 7.94 (s, 1H), 7.20 (d, J=2.0 Hz, 1H), 6.97 (d, J=8.2 Hz, 1H), 6.89 (dd, J=8.2, 2.0 Hz, 1H), 6.69 (s, 1H), 4.08-4.01 (m, 2H), 3.50-3.42 (m, 5H), 2.01-1.94 (m, 2H), 1.30 (s, 6H), 1.24 (t, J=7.3 Hz, 3H). OH not clearly observed.

Example 15a: 5-[[5-Chloro-2-(3,5-dimethylpyrazol-1-yl)pyrimidin-4-yl]amino]-3-(3-hydroxy-3-methyl-butyl)-1-methyl-benzimidazol-2-one

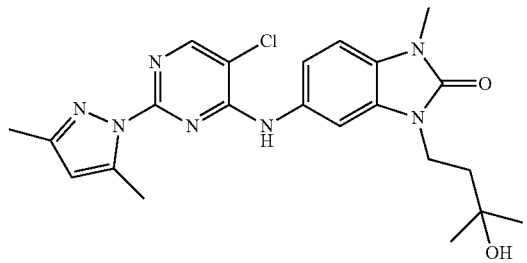 [SMILES: Cc1cc(C)n(-c2ncc(Cl)c(Nc3ccc4c(c3)n(CCC(C)(C)O)c(=O)n4C)n2)n1]

A mixture of 5-[(2,5-dichloropyrimidin-4-yl)amino]-3-(3-hydroxy-3-methyl-butyl)-1-methyl-benzimidazol-2-one (Intermediate D2a, 12.7 mg, 0.032 mmol), 3,5-dimethyl-1H-pyrazole (30 mg, 0.31 mmol) and cesium carbonate (100 mg, 0.31 mmol) in NMP (0.5 mL) was heated in the microwave to 170° C. for 1 h, then partitioned between DCM and water and pH adjusted to 5 using 10% citric acid before separation and extraction with further DCM. Organic layers were combined and evaporated, and the resulting NMP solution was purified, first by preparative HPLC (ACE 5 C18-PFP column (5μ, 250×21.2 mm), 15 minute gradient elution from 40:60 to 25:75 water:methanol (both modified with 0.1% formic acid) at a flow rate of 20 mL/min) then further purified by flash column chromatography (12 g KP-SIL, 0-6% methanol in DCM) to give the title compound (6 mg) as a white solid. LCMS (Method X4) Rt 2.71 min; m/z 456.1928 expected 456.1915 for $C_{22}H_{27}ClN_7O_2$ [M+H]$^+$. $^1$H NMR (500 MHz, chloroform-d) δ 8.37 (s, 1H), 7.44 (d, J=1.9 Hz, 1H), 7.22 (s, 1H), 7.13 (dd, J=1.9, 8.2 Hz, 1H), 6.98 (d, J=8.2 Hz, 1H), 5.95 (s, 1H), 4.08 (t, J=7.3 Hz, 2H), 3.45 (s, 3H), 2.36 (br m, 1H), 2.33 (s, 3H), 2.31 (s, 3H), 1.89 (t, J=7.4 Hz, 2H), 1.35-1.22 (m, 6H).

The following tabulated examples were prepared by a method analogous to that used for the preparation of example 15a, using the intermediate shown in Table 5 and the appropriate amine or heterocycle obtained from commercial vendors.

TABLE 5

Compounds prepared by a method analogous to that used for the preparation of Example 15a

| Example | Data | Intermediates |
|---|---|---|
| Example 15b: ethyl 1-(5-chloro-4-((3-(3-hydroxy-3-methylbutyl)-1-methyl-2-oxo-2,3-dihydro-1H-benzo[d]imidazol-5-yl)amino)pyrimidin-2-yl)-1H-pyrazole-4-carboxylate | $^1$H NMR (500 MHz, Chloroform-d) δ 8.94 (d, J = 0.8 Hz, 1H), 8.36 (s, 1H), 8.12 (d, J = 0.8 Hz, 1H), 7.85 (d, J = 2.0 Hz, 1H), 7.42 (s, 1H), 7.05 (dd, J = 8.3, 2.0 Hz, 1H), 6.99 (d, J = 8.3 Hz, 1H), 4.33 (q, J = 7.1 Hz, 2H), 4.16-4.06 (m, 2H), 3.45 (s, 3H), 2.01-1.94 (m, 2H), 1.37 (t, J = 7.1 Hz, 3H), 1.29 (s, 6H). OH not clearly observed. LCMS (Method T4) Rt 2.90 min; m/z 500.1802, expected 500.1808 for $C_{23}H_{27}ClN_7O_4^+$ [M + H]$^+$. | Intermediate D2a: 5-[(2,5-dichloro-pyrimidin-4-yl)amino]-3-(3-hydroxy-3-methyl-butyl)-1-methyl-benzimidazol-2-one |
| Example 15c: ethyl 1-(5-chloro-4-((3-(3-hydroxy-3-methylbutyl)-1-methyl-2-oxo-2,3-dihydro-1H-benzo[d]imidazol-5-yl)amino)pyrimidin-2-yl)-3,5-dimethyl-1H-pyrazole-4-carboxylate | $^1$H NMR (500 MHz, Chloroform-d) δ 8.39 (s, 1H), 7.39 (d, J = 2.0 Hz, 1H), 7.33 (s, 1H), 7.13 (dd, J = 8.3, 2.0 Hz, 1H), 6.97 (d, J = 8.3 Hz, 1H), 4.29 (q, J = 7.2 Hz, 2H), 4.04 (m, 2H), 3.43 (s, 3H), 2.66 (s, 3H), 2.48 (s, 3H), 1.91-1.84 (m, 2H), 1.35 (t, J = 7.2 Hz, 3H), 1.25 (s, 6H). OH not clearly observed, LCMS (Method T4) Rt 2.92 min; m/z 528.2113, expected 528.2121 for $C_{25}H_{31}ClN_7O_4^+$ [M + H]$^+$. | Intermediate D2a: 5-[(2,5-dichloro-pyrimidin-4-yl)amino]-3-(3-hydroxy-3-methyl-butyl)-1-methyl-benzimidazol-2-one |

TABLE 5-continued

Compounds prepared by a method analogous to that used for the preparation of Example 15a

| Example | Data | Intermediates |
| --- | --- | --- |
| Example 15d: 5-((5-chloro-2-(3-(trifluoromethyl)-1H-pyrazol-1-yl)pyrimidin-4-yl)amino)-3-(3-hydroxy-3-methylbutyl)-1-methyl-1,3-dihydro-2H-benzo[d]imidazol-2-one | $^1$H NMR (500 MHz, Chloroform-d) δ 8.49-8.44 (m, 1H), 8.37 (s, 1H), 7.80 (d, J = 2.0 Hz, 1H), 7.41 (s, 1H), 7.12 (dd, J = 8.3, 2.0 Hz, 1H), 7.00 (d, J = 8.3 Hz, 1H), 6.68 (d, J = 2.7 Hz, 1H), 4.12 (t, J = 7.0 Hz, 2H), 3.45 (s, 3H), 1.92 (t, J = 7.0 Hz, 2H), 1.27 (s, 6H). OH not clearly observed. LCMS (Method T4) Rt 2.97 min; m/z 496.1461, expected 496.1470 for $C_{21}H_{22}ClF_3N_7O_2^+$ [M + H]$^+$. | Intermediate D2a: 5-[(2,5-dichloro-pyrimidin-4-yl)amino]-3-(3-hydroxy-3-methyl-butyl)-1-methyl-benzimidazol-2-one |
| Example 15e: 5-((5-chloro-2-(3,5-dimethyl-1H-pyrazol-1-yl)pyrimidin-4-yl)amino)-3-(3,5-dihydroxy-3-methylpentyl)-1-methyl-1,3-dihydro-2H-benzo[d]imidazol-2-one | $^1$H NMR (500 MHz, acetone-d$_6$) δ 8.63 (0.6H, br, NH partly exchanged), 8.36 (1H, s), 7.83 (1H, d, J 2.2 Hz), 7.36 (1H, dd, J 8.3, 2.2 Hz), 7.09 (1H, d, J 8.3 Hz), 6.01 (1H, s), 4.09 (2H, m), 3.75 (2H, m), 3.40 (3H, s), 2.42 (3H, s), 2.23 (3H, s), 1.90 (2H, m), 1.76 (2H, m), 1.25 (3H, s). OHs not seen. LCMS (Method T4): Rt 2.66 min, m/z 486.1998, expected 486.2015 for $C_{23}H_{29}ClN_7O_3$ [M + H]$^+$. | Intermediate D4: 5-[(2,5-dichloro-pyrimidin-4-yl)amino]-3-(3,5-dihydroxy-3-methyl-pentyl)-1-methyl-benzimidazol-2-one |
| Example 15f: 5-((5-chloro-2-(3,5-dimethyl-1H-pyrazol-1-yl)pyrimidin-4-yl)amino)-3-(3-hydroxy-3-methylpentyl)-1-methyl-1,3-dihydro-2H-benzo[d]imidazol-2-one | $^1$H NMR (500 MHz, acetone-d$_6$) δ 8.66 (0.7H, br, NH partly exchanged), 8.33 (1H, s), 7.72 (1H, m), 7.36 (1H, dd, J 8.3, 1.8 Hz), 7.08 (1H, d, J 8.3 Hz), 6.00 (1H, s), 4.03 (2H, t, J 7.2 Hz), 3.39 (3H, s), 2.39 (3H, s), 2.20 (3H, s), 1.81 (2H, m), 1.51 (2H, q, J 8.0 Hz), 1.15 (3H, s), 0.86 (3H, t, J 8.0 Hz). OH not seen. LCMS (Method T4): Rt 2.85 min, m/z 470.2059, expected 470.2066 for $C_{23}H_{29}ClN_7O_2$ [M + H]$^+$. | Example 22g: 5-((2,5-dichloro-pyrimidin-4-yl)amino)-3-(3-hydroxy-3-methylpentyl)-1-methyl-1,3-dihydro-2H-benzo[d]imidazol-2-one |
| Example 15g: 5-((5-chloro-2-(dimethylamino)pyrimidin-4-yl)amino)-3-(3-hydroxy-3-methylbutyl)-1-methyl-1,3-dihydro-2H-benzo[d]imidazol-2-one | $^1$H NMR (500 MHz, acetone-d$_6$) δ 7.96 (1H, s), overlapping with 7.98-7.94 (0.6H, partly exchanged NH), 7.73 (1H, d, J 1.7 Hz), 7.35 (1H, dd, J 8.1, 1.7 Hz), 7.05 (1H, d, J 8.1 Hz), 4.02 (2H, t, J 7.9 Hz), 3.38 (3H, s), 3.13 (6H, s), 1.85 (2H, t, J 7.9 Hz), 1.25 (6H, s). OH not observed. LCMS (Method T4): Rt 2.22 min, m/z 405.1790, expected 405.1800 for $C_{19}H_{26}ClN_6O_2$ [M + H]$^+$. | Intermediate D2a: 5-[(2,5-dichloro-pyrimidin-4-yl)amino]-3-(3-hydroxy-3-methyl-butyl)-1-methyl-benzimidazol-2-one |

TABLE 5-continued

Compounds prepared by a method analogous to that used for the preparation of Example 15a

| Example | Data | Intermediates |
|---|---|---|
| Example 15h: 5-((5-chloro-2-(3,5-dimethyl-1H-pyrazol-1-yl)pyrimidin-4-yl)amino)-1-methyl-1,3-dihydro-2H-benzo[d]imidazol-2-one 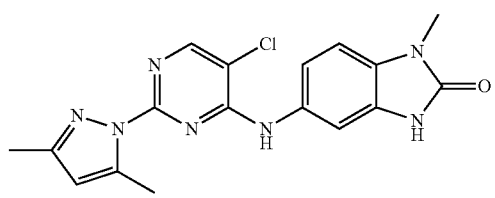 | $^1$H NMR (500 MHz, DMSO-$d_6$) δ 10.90 (1H, s, NH), 9.27 (1H,s, NH), 8.40 (1H, s), 7.28 (1H, d, J 1.7 Hz), 7.22 (1H, dd, J 8.3, 1.7 Hz), 7.07 (1H, d, J 8.3 Hz), 6.01 (1H, s), 3.28 (3H, s), 2.25 (3H, s), 2.14 (3H, s). LCMS (Method T4): Rt 2.68 min, m/z 370.1127, expected 370.1178 for $C_{17}H_{17}ClN_7O$ [M + H]$^+$. | Intermediate D3c: 6-[(2,5-dichloro-pyrimidin-4-yl)amino]-3-methyl-1H-benzimidazol-2-one |
| Example 15i: 1-(5-chloro-4-((3-(3-hydroxy-4-methoxy-3-methylbutyl)-1-methyl-2-oxo-2,3-dihydro-1H-benzo[d]imidazol-5-yl)amino)pyrimidin-2-yl)-N,N-dimethylpiperidine-4-carboxamide 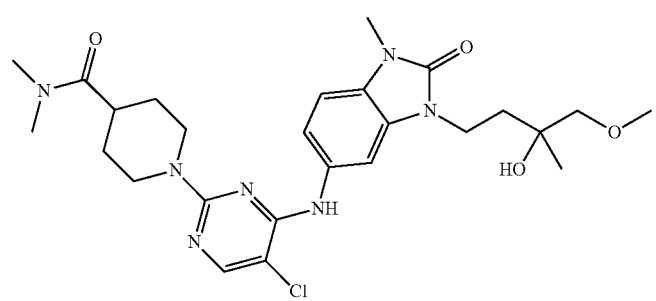 | $^1$H NMR (500 MHz, acetone-$d_6$) δ 8.17 (0.8H, br, partly exchanged NH), 7.97 (1H, s), 7.60 (1H, d, J 1.9 Hz), 7.27 (1H, dd, J 8.4, 1.9 Hz), 7.05 (1H, d, J 8.4 Hz), 4.68 (2H, m), 4.00 (2H, m), 3.37 (3H, s), 2.99 (3H, s), 3.26 (2H, m), 3.13 (3H, s), 3.00-2.91 (3H, m), 2.87 (3H, s), 1.87 (2H, m), 1.77-1.57 (4H, m), 1.22 (3H, s). OH not observed. LCMS (Method T4): Rt 2.42 min, m/z 546.2579, expected 546.2590 for $C_{26}H_{37}ClN_7O_4$ [M + H]$^+$. | Intermediate D2b: 5-[(2,5-dichloro-pyrimidin-4-yl)amino]-3-(3-hydroxy-4-methoxy-3-methyl-butyl)-1-methyl-benzimidazol-2-one |
| Example 15j: 5-((5-chloro-2-(3,5-dimethyl-1H-pyrazol-1-yl)pyrimidin-4-yl)amino)-3-(3-hydroxy-4-methoxy-3-methylbutyl)-1-methyl-1,3-dihydro-2H-benzo[d]imidazol-2-one 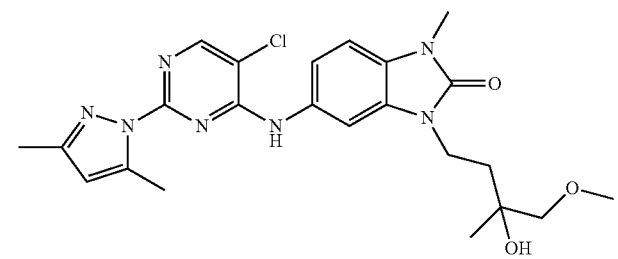 | $^1$H NMR (500 MHz, acetone-$d_6$) δ 8.63 (0.8H, br, partly exchanged NH), 8.36 (1H, s), 7.78 (1H, d, J 1.9 Hz), 7.38 (1H, dd, J 8.1, 1.9 Hz), 7.10 (1H, d, J 8.1 Hz), 6.04 (1H, s), 4.7 (2H, app t, J 7.5 Hz), 3.40 (3H, s), 3.37 (2H, m), 3.25 (3H, s), 2.41 (3H, s), 2.22 (3H, s), 1.93 (1H, m), 1.84 (1H, m), 1.17 (3H, s). LCMS (Method T4): Rt 2.93 min, m/z 486.1992, expected 486.2015 for $C_{23}H_{29}ClN_7O_3$ [M + H]$^+$. | Intermediate D2b: 5-[(2,5-dichloro-pyrimidin-4-yl)amino]-3-(3-hydroxy-4-methoxy-3-methyl-butyl)-1-methyl-benzimidazol-2-one |
| Example 15k: 1-(5-chloro-4-((3-(3,5-dihydroxy-3-methylpentyl)-1-methyl-2-oxo-2,3-dihydro-1H-benzo[d]imidazol-5-yl)amino)pyrimidin-2-yl)-N,N-dimethylpiperidine-4-carboxamide 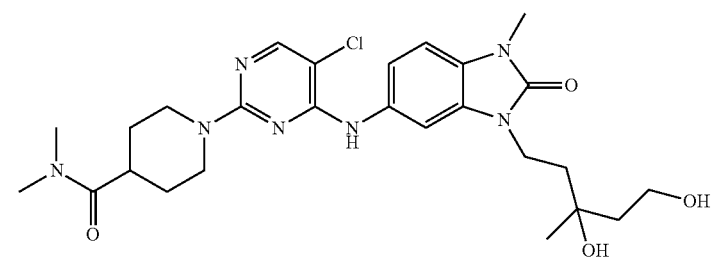 | $^1$H NMR (500 MHz, acetone-$d_6$) δ 8.02 (0.6H, br, partly exchanged NH), 7.97 (1H, s), 7.63 (1H, d, J 1.9 Hz), 7.24 (1H, dd, J 8.3, 1.9 Hz), 7.05 (1H, d J 8.3 Hz), 4.69 (2H, br d, J 13.8 Hz), 4.04-3.99 (2H, m), 3.84-3.76 (2H, m), 3.38 (3H, s), 3.14 (3H, s), 2.99-2.92 (4H, m), 2.87 (3H, s), 1.91-1.81 (3H, m), 1.78-1.72 (2H, m), 1.69-1.62 (2H, m), 1.27 (3H, s). OHs not observed. LCMS (Method T4): Rt 2.30 min, m/z 546.2580, expected 546.2590 for $C_{26}H_{37}ClN_7O_4$ [M + H]$^+$. | Intermediate D4: 5-[(2,5-dichloro-pyrimidin-4-yl)amino]-3-(3,5-dihydroxy-3-methyl-pentyl)-1-methyl-benzimidazol-2-one |

TABLE 5-continued

Compounds prepared by a method analogous to that used for the preparation of Example 15a

| Example | Data | Intermediates |
|---|---|---|
| Example 15l: 1-(5-chloro-4-((3-(3-hydroxy-3-methylpentyl)-1-methyl-2-oxo-2,3-dihydro-1H-benzo[d]imidazol-5-yl)amino)pyrimidin-2-yl)-N,N-dimethylpiperidine-4-carboxamide | $^1$H NMR (600 MHz, acetone-d$_6$) δ 8.02 (0.7H, br, partly exchanged NH), 7.98 (1H, s), 7.61 (1H, d, J 1.9 Hz), 7.28 (1H, dd, J 8.4, 1.9 Hz), 7.06 (1H, d J 8.4 Hz), 4.69 (2H, br d, J 12.9 Hz), 4.00 (2H, t, J 7.9 Hz), 3.39 (3H, s), 3.14 (3H, s), 3.00-2.94 (4H, m), 2.88 (3H, s), 1.85-1.80 (2H, m), 1.78-1.72 (2H, m), 1.69-1.62 (2H, m), 1.55 (2H, q, J 7.5 Hz), 1.20 (3H, s), 0.92 (3H, t, J 7.5 Hz). LCMS (Method T4): Rt 2. 52 min, m/z 530.2635, expected 530.2641 for C$_{26}$H$_{37}$ClN$_7$O$_3$ [M + H]$^+$. | Example 22g: 5-((2,5-dichloro-pyrimidin-4-yl)amino)-3-(3-hydroxy-3-methylpentyl)-1-methyl-1,3-dihydro-2H-benzo[d]imidazol-2-one |
| Example 15m: 5-((5-chloro-2-(1H-pyrazol-1-yl)pyrimidin-4-yl)amino)-3-(3-hydroxy-3-methylbutyl)-1-methyl-1,3-dihydro-2H-benzo[d]imidazol-2-one | $^1$H NMR (500 MHz, DMSO-d$_6$) δ 9.42 (1H, br), 8.45 (1H, s), 8.38 (1H, d, J 2.2 Hz), 7.79 (1H, s), 7.63 (1H, d, J 2.2 Hz), 7.42 (1H, dd, J 8.4, 2.2 Hz), 7.17 (1H, d, J 8.4 Hz), 6.52 (1H, s), 3.91 (2H, t, J 7.6 Hz), 3.34 (3H, s), 1.75 (2H, t, J 7.6 Hz), 1.14 (6H, s). OH not observed. LCMS (Method T4): Rt 2.73 min, m/z 428.1552, expected 428.1596 for C$_{20}$H$_{23}$ClN$_7$O$_2$ [M + H]$^+$. | Intermediate D2a: 5-[(2,5-dichloro-pyrimidin-4-yl)amino]-3-(3-hydroxy-3-methyl-butyl)-1-methyl-benzimidazol-2-one |
| Example 15n: 5-((5-chloro-2-(4-chloro-3,5-dimethyl-1H-pyrazol-1-yl)pyrimidin-4-yl)amino)-3-(3-hydroxy-3-methylbutyl)-1-methyl-1,3-dihydro-2H-benzo[d]imidazol-2-one | $^1$H NMR (500 MHz, chloroform-d) δ 9.47 (1H, s), 8.44 (1H, s), 7.42 (1H, d, J 1.8 Hz), 7.25 (1H, dd, J 8.4, 1.8 Hz), 7.15 (1H, d, J 8.4 Hz), 3.89 (2H, t, J 7.7 Hz), 3.34 (3H, s), 2.25 (3H, s), 2.17 (3H, s), 1.68 (2H, t, J 7.7 Hz), 1.10 (6H, s). OH not observed. LCMS (Method T4): Rt 3.02 min; m/z 490.1509 expected 490.1520 for C$_{22}$H$_{26}$Cl$_2$N$_7$O$_2$ [M + H]$^+$. | Intermediate D2a: 5-[(2,5-dichloro-pyrimidin-4-yl)amino]-3-(3-hydroxy-3-methyl-butyl)-1-methyl-benzimidazol-2-one |
| Example 15o: 6-(3,5-dimethyl-1H-pyrazol-1-yl)-4-((3-(3-hydroxy-3-methylbutyl)-1-methyl-2-oxo-2,3-dihydro-1H-benzo[d]imidazol-5-yl)amino)nicotinonitrile | $^1$H NMR (500 MHz, acetone-d$_6$) δ 8.46 (1H, s), 8.28 (0.6H, br s, partly exchanged NH), 7.41 (1H, s), 7.22 (1H, d, J 1.5 Hz), 7.19 (1H, d, J 8.3 Hz), 7.14 (1H, dd, J 8.3, 1.5 Hz), 6.04 (1H, s), 4.04 (2H, t, J 7.8 Hz), 3.43 (3H, s), 2.62 (3H, s), 2.11 (3H, s), 1.87 (2H, t, J 7.8 Hz), 1.23 (6H, s). OH not observed. LCMS (Method T4): Rt 3.00 min, m/z 446.2265, expected expected 446.2299 for C$_{24}$H$_{28}$N$_7$O$_2$ [M + H]$^+$. | Intermediate D3a: 6-chloro-4-[[3-(3-hydroxy-3-methyl-butyl)-1-methyl-2-oxo-benzimidazol-5-yl]amino]pyridine-3-carbonitrile |

TABLE 5-continued

Compounds prepared by a method analogous to that used for the preparation of Example 15a

| Example | Data | Intermediates |
|---|---|---|
| Example 15p: 5-((5-chloro-2-(3,5-dimethyl-1H-pyrazol-1-yl)-6-methylpyrimidin-4-yl)amino)-3-(3-hydroxy-3-methylbutyl)-1-methyl-1,3-dihydro-2H-benzo[d]imidazol-2-one | $^1$H NMR (500 MHz, Chloroform-d) δ 7.46 (d, J = 2.0 Hz, 1H), 7.27 (s, 1H, NH), 7.11 (dd, J = 8.3, 2.0 Hz, 1H), 6.97 (d, J = 8.3 Hz, 1H), 5.94 (s, 1H), 4.11-4.04 (m, 2H), 3.45 (s, 3H), 2.63 (s, 3H), 2.39 (s, 1H, OH), 2.34 (s, 3H), 2.31 (s, 3H), 1.93-1.86 (m, 2H), 1.26 (s, 6H). LCMS (Method X4) Rt 2.88 min; m/z 470.2097 expected 470.2071 for $C_{23}H_{29}ClN_7O_2$ [M + H]$^+$. | Intermediate D3h: 5-[(2,5-dichloro-6-methyl-pyrimidin-4-yl)amino]-3-(3-hydroxy-3-methyl-butyl)-1-methyl-benzimidazol-2-one |
| Example 15q: 5-((5-bromo-2-(3,5-dimethyl-1H-pyrazol-1-yl)pyrimidin-4-yl)amino)-3-(3-hydroxy-3-methylbutyl)-1-methyl-1,3-dihydro-2H-benzo[d]imidazol-2-one | $^1$H NMR (500 MHz, Chloroform-d) δ 8.46 (s, 1H), 7.41 (d, J = 2.0 Hz, 1H), 7.24 (s, 1H), 7.12 (dd, J = 8.3, 2.0 Hz, 1H), 6.98 (d, J = 8.3 Hz, 1H), 5.94 (s, 1H), 4.11-4.04 (m, 2H), 3.45 (s, 3H), 2.30 (s, 6H), 1.89 (m, 2H), 1.27 (s, 6H). OH not clearly observed. LCMS (Method X2) Rt 1.32 min; m/z 500.1422 expected 500.1410 for $C_{22}H_{27}BrN_7O_2$ [M + H]$^+$. | Intermediate D3g: 5-[(5-bromo-2-chloro-pyrimidin-4-yl)amino]-3-(3-hydroxy-3-methyl-butyl)-1-methyl-benzimidazol-2-one |

Example 16a: 5-((5-chloro-2-(3-methyl-1H-pyrazol-1-yl)pyrimidin-4-yl)amino)-3-(3-hydroxy-3-methyl-butyl)-1-methyl-1,3-dihydro-2H-benzo[d]imidazol-2-one and Example 16b: 5-((5-chloro-2-(5-methyl-1H-pyrazol-1-yl)pyrimidin-4-yl)amino)-3-(3-hydroxy-3-methylbutyl)-1-methyl-1,3-dihydro-2H-benzo[d]imidazol-2-one

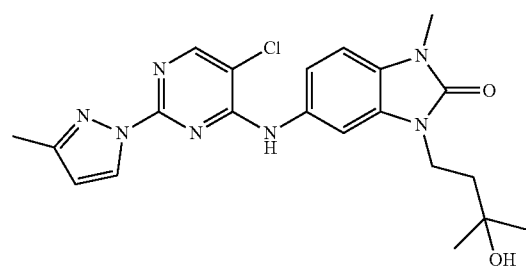

and

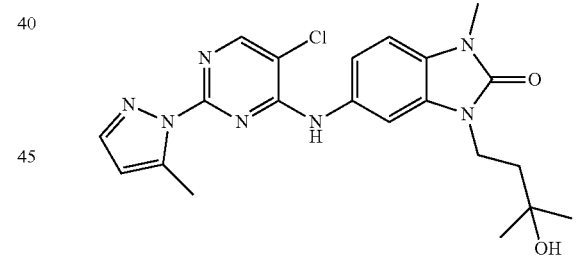

A mixture of 5-[(2,5-dichloropyrimidin-4-yl)amino]-3-(3-hydroxy-3-methyl-butyl)-1-methyl-benzimidazol-2-one (Intermediate D2a, 25 mg, 0.063 mmol), 3-methylpyrazole (0.05 mL, 0.62 mmol) and dicesium carbonate (100 mg, 0.31 mmol) in NMP (0.5 mL) was heated in the microwave to 170° C. for 1 hour, then partitioned between DCM and water and pH adjusted to 5 using 10% citric acid before separation and extraction with further DCM. Organic layers were combined and evaporated to give crude material as a solution in NMP. Regioisomers were separated by preparative HPLC (ACE 5 C18-PFP column (5μ, 250×21.2 mm), 15 minute gradient elution from 45:55 to 20:80 water:methanol (both modified with 0.1% formic acid) at a flow rate of 20 mL/min). The major, later eluting product was assigned as Example 16a 5-[[5-chloro-2-(3-methylpyrazol-1-yl)pyrimidin-4-yl]amino]-3-(3-hydroxy-3-methyl-butyl)-1-methyl-benzimidazol-2-one (18 mg).

$^1$H NMR (500 MHz, Chloroform-d) δ 8.34 (s, 1H), 8.27 (d, J=2.6 Hz, 1H), 7.63 (d, J=2.0 Hz, 1H), 7.32 (s, 1H, NH), 7.18 (dd, J=8.3, 2.0 Hz, 1H), 7.02 (d, J=8.3 Hz, 1H), 6.23 (d, J=2.6 Hz, 1H), 4.15-4.08 (m, 2H), 3.47 (s, 3H), 2.40 (s, 3H), 1.94 (t, J=7.3 Hz, 2H), 1.30 (s, 6H). OH not clearly observed. LCMS (Method X2) Rt 1.33 min; m/z 442.1755 expected 442.1758 for $C_{21}H_{25}ClN_7O_2$ [M+H]$^+$.

The minor, earlier eluting product was assigned as Example 16b 5-[[5-chloro-2-(5-methylpyrazol-1-yl)pyrimidin-4-yl]amino]-3-(3-hydroxy-3-methyl-butyl)-1-methyl-benzimidazol-2-one (2.5 mg)

$^1$H NMR (500 MHz, Chloroform-d) δ 8.37 (s, 1H), 7.74 (d, J=2.0 Hz, 1H), 7.63 (m, 1H), 7.29 (s, 1H, NH), 7.08 (dd, J=8.3, 2.0 Hz, 1H), 6.98 (d, J=8.3 Hz, 1H), 6.16 (s, 1H), 4.13-4.06 (m, 2H), 3.45 (s, 3H), 2.46 (s, 3H), 1.97-1.91 (m, 2H), 1.29 (s, 6H). OH not clearly observed. LCMS (Method X2) Rt 1.26 min m/z 442.1756 expected 442.1758 for $C_{21}H_{25}ClN_7O_2$ [M+H]$^+$.

Example 17a 5-((5-chloro-2-(1H-indazol-3-yl)pyrimidin-4-yl)amino)-3-(3-hydroxy-3-methylbutyl)-1-methyl-1,3-dihydro-2H-benzo[d]imidazol-2-one and Example 17b: 5-((5-chloro-2-(1H-indazol-1-yl)pyrimidin-4-yl)amino)-3-(3-hydroxy-3-methylbutyl)-1-methyl-1,3-dihydro-2H-benzo[d]imidazol-2-one

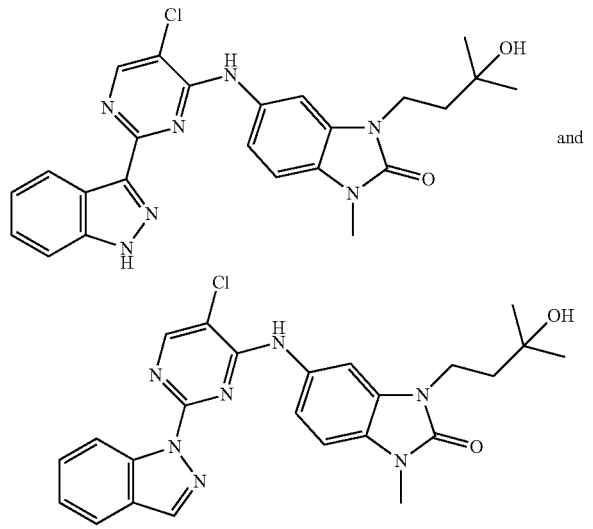

and

A mixture of 5-[(2,5-dichloropyrimidin-4-yl)amino]-3-(3-hydroxy-3-methyl-butyl)-1-methyl-benzimidazol-2-one (Intermediate D2a, 20 mg, 0.05 mmol), indazole (60 mg, 0.50 mmol) and cesium carbonate (164 mg, 0.50 mmol) in NMP (0.63 mL) was heated in the microwave to 180° C. for 1 hour. Once cooled the mixture was diluted with DMSO (0.5 mL) then purified using reverse-phase C18 column eluting from 10-100% methanol in water (each containing 0.1% formic acid). The later eluting product was assigned as Example 17b 5-[(5-chloro-2-indazol-1-yl-pyrimidin-4-yl)amino]-3-(3-hydroxy-3-methyl-butyl)-1-methyl-benzimidazol-2-one (4 mg)

$^1$H NMR (500 MHz, Methanol-d$_4$) δ 8.34 (s, 1H), 8.26 (s, 1H), 8.01-7.95 (m, 1H), 7.79-7.72 (m, 1H), 7.51 (d, J=1.8 Hz, 1H), 7.30 (dd, J=8.3, 1.8 Hz, 1H), 7.25 (d, J=8.3 Hz, 1H), 7.25-7.16 (m, 1H), 7.07-6.99 (m, 1H), 3.99-3.92 (m, 2H), 3.51 (s, 3H), 1.74-1.67 (m, 2H), 1.05 (s, 6H). LCMS (Method T4) Rt 2.88 min m/z 478.1737 expected 478.1753 for $C_{24}H_{25}ClN_7O_2$ [M+H]$^+$.

The earlier eluting compound required further purification by preparative HPLC (ACE 5 C18-PFP column (5μ, 250× 21.2 mm), 15 minute gradient elution from 60:40 to 0:100 water:methanol (both modified with 0.1% formic acid) at a flow rate of 20 mL/min). This compound was assigned as Example 17a 5-[[5-chloro-2-(1H-indazol-3-yl)pyrimidin-4-yl]amino]-3-(3-hydroxy-3-methyl-butyl)-1-methyl-benzimidazol-2-one (3 mg).

$^1$H NMR (500 MHz, DMSO-d$_6$) δ 9.16 (s, 1H), 8.92 (s, 1H), 8.10 (s, 1H), 7.68 (dd, J=7.8, 1.6 Hz, 1H), 7.63-7.58 (m, 1H), 7.53-7.48 (m, 1H), 7.31-7.26 (m, 2H), 7.22-7.17 (m, 1H), 7.07-7.01 (m, 1H), 3.83-3.76 (m, 2H), 3.32 (s, 3H), 1.68-1.61 (m, 2H), 1.12 (s, 6H). OH not clearly observed. LCMS (Method T4) Rt 2.30 min m/z 478.1750 expected 478.1753 for $C_{24}H_{25}ClN_7O_2$ [M+H]$^+$.

Example 18a: 2-chloro-4-((3-(2-(1-hydroxycyclobutyl)ethyl)-1-methyl-2-oxo-2,3-dihydro-1H-benzo[d]imidazol-5-yl)amino)nicotinonitrile

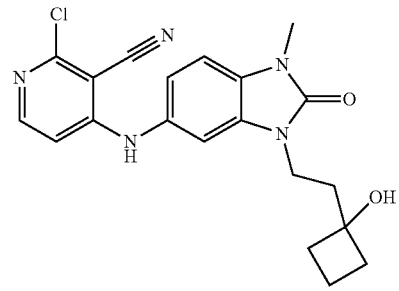 [SMILES: Cn1c(=O)n(CCC2(O)CCC2)c2cc(Nc3ccnc(Cl)c3C#N)ccc21]

To a suspension of 2-chloro-4-[(1-methyl-2-oxo-3H-benzimidazol-5-yl)amino]pyridine-3-carbonitrile (Intermediate D1, 25 mg, 0.083 mmol) in acetonitrile (1 mL) and DMF (0.2 mL) was added dicesium carbonate (60 mg, 0.18 mmol) and 1-(2-bromoethyl)cyclobutan-1-ol (20 mg, 0.11 mmol) and the resulting mixture was heated to 100° C. in the microwave for 1 h. The resulting mixture was partitioned water and DCM, then acidified to pH6 with 10% citric acid, and passed through phase separator to separate layers. The organic layer was evaporated, then redissolved in DMSO and purified using reverse phase flash chromatography (12 g SNAP Ultra C18, 50-65% methanol in water, 0.1% formic acid modifier) to give 2-chloro-4-[[3-[2-(1-hydroxycyclobutyl)ethyl]-1-methyl-2-oxo-benzimidazol-5-yl]amino]pyridine-3-carbonitrile (19 mg). $^1$H NMR (600 MHz, Chloroform-d) δ 8.05 (d, J=6.1 Hz, 1H), 7.06 (d, J=8.2 Hz, 1H), 7.04-7.01 (m, 2H), 7.00 (d, J=1.9 Hz, 1H), 6.63 (d, J=6.1 Hz, 1H), 4.07 (t, J=6.7 Hz, 2H), 3.48 (s, 3H, NMe), 2.14-1.87 (m, 6H), 1.82 (m, 1H) and 1.56 (m, 1H). OH not clearly observed. LCMS (2 min) Rt 1.26 min; m/z 398.1372 expected 398.1384 for $C_{20}H_{21}N_5O_2Cl$ [M+H]$^+$.

Example 18b: 2-chloro-4-((1-methyl-3-(2-(methylsulfonyl)ethyl)-2-oxo-2,3-dihydro-1H-benzo[d]imidazol-5-yl)amino)nicotinonitrile

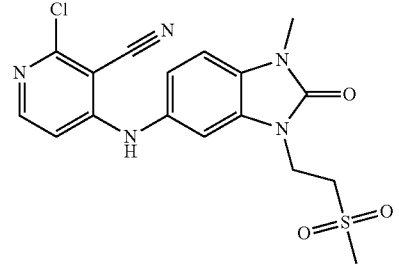 [SMILES: Cn1c(=O)n(CCS(C)(=O)=O)c2cc(Nc3ccnc(Cl)c3C#N)ccc21]

Prepared, from 2-bromoethyl methyl sulfone, using an analogous method to that used for the preparation of example 18a.

$^1$H NMR (600 MHz, Chloroform-d) δ 8.07 (d, J=6.1 Hz, 1H), 7.11 (d, J=1.9 Hz, 1H), 7.07 (d, J=8.2 Hz, 1H), 7.02

(dd, J=8.2, 1.9 Hz, 1H), 6.91 (s, 1H, NH), 6.71 (d, J=6.1 Hz, 1H), 4.40 (t, J=6.3 Hz, 2H), 3.54 (t, J=6.3 Hz, 2H), 3.48 (s, 3H), 2.95 (s, 3H). LCMS (Method X2) Rt 1.05 min; m/z 406.0742 expected 406.0741 for $C_{17}H_{17}ClN_5O_3S$ [M+H]$^+$.

Example 19a: 2-chloro-4-((1-methyl-2-oxo-3-(3-oxopentyl)-2,3-dihydro-1H-benzo[d]imidazol-5-yl)amino)nicotinonitrile

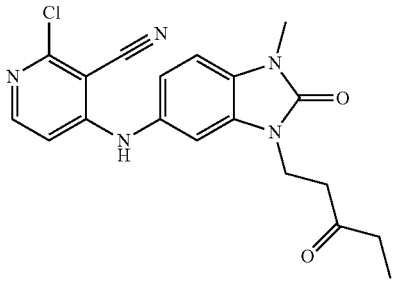 [SMILES: CCC(=O)CCn1c(=O)n(C)c2ccc(Nc3ccnc(Cl)c3C#N)cc21]

To a solution of 2-chloro-4-[(1-methyl-2-oxo-3H-benzimidazol-5-yl)amino]pyridine-3-carbonitrile (Intermediate D1, 20 mg, 0.067 mmol) in DMF (0.5 mL) was added polymer-bound macroporous tetraalkylammonium carbonate, 18-50 mesh (2.5-3.5 mmol/g loading, 50 mg). After 15 minutes, 1-bromopentan-3-one (14 mg, 0.085 mmol) was added, and the resulting mixture was heated to 90° C. for 4 days. Water (0.1 mL) was added, and the solution was removed by syringe, diluted with DMSO to give a total volume of 1 mL, filtered, then purified using reverse phase flash chromatography (Biotage SNAP Ultra C18, 50-80% methanol in water each containing 0.1% formic acid modifier), to give the title compound as a white solid (20 mg). $^1$H NMR (600 MHz, Chloroform-d) δ 8.06 (d, J=6.1 Hz, 1H), 7.16 (d, J=1.9 Hz, 1H), 7.03 (br m, 1H), 7.01 (d, J=8.2 Hz, 1H), 6.98 (dd, J=8.2, 1.9 Hz, 1H), 6.73 (d, J=6.1 Hz, 1H), 4.13 (t, J=6.3 Hz, 2H), 3.45 (s, 3H), 2.97 (t, J=6.3 Hz, 2H), 2.45 (q, J=7.3 Hz, 2H), 1.04 (t, J=7.3 Hz, 3H). LCMS (Method X4) Rt 2.52 min; m/z 384.1212 expected 384.1227 for $C_{19}H_{19}ClN_5O_2$ [M+H]$^+$.

The following tabulated examples were prepared by a method analogous to that used for the preparation of example 19a, using an appropriate alkyl bromide obtained from commercial vendors.

TABLE 6

Compounds prepared by a method analogous to that used for the preparation of Example 19a

| Example | Data |
|---|---|
| Example 19b: 2-chloro-4-((1-methyl-3-((2-methyltetrahydrofuran-3-yl)methyl)-2-oxo-2,3-dihydro-1H-benzo[d]imidazol-5-yl)amino)nicotinonitrile, 2:1 mixture of cis:trans diastereoisomers, racemic | LCMS (Method X4) Rt 2.46 min; m/z 398.1396 expected 398.1384 for $C_{20}H_{21}ClN_5O_2$ [M + H]$^+$. NMR shows mixture of diastereoisomers, ratio ~2:1. Major product, assigned as cis based on NOE between THF C2 and C3 hydrogens, and between C2 methyl and C3 methylene: $^1$H NMR (600 MHz, Chloroform-d) δ 8.05 (d, J = 6.1 Hz, 1H), 7.06 (d, J = 8.2 Hz, 1H), 7.02 (dd, J = 8.2, 1.8 Hz, 1H), 6.90 (br s, 1H, NH), 6.89 (d, J = 1.8 Hz, 1H), 6.60 (d, J = 6.1 Hz, 1H), 4.12 (app p, J = 6.4 Hz, 1H), 4.07 (td, J = 8.3, 5.4 Hz, 1H), 3.98-3.84 (m, 2H), 3.77 (td, J = 8.4, 6.7 Hz, 1H), 3.49 (s, 3H), 2.79-2.70 (m, 1H), 1.95 (m, 1H), 1.83 (m, 1H), 1.32 (d, J = 6.5 Hz, 3H). Minor product, assigned as trans: $^1$H NMR (600 MHz, Chloroform-d) δ 8.05 (d, J = 6.1 Hz, 1H), 7.06 (d, J = 8.2 Hz, 1H), 7.02 (dd, J = 8.2, 1.8 Hz, 1H), 6.92 (br s 1H, NH), 6.89 (d, J = 1.8 Hz, 1H), 6.61 (d, J = 6.1 Hz, 1H), 3.98 - 3.84 (m, 4H), 3.82 (app p, J = 6.2 Hz, 1H), 3.49 (s, 3H), 2.33 (m, 1H), 2.11 (m, 1H), 1.83 (m, 1H), 1.20 (d, J = 6.1 Hz, 3H). |
| Example 19c: 2-chloro-4-((1-methyl-3-(2-(2-methyl-1,3-dioxolan-2-yl)ethyl)-2-oxo-2,3-dihydro-1H-benzo[d]imidazol-5-yl)amino)nicotinonitrile | $^1$H NMR (600 MHz, Chloroform-d) δ 8.05 (d, J = 6.1 Hz, 1H), 7.03 (d, J = 8.2 Hz, 1H), 6.99 (dd, J = 8.3, 1.9 Hz, 1H), 6.91 (d, J = 1.9 Hz, 1H), 6.89 (s, 1H, NH), 6.62 (d, J = 6.1 Hz, 1H), 4.05-3.95 (m, 6H), 3.47 (s, 3H), 2.15-2.09 (m, 2H), 1.39 (s, 3H). LCMS (Method X4) Rt 2.5 min; m/z 414.1340 expected 414.1433 for $C_{20}H_{21}ClN_5O_3$ [M + H]$^+$. |

TABLE 6-continued

Compounds prepared by a method analogous to that used for the preparation of Example 19a

| Example | Data |
|---|---|
| Example 19d: tert-butyl 2-((6-((2-chloro-3-cyanopyridin-4-yl)amino)-3-methyl-2-oxo-2,3-dihydro-1H-benzo[d]imidazol-1-yl)methyl)azetidine-1-carboxylate 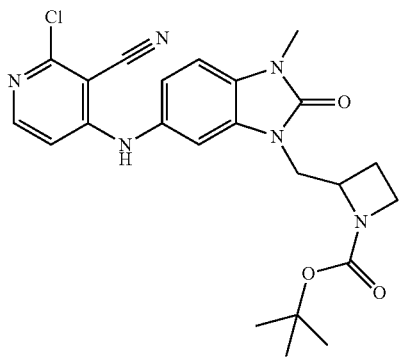 | $^1$H NMR (600 MHz, Chloroform-d) δ 8.04 (d, J = 6.1 Hz, 1H), 7.12 (s, 1H), 7.04 (d, J = 8.2 Hz, 1H), 6.99 (dd, J = 8.2, 2.0 Hz, 1H) overlapping with 6.99 (s, 1H, NH), 6.63 (d, J = 6.1 Hz, 1H), 4.60-4.52 (m, 1H), 4.21 (m, 1H), 4.17-4.11 (m, 1H), 3.87-3.81 (m, 1H), 3.67 (m, 1H), 3.49 (s, 3H), 2.32 (s, 1H), 2.21 (s, 1H), 1.33 (s, 9H). LCMS (Method X4) Rt 2.76 min; m/z 469.1744 expected 469.1755 for $C_{23}H_{26}ClN_6O_3$ [M + H]$^+$. |

Example 20a: 5-((5-chloro-2-((3R,5S)-4,4-difluoro-3,5-dimethylpiperidin-1-yl)pyrimidin-4-yl)amino)-3-(3-hydroxy-3-methylbutyl)-1-methyl-1,3-dihydro-2H-benzo[d]imidazol-2-one

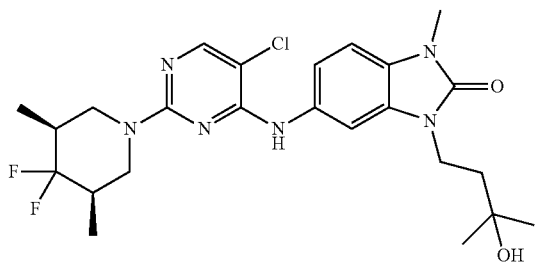 [SMILES: C[C@@H]1CN(c2ncc(Cl)c(Nc3ccc4c(c3)n(CCC(C)(C)O)c(=O)n4C)n2)C[C@H](C)C1(F)F]

A mixture of (3R,5S)-4,4-difluoro-3,5-dimethyl-piperidine (0.03 mL, 0.13 mmol), 5-[(2,5-dichloropyrimidin-4-yl)amino]-3-(3-hydroxy-3-methyl-butyl)-1-methyl-benzimidazol-2-one (intermediate D2a, 20 mg, 0.05 mmol) and N,N-diisopropylethylamine (0.04 mL, 0.25 mmol) in NMP (1 mL) was heated in the microwave to 170° C. for 1 hour. The mixture was partitioned between DCM and water, the aqueous layer was extracted with DCM and the combined organics were washed with brine. The organic layers were combined and evaporated, and the resulting NMP solution was purified by preparative HPLC (ACE 5 C18-PFP column (5μ, 250×2.2 mm), 15 minute gradient elution from 40:60 to 25:75 water:methanol (both modified with 0.1% formic acid) at a flow rate of 20 mL/min) to give the title compound (19 mg) as a solid. LCMS (Method T4): Rt 3.15 min m/z 509.2212, expected 509.2238 for $C_{24}H_{32}ClF_2NO_2$ [M+H]$^+$. $^1$H NMR (acetone-d$_6$, 500 MHz): δ 8.14 (1H, s), 8.00 (1H, s), 7.46 (1H, d, J 1.4 Hz), 7.37 (1H, dd, J 8.0, 1.4 Hz), 7.09 (1H, d, J 8.0 Hz), 4.65 (2H, br d, J 11.4 Hz), 4.03 (2H, m), 3.38 (3H, s), 2.71 (2H, t, J 11.3 Hz), 1.99 (2H, m), 1.85 (2H, m), 1.26 (6H, s), 1.02 (6H, d, J 6.6 Hz). OH not observed. $^{19}$F NMR (acetone-d6, 471 MHz): δ−108.7 (dt, J 235.3 Hz), −135.3 (dt, J 235, 27 Hz).

The following tabulated examples were prepared by a method analogous to that used for the preparation of example 20a, using the intermediate shown in Table 7 and the appropriate amine or heterocycle obtained from commercial vendors.

TABLE 7

Compounds prepared by a method analogous to that used for the preparation of Example 20a

| Example | Data | Intermediates |
| --- | --- | --- |
| Example 20b: 5-((6-((5-chloro-2-(2,2,6,6-tetramethylmorpholino)pyrimidin-4-yl)amino)-3-methyl-2-oxo-2,3-dihydro-1H-benzo[d]imidazol-1-yl)methyl)-5-(2-hydroxypropan-2-yl)-3-methyloxazolidin-2-one | $^1$H NMR (600 MHz, DMSO-$d_6$): δ 8.72 (1H, s), 8.02 (1H, s), 7.45 (1H, d, J 1.8 Hz), 7.39 (1H, dd, J 8.5, 1.8 Hz), 7.12 (1H, d, J 8.5 Hz), 4.27 (1H, d, J 15.4 Hz), 3.98 (1H, d, J 15.4 Hz), 3.60 (1H, d, J 9.5 Hz), 3.56 (1H, d, J 9.5 Hz), 3.52 (4H, s), 3.36 (3H, s), 2.70 (3H, s), 1.26 (3H, s), 1.22 (3H, s), 1.15 (6H, s), 1.12 (6H, s). OH not clearly observed. LCMS (Method T4): Rt 2.67 min, m/z 588.2678, expected 588.2696 for $C_{28}H_{39}ClN_7O_5$ [M + H]$^+$. | Intermediate D3j: 5-((6-((2,5-dichloropyrimidin-4-yl)amino)-3-methyl-2-oxo-2,3-dihydro-1H-benzo[d]imidazol-1-yl)methyl)-5-(2-hydroxypropan-2-yl)-3-methyloxazolidin-2-one |
| Example 20c: 1-(5-chloro-4-((3-(3-hydroxy-3-methylpentyl)-1-methyl-2-oxo-2,3-dihydro-1H-benzo[d]imidazol-5-yl)amino)pyrimidin-2-yl)-N,N-dimethylpiperidine-4-carboxamide | $^1$H NMR (500 MHz, acetone-$d_6$): δ 8.16 (0.6H, br, partly exchanged NH), 7.97 (1H, s), 7.61 (1H,d, J 1.8 Hz), 7.28 (1H, dd, J 7.7, 1.8 Hz), 7.05 (1H, d, J 7.7 Hz), 4.68 (2H, br d, J 13.3 Hz), 4.01 (2H, t, J 8.0 Hz), 3.37 (3H, s), 3.12 (3H, s), 3.00-2.91 (3H, m), 2.87 (3H, s), 1.85 (2H, t, J 8.0 Hz), 1.77-1.71 (2H, m), 1.70-1.59 (2H, m), 1.25 (6H, s). OH not observed. LCMS (Method T4): Rt 2.40 min, m/z 516.2617, expected 516.2484 for $C_{25}H_{35}ClN_7O_3$ [M + H]$^+$. | Intermediate D2a: 5-[(2,5-dichloropyrimidin-4-yl)amino]-3-(3-hydroxy-3-methyl-butyl)-1-methyl-benzimidazol-2-one |
| Example 20d: 5-((5-chloro-2-(piperidin-1-yl)pyrimidin-4-yl)amino)-3-(3-hydroxy-3-methylbutyl)-1-methyl-1,3-dihydro-2H-benzo[d]imidazol-2-one | $^1$H NMR (500 MHz, acetone-$d_6$): δ 7.97 (0.3H, br, partly exchanged NH), 7.96 (1H, s), 7.61 (1H, d, J 1.8 Hz), 7.31 (1H, dd, J 8.7, 1.3 Hz), 7.05 (1H, d, J 8.7 Hz), 4.02 (2H, m), 3.73 (4H, br t, J 4.8 Hz), 3.38 (3H, s), 1.86 (2H, m), 1.67-1.62 (2H, m), 1.59-1.52 (4H, m), 1.25 (6H, s). OH not observed. LCMS (Method T4): Rt 2.60 min, m/z 445.2111, expected 445.2113 for $C_{22}H_{30}ClN_6O_2$ [M + H]$^+$. | Intermediate D2a: 5-[(2,5-dichloropyrimidin-4-yl)amino]-3-(3-hydroxy-3-methyl-butyl)-1-methyl-benzimidazol-2-one |

TABLE 7-continued

Compounds prepared by a method analogous to that used for the preparation of Example 20a

| Example | Data | Intermediates |
| --- | --- | --- |
| Example 20e: 5-((5-chloro-2-((3S,5R)-3,5-dimethylpiperidin-1-yl)pyrimidin-4-yl)amino)-3-(3-hydroxy-3-methylbutyl)-1-methyl-1,3-dihydro-2H-benzo[d]imidazol-2-one:formic acid (1:1) | $^1$H NMR (500 MHz, acetone-d$_6$): δ 8.31 (0.6 H, b rs, partly exchanged NH), 8.13 (1H, s), 7.96 (1H, s), 7.51 (1H, d, J 2.0 Hz), 7.39 (1H, dd, J 8.4, 2.0 Hz), 7.09 (1H, d, J, 8.4 Hz), 4.66 (2H, br d, J 11.9 Hz), 4.04 (2H, m), 3.39 (3H, s), 2.33 (2H, dd, J 12.6, 11.6 Hz), 1.86 (2H, m), 1.81 (1H, m), 1.64-1.55 (2H, m), 1.26 (6H, s), 0.90 (6H, d, J 6.5 Hz), 0.82 (1H, m). LCMS (Method T4): Rt 2.86 min, m/z 473.2392, expected 473.2426 for C$_{24}$H$_{34}$ClN$_6$O$_2$ [M + H]$^+$. | Intermediate D2a: 5-[(2,5-dichloropyrimidin-4-yl)amino]-3-(3-hydroxy-3-methyl-butyl)-1-methyl-benzimidazol-2-one |
| Example 20f: 5-((5-chloro-2-(isopropylamino)pyrimidin-4-yl)amino)-3-(3-hydroxy-3-methylbutyl)-1-methyl-1,3-dihydro-2H-benzo[d]imidazol-2-one | LCMS (Method T4): Rt 2.37 min, m/z 419.1904, expected 419.1957 for C$_{20}$H$_{28}$ClN$_6$O$_2$ [M + H]$^+$. $^1$H NMR (500 MHz, Methanol-d4): δ 7.85 (1H, s), 7.62 (1H, br s), 7.37 (1H, br d, J 7.8 Hz), 7.13 (1H, d, J 7.8 Hz), 4.05 (2H, m), 3.97 (1H, sept, J 6.6 Hz), 3.44 (3H, s), 1.88 (2H, m), 1.29 (6H, s), 1.18 (6H, d, J 6.6 Hz). | Intermediate D2a: 5-[(2,5-dichloropyrimidin-4-yl)amino]-3-(3-hydroxy-3-methyl-butyl)-1-methyl-benzimidazol-2-one |
| Example 20g: 5-((5-chloro-2-(3-methylpiperidin-1-yl)pyrimidin-4-yl)amino)-3-(3-hydroxy-3-methylbutyl)-1-methyl-1,3-dihydro-2H-benzo[d]imidazol-2-one:formic acid (1:1) | LCMS (Method T4): Rt 2.66 min, m/z 459.2239, expected 459.2275 for C$_{23}$H$_{32}$ClN$_6$O$_2$ [M + H]$^+$. $^1$H NMR (500 MHz, acetone-d$_6$): δ 8.14 (1H, s, formate), 7.98 (0.8H, br, partly exchanged NH), 7.95 (1H, s), 7.57 (1H, d, J 2.0 Hz), 7.35 (1H, dd, J 8.8, 2.0 Hz), 7.06 (1H, d, J 8.8 Hz), 4.59-4.50 (2H, m), 4.01 (2H, m), 3.37 (3H, s), 2.83 (1H, td, J 12.8, 2.5 Hz), 2.51 (1H, dd, J 12.8, 10.2 Hz), 1.89-1.77 (3H, m), 1.68 (1H, m), 1.57 (1H, m), 1.46 (1H, m), 1.25 (6H, s), 1.16 (1H, m), 0.90 (3H, d, J 6.1 Hz). Other exchangables not observed. | Intermediate D2a: 5-[(2,5-dichloropyrimidin-4-yl)amino]-3-(3-hydroxy-3-methyl-butyl)-1-methyl-benzimidazol-2-one |

TABLE 7-continued

Compounds prepared by a method analogous to that used for the preparation of Example 20a

| Example | Data | Intermediates |
| --- | --- | --- |
| Example 20h: 5-((5-chloro-2-(3-trifluoromethyl)piperidin-1-yl)pyrimidin-4-yl)amino)-3-(3-hydroxy-3-methylbutyl)-1-methyl-1,3-dihydro-2H-benzo[d]imidazol-2-one | LCMS (Method T4): Rt 2.98 min, m/z 513.1980, expected 513.1987 for $C_{23}H_{29}ClF_3N_6O_2$ [M + H]$^+$. $^1$H NMR (500 MHz, acetone-$d_6$): δ 8.11 (1H, br s), 8.00 (1H, s), 7.49 (1H, d, J 1.6 Hz), 7.37 (1H, dd, J 8.4, 1.6 Hz), 7.05 (1H, d, J 8.4 Hz), 4.88 (1H, m), 4.63 (1H, m), 4.06-3.98 (2H, m), 3.38 (3H, s), 2.96-2.85 (3H, m), 2.40 (1H, m), 1.88-1.79 (3H, m), 1.66-1.50 (2H, m), 1.29 (6H, s). OH not observed. | Intermediate D2a: 5-[(2,5-dichloropyrimidin-4-yl)amino]-3-(3-hydroxy-3-methyl-butyl)-1-methyl-benzimidazol-2-one |
| Example 20i: 5-((5-chloro-2-(ethyl(methyl)amino)pyrimidin-4-yl)amino)-3-(3-hydroxy-3-methylbutyl)-1-methyl-1,3-dihydro-2H-benzo[d]imidazol-2-one | LCMS (Method T4): Rt 2.40 min, m/z 419.1945, expected 419.1957 for $C_{20}H_{28}ClN_6O_2$ [M + H]$^+$. $^1$H NMR (500 MHz, acetone-$d_6$): δ 7.96 (1H, s), 7.94 (1H, s), 7.67 (1H, d, J 1.6 Hz), 7.37 (1H, dd, J 8.4, 1.6 Hz), 7.05 (1H, d, J 8.4 Hz), 4.02 (2H, m), 3.63 (2H, q, J 7.1 Hz), 3.38 (3H, s), 3.11 (3H, s), 1.86 (2H, m), 1.26 (6H, s), 1.12 (3H, t, J 7.1 Hz). OH not observed. | Intermediate D2a: 5-[(2,5-dichloropyrimidin-4-yl)amino]-3-(3-hydroxy-3-methyl-butyl)-1-methyl-benzimidazol-2-one |
| Example 20j: 5-((5-chloro-2-((2R,6S)-2,6-dimethylmorpholino)pyrimidin-4-yl)amino)-3-(3-hydroxy-3-methylbutyl)-1-methyl-1,3-dihydro-2H-benzo[d]imidazol-2-one | LCMS (Method T4): Rt 2.83 min, m/z 475.2169, expected 475.2219 for $C_{23}H_{32}ClN_6O_3$ [M + H]$^+$. $^1$H NMR (500 MHz, acetone-$d_6$): δ 8.07 (1H, br), 7.98 (1H, s), 7.57 (1H, d, J 1.8 Hz), 7.31 (1H, dd, J 8.7, 1.8 Hz), 7.07 (1H, d, J 8.7 Hz), 4.46 (2H, br d, J 13.1 Hz), 4.03 (2H, t, J 8.0 Hz), 3.55 (2H, m), 3.37 (3H, s), 2.48 (2H, dd, J 13.0, 10.5 Hz), 1.86 (2H, t, J 8.0 Hz), 1.26 (6H, s), 1.16 (6H, d, J 6.6 Hz). OH not observed. | Intermediate D2a: 5-[(2,5-dichloropyrimidin-4-yl)amino]-3-(3-hydroxy-3-methyl-butyl)-1-methyl-benzimidazol-2-one |
| Example 20k: 5-((5-chloro-2-(2,2-dimethyl-6-(trifluoromethyl)morpholino)pyrimidin-4-yl)amino)-3-(3-hydroxy-3-methylbutyl)-1-methyl-1,3-dihydro-2H-benzo[d]imidazol-2-one | LCMS (Method T4): Rt 3.14 min, m/z 543.2041, expected 543.2093 for $C_{24}H_{31}ClF_3N_6O_3$ [M + H]$^+$. $^1$H NMR (500 MHz, methanol-$d_4$): δ 7.95 (1H, s), 7.39 (1H, d, J 1.9 Hz), 7.35 (1H, dd, J 8.8, 1.9 Hz), 7.11 (1H, d, J 8.8 Hz), 4.69 (1H, m), 4.35 (1H, dd, J 13.2, 1.4 Hz), 4.21 (1H, m), 4.01 (2H, m), 3.43 (3H, s), 2.84 (1H, dd, J 12.9, 11.2 Hz), 2.79 (1H, br d, J 13.3 Hz), 1.85 (2H, m), 1.28 (6H, s), 1.26 (3H, s), 1.19 (3H, s). | Intermediate D2a: 5-[(2,5-dichloropyrimidin-4-yl)amino]-3-(3-hydroxy-3-methyl-butyl)-1-methyl-benzimidazol-2-one |

TABLE 7-continued

Compounds prepared by a method analogous to that used for the preparation of Example 20a

| Example | Data | Intermediates |
|---|---|---|
| Example 20l: 5-((6-((5-chloro-2-((2R,6S)-2,6-dimethylmorpholino)pyrimidin-4-yl)amino)-3-methyl-2-oxo-2,3-dihydro-1H-benzo[d]imidazol-1-yl)methyl)-5-ethyl-3-methyloxazolidin-2-one | LCMS (Method T4): Rt 2.64 min, m/z 530.2202, expected 530.2277 for $C_{25}H_{33}ClN_7O_4$ [M + H]$^+$. $^1$H NMR (500 MHz, DMSO-d$_6$): δ 8.71 (1H, s), 8.03 (1H, s), 7.56 (1H, d, J 1.8 Hz), 7.31 (1H, dd, J 8.4, 1.8 Hz), 7.11 (1H, d, J 8.4 Hz), 4.33 (2H, br d, J 12.6 Hz), 4.01 (1H, d, J 15.2 Hz), 3.90 (1H, d, J 15.2 Hz), 3.59 (1H, d, J 9.4 Hz), 3.51 (2H, m), 3.40 (1H, d, J 9.4 Hz), 3.34 (3H, s), 2.64 (3H, s), 2.44 (2H, m), 1.72 (2H, m), 1.10 (6H, d, J 6.1 Hz), 0.92 (3H, t, J 7.1 Hz). | Intermediate D3d: 5-[[6-[(2,5-dichloropyrimidin-4-yl)amino]-3-methyl-2-oxo-benzimidazol-1-yl]methyl]-5-ethyl-3-methyl-oxazolidin-2-one |
| Example 20m: 5-((6-((5-chloro-2-(3-(trifluoromethyl)-1H-pyrazol-1-yl)pyrimidin-4-yl)amino)-3-methyl-2-oxo-2,3-dihydro-1H-benzo[d]imidazol-1-yl)methyl)-5-ethyl-3-methyloxazolidin-2-one | LCMS (Method T4): 2.93 min, m/z 551.1476, expected 551.1528 for $C_{23}H_{23}ClF_3N_8O_3$ [M + H]$^+$. $^1$H NMR (500 MHz, DMSO-d$_6$): δ 9.60 (1H, s), 8.62 (1H, br d, J 2.7 Hz), 8.52 (1H, s), 7.77 (1H, d, J 2.0 Hz), 7.34 (1H, dd, J 8.4, 2.0 Hz), 7.18 (1H, d, J 8.4 Hz), 6.96 (1H, d, J 2.7 Hz), 4.06 (1H, d, J 14.6 Hz), 4.01 (1H, d, J 14.6 Hz), 3.60 (1H, d, J 7.9 Hz), 3.38 (1H, d, J 7.9 Hz), 3.36 (3H, s), 2.57 (3H, s), 1.70 (2H, m), 0.87 (3H, t, J 7.9 Hz). | Intermediate D3d: 5-[[6-[(2,5-dichloropyrimidin-4-yl)amino]-3-methyl-2-oxo-benzimidazol-1-yl]methyl]-5-ethyl-3-methyl-oxazolidin-2-one |
| Example 20n: 5-((6-((5-chloro-2-((2R,6S)-2,6-dimethylmorpholino)pyrimidin-4-yl)amino)-3-methyl-2-oxo-2,3-dihydro-1H-benzo[d]imidazol-1-yl)methyl)-5-ethyloxazolidin-2-one | LCMS (Method T4): 2.59 min, m/z 516.2088, expected 516.2121 for $C_{24}H_{31}ClN_7O_4$ [M + H]$^+$. $^1$H NMR (500 MHz, DMSO-d$_6$): δ 8.72 (1H, s), 8.03 (1H, s), 7.60 (1H, d, J 1.9 Hz), 7.43 (1H, s), 7.31 (1H, dd, J 8.3, 1.9 Hz), 7.11 (1H, d, J, 8.3 Hz), 4.33 (2H, m), 4.01 (1H, d, J 14.8 Hz), 3.87 (1H, d, J 14.8 Hz), 3.55-3.48 (3H, m), 3.34 (3H, s), 3.29 (1H, m), 2.46 (2H, m), 1.79-1.68 (2H, m), 1.12 (6H, d, J 6.5 Hz), 0.94 (3H, t, J 7.6 Hz). | Intermediate D3e: 5-[[6-[(2,5-dichloropyrimidin-4-yl)amino]-3-methyl-2-oxo-benzimidazol-1-yl]methyl]-5-ethyl-oxazolidin-2-one |
| Example 20o: 5-((6-((5-chloro-2-(3-(trifluoromethyl)-1H-pyrazol-1-yl)pyrimidin-4-yl)amino)-3-methyl-2-oxo-2,3-dihydro-1H-benzo[d]imidazol-1-yl)methyl)-5-ethyloxazolidin-2-one | LCMS (Method T4): Rt 3.00 min, m/z 537.1351, expected 537.1372 for $C_{22}H_{21}ClF_3N_8O_3$ [M + H]$^+$. $^1$H NMR (500 MHz, DMSO-d$_6$): δ 9.61 (1H, s), 8.63 (1H, m), 8.52 (1H, s), 7.75 (1H, d, J 2.0 Hz), 7.38 (1H, s), 7.36 (1H, dd, J 8.5, 2.0 Hz), 7.18 (1H, d, J 8.5 Hz), 6.96 (1H, d, J 2.7 Hz), 4.07 (1H, d, J 15.3 Hz), 3.98 (1H, d, J 15.3 Hz), 3.58 (1H, d, J 8.2 Hz), 3.37 (3H, s), 3.30 (1H, d, J 8.2 Hz), 1.77-1.67 (2H, m), 0.90 (3H, t, J 7.2 Hz). | Intermediate D3e: 5-[[6-[(2,5-dichloropyrimidin-4-yl)amino]-3-methyl-2-oxo-benzimidazol-1-yl]methyl]-5-ethyl-oxazolidin-2-one |

TABLE 7-continued

Compounds prepared by a method analogous to that used for the preparation of Example 20a

| Example | Data | Intermediates |
|---|---|---|
| Example 20p: 5-((5-chloro-2-((2R,6S)-2,6-dimethylmorpholino)pyrimidin-4-yl)amino)-6-fluoro-3-(3-hydroxy-3-methylbutyl)-1-methyl-1,3-dihydro-2H-benzo[d]imidazol-2-one 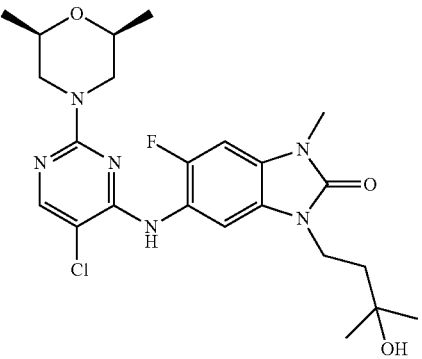 | LCMS (Method T4): Rt 2.88 min, m/z 493.2071, expected 493.2125 for $C_{23}H_{31}ClFN_6O_3$ [M + H]$^+$. $^1$H NMR (500 MHz, acetone-$d_6$): δ 8.02 (1H, s), 7.76 (1H, br), 7.59 (1H, d, J, 6.0 Hz), 7.10 (1H, d, J 11.0 Hz), 4.39 (2H, m), 4.03 (2H, m), 3.52 (2H, m), 3.39 (3H, s), 2.45 (2H, dd, J 13.2, 10.6 Hz), 1.86 (2H, m), 1.26 (6H, s), 1.13 (6H, d, J 6.5 Hz). OH not observed. | Intermediate D3f: 6-[(2,5-dichloropyrimidin-4-yl)amino]-5-fluoro-1-(3-hydroxy-3-methyl-butyl)-3-methyl-benzimidazol-2-one |
| Example 20q: 5-((5-chloro-2-((3S,5R)-3,5-dimethylpiperidin-1-yl)pyrimidin-4-yl)amino)-6-fluoro-3-(3-hydroxy-3-methylbutyl)-1-methyl-1,3-dihydro-2H-benzo[d]imidazol-2-one: formic acid (1:1) 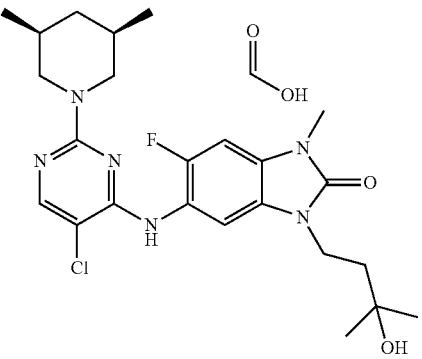 | LCMS (Method T4): Rt 2.93 min, m/z 491.2273, expected 491.2332 for $C_{24}H_{33}ClFN_6O_2$ [M + H]$^+$. $^1$H NMR (500 MHz, acetone-$d_6$): δ 8.13 (1H, s), 7.98 (1H, s), 7.71 (1H, br), 7.54 (1H, d, J 6.5 Hz), 7.10 (1H, d, J 9.9 Hz), 4.61-4.52 (2H, m), 4.04 (2H, m), 3.39 (3H, s), 2.22 (2H, dd, J 12.9, 11.4 Hz), 1.86 (2H, m), 1.77 (1H, m), 1.57-1.47 (2H, m), 1.26 (6H, s), 0.85 (6H, d, J 7.0 Hz), 0.76 (1H, m). OH, protonated N not observed. | Intermediate D3f: 6-[(2,5-dichloropyrimidin-4-yl)amino]-5-fluoro-1-(3-hydroxy-3-methyl-butyl)-3-methyl-benzimidazol-2-one |
| Example 20r: 5-((5-chloro-2-(3-(trifluoromethyl)-1H-pyrazol-1-yl)pyrimidin-4-yl)amino)-6-fluoro-3-(3-hydroxy-3-methylbutyl)-1-methyl-1,3-dihydro-2H-benzo[d]imidazol-2-one 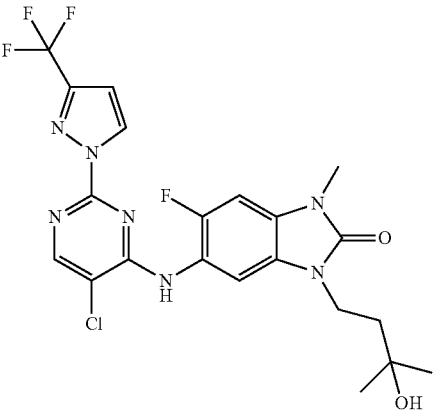 | LCMS (Method T4): Rt 2.97 min, m/z 514.1360, expected 514.1376 for $C_{21}H_{21}ClF_4N_7O_2$ [M + H]$^+$. $^1$H NMR (500 MHz, acetone-$d_6$): δ 8.67 (0.5H, br), 8.51-8.48 (2H, m), 7.63 (1H, d, J 6.5 Hz), 7.17 (1H, d, J 10.2 Hz), 6.85 (1H, d, J 2.6 Hz), 4.06 (2H, m), 3.42 (3H, s), 1.86 (2H, m), 1.21 (6H, s). OH not observed. | Intermediate D3f: 6-[(2,5-dichloropyrimidin-4-yl)amino]-5-fluoro-1-(3-hydroxy-3-methyl-butyl)-3-methyl-benzimidazol-2-one |

TABLE 7-continued

Compounds prepared by a method analogous to that used for the preparation of Example 20a

| Example | Data | Intermediates |
|---|---|---|
| Example 20s: 5-((5-chloro-2-(4-(trifluoromethyl)-1H-pyrazol-1-yl)pyrimidin-4-yl)amino)-3-(3-hydroxy-3-methylbutyl)-1-methyl-1,3-dihydro-2H-benzo[d]imidazol-2-one | LCMS (Method T4): Rt 3.00 min, m/z 496.1463, expected 496.1470 for $C_{21}H_{22}ClF_3N_7O_2$ [M + H]$^+$. $^1$H NMR (500 MHz, acetone-$d_6$): δ 8.91 (1H, s), 8.84 (0.5H, br, partly exchanged NH), 8.43 (1H, s), 8.16 (1H, s), 7.97 (1H, d, J 1.9 Hz), 7.45 (1H, dd, J 8.4, 1.9 Hz), 7.12 (1H, d, J 8.4 Hz), 4.07 (2H, t, J 8.0 Hz), 3.40 (3H, s), 1.92 (2H, t, J 8.0 Hz), 1.24 (6H, s). OH not observed. | Intermediate D2a: 5-[(2,5-dichloropyrimidin-4-yl)amino]-3-(3-hydroxy-3-methyl-butyl)-1-methyl-benzimidazol-2-one |
| Example 20t: 5-((5-chloro-2-morpholinopyrimidin-4-yl)amino)-3-(3-hydroxy-3-methylbutyl)-1-methyl-1,3-dihydro-2H-benzo[d]imidazol-2-one | LCMS (Method T4): Rt 2.51 min, m/z 447.1897, expected 447.1906 for $C_{21}H_{28}ClN_6O_3$ [M + H]$^+$. $^1$H NMR (500 MHz, methanol-$d_4$): δ 7.92 (1H, s), 7.47 (1H, d, J 1.7 Hz), 7.31 (1H, dd, J 8.4, 1.7 Hz), 7.10 (1H, d, J 8.4 Hz), 4.00 (2H, m), 3.70-3.67 (4H, m), 3.66-3.62 (4H, m), 3.41 (3H, s), 1.84 (2H, m), 1.28 (6H, s). | Intermediate D2a: 5-[(2,5-dichloropyrimidin-4-yl)amino]-3-(3-hydroxy-3-methyl-butyl)-1-methyl-benzimidazol-2-one |

Example 21a: 5-((5-chloro-2-((2S,6R)-2-cyclopropyl-6-methylmorpholino)pyrimidin-4-yl)amino)-3-(3-hydroxy-3-methylbutyl)-1-methyl-1,3-dihydro-2H-benzo[d]imidazol-2-one and Example 21b: 5-((5-chloro-2-((2R,6R)-2-cyclopropyl-6-methylmorpholino)pyrimidin-4-yl)amino)-3-(3-hydroxy-3-methylbutyl)-1-methyl-1,3-dihydro-2H-benzo[d]imidazol-2-one A mixture of 2-cyclopropyl-6-methyl-morpholine (36 mg, 0.25 mmol, mixture of diastereomers), 5-[(2,5-dichloropyrimidin-4-yl)amino]-3-(3-hydroxy-3-methyl-butyl)-1-methyl-benzimidazol-2-one (intermediate D2a, 20 mg, 0.05 mmol) and N,N-diisopropylethylamine (0.04 mL, 0.25 mmol) in NMP (1 mL) was heated in the microwave to 170° C. for 1 hour The mixture was partitioned between DCM and water, the aqueous layer was extracted with DCM and the combined organics were washed with brine. The organic layers were combined and evaporated, and the resulting NMP solution was purified by preparative HPLC (ACE 5 C18-PFP column (5μ, 250×21.2 mm), 15 minute gradient elution from 40:60 to 25:75 water:methanol (both modified with 0.1% formic acid) at a flow rate of 20 mL/min).

The earlier eluting product was assigned as Example 21b: 5-((5-chloro-2-((2R,6R)-2-cyclopropyl-6-methylmorpholino)pyrimidin-4-yl)amino)-3-(3-hydroxy-3-methyl-butyl)-1-methyl-1,3-dihydro-2H-benzo[d]imidazol-2-one (7 mg, 24%, 0.012 mmol).

$^1$H NMR (500 MHz, methanol-d$_4$) δ 7.92 (1H, s), 7.43 (1H, d, J 1.9 Hz), 7.39 (1H, dd, J 8.1, 1.9 Hz), 7.12 (1H, d, J 8.1 Hz), 4.10 (1H, m), 4.03 (2H, t, J 8.3 Hz), 3.90 (1H, dd, J 12.5, 3.3 Hz), 3.77 (1H, dd, J 13.0, 5.0 Hz), 3.71 (1H, dd, J 13.0, 3.7 Hz), 3.44 (3H, s), 3.29 (1H, dd, J 12.5, 7.0 Hz), 2.99 (1H, m), 1.86 (2H, t, J 8.3 Hz), 1.29 (6H, s), 1.15 (3H, d, J 6.1 Hz), 1.08 (1H, m), 0.52 (1H, m), 0.47 (1H, m), 0.31 (1H, m), 0.18 (1H, m). LCMS (Method T4) Rt 2.78 min, m/z 501.2316, expected 501.2375 for C$_{25}$H$_{34}$ClN$_6$O$_3$ [M+H]$^+$.

The later eluting product was assigned as Example 21a: 5-((5-chloro-2-((2S,6R)-2-cyclopropyl-6-methylmorpholino)pyrimidin-4-yl)amino)-3-(3-hydroxy-3-methyl-butyl)-1-methyl-1,3-dihydro-2H-benzo[d]imidazol-2-one (9 mg, 30%, 0.015 mmol).

$^1$H NMR (500 MHz, methanol-d$_4$) δ 7.91 (1H s), 7.45 (1H, d, J 1.8 Hz), 7.33 (1H, dd, J 8.4, 1.8 Hz), 7.11 (1H, d, J 8.4 Hz), 4.48 (1H, m), 4.34 (1H, m), 4.03 (2H, m), 3.50 (1H, m), 3.44 (3H, s), 2.75-2.66 (2H, m), 2.53 (1H, dd, J 13.0, 10.7 Hz), 1.86 (2H, m), 1.29 (6H, s), 1.18 (3H, d, J 6.3 Hz), 0.85 (1H, m), 0.53 (1H, m), 0.47 (1H, m), 0.35 (1H, m), 0.16 (1H, m). LCMS (Method T4) Rt 2.82 min, m/z 501.2306, expected 501.2375 for C$_{25}$H$_{34}$ClN$_6$O$_3$ [M+H]$^+$.

Example 22a: 5-((5-chloro-2-(methylthio)pyrimidin-4-yl)amino)-3-(3-hydroxy-3-methylbutyl)-1-methyl-1,3-dihydro-2H-benzo[d]imidazol-2-one

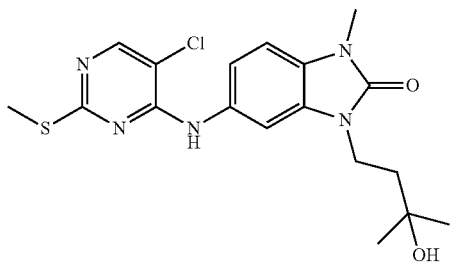 [SMILES: CSc1ncc(Cl)c(Nc2ccc3c(c2)n(CCC(C)(C)O)c(=O)n3C)n1]

A mixture of 4,5-dichloro-2-methylsulfanyl-pyrimidine (18 mg, 0.09 mmol), 5-amino-3-(3-hydroxy-3-methyl-butyl)-1-methyl-benzimidazol-2-one (intermediate A1, 20 mg, 0.08 mmol) and N-ethyl-N-isopropyl-propan-2-amine (20.5 μL, 0.12 mmol) in DMF (0.50 mL, 0.16 M) was heated in the microwave to 120° C. for 30 minutes. The mixture was diluted with water, acidified to pH 5 by addition of 10% citric acid and extracted with DCM (5 mL×3). The combined organics were evaporated under reduced pressure. The product was purified by prep HPLC (ACE 5 C18-PFP column (5μ, 250×21.2 mm), 15 minute gradient elution from 40:60 to 25:75 water:methanol (both modified with 0.1% formic acid) at a flow rate of 20 mL/min) to give 5-[(5-chloro-2-methylsulfanyl-pyrimidin-4-yl)amino]-3-(3-hydroxy-3-methyl-butyl)-1-methyl-benzimidazol-2-one (27 mg) as a white solid. $^1$H NMR (DMSO-d$_6$, 500 MHz): δ 8.43 (1H, br s), 8.24 (1H, s), 7.41 (1H, d, J 1.6 Hz), 7.27 (1H, dd, J 8.4, 1.6 Hz), 7.13 (1H, d, J 8.4 Hz), 3.87 (2H, m), 3.32 (3H, s), 2.38 (3H, s), 1.72 (2H, m), 1.17 (6H, s). OH not observed. LCMS (Method T4) Rt 2.80 min, m/z 408.1208, expected 408.1255 for C$_{18}$H$_{23}$ClN$_5$O$_2$S [M+H]$^+$.

The following tabulated examples were prepared by a method analogous to that used for the preparation of example 22a, using the intermediates shown in Table 8, in NMP, DMA or DMF, and using DIPEA or triethylamine as a base. For examples 22b and 22g, reactions were heated to 180° C. for 1 hour. For example 22f, additional heating to 130° C. for 2 hours and 140° C. for 2 hours was required. For examples 22i, 22j, 22k, a lower temperature of 80° C. was used. For examples 22m and 22n, a higher temperature of 160° C. was used.

TABLE 8

Compounds prepared by a method analogous to that used for the preparation of Example 22a.

| Example | Data | Intermediates |
|---|---|---|
| Example 22b: 5-((2-bromo-5-chloropyridin-4-yl)amino)-3-(3-hydroxy-3-methylbutyl)-1-methyl-1,3-dihydro-2H-benzo[d]imidazol-2-one | LCMS (Method T4) Rt 2.78 min, m/z 439.0512, expected 439.0531 for C$_{18}$H$_{21}$BrClN$_4$O$_2$ [M + H]$^+$. $^1$H NMR (acetone-d$_6$, 500 MHz): δ 8.08 (1H, s), 7.92 (0.6H, br, partly exchanged NH), 7.17 (1H, d, J 8.4 Hz), 7.15 (1H, m), 7.08 (1H, dt, J 8.4, 1.7 Hz), 6.83 (1H, d, J 4.3 Hz), 4.04 (2H, m), 3.42 (3H, s), 1.86 (2H, m), 1.26 (6H, s). OH not observed. | Intermediate A1: 5-amino-3-(3-hydroxy-3-methyl-butyl)-1-methyl-benzimidazol-2-one and 2,4-dibromo-5-chloropyridine |

TABLE 8-continued

Compounds prepared by a method analogous to that used for the preparation of Example 22a.

| Example | Data | Intermediates |
| --- | --- | --- |
| Example 22c: 2-chloro-4-((3-((5-ethyl-2-oxooxazolidin-5-yl)methyl)-1-methyl-2-oxo-2,3-dihydro-1H-benzo[d]imidazol-5-yl)amino)nicotinonitrile | LCMS (Method T4) Rt 2.51 min, m/z 427.1207, expected 427.1280 for $C_{20}H_{20}ClN_6O_3$ [M + H]$^+$. $^1$H NMR (500 MHz, DMSO-d$_6$): δ 9.51 (1H, s), 7.96 (1H, d, J 6.2 Hz), 7.39 (1H, s), 7.22-7.19 (2H, m), 7.00 (1H, dd, J 8.3, 1.8 Hz), 6.88 (1H, d, J 6.2 Hz), 4.08 (1H, d, J 15.3 Hz), 3.99 (1H, d, J 15.3 Hz), 3.51 (1H, d, J 9.4 Hz), 3.37 (3H, s), 3.31 (1H, d, J 9.4 Hz), 1.74 (2H, m), 0.93 (3H, t, J 7.4 Hz). | Intermediate A6c: 5-[(6-amino-3-methyl-2-oxo-benzimidazol-1-yl)methyl]-5-ethyl-oxazolidin-2-one and 2,4-dichloropyridine-3-carbonitrile |
| Example 22d: 4-chloro-6-((6-fluoro-3-(3-hydroxy-3-methylbutyl)-1-methyl-2-oxo-2,3-dihydro-1H-benzo[d]imidazol-5-yl)amino)pyrimidine-5-carbonitrile | LCMS (Method T4) Rt 2.62 min, m/z 405.1237, expected 405.1237 for $C_{18}H_{19}ClFN_6O_2$ [M + H]$^+$. $^1$H NMR (500 MHz, methanol-d$_4$): δ 8.41 (1H, s), 7.28 (1H, d, J 6.4 Hz), 7.14 (1H, d, J 9.9 Hz), 4.02 (2H, t, J 7.5 Hz), 3.43 (3H, s), 1.85 (2H, t, J 7.5 Hz), 1.28 (6H, s). | Intermediate A6a: 6-amino-5-fluoro-1-(3-hydroxy-3-methyl-butyl)-3-methyl-benzimidazol-2-one and 4,6-dichloropyrimidine-5-carbonitrile |
| Example 22e: 2-chloro-4-((3-((5-ethyl-3-methyl-2-oxooxazolidin-5-yl)methyl)-1-methyl-2-oxo-2,3-dihydro-1H-benzo[d]imidazol-5-yl)amino)nicotinonitrile | LCMS (Method T4) Rt 2.55 min, m/z 441.1421, expected 441.1436 for $C_{21}H_{22}ClN_6O_3$ [M + H]$^+$. $^1$H NMR (500 MHz, DMSO-d$_6$): δ 9.51 (1H, s), 7.98 (1H, d, J 6.1 Hz), 7.22-7.19 (2H, m), 7.00 (1H, dd, J 8.3, 2.0 Hz), 6.84 (1H, d, J 6.1 Hz), 4.10 (1H, d, J 14.8 Hz), 4.01 (1H, d, J 14.8 Hz), 3.56 (1H, d, J 9.0 Hz), 3.40-3.36 (4H, m), 2.63 (3H, s), 1.77-1.67 (2H, m), 0.90 (3H, t, J 7.3 Hz). | Intermediate A6b: 5-[(6-amino-3-methyl-2-oxo-benzimidazol-1-yl)methyl]-5-ethyl-3-methyl-oxazolidin-2-one and 2,4-dichloropyridine-3-carbonitrile |
| Example 22f: 2-chloro-4-((6-fluoro-3-(3-hydroxy-3-methylbutyl)-1-methyl-2-oxo-2,3-dihydro-1H-benzo[d]imidazol-5-yl)amino)nicotinonitrile | LCMS (Method T4) Rt 2.67 min, m/z 404.1228, expected 404.1284 for $C_{19}H_{20}ClFN_5O_2$ [M + H]$^+$. $^1$H NMR (600 MHz, methanol-d$_4$): δ 8.00 (1H, d, J 6.3 Hz), 7.22 (1H, d, J 1.1 Hz), 7.21 (1H, d, J 4.7 Hz), 6.52 (1H, dd, J 6.3, 1.8 Hz), 4.03 (2H, t, J 8.2 Hz), 3.45 (3H, s), 1.86 (2H, t, J 8.2 Hz), 1.28 (6H, s). | Intermediate A6a: 6-amino-5-fluoro-1-(3-hydroxy-3-methyl-butyl)-3-methyl-benzimidazol-2-one and 2,4-dichloropyridine-3-carbonitrile |

TABLE 8-continued

Compounds prepared by a method analogous to that used for the preparation of Example 22a.

| Example | Data | Intermediates |
|---|---|---|
| Example 22g: 5-((2,5-dichloropyrimidin-4-yl)amino)-3-(3-hydroxy-3-methylpentyl)-1-methyl-1,3-dihydro-2H-benzo[d]imidazol-2-one | LCMS (Method T4) Rt 2.78 min, m/z 410.1146, expected 410.1145 for $C_{18}H_{22}Cl_2N_5O_2$ [M + H]$^+$. $^1$H NMR (500 MHz, acetone-d$_6$): δ 8.80 (0.4H, partly exchanged NH), 8.28 (1H, s), 7.52 (1H, dd, J 6.9, 2.0 Hz), 7.30 (1H, ddd, J 8.7, 5.2, 2.0 Hz), 7.11 (1H, d, J 8.4 Hz), 4.02 (2H, m), 3.41 (3H, s), 1.86 (2H, m), 1.58 (2H, q, J 7.8 Hz), 1.24 (3H, s), 0.94 (3H, t, J 7.8 Hz). OH not observed. | Intermediate A7a: 5-amino-3-(3-hydroxy-3-methylpentyl)-1-methyl-benzimidazol-2-one and 2,4,5-trichloro pyrimidine |
| Example 22h: 5-((5-chloropyrazolo[1,5-a]pyrimidin-7-yl)amino)-3-(3-hydroxy-3-methylbutyl)-1-methyl-1,3-dihydro-2H-benzo[d]imidazol-2-one | $^1$H NMR (600 MHz, DMSO-d$_6$): δ 10.34 (s, 1H, NH), 8.24 (d, J = 2.2 Hz, 1H), 7.27 (d, J = 2.0 Hz, 1H), 7.25 (d, J = 8.2 Hz, 1H), 7.16 (dd, J = 8.2, 2.0 Hz, 1H), 6.52 (d, J = 2.3 Hz, 1H), 5.97 (s, 1H), 4.46 (s, 1H, OH), 3.94-3.88 (m, 2H), 3.37 (s, 3H), 1.74-1.68 (m, 2H), 1.16 (s, 6H). LCMS (Method X4) rt 2.63 m/z 401.149 expected 401.149 for $C_{19}H_{22}ClN_6O_2$ [M + H]$^+$. | Intermediate A1: 5-amino-3-(3-hydroxy-3-methyl-butyl)-1-methyl-benzimidazol-2-one and 5,7-dichloropyrazolo[1,5-a]pyrimidine |
| Example 22i: 3-(3-hydroxy-3-methylbutyl)-1-methyl-5-((2,5,6-trichloropyrimidin-4-yl)amino)-1,3-dihydro-2H-benzo[d]imidazol-2-one | $^1$H NMR (600 MHz, Chloroform-d) δ 7.56 (d, J = 2.0 Hz, 1H), 7.47 (s, 1H, NH), 7.09 (dd, J = 8.3, 2.0 Hz, 1H), 7.00 (d, J = 8.3 Hz, 1H), 4.13-4.07 (m, 2H), 3.46 (s, 3H), 1.98-1.92 (m, 2H), 1.34 (s, 6H). LCMS (Method X4) rt 3.01 min; m/z 452.0427 expected 452.0424 for $C_{17}H_{18}Cl_3N_5O_2Na$ [M + Na]$^+$. | Intermediate A1: 5-amino-3-(3-hydroxy-3-methyl-butyl)-1-methyl-benzimidazol-2-one and 2,4,5,6-tetrachloro-pyrimidine |
| Example 22j: (R)-6-chloro-5-cyano-4-((3-(3-methoxybutyl)-1-methyl-2-oxo-2,3-dihydro-1H-benzo[d]imidazol-5-yl)amino)-N-methylpicolinamide | $^1$H NMR (500 MHz, chloroform-d) δ 7.77 (br q, 1H), 7.47 (s, 1H), 7.04 (s, 1H, NH), 7.02 (d, J = 8.2 Hz, 1H), 6.98 (dd, J = 8.2 and 1.9 Hz, 1H), 6.92 (d, J = 1.6 Hz, 1H), 4.06-3.86 (m, 2H), 3.47 (s, 3H), 3.41-3.32 (m, 1H), 3.30 (s, 3H, OMe), 2.97 (d, J = 5.0 Hz, 3H), 1.96-1.73 (m, 2H), 1.18 (d, J = 6.0 Hz, 3H). LCMS (Method X4) Rt 2.58 min; m/z 465.1401 expected 465.1418 for $C_{21}H_{23}ClN_6O_3Na$ [M + Na]$^+$. | Intermediate A7d: 5-amino-3-[(3R)-3-methoxybutyl]-1-methyl-benzimidazol-2-one (used without purification) and Intermediate E1: 4,6-dichloro-5-cyano-N-methyl-pyridine-2-carboxamide |

TABLE 8-continued

Compounds prepared by a method analogous to that used for the preparation of Example 22a.

| Example | Data | Intermediates |
|---|---|---|
| Example 22k: 4-((3-(3-acetamido-3-methylbutyl)-1-methyl-2-oxo-2,3-dihydro-1H-benzo[d]imidazol-5-yl)amino)-6-chloro-5-cyano-N-methylpicolinamide | $^1$H NMR (500 MHz, Chloroform-d) δ 7.80 (q, J = 5.6 Hz, 1H), 7.57 (s, 1H), 7.51 (s, 1H, NH), 7.01 (m, 2H), 6.99 (dd, J = 8.3, 1.8 Hz, 1H), 5.69 (s, 1H), 3.95-3.88 (m, 2H), 3.46 (s, 3H), 3.04-2.95 (d, 3H), 2.29-2.22 (m, 2H), 1.87 (s, 3H), 1.36 (s, 6H). LCMS (Method X2) rt 1.24 min m/z 484.1880 expected 484.1864 for $C_{23}H_{27}ClN_7O_3$ [M + H]$^+$. | Intermediate A4b: N-[3-(6-amino-3-methyl-2-oxo-benzimidazol-1-yl)-1,1-dimethyl-propyl]acetamide and Intermediate E1: 4,6-dichloro-5-cyano-N-methyl-pyridine-2-carboxamide |
| Example 22l: 5-((5,6-dichloropyrimidin-4-yl)amino)-3-(3-hydroxy-3-methylbutyl)-1-methyl-1,3-dihydro-2H-benzo[d]imidazol-2-one | $^1$H NMR (500 MHz, DMSO-d$_6$) δ 9.46 (s, 1H, NH), 8.26 (s, 1H), 7.30 (d, J = 2.0 Hz, 1H), 7.21 (dd, J = 8.4, 2.0 Hz, 1H), 7.13 (d, J = 8.4 Hz, 1H), 4.45 (s, 1H, OH), 3.91-3.84 (m, 2H), 3.33 (s, 3H, obscured by solvent), 1.74-1.66 (m, 2H), 1.16 (s, 6H). LCMS (Method X4) Rt 2.59 min; m/z 396.0997 expected 396.0994 for $C_{17}H_{20}Cl_2N_5O_2$ [M + H]$^+$. | Intermediate A1: 5-amino-3-(3-hydroxy-3-methyl-butyl)-1-methyl-benzimidazol-2-one and 4,5,6-trichloro-pyrimidine |
| Example 22m: rac-2-chloro-4-((3-(((1S,2S)-2-ethyl-2-hydroxycyclopentyl)methyl)-1-methyl-2-oxo-2,3-dihydro-1H-benzo[d]imidazol-5-yl)amino)nicotinonitrile | $^1$H NMR (600 MHz, Chloroform-d) δ 8.02 (d, J = 6.1 Hz, 1H), 7.04 (d, J = 8.3 Hz, 1H), 7.00 (dd, J = 8.3, 2.0 Hz, 1H), 6.96 (s, 1H), 6.93 (d, J = 2.0 Hz, 1H), 6.59 (d, J = 6.1 Hz, 1H), 4.14 (dd, J = 14.9, 8.7 Hz, 1H), 3.80 (dd, J = 14.9, 5.7 Hz, 1H), 3.47 (s, 3H), 2.16-2.06 (m, 1H), 1.85-1.77 (m, 2H), 1.75-1.58 (m, 3H), 1.57-1.42 (m, 2H), 1.31-1.18 (m, 2H), 0.84 (t, J = 7.4 Hz, 3H). LCMS (Method X4) Rt 2.87 m/z 426.1693 expected 426.1697 for $C_{22}H_{25}ClN_5O_2$ [M + H]$^+$. | Intermediate A8b: 5-amino-3-(((1S,2S)-2-ethyl-2-hydroxycyclopentyl) methyl)-1-methyl-1,3-dihydro-2H-benzo[d]imidazol-2-one and 2,4-dichloropyridine-3-carbonitrile |

TABLE 8-continued

Compounds prepared by a method analogous to that used for the preparation of Example 22a.

| Example | Data | Intermediates |
| --- | --- | --- |
| Example 22n: rac-2-chloro-4-((3-(((1S,2S)-2-hydroxy-2-methylcyclopentyl)methyl)-1-methyl-2-oxo-2,3-dihydro-1H-benzo[d]imidazol-5-yl)amino)nicotinonitrile 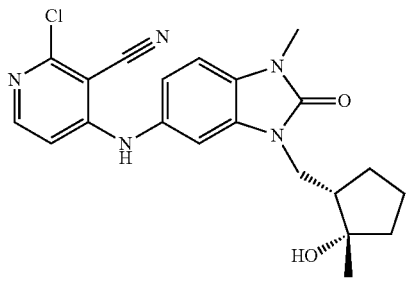 | $^1$H NMR (600 MHz, Chloroform-d) δ 8.03 (d, J = 6.1 Hz, 1H), 7.05 (d, J = 8.3 Hz, 1H), 7.01 (dd, J = 8.3, 1.9 Hz, 1H), 6.94 (d, J = 1.9 Hz, 1H), 6.93 (s, 1H), 6.60 (d, J = 6.1 Hz, 1H), 4.16 (dd, J = 14.9, 9.4 Hz, 1H), 3.81 (dd, J = 14.9, 5.3 Hz, 1H), 3.48 (s, 3H), 2.13-2.03 (m, 1H), 1.89-1.75 (m, 3H), 1.71-1.50 (m, 3H), 1.10 (s, 3H). OH not clearly observed. LCMS (Method T4) Rt 2.73 m/z 412.1517 expected 412.1535 for $C_{21}H_{23}ClN_5O_2$ [M + H]$^+$. | Intermediate A8a: 5-amino-3-[[(1S,2S)-2-hydroxy-2-methyl-cyclopentyl]methyl]-1-methyl-benzimidazol-2-one mlloyd and 2,4-dichloropyridine-3-carbonitrile |

Example 23a: 5-((5-chloro-2-(1-methyl-1H-pyrazol-3-yl)pyrimidin-4-yl)amino)-3-(3-hydroxy-3-methyl-butyl)-1-methyl-1,3-dihydro-2H-benzo[d]imidazol-2-one A mixture of 5-[(2,5-dichloropyrimidin-4-yl)amino]-3-(3-hydroxy-3-methyl-butyl)-1-methyl-benzimidazol-2-one (intermediate D2a, 20 mg, 0.05 mmol), 1-methyl-3-(4,4,5,5-tetramethyl-1,3,2-dioxaborolan-2-yl)-1H-pyrazole (12.6 mg, 0.06 mmol), sodium carbonate (11 mg, 0.10 mmol) and bis(triphenylphosphine)palladium (II) chloride (1.8 mg, 0.0025 mmol) in dioxane:water 1:1 (1 mL in total) was heated in the microwave at 130° C. for 30 min. The mixture was partitioned between DCM and water and pH adjusted to 5 using 10% citric acid before separation and extraction with further DCM. The organic layers were combined and evaporated, and the resulting solution was purified by preparative HPLC (ACE 5 C18-PFP column (5μ, 250×21.2 mm), 15 minute gradient elution from 40:60 to 25:75 water:methanol (both modified with 0.1% formic acid) at a flow rate of 20 mL/min) to give yellow solid that required further purification by normal phase chromatography (0 to 6% MeOH in DCM, 10 g column) to obtain 5-[[5-chloro-2-(1-methylpyra-zol-3-yl)pyrimidin-4-yl]amino]-3-(3-hydroxy-3-methyl-butyl)-1-methyl-benzimidazol-2-one (10 mg, 40%, 0.0204 mmol) as a solid. LCMS (Method T4) Rt 2.63 min, m/z 442.1738, expected 442.1753 for $C_{21}H_{25}ClN_7O_2$ [M+H]$^+$. $^1$H NMR (500 MHz, acetone-d$_6$): δ 8.42-8.36 (1.4H, br m, including partly exchanged NH), 8.00 (1H, d, J 2.0 Hz), 7.65 (1H, br s), 7.48 (1H, dd, J 8.4, 2.0 Hz), 7.08 (1H, d, J 8.4 Hz), 6.88 (1H, br s), 4.09 (2H, m), 3.98 (3H, s), 3.39 (3H, s), 1.90 (2H, m), 1.22 (6H, s). OH not observed.

The following tabulated examples were prepared by a method analogous to that used for the preparation of example 23a using an appropriate boronic acid or ester obtained from commercial vendors

TABLE 9

Compounds prepared by a method analogous to that used for the preparation of Example 23a

| Example | Data |
|---|---|
| Example 23b: 5-((5-chloro-2-(1,3-dimethyl-1H-pyrazol-5-yl)pyrimidin-4-yl)amino)-3-(3-hydroxy-3-methylbutyl)-1-methyl-1,3-dihydro-2H-benzo[d]imidazol-2-one | LCMS (Method T4) Rt 2.84 min, m/z 456.1903, expected 456.1909 for $C_{22}H_{27}ClN_7O_2$ [M + H]$^+$. $^1$H NMR (500 MHz, acetone-$d_6$): δ 8.41 (1H, s), 8.15 (0.4H, partly exchanged NH), 7.48 (1H, d, J 1.9 Hz), 7.37 (1H, dd, J 8.1, 1.9 Hz), 7.13 (1H, d, J 8.1 Hz), 6.70 (1H, s), 4.04 (2H, t, J 8.0 Hz), 4.02 (3H, s), 3.40 (3H, s), 2.18 (3H, s), 1.86 (2H, t, J 8.0 Hz), 1.23 (6H, s). OH not observed. |
| Example 23c: 5-((5-chloro-2-(2,4-dimethylthiazol-5-yl)pyrimidin-4-yl)amino)-3-(3-hydroxy-3-methylbutyl)-1-methyl-1,3-dihydro-2H-benzo[d]imidazol-2-one | LCMS (Method T4) Rt 2.95 min, m/z 473.1501, expected 473.1521 for $C_{22}H_{26}ClN_6O_2S$ [M + H]$^+$. $^1$H NMR (500 MHz, acetone-$d_6$): δ 8.50 (1H, br), 8.38 (1H, s), 7.54 (1H, d, J 1.8 Hz), 7.34 (1H, dd, J 8.3, 1.8 Hz), 7.13 (1H, d, J 8.3 Hz), 4.07 (2H, t, J 7.9 Hz), 3.41 (3H, s), 2.63 (3H, s), 2.60 (3H, s), 1.89 (2H, t, J 7.9 Hz), 1.24 (6H, s). OH not observed. |
| Example 23d: 5-((5-chloro-2-(thiophen-2-yl)pyrimidin-4-yl)amino)-3-(3-hydroxy-3-methylbutyl)-1-methyl-1,3-dihydro-2H-benzo[d]imidazol-2-one | LCMS (Method T4) Rt 2.97 min, m/z 444.1245, expected 444.1255 for $C_{21}H_{23}ClN_5O_2S$ [M + H]$^+$. $^1$H NMR (500 MHz, acetone-$d_6$): δ 8.47 (0.7H, br, partly exchanged NH), 8.35 (1H, s), 7.89 (1H, dd, J 3.8, 1.3 Hz), 7.76 (1H, d, J 2.0 Hz), 7.61 (1H, dd, J 5.1, 1.3 Hz), 7.42 (1H, dd, J 8.3, 1.7 Hz), 7.15 (1H, dd, J 5.1, 3.7 Hz), 7.12 (1H, d, J 8.3 Hz), 4.09 (2H, t, J 8.0 Hz), 3.41 (3H, s), 1.92 (2H, t, J 8.0 Hz), 1.25 (6H, s). OH not observed. |

Example 24a: 5-((5-chloro-2-(1-methyl-1H-imidazol-2-yl)pyrimidin-4-yl)amino)-3-(3-hydroxy-3-methylbutyl)-1-methyl-1,3-dihydro-2H-benzo[d]imidazol-2-one:formic acid (1:1)

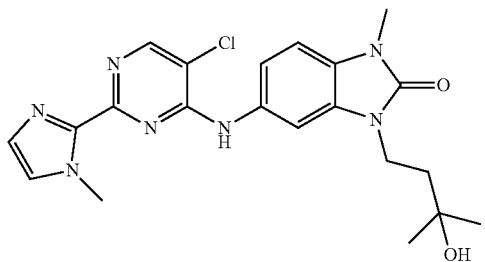 [SMILES: Cn1ccnc1-c1ncc(Cl)c(Nc2ccc3c(c2)n(CCC(C)(C)O)c(=O)n3C)n1]

A mixture of 1-methyl-2-(tri-n-butylstannyl)imidazole (21 mg, 0.06 mmol), 5-[(2,5-dichloropyrimidin-4-yl)amino]-3-(3-hydroxy-3-methyl-butyl)-1-methyl-benzimidazol-2-one (intermediate D2a, 20 mg, 0.05 mmol), and bis(triphenylphosphine)palladium (II) chloride (3.5 mg, 0.005 mmol) in 1,4-dioxane (1 mL) was heated at atmospheric pressure for 18 h at 90° C. The mixture was partitioned between DCM and water and pH adjusted to 5 using 10% citric acid before separation and extraction with further DCM. The organic layers were combined and evaporated, and the resulting solution was purified by preparative HPLC (ACE 5 C18-PFP column (5µ, 250×21.2 mm), 15 minute gradient elution from 40:60 to 25:75 water:methanol (both modified with 0.1% formic acid) at a flow rate of 20 mL/min) to give the title product (3 mg, 13%, 0.0068 mmol), as a solid. LCMS (Method T4) Rt 2.20 min, m/z 442.1740, expected 442.1753 for $C_{21}H_{25}ClN_7O_2$ [M+H]$^+$. $^1$H NMR (500 MHz, acetone-$d_6$): δ 8.50 (1H, br), 8.37 (1H, s), 8.12 (1H, s), 7.74 (1H, br s), 7.64 (1H, br s), 7.55 (1H, d, J 2.0 Hz), 7.35 (1H, dd, J 8.6, 2.0 Hz), 7.14 (1H, d, J 8.6 Hz), 4.04 (2H, t, J 8.3 Hz), 3.91 (3H, s), 3.40 (3H, s), 1.88 (2H, t, J 8.3 Hz), 1.24 (6H, s). OH not observed.

Example 25a: 2-chloro-4-((1-methyl-2-oxo-3-((4-(2,2,2-trifluoroethyl)morpholin-3-yl)methyl)-2,3-dihydro-1H-benzo[d]imidazol-5-yl)amino)nicotinonitrile

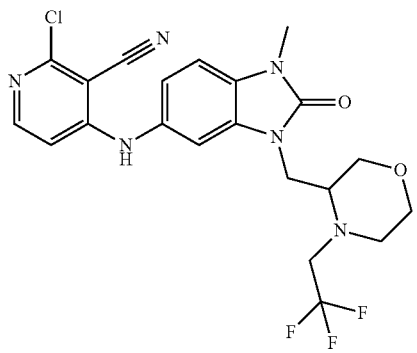 [SMILES: Cn1c(=O)n(CC2COCCN2CC(F)(F)F)c2cc(Nc3ccnc(Cl)c3C#N)ccc21]

4-(2,2,2-trifluoroethyl)morpholin-3-yl]methanol (15 mg, 0.076 mmol) in THF (0.5 mL) and cyanomethyl-tributylphosphorane (33% w/v solution in THF, 135 uL, 0.19 mmol) were added sequentially to a suspension of 2-chloro-4-[(1-methyl-2-oxo-3H-benzimidazol-5-yl)amino]pyridine-3-carbonitrile (Intermediate D1, 20 mg, 0.067 mmol) in DMF (0.2 mL). The resulting mixture was heated in the microwave to 100° C. for 1 hour. Added water (0.1 mL) and solvent removed, purified using reverse phase flash chromatography (Biotage 12 g SNAP Ultra C18, 20-100% methanol in water, 0.1% formic acid modifier) then further purified by flash column chromatography (10 g KP-SIL, 2-4% methanol in DCM) to give the title compound (5.3 mg). $^1$H NMR (600 MHz, Chloroform-d) δ 8.05 (d, J=6.1 Hz, 1H), 7.05 (d, J=8.2 Hz, 1H), 7.01 (dd, J=8.3, 2.0 Hz, 1H), 6.99 (d, J=1.9 Hz, 1H), 6.91 (s, 1H, NH), 6.64 (d, J=6.1 Hz, 1H), 4.13-4.02 (m, 2H), 3.84 (dt, J=11.3, 3.4 Hz, 1H), 3.76-3.69 (m, 2H), 3.55 (dd, J=11.7, 3.2 Hz, 1H), 3.48 (s, 3H, NMe), 3.40-3.20 (m, 2H), 3.16 (ddd, J=12.4, 9.6, 3.4 Hz, 1H), 3.09 (m, 1H), 2.73 (dt, J=12.2, 3.3 Hz, 1H). LCMS (Method X2) Rt 1.34 min; m/z 481.1381 expected 481.1367 for $C_{21}H_{21}N_6O_2F_3Cl$ [M+H]$^+$.

The following tabulated examples were prepared by a method analogous to that used for the preparation of example 25a, using the alcohol intermediates shown in Table 10.

TABLE 10

Compounds prepared by a method analogous to that used for the preparation of Example 25a

| Example | Data | Intermediate |
|---------|------|--------------|
| Example 25b: 2-chloro-4-((3-(2-(dimethylamino)butyl)-1-methyl-2-oxo-2,3-dihydro-1H-benzo[d]imidazol-5-yl)amino)nicotinonitrile: formic acid (1:1) | $^1$H NMR (600 MHz, Chloroform-d) δ 8.24 (s, 1H, formate), 8.04 (d, J = 6.1 Hz, 1H), 7.44 (s, 1H, NH), 7.05-7.01 (m, 3H), 6.69 (d, J = 6.1 Hz, 1H), 4.19 (dd, J = 14.8, 7.6 Hz, 1H), 3.94 (dd, J = 14.8, 6.3 Hz, 1H), 3.47 (s, 3H), 3.31 (m, 1H), 2.56 (s, 6H), 1.79 (m, 1H), 1.53(m, 1H), 1.06 (t, J = 7.5 Hz, 3H). Protonated nitrogen not seen; likely masked by / exchanging with broad water peak at 4.4 ppm. LCMS (Method X2) Rt 0.89 min; m/z 399.1698 expected 399.1700 for $C_{20}H_{24}N_6OCl$ [M + H]$^+$. | 2-(dimethylamino)-1-butanol |
| Example 25c: (S)-2-chloro-4-((3-((1-ethylpyrrolidin-2-yl)methyl)-1-methyl-2-oxo-2,3-dihydro-1H-benzo[d]imidazol-5-yl)amino)nicotinonitrile | $^1$H NMR (600 MHz, Chloroform-d) δ 8.04 (d, 1H, J = 6.1 Hz), 7.02 (d, J = 8.1 Hz, 1H), 7.00 (d, J = 1.9 Hz, 1H), 6.98 (dd, J = 8.1, 2.0 Hz, 1H), 6.92 (s, 1H, NH), 6.62 (d, J = 6.1 Hz, 1H), 3.91 (dd, J = 14.3, 4.8 Hz, 1H), 3.83 (dd, J = 14.2, 7.4 Hz, 1H), 3.47 (s, 3H), 3.17 (m, 1H), 2.95-2.89 (m, 1H), 2.89-2.82 (m, 1H), 2.41 (dq, J = 11.8, 7.1 Hz, 1H), 2.24 (m, 1H), 1.86 (m, 1H), 1.80 (m, 2H), 1.74 (m, 1H), 1.09 (t, J = 7.2 Hz, 3H, CH3) LCMS (Method X4) Rt 1.73 min; m/z 411.1697 expected 411.1700 for $C_{21}H_{24}N_6OCl$ [M + H]$^+$. | [(2S)-1-ethyl-2-pyrrolidinyl] methanol |

TABLE 10-continued

Compounds prepared by a method analogous to that used for the preparation of Example 25a

| Example | Data | Intermediate |
| --- | --- | --- |
| Example 25e: 2-chloro-4-((1-methyl-2-oxo-3-((1-(2,2,2-trifluoroethyl)piperidin-2-yl)methyl)-2,3-dihydro-1H-benzo[d]imidazol-5-yl)amino)nicotinonitrile | $^1$H NMR (600 MHz, Chloroform-d) δ 8.04 (d, J = 6.1 Hz, 1H), 7.04 (d, J = 8.2 Hz, 1H), 7.00 (dd, J = 8Hz, 2Hz, 1H), 6.88 (m, 2H), 6.59 (d, J = 6.1 Hz, 1H), 4.19-4.09 (m, 1H), 3.85 (dd, J = 14.4, 8.1 Hz, 1H), 3.48 (s, 3H), 3.28 (m, 1H), 3.21-3.10 (m, 2H), 3.08 (m, 1H), 2.70-2.62 (m, 1H), 1.75-1.65 (m, 2H), 1.57 (m, 2H), 1.53-1.40 (m, 2H), LCMS (Method X4) Rt 1.43 min; m/z 479.1581 expected 479.1574 for $C_{22}H_{23}ClF_3N_6O$ [M + H]$^+$. | Intermediate G4c: [1-(2,2,2-trifluoroethyl)-2-piperidyl]methanol |
| Example 25f: (S)-2-chloro-4-((3-((1-(2-fluoroethyl)pyrrolidin-2-yl)methyl)-1-methyl-2-oxo-2,3-dihydro-1H-benzo[d]imidazol-5-yl)amino)nicotinonitrile: formic acid (1:1) | $^1$H NMR (600 MHz, Chloroform-d) δ 8.22 (s, 1H), 8.05 (d, J = 6.1 Hz, 1H), 7.14 (d, J = 1.8 Hz, 1H), 7.10 (s, 1H), 7.06-6.98 (m, 2H), 6.66 (d, J = 6.1 Hz, 1H), 4.72-4.54 (m, 2H), 4.04 (m, 2H), 3.48 (s, 3H), 3.39 (m, 1H), 3.33-3.21 (m, 2H), 2.92 (m, 1H), 2.63-2.55 (m, 1H), 1.99-1.81 (m, 4H). Protonated amine NH not observed due to rapid exchange. LCMS (Method X2) Rt 0.90 min; m/z 429.1611 expected 429.1606 for $C_{21}H_{23}N_6OFCl$ [M + H]$^+$. | Intermediate G4g: [(2S)-1-(2-fluoroethyl)pyrrolidin-2-yl]methanol |
| Example 25g: (S)-2-chloro-4-((3-((1-(2-hydroxyethyl)pyrrolidin-2-yl)methyl)-1-methyl-2-oxo-2,3-dihydro-1H-benzo[d]imidazol-5-yl)amino)nicotinonitrile: formic acid (1:1) | Note that silyl protecting group was removed during reverse phase chromatography. $^1$H NMR (600 MHz, Methanol-d4) δ 8.32 (s, 1H), 7.98 (d, J =6.2 Hz, 1H), 7.31-7.22 (m, 2H), 7.15 (dd, J = 8.3, 2.0 Hz, 1H), 6.71 (d, J = 6.2 Hz, 1H), 4.30-4.20 (m, 2H), 3.83 (m, 2H), 3.74-3.69 (m, 1H), 3.67-3.59 (m, 1H), 3.49 (s, 3H), 3.50-3.44 (m, 1H), 3.11-3.00 (m, 2H), 2.16 (m, 1H), 2.07-1.91 (m, 2H), 1.89-1.80 (m, 1H). LCMS (2 min) Rt 0.88 min; m/z 427.1653 expected 427.1649 for $C_{21}H_{24}N_6O_2Cl$ [M + H]$^+$. | Intermediate G4f: [(2S)-1-[2-[tert-butyl(dimethyl)silyl]oxyethyl]pyrrolidin-2-yl]methanol |

TABLE 10-continued

Compounds prepared by a method analogous to that used for the preparation of Example 25a

| Example | Data | Intermediate |
|---|---|---|
| Example 25h: 2-chloro-4-((3-(((2R,4S)-4-fluoro-1-(2,2,2-trifluoroethyl)pyrrolidin-2-yl)methyl)-1-methyl-2-oxo-2,3-dihydro-1H-benzo[d]imidazol-5-yl)amino)nicotinonitrile 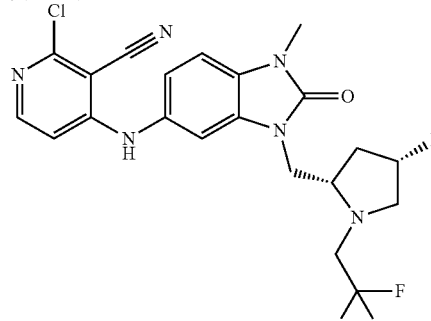 | LCMS (Method T4) Rt 2.89 min, m/z 483.1301, expected for $C_{21}H_{20}ClF_4N_6O$ [M + H]$^+$. $^1$H NMR (500 MHz, Methanol-d4) δ 7.94 (1H, d, J 6.4 Hz), 7.23 (1H, d, J 8.1 Hz), 7.20 (1H, d, J 1.9 Hz), 7.08 (1H, dd, J 8.1, 1.9 Hz), 6.69 (1H, d, J 6.4 Hz), 5.20 (1H, m), 4.02 (1H, dd, J 14.5, 5.8 Hz), 3.90 (1H, dd, J 14.5, 8.0 Hz), 3.54-3.40 (5H, m), 3.19 (1H, m), 2.89 (1H, m), 2.81 (1H, m) 2.21 (1H, m), 2.03 (1H, m). | Intermediate G4d: [(2S,4S)-4-fluoro-1-(2,2,2-trifluoroethyl)pyrrolidin-2-yl]methanol |
| Example 25i: (S)-2-chloro-4-((3-((1-(2,2-difluoroethyl)pyrrolidin-2-yl)methyl)-1-methyl-2-oxo-2,3-dihydro-1H-benzo[d]imidazol-5-yl)amino)nicotinonitrile 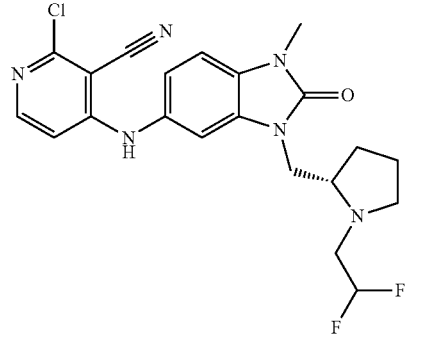 [SMILES: Cn1c(=O)n(C[C@@H]2CCCN2CC(F)F)c2cc(Nc3ccnc(Cl)c3C#N)ccc21] | LCMS (Method T4) Rt 2.22 min, m/z 447.1493, expected 447.1506 for $C_{21}H_{22}ClF_2N_6O$ [M + H]$^+$. $^1$H NMR (600 MHz, Methanol-d4) δ 7.96 (1H, d, J 6.2 Hz), 7.26-7.23 (2H, m), 7.10 (1H, dd, J 8.1, 1.8 Hz), 6.69 (1H, d, J 6.2 Hz), 5.79 (1H, tt, J 56.4, 4.2 Hz), 3.92 (1H, dd, J 14.1, 5.7 Hz), 3.89 (1H, dd, J 14.1, 6.6 Hz), 3.47 (3H, s), 3.20 (1H, m), 3.17-3.10 (2H, m), 2.81 (1H, ap. qd, J 14.1, 4.2 Hz), 2.47 (1H, ap. q, J 8.0 Hz), 1.86 (1H, m), 1.82-1.76 (2H, m), 1.70 (1H, m). | Intermediate G4e: [(2S)-1-(2,2-difluoroethyl)pyrrolidin-2-yl]methanol |

Example 26a: 2-chloro-4-((3-(3-(ethylamino)butyl)-1-methyl-2-oxo-2,3-dihydro-1H-benzo[d]imidazol-5-yl)amino)nicotinonitrile hydrochloride

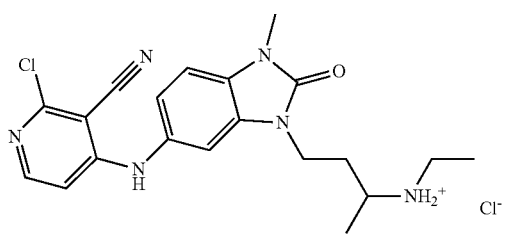 [SMILES: CC[NH2+]C(C)CCn1c(=O)n(C)c2ccc(Nc3ccnc(Cl)c3C#N)cc21 ; [Cl-]]

Cyanomethyltributylphosphorane (50 mg, 0.21 mmol, as 0.15 mL of a 33% solution in THF) was added dropwise to a mixture of tert-butyl N-ethyl-N-(3-hydroxy-1-methyl-propyl)carbamate (Intermediate G5, 19 mg, 0.09 mmol) and 2-chloro-4-[(1-methyl-2-oxo-3H-benzimidazol-5-yl)amino] pyridine-3-carbonitrile (Intermediate 1, 20 mg, 0.067 mmol) in DMF (0.2 mL) and THF (0.4 mL). The resulting mixture was heated in the microwave to 100° C. for 1 hour. Added water (0.1 mL), evaporated under reduced pressure and purified using reverse phase flash chromatography (Biotage 12 g SNAP Ultra C18, 20-100% methanol in water, 0.1% formic acid modifier). Resulting material was dissolved in THF and treated with hydrogen chloride in dioxane (4M, 1 mL) at room temperature overnight. The resulting precipitate was collected by filtration and washed with THF, dried on the filter and under vacuum to give the title compound (3 mg). $^1$H NMR (600 MHz, DMSO-d$_6$) δ 9.54 (s, 1H), 8.63 (s, 1H), 8.53 (s, 1H), 8.03 (d, J=6.2 Hz, 1H), 7.28 (d, J=1.9 Hz, 1H), 7.24 (d, J=8.3 Hz, 1H), 7.03 (dd, J=8.2, 1.9 Hz, 1H), 6.71 (d, J=6.2 Hz, 1H), 3.94 (t, J=7.1 Hz, 2H), 3.37 (s, 3H), 3.17 (m, 1H), 3.00-2.85 (m, 2H), 2.17-2.08 (m, 1H), 1.77 (m, 1H), 1.31 (d, J=6.5 Hz, 3H), 1.17 (t, J=7.2 Hz, 3H). LCMS (Method T4) Rt 2.03 min; m/z 399.1690 expected 399.1700 for $C_{20}H_{24}ClN_6O$ [M+H]$^+$.

Example 27a: 2-chloro-4-((3-(3-hydroxy-3-methyl-hex-5-yn-1-yl)-1-methyl-2-oxo-2,3-dihydro-1H-benzo[d]imidazol-5-yl)amino)nicotinonitrile

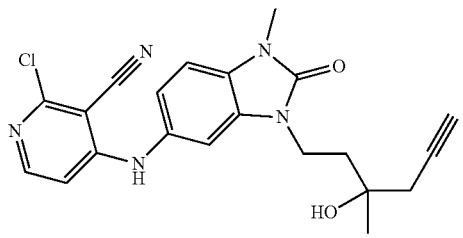 [SMILES: C#CCC(C)(O)CCn1c(=O)n(C)c2ccc(Nc3ccnc(Cl)c3C#N)cc21]

To a solution of (3-hydroxy-3-methyl-hex-5-ynyl) 4-methylbenzenesulfonate (intermediate C5c, 38 mg, 0.11 mmol) in acetonitrile (1 mL) was added 2-chloro-4-[(1-methyl-2-oxo-3H-benzimidazol-5-yl)amino]pyridine-3-carbonitrile (intermediate D1, 25 mg, 0.08 mmol) and cesium carbonate (60 mg, 0.18 mmol) and the resulting mixture was heated to 85° C. for 18 h. The mixture was partitioned between DCM and water, neutralised to pH 6 with citric acid and separated, extracting the aqueous layer with further DCM. The combined organics were washed with brine, dried over MgSO$_4$ and evaporated under reduced pressure. Purification by preparative HPLC (ACE 5 C18-PFP column (5μ, 250×21.2 mm), 15 minute gradient elution from 40:60 to 25:75 water:methanol (both modified with 0.1% formic acid) at a flow rate of 20 mL/min) gave the title compound (22 mg, 64%, 0.0537 mmol) as a solid. LCMS (Method T4) Rt 2.81 min; m/z 414.1676, expected 414.1691 for $C_{21}H_{21}ClN_5O_2[M+H]^+$. $^1$H NMR (500 MHz, acetone-d$_6$) δ 8.51 (1H, br), 8.03 (1H, d, J 6.1 Hz), 7.24 (1H, d, J 1.9 Hz), 7.20 (1H, d, J 8.7 Hz), 7.11 (1H, dd, J 8.7, 1.9 Hz), 6.79 (1H, d, J 6.1 Hz), 4.06 (2H, m), 3.41 (3H, s), 2.47 (1H, m), 2.42-2.38 (2H, m), 2.04-1.93 (2H, m), 1.34 (3H, s). OH not observed.

The following tabulated examples were prepared by a method analogous to that used for the preparation of example 27a, using the tosylate intermediates shown in Table 11. Example 27d was carried out using microwave heating at 100° C. for 30 minutes.

TABLE 11

Compounds prepared by a method analogous to that used for the preparation of Example 27a

| Example | Data | Intermediate |
| --- | --- | --- |
| Example 27b: 2-chloro-4-((3-(3-hydroxy-4-methoxy-3-methylbutyl)-1-methyl-2-oxo-2,3-dihydro-1H-benzo[d]imidazol-5-yl)amino)nicotinonitrile | LCMS (Method T4) Rt 2.58 min; m/z 416.1471, expected 416.1484 for $C_{20}H_{23}ClN_5O_3$ [M + H]$^+$. $^1$H NMR (500 MHz, acetone-d$_6$) δ 8.52 (1H, br s), 8.03 (1H, d, J 6.1 Hz), 7.20-7.17 (2H, m), 7.10 (1H, dd, J 8.1, 1.9 Hz), 6.79 (1H, d, J 6.1 Hz), 4.02 (2H, m), 3.41 (3H, s), 3.30 (3H, s), 3.28 (1H, d, J 9.6 Hz), 3.24 (1H, d, J 9.6 Hz), 1.91 (1H, m), 1.83 (1H, d), 1.21 (3H, s). OH not observed. | Intermediate C6a: (3-hydroxy-4-methoxy-3-methyl-butyl) 4-methylbenzene-sulfonate |
| Example 27c: 2-chloro-4-((3-(3-hydroxy-3-methylpentyl)-1-methyl-2-oxo-2,3-dihydro-1H-benzo[d]imidazol-5-yl)amino)nicotinonitrile | LCMS (Method T4) Rt 2.69 min; m/z 400.1531, expected 400.1535 for $C_{20}H_{23}ClN_5O_2$ [M + H]$^+$. $^1$H NMR (500 MHz, methanol-d$_4$) δ 7.96 (1H, d, J 6.4 Hz), 7.23 (1H, d, J 8.2 Hz), 7.18 (1H, d, J 2.0 Hz), 7.09 (1H, dd, J 8.2, 2.0 Hz), 6.70 (1H, d, J 6.4 Hz), 4.02 (2H, m), 3.46 (3H, s), 1.84 (2H, m), 1.57 (2H, m), 1.23 (3H, s), 0.84 (3H, t, J 7.0 Hz). | Intermediate C5a: (3-hydroxy-3-methyl-pentyl) 4-methylbenzene-sulfonate |

TABLE 11-continued

Compounds prepared by a method analogous to that used for the preparation of Example 27a

| Example | Data | Intermediate |
|---|---|---|
| Example 27d: 2-chloro-4-((1-methyl-2-oxo-3-(4,4,4-trifluoro-3-hydroxy-3-methylbutyl)-2,3-dihydro-1H-benzo[d]imidazol-5-yl)amino)nicotinonitrile 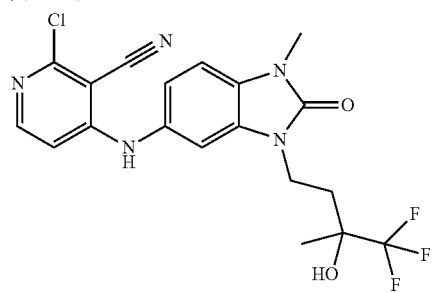 | $^{1}$H NMR (600 MHz, DMSO-d6) δ9.51 (s, 1H), 8.00 (d, J = 6.2 Hz, 1H), 7.22 (d, J = 8.2 Hz, 1H), 7.18 (d, J = 1.9 Hz, 1H), 7.02 (dd, J = 8.2, 2.0 Hz, 1H), 6.68 (d, J = 6.2 Hz, 1H), 6.13 (s, 1H), 4.03-3.90 (m, 2H), 3.35 (s, 3H), 1.97 (ddd, J =13.4, 10.5, 5.6 Hz, 1H), 1.84 (ddd, J =13.5, 10.5, 5.6 Hz, 1H), 1.36 (s, 3H). LCMS (Method X2) Rt 1.29 min; observed 440.1083, expected 440.1101 for $C_{19}H_{18}ClF_3N_5O_2$ [M + H]$^+$. | Intermediate C1c: (4,4,4-trifluoro-3-hydroxy-3-methyl-butyl) 4-methylbenzene-sulfonate |
| Example 27e: 2-chloro-4-((3-(3-hydroxy-2,3-dimethylbutyl)-1-methyl-2-oxo-2,3-dihydro-1H-benzo[d]imidazol-5-yl)amino)nicotinonitrile 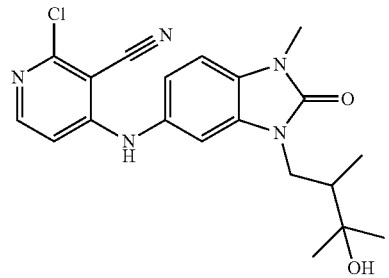 [SMILES: CC(Cn1c(=O)n(C)c2ccc(Nc3ccnc(Cl)c3C#N)cc21)C(C)(C)O] | $^{1}$H NMR (600 MHz, Chloroform-d) δ 8.04 (d, J = 6.1 Hz, 1H), 7.04 (d, J = 8.2 Hz, 1H), 7.03-6.95 (m, 2H), 6.94 (s, 1H), 6.63 (d, J = 6.1 Hz, 1H), 4.14 (dd, J = 14.3, 3.8 Hz, 1H), 3.81 (dd, J =14.2, 9.4 Hz, 1H), 3.48 (s, 3H), 2.10-2.01 (m, 2H), 1.32 (s, 3H), 1.27 (s, 3H), 0.97 (d, J = 7.0 Hz, 3H). LCMS (Method X2) Rt 1.26 min, m/z 400.1540 expected 400.1540 for $C_{20}H_{23}ClN_5O_2$ [M + H]$^+$ | Intermediate C1b: (3-hydroxy-2,3-dimethyl-butyl) 4-methylbenzene-sulfonate |
| Example 27f: 2-chloro-4-((3-(3-hydroxy-3,4-dimethylpentyl)-1-methyl-2-oxo-2,3-dihydro-1H-benzo[d]imidazol-5-yl)amino)nicotinonitrile 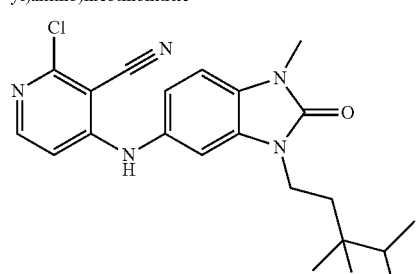 | LCMS (Method T4) Rt 2.81 min; m/z 414.1676, expected 414.1691 for $C_{21}H_{25}ClN_5O_2$ [M + H]$^+$. $^{1}$H NMR (500 MHz, methanol-d$_4$) δ 8.03 (1H, d, J 6.3 Hz), 7.22-7.19 (2H, m), 7.11 (1H, dd, J 8.1, 1.5 Hz), 6.79 (1H, d, J 6.3 Hz), 4.05 (2H, m), 3.43 (3H, s), 1.85 (2H, m), 1.76 (1H, app hept, J 7.0 Hz), 1.15 (3H, s), 0.95 (3H, d, J 7.0 Hz), 0.92 (3H, d, J 7.0 Hz). | Intermediate C5b: (3-hydroxy-3,4-dimethyl-pentyl) 4-methylbenzene sulfonate N5074-67 avarela |

Example 28a: 5-((5-chloro-2-(2,2,6,6-tetramethyl-morpholino)pyrimidin-4-yl)amino)-3-(3-hydroxy-3-methylbutyl)-1-methyl-1,3-dihydro-2H-benzo[d]imidazol-2-one

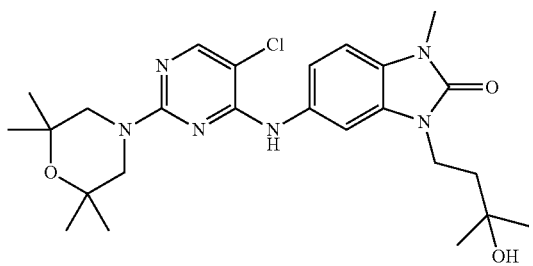 [SMILES: Cn1c(=O)n(CCC(C)(C)O)c2cc(Nc3nc(N4CC(C)(C)OC(C)(C)C4)ncc3Cl)ccc21]

A mixture of 5-[(2,5-dichloropyrimidin-4-yl)amino]-3-(3-hydroxy-3-methyl-butyl)-1-methyl-benzimidazol-2-one (Intermediate D2a, 30 mg, 0.076 mmol), 2,2,6,6-tetramethylmorpholine (22 mg, 0.15 mmol) and DIPEA (40 uL, 0.23 mmol) in NMP (0.67 mL) was heated in the microwave to 140° C. for 2 hours. Once cooled the mixture was diluted with DMSO (0.5 mL) then purified using reverse-phase C18 column eluting from 30-100% methanol in water (each containing 0.1% formic acid) to give the title compound (32 mg) as a pale brown solid. $^1$H NMR (600 MHz, Chloroform-d) δ 7.97 (s, 1H), 7.36 (d, J=2.0 Hz, 1H), 7.24 (dd, J=8.4, 2.0 Hz, 1H), 7.00 (s, 1H), 6.93 (d, J=8.4 Hz, 1H), 4.04 (t, J=7.2 Hz, 2H), 3.58 (s, 4H), 3.42 (s, 3H), 1.89 (t, J=7.2 Hz, 2H), 1.28 (s, 6H), 1.23 (s, 12H). OH not clearly observed. LCMS (Method X4) Rt 3.08 min, m/z 503.2521 expected 503.2537 for $C_{25}H_{36}ClN_6O_3$ [M+H]$^+$.

Example 28b: 5-((5-chloro-2-(2-(trifluoromethyl)morpholino)pyrimidin-4-yl)amino)-3-(3-hydroxy-3-methylbutyl)-1-methyl-1,3-dihydro-2H-benzo[d]imidazol-2-one

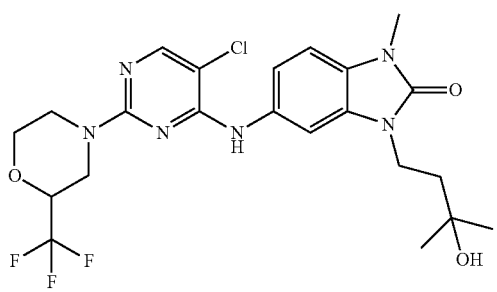 [SMILES: Cn1c(=O)n(CCC(C)(C)O)c2cc(Nc3nc(N4CCOC(C(F)(F)F)C4)ncc3Cl)ccc21]

A mixture of 5-[(2,5-dichloropyrimidin-4-yl)amino]-3-(3-hydroxy-3-methyl-butyl)-1-methyl-benzimidazol-2-one (Intermediate D2a, 30 mg, 0.076 mmol), 2-(trifluoromethyl)morpholine hydrochloride (29 mg, 0.15 mmol) and DIPEA (53 uL, 0.30 mmol) in NMP (0.67 mL) was heated in the microwave to 140° C. for 2 hours. Once cooled the mixture was diluted with DMSO (0.5 mL) then purified using reverse-phase C18 column eluting from 30-100% methanol in water (each containing 0.1% formic acid) to give the title compound (34 mg) as a pale brown solid. $^1$H NMR (600 MHz, Chloroform-d) δ 8.00 (s, 1H), 7.35 (d, J=2.0 Hz, 1H), 7.16 (dd, J=8.3, 2.0 Hz, 1H), 7.05 (s, 1H), 6.94 (d, J=8.3 Hz, 1H), 4.67 (d, J=13.0 Hz, 1H), 4.40 (d, J=13.4 Hz, 1H), 4.10-3.97 (m, 3H), 3.93-3.85 (m, 1H), 3.64 (td, J=11.6, 2.9 Hz, 1H), 3.42 (s, 3H), 3.15-3.08 (m, 1H), 3.04 (dd, J=13.0, 10.7 Hz, 1H), 2.35 (s, 1H), 1.87 (t, J=7.4 Hz, 2H), 1.29 (s, 6H). LCMS (Method X4) Rt 3.16 min, m/z 515.1773 expected 515.1785 for $C_{22}H_{27}ClF_3N_6O_3$ [M+H]$^+$.

Example 29a: 5-((3-chloro-2-fluoropyridin-4-yl)amino)-3-(3-hydroxy-3-methylbutyl)-1-methyl-1,3-dihydro-2H-benzo[d]imidazol-2-one

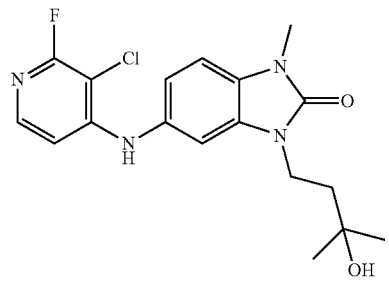 [SMILES: Cn1c(=O)n(CCC(C)(C)O)c2cc(Nc3ccnc(F)c3Cl)ccc21]

A mixture of 5-amino-3-(3-hydroxy-3-methyl-butyl)-1-methyl-benzimidazol-2-one (Intermediate A1, 20 mg, 0.08 mmol), Xantphos (12 mg, 0.02 mmol), 4-bromo-3-chloro-2-fluoropyridine (24 mg, 0.11 mmol), tris(dibenzylideneacetone)dipalladium(0) (2.3 mg, 0.004 mmol), and 4-bromo-3-chloro-2-fluoropyridine (24.00 mg, 0.1141 mmol) in NMP (0.9 mL), and toluene (0.9 mL) was degassed and heated in the microwave under a nitrogen atmosphere to 140° C. for 1 hour, then purified by SCX-2 column, eluting with DCM, methanol then methanolic ammonia. Compound eluted in the non-basic fractions, and was purified further by reverse phase chromatography (Biotage Snap Ultra C18 12 g, 40-80% methanol in water, 0.1% formic acid modifier) to give 5-[(3-chloro-2-fluoro-4-pyridyl)amino]-3-(3-hydroxy-3-methyl-butyl)-1-methyl-benzimidazol-2-one (20 mg, 66%, 0.053 mmol)

$^1$H NMR (500 MHz, Chloroform-d) δ 7.73 (d, J=6.0 Hz, 1H), 7.02 (app s, 2H), 6.94 (s, 1H), 6.64 (s, 1H, NH), 6.59 (d, J=6 Hz, 1H), 4.09-4.02 (m, 2H), 3.46 (s, 3H), 2.18 (v br, 1H, OH), 1.92-1.86 (m, 2H), 1.31 (s, 6H). LCMS (Method X4) Rt 2.57 min; m/z 379.1336 expected 379.1337 for $C_{18}H_{21}ClFN_4O_2$[M+H]$^+$.

The following tabulated examples were prepared by a method analogous to that used for the preparation of example 29a, using the heteroaryl halides shown in Table 12.

TABLE 12

Compounds prepared by a method analogous to that used for the preparation of Example 29a

| Example | Data | Intermediate |
|---|---|---|
| Example 29b: 5-((2,3-dichloropyridin-4-yl)amino)-3-(3-hydroxy-3-methylbutyl)-1-methyl-1,3-dihydro-2H-benzo[d]imidazol-2-one | $^1$H NMR (600 MHz, Chloroform-d) δ 7.90 (d, J = 5.6 Hz, 1H), 7.03 (d, J = 8.2 Hz, 1H), 7.01 (dd, J = 8.2, 1.8 Hz, 1H), 6.95 (d, J = 1.8 Hz, 1H), 6.68 (s, 1H), 6.64 (d, J = 5.7 Hz, 1H), 4.09-4.03 (m, 2H), 3.46 (s, 3H), 1.93-1.87 (m, 2H), 1.32 (s, 6H). OH not clearly observed. LCMS (Method X4) Rt 2.67 min; m/z 395.1038 expected 395.1042 for $C_{18}H_{21}Cl_2N_4O_2$ [M + H]$^+$. | 2,3-dichloro-4-iodopyridine |
| Example 29c: 5-((3-bromopyridin-4-yl)amino)-3-(3-hydroxy-3-methylbutyl)-1-methyl-1,3-dihydro-2H-benzo[d]imidazol-2-one: formic acid (1:1) | $^1$H NMR (600 MHz, Chloroform-d) δ 8.51 (s, 1H), 8.27 (s, 1H), 8.14 (d, J = 6.1 Hz, 1H), 7.06 (d, J = 8.2 Hz, 1H), 7.03 (dd, J = 8.2, 1.9 Hz, 1H), 6.99 (d, J = 1.9 Hz, 1H), 6.90 (s, 1H), 6.74 (d, J = 6.0 Hz, 1H), 4.07 (m, 2H), 3.48 (s, 3H), 1.90 (m, 2H), 1.32 (s, 6H). NH+, OH not clearly observed, exchanging with water (broad peak at 5.43 ppm). LCMS (Method T4) Rt 1.84 min; m/z 405.0912 expected 405.0921 for $C_{18}H_{22}BrN_4O_2$ [M + H]$^+$. | 3,4-dibromopyridine |
| Example 29d: 5-((5-chloro-2-(trifluoromethyl)pyridin-4-yl)amino)-3-(3-hydroxy-3-methylbutyl)-1-methyl-1,3-dihydro-2H-benzo[d]imidazol-2-one | LCMS (Method T4) Rt 2.84 min; m/z 429.1331, expected 429.1329 for $C_{19}H_{21}ClF_3N_4O_2$ [M + H]$^+$. $^1$H NMR (500 MHz, acetone-d$_6$) δ 8.42 (1H, s), 8.16 (0.3H, partly exchanged NH), 7.21-7.17 (2H, m), 7.12-7.09 (2H, m), 4.04 (2H, t, J 8.0 Hz), 3.42 (3H, s), 1.85 (2H, t, J 8.0 Hz), 1.25 (6H, s). OH not observed. | 5-chloro-4-iodo-2-(trifluoromethyl)pyridine |
| Example 29e: 5-((3-chloropyridin-4-yl)amino)-3-(3-hydroxy-3-methylbutyl)-1-methyl-1,3-dihydro-2H-benzo[d]imidazol-2-one: formic acid (1:1) | LCMS (Method T4) Rt 1.81 min; m/z 361.1422, expected 361.1426 for $C_{18}H_{22}ClN_4O_2$ [M + H]$^+$. $^1$H NMR (500 MHz, acetone-d$_6$) δ 8.30 (1H, s), 8.16 (1H, s), 8.06 (1H, d, J 5.7 Hz), 7.18-7.13 (2H, m), 7.06 (1H, dd, J 8.1, 2.0 Hz), 6.84 (1H, d, J 5.7 Hz), 4.03 (2H, t, J 8.2 Hz), 3.41 (3H, s), 1.85 (2H, t, d 8.2 Hz), 1.25 (6H, s). NH, OH not observed. | 4-bromo-3-chloropyridine |

The following tabulated examples were prepared by a method analogous to that used for the preparation of example 29a, using the coupling partners shown in Table 13.

TABLE 13

Compounds prepared by a method analogous to that used for the preparation of Example 29a

| Example | Data | Intermediates |
|---|---|---|
| Example 30a: 5-((5-chloro-2-(3,5-dimethyl-1H-pyrazol-1-yl)pyridin-4-yl)amino)-3-(3-hydroxy-3-methylbutyl)-1-methyl-1,3-dihydro-2H-benzo[d]imidazol-2-one | LCMS (Method T4) Rt 2.97 min; m/z 455.1943, expected 455.1957 for $C_{23}H_{28}ClN_6O_2$ [M + H]$^+$. $^1$H NMR (500 MHz, acetone-d$_6$) δ 8.19-8.14 (1.6H, m, includes partly exchanged NH), 7.39 (1H, s), 7.19-7.16 (2H, m), 7.09 (1H, dd, J 8.2, 2.0 Hz), 5.97 (1H, s), 4.03 (2H, t, J 7.9 Hz), 3.42 (3H, s), 2.57 (3H, s), 2.10 (3H, s), 1.87 (2H, t, J 7.9 Hz), 1.23 (6H, s). OH not observed. | Example 22b: 5-((2-bromo-5-chloropyridin-4-yl)amino)-3-(3-hydroxy-3-methylbutyl)-1-methyl-1,3-dihydro-2H-benzo[d]imidazol-2-one and 3,5-dimethyl-1H-pyrazole |
| Example 30b: 5-((5-chloro-2-(2-oxopyrrolidin-1-yl)pyrimidin-4-yl)amino)-3-(3-hydroxy-3-methylbutyl)-1-methyl-1,3-dihydro-2H-benzo[d]imidazol-2-one | LCMS (Method T4) Rt 2.49 min; m/z 445.1746, expected 445.1749 for $C_{21}H_{26}ClN_6O_3$ [M + H]$^+$. $^1$H NMR (500 MHz, acetone-d$_6$) δ 8.88 (1H, d, J 2.1 Hz), 8.25 (1H, s), 8.23 (0.5 H, br s, partly exchanged NH), 7.25 (1H, dd, J 8.3, 2.1 Hz) 7.01 (1H, d, J 8.3 Hz), 4.17 (2H, m), 4.05 (2H, t, J 7.0 Hz), 3.36 (3H, s), 2.65 (2H, t, J 8.1 Hz), 2.14 (2H, m), 1.91 (2H, m), 1.25 (6H, s). OH not observed. | Intermediate D2a: 5-[(2,5-dichloropyrimidin-4-yl)amino]-3-(3-hydroxy-3-methyl-butyl)-1-methyl-benzimidazol-2-one and 2-pyrrolidinone |

Example 31a: (S)-5-((5-chloro-2-(2-(hydroxymethyl)pyrrolidin-1-yl)pyrimidin-4-yl)amino)-3-(3-hydroxy-3-methylbutyl)-1-methyl-1,3-dihydro-2H-benzo[d]imidazol-2-one

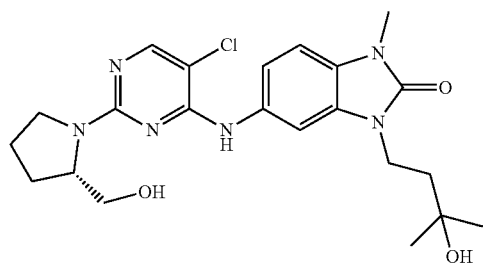 [SMILES: Cn1c(=O)n(CCC(C)(C)O)c2cc(Nc3nc(N4CCC[C@H]4CO)ncc3Cl)ccc21]

A mixture of 5-[(2,5-dichloropyrimidin-4-yl)amino]-3-(3-hydroxy-3-methyl-butyl)-1-methyl-benzimidazol-2-one (Intermediate D2a, 7.4 mg, 0.019 mmol), [(2S)-pyrrolidin-2-yl]methanol (7 uL, 0.07 mmol), N-ethyl-N-isopropyl-propan-2-amine (13 uL, 0.075 mmol) in DMF (0.5 mL) was heated to 100° C. for 1 h in the microwave, then partitioned between DCM and water, adjusted to pH 5 by addition of 10% citric acid, layers separated and aqueous further extracted with DCM. Combined organics were evaporated and purified by preparative HPLC (ACE 5C18-PFP column (5μ, 250×21.2 mm), 15 minute gradient elution from 60:40 to 0:100 water:methanol (both modified with 0.1% formic acid) at a flow rate of 2 mL/min), yielding 5-[[5-chloro-2-[(2S)-2-(hydroxymethyl)pyrrolidin-1-yl]pyrimidin-4-yl]amino]-3-(3-hydroxy-3-methyl-butyl)-1-methyl-benzimidazol-2-one (5 mg). $^1$H NMR (500 MHz, Methanol-d4) δ 7.91 (s, 1H), 7.59 (br s, 1H), 7.37 (dd, J=8.4, 1.9 Hz, 1H), 7.12 (d, J=8.5 Hz, 1H), 4.12 (m, 1H), 4.08-4.00 (m, 2H), 3.66-3.60 (m, 1H), 3.60-3.50 (m, 3H), 3.43 (s, 3H), 2.08-1.9 (m, 4H), 1.87 (m, 2H), 1.29 (s, 6H). LCMS (Method T4) Rt 2.22 min; m/z 461.2050 expected 461.2062 for $C_{22}H_{30}ClN_6O_3$ [M+H]$^+$.

Example 31b: (S)-7-((3-(3-hydroxy-3-methylbutyl)-1-methyl-2-oxo-2,3-dihydro-1H-benzo[d]imidazol-5-yl)amino)-5-(2-(hydroxymethyl)pyrrolidin-1-yl)pyrazolo[1,5-a]pyrimidine-3-carbonitrile

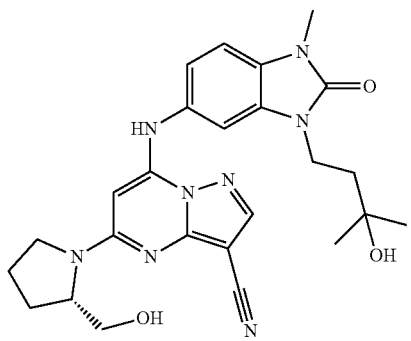 [SMILES: Cn1c(=O)n(CCC(C)(C)O)c2cc(Nc3cc(N4CCC[C@H]4CO)nc4c(C#N)cnn34)ccc21]

Prepared by a method analogous to that used for the preparation of Example 31a, starting from 5-chloro-7-[[3-(3-hydroxy-3-methyl-butyl)-1-methyl-2-oxo-benzimidazol-5-yl]amino]pyrazolo[1,5-a]pyrimidine-3-carbonitrile (Intermediate D3i, 8 mg) and yielding the title compound (7 mg). NMR signals very broad and poorly defined, due to rotation around C—N bond linking pyrrolidine to heteroaromatic ring. $^1$H NMR (600 MHz, DMSO-d6) δ 9.64 (s, 1H), 8.38 (s, 1H), 7.26 (d, J=1.9 Hz, 1H), 7.21 (d, J=8.3 Hz, 1H), 7.13 (dd, J=8.2, 2.0 Hz, 1H), 5.9-5.3 and 4.4-4.2 (br m, total 2H), 4.81 (1H, br m), 4.45 (1H, s), 3.90 (2H, m), 3.85-3.0 (4H, v br), 3.35 (3H, s), 2.04-1.91 (2H, br m), 1.90-1.82 (2H, br m,), 1.72 (2H, t, J=8.2 Hz), 1.16 (6H, s). LCMS (Method T4) Rt 2.73 min; m/z 491.2508 expected 491.2514 for $C_{25}H_{31}N_8O_3$ [M+H]$^+$.

Example 32: 2-chloro-4-((1-methyl-3-(2-(2-methyloxiran-2-yl)ethyl)-2-oxo-2,3-dihydro-1H-benzo[d]imidazol-5-yl)amino)nicotinonitrile

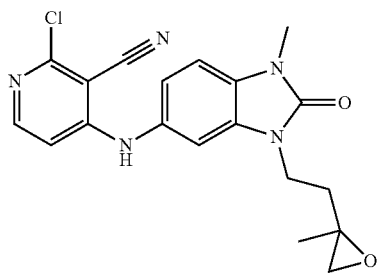 [SMILES: Cn1c(=O)n(CCC2(C)CO2)c2cc(Nc3ccnc(Cl)c3C#N)ccc21]

Step 1: 2-choro-4-[[1-methyl-3-(3-methylbut-3-enyl)-2-oxo-benzimidazol-5-yl]amino]pyridine-3-carbonitrile To a solution of 3-methylbut-3-enyl 4-methylbenzenesulfonate (intermediate C6b, 156 mg, 0.65 mmol) in acetonitrile (5 mL) were added: 2-chloro-4-[(1-methyl-2-oxo-3H-benzimidazol-5-yl)amino]pyridine-3-carbonitrile (intermediate D1, 150 mg, 0.50 mmol) and cesium carbonate (360 mg, 1.11 mmol) and the resulting mixture was heated under reflux for 6 h. The mixture was partitioned between DCM and water, neutralised to pH 6 with citric acid and separated, extracting the aqueous layer with further DCM. The combined organics were washed with brine, dried over MgSO$_4$ and evaporated under reduced pressure. Purification by reverse phase chromatography (Biotage Snap Ultra C18 12 g, 30-80% methanol in water, 0.1% formic acid modifier) gave 2-chloro-4-[[1-methyl-3-(3-methylbut-3-enyl)-2-oxo-benzimidazol-5-yl]amino]pyridine-3-carbonitrile (80 mg, 37%, 0.1849 mmol) as an oil. LCMS (Method T2) Rt 1.47 min; m/z 368.1247, expected 368.1273 for $C_{19}H_{18}ClN_5O$ [M+H]$^+$.

Step 2: 2-chloro-4-((1-methyl-3-(2-(2-methyloxiran-2-yl)ethyl)-2-oxo-2,3-dihydro-1H-benzo [d]imidazol-5-yl)amino)nicotinonitrile To a solution of 2-chloro-4-[[1-methyl-3-(3-methylbut-3-enyl)-2-oxo-benzimidazol-5-yl]amino]pyridine-3-carbonitrile (80 mg, 0.22 mmol) in DCM (2 mL) was added m-CPBA (56 mg, 0.33 mmol). The mixture was stirred for 2 h at room temperature, then a second portion of m-CPBA (37.5 mg, 0.22 mmol) was added and the mixture was stirred for another hour.

Saturated aqueous Na$_2$S$_2$O$_3$ was added, the layers were separated and the organic layer was washed with aqueous NaHCO$_3$. The combined aqueous layers were extracted with further DCM and the combined organic layers were dried over MgSO$_4$, filtered and concentrated under vacuum, affording the title compound as an orange solid. LCMS (Method T2) Rt 1.33 min; m/z 384.1179, expected 384.1222 for $C_{19}H_{19}ClN_5O_2$ [M+H]$^+$. $^1$H NMR (500 MHz, methanol-d$_4$) δ 7.96 (1H, d, J 6.4 Hz), 7.25 (1H, d, J 8.2 Hz), 7.17 (1H, d, J 1.6 Hz), 7.11 (1H, dd, J 8.2, 1.6 Hz), 6.70 (1H, d, J 6.4 Hz), 4.08 (2H, m), 3.47 (3H, s), 2.56 (2H, s), 2.00 (2H, m), 1.41 (3H, s).

Example 33: 2-chloro-4-((3-(2-(3,5-dimethyl-2-oxooxazolidin-5-yl)ethyl)-1-methyl-2-oxo-2,3-dihydro-1H-benzo[d]imidazol-5-yl)amino)nicotinonitrile

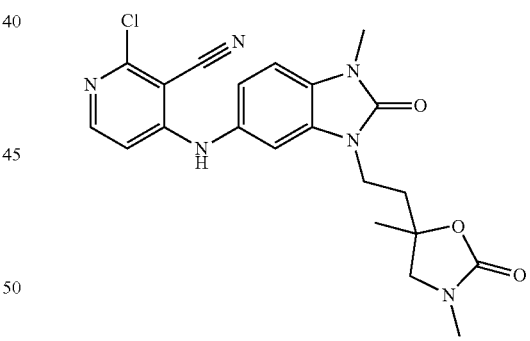

To a solution of 2-chloro-4-((1-methyl-3-(2-(2-methyloxiran-2-yl)ethyl)-2-oxo-2,3-dihydro-1H-benzo[d]imidazol-5-yl)amino)nicotinonitrile (Example 32, 10 mg, 0.03 mmol) in EtOH (1.00 mL) in a sealed tube was added methylamine (2 M in THF, 0.07 mL, 0.13 mmol). The mixture was stirred at 78° C. for 4 h, then it was cooled to room temperature, the solvent was evaporated and the mixture was dissolved in THF (1 mL). Disuccinimidyl carbonate (33 mg, 0.13 mmol) and triethylamine (0.02 mL, 0.13 mmol) were added and the mixture was heated to 66° C. for 26 h. Aqueous NH$_4$Cl and EtOAc were added, the layers were separated and the aqueous layer was extracted with further EtOAc. Purification by preparative HPLC (ACE 5 C18-PFP column (5μ, 250×21.2 mm), 15 minute gradient elution from 60:40 to 0:100 water:methanol (both modified with 0.1% formic acid) at a flow rate of 20 mL/min) gave the title compound (3 mg) as a white solid. LCMS (Method T4) Rt 2.47 min; m/z 441.1424, expected 441.1436 for $C_{21}H_{22}ClN_6O_3$ [M+H]$^+$. $^1$H NMR (500 MHz, methanol-d$_4$) δ 7.95 (1H, d, J 7.2 Hz), 7.24 (1H, d, J 8.4 Hz), 7.17 (1H, d, J 1.7 Hz), 7.10 (1H, dd, J 8.4, 1.7 Hz), 6.70 (1H, d, J 7.2 Hz), 4.08 (2H, m), 3.55 (1H, d, J 8.8 Hz), 3.46 (3H, s), 3.38 (1H, d, J 8.8 Hz), 2.84 (3H, s), 2.16 (2H, m), 1.50 (3H, s).

Example 34: 2-chloro-4-((1-methyl-3-((5-methyl-2-oxooxazolidin-4-yl)methyl)-2-oxo-2,3-dihydro-1H-benzo[d]imidazol-5-yl)amino)nicotinonitrile

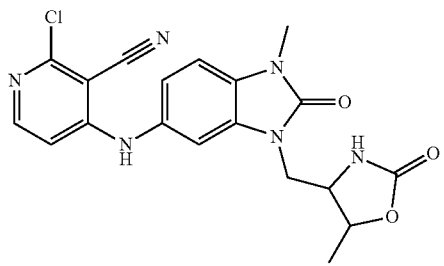 [SMILES: CC1OC(=O)NC1Cn1c(=O)n(C)c2ccc(Nc3ccnc(Cl)c3C#N)cc21]

Step 1: tert-butyl 4-[[6-[(2-choro-3-cyano-4-pyridyl)amino]-3-methyl-2-oxo-benzimidazol-1-yl]methyl]-2,2,5-trimethyl-oxazolidine-3-carboxylate Cyanomethyltributylphosphorane (90 mg, 0.37 mmol, as 135 uL of a 33% solution in THF) was added dropwise to a mixture of 2-chloro-4-[(1-methyl-2-oxo-3H-benzimidazol-5-yl)amino]pyridine-3-carbonitrile (intermediate D1, 40 mg, 0.13 mmol) and tert-butyl 4-(hydroxymethyl)-2,2,5-trimethyl-oxazolidine-3-carboxylate (43 mg, 0.17 mmol) in DMF (0.5 mL). The resulting mixture was heated in the microwave to 100° C. for 1 hour. Water (0.1 mL) was added and the solvent was evaporated under reduced pressure. The resulting DMF solution was diluted with DMSO then purified using reverse phase flash chromatography (Biotage 10 g SNAP Ultra C18, 10-100% methanol in water, 0.1% formic acid modifier) giving the title compound (70 mg, 85%, 0.1129 mmol) as a solid. LCMS (Method T2) Rt 1.56 min; m/z 427.1633 [M-Boc+H]$^+$.

Step 2: 4-[[3-(2-amino-3-hydroxy-butyl)-1-methyl-2-oxo-benzimidazol-5-yl]amino]-2-choro-pyridine-3-carbonitrile To a solution of tert-butyl 4-[[6-[(2-chloro-3-cyano-4-pyridyl)amino]-3-methyl-2-oxo-benzimidazol-1-yl]methyl]-2,2,5-trimethyl-oxazolidine-3-carboxylate (70 mg, 0.13 mmol) in DCM (2 mL) was added TFA (0.1 mL, 1.33 mmol) dropwise at room temperature. The mixture was stirred for 2 h at room temperature. The mixture was cooled to 0° C. and ammonia (7 M in MeOH) was added dropwise until basic pH. Water and DCM were added, the layers separated and the aqueous layer extracted with further DCM (adding a few drops of MeOH to aid extraction of amino alcohol). The solvent was evaporated and the crude was taken to the next step without further purification. LCMS (Method T2) Rt 1.01 min; m/z 387.1330 [M+H]$^+$.

Step 3: 2-choro-4-[[1-methyl-3-[(5-methyl-2-oxo-oxazolidin-4-yl)methyl]-2-oxo-benzimidazol-5-yl]amino]pyridine-3-carbonitrile To a solution of 4-[[3-(2-amino-3-hydroxy-butyl)-1-methyl-2-oxo-benzimidazol-5-yl]amino]-2-chloro-pyridine-3-carbonitrile (50 mg, 0.13 mmol) in THF (2 mL) was added triphosgene (107 mg, 0.36 mmol). The mixture was stirred at room temperature in a sealed tube for 18 h. The reaction was quenched by slow dropwise addition of 2 M NaOH, then EtOAc was added and the layers were separated. The aqueous layer was extracted with further EtOAc and the combined organic layers were washed with Brine, dried over MgSO$_4$ and concentrated under reduced pressure. Purification by preparative HPLC (ACE 5 C18-PFP column (5μ, 250×21.2 mm), 15 minute gradient elution from 60:40 to 0:100 water:methanol (both modified with 0.1% formic acid) at a flow rate of 20 mL/min) gave the title compound (7 mg, 13%, 0.017 mmol) as a solid, 3:1 mixture of diastereomers by $^1$H NMR. LCMS (Method T4) Rt 2.36 min; m/z 413.1115, expected 413.1123 for $C_{19}H_{18}ClN_6O_3$ [M+H]$^+$. $^1$H NMR (500 MHz, acetone-d6, major diastereomer) δ 8.53 (0.5H, br, partly exchanged NH), 8.02 (1H, d, J 6.0 Hz), 7.39 (1H, d, J 2.1 Hz), 7.21 (1H, d, J 8.5 Hz), 7.12 (1H, dd, J 8.5, 2.1 Hz), 6.82 (1H, d, J 6.0 Hz), 6.79 (0.4H, br, partyl exchanged NH), 4.60 (1H, m), 4.14 (1H, dd, J 14.7, 5.8 Hz), 4.08 (1H, dd, J 14.7, 4.4 Hz), 3.94 (1H, m), 3.43 (3H, s), 1.38 (3H, d, J 6.5 Hz).

Example 35a: 5-((5-chloro-2-(4,4-difluoro-3-(hydroxymethyl)piperidin-1-yl)pyrimidin-4-yl)amino)-3-(3-hydroxy-3-methylbutyl)-1-methyl-1,3-dihydro-2H-benzo[d]imidazol-2-one: formic acid (1:1)

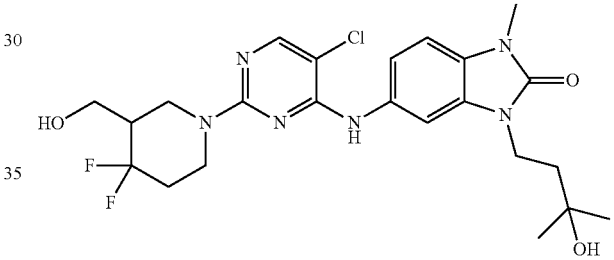

A mixture of 5-[(2,5-dichloropyrimidin-4-yl)amino]-3-(3-hydroxy-3-methyl-butyl)-1-methyl-benzimidazol-2-one (Intermediate D2a, 15.4 mg, 0.039 mmol) and (4,4-difluoro-3-piperidyl)methanol (prepared by hydrogenation of commercial (1-benzyl-4,4-difluoro-3-piperidyl)methanol using palladium hydroxide in ethanol, 17.6 mg, 0.117 mmol) in NMP (1.5 mL) was stirred under microwave irradiation at 140° C. for 1 h. HPLC purification gave 5-[[5-chloro-2-[4,4-difluoro-3-(hydroxymethyl)-1-piperidyl]pyrimidin-4-yl]amino]-3-(3-hydroxy-3-methyl-butyl)-1-methyl-benzimidazol-2-one (13 mg) as a yellow wax. $^1$H NMR (600 MHz, methanol-d$_4$) δ 8.22 (s, ~1H), 7.95 (s, 1H), 7.43 (d, J=1.9 Hz, 1H), 7.41 (dd, J=8.4, 1.9 Hz, 1H), 7.12 (d, J=8.4 Hz, 1H), 4.55-4.44 (m, 1H), 4.31-4.23 (m, 1H), 4.12-3.95 (m, 2H), 3.88 (dd, J=11.2, 4.1 Hz, 1H), 3.48 (dd, J=11.2, 9.2 Hz, 1H), 3.46-3.44 (m, 1H), 3.43 (s, 3H), 3.31-3.28 (m, 1H), 2.20-2.06 (m, 1H), 2.06-1.96 (m, 1H), 1.96-1.89 (m, 1H), 1.93-1.73 (m, 2H), 1.30 (s, 6H). LCMS (Method T4) Rt=2.70 mins, m/z 511.2097.2108 [M+H]$^+$ expected 511.2030 for $C_{23}H_{30}ClF_2N_6O_3$.

The following tabulated examples were prepared by a method analogous to that used for the preparation of example 35a. Example 35b used 4,4-difluoro-3-(methoxymethyl)piperidine; prepared by methylation of commercial (1-benzyl-4,4-difluoro-3-piperidyl)methanol using sodium hydride and dimethylsulfate in DMF, followed by hydrogenation with palladium hydroxide in ethanol. For Examples 35e and 35t, 8 h heating was required. For examples 35m and 35n 4 h heating was required.

TABLE 14

Compounds prepared by a method analogous to that used for the preparation of Example 35a

| Example | Data | Intermediates |
|---|---|---|
| Example 35b: 5-((5-chloro-2-(4,4-difluoro-3-(methoxymethyl)piperidin-1-yl)pyrimidin-4-yl)amino)-3-(3-hydroxy-3-methylbutyl)-1-methyl-1,3-dihydro-2H-benzo[d]imidazol-2-one: formic acid (1:2) | $^1$H NMR (600 MHz, Methanol-d$_4$) δ 8.22 (s, 2H, formic), 7.96 (s, 1H), 7.47 (d, J = 1.9 Hz, 1H), 7.36 (dd, J = 8.4, 1.9 Hz, 1H), 7.12 (d, J = 8.4 Hz, 1H), 4.56-4.46 (m, 1H), 4.39-4.29 (m, 1H), 4.10-4.00 (m, 2H), 3.66 (dd, J = 9.6, 3.6 Hz, 1H), 3.45 (s, 3H), 3.41-3.35 (m, 1H), 3.32-3.33 (m, 1H), 3.27-3.23 (m, 1H), 3.22 (s, 3H), 2.28-2.17 (m, 1H), 2.07-1.97(m, 1H), 1.97-1.90 (m, 1H), 1.87 (dd, J = 9.1, 7.3 Hz, 2H), 1.30 (s, 6H). LCMS (Method T4) Rt = 2.94 mins, m/z 525.2243 [M + H]$^+$ expected 525.2187 for C$_{24}$H$_{32}$ClF$_2$N$_6$O$_3$ | 4,4-difluoro-3-(methoxymethyl) piperidine and Intermediate D2a: 5-[(2,5-dichloropyrimidin-4-yl)amino]-3-(3-hydroxy-3-methyl-butyl)-1-methyl-benzimidazol-2-one |
| Example 35c: 5-((5-chloro-2-(4,4-difluoro-3-methylpiperidin-1-yl)pyrimidin-4-yl)amino)-3-(3-hydroxy-3-methylbutyl)-1-methyl-1,3-dihydro-2H-benzo[d]imidazol-2-one: formic acid (1:0.5) | $^1$H NMR (600 MHz, Methanol-d$_4$) δ 8.28 (s, 0.5H, formic), 7.94 (s, 1H), 7.42 (d, J = 1.9 Hz, 1H), 7.35 (dd, J = 8.4, 2.0 Hz, 1H), 7.13 (d, J = 8.4 Hz, 1H), 4.45-4.36 (m, 1H), 4.35-4.27 (m, 1H), 4.09-3.96 (m, 2H), 3.44 (s, 3H), 3.28 (ddd, J = 14.1, 11.3, 3.4 Hz, 1H), 2.98 (ddd, J = 13.5, 10.2, 1.3 Hz, 1H), 2.15-1.95(m, 2H), 1.97-1.76 (m, 2H), 1.84-1.78 (m, 1H), 1.29 (s, 6H), 1.00 (d, J = 6.8 Hz, 3H). LCMS (Method T4) Rt = 3.01 mins, m/z 495.2131 [M + H]$^+$ expected 495.2081 for C$_{23}$H$_{30}$ClF$_2$N$_6$O$_2$ | 4,4-difluoro-3-methyl-piperidine and Intermediate D2a: 5-[(2,5-dichloropyrimidin-4-yl)amino]-3-(3-hydroxy-3-methyl-butyl)-1-methyl-benzimidazol-2-one |
| Example 35d: 5-((5-chloro-2-(4,4-difluoropiperidin-1-yl)pyrimidin-4-yl)amino)-3-(3-hydroxy-3-methylbutyl)-1-methyl-1,3-dihydro-2H-benzo[d]imidazol-2-one | $^1$H NMR (600 MHz, methanol-d$_4$) δ 7.94 (s, 1H), 7.44 (d, J = 1.9 Hz, 1H), 7.32 (dd, J = 8.4, 2.0 Hz, 1H), 7.12 (d, J = 8.4 Hz, 1H), 4.11-3.95 (m, 2H), 3.88-3.75 (m, 4H), 3.43 (s, 3H), 2.00-1.90 (m, 4H), 1.89-1.79 (m, 2H), 1.29 (s, 6H). LCMS (Method T4) Rt = 2.89 mins, m/z 503.1729 [M + Na]$^+$ expected 503.1744 for C$_{22}$H$_{27}$ClF$_2$N$_6$NaO$_2$ | 4,4-difluoropiperidine and Intermediate D2a: 5-[(2,5-dichloropyrimidin-4-yl)amino]-3-(3-hydroxy-3-methyl-butyl)-1-methyl-benzimidazol-2-one |
| Example 35e: 5-((5-chloro-2-(3,3-difluoro-8-azabicyclo[3.2.1]octan-8-yl)pyrimidin-4-yl)amino)-3-(3-hydroxy-3-methylbutyl)-1-methyl-1,3-dihydro-2H-benzo[d]imidazol-2-one | $^1$H NMR (600 MHz, DMF-d$_7$) δ 8.84 (s, 1H), 8.14 (s, 1H), 7.66 (d, J = 1.9 Hz, 1H), 7.47 (dd, J = 8.4, 2.0 Hz, 1H), 7.18 (d, J = 8.4 Hz, 1H), 4.76-4.64 (m, 2H), 4.52 (s, 1H), 4.12-3.97 (m, 2H), 3.42 (s, 3H), 2.33-2.12 (m, 4H), 2.09-2.00 (m, 2H), 1.99-1.93 (m, 2H), 1.89-1.79 (m, 2H), 1.26 (s, 6H). LCMS (Method T4) Rt = 2.91 mins, m/z 507.2151 [M + H]$^+$ expected 507.2081 for C$_{24}$H$_{30}$ClF$_2$N$_6$O$_2$ | 3,3-difluoro-8-azabicyclo[3.2.1] octane hydrochloride and Intermediate D2a: 5-[(2,5-dichloropyrimidin-4-yl)amino]-3-(3-hydroxy-3-methyl-butyl)-1-methyl-benzimidazol-2-one |
| Example 35f: 5-((5-chloro-2-(2,2-difluoro-7-azaspiro[3.5]nonan-7-yl)pyrimidin-4-yl)amino)-3-(3-hydroxy- | $^1$H NMR (600 MHz, Methanol-d$_4$) δ 7.91 (s, 1H), 7.50 (d, J = 1.9 Hz, 1H), 7.32 (dd, J = 8.4, 2.0 Hz, 1H), 7.12 (d, | 2,2-difluoro-7-azaspiro[3.5]non ane and |

TABLE 14-continued

Compounds prepared by a method analogous to that used for the preparation of Example 35a

| Example | Data | Intermediates |
|---|---|---|
| 3-methylbutyl)-1-methyl-1,3-dihydro-2H-benzo[d]imidazol-2-one | J = 8.4 Hz, 1H), 4.12-3.94 (m, 2H), 3.72-3.57 (m, 4H), 3.44 (s, 3H), 2.39 (t, J = 12.7 Hz, 4H), 1.92-1.77 (m, 2H), 1.72-1.55 (m, 4H), 1.30 (s, 6H). LCMS (Method T4) Rt = 3.09 mins, m/z 521.2226 [M + H]$^+$ expected 521.2238 for $C_{25}H_{32}ClF_2N_6O_2$ | Intermediate D2a: 5-[(2,5-dichloropyrimidin-4-yl)amino]-3-(3-hydroxy-3-methyl-butyl)-1-methyl-benzimidazol-2-one |
| Example 35g: 5-((5-chloro-2-(4-(trifluoromethyl)piperidin-1-yl)pyrimidin-4-yl)amino)-3-(3-hydroxy-3-methylbutyl)-1-methyl-1,3-dihydro-2H-benzo[d]imidazol-2-one: formic acid (1:1.5) | $^1$H NMR (600 MHz, Methanol-d4) δ 8.21 (s, 1.5H, formic), 7.92 (s, 1H), 7.46 (d, J = 1.9 Hz, 1H), 7.33 (dd, J = 8.4, 1.9 Hz, 1H), 7.11 (d, J = 8.4 Hz, 1H), 4.68 (dt, J = 13.5, 2.8 Hz, 2H), 4.08-3.93 (m, 2H), 3.43 (s, 3H), 2.85 (td, J = 13.1, 2.6 Hz, 2H), 2.42 (ddp, J =12.1, 8.4, 3.8 Hz, 1H), 1.95-1.77 (m, 4H), 1.46 (qd, J = 12.6, 4.4 Hz, 2H), 1.29 (s, 6H). LCMS (Method T4) Rt = 2.95 mins, m/z 535.1787 [M + Na]$^+$ expected 535.1807 for $C_{23}H_{28}ClF_3N_6NaO_2$ | 4-(trifluoromethyl)piperidine and Intermediate D2a: 5-[(2,5-dichloropyrimidin-4-yl)amino]-3-(3-hydroxy-3-methyl-butyl)-1-methyl-benzimidazol-2-one |
| Example 35h: 5-((5-chloro-2-((3R,4S)-3,4-difluoropyrrolidin-1-yl)pyrimidin-4-yl)amino)-3-(3-hydroxy-3-methylbutyl)-1-methyl-1,3-dihydro-2H-benzo[d]imidazol-2-one: formic acid (1:1) | $^1$H NMR (600 MHz, Methanol-d$_4$) δ 8.18 (s, 1H), 7.93 (s, 1H), 7.63 (d, J = 1.9 Hz, 1H), 7.39 (dd, J = 8.4, 1.9 Hz, 1H), 7.11 (d, J = 8.4 Hz, 1H), 5.35-5.25 (m, 1H), 5.25-5.17 (m, 1H), 4.15-3.96 (m, 2H), 3.89 (ddd, J = 20.2, 11.9, 5.4 Hz, 2H), 3.68 (ddt, J = 19.4, 11.9, 3.4 Hz, 2H), 3.43 (s, 3H), 2.04-1.64 (m, 2H), 1.29 (s, 6H). LCMS (Method T4) Rt = 2.60 mins, m/z 467.1787 [M + H]$^+$ expected 467.1768 for $C_{21}H_{26}ClF_2N_6O_2$ | (3R,4S)-3,4-difluoropyrrolidine hydrochloride and Intermediate D2a: 5-[(2,5-dichloropyrimidin-4-yl)amino]-3-(3-hydroxy-3-methyl-butyl)-1-methyl-benzimidazol-2-one |
| Example 35i: (S)-5-((5-chloro-2-(2,2,6,6-tetramethylmorpholino)pyrimidin-4-yl)amino)-1-methyl-3-((1-(2,2,2-trifluoroethyl)pyrrolidin-2-yl)methyl)-1,3-dihydro-2H-benzo[d]imidazol-2-one | $^1$H NMR (500 MHz, Chloroform-d) δ 8.00 (s, 1H), 7.38 (d, J = 2.0 Hz, 1H), 7.28 (dd, J = 8.4, 2.0 Hz, 1H), 6.99 (s, 1H), 6.94 (d, J = 8.4 Hz, 1H), 3.93 (dd, J = 14.2, 4.6 Hz, 1H), 3.71 (dd, J = 14.2, 8.4 Hz, 1H), 3.60 (s, 4H), 3.45 (s, 3H), 3.46-3.40 (m, 1H), 3.35-3.30 (m. 1H), 3.21 (m, 1H), 3.20-3.05 (m, 1H), 2.54 (q, J = 8.5 Hz, 1H), 1.90-1.68 (m, 4H), 1.25 (s, 6H), 1.25 (s, 6H). LCMS (Method X2) Rt 1.65 min; m/z 582.2588 expected 582.2571 for $C_{27}H_{36}N_7O_2F_3Cl$ [M + H]$^+$. | 2,2,6,6-tetramethylmorpholine and Intermediate D2c: (S)-5-((2,5-dichloropyrimidin-4-yl)amino)-1-methyl-3-((1-(2,2,2-trifluoroethyl)pyrrolidin-2-yl)methyl)-1,3-dihydro-2H-benzo[d]imidazol-2-one |
| Example 35j: 5-((5-chloro-2-((3R,5S)-4,4-difluoro-3,5-dimethylpiperidin-1- | $^1$H NMR (500 MHz, Chloroform-d) δ 8.01 (s, 1H), 7.39 (d, J = 2 Hz, 1H), | (3R,5S)-4,4-difluoro-3,5- |

TABLE 14-continued

Compounds prepared by a method analogous to that used for the preparation of Example 35a

| Example | Data | Intermediates |
|---|---|---|
| yl)pyrimidin-4-yl)amino)-1,3-bis(3-hydroxy-3-methylbutyl)-1,3-dihydro-2H-benzo[d]imidazol-2-one | 7.23 (dd, J = 8.5, 2 Hz, 1H), 7.05-7.00 (m, 2H), 4.62 (br d, J = 13 Hz, 2H), 4.08 (m, 4H), 2.76 (app t, J = 12.7 Hz, 2H), 2.05-1.9 (m, 2H, partly obscured by next peak), 1.95-1.88 (m, 4H), 1.33 (s, 6H), 1.32 (s, 6H), 1.08 (d, J = 6.7 Hz, 6H). OHs may be under broad peak between 2.7 and 1.7 ppm. LCMS (Method X2) Rt 1.60 min; m/z 581.2833 expected 581.2818 for $C_{28}H_{40}N_6O_3F_2Cl$ [M + H]$^+$. | dimethyl-piperidine and Intermediate D2d: 5-((2,5-dichloropyrimidin-4-yl)amino)-1,3-bis(3-hydroxy-3-methylbutyl)-1,3-dihydro-2H-benzo[d]imidazol-2-one |
| Example 35k: 5-((5-chloro-2-(2,2,6,6-tetramethylmorpholino)pyrimidin-4-yl)amino)-1,3-bis(3-hydroxy-3-methylbutyl)-1,3-dihydro-2H-benzo[d]imidazol-2-one | $^1$H NMR (500 MHz, Chloroform-d) δ 8.01 (s, 1H), 7.44 (d, J = 2 Hz, 1H), 7.24 (dd, J = 8.4, 2 Hz, 1H), 7.02 (s, 1H) overlapping with 7.02 (d, J = 8.1 Hz, 1H), 4.08 (m, 4H), 3.61 (s, 4H), 2.66 (s, 1H), 1.96-1.88 (m, 4H), 1.33 (s, 6H), 1.31 (s, 6H), 1.26 (s, 12H). OHs may be under broad peak between 2.5 and 2ppm. LCMS (Method X2) Rt 1.48min; m/z 575.3108 expected 575.3113 for $C_{29}H_{44}N_6O_4Cl$ [M + H]$^+$. | 2,2,6,6-tetramethylmorph oline and Intermediate D2d: 5-((2,5-dichloropyrimidin-4-yl)amino)-1,3-bis(3-hydroxy-3-methylbutyl)-1,3-dihydro-2H-benzo[d]imidazol-2-one |
| Example 35l: 5-((5-chloro-2-((3S,5R)-3,4,5-trimethylpiperazin-1-yl)pyrimidin-4-yl)amino)-3-(3-hydroxy-3-methylbutyl)-1-methyl-1,3-dihydro-2H-benzo[d]imidazol-2-one | $^1$H NMR (600 MHz, Methanol-d$_4$) δ 7.94 (s, 1H), 7.43 (d, J = 2.0 Hz, 1H), 7.37 (dd, J = 8.4, 2.0 Hz, 1H), 7.14 (d, J = 8.4 Hz, 1H), 4.40 (dq, J = 13.5, 1.8 Hz, 2H), 4.13-3.97 (m, 2H), 3.45 (s, 3H), 2.70 (dd, J = 13.4, 11.0 Hz, 2H), 2.34 (s, 3H), 2.32-2.22 (m, 2H), 1.91-1.82 (m, 2H), 1.30 (s, 6H), 1.15 (d, J = 6.2 Hz, 6H). LCMS (Method T4) Rt 2.22 min; m/z 488.2518 expected 488.2535 for $C_{24}H_{35}N_7O_2Cl$ [M + H]$^+$. | (2R,6S)-1,2,6-trimethylpiperazin e and Intermediate D2a: 5-[(2,5-dichloropyrimidin-4-yl)amino]-3-(3-hydroxy-3-methyl-butyl)-1-methyl-benzimidazol-2-one |
| Example 35m: 5-((2-((1R,5S)-8-azabicyclo[3.2.1]octan-8-yl)-5-chloropyrimidin-4-yl)amino)-3-(3-hydroxy-3-methylbutyl)-1-methyl-1,3-dihydro-2H-benzo[d]imidazol-2-one: formic acid (1:2) | $^1$H NMR (600 MHz, Methanol-d$_4$) δ 8.19 (s, 2H, formic), 7.91 (s, 1H), 7.51 (d, J = 1.9 Hz, 1H), 7.39 (dd, J = 8.4, 1.9 Hz, 1H), 7.12 (d, J = 8.4 Hz, 1H), 4.56-4.46 (m, 2H), 4.09-3.94 (m, 2H), 3.43 (s, 3H), 2.06-1.98 (m, 2H), | 8-azabicyclo[3.2.1] octane hydrochloride and Intermediate D2a: 5-[(2,5- |

TABLE 14-continued

Compounds prepared by a method analogous to that used for the preparation of Example 35a

| Example | Data | Intermediates |
|---|---|---|
| (structure shown) | 1.97-1.89 (m, 1H), 1.89-1.77 (m, 6H), 1.61-1.52 (m, 1H), 1.52-1.43 (m, 2H), 1.28 (s, 6H). LCMS (Method T4) Rt 2.49 min; m/z 471.2283 expected 471.2270 for $C_{24}H_{32}N_6O_2Cl$ [M + H]$^+$. | dichloropyrimidin-4-yl)amino]-3-(3-hydroxy-3-methyl-butyl)-1-methyl-benzimidazol-2-one |
| Example 35n: 5-((2-((1R,5S)-3-azabicyclo[3.2.1]octan-3-yl)-5-chloropyrimidin-4-yl)amino)-3-(3-hydroxy-3-methylbutyl)-1-methyl-1,3-dihydro-2H-benzo[d]imidazol-2-one formic acid (1:1.5) (structure shown) | $^1$H NMR (600 MHz, Methanol-d$_4$) δ 8.16 (s, 1.5H, formic), 7.89 (s, 1H), 7.54 (d, J = 2.0 Hz, 1H), 7.34 (dd, J = 8.4, 2.0 Hz, 1H), 7.11 (d, J = 8.4 Hz, 1H), 4.22-4.11 (m, 2H), 4.07-3.93 (m, 2H), 3.43 (s, 3H), 3.01-2.88 (m, 2H), 2.37 - 2.21 (m, 2H), 1.96-1.81 (m, 2H), 1.71-1.65 (m, 2H), 1.64-1.60 (m, 2H), 1.56-1.45 (m, 2H), 1.29 (s, 6H). LCMS (Method T4) Rt 2.65 min; m/z 471.2296 expected 471.2270 for $C_{24}H_{32}N_6O_2Cl$ [M + H]$^+$. | 3-azabicyclo[3.2.1]octane hydrochloride and Intermediate D2a: 5-[(2,5-dichloropyrimidin-4-yl)amino]-3-(3-hydroxy-3-methyl-butyl)-1-methyl-benzimidazol-2-one |
| Example 35o: 5-((5-chloro-2-((3aR,7aS)-octahydro-2H-isoindol-2-yl)pyrimidin-4-yl)amino)-3-(3-hydroxy-3-methylbutyl)-1-methyl-1,3-dihydro-2H-benzo[d]imidazol-2-one: formic acid (1:3) (structure shown) | $^1$H NMR (600 MHz, Methanol-d$_4$) δ 8.16 (s, 3H, formic), 7.89 (s, 1H), 7.67 (d, J = 2.0 Hz, 1H), 7.42 (dd, J =8.4, 2.0 Hz, 1H), 7.11 (d, J = 8.4 Hz, 1H), 4.12-3.93 (m, 2H), 3.60-3.45 (m, 2H), 3.43 (s, 3H), 3.41-3.36 (m, 2H), 2.41-2.23 (m, 2H), 1.87 (dd, J = 9.5, 6.6 Hz, 2H), 1.71-1.61 (m, 2H), 1.60-1.33 (m, 6H), 1.28 (s, 6H). LCMS (Method T4) Rt 2.64 min; m/z 485.2427 expected 485.2426 for $C_{25}H_{34}N_6O_2Cl$ [M + H]$^+$. | (3aR,7aS)-octahydro-1H-isoindole hydrochloride and Intermediate D2a: 5-[(2,5-dichloropyrimidin-4-yl)amino]-3-(3-hydroxy-3-methyl-butyl)-1-methyl-benzimidazol-2-one |
| Example 35p: 5-((5-chloro-2-((3R,4S)-3,4-dimethylpyrrolidin-1-yl)pyrimidin-4-yl)amino)-3-(3-hydroxy-3-methylbutyl)-1-methyl-1,3-dihydro-2H-benzo[d]imidazol-2-one: formic acid (1:1) (structure shown) | $^1$H NMR (600 MHz, Methanol-d$_4$) δ 8.17 (s, 1H), 7.89 (s, 1H), 7.68 (d, J = 2.0 Hz, 1H), 7.41 (dd, J = 8.4, 2.0 Hz, 1H), 7.11 (d, J = 8.4 Hz, 1H), 4.12-3.89 (m, 2H), 3.70-3.55 (m, 2H), 3.43 (s, 3H), 3.27-3.15 (m, 2H), 2.57-2.27 (m, 2H), 1.94-1.76 (m, 2H), 1.29 (s, 6H), 1.00 (d, J = 6.7 Hz, 6H). LCMS (Method T4) Rt 2.50 min; m/z 459.2300 expected 459.2270 for $C_{23}H_{32}N_6O_2Cl$ [M + H]$^+$. | (3R,4S)-3,4-dimethylpyrrolidine hydrochloride and Intermediate D2a: 5-[(2,5-dichloropyrimidin-4-yl)amino]-3-(3-hydroxy-3-methyl-butyl)-1-methyl-benzimidazol-2-one |
| Example 35q: 6-((5-chloro-2-(2,2,6,6-tetramethylmorpholino)pyrimidin-4-yl)amino)-1,3-bis(3-hydroxy-3-methylbutyl)-1,3-dihydro-2H-imidazo[4,5-b]pyridin-2-one | $^1$H NMR (500 MHz, Chloroform-d) δ 8.13 (d, J = 2.1 Hz, 1H), 8.02 (s, 1H), 7.67 (d, J = 2.2 Hz, 1H), 6.94 (s, 1H), 4.18 (m, 2H), 4.05 (m, 2H), 3.58 (s, 4H), 2.00 (m, 2H), 1.93-1.86 (m, 2H), | 6-((2,5-dichloropyrimidin-4-yl)amino)-1,3-bis(3-hydroxy-3-methylbutyl)-1,3- |

TABLE 14-continued

Compounds prepared by a method analogous to that used for the preparation of Example 35a

| Example | Data | Intermediates |
|---|---|---|
| 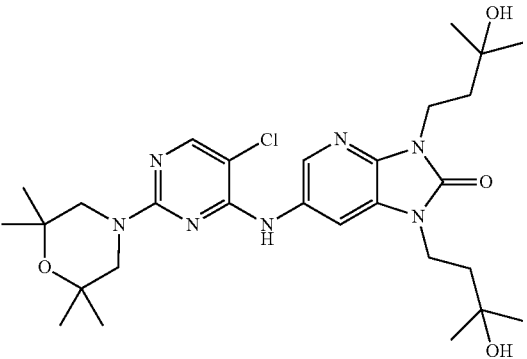 [SMILES: CC(C)(O)CCn1c(=O)n(CCC(C)(C)O)c2ncc(Nc3nc(N4CC(C)(C)OC(C)(C)C4)ncc3Cl)cc21] | 1.31 (s, 6H), 1.30 (s, 6H), 1.24 (s, 12H). OHs not observed. LCMS (Method X4) Rt 3.19 min; m/z 576.3071 expected 576.3065 for $C_{28}H_{43}ClN_7O_4$ [M + H]$^+$ | dihydro-2H-imidazo[4,5-b]pyridin-2-one (Intermediate D3I) and 2,2,6,6-tetramethylmorpholine |
| Example 35r: 6-((5-chloro-2-((3R,5S)-4,4-difluoro-3,5-dimethylpiperidin-1-yl)pyrimidin-4-yl)amino)-1,3-bis(3-hydroxy-3-methylbutyl)-1,3-dihydro-2H-imidazo[4,5-b]pyridin-2-one 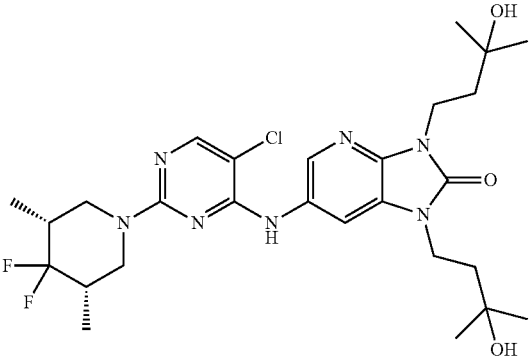 [SMILES: C[C@@H]1CN(c2ncc(Cl)c(Nc3cnc4c(c3)n(CCC(C)(C)O)c(=O)n4CCC(C)(C)O)n2)C[C@H](C)C1(F)F] | $^1$H NMR (500 MHz, Chloroform-d) δ 8.15 (d, J = 2.1 Hz, 1H), 8.02 (s, 1H), 7.62 (d, J = 2.1 Hz, 1H), 6.95 (s, 1H), 4.57 (br d, J = 13 Hz, 2H), 4.18 (t, J = 7 Hz, 2H), 4.09-4.02 (m, 2H), 2.74 (br t, J = 13 Hz, 2H), 2.04-1.86 (m, 6H), 1.32 (s, 6H), 1.31 (s, 6H), 1.06 (d, J = 6.7 Hz, 6H). LCMS (Method X4) Rt 3.44 min; m/z 582.2802 expected 582.2771 for $C_{27}H_{39}ClF_2N_7O_3$ [M + H]$^+$ | 6-((2,5-dichloropyrimidin-4-yl)amino)-1,3-bis(3-hydroxy-3-methylbutyl)-1,3-dihydro-2H-imidazo[4,5-b]pyridin-2-one (Intermediate D3I) and (3R,5S)-4,4-difluoro-3,5-dimethylpiperidine |
| Example 35s: 5-((5-chloro-2-(8,8-difluoro-3-azabicyclo[3.2.1]octan-3-yl)pyrimidin-4-yl)amino)-3-(3-hydroxy-3-methylbutyl)-1-methyl-1,3-dihydro-2H-benzo[d]imidazol-2-one: formic acid (1:0.5) 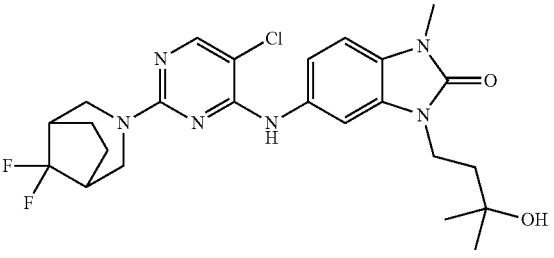 [SMILES: Cn1c(=O)n(CCC(C)(C)O)c2cc(Nc3nc(N4CC5CCC(C4)C5(F)F)ncc3Cl)ccc21] | $^1$H NMR (600 MHz, Methanol-d$_4$) δ 8.19 (s, 0.5H, formic), 7.94 (s, 1H), 7.47 (d, J = 2.0 Hz, 1H), 7.33 (dd, J = 8.4, 2.0 Hz, 1H), 7.12 (d, J = 8.4 Hz, 1H), 4.47-4.35 (m, 2H), 4.10-3.93 (m, 2H), 3.43 (s, 3H), 3.23 (d, J = 12.9 Hz, 2H), 2.36-2.21 (m, 2H), 1.94-1.77 (m, 4H), 1.65-1.53 (m, 2H), 1.29 (s, 6H). LCMS (Method T4) Rt 2.99 min; m/z 507.2073 expected 507.2081 for $C_{24}H_{30}F_2N_6O_2Cl$ [M + H]$^+$. | 8,8-difluoro-3-azabicyclo[3.2.1]octane hydrochloride and Intermediate D2a: 5-[(2,5-dichloropyrimidin-4-yl)amino]-3-(3-hydroxy-3-methyl-butyl)-1-methyl-benzimidazol-2-one |
| Example 35t: 5-((2-((1r,3r,5r,7r)-2-azaadamantan-2-yl)-5-chloropyrimidin-4-yl)amino)-3-(3-hydroxy-3-methylbutyl)-1-methyl-1,3-dihydro-2H-benzo[d]imidazol-2-one: formic acid (1:3) | $^1$H NMR (600 MHz, Methanol-d$_4$) δ 8.15 (s, 3H, formic), 7.91 (s, 1H), 7.44 (d, J = 1.9 Hz, 1H), 7.34 (dd, J = 8.4, 1.9 Hz, 1H), 7.13 (d, J = 8.4 Hz, 1H), 4.79-4.67 (m, 2H), 4.13-3.91 (m, 2H), 3.45 (s, 3H), 2.11-2.05 (m, 2H), | 2-azaadamantane (from Raney Nickel hydrogenation of commercial 2- |

TABLE 14-continued

Compounds prepared by a method analogous to that used for the preparation of Example 35a

| Example | Data | Intermediates |
|---|---|---|
| | 1.98-1.93 (m, 2H), 1.93-1.74 (m, 10H), 1.29 (s, 6H). LCMS (Method T4) Rt 2.69 min; m/z 497.2435 expected 497.2426 for $C_{26}H_{34}N_6O_2Cl$ [M + H]⁺. | Hydroxy-2-azaadamantane) and Intermediate D2a: 5-[(2,5-dichloropyrimidin-4-yl)amino]-3-(3-hydroxy-3-methyl-butyl)-1-methyl-benzimidazol-2-one |
| Example 35u: 4-chloro-6-((5-chloro-2-(2,2,6,6-tetramethylmorpholino)pyrimidin-4-yl)amino)-1,3-bis(3-hydroxy-3-methylbutyl)-1,3-dihydro-2H-benzo[d]imidazol-2-one | ¹H NMR (500 MHz, Chloroform-d) δ 8.01 (s, 1H), 7.74 (d, J = 1.9 Hz, 1H), 7.00 (s, 1H), 6.98 (d, J = 2.0 Hz, 1H), 4.38 (m, 2H), 4.04 (m, 2H), 3.63 (s, 4H), 2.01-1.94 (m, 2H), 1.92-1.85 (m, 2H), 1.32 (s, 6H), 1.31 (s, 6H), 1.29 (s, 12H). OHs not observed. LCMS (Method X4) Rt 3.65 min m/z 609.2708 expected 609.2723 for $C_{29}H_{43}Cl_2N_6O_4$ [M + H]⁺ | 4-chloro-6-((2,5-dichloropyrimidin-4-yl)amino)-1,3-bis(3-hydroxy-3-methylbutyl)-1,3-dihydro-2H-benzo[d]imidazol-2-one (Intermediate D3k) and 2,2,6,6-tetramethyl-morpholine |
| Example 35v: 5-((5-chloro-2-(3-(methoxymethyl)piperidin-1-yl)pyrimidin-4-yl)amino)-3-(3-hydroxy-3-methylbutyl)-1-methyl-1,3-dihydro-2H-benzo[d]imidazol-2-one: formic acid (1:1) | ¹H NMR (600 MHz, Methanol-d₄) δ 8.18 (s, 1H), 7.89 (s, 1H), 7.49 (d, J = 2.0 Hz, 1H), 7.36 (dd, J = 8.4, 2.0 Hz, 1H), 7.10 (d, J= 8.4 Hz, 1H), 4.55-4.45 (m, 1H), 4.41-4.30 (m, 1H), 4.09-3.97 (m, 2H), 3.44 (s, 3H), 3.25 (s, 3H), 3.30-3.19 (m, 2H), 2.99-2.92 (m, 2H), 2.75 (dd, J = 13.1, 10.0 Hz, 1H), 1.87 (dd, J = 8.9, 7.5 Hz, 2H), 1.83-1.75 (m, 2H), 1.73-1.66 (m, 1H), 1.56-1.43 (m, 1H), 1.29 (s, 6H). LCMS (Method T4) Rt = 2.54 mins, m/z 489.2374 [M + H]⁺ expected 489.2375 for $C_{24}H_{34}ClN_6O_3$ | 3-(methoxymethyl)piperidine and Intermediate D2a: 5-[(2,5-dichloropyrimidin-4-yl)amino]-3-(3-hydroxy-3-methyl-butyl)-1-methyl-benzimidazol-2-one |
| Example 35w: 5-((5-chloro-2-(6,6-difluoro-3-azabicyclo[3.1.1]heptan-3-yl)pyrimidin-4-yl)amino)-3-(3-hydroxy-3-methylbutyl)-1-methyl-1,3-dihydro-2H-benzo[d]imidazol-2-one: formic acid (1:0.5) | ¹H NMR (600 MHz, Methanol-d₄) δ 8.13 (s, 0.5H, formic), 7.94 (s, 1H), 7.62 (d, J = 2.0 Hz, 1H), 7.37 (dd, J = 8.4, 2.0 Hz, 1H), 7.09 (d, J = 8.4 Hz, 1H), 4.03 (d, J = 12.0 Hz, 2H), 4.01-3.91 (m, 2H), 3.73 (d, J = 12.0 Hz, | 6,6-difluoro-3-azabicyclo[3.1.1] heptane and Intermediate D2a: 5-[(2,5-dichloropyrimidin- |

TABLE 14-continued

Compounds prepared by a method analogous to that used for the preparation of Example 35a

| Example | Data | Intermediates |
|---|---|---|
| (structure shown) | 2H), 3.41 (s, 3H), 2.98-2.88 (m, 2H), 2.10-2.02 (m, 1H), 1.92-1.79 (m, 2H), 1.56 (dd, J = 17.0, 9.7 Hz, 1H), 1.28 (s, 6H). LCMS (Method T4) Rt = 2.74 mins, m/z 493.1936 [M + H]$^+$ expected 493.1925 for $C_{23}H_{28}ClF_2N_6O_2$ | 4-yl)amino]-3-(3-hydroxy-3-methyl-butyl)-1-methyl-benzimidazol-2-one |
| Example 35x: 5-((5-chloro-2-((3S,5R)-3-hydroxy-5-methylpiperidin-1-yl)pyrimidin-4-yl)amino)-3-(3-hydroxy-3-methylbutyl)-1-methyl-1,3-dihydro-2H-benzo[d]imidazol-2-one formic acid (1:1.5) | $^1$H NMR (600 MHz, Methanol-d$_4$) δ 8.14 (s, 1.5H), 7.90 (s, 1H), 7.51 (d, J = 2.0 Hz, 1H), 7.33 (dd, J = 8.4, 2.0 Hz, 1H), 7.12 (d, J = 8.4 Hz, 1H), 4.73 (ddt, J = 12.4, 5.0, 1.8 Hz, 1H), 4.48 (ddt, J = 13.0, 3.9, 1.7 Hz, 1H), 4.13-3.97 (m, 2H), 3.54 (tt, J = 10.6, 4.6 Hz, 1H), 3.43 (s, 3H), 2.48 (dd, J = 12.4, 10.6 Hz, 1H), 2.29 (dd, J = 13.0, 11.4 Hz, 1H), 2.11-2.03 (m, 1H), 1.94-1.82 (m, 2H), 1.68-1.57 (m, 1H), 1.29 (s, 6H), 1.07 (q, J = 11.4 Hz, 1H), 0.95 (d, J = 6.6 Hz, 3H). LCMS (Method T4) Rt = 2.48 min, m/z 475.2235 [M + H]$^+$ expected 475.2224 for $C_{23}H_{32}ClN_6O_3$ | (3S,5R)-5-methylpiperidin-3-ol and Intermediate D2a: 5-[(2,5-dichloropyrimidin-4-yl)amino]-3-(3-hydroxy-3-methyl-butyl)-1-methyl-benzimidazol-2-one |
| Example 35y: 5-((5-chloro-2-((3R,5S)-3,5-dimethylazepan-1-yl)pyrimidin-4-yl)amino)-3-(3-hydroxy-3-methylbutyl)-1-methyl-1,3-dihydro-2H-benzo[d]imidazol-2-one: formic acid (1:1) | $^1$H NMR (600 MHz, Methanol-d$_4$) δ 8.16 (s, 1H), 7.89 (s, 1H), 7.44 (d, J = 8.4 Hz, 1H), 7.41 (v. br, 1H), 7.11 (d, J =8.4 Hz, 1H), 4.09-3.99 (m, 2H), 3.91 (ddd, J = 13.7, 4.2, 1.5 Hz, 1H), 3.86-3.77 (m, 1H), 3.53-3.44 (m, 1H), 3.44 (s, 3H), 3.03-2.88 (m, 1H), 2.00-1.75 (m, 4H), 1.59-1.47 (m, 2H), 1.44-1.34 (m, 1H), 1.29 (s, 6H), 1.15-0.68 (m, 1H), 0.92 (v br m, 6H). LCMS (Method T4) Rt = 2.77 mins, m/z 487.2663 [M + H]$^+$ expected 487.2583 for $C_{25}H_{36}ClN_6O_2$ | (3R,5S)-3,5-dimethylazepane and Intermediate D2a: 5-[(2,5-dichloropyrimidin-4-yl)amino]-3-(3-hydroxy-3-methyl-butyl)-1-methyl-benzimidazol-2-one |
| Example 35za: 5-((5-chloro-2-(3-phenylpiperidin-1-yl)pyrimidin-4-yl)amino)-3-(3-hydroxy-3-methylbutyl)-1-methyl-1,3-dihydro-2H-benzo[d]imidazol-2-one: formic acid (1:0.5) | $^1$H NMR (600 MHz, Methanol-d$_4$) δ 8.20 (s, 0.5H, formic), 7.91 (s, 1H), 7.46 (d, J = 1.9 Hz, 1H), 7.28 (dd, J = 8.4, 1.9 Hz, 1H), 7.24-7.16 (m, 3H), 7.12-7.05 (m, 2H), 7.02 (d, J = 8.4 Hz, 1H), 4.68-4.56 (m, 2H), 3.88-3.63 (m, 2H), 3.41 (s, 3H), 2.90 (td, J = 13.0, 2.7 Hz, 1H), 2.81 (dd, J = 13.0, 11.4 Hz, 1H), 2.61 (tt, J = 11.4, 3.7 Hz, 1H), 2.06-1.93 (m, 1H), 1.90-1.75 (m, 2H), 1.75-1.64 (m, 2H), 1.64-1.52 (m, 1H), 1.22 (s, 6H). LCMS (Method T4) Rt 2.90 min; m/z 521.2416 expected 521.2426 for $C_{28}H_{34}N_6O_2Cl$ [M + H]$^+$. | 3-phenylpiperidine and Intermediate D2a: 5-[(2,5-dichloropyrimidin-4-yl)amino]-3-(3-hydroxy-3-methyl-butyl)-1-methyl-benzimidazol-2-one |
| Example 35zb: 5-((2-(4-((1H-pyrazol-1- | $^1$H NMR (600 MHz, Methanol-d$_4$) δ 8.14 (s, 1.5H, formic), 7.90 (s, 1H), | 4-(1H-pyrazol-1-ylmethyl)piperidine |

TABLE 14-continued

Compounds prepared by a method analogous to that used for the preparation of Example 35a

| Example | Data | Intermediates |
| --- | --- | --- |
| yl)methyl)piperidin-1-yl)-5-chloropyrimidin-4-yl)amino)-3-(3-hydroxy-3-methylbutyl)-1-methyl-1,3-dihydro-2H-benzo[d]imidazol-2-one: formic acid (1:1.5)<br><br>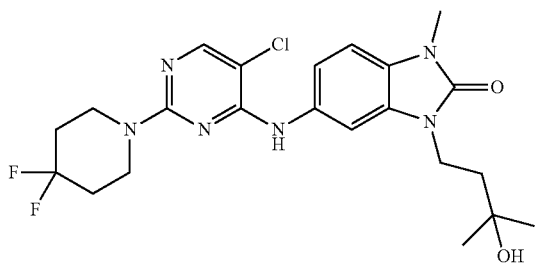 | 7.61 (d, J = 1.9 Hz, 1H), 7.51-7.48 (m, 2H), 7.32 (dd, J = 8.4, 1.9 Hz, 1H), 7.11 (d, J = 8.4 Hz, 1H), 6.29 (t, J = 2.1 Hz, 1H), 4.62-4.52 (m, 2H), 4.04 (d, J = 7.3 Hz, 2H), 4.04-3.97 (m, 2H), 3.43 (s, 3H), 2.91-2.77 (m, 2H), 2.19-2.09 (m, 1H), 1.92-1.78 (m, 2H), 1.61-1.46 (m, 2H), 1.28 (s, 6H), 1.21 (qd, J = 12.4, 4.4 Hz, 2H). LCMS (Method T4) Rt 2.54 min; m/z 525.2474 expected 525.2488 for $C_{26}H_{34}N_{18}O_2Cl$ [M + H]⁺. | hydrochloride and Intermediate D2a: 5-[(2,5-dichloropyrimidin-4-yl)amino]-3-(3-hydroxy-3-methyl-butyl)-1-methyl-benzimidazol-2-one |

Example 36a: 5-((5-chloro-2-(4,4-difluoropiperidin-1-yl)pyridin-4-yl)amino)-3-(3-hydroxy-3-methyl-butyl)-1-methyl-1,3-dihydro-2H-benzo[d]imidazol-2-one A mixture of 5-amino-3-(3-hydroxy-3-methyl-butyl)-1-methyl-benzimidazol-2-one (intermediate A1, 15 mg, 0.06 mmol), 5-chloro-2-(4,4-difluoro-1-piperidyl)-4-iodo-pyridine (Intermediate E3b, 26 mg, 0.07 mmol), cesium carbonate (157 mg, 0.48 mmol), Xantphos (21 mg, 0.04 mmol) and Tris(dibenzylideneacetone)dipalladium (0) (5.5 mg, 0.006 mmol) in toluene:DMF (3:1 v/v, 0.80 mL, 0.08 M) was heated at 80° C. under microwave irradiation for 1 h. Water (10 mL) was added and the aqueous mixture was extracted with EtOAc (3×10 mL). The organic extracts were combined, washed with brine (10 mL), dried (MgSO4) and concentrated in vacuo. Purification by column chromatography (Biotage 10 g KP-Sil column, 0 to 10% MeOH in DCM) gave the desired product containing unknown impurities which were removed by preparative HPLC purification (ACE 5 C18-PFP column (5µ, 250×21.2 mm), 15 minute gradient elution from 40:60 to 25:75 water:methanol (both modified with 0.1% formic acid) at a flow rate of 20 mL/min) to give the title compound (4 mg, 14%, 0.0083 mmol) as a solid. LCMS (Method T4): Rt 2.35 min, m/z 480.1959, expected 480.1972 for $C_{23}H_{29}ClF_2N_5O_3$ [M+H]⁺. ¹H NMR (500 MHz, Methanol-d4): δ 7.87 (1H, s), 7.20 (1H, d, J 8.4 Hz), 7.16 (1H, d, J 1.8 Hz), 7.09 (1H, dd, J 8.4, 1.8 Hz), 6.20 (1H, s), 4.03 (2H, m), 3.50-3.46 (4H, m), 3.45 (3H, s), 1.99-1.89 (4H, m), 1.86 (2H, m), 1.28 (6H, s).

The following tabulated examples were prepared by a method analogous to that used for the preparation of example 36a, using the intermediates shown. Examples 36e and 36f were heated to 140° C.

TABLE 15

Compounds prepared by a method analogous to that used for the preparation of Example 36a.

| Example | Data | Intermediates |
| --- | --- | --- |
| Example 36b: 5-((5-chloro-2-((2R,6S)-2,6-dimethylmorpholino)pyridin-4-yl)amino)-3-(3-hydroxy-3-methylbutyl)-1-methyl-1,3-dihydro-2H-benzo[d]imidazol-2-one | LCMS (Method T4): Rt 2.32 min, m/z 474.2246, expected 474.2266 for $C_{24}H_{33}ClN_5O_3$ [M + H]⁺. ¹H NMR (500 MHz, Methanol-d4): δ 7.86 (1H, s), 7.21 (1H, d, J 8.3 Hz), 7.16 (1H, d, J 1.6 Hz), 7.09 (1H, dd, J 8.3, 1.6 Hz), 6.13 (1H, s), 4.03 (2H, m), 3.73 (2H, m), 3.63 (2H, m), 3.46 (3H, s), 2.33 (2H, dd, J 12.6, 10.7 Hz), 1.86 (2H, m), 1.29 (6H, s), 1.16 (6H, d, J 6.3 Hz). | 5-amino-3-(3-hydroxy-3-methyl-butyl)-1-methyl-benzimidazol-2-one (intermediate A1) and (2S,6R)-4-(5-chloro-4-iodo-2-pyridyl)-2,6-dimethyl-morpholine (Intermediate E3c) |

TABLE 15-continued

Compounds prepared by a method analogous to that used for the preparation of Example 36a.

| Example | Data | Intermediates |
| --- | --- | --- |
| Example 36c: 1-(5-chloro-4-((3-(3-hydroxy-3-methylbutyl)-1-methyl-2-oxo-2,3-dihydro-1H-benzo[d]imidazol-5-yl)amino)pyridin-2-yl)-N,N-dimethylpiperidine-4-carboxamide 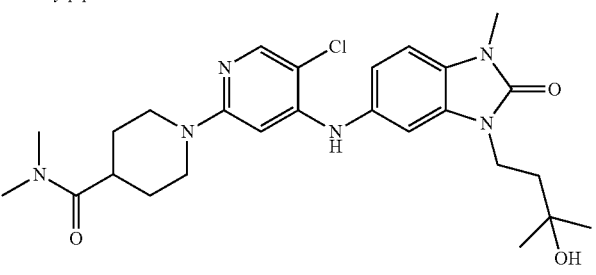 | LCMS (Method T4): Rt 2.14 min, m/z 515.2515, expected 515.2532 for $C_{26}H_{36}ClN_6O_3$ [M + H]$^+$. $^1$H NMR (500 MHz, Methanol-d4): δ 7.84 (1H, s), 7.20 (1H, d, J 8.1 Hz), 7.17 (1H, d, J 1.7 Hz), 7.09 (1H, dd, J 8.1, 1.7 Hz), 6.14 (1H, s), 4.03 (2H, m), 3.98 (2H, m), 3.45 (3H, s), 3.12 (3H, s), 2.92 (3H, s), 2.89-2.78 (3H, m), 1.86 (2H, m), 1.73-1.60 (4H, m), 1.28 (6H, s). | 5-amino-3-(3-hydroxy-3-methyl-butyl)-1-methyl-benzimidazol-2-one (intermediate A1) and 1-(5-chloro-4-iodo-2-pyridyl)-N,N-dimethyl-piperidine-4-carboxamide (Intermediate E3d) |
| Example 36d: 5-((5-chloro-2-((3S,5R)-3,5-dimethylpiperidin-1-yl)pyridin-4-yl)amino)-3-(3-hydroxy-3-methylbutyl)-1-methyl-1,3-dihydro-2H-benzo[d]imidazol-2-one: formic acid (1:1) 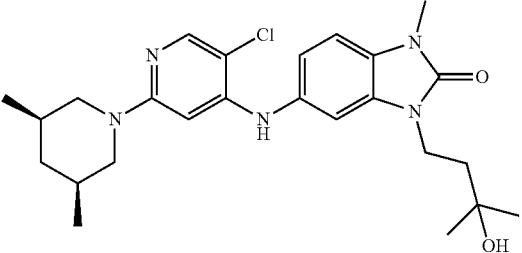 [SMILES: C[C@@H]1C[C@H](C)CN(c2cc(Nc3ccc4c(c3)n(CCC(C)(C)O)c(=O)n4C)c(Cl)cn2)C1] | LCMS (Method T4): Rt 2.52 min, m/z 472.2482, expected 472.2474 for $C_{25}H_{35}ClN_5O_2$ [M + H]$^+$. $^1$H NMR (500 MHz, Methanol-d4): δ 8.27 (1H, br), 7.84 (1H, s), 7.22 (1H, d, J 8.3 Hz), 7.18 (1H, d, J 1.8 Hz), 7.10 (1H, dd, J 8.3, 1.8 Hz), 6.12 (1H, s), 4.03 (2H, m), 3.81 (2H, m), 3.46 (3H, s), 2.30 (2H, dd, J 12.6, 11.8 Hz), 1.86 (2H, m), 1.80 (1H, m), 1.62 (2H, m), 1.28 (6H, s), 0.87 (6H, d, J 6.6 Hz), 0.76 (1H, m). | 5-amino-3-(3-hydroxy-3-methyl-butyl)-1-methyl-benzimidazol-2-one (intermediate A1) and 5-chloro-2-[(3S,5R)-3,5-dimethyl-1-piperidyl]-4-iodo-pyridine (Intermediate E3a) |
| Example 36e: 5-((5-chloro-2-((3R,5S)-3,5-dimethylpiperidine-1-carbonyl)pyridin-4-yl)amino)-3-(3-hydroxy-3-methylbutyl)-1-methyl-1,3-dihydro-2H-benzo[d]imidazol-2-one: formic acid (1:1) 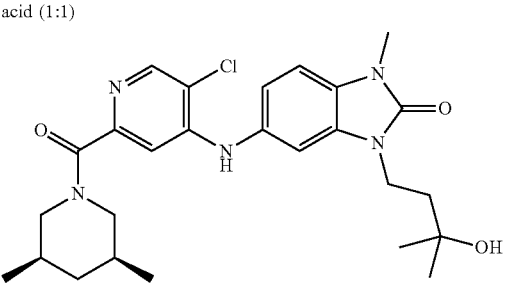 | $^1$H NMR (600 MHz, Methanol-d$_4$) δ 8.32 (s, 1H), 8.28 (s, 1H), 7.23 (d, J = 8.3 Hz, 1H), 7.19 (d, J = 2.0 Hz, 1H), 7.10 (dd, J = 8.3, 2.0 Hz, 1H), 6.84 (s, 1H), 4.53-4.44 (m, 1H), 4.10-3.96 (m, 2H), 3.62-3.56 (m, 1H), 3.47 (s, 3H), 2.59-2.51 (m, 1H), 2.28-2.19 (m, 1H), 1.96-1.78 (m, 3H), 1.69-1.57 (m, 2H), 1.29 (s, 6H), 0.95 (d, J = 6.6 Hz, 3H), 0.88-0.82 (m, 1H), 0.81 (d, J =6.6 Hz, 3H). LCMS (Method T4): Rt 2.89 min, m/z 500.2407, expected 500.2423 for $C_{26}H_{35}ClN_5O_3$ [M + H]$^+$. | 5-amino-3-(3-hydroxy-3-methyl-butyl)-1-methyl-benzimidazol-2-one (intermediate A1) and (4,5-dichloro-2-pyridyl)-[(3R,5S)-3,5-dimethyl-1-piperidyl] methanone (prepared from 4,5-dichloropicolinic acid and (3S,5R)-3,5-dimethyl-piperidine) |
| Example 36f: 5-((5-chloro-2-((3S,5R)-4,4-difluoro-3,5-dimethylpiperidine-1-carbonyl)pyridin-4-yl)amino)-3-(3-hydroxy-3-methylbutyl)-1-methyl-1,3-dihydro-2H-benzo[d]imidazol-2-one | 1H NMR (600 MHz, Methanol-d$_4$) δ 8.29 (s, 1H), 7.23 (d, J = 8.2 Hz, 1H), 7.19 (d, J = 2.0 Hz, 1H), 7.11 (dd, J = 8.2, 2.0 Hz, 1H), 6.95 (s, 1H), 4.58-4.48 (m, 1H), 4.12-3.96 (m, 2H), 3.82-3.73 (m, 1H), 3.46 | 5-amino-3-(3-hydroxy-3-methyl-butyl)-1-methyl-benzimidazol-2-one |

TABLE 15-continued

Compounds prepared by a method analogous to that used for the preparation of Example 36a.

| Example | Data | Intermediates |
|---|---|---|
| ![structure] | (s, 3H), 3.02-2.84 (m, 1H), 2.65 (t, J = 12.8 Hz, 1H), 2.23-1.99 (m, 2H), 1.93-1.77 (m, 2H), 1.29 (s, 6H), 1.07 (d, J = 6.8 Hz, 3H), 0.94 (d, J = 6.8 Hz, 3H). LCMS (Method T4) Rt 2.96 min; m/z 536.2232 expected 536.2235 for $C_{26}H_{33}F_2N_5O_3Cl$ $[M + H]^+$. | (intermediate A1) and (4,5-dichloro-2-pyridyl)-[(3R,5S)-4,4-difluoro-3,5-dimethyl-1-piperidyl]methanone (prepared from 4,5-dichloropicolinic acid and (3S,5R)-4,4-difluoro-3,5-dimethyl-piperidine) |

Example 37a: 5-((5-chloro-2-((3S,5R)-4,4-difluoro-3,5-dimethylpiperidin-1-yl)pyrimidin-4-yl)amino)-1-(2-(dimethylamino)ethyl)-3-(3-hydroxy-3-methyl-butyl)-1,3-dihydro-2H-benzo[d]imidazol-2-one: formic acid (1:2)

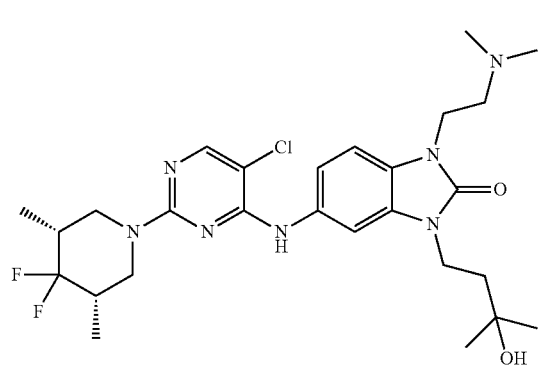 [SMILES: C[C@@H]1CN(c2ncc(Cl)c(Nc3ccc4c(c3)n(CCC(C)(C)O)c(=O)n4CCN(C)C)n2)C[C@H](C)C1(F)F]

To a solution of 2-(5-((5-chloro-2-((3S,5R)-4,4-difluoro-3,5-dimethylpiperidin-1-yl)pyrimidin-4-yl)amino)-3-(3-hydroxy-3-methylbutyl)-2-oxo-2,3-dihydro-1H-benzo[d]imidazol-1-yl)acetaldehyde (Intermediate H1, 30 mg, 0.056 mmol) in THF (1.1 mL) was added dimethylamine solution in THF (56 uL, 0.11 mmol). The reaction mixture was stirred at rt for 20 mins. Sodium triacetoxyborohydride (18 mg, 0.084 mmol) was then added. The reaction mixture was stirred at rt for 24 h. A couple of drops of water were added to the reaction mixture before concentrating in vacuo. The residue was then taken up in DMSO (1 mL) and purified directly using Biotage reverse-phase 12 g C-18 column eluting 10-100% MeOH in water (each containing 0.1% formic acid) affording the title compound (19 mg) as a pale yellow solid. $^1$H NMR (600 MHz, Chloroform-d) δ 8.26 (s, 2H, formic), 7.98 (s, 1H), 7.39 (d, J=2.0 Hz, 1H), 7.22 (dd, J=8.4, 2.0 Hz, 1H), 7.15 (d, J=8.4 Hz, 1H), 7.06 (s, 1H), 4.58 (dt, J=13.1, 4.0 Hz, 2H), 4.26 (t, J=7.2 Hz, 2H), 4.02 (t, J=7.4 Hz, 2H), 3.22 (t, J=7.2 Hz, 2H), 2.79-2.68 (m, 8H), 2.01-1.85 (m, 4H), 1.29 (s, 6H), 1.04 (d, J=6.8 Hz, 6H). OH not observed; LCMS (Method X4) Rt=2.71 mins, m/z 566.2831 [M+H]1 expected 566.2822 for $C_{27}H_{39}ClF_2N_7O_2^+$.

Example 37b: 5-((5-chloro-2-((3S,5R)-4,4-difluoro-3,5-dimethylpiperidin-1-yl)pyrimidin-4-yl)amino)-3-(3-hydroxy-3-methylbutyl)-1-(2-morpholinoethyl)-1,3-dihydro-2H-benzo[d]imidazol-2-one:formic acid (1:2)

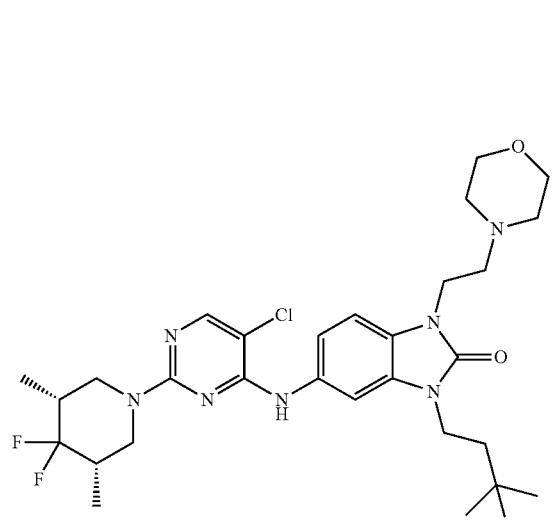

Prepared by a method analogous to that used in the preparation of Example 37a, using morpholine.

$^1$H NMR (600 MHz, Chloroform-d) δ 8.13 (s, 2H, formate), 7.99 (s, 1H), 7.37 (d, J=2.0 Hz, 1H), 7.22 (dd, J=8.4, 2.0 Hz, 1H), 7.09-7.03 (m, 2H), 4.59-4.54 (m, 2H), 4.17 (t, J=7.1 Hz, 2H), 4.03 (t, J=7.3 Hz, 2H), 3.81 (t, J=4.7 Hz, 4H), 3.01 (t, J=7.1 Hz, 2H), 2.91 (br. s, 4H), 2.73 (t, J=12.7 Hz, 2H), 2.02-1.86 (m, 4H), 1.30 (s, 6H), 1.04 (d, J=6.7 Hz, 6H), OH not observed; LCMS (Method X4) Rt=2.77 mins, m/z 608.2951 [M+H]$^+$ expected 608.2927 for $C_{29}H_{41}ClF_2N_7O_3^+$.

Example 38a: ethyl(E)-4-(5-((5-chloro-2-((3S,5R)-4,4-difluoro-3,5-dimethylpiperidin-1-yl)pyrimidin-4-yl)amino)-3-(3-hydroxy-3-methylbutyl)-2-oxo-2,3-dihydro-1H-benzo[d]imidazol-1-yl)but-2-enoate

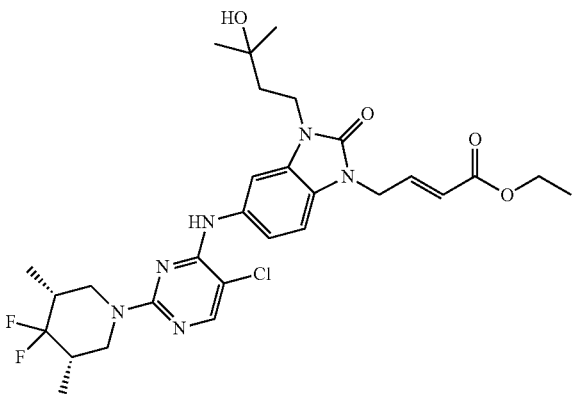 [SMILES: CCOC(=O)/C=C/Cn1c(=O)n(CCC(C)(C)O)c2cc(Nc3nc(N4C[C@@H](C)C(F)(F)[C@@H](C)C4)ncc3Cl)ccc21]

A mixture of 2-(5-((5-chloro-2-((3S,5R)-4,4-difluoro-3,5-dimethylpiperidin-1-yl)pyrimidin-4-yl)amino)-3-(3-hydroxy-3-methylbutyl)-2-oxo-2,3-dihydro-1H-benzo[d]imidazol-1-yl)acetaldehyde (Intermediate H1, 30 mg, 0.056 mmol) and Carbethoxymethylene)triphenylphosphorane (23 mg, 0.067 mmol) in THF (1.1 mL) was refluxed for 16 h. The solvent was removed in vacuo then the residue was then taken up in DMSO (1 mL) and purified directly using Biotage reverse-phase 12 g C-18 column eluting 10-100% MeOH in water (each containing 0.1% formic acid) affording the title compound (16 mg,) as a yellow solid.

$^1$H NMR (500 MHz, Chloroform-d) δ 7.98 (s, 1H), 7.37 (d, J=2.0 Hz, 1H), 7.19 (dd, J=8.4, 2.0 Hz, 1H), 7.03-6.95 (m, 2H), 6.86 (d, J=8.4 Hz, 1H), 5.81 (dt, J=15.7, 1.9 Hz, 1H), 4.66 (dd, J=4.8, 1.9 Hz, 2H), 4.62-4.56 (m, 2H), 4.17 (q, J=7.1 Hz, 2H), 4.08-4.04 (m, 2H), 2.73 (t, J=12.7 Hz, 2H), 2.03-1.87 (m, 4H), 1.30 (s, 6H), 1.25 (t, J=7.1 Hz, 3H), 1.04 (d, J=6.7 Hz, 6H), OH not observed; LCMS (Method X4) Rt=3.47 mins, m/z 607.2627 [M+H]$^+$ expected 607.2611 for $C_{29}H_{38}ClF_2N_6O_4^+$.

Example 39a: 5-((5-Chloro-2-(2,2,2-trifluoroethoxy)pyrimidin-4-yl)amino)-3-(3-hydroxy-3-methyl-butyl)-1-methyl-1,3-dihydro-2H-benzo[d]imidazol-2-one

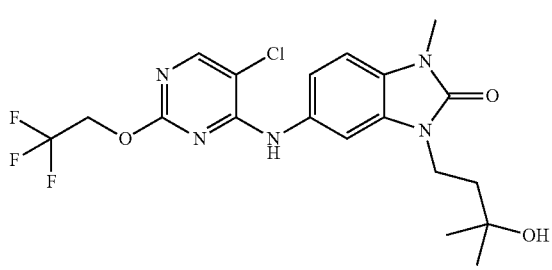 [SMILES: Cn1c(=O)n(CCC(C)(C)O)c2cc(Nc3nc(OCC(F)(F)F)ncc3Cl)ccc21]

A mixture of 5-[(2,5-dichloropyrimidin-4-yl)amino]-3-(3-hydroxy-3-methyl-butyl)-1-methyl-benzimidazol-2-one (11.5 mg, 0.029 mmol), sodium hydride (3.5 mg, 0.087 mmol) and 2,2,2 trifluoroethanol (100 uL) in NMP (1.5 mL) was stirred at rt for 15 min and then under microwave irradiation at 120° C. for 30 min. Hplc purification gave 5-[[5-chloro-2-(2,2,2-trifluoroethoxy)-pyrimidin-4-yl]amino]-3-(3-hydroxy-3-methyl-butyl)-1-methyl-benzimidazol-2-one (7 mg, 52%, 0.015 mmol) as a white solid.

$^1$H NMR (600 MHz, Methanol-d$_4$) δ 8.15 (s, 1H), 7.47 (d, J=2.0 Hz, 1H), 7.32 (dd, J=8.4, 2.0 Hz, 1H), 7.17 (d, J=8.4 Hz, 1H), 4.75 (q, J=8.7 Hz, 2H), 4.14-3.85 (m, 2H), 3.45 (s, 3H), 2.01-1.70 (m, 2H), 1.30 (s, 6H).

LCMS (Method T4) Rt=2.86 mins, m/z 460.1375 [M+H]$^+$ expected 460.1358 for $C_{19}H_{22}ClF_3N_5O_3$.

Example 40a: 5-[[5-chloro-2-[(3S,5R)-4,4-difluoro-3,5-dimethyl-1-piperidyl]pyrimidin-4-yl]amino]-1-(2-hydroxyethyl)-3-(3-hydroxy-3-methyl-butyl)benzimidazol-2-one

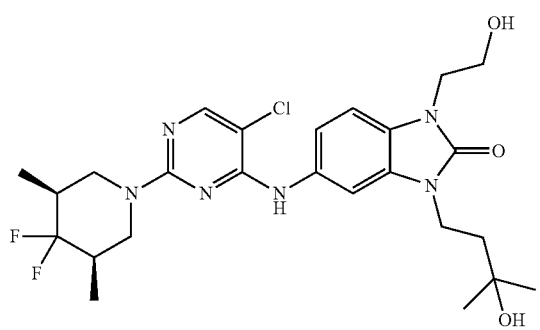 [SMILES: C[C@@H]1CN(c2ncc(Cl)c(Nc3ccc4c(c3)n(CCC(C)(C)O)c(=O)n4CCO)n2)C[C@H](C)C1(F)F]

To a solution of 2-[5-[[5-chloro-2-[(3S,5R)-4,4-difluoro-3,5-dimethyl-1-piperidyl]pyrimidin-4-yl]amino]-3-(3-hydroxy-3-methyl-butyl)-2-oxo-benzimidazol-1-yl]acetaldehyde (Intermediate H1, 20 mg, 0.034 mmol) in MeOH (1 mL) at rt was added sodium borohydride (3 mg, 0.07 mmol). The mixture was stirred for 2 h. The mixture was quenched by the dropwise addition of 2M aqueous HCl, then EtOAc was added, the layers were separated and the aqueous layer was extracted with further EtOAc. The combined organic layers were washed with brine, dried over MgSO4, filtered and concentrated under reduced pressure. Purification by preparative HPLC (ACE 5 C18-PFP column (5µ, 250×21.2 mm), 15 minute gradient elution from 60:40 to 0:100 water:methanol (both modified with 0.1% formic acid) at a flow rate of 20 mL/min) gave 5-[[5-chloro-2-[(3S,5R)-4,4-difluoro-3,5-dimethyl-1-piperidyl]pyrimidin-4-yl]amino]-1-(2-hydroxyethyl)-3-(3-hydroxy-3-methyl-butyl)benzimidazol-2-one (7 mg) as a white solid.

LCMS (Method X4): Rt 3.17 min, m/z 539.2350, expected 539.2349 for $C_{25}H_{34}ClF_2N_6O_3$ [M+H]$^+$.

$^1$H NMR (500 MHz, Methanol-d4): δ 7.94 (1H, s), 7.38 (1H, d, J 1.6 Hz), 7.35 (1H, dd, J 8.5, 1.6 Hz), 7.21 (1H, d, J 8.5 Hz), 4.54 (2H, br d, J 13.3 Hz), 4.08-3.99 (4H, m), 3.85 (2H, t, J 5.5 Hz), 2.70 (2H, t, J 12.6 Hz), 2.02-1.84 (4H m), 1.29 (6H, s), 1.01 (6H, d, J 6.6 Hz).

Example 41a: 5-((5-chloro-2-((3S,5R)-4,4-difluoro-3,5-dimethylpiperidin-1-yl)pyrimidin-4-yl)amino)-1-(2,2-dimethoxyethyl)-3-(3-hydroxy-3-methylbutyl)-1,3-dihydro-2H-benzo[d]imidazol-2-one

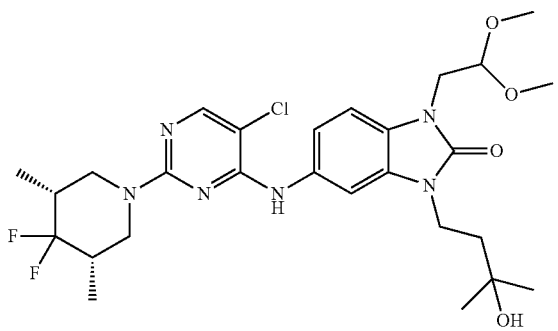 [SMILES: COC(Cn1c(=O)n(CCC(C)(C)O)c2cc(Nc3nc(N4C[C@@H](C)C(F)(F)[C@@H](C)C4)ncc3Cl)ccc21)OC]

Step 1:
N1-(2,2-dimethoxyethyl)-4-nitrobenzene-1,2-diamine

A mixture of 2-fluoro-5-nitroaniline (2.1 g, 13.5 mmol), aminoacetaldehyde dimethyl acetal (2.18 mL, 20.2 mmol) and DIPEA (4.7 mL, 26.9 mmol) in NMP (13.5 mL) was heated at 180° C. overnight. LCMS (Method T2) Rt=1.10 mins, m/z 242.11 [M+H]+. The mixture was allowed to cool to rt then poured into ice-water, then extracted with EtOAc. The combined organic extracts were thoroughly washed with water to remove NMP, then brine then dried over MgSO4. No further purification was performed.

Step 2: 1-(2,2-dimethoxyethyl)-5-nitro-1,3-dihydro-2H-benzo[d]imidazol-2-one

To a solution of N1-(2,2-dimethoxyethyl)-4-nitrobenzene-1,2-diamine (step 1, 3.25 g) in acetonitrile (110 mL) was added disuccinimidyl carbonate (10.3 g, 40.4 mmol) followed by triethylamine (7.5 mL, 54 mmol). The mixture was stirred at rt for 2 hours. The mixture was poured into ice-water, then concentrated in vacuo in order to remove the MeCN before extraction with EtOAc. The organic extracts were washed with brine, dried over MgSO4. The crude residue was purified by Biotage KP-Sil 340 g eluting 20-100% EtOAc in cyclohexane affording the title compound (0.77 g, 21%, 2.8888 mmol) as a pale yellow solid. 1H NMR (500 MHz, DMSO-d6) δ 11.49 (s, 1H), 8.00 (dd, J=8.8, 2.3 Hz, 1H), 7.76 (d, J=2.3 Hz, 1H), 7.37 (d, J=8.8 Hz, 1H), 4.65 (t, J=5.3 Hz, 1H), 3.96 (d, J=5.3 Hz, 2H), 3.29 (s, 6H).

Step 3: 1-(2,2-dimethoxyethyl)-3-(3-hydroxy-3-methybutyl)-5-nitro-1,3-dihydro-2H-benzo[d]imidazol-2-one A mixture of (3-hydroxy-3-methyl-butyl) 4-methylbenzenesulfonate (Intermediate C1a, 1.12 g, 4.3 mmol), cesium carbonate (1.88 g, 5.8 mmol), 3-(2,2-dimethoxyethyl)-6-nitro-1H-benzimidazol-2-one (step 2, 0.77 g, 2.88 mmol) and acetonitrile (14.4 mL) was refluxed for 1 hour. The mixture was concentrated in vacuo to remove MeCN. The residue was then diluted with water and extracted with EtOAc. The organic extracts were dried over MgSO4 and concentrated. The residue was then purified by Biotage KP-Sil 25 g eluting 40-80% EtOAc in cyclohexane affording 1-(2,2-dimethoxyethyl)-3-(3-hydroxy-3-methyl-butyl)-5-nitro-benzimidazol-2-one (1 g) as a yellow sticky oil which crystallised under vacuum. 1H NMR (500 MHz, Chloroform-d) δ 8.07 (dd, J=8.7, 2.2 Hz, 1H), 7.92 (d, J=2.2 Hz, 1H), 7.20 (d, J=8.7 Hz, 1H), 4.58 (t, J=5.2 Hz, 1H), 4.14-4.08 (m, 2H), 4.01 (d, J=5.1 Hz, 2H), 3.40 (s, 6H), 1.95-1.89 (m, 2H), 1.31 (s, 6H); LCMS (Method T2) Rt=1.34 mins, m/z 354.17 [M+H]+.

Step 4: 5-amino-1-(2,2-dimethoxyethyl)-3-(3-hydroxy-3-methybutyl)-1,3-dihydro-2H-benzo[d]imidazol-2-one Pd/C (10 wt %) (50 mg, 0.047 mmol) was added to a solution of 1-(2,2-dimethoxyethyl)-3-(3-hydroxy-3-methyl-butyl)-5-nitro-benzimidazol-2-one (step 3, 0.62 g, 1.77 mmol) in ethyl acetate (8.8 mL) then placed under an atmosphere of hydrogen and stirred at 60° C. overnight. The mixture was reintroduced to an atmosphere of nitrogen then filtered through a pad of Celite™ and washed through with ethyl acetate then concentrated in vacuo affording 5-amino-1-(2,2-dimethoxyethyl)-3-(3-hydroxy-3-methyl-butyl)benzimidazol-2-one (598 mg) as a pale brown oil with trace residual solvent present. LCMS (Method T2) Rt=0.74 mins, m/z 324.22 [M+H]+.

Step 5: 5-((5-choro-2-((3S,5R)-4,4-difluoro-3,5-dimethylpiperidin-1-yl)pyrimidin-4-yl)amino)-1-(2,2-dimethoxyethyl)-3-(3-hydroxy-3-methybutyl)-1,3-dihydro-2H-benzo[d]imidazol-2-one A mixture of 5-amino-1-(2,2-dimethoxyethyl)-3-(3-hydroxy-3-methyl-butyl)benzimidazol-2-one (step 4, 284 mg, 0.88 mmol), 2,4,5-trichloropyrimidine (0.24 g, 1.32 mmol), and DIPEA (0.38 mL, 2.2 mmol) in NMP (4.4 mL) was heated in the microwave for 1 h at 140° C. (3R,5S)-4,4-difluoro-3,5-dimethyl-piperidinehydrochloride (0.36 g, 1.93 mmol) was added to the mixture which was then further heated in the microwave for 2 h at 140° C. The resulting mixture was purified in 2 batches, using reverse-phase chromatography (30 g C18 column eluting from 10-100% MeOH in water (containing 0.1% formic acid)) affording the title compound (375 mg) as a yellow solid.
1H NMR (600 MHz, Chloroform-d) δ 7.98 (s, 1H), 7.32 (d, J=2.0 Hz, 1H), 7.20 (dd, J=8.4, 2.0 Hz, 1H), 7.10 (d, J=8.4 Hz, 1H), 7.00 (s, 1H), 4.63 (t, J=5.3 Hz, 1H), 4.61-4.55 (m, 2H), 4.05 (t, J=7.3 Hz, 2H), 3.98 (d, J=5.3 Hz, 2H), 3.41 (s, 6H), 2.73 (t, J=12.7 Hz, 2H), 2.02-1.86 (m, 4H), 1.29 (s, 6H), 1.05 (d, J=6.8 Hz, 6H), OH not observed; LCMS (Method X4) Rt=3.47 mins, m/z 583.2621 [M+H]1 expected 583.2611 for $C_{27}H_{38}ClF_2N_6O_4^+$.

The following tabulated examples were prepared by a method analogous to that used for the preparation of example 35a, using intermediate 2a (5-[(2,5-dichloropyrimidin-4-yl)amino]-3-(3-hydroxy-3-methyl-butyl)-1-methyl-benzimidazol-2-one) and the appropriate amine as free base or salt, obtained from commercial vendors or prepared by known methods.

TABLE 15B

Compounds prepared by a method analogous to that used for the preparation of Example 35a

| Example | Structure | Data |
| --- | --- | --- |
| Example 42a: 1-(5-chloro-4-((3-(3-hydroxy-3-methylbutyl)-1-methyl-2-oxo-2,3-dihydro-1H-benzo[d]imidazol-5-yl)amino)pyrimidin-2-yl)piperidine-4-carbonitrile | 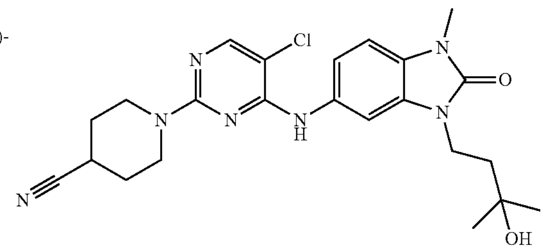 | LCMS (Method T4) Rt 2.53 min. m/z 470.2069 for $C_{23}H_{29}ClN_7O_2$ $[M + H]^+$ expected 470.2066 |
| Example 42b: 1-(5-chloro-4-((3-(3-hydroxy-3-methylbutyl)-1-methyl-2-oxo-2,3-dihydro-1H-benzo[d]imidazol-5-yl)amino)pyrimidin-2-yl)piperidine-3-carbonitrile | 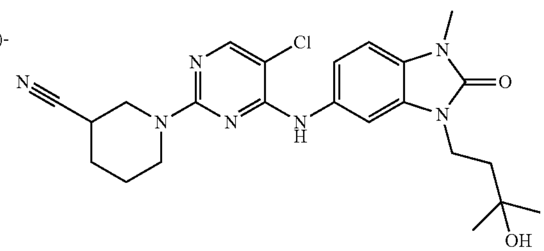 | LCMS (Method T4) Rt 2.56 min. m/z 492.1867 for $C_{23}H_{28}ClN_7O_2Na$ $[M + Na]^+$ expected 492.1885 |
| Example 42c: 5-((5-chloro-2-(4-(morpholinomethyl)piperidin-1-yl)pyrimidin-4-yl)amino)-3-(3-hydroxy-3-methylbutyl)-1-methyl-1,3-dihydro-2H-benzo[d]imidazol-2-one | 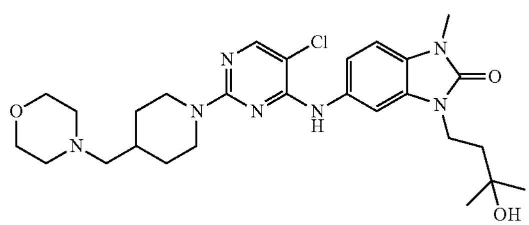 [SMILES: Cn1c(=O)n(CCC(C)(C)O)c2cc(Nc3nc(N4CCC(CN5CCOCC5)CC4)ncc3Cl)ccc21] | LCMS (Method T4) Rt 1.96 min. m/z 544.2852 for $C_{27}H_{39}ClN_7O_3$ $[M + H]^+$ expected 544.2803 |
| Example 42d: 5-((5-chloro-2-(3-(morpholinomethyl)piperidin-1-yl)pyrimidin-4-yl)amino)-3-(3-hydroxy-3-methylbutyl)-1-methyl-1,3-dihydro-2H-benzo[d]imidazol-2-one | 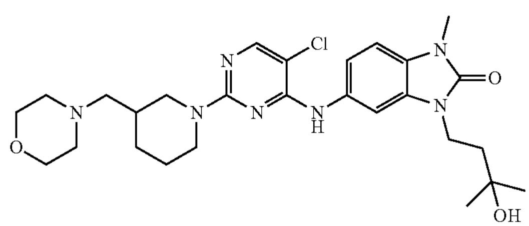 [SMILES: Cn1c(=O)n(CCC(C)(C)O)c2cc(Nc3nc(N4CCCC(CN5CCOCC5)C4)ncc3Cl)ccc21] | LCMS (Method T4) Rt 2.11 min. m/z 544.2818 for $C_{27}H_{39}ClN_7O_3$ $[M + H]^+$ expected 544.2803 |
| Example 42e: 5-((5-chloro-2-(2-methyl-2,4,5,7-tetrahydro-6H-pyrazolo[3,4-c]pyridin-6-yl)pyrimidin-4-yl)amino)-3-(3-hydroxy-3-methylbutyl)-1-methyl-1,3-dihydro-2H-benzo[d]imidazol-2-one | 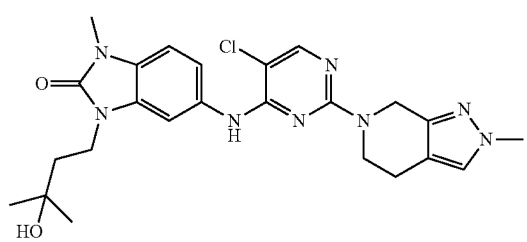 [SMILES: Cn1cc2c(n1)CN(c1ncc(Cl)c(Nc3ccc4c(c3)n(CCC(C)(C)O)c(=O)n4C)n1)CC2] | LCMS (Method X4) Rt 2.49 min. m/z 497.2186 for $C_{24}H_{30}ClN_8O_2$ $[M + H]^+$ expected 497.218 |
| Example 42f: 5-((5-chloro-2-(1-methyl-1,4,5,7-tetrahydro-6H-pyrazolo[3,4-c]pyridin-6-yl)pyrimidin-4-yl)amino)-3-(3-hydroxy-3-methylbutyl)-1-methyl-1,3-dihydro-2H-benzo[d]imidazol-2-one | 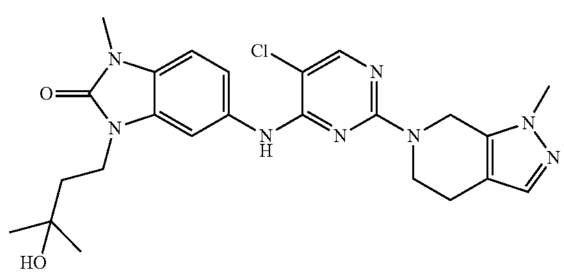 [SMILES: Cn1ncc2c1CN(c1ncc(Cl)c(Nc3ccc4c(c3)n(CCC(C)(C)O)c(=O)n4C)n1)CC2] | LCMS (Method X4) Rt 2.49 min. m/z 497.2183 for $C_{24}H_{30}ClN_8O_2$ $[M + H]^+$ expected 497.218 |

TABLE 15B-continued

Compounds prepared by a method analogous to that used for the preparation of Example 35a

| Example | Structure | Data |
|---|---|---|
| Example 42g: 5-((5-chloro-2-(3-(hydroxymethyl)piperidin-1-yl)pyrimidin-4-yl)amino)-3-(3-hydroxy-3-methylbutyl)-1-methyl-1,3-dihydro-2H-benzo[d]imidazol-2-one | 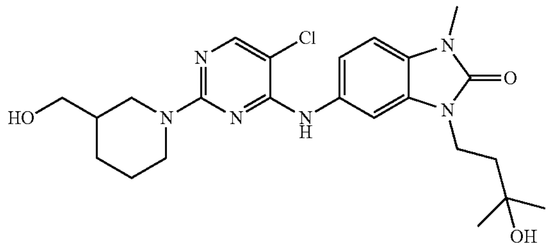 | LCMS (Method X4) Rt 2.11 min. m/z 475.2224 for $C_{23}H_{32}ClN_6O_3$ $[M + H]^+$ expected 475.2224 |
| Example 42h: 5-((5-chloro-2-(4-morpholinopiperidin-1-yl)pyrimidin-4-yl)amino)-3-(3-hydroxy-3-methylbutyl)-1-methyl-1,3-dihydro-2H-benzo[d]imidazol-2-one | 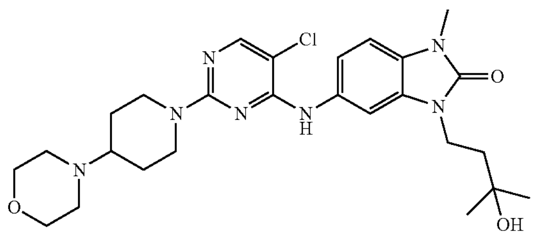 [SMILES: Cn1c(=O)n(CCC(C)(C)O)c2cc(Nc3nc(N4CCC(N5CCOCC5)CC4)ncc3Cl)ccc21] | LCMS (Method X4) Rt 1.88 min. m/z 530.265 for $C_{26}H_{37}ClN_7O_3$ $[M + H]^+$ expected 530.2646 |
| Example 42i: 5-((2-(4-(1H-pyrazol-1-yl)piperidin-1-yl)-5-chloropyrimidin-4-yl)amino)-3-(3-hydroxy-3-methylbutyl)-1-methyl-1,3-dihydro-2H-benzo[d]imidazol-2-one | 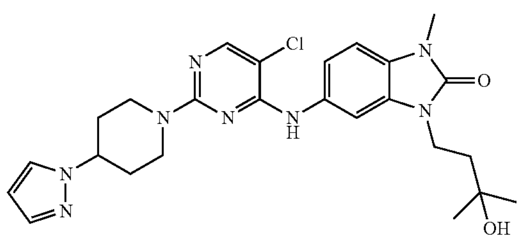 [SMILES: Cn1c(=O)n(CCC(C)(C)O)c2cc(Nc3nc(N4CCC(n5cccn5)CC4)ncc3Cl)ccc21] | LCMS (Method X4) Rt 2.48 min. m/z 511.2339 for $C_{25}H_{32}ClN_8O_2$ $[M + H]^+$ expected 511.2337 |
| Example 42j: 5-((5-chloro-2-(2-(hydroxymethyl)morpholino)pyrimidin-4-yl)amino)-3-(3-hydroxy-3-methylbutyl)-1-methyl-1,3-dihydro-2H-benzo[d]imidazol-2-one | 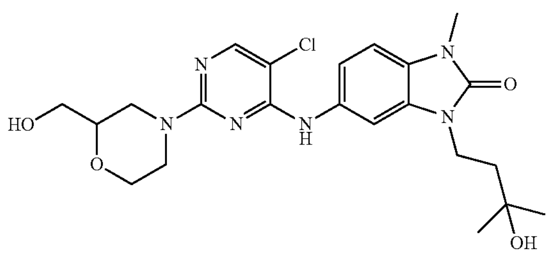 [SMILES: Cn1c(=O)n(CCC(C)(C)O)c2cc(Nc3nc(N4CCOC(CO)C4)ncc3Cl)ccc21] | LCMS (Method X4) Rt 2.25 min. m/z 477.2011 for $C_{22}H_{30}ClN_6O_4$ $[M + H]^+$ expected 477.2017 |

Intermediates Used in the Preparation of Examples

Intermediate A1: 5-amino-3-(3-hydroxy-3-methyl-butyl)-1-methyl-benzimidazol-2-one

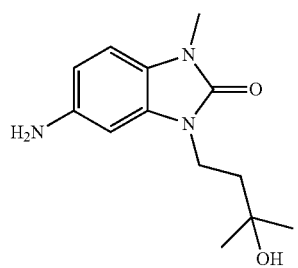 [SMILES: Cn1c(=O)n(CCC(C)(C)O)c2cc(N)ccc21]

Palladium on activated charcoal (10% Pd, 28 mg, 0.27 mmol) was added to a stirring mixture of ammonium formate (4.0 g, 63.4 mmol) and 3-(3-hydroxy-3-methyl-butyl)-1-methyl-5-nitro-benzimidazol-2-one (intermediate B1a, 2.53 g, 9.1 mmol) in ethanol (20 mL) under an argon atmosphere. The resulting mixture was heated to 60° C. for 45 minutes, then allowed to cool to room temperature and filtered (under argon) through a pad of Celite™, washing with further ethanol (60 mL). The resulting solution was evaporated under reduced pressure. Et$_2$O:EtOAc (1:1) was added and the resulting precipitate was removed by filtration. The solvent was evaporated under reduced pressure, affording the title compound (2.15 g) as yellow foam. $^1$H NMR (500 MHz, Methanol-d$_4$): δ 6.90 (1H, d, J, 8.1 Hz), 6.63 (1H, d, J 1.9 Hz), 6.58 (1H, dd, J 8.1, 1.9 Hz), 3.95 (2H, m), 3.36 (3H, s), 1.84 (2H, m), 1.29 (6H, s). LCMS (Method T2) Rt 0.18 min; m/z 250.1543 [M+H]$^+$.

Intermediate A2: 5-Amino-1-methyl-3-[(3S)-3-pyrazol-1-ylbutyl]benzimidazol-2-one

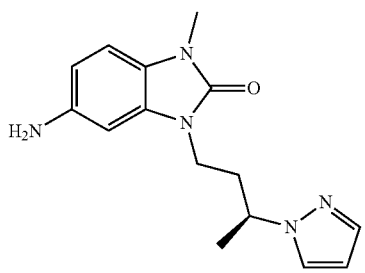 [SMILES: C[C@@H](CCn1c(=O)n(C)c2ccc(N)cc21)n1cccn1]

1-methyl-5-nitro-3-[(3S)-3-pyrazol-1-ylbutyl]benzimidazol-2-one (Intermediate B2, 15 mg, 0.048 mmol) in ethanol (0.5 mL) was added dropwise to an oven dried sealed vial charged with Pd/C (10 wt %) (2 mg) and ammonium formate (30 mg, 0.48 mmol) under a nitrogen atmosphere. The resulting mixture was heated to 60° C. for 60 min then allowed to cool, and passed through a pad of Celite™ and a PL-HCO$_3$ column (200 mg), washing with further ethanol (12 mL), then evaporated under reduced pressure. The mixture was re-dissolved in DCM, and washed with sat. aq sodium bicarbonate to ensure all formic acid removed. Following evaporation, material was used without further purification. LCMS (Method T2) Rt 0.58 min; m/z 286.17 [M+H]$^+$.

Intermediate A3a: Methyl 4-(6-amino-3-methyl-2-oxo-benzimidazol-1-yl)-2-methyl-butanoate

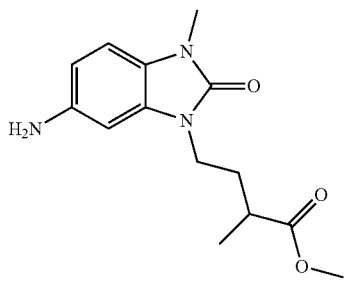 [SMILES: COC(=O)C(C)CCn1c(=O)n(C)c2ccc(N)cc21]

A mixture of methyl 2-methyl-4-(3-methyl-6-nitro-2-oxo-benzimidazol-1-yl)butanoate (Intermediate B3a, 309 mg, 1.0 mmol), ammonium formate (379 mg, 6.0 mmol) and 10 wt % Pd/C (29 mg, 0.03 mmol) in methanol (10 mL) under argon was heated at 100° C. under microwave irradiation for 90 min. The crude reaction mixture was filtered through Celite™ and the precipitate washed with methanol (120 mL). The filtrate was concentrated in vacuo to give the title compound (275 mg) as a brown solid which was used without further purification. $^1$H NMR (500 MHz, Methanol-d$_4$) δ 6.89 (d, J=8.3 Hz, 1H), 6.61 (d, J=2.0 Hz, 1H), 6.57 (dd, J=8.3, 2.0 Hz, 1H), 3.93-3.82 (m, 2H), 3.58 (s, 3H), 3.35 (s, 3H), 2.55-2.47 (m, 1H), 2.16-2.07 (m, 1H), 1.85-1.76 (m, 1H), 1.21 (d, J=7.1 Hz, 3H).

Intermediate A3b: Methyl 3-(6-amino-3-methyl-2-oxo-benzimidazol-1-yl)-2-methyl-propanoate

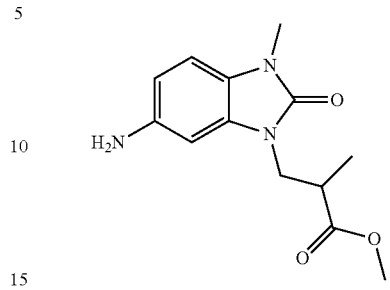

Prepared by a method analogous to that used for the preparation of Intermediate A3a, with additional heating at 120° C. for 45 min, using methyl 2-methyl-3-(3-methyl-6-nitro-2-oxo-benzimidazol-1-yl)propanoate (Intermediate B3b). $^1$H NMR (500 MHz, Methanol-d$_4$) δ 6.89 (d, J=8.2 Hz, 1H), 6.60 (d, J=2.0 Hz, 1H), 6.57 (dd, J=8.2, 2.0 Hz, 1H), 4.06 (dd, J=14.4, 7.9 Hz, 1H), 3.91 (dd, J=14.4, 6.8 Hz, 1H), 3.59 (s, 3H), 3.34 (s, 3H), 3.05-2.97 (m, 1H), 1.18 (d, J=7.1 Hz, 3H).

Intermediate A3c: 5-Amino-3-[(3R)-3-hydroxybutyl]-1-methyl-benzimidazol-2-one

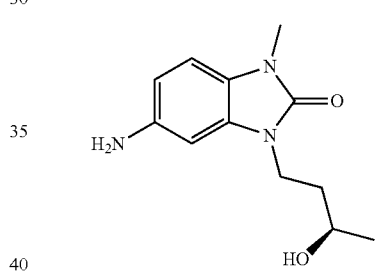

Prepared by a method analogous to that used for the preparation of Intermediate A3a, using Intermediate B1b 3-[(3R)-3-hydroxybutyl]-1-methyl-5-nitro-benzimidazol-2-one and ethanol as solvent. LCMS (Method X2) Rt 0.47 min: m/z 258.12 [M+Na]$^+$.

Intermediate A4a: 5-Amino-3-(3-hydroxy-3-methylbutyl)-1-(tetrahydropyran-4-ylmethyl)benzimidazol-2-one

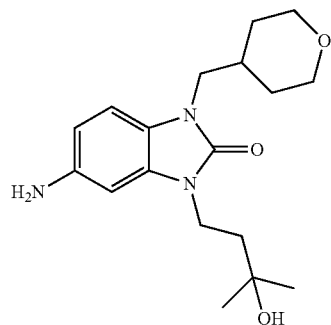 [SMILES: CC(C)(O)CCn1c(=O)n(CC2CCOCC2)c2ccc(N)cc21]

3-(3-Hydroxy-3-methyl-butyl)-5-nitro-1-(tetrahydropyran-4-ylmethyl)benzimidazol-2-one (Intermediate B7, 50 mg, 0.14 mmol) in ethanol (3 mL) was added dropwise to an oven dried sealed vial charged with Pd/C (10 wt %) (3.7 mg, 0.0035 mmol) and ammonium formate (40 mg, 0.63 mmol) under an argon atmosphere. The resulting mixture was evacuated and refilled with argon three times, then heated to 60° C. for 30 min. Cooled to room temperature, filtered through Celite™ washing with further ethanol into a flask containing MP-carbonate resin (100 mg). After 10 mins standing, decanted liquid to remove resin and evaporated under reduced pressure to give title compound (42 mg) as a clear oil which turned slowly brown on standing. LCMS (Method X2) Rt 0.70 min; m/z 334.21.

Intermediate A4b: N-[3-(6-amino-3-methyl-2-oxo-benzimidazol-1-yl)-1,1-dimethyl-propyl]acetamide
N5041-91 bbellenie

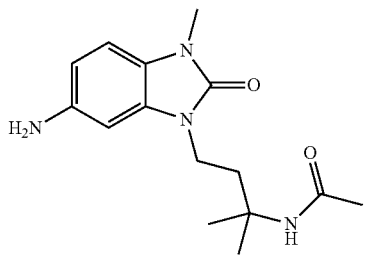 [SMILES: CC(=O)NC(C)(C)CCn1c(=O)n(C)c2ccc(N)cc21]

Prepared from N-[1,1-dimethyl-3-(3-methyl-6-nitro-2-oxo-benzimidazol-1-yl)propyl]acetamide (Intermediate E11) using a method analogous to that used for the preparation of Intermediate A4a, heating at 70° C. for 20 minutes. LCMS (Method X2) Rt 0.63 min: m/z 291.18.

Intermediate A5: 5-Amino-3-(2-hydroxybutyl)-1-methyl-1H-benzo[d]imidazol-2(3H)-one

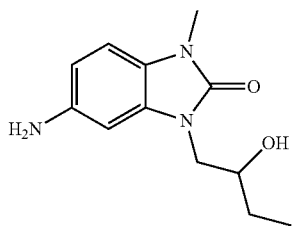 [SMILES: CCC(O)Cn1c(=O)n(C)c2ccc(N)cc21]

To a solution of 3-(2-hydroxybutyl)-1-methyl-5-nitro-1H-benzo[d]imidazol-2(3H)-one (Intermediate B5, 100 mg, 0.38 mmol) in ethanol (10 mL) was added Pd/C (2 mg) and the resulting mixture stirred under a hydrogen atmosphere for 3 h, then filtered through Celite™ and concentrated under reduced pressure to give the title compound (76 mg). $^1$H NMR (500 MHz, Methanol-d4) δ 6.90 (d, J=8.5 Hz, 1H), 6.67 (d, J=2.1 Hz, 1H), 6.58 (dd, J=8.5, 2.1 Hz, 1H), 3.87-3.76 (m, 3H), 3.37 (s, 3H), 1.59 (m, 1H), 1.47 (m, 1H), 1.02 (t, J=7.6 Hz, 3H).

Intermediate A6a: 6-amino-5-fluoro-1-(3-hydroxy-3-methyl-butyl)-3-methyl-benzimidazol-2-one

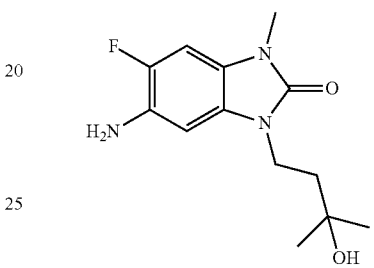

To a suspension of 5-fluoro-1-(3-hydroxy-3-methyl-butyl)-3-methyl-6-nitro-benzimidazol-2-one (intermediate B10, 115 mg, 0.39 mmol) in ethanol (2 mL) degassed and placed under nitrogen was added Pd/C (10 wt %) (14 mg, 0.013 mmol). Nitrogen was replaced with hydrogen and the resulting mixture stirred under a $H_2$ atmosphere for 5 hours. The hydrogen atmosphere was replaced with nitrogen, and the suspension was filtered through Celite™ washing with EtOAc and MeOH. The solvent was evaporated under reduced pressure affording the title compound (85 mg) as a foam. LCMS (Method T2) Rt 0.89 min, m/z 268 [M+H]$^+$ The following tabulated intermediates were prepared by a method analogous to that used for the preparation of intermediate A6a, using the nitro intermediates shown in Table 16. For intermediate A6i a short reaction time of 35 minutes was used to avoid reduction of chloro group.

TABLE 16

Compounds prepared by a method analogous to that used for the preparation of Intermediate A6a

| Product | Data | Intermediates |
|---|---|---|
| Intermediate A6b: 5-[(6-amino-3-methyl-2-oxo-benzimidazol-1-yl)methyl]-5-ethyl-3-methyl-oxazolidin-2-one | LCMS (Method T2) Rt 0.22 min, m/z 305.16 [M + H]$^+$ | Intermediate B9b: 5-ethyl-3-methyl-5-[(3-methyl-6-nitro-2-oxo-benzimidazol-1-yl)methyl]oxazolidin-2-one |

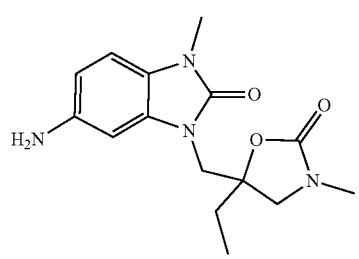 [SMILES: CCC1(Cn2c(=O)n(C)c3ccc(N)cc32)CN(C)C(=O)O1]

TABLE 16-continued

Compounds prepared by a method analogous to that used for the preparation of Intermediate A6a

| Product | Data | Intermediates |
| --- | --- | --- |
| Intermediate A6c: 5-[(6-amino-3-methyl-2-oxo-benzimidazol-1-yl)methyl]-5-ethyl-oxazolidin-2-one | LCMS (Method T2) Rt 0.16 min, m/z 291.14 [M + H]$^+$ | Intermediate B9a: 5-ethyl-5-[(3-methyl-6-nitro-2-oxo-benzimidazol-1-yl)methyl]oxazolidin-2-one |
| Intermediate A6d: 5-[(6-amino-3-methyl-2-oxo-benzimidazol-1-yl)methyl]-3,5-dimethyl-oxazolidin-2-one | LCMS (Method T2) Rt 0.16 min, m/z 291.15 [M + H]$^+$ | Intermediate B9c: 3,5-dimethyl-5-[(3-methyl-6-nitro-2-oxo-benzimidazol-1-yl)methyl]oxazolidin-2-one |
| Intermediate A6e: 5-((6-amino-3-methyl-2-oxo-2,3-dihydro-1H-benzo[d]imidazol-1-yl)methyl)-5-(2-hydroxypropan-2-yl)-3-methyloxazolidin-2-one | LCMS (Method T2) Rt 0.19 min, m/z 335.17 [M + H]$^+$ | Intermediate B9d: 5-(2-hydroxypropan-2-yl)-3-methyl-5-((3-methyl-6-nitro-2-oxo-2,3-dihydro-1H-benzo[d]imidazol-1-yl)methyl)oxazolidin-2-one |
| Intermediate A6f: (S)-5-amino-1-methyl-3-((1-(2,2,2-trifluoroethyl)pyrrolidin-2-yl)methyl)-1,3-dihydro-2H-benzo[d]imidazol-2-one | LCMS (Method X2) Rt 0.81 min; m/z 329.1590 expected 329.1589 for C$_{15}$H$_{20}$N$_4$OF$_3$ [M + H]$^+$ | Intermediate B12: (S)-1-methyl-5-nitro-3-((1-(2,2,2-trifluoroethyl)pyrrolidin-2-yl)methyl)-1,3-dihydro-2H-benzo[d]imidazol-2-one |

TABLE 16-continued

Compounds prepared by a method analogous to that used for the preparation of Intermediate A6a

| Product | Data | Intermediates |
| --- | --- | --- |
| Intermediate A6g: 5-amino-1,3-bis(3-hydroxy-3-methylbutyl)-1,3-dihydro-2H-benzo[d]imidazol-2-one | LCMS (Method X2) Rt 0.76 min; m/z 344.1939 expcted 344.1950 for $C_{17}H_{27}N_3O_3Na$ [M + Na]$^+$. | Intermediate B13A: 1,3-bis(3-hydroxy-3-methylbutyl)-5-nitro-1,3-dihydro-2H-benzo[d]imidazol-2-one |
| Intermediate A6h: 6-amino-1,3-bis(3-hydroxy-3-methylbutyl)-1,3-dihydro-2H-imidazo[4,5-b]pyridin-2-one | LCMS (Method X2) Rt 0.83 min; m/z 345.1910 expected 345.1903 for $C_{16}H_{26}N_4O_3Na$ [M + Na]$^+$. | Intermediate B13b: 1,3-bis(3-hydroxy-3-methylbutyl)-6-nitro-1,3-dihydro-2H-imidazo[4,5-b]pyridin-2-one N5127-38 |
| Intermediate A6i: 6-amino-4-chloro-1,3-bis(3-hydroxy-3-methylbutyl)-1,3-dihydro-2H-benzo[d]imidazol-2-one | LCMS (Method X2) Rt 1.03 min; m/z 378.1557 expected 378.1560 for $C_{17}H_{26}ClN_3O_3Na$ [M + Na]$^+$. | Intermediate B13c: 4-chloro-1,3-bis(3-hydroxy-3-methyl-butyl)-6-nitro-benzimidazol-2-one N5127-27 |

Intermediate A7a: 5-amino-3-(3-hydroxy-3-methyl-pentyl)-1-methyl-benzimidazol-2-one

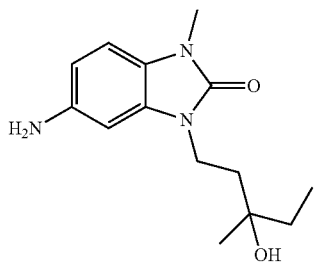 [SMILES: CCC(C)(O)CCn1c(=O)n(C)c2ccc(N)cc21]

Palladium on activated charcoal (10% wt Pd, 39 mg, 0.04 mmol) was added to a stirring mixture of ammonium formate (534 mg, 8.47 mmol) and 3-(3-hydroxy-3-methyl-pentyl)-1-methyl-5-nitro-benzimidazol-2-one (intermediate B1d, 355 mg, 1.21 mmol) in ethanol (20 mL) under an Ar atmosphere. The resulting mixture was heated to 60 C for 45 minutes, then allowed to cool to room temperature and filtered (under argon) through a pad of Celite™, washing with further ethanol (60 mL). The resulting solution was evaporated under reduced pressure to give a yellow oil. Et$_2$O:EtOAc (1:1) was added, the resulting precipitate was removed by filtration and the solvent was evaporated to give the title compound (314 mg) as a foam. LCMS (Method T2): Rt 0.51 min, m/z 264.17 [M+H]$^+$. The following tabulated intermediates were prepared by a method analogous to that used for the preparation of intermediate A7a, using the nitro intermediates shown in Table 17.

TABLE 17

Compounds prepared by a method analogous to that used for the preparation of Intermediate A7a

| Product | Data | Intermediates |
|---|---|---|
| Intermediate A7b: 5-amino-3-(3-hydroxy-4-methoxy-3-methyl-butyl)-1-methyl-benzimidazol-2-one | LCMS (Method T2) Rt 0.31 m/z 280.17 [M + H]$^+$ | Intermediate B1e: 3-(3-hydroxy-4-methoxy-3-methyl-butyl)-1-methyl-5-nitro-benzimidazol-2-one |
| Intermediate A7c: 5-amino-1-methyl-3-[2-(4-methyl-2-phenyl-1,3-dioxan-4-yl)ethyl]benzimidazol-2-one | LCMS (Method T2) Rt 1.05 min, m/z 368.19 [M + H]$^+$ | Intermediate B1c: 1-methyl-3-[2-(4-methyl-2-phenyl-1,3-dioxan-4-yl)ethyl]-5-nitro-benzimidazol-2-one |

TABLE 17-continued

Compounds prepared by a method analogous to that used for the preparation of Intermediate A7a

| Product | Data | Intermediates |
| --- | --- | --- |
| Intermediate A7d: 5-amino-3-[[(3R)-3-methoxybutyl]-1-methyl-benzimidazol-2-one 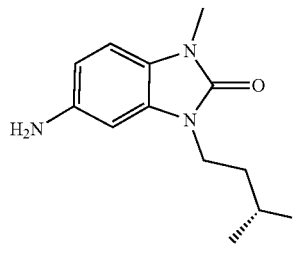 | LCMS (Method X2) Rt 0.59 min; m/z 250.16 [M + H]$^+$. | Intermediate B6: 3-[(3R)-3-methoxybutyl]-1-methyl-5-nitro-benzimidazol-2-one |

Intermediate A8a: 5-amino-3-[[(1S,2S)-2-hydroxy-2-methyl-cyclopentyl]methyl]-1-methyl-benzimidazol-2-one

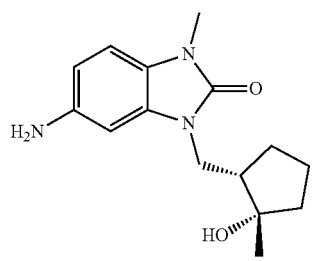 [SMILES: Cn1c(=O)n(C[C@@H]2CCC[C@]2(C)O)c2cc(N)ccc21]

Step 1: 2-[[tert-butyl(dimethyl)silyl]oxymethyl]cyclopent-2-en-1-one

To a solution of 2-(hydroxymethyl)cyclopent-2-en-1-one (0.5 g, 4.5 mmol) in DCM (45 mL) cooled to 0° C. was added TBSCl (0.94 g, 6.2 mmol) followed by Imidazole (0.67 g, 9.8 mmol). The solution immediately became cloudy and was allowed to stir with warming to rt overnight. TLC analysis indicated full conversion. The mixture was washed with 10% aq. citric acid and brine. The organic extracts were dried over MgSO$_4$, filtered and concentrated. The residue was purified by Biotage KP-Sil 25 g eluting 5-30% EtOAc in cyclohexane. 2-[[tert-butyl(dimethyl)silyl]oxymethyl]cyclopent-2-en-1-one (1 g) was obtained as a colourless oil. $^1$H NMR (500 MHz, Chloroform-d) δ 7.53-7.50 (m, 1H), 4.36-4.34 (m, 2H), 2.62-2.57 (m, 2H), 2.44-2.41 (m, 2H), 0.90 (s, 9H), 0.06 (s, 6H).

Step 2: 2-[[tert-butyl(dimethyl)silyl]oxymethyl]cyclopentanone

A vessel containing Pd/C (10 wt %) (0.24 g, 0.22 mmol) and a stirrer bar was placed under vacuum and gently heated. The vessel was then refilled with argon. A solution of 2-[[tert-butyl(dimethyl)silyl]oxymethyl]cyclopent-2-en-1-one (step 1, 1 g, 4.4 mmol) in EtOAc (20 mL) was added then was stirred under an atmosphere of hydrogen for 1 hour at 25° C. An aliquot was then taken, filtered and concentrated in vacuo. $^1$H NMR analysis of the crude mixture showed complete conversion. The rest of the mixture was resubmitted to a nitrogen atmosphere then filtered through a pad of Celite™ and washed through with EtOAc. The filtrate was concentrated in vacuo affording 2-[[tert-butyl(dimethyl)silyl]oxymethyl]cyclopentanone (0.99 g) as a colourless oil. $^1$H NMR (500 MHz, Chloroform-d) δ 3.84 (dd, J=9.9, 4.9 Hz, 1H), 3.72 (dd, J=9.9, 3.4 Hz, 1H), 2.31-1.89 (m, 6H), 1.85-1.70 (m, 1H), 0.85 (s, 9H), 0.02 (s, 3H), 0.01 (s, 3H).

Step 3: (1R,2R)-2-[[tert-butyl(dimethyl)silyl]oxymethyl]-1-methyl-cyclopentanol

A solution of 2-[[tert-butyl(dimethyl)silyl]oxymethyl]cyclopentanone (0.5 g, 2.2 mmol) in diethyl ether (11 mL) was cooled to 0° C. Methylmagnesium bromide (0.44 mL, 3M solution in diethyl ether) was added and the solution allowed to warm to rt. After stirring for 2 hours a further addition of Methylmagnesium bromide (1 mL, 3M) was made. After stirring for an additional 1 hour the mixture was quenched by careful and slow addition of water. The mixture was extracted with DCM and the organic extracts washed with brine then dried over MgSO$_4$. The solvent was removed under vacuum and the crude residue purified using a Biotage KP-Sil 25 g eluting 1-10% EtOAc in cyclohexane. (1R,2R)-2-[[tert-butyl(dimethyl)silyl]oxymethyl]-1-methyl-cyclopentanol (150 mg) was obtained as a mixture of diastereomers, ~3.5:1 in favour of R/R diastereomer. A small sample was repurified as above in order to obtain characterisation data.

(1S,2S)-2-[[tert-butyl(dimethyl)silyl]oxymethyl]-1-methyl-cyclopentanol: $^1$H NMR (500 MHz, Chloroform-d) δ 3.93-3.88 (m, 1H), 3.77-3.72 (m, 1H), 3.56 (s, 1H), 1.79-1.64 (m, 5H), 1.61-1.49 (m, 2H), 1.32 (s, 3H), 0.89 (s, 9H), 0.07 (s, 3H), 0.06 (s, 3H).

(1R,2S)-2-[[tert-butyl(dimethyl)silyl]oxymethyl]-1-methyl-cyclopentanol: 1H NMR (500 MHz, Chloroform-d) δ 3.73 (dd, J=10.0, 5.4 Hz, 1H), 3.57 (app. t, J=10.0 Hz, 1H), 2.62 (br. s, 1H), 2.13-2.02 (m, 1H), 1.81-1.62 (m, 4H), 1.61-1.49 (m, 1H), 1.21 (s, 3H), 1.19-1.10 (m, 1H), 0.89 (s, 9H), 0.07 (s, 3H), 0.06 (s, 3H).

Step 4: (1S,2S)-2-(hydroxymethyl)-1-methyl-cyclopentanol

To a solution of (1S,2S)-2-[[tert-butyl(dimethyl)silyl]oxymethyl]-1-methyl-cyclopentanol (3.5:1 mixture of diastereomers, 150 mg, 0.61 mmol) in THF (6.1 mL) under argon and cooled to 0° C. was added TBAF (1.0 M in THF, 1.84 mL, 1.84 mmol) dropwise. The solution was allowed to warm to rt and stirred for 2 hours. The reaction was quenched with sat. aq. NH$_4$Cl (10 mL) and extracted with EtOAc. The combined organic extracts were dried over MgSO$_4$ and concentrated in vacuo. The residue was purified by column chromatography (Biotage KP-Sil 10 g eluting 20-80% EtOAc in cyclohexane) affording (1S,2S)-2-(hydroxymethyl)-1-methyl-cyclopentanol (52 mg) as a single diastereoisomer, as a colourless oil. $^1$H NMR (500 MHz, Chloroform-d) δ 3.90-3.84 (m, 1H), 3.76-3.69 (m, 1H), 2.92 (s, 1H), 2.44 (s, 1H), 1.81-1.63 (m, 6H), 1.62-1.51 (m, 1H), 1.36 (s, 3H).

Step 5: [(1S,2S)-2-hydroxy-2-methyl-cyclopentyl]methyl 4-methylbenzenesulfonate

A mixture of (1S,2S)-2-(hydroxymethyl)-1-methyl-cyclopentanol (54 mg, 0.41 mmol), p-toluene-sulfonyl-chloride (0.12 g, 0.62 mmol), in pyridine (3 mL) was stirred at 0° C. for 2 hours. A further addition of p-toluene-sulfonyl-chloride (80 mg) was made and the solution stirred for a further 1 hour. The reaction mixture was poured into 5% aq. HCl then extracted with DCM. Combined organic phase was washed with HCl, brine, dried over MgSO$_4$ and concentrated. The residue was purified by column chromatography (Biotage KP-Sil 10 g eluting 20-50% EtOAc in cyclohexane) affording [(1S,2S)-2-hydroxy-2-methyl-cyclopentyl]methyl 4-methylbenzenesulfonate (85 mg) as a colourless oil. $^1$H NMR (500 MHz, Chloroform-d) δ 7.81-7.74 (m, 2H), 7.36-7.30 (m, 2H), 4.24 (dd, J=9.8, 7.2 Hz, 1H), 3.98 (dd, J=9.8, 6.8 Hz, 1H), 2.43 (s, 3H), 2.00-1.90 (m, 1H), 1.84-1.74 (m, 1H), 1.77-1.64 (m, 3H), 1.59-1.48 (m, 1H), 1.46 (s, 1H), 1.45-1.33 (m, 1H), 1.32 (s, 3H).

Step 6: 3-[[(1S,2S)-2-hydroxy-2-methyl-cyclopentyl]methyl]-1-methyl-5-nitro-benzimidazol-2-one A mixture of [(1S,2S)-2-hydroxy-2-methyl-cyclopentyl]methyl 4-methylbenzenesulfonate (85 mg, 0.30 mmol), 1-methyl-5-nitro-1,3-dihydro-2H-benzo[d]imidazol-2-one (45 mg, 0.23 mmol), cesium carbonate (0.19 g, 0.58 mmol) and acetonitrile (2.3 mL) was heated to 80° C. for 2 h in the microwave. The mixture was diluted with water and extracted with DCM and the combined organic extracts were concentrated. The residue (dissolved in 1 mL DMSO) was purified using reverse-phase C18 column eluting from 10-100% methanol in water (each containing 0.1% formic acid). The first eluting compound, 3-[[(1S,2S)-2-hydroxy-2-methyl-cyclopentyl]methyl]-1-methyl-5-nitro-benzimidazol-2-one (18 mg) was obtained as a yellow oil. $^1$H NMR (500 MHz, Chloroform-d) δ 8.14 (dd, J=8.6, 2.2 Hz, 1H), 7.97 (d, J=2.2 Hz, 1H), 7.08 (d, J=8.6 Hz, 1H), 4.22 (dd, J=14.9, 9.1 Hz, 1H), 3.92 (dd, J=14.9, 5.6 Hz, 1H), 3.52 (s, 3H), 2.20-2.09 (m, 1H), 1.94-1.79 (m, 3H), 1.76-1.54 (m, 3H), 1.13 (s, 3H).

Step 7: 5-amino-3-[[(1S,2S)-2-hydroxy-2-methyl-cyclopentyl]methyl]-1-methyl-benzimidazol-2-one To a solution of 3-[[(1S,2S)-2-hydroxy-2-methyl-cyclopentyl]methyl]-1-methyl-5-nitro-benzimidazol-2-one (18 mg, 0.06 mmol) in Ethanol (1.5 mL) was added ammonium formate (37 mg, 0.59 mmol) and Pd/C (10 wt %) (10 mg, 0.0094 mmol). The vial was sealed and evacuated then refilled with argon three times. The vial was then placed into a drysyn block preheated to 60° C. and stirred for 1 hour. Once cooled, the mixture was purified using a 2 g SCX column affording 5-amino-3-[[(1S,2S)-2-hydroxy-2-methyl-cyclopentyl]methyl]-1-methyl-benzimidazol-2-one (Intermediate A8a, 16 mg) as a pale orange solid. LCMS (Method T2) Rt 0.80 min; m/z 276.1698 [M+H]$^+$.

Intermediate A8b: 5-amino-3-(((1S,2S)-2-ethyl-2-hydroxycyclopentyl)methyl)-1-methyl-1,3-dihydro-2H-benzo[d]imidazol-2-one

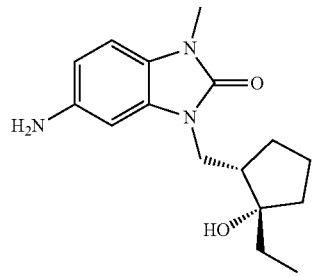 [SMILES: CC[C@]1(O)CCC[C@H]1Cn1c(=O)n(C)c2ccc(N)cc21]

Prepared by an analogous method to that used in the preparation of Intermediate A8a. LCMS (Method T2) Rt 0.93 min: m/z 290.1832 [M+H]$^+$.

Intermediate B1a: 3-(3-Hydroxy-3-methyl-butyl)-1-methyl-5-nitro-benzimidazol-2-one

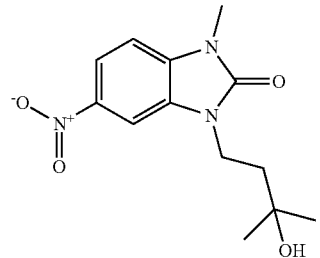

To a mixture of 3-methyl-6-nitro-1H-benzimidazol-2-one (2.50 g, 12.94 mmol) and cesium carbonate (11.4 g, 35.10 mmol) in acetonitrile (20 mL) was added a solution of (3-hydroxy-3-methyl-butyl) 4-methylbenzenesulfonate (intermediate C1a, 5.9 g, 22.63 mmol) in acetonitrile (10 mL) and the resulting mixture heated to 85 C for 18 h. Upon cooling to room temperature, the mixture was diluted with DCM and the solids filtered through filter paper. The resulting solution was partitioned between DCM and water, neutralised to pH 6 with citric acid and separated, extracting the aqueous layer with further DCM. The combined organics were washed with brine, dried over MgSO$_4$ and evaporated under reduced pressure. Purification by column chromatography (100 g column, DCM:MeOH 0-5%) gave the title compound (2.11 g, 58%, 7.55 mmol) as an orange solid. LCMS (Method T2): Rt 1.25 min, m/z 262.12 [M-water+H]$^+$. $^1$H NMR (500 MHz, chloroform-d): δ 8.13 (1H, dd, J 8.7, 2.0 Hz), 7.95 (1H, d, J 2.0 Hz), 7.04 (1H, d, J 8.7 Hz), 4.13 (2H, m), 3.50 (3H, s), 1.93 (2H, m), 1.34 (6H, s).

The following tabulated intermediates were prepared by a method analogous to that used for the preparation of intermediate B1a, using the alkyl tosylate shown in Table 18. For the preparation of intermediate B1f, 5-fluoro-3-methyl-6-nitro-1H-benzimidazol-2-one (Intermediate B10) was used in place of 3-methyl-6-nitro-1H-benzimidazol-2-one.

TABLE 18

Compounds prepared by a method analogous to that used for the preparation of Intermediate B1a

| Product | Data | Tosylate |
|---|---|---|
| Intermediate B1b: 3-[(3R)-3-hydroxybutyl]-1-methyl-5-nitro-benzimidazol-2-one | $^1$H NMR (500 MHz, DMSO-d$_6$) δ 8.10 (d, J = 2.2 Hz, 1H), 8.07 (dd, J = 8.6, 2.2 Hz, 1H), 7.37 (d, J = 8.6 Hz, 1H), 4.63 (d, J = 4.9 Hz, 1H), 4.05-3.91 (m, 2H), 3.70-3.54 (m, 1H), 3.41 (s, 3H), 1.73 (m, 1H), 1.65 (m, 1H), 1.09 (d, J = 6.2 Hz, 3H). | Intermediate C2: [(3R)-3-hydroxybutyl] 4-methylbenzenesulfonate |
| Intermediate B1c: 1-methyl-3-[2-(4-methyl-2-phenyl-1,3-dioxan-4-yl)ethyl]-5-nitro-benzimidazol-2-one | $^1$H NMR (Chloroform-d, 500 MHz, 2:1 mixture of diastereomers):<br>Major diastereomer d 8.10 (1H, dd, J 8.8, 2.0 Hz), 7.93 (1H, d, J 2.0 Hz), 7.43-7.32 (5H, m), 6.95 (d, J = 8.6 Hz, 1H), 5.72 (1H, s), 4.18-4.08 (4H, m), 3.35 (3H, s), 2.19-2.07 (4H, m), 1.58 (3H, s).<br>Minor diastereomer d 8.11 (1H, dd, J 8.8, 2.0 Hz), 7.90 (1H, d, J 2.0 Hz), 7.43-7.32 (5H, m), 6.98 (d, J = 8.6 Hz, 1H), 5.71 (1H, s), 4.27-4.20 (4H, m), 3.43 (3H, s), 2.06-2.00 (4H, m), 1.51 (3H, s). | Intermediate C6c: 2-(4-methyl-2-phenyl-1,3-dioxan-4-yl)ethyl 4-methylbenzenesulfonate |
| Intermediate B1d: 3-(3-hydroxy-3-methyl-pentyl)-1-methyl-5-nitro-benzimidazol-2-one | LCMS (Method T2): Rt 1.37 min, m/z 294.14 [M + H]$^+$. | Intermediate C5a: (3-hydroxy-3-methyl-pentyl) 4-methylbenzenesulfonate |
| Intermediate B1e: 3-(3-hydroxy-4-methoxy-3-methyl-butyl)-1-methyl-5-nitro-benzimidazol-2-one | LCMS (Method T2): Rt 1.28 min, m/z 310.12 [M + H]$^+$. | Intermediate C6a: (3-hydroxy-4-methoxy-3-methyl-butyl) 4-methylbenzenesulfonate |

TABLE 18-continued

Compounds prepared by a method analogous to that used for the preparation of Intermediate B1a

| Product | Data | Tosylate |
| --- | --- | --- |
| Intermediate B1f: 5-fluoro-1-(3-hydroxy-3-methyl-butyl)-3-methyl-6-nitro-benzimidazol-2-one | LCMS (Method T2): Rt 1.25 min, m/z 298.12 [M + H]$^+$. | Intermediate C1a: (3-hydroxy-3-methyl-butyl) 4-methylbenzenesulfonate |

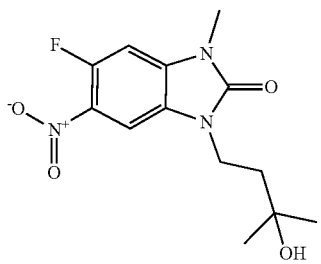

Intermediate B2: 1-Methyl-5-nitro-3-[(3S)-3-pyrazol-1-ylbutyl]benzimidazol-2-one

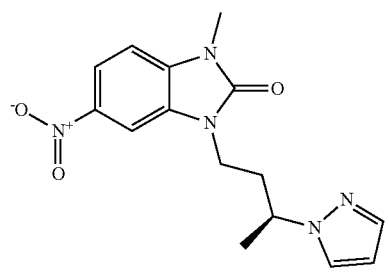

Step 1: [(1R)-1-methyl-3-(3-methyl-6-nitro-2-oxo-benzimidazol-1-yl)propyl] 4-methylbenzenesulfonate To a mixture of 3-methyl-6-nitro-1H-benzimidazol-2-one (59 mg, 0.3 mmol) and cesium carbonate (232 mg, 0.71 mmol) in acetonitrile (1 mL) was added a solution of [(3R)-3-(p-tolylsulfonyloxy)butyl] 4-methylbenzenesulfonate (Intermediate C3, 155 mg, 0.39 mmol) in acetonitrile (1 mL) and the resulting mixture heated to 60° C. for 2 h. The resulting mixture was partitioned between DCM and water, acidified to pH4 using 10% citric acid and separated and dried using a phase separator. The resulting bright orange solution was evaporated under reduced pressure onto silica gel and purified by flash column chromatography (10 g KP-SIL, 20-60% ethyl acetate in cyclohexane) to give [(1R)-1-methyl-3-(3-methyl-6-nitro-2-oxo-benzimidazol-1-yl)propyl] 4-methylbenzenesulfonate (42 mg, est. 70% purity). LCMS (Method T2) Rt 1.47 min; m/z 420.12.

Step 2: 1-methyl-5-nitro-3-[(3S)-3-pyrazol-1-yl-butyl]benzimidazol-2-one

To a solution of [(1R)-1-methyl-3-(3-methyl-6-nitro-2-oxo-benzimidazol-1-yl)propyl]4-methylbenzenesulfonate (20 mg, from Step 1) in DMF (0.5 mL) was added 1H-pyrazole (20 mg, 0.29 mmol). The mixture was heated in the microwave to 120° C. for 1 h, then partitioned between DCM and water (pH adjusted to 5 using 10% aq citric acid), and separated using a phase separator, extracting with further DCM. Combined organics evaporated under reduced pressure to give the title compound as a yellow oil (15 mg). LCMS (Method T2) Rt 1.31 min; m/z 316.14.

Intermediate B3a: Methyl 2-methyl-4-(3-methyl-6-nitro-2-oxo-benzimidazol-1-yl)butanoate

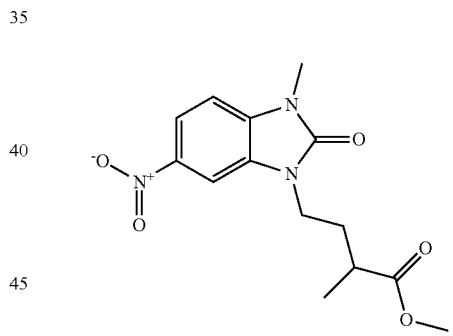

Methyl 4-chloro-2-methyl-butanoate (0.26 mL, 1.86 mmol) was added dropwise to a stirred solution of 3-methyl-6-nitro-1H-benzimidazol-2-one (300 mg, 1.55 mmol), cesium carbonate (603 mg, 1.85 mmol) and potassium iodide (23 mg, 0.14 mmol) in DMF (15 mL) at 100° C. After 1 hour the reaction mixture was allowed to cool to rt. Water (100 mL) was added, and the aqueous mixture was extracted with ethyl acetate (4×25 mL). The organic extracts were combined, dried (sodium sulfate) and concentrated in vacuo. Purification by flash chromatography (50 g KP-SIL; 0-70% EtOAc in cyclohexane) afforded the title compound (456 mg) as a yellow solid. $^1$H NMR (500 MHz, chloroform-d) δ 8.13 (dd, J=8.7, 2.2 Hz, 1H), 7.95 (d, J=2.2 Hz, 1H), 7.03 (d, J=8.7 Hz, 1H), 3.99 (t, J=7.0 Hz, 2H), 3.73 (s, 3H), 3.49 (s, 3H), 2.58-2.50 (m, 1H), 2.22-2.13 (m, 1H), 1.94-1.86 (m, 1H), 1.27 (d, J=7.2 Hz, 3H).

Intermediate B3b: Methyl 2-methyl-3-(3-methyl-6-nitro-2-oxo-benzimidazol-1-yl)propanoate

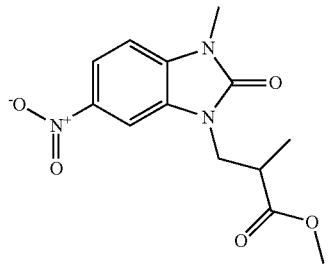

Prepared by a method analogous to that used for the preparation of Intermediate B3a using methyl 3-bromo-2-methyl-propanoate. $^1$H NMR (500 MHz, Chloroform-d) δ 8.12 (dd, J=8.7, 2.2 Hz, 1H), 7.97 (d, J=2.2 Hz, 1H), 7.03 (d, J=8.7 Hz, 1H), 4.19 (dd, J=14.4, 8.0 Hz, 1H), 4.03 (dd, J=14.4, 6.3 Hz, 1H), 3.66 (s, 3H), 3.49 (s, 3H), 3.15-3.07 (m, 1H), 1.29 (d, J=7.2 Hz, 3H).

Intermediate B4a: 1-methyl-3-(2-methylenebutyl)-5-nitro-benzimidazol-2-one

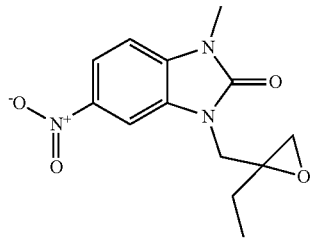

Step 1: 1-methyl-3-(2-methylenebutyl)-5-nitro-benzimidazol-2-one

A solution of 1-methyl-5-nitro-2,3-dihydro-1H-1,3-benzodiazol-2-one (325 mg, 1.68 mmol), 2-(bromomethyl)but-1-ene (251 mg, 1.68 mmol) and cesium carbonate (658 mg, 2.02 mmol) in acetonitrile (5.00 mL) was stirred at room temperature for 18 h. DCM and 10% citric acid were added, the layers separated and the aqueous layer extracted with further DCM. Purification by column chromatography (50 g column, 0 to 10% MeOH in DCM) gave the title compound (379 mg, 86%, 1.4506 mmol) as a yellow solid. LCMS (method T2): Rt 1.43 min, m/z 262.12 [M+H]*.

Step 2: 3-[(2-ethyloxiran-2-yl)methyl]-1-methyl-5-nitro-benzimidazol-2-one

To a solution of 1-methyl-3-(2-methylenebutyl)-5-nitro-benzimidazol-2-one (from previous step, 379 mg, 1.45 mmol) in DCM (10.00 mL) was added m-CPBA (626 mg, 3.63 mmol). The mixture was stirred for 18 h at room temperature, then it was quenched with saturated aqueous $Na_2S_2O_3$ and the layers were separated. The organic layer was washed with $NaHCO_3$; the aqueous layers were combined and extracted with DCM. The organic layers were combined, dried over $MgSO_4$, filtered and concentrated under reduced pressure to give the title compound (374 mg, 93%, 1.35 mmol) as an orange solid. LCMS (Method T2): Rt 1.27 min, m/z 278.12 [M+H]$^+$.

Intermediate B4b: 1-methyl-3-[(2-methyloxiran-2-yl)methyl]-5-nitro-benzimidazol-2-one

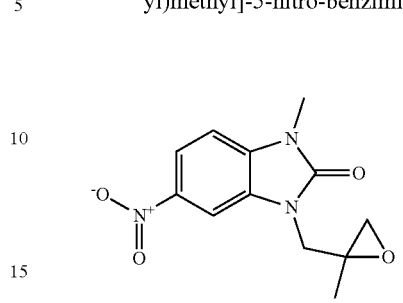

Prepared by an analogous 2 step procedure to that used in the synthesis of intermediate B4a, starting from 3-bromo-2-methylpropene. LCMS (Method T2): Rt 1.35 min, m/z 264.09 [M+H]$^+$.

Intermediate B4c: 3-((2-(2-hydroxypropan-2-yl)oxiran-2-yl)methyl)-1-methyl-5-nitro-1,3-dihydro-2H-benzo[d]imidazol-2-one

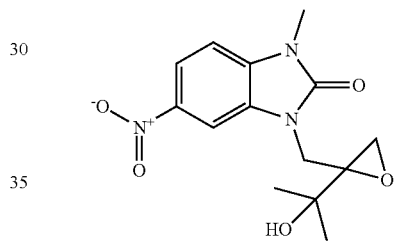

Prepared by an analogous 2 step procedure to that used in the synthesis of intermediate B4a, starting from intermediate C6d. LCMS (Method T2): Rt 1.18 min, m/z 308.12 [M+H]$^+$.

Intermediate B5: 3-(2-Hydroxybutyl)-1-methyl-5-nitro-1H-benzo[d]imidazol-2(3H)-one

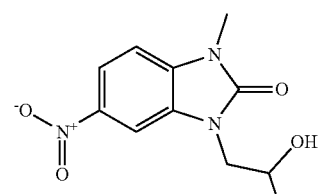

To a mixture of 1-methyl-5-nitro-1H-benzo[d]imidazol-2(3H)-one (240 mg, 1.242 mmol) and cesium carbonate (485 mg, 1.489 mmol) in DMF (3 mL) was added 2-ethyloxirane (0.119 ml, 1.367 mmol) and the resulting mixture heated in the microwave to 120° C. for 1 h, then added to water (10 mL). The resulting mixture was extracted with DCM, combined organics were dried over sodium sulfate, filtered and evaporated onto silica gel for purification by flash column chromatography (10 g silica, 40-60% ethyl acetate in cyclohexane). Fractions were combined and evaporated to give the title compound (200 mg) as a yellow-orange oil which solidified on standing. ¹H NMR (500 MHz, DMSO-d₆) δ 8.13 (d, J=2.2 Hz, 1H), 8.05 (dd, J=8.7, 2.3 Hz, 1H), 7.36 (d, J=8.8 Hz, 1H), 4.90 (d, J=5.4 Hz, 1H), 3.88 (dd, J=14.2, 4.2 Hz, 1H), 3.82 (dd, J=14.2, 7.4 Hz, 1H), 3.70 (m, 1H), 3.41 (s, 3H), 1.49 (m, 1H), 1.37 (m, 1H), 0.92 (t, J=7.4 Hz, 3H).

Intermediate B6: 3-[(3R)-3-Methoxybutyl]-1-methyl-5-nitro-benzimidazol-2-one

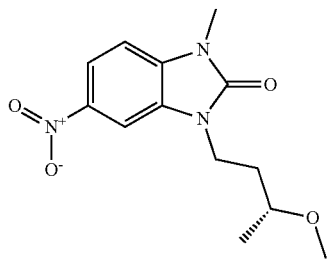 [SMILES: CO[C@H](C)CCn1c(=O)n(C)c2ccc([N+](=O)[O-])cc21]

Sodium hydride 60% in mineral oil (7.6 mg, 0.19 mmol) was suspended in dry THF (1 mL) under nitrogen and cooled to 0° C. After 5 minutes, a solution of 3-[(3R)-3-hydroxybutyl]-1-methyl-5-nitro-benzimidazol-2-one (Intermediate B1B, 40 mg, 0.1508 mmol) in dry THF (2 mL) was added dropwise over 10 minutes. Iodomethane (13 uL, 0.21 mmol) was added and the mixture allowed to warm to room temperature, then stirred overnight. Opened to air and cooled to 0° C., added water, then neutralised with dilute HCl to pH-7 and extracted with DCM. Purified by flash column chromatography (10 g silica, DCM, then 6% ethyl acetate in DCM, then 100% ethyl acetate) to give the title compound (24 mg) LCMS (Method X2) Rt 1.16 min: m/z 302.11 [M+Na]⁺.

Intermediate B7: 3-(3-Hydroxy-3-methyl-butyl)-5-nitro-1-(tetrahydropyran-4-ylmethyl)benzimidazol-2-one

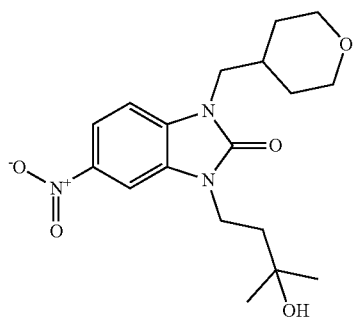

Prepared by a method analogous to that used for the preparation of Intermediate B1a, using microwave heating at 100° C. for 30 minutes, starting from 5-nitro-1-((tetrahydro-2H-pyran-4-yl)methyl)-1H-benzo[d]imidazol-2(3H)-one (Intermediate B8). ¹H NMR (500 MHz, DMSO-d₆) δ 8.06 (dd, J=8.7, 2.2 Hz, 1H), 8.02 (d, J=2.2 Hz, 1H), 7.49 (d, J=8.7 Hz, 1H), 4.51 (s, 1H), 4.04-3.96 (m, 2H), 3.81 (m, 4H), 3.21 (td, J=11.7, 2.1 Hz, 2H), 2.02 (br m, 1H), 1.77-1.70 (m, 2H), 1.46 (d, J=11.7 Hz, 2H), 1.29 (qd, J=12.1, 4.5 Hz, 2H), 1.17 (s, 6H).

Intermediate B8: 5-Nitro-1-((tetrahydro-2H-pyran-4-yl)methyl)-1H-benzo[d]imidazol-2(3H)-one

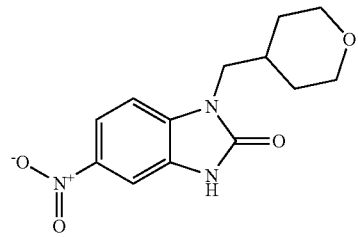

A mixture of (tetrahydro-2H-pyran-4-yl)methanamine (0.43 mL, 3.52 mmol), 2-fluoro-5-nitroaniline (539 mg, 3.45 mmol) and DIPEA (0.60 mL, 3.4 mmol) in NMP (3.5 mL) was heated in the microwave to 180° C. for 2.5 h. Further (tetrahydro-2H-pyran-4-yl)methanamine (0.21 mL, 1.72 mmol) was added and the mixture returned to the microwave at 180° C. for 2 h. After cooling, the reaction was partitioned between DCM and saturated sodium bicarbonate. The organic phase was washed twice with water, dried over sodium sulfate, filtered and evaporated under reduced pressure to give a crude mixture of 4-nitro-N1-((tetrahydro-2H-pyran-4-yl)methyl)benzene-1,2-diamine and by-products in NMP. This was diluted with acetonitrile (10 mL), and bis(2,5-dioxopyrrolidin-1-yl) carbonate (810 mg, 3.16 mmol) was added. The resulting mixture was stirred for 20 h at room temperature, then poured into water (15 mL) and the precipitate resulting was collected by filtration, washing with water, diethyl ether and DCM to give the title compound (0.38 g) as a beige solid. LCMS (Method T2) Rt 1.21, m/z 278.11.

Intermediate B9a: 5-ethyl-5-[(3-methyl-6-nitro-2-oxo-benzimidazol-1-yl)methyl]oxazolidin-2-one

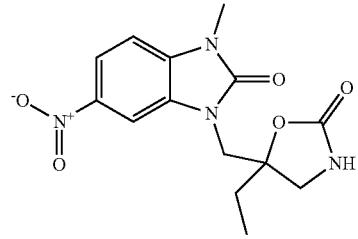

To a solution of 3-((2-ethyloxiran-2-yl)methyl)-1-methyl-5-nitro-1,3-dihydro-2H-benzo[d]imidazol-2-one (intermediate B4a, 142 mg, 0.51 mmol) in EtOH (2 mL) in a sealed tube was added ammonia (7 M in MeOH, 0.59 mL, 4.10 mmol). The mixture was stirred at 100 C for 1 h in the microwave. After cooling to room temperature, the solvent was evaporated under reduced pressure and the mixture was dissolved in THF (3 mL). Triphosgene (760 mg, 2.56 mmol) was added and the mixture was stirred at room temperature for 18 h in a sealed tube. The reaction was quenched by the slow addition of 2M NaOH, the layers were separated and the aqueous layer was extracted with EtOAc. Purification by column chromatography (25 g column, 0 to 10% MeOH in DCM) the title compound (136 mg, 83%, 0.42 mmol) as an oil. LCMS (Method T2): Rt 1.13 min, m/z 321.12 [M+H]⁺.

The following tabulated intermediates were prepared by a method analogous to that used for the preparation of intermediate B9a, using the epoxide shown in Table 19 and methylamine.

TABLE 19

Compounds prepared by a method analogous to that used for the preparation of Intermediate B9a

| Product | Data | Intermediates |
|---|---|---|
| Intermediate B9b: 5-ethyl-3-methyl-5-[(3-methyl-6-nitro-2-oxo-benzimidazol-1-yl)methyl]oxazolidin-2-one | LCMS (Method T2): Rt 1.16 min, m/z 335.13 [M + H]⁺. | Intermediate B4a: 3-((2-ethyloxiran-2-yl)methyl)-1-methyl-5-nitro-1,3-dihydro-2H-benzo[d]imidazol-2-one |
| Intermediate B9c: 3,5-dimethyl-5-[(3-methyl-6-nitro-2-oxo-benzimidazol-1-yl)methyl]oxazolidin-2-one | LCMS (Method T2): Rt 1.08 min, m/z 321.12 [M + H]⁺. | Intermediate B4b: 1-methyl-3-[(2-methyloxiran-2-yl)methyl]-5-nitro-benzimidazol-2-one |
| Intermediate B9d: 5-(2-hydroxypropan-2-yl)-3-methyl-5-((3-methyl-6-nitro-2-oxo-2,3-dihydro-1H-benzo[d]imidazol-1-yl)methyl)oxazolidin-2-one | LCMS (Method T2): Rt 1.09 min, m/z 365.14 [M + H]⁺. | Intermediate B4c: 3-((2-(2-hydroxypropan-2-yl)oxiran-2-yl)methyl)-1-methyl-5-nitro-1,3-dihydro-2H-benzo[d]imidazol-2-one |

Intermediate B10:
5-fluoro-3-methyl-6-nitro-1H-benzimidazol-2-one

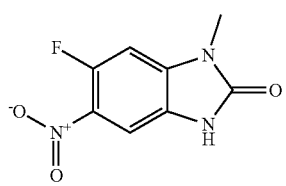

A suspension of 5-fluoro-3-methyl-1H-benzimidazol-2-one (0.5 g, 3 mmol) in acetic anhydride (7.5 mL) under N₂ was cooled to −30° C. and fuming nitric acid (0.14 mL, 3.04 mmol) was added dropwise. The mixture was stirred for 1 h, allowing slow warming up to 0 C. The mixture was then poured into a stirring mixture of ice water (10 mL) and EtOAc (1 mL), and the mixture was stirred for 30 min at room temperature. Further EtOAc was added and the layers were separated. The aqueous layer was extracted with further EtOAc. The organic layers were combined, dried over MgSO₄ and evaporated under reduced pressure to afford the title compound (500 mg) as a black solid. LCMS (Method T2): Rt 0.97 min m/z 212.04 [M+H]⁺.

Intermediate B11: N-(2-methyl-4-(3-methyl-6-nitro-2-oxo-2,3-dihydro-1H-benzo[d]imidazol-1-yl)butan-2-yl)acetamide

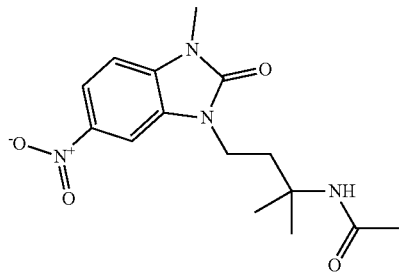

3-(3-hydroxy-3-methyl-butyl)-1-methyl-5-nitro-benzimidazol-2-one (Intermediate B1a, 50 mg, 0.18 mmol) was dissolved in MeCN (1 mL) and sulfuric acid (0.10 mL, 1.876 mmol) was added dropwise at 0° C., and the resulting mixture stirred overnight at rt. Added water (2 mL) dropwise, then carefully added sat. aq. sodium bicarbonate until pH 6 was reached. Extracted twice with DCM, combined organics dried and evaporated and purified by flash column chromatography (10 g KP-SIL, 0-3% methanol in DCM) to give the title compound (32 mg, 56%, 0.1 mmol). LCMS (Method X2) Rt 1.10 min; m/z 321.1564 expected 321.1563 for $C_{15}H_{21}N_4O_4$ [M+H]$^+$.

Intermediate B12: (S)-1-methyl-5-nitro-3-((1-(2,2,2-trifluoroethyl)pyrrolidin-2-yl)methyl)-1,3-dihydro-2H-benzo[d]imidazol-2-one

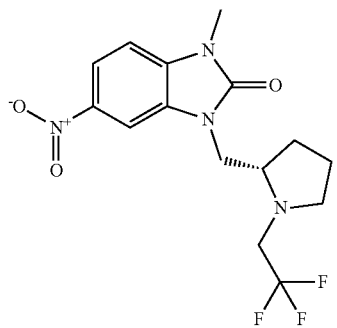

[(2S)-1-(2,2,2-trifluoroethyl)pyrrolidin-2-yl]methanol (Intermediate G4a, 90 mg, 0.49 mmol) in THF (2 mL) and cyanomethyltributylphosphorane (33% w/v solution in THF) (0.75 mL, 1.04 mmol) were added sequentially to a suspension of 1-methyl-5-nitro-2,3-dihydro-1H-1,3-benzodiazol-2-one (80 mg, 0.41 mmol) in DMF (0.3 mL) under argon. The resulting mixture was heated to 60° C. for 2 hours, then in the microwave at 100° C. for 1 h. After cooling, the mixture was partitioned between DCM and water, acidified to pH4 with 10% citric acid, and layers separated. The organic layer was evaporated onto silica, purified by flash column chromatography (10 g KP-SIL, 20-60% ethyl acetate in cyclohexane). The resulting red gum was triturated with diethyl ether, and the resulting solid was then dissolved in DCM and re-evaporated and dried to give a beige solid. LCMS (Method X2) Rt 1.37 min m/z 359.1325 expected 359.1331 for $C_{15}H_{18}N_4O_3F_3$ [M+H]$^+$.

Intermediate B13a: 1,3-bis(3-hydroxy-3-methyl-butyl)-5-nitro-1,3-dihydro-2H-benzo[d]imidazol-2-one

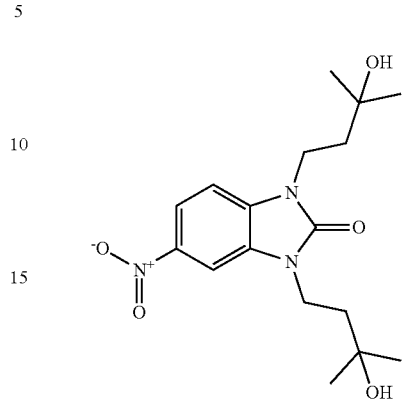

To a mixture of 5-nitro-2-benzimidazolinone (300 mg, 1.62 mmol) and dicesium carbonate (0.75 g, 2.3 mmol) in acetonitrile (8 mL) and DMF (2 mL) was added (3-hydroxy-3-methyl-butyl) 4-methylbenzenesulfonate (Intermediate C1a, 450 mg, 1.74 mmol) and the resulting mixture was heated to 100° C. for 1 h in the microwave. After cooling, the mixture was partitioned between DCM and water, acidified to pH8 with 10% citric acid, and layers separated. Organic phase evaporated under reduced pressure, then purified using reverse phase flash chromatography (Biotage 12 g SNAP Ultra C18, 30-65% methanol in water, 0.1% formic acid modifier). $^1$H NMR (600 MHz, Chloroform-d) δ 8.13 (dd, J=8.6, 2.2 Hz, 1H), 7.97 (d, J=2.2 Hz, 1H), 7.12 (d, J=8.7 Hz, 1H), 4.16-4.09 (m, 4H), 1.96-1.88 (m, 4H), 1.34 (s, 6H), 1.33 (s, 6H).

Intermediate B13b: 1,3-bis(3-hydroxy-3-methyl-butyl)-6-nitro-1,3-dihydro-2H-imidazo[4,5-b]pyridin-2-one

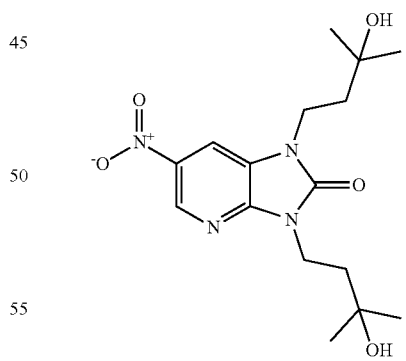

Prepared by an analogous method to that used for the preparation of intermediate B13a, using DMF as a solvent and heating to 120° C., starting from 6-nitro-1,3-dihydro-2H-imidazo[4,5-b]pyridin-2-one, which was prepared as follows: to 5-nitropyridine-2,3-diamine (125 mg, 0.81 mmol) in acetonitrile (15 mL) at room temperature was added portionwise bis(2,5-dioxopyrrolidin-1-yl) carbonate (0.30 g, 1.17 mmol) over 3 minutes. The resulting mixture was stirred at room temperature for 10 minutes, then heated in the microwave to 120° C. for 1 hour. Solid material was collected by filtration, washed with acetonitrile and dried on the filter to give 6-nitro-1,3-dihydroimidazo[4,5-b]pyridin-2-one (0.09 g) as brown solid. LCMS (Method X2) Rt 1.39 min; m/z 408.13 [M+Na]$^+$.

Intermediate B13c: 4-chloro-1,3-bis(3-hydroxy-3-methyl-butyl)-6-nitro-benzimidazol-2-one

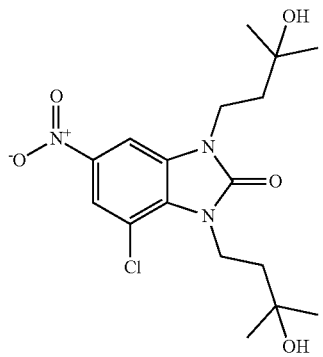

Prepared by an analogous method to that used for the preparation of intermediate B13a, using DMF as a solvent and starting from 4-chloro-6-nitro-1,3-dihydro-2H-benzo[d]imidazol-2-one. LCMS (Method X2) Rt 1.39 min; m/z 408.13 [M+Na]$^+$.

Intermediate C1a: (3-Hydroxy-3-methyl-butyl) 4-methylbenzenesulfonate

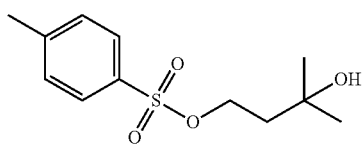 [SMILES: Cc1ccc(S(=O)(=O)OCCC(C)(C)O)cc1]

A mixture of 3-methylbutane-1,3-diol (6.6 g, 63.4 mmol), 4-methylbenzenesulfonyl chloride (18 g, 94 mmol), in dry pyridine (60 mL) was stirred at 0° C. for 2 hours, then poured into cold HCl (2M, 150 mL) and extracted with ethyl acetate (3×180 mL). Combined organic phase was washed with HCl (2M, 4×180 mL), brine (90 mL), dried over magnesium sulfate and evaporated to dryness. Purified by flash column chromatography (divided material into two halves, purified each using 100 g silica, 0-50% ethyl acetate in cyclohexane), recombined pure fractions from each column to give the title compound (12 g, 73%, 46.5 mmol) as a clear oil. $^1$H NMR (500 MHz, chloroform-d) δ 7.81 (d, J=8.2 Hz, 2H), 7.34 (d, J=7.6 Hz, 2H), 4.22 (t, J=6.9 Hz, 2H), 2.46 (s, 3H), 1.87 (t, J=6.9 Hz, 2H), 1.23 (s, 6H).

Intermediate C1b: (3-hydroxy-2,3-dimethyl-butyl) 4-methylbenzenesulfonate

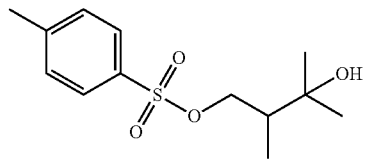 [SMILES: Cc1ccc(S(=O)(=O)OCC(C)C(C)(C)O)cc1]

Prepared from 2,3-dimethylbutane-1,3-diol (Intermediate G6a) using a method analogous to that used for the preparation of intermediate C1a. LCMS (Method X2) Rt 1.23 min; m/z 295.0977 [M+Na]$^+$.

Intermediate C1c: (4,4,4-trifluoro-3-hydroxy-3-methyl-butyl) 4-methylbenzenesulfonate

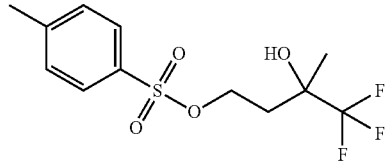 [SMILES: Cc1ccc(S(=O)(=O)OCCC(C)(O)C(F)(F)F)cc1]

Prepared from 4,4,4-trifluoro-3-methyl-butane-1,3-diol (Intermediate G6b) using a method analogous to that used for the preparation of intermediate C1a. $^1$H NMR (500 MHz, chloroform-d) δ 7.81 (d, J=8 Hz, 2H), 7.38 (d, J=8.1 Hz, 2H), 4.31 (dt, J=10.4, 6.8 Hz, 1H), 4.23 (dt, J=10.4, 6.3 Hz, 1H), 2.48 (s, 3H), 2.18-1.97 (m, 3H), 1.39 (s, 3H).

Intermediate C2: [(3R)-3-Hydroxybutyl] 4-methylbenzenesulfonate and

Intermediate C3: [(3R)-3-(p-Tolylsulfonyloxy)butyl] 4-methylbenzenesulfonate

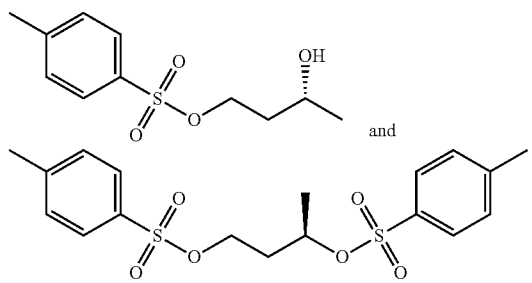

A solution of (3R)-butane-1,3-diol (0.86 mL, 9.5 mmol) in dry dichloromethane (10 mL) under a nitrogen atmosphere was cooled in a salt-ice bath (bath temp −12° C.). Triethylamine (2.25 mL, 16.1 mmol) was added followed by a solution of 4-methylbenzenesulfonyl chloride (2 g, 10.5 mmol) in dry dichloromethane (6 mL) over 10 minutes. The resulting mixture was allowed to warm slowly to room temperature and stirred for 20 h, then diluted with DCM, washed with 10% citric acid, sat. sodium bicarbonate solution, brine, dried over sodium sulfate, filtered and evaporated under reduced pressure to give a clear oil. This was purified by flash column chromatography (50 g silica, 10-30% ethyl acetate in cyclohexane). Two products obtained: Intermediate C2: [(3R)-3-hydroxybutyl] 4-methylbenzenesulfonate (1.65 g) as clear oil [$^1$H NMR (500 MHz, chloroform-d) δ 7.82 (br d, J=8.3 Hz, 2H), 7.37 (br d, J=7.9 Hz, 2H), 4.26 (ddd, J=10.0, 8.7, 5.0 Hz, 1H), 4.13 (dt, J=10.0, 5.5 Hz, 1H), 3.96 (dqd, J=9.7, 6.2, 3.5 Hz, 1H), 2.47 (s, 3H), 1.85 (dddd, J=14.5, 8.7, 5.8, 3.6 Hz, 1H), 1.71 (ddt, J=14.2, 8.9, 5.0 Hz, 1H), 1.21 (d, J=6.3 Hz, 3H)] and Intermediate C3: [(3R)-3-(p-tolylsulfonyloxy)butyl] 4-methylbenzenesulfonate (155 mg) as clear oil. [1H NMR (500 MHz, chloroform-d) δ 7.80-7.73 (m, 4H), 7.40-7.32 (m, 4H), 4.71 (dqd, J=8.0, 6.3, 4.5 Hz, 1H), 4.04 (dt, J=10.2, 5.8 Hz, 1H), 3.94 (ddd, J=10.4, 7.7, 5.6 Hz, 1H), 2.48 (s, 3H), 2.47 (s, 3H), 2.02-1.85 (m, 2H), 1.26 (d, J=6.3 Hz, 3H).

Intermediate C4a: Methyl 2-methoxy-4-(p-tolylsulfonyloxy)butanoate

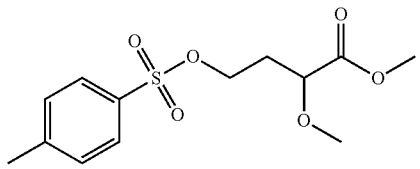

Step 1: 3-methoxytetrahydrofuran-2-one

Silver oxide (520 mg, 2.2 mmol) was added portionwise to a stirred solution of 3-hydroxytetrahydrofuran-2-one (0.15 mL, 1.9 mmol) and iodomethane (0.36 mL, 5.8 mmol) in acetonitrile (5 mL) at rt under Ar. The reaction mixture was subsequently stirred at 75° C. for 4 h. The reaction mixture was allowed to cool to rt, filtered and the solid residue was washed with Et$_2$O (3×15 mL). The filtrate was concentrated in vacuo and directly dry loaded onto silica gel. Purification by flash chromatography (50 g KP-SIL; 60% EtOAc in cyclohexane to 100% EtOAc) afforded 3-methoxytetrahydrofuran-2-one (168 mg, 75%) as a colourless oil. $^1$H NMR (500 MHz, chloroform-d) δ 4.43 (ddd, J=9.1, 8.1, 4.3 Hz, 1H), 4.26 (ddd, J=9.1, 8.0, 6.9 Hz, 1H), 4.03 (t, J=7.6 Hz, 1H), 3.59 (s, 3H), 2.56-2.48 (m, 1H), 2.30-2.21 (m, 1H).

Step 2: methyl 4-hydroxy-2-methoxy-butanoate

4N HCl in dioxane (50 uL, 0.2 mmol) was added to a stirred solution of 3-methoxytetrahydrofuran-2-one (166 mg, 1.4 mmol, from step 1) in anhydrous methanol (4.5 mL) under Ar. The reaction mixture was stirred at 60° C. for 3 h. The reaction mixture was allowed to cool to rt, concentrated in vacuo and directly dry loaded onto silica gel. Purification by flash chromatography (KP-SIL 25 g; 50% EtOAc in cyclohexane to 100% EtOAc) afforded methyl 4-hydroxy-2-methoxy-butanoate (117 mg, 55%) as a colourless oil. $^1$H NMR (500 MHz, chloroform-d) δ 4.01 (dd, J=7.7, 4.6 Hz, 1H), 3.81-3.77 (m, 5H), 3.44 (s, 3H), 2.08-1.95 (m, 3H).

Step 3: methyl 2-methoxy-4-(p-tolylsulfonyloxy)butanoate

Triethylamine (0.16 mL, 1.17 mmol), pyridine (10 uL, 0.12 mmol) and tosyl chloride (179 mg, 0.94 mmol) were added sequentially to a stirred solution of methyl 4-hydroxy-2-methoxy-butanoate (115 mg, 0.78 mmol, from step 2) in DCM (2 mL) under Ar. The reaction mixture was then stirred at 30° C. for 5 h. Water was added to the reaction mixture. The layers were separated and the aqueous layer was further extracted with DCM (3×10 mL). The organic extracts were combined, washed with brine (5 mL), dried (sodium sulfate) and concentrated in vacuo. Purification by flash chromatography (25 g KP-SIL; 0% to 60% EtOAc in cyclohexane) afforded methyl 2-methoxy-4-(p-tolylsulfonyloxy)butanoate (204 mg, 87%) as a pale yellow oil. $^1$H NMR (500 MHz, chloroform-d) δ 7.83-7.79 (m, 2H), 7.39-7.34 (m, 2H), 4.24-4.18 (m, 1H), 4.14-4.09 (m, 1H), 3.85 (dd, J=9.1, 3.9 Hz, 1H), 3.75 (s, 3H), 3.33 (s, 3H), 2.46 (s, 3H), 2.19-2.10 (m, 1H), 2.01-1.92 (m, 1H).

Intermediate C4b: Methyl 2-ethoxy-4-(p-tolylsulfonyloxy)butanoate

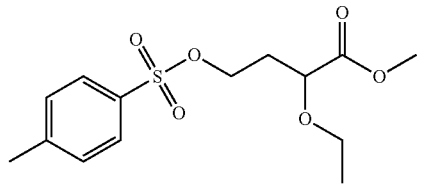

Prepared by a method analogous to that used for the preparation of Intermediate C4a. $^1$H NMR (500 MHz, chloroform-d) δ 7.82-7.79 (m, 2H), 7.38-7.34 (m, 2H), 4.25-4.19 (m, 1H), 4.15-4.09 (m, 1H), 3.94 (dd, J=9.5, 3.7 Hz, 1H), 3.73 (s, 3H), 3.63 (dq, J=9.0, 7.0 Hz, 1H), 3.28 (dq, J=9.0, 7.0 Hz, 1H), 2.46 (s, 3H), 2.18-2.09 (m, 1H), 1.99-1.91 (m, 1H), 1.13 (t, J=7.0 Hz, 3H).

Intermediate C4c: Methyl 2-(cyclopropylmethoxy)-4-(p-tolylsulfonyloxy)butanoate

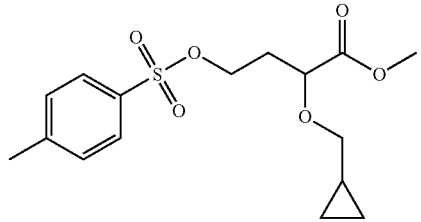

Prepared by a method analogous to that used for the preparation of Intermediate C4a. Alkylation of 3-hydroxytetrahydrofuran-2-one in Step 1 was achieved using NaH and (bromomethyl)cyclopropane. $^1$H NMR (500 MHz, chloroform-d) δ 7.82-7.79 (m, 2H), 7.38-7.34 (m, 2H), 4.29-4.22 (m, 1H), 4.15-4.10 (m, 1H), 3.99 (dd, J=9.7, 3.6 Hz, 1H), 3.73 (s, 3H), 3.34 (dd, J=10.0, 7.2 Hz, 1H), 3.17 (dd, J=10.0, 6.8 Hz, 1H), 2.46 (s, 3H), 2.19-2.10 (m, 1H), 2.01-1.93 (m, 1H), 1.02-0.93 (m, 1H), 0.54-0.47 (m, 2H), 0.22-0.10 (m, 2H).

Intermediate C5a: (3-hydroxy-3-methyl-pentyl) 4-methylbenzenesulfonate

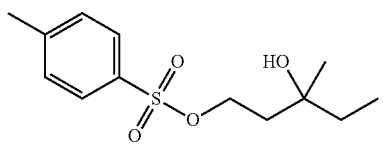 [SMILES: CCC(C)(O)CCOS(=O)(=O)c1ccc(C)cc1]

Step 1: 3-methylpentane-1,3-diol

To a solution of 1-[tert-butyl(dimethyl)silyl]oxy-3-methyl-pentan-3-ol (Intermediate G1a, 570 mg, 2.45 mmol) in MeOH (25 mL) was added HCl (5.70 mL, 11.4 mmol) dropwise at room temperature. The mixture was stirred for 2 h, then it was quenched by the addition of solid $NaHCO_3$. The salts were filtered washing with DCM, and the solvent was removed under reduced pressure to give the title compound (290 mg, 100% yield, 2.45 mmol) as a clear oil, which was used in the next step without further purification.

Step 2: (3-hydroxy-3-methyl-pentyl) 4-methylbenzenesulfonate

A mixture of 4-methylbenzenesulfonyl chloride (515 mg, 2.70 mmol), 3-methylpentane-1,3-diol (from step 1, 290 mg, 2.45 mmol), triethylamine (0.68 mL, 4.91 mmol) and DMAP (30 mg, 0.25 mmol) in DCM (12 mL) was stirred at 0° C. for 2 hours. Aqueous 10% citric acid was added, the layers were separated and the aqueous layer was extracted with DCM. The organic layers were combined, dried over $MgSO_4$ and concentrated under reduced pressure. Purification by flash column chromatography (50 g KP-SIL, 0-50% ethyl acetate in cyclohexane) gave the title compound (426 mg, 64%, 1.5 mmol) as a colourless oil. $^1H$ NMR (500 MHz, Chloroform-d): δ 7.81 (2H, d, J 8.8 Hz), 7.36 (2H, d, J 8.8 Hz), 4.25-4.19 (2H, m), 2.46 (3H, s), 1.90-1.80 (2H, m), 1.48 (2H, q, J 7.6 Hz), 1.15 (3H, s), 0.88 (3H, t, d, J 7.6 Hz).

The following tabulated intermediates were prepared by a method analogous to that used for the preparation of intermediate C5a, using the alcohol shown in Table 20.

TABLE 20

Compounds prepared by a method analogous to that used for the preparation of Intermediate C5a

| Product | Data | Intermediates |
|---|---|---|
| Intermediate C5b: (3-hydroxy-3,4-dimethyl-pentyl) 4-methylbenzenesulfonate | $^1H$ NMR (500 MHz, Chloroform-d): d 7.82 (2H, d, J 7.9 Hz), 7.36 (2H, d, J 7.9 Hz), 4.27-4.22 (2H, m), 2.46 (3H, s), 1.91-1.80 (2H, m), 1.65 (1H, m), 1.09 (3H, s), 0.90 (3H, d, J 6.9 Hz), 0.88 (3H, d, J 6.9 Hz). | Intermediate G113: 1-((tert-butyldimethylsilyl)oxy)-3,4-dimethylpentan-3-ol |
| Intermediate C5c: (3-hydroxy-3-methyl-6-trimethylsilyl-hex-5-ynyl) 4-methylbenzenesulfonate | $^1H$ NMR (500 MHz, Chloroform-d): d 7.80 (2H, d, J 8.3 Hz), 7.36 (2H, d, J 8.3 Hz), 4.26-4.18 (2H, m), 2.46 (3H, s), 2.41 (1H, d, J 16.3 Hz), 2.36 (1H, d, J 16.3 Hz), 2.03-1.89 (2H, m), 1.25 (3H, s), 0.15 (9H, s). | Intermediate G2: 1-((tert-butyldimethylsilyl)oxy)-3-methyl-6-(trimethylsilyl)hex-5-yn-3-ol |

The following tabulated intermediates were prepared by a method analogous to the second step described for the preparation of intermediate C5a, using the alcohol shown in Table 21.

TABLE 21

Compounds prepared by a method analogous to that used in the second step of the preparation of Intermediate C5a

| Product | Data | Intermediates |
|---|---|---|
| Intermediate C6a: (3-hydroxy-4-methoxy-3-methyl-butyl) 4-methylbenzenesulfonate | $^1H$ NMR (500 MHz, Chloroform-d): d 7.81 (2H, d, J 8.4 Hz), 7.36 (2H, d, J 8.4 Hz), 4.27-4.19 (2H, m), 3.36 (3H, s), 3.28 (1H, d, J 9.0 Hz), 3.24 (1H, d, J 9.0 Hz), 2.47 (3H, s), 1.98-1.88 (2H, m), 1.15 (3H, s). | Intermediate G8: 4-methoxy-3-methyl-butane-1,3-diol |

TABLE 21-continued

Compounds prepared by a method analogous to that used in the second step of the preparation of Intermediate C5a

| Product | Data | Intermediates |
|---|---|---|
| Intermediate C6b: 3-methylbut-3-enyl 4-methylbenzenesulfonate 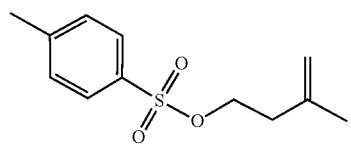 [SMILES: C=C(C)CCOS(=O)(=O)c1ccc(C)cc1] | ¹H NMR (500 MHz, Chloroform-d): d 7.82 (2H, d, J 8.4 Hz), 7.37 (2H, d, J 8.4 Hz), 4.81 (1H, s), 4.70 (1H, s), 4.15 (2H, t, J 7.0 Hz), 2.48 (3H, s), 2.38 (2H, t, J 7.0 Hz), 1.69 (3H, s). | 3-methylbut-3-en-1-ol |
| Intermediate C6c: 2-(4-methyl-2-phenyl-1,3-dioxan-4-yl)ethyl 4-methylbenzenesulfonate 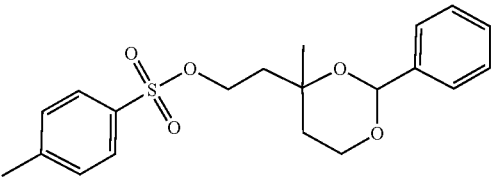 [SMILES: Cc1ccc(S(=O)(=O)OCCC2(C)CCOC(c3ccccc3)O2)cc1] | LCMS (Method T2): Rt 1.56 min, m/z 399.12 [M + Na]⁺. | Intermediate G3: 2-(4-methyl-2-phenyl-1,3-dioxan-4-yl)ethanol |
| Intermediate C6d: 3-hydroxy-3-methyl-2-methylenebutyl 4-methylbenzenesulfonate 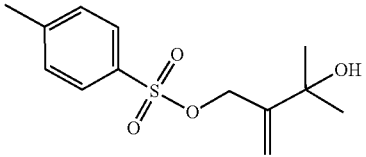 [SMILES: C=C(COS(=O)(=O)c1ccc(C)cc1)C(C)(C)O] | ¹H NMR (500 MHz, Chloroform-d): d 7.83 (2H, d, J 8.3 Hz), 7.36 (2H, d, J 8.3 Hz), 5.30 (1H, s), 5.19 (1H, s), 4.66 (2H, s), 2.47 (3H, s), 1.35 (6H, s). | Intermediate G7: 3-methyl-2-methylene-butane-1,3-diol |

Intermediate D1: 2-Chloro-4-[(1-methyl-2-oxo-3H-benzimidazol-5-yl)amino]pyridine-3-carbonitrile

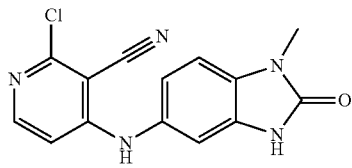 [SMILES: Cn1c(=O)[nH]c2cc(Nc3ccnc(Cl)c3C#N)ccc21]

To a mixture of 5-amino-1-methyl-1H-benzo[d]imidazol-2(3H)-one (750 mg, 4.6 mmol) and 2,4-dichloropyridine-3-carbonitrile (760 mg, 4.4 mmol) under argon was added DMA (10 mL) followed by DIPEA (0.90 mL, 5.19 mmol). The reaction mixture was heated at 120° C. under microwave irradiation for 45 min then allowed to cool to rt and added dropwise to a stirring mixture of methanol:water (1:1; 120 mL). The resulting precipitate was filtered, washed with water (2×25 mL) and diethyl ether (2×30 mL) affording 2-chloro-4-[(1-methyl-2-oxo-3H-benzimidazol-5-yl)amino]pyridine-3-carbonitrile (1297 mg, 99%, 4.3 mmol) as a beige solid. ¹H NMR (500 MHz, DMSO-d₆) δ 10.95 (br s, 1H), 9.39 (br s, 1H), 7.99 (d, J=6.2 Hz, 1H), 7.13 (d, J=8.3 Hz, 1H), 6.95 (dd, J=8.3, 1.9 Hz, 1H), 6.90 (d, J=1.9 Hz, 1H), 6.65 (d, J=6.2 Hz, 1H).

Intermediate D2a: 5-[(2,5-dichloropyrimidin-4-yl)amino]-3-(3-hydroxy-3-methyl-butyl)-1-methyl-benzimidazol-2-one

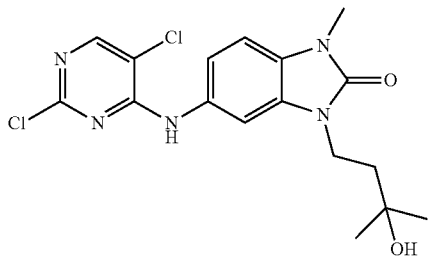 [SMILES: Cn1c(=O)n(CCC(C)(C)O)c2cc(Nc3nc(Cl)ncc3Cl)ccc21]

A mixture of 5-amino-3-(3-hydroxy-3-methyl-butyl)-1-methyl-benzimidazol-2-one (intermediate A1, 1.61 g, 6.47 mmol), 2,4,5-trichloropyrimidine (0.88 mL, 7.69 mmol) and cesium carbonate (4.21 g, 12.93 mmol) in DMF (15 mL) was heated in the microwave to 120° C. for 30 minutes. The resulting mixture was diluted with water, acidified to pH5 by addition of 10% citric acid and extracted with DCM. The combined organics were evaporated under reduced pressure, and the resulting sticky solid was dissolved in a minimum volume of ethyl acetate and precipitated by addition of diethyl ether. The resulting solid was collected by filtration and washed with diethyl ether and dried under reduced pressure, giving the title product (1.96 mg, 72%, 4.69 mmol) as a solid. ¹H NMR (500 MHz, DMSO-d6): δ 9.57 (1H, s), 8.34 (1H, s), 7.35 (1H, d, J 1.9 Hz), 7.19 (1H, dd, J 8.4, 1.9 Hz), 7.15 (1H, d, J=8.4 Hz), 4.44 (1H, s), 3.92-3.86 (2H, m), 3.33 (3H, s), 1.76-1.69 (2H, m), 1.17 (6H, s). LCMS (Method T2): Rt 1.43 min, m/z 396.10 [M+H]⁺.

Intermediate D2b: 5-[(2,5-dichloropyrimidin-4-yl)amino]-3-(3-hydroxy-4-methoxy-3-methyl-butyl)-1-methyl-benzimidazol-2-one N5092-29 Avarela

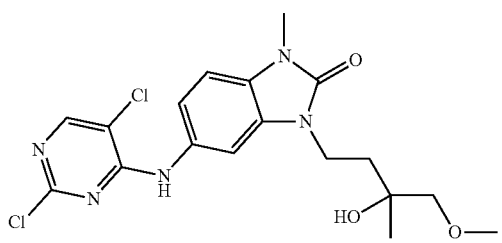 [SMILES: COCC(C)(O)CCn1c(=O)n(C)c2ccc(Nc3nc(Cl)ncc3Cl)cc21]

Prepared from 5-amino-3-(3-hydroxy-4-methoxy-3-methyl-butyl)-1-methyl-benzimidazol-2-one (Intermediate A7b) by an analogous method to that used for the preparation of Intermediate D2a. LCMS (Method T2): Rt 1.39 min, m/z 426.11 [M+H]⁺.

Intermediate D2c: (S)-5-((2,5-dichloropyrimidin-4-yl)amino)-1-methyl-3-((1-(2,2,2-trifluoroethyl)pyrrolidin-2-yl)methyl)-1,3-dihydro-2H-benzo[d]imidazol-2-one N5127-12

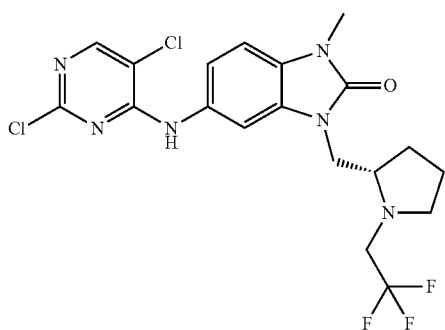 [SMILES: Cn1c(=O)n(C[C@@H]2CCCN2CC(F)(F)F)c2cc(Nc3nc(Cl)ncc3Cl)ccc21]

Prepared from 5-amino-1-methyl-3-[[(2S)-1-(2,2,2-trifluoroethyl)pyrrolidin-2-yl]methyl]benzimidazol-2-one (Intermediate A6f) by an analogous method to that used for the preparation of Intermediate D2a. LCMS (Method X2) Rt 1.47 min; m/z 475.1033 expected 475.1028 for $C_{19}H_{20}N_6OF_3Cl_2$ [M+H]⁺.

Intermediate D2d: 5-((2,5-dichloropyrimidin-4-yl)amino)-1,3-bis(3-hydroxy-3-methylbutyl)-1,3-dihydro-2H-benzo[d]imidazol-2-one

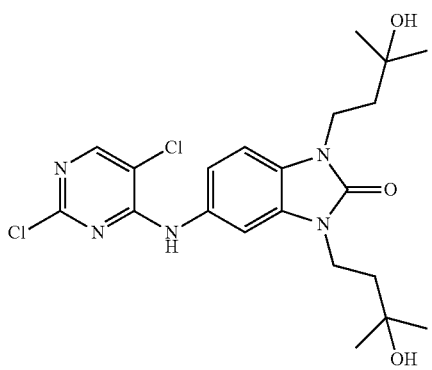 [SMILES: CC(C)(O)CCn1c(=O)n(CCC(C)(C)O)c2cc(Nc3nc(Cl)ncc3Cl)ccc21]

Prepared from 5-amino-1,3-bis(3-hydroxy-3-methyl-butyl)benzimidazol-2-one (Intermediate A6g) by an analogous method to that used for the preparation of Intermediate D2a. ¹H NMR (500 MHz, Chloroform-d) δ 8.21 (s, 1H), 7.64 (d, J=2.0 Hz, 1H), 7.31 (s, 1H), 7.09 (dd, J=8.4, 2.0 Hz, 1H), 7.04 (d, J=8.3 Hz, 1H), 4.12-4.03 (m, 4H), 1.99-1.88 (m, 4H), 1.33 (s, 6H), 1.32 (s, 6H).

The following tabulated intermediates were prepared by a method analogous to that used for the preparation of example 22a, using the intermediates shown in Table 22. NMP, DMA or DMF were used as solvent. For the preparation of intermediate D3a, 1 hour heating at 140° C. in NMP was used. For the preparation of intermediate D3b, 1 hour heating at 180° C. in NMP was used.

TABLE 22

Compounds prepared by a method analogous to that used for the preparation of Example 22a

| Intermediate | Data | Starting from |
| --- | --- | --- |
| Intermediate D3a: 6-chloro-4-[[3-(3-hydroxy-3-methyl-butyl)-1-methyl-2-oxo-benzimidazol-5-yl]amino]pyridine-3-carbonitrile | LCMS (Method T2): Rt 1.39 min, m/z 386.13 [M + H]⁺. | Intermediate A1: 5-amino-3-(3-hydroxy-3-methyl-butyl)-1-methyl-benzimidazol-2-one and 4,6-dichloropyridine-3-carbonitrile |

TABLE 22-continued

Compounds prepared by a method analogous to that used for the preparation of Example 22a

| Intermediate | Data | Starting from |
| --- | --- | --- |
| Intermediate D3b: 5-[(2,5-dichloropyrimidin-4-yl)amino]-1-methyl-3-[2-(4-methyl-2-phenyl-1,3-dioxan-4-yl)ethyl]benzimidazol-2-one | LCMS (Method T2): Rt 1.56 min, m/z 408.09 [M − BnO]⁺. | Intermediate A7c: 5-amino-1-methyl-3-[2-(4-methyl-2-phenyl-1,3-dioxan-4-yl)ethyl]benzimidazol-2-one and 2,4,5-trichloro pyrimidine |
| Intermediate D3c: 6-[(2,5-dichloropyrimidin-4-yl)amino]-3-methyl-1H-benzimidazol-2-one | LCMS (Method T2): Rt 1.26 min, m/z 310.02 [M + H]⁺. | 5-amino-1-methyl-2,3-dihydro-1H-1,3-benzodiazol-2-one and 2,4,5-trichloro pyrimidine |
| Intermediate D3d: 5-[[6-[(2,5-dichloropyrimidin-4-yl)amino]-3-methyl-2-oxo-benzimidazol-1-yl]methyl]-5-ethyl-3-methyl-oxazolidin-2-one | LCMS (Method T2): Rt 1.37 min, m/z 451.10 [M + H]⁺. | Intermediate A6d: 5-[(6-amino-3-methyl-2-oxo-benzimidazol-1-yl)methyl]-3,5-dimethyl-oxazolidin-2-one and 2,4,5-trichloro pyrimidine |
| Intermediate D3e: 5-[[6-[(2,5-dichloropyrimidin-4-yl)amino]-3-methyl-2-oxo-benzimidazol-1-yl]methyl]-5-ethyl-oxazolidin-2-one | LCMS (Method T2): Rt 1.34 min, m/z 437.08 [M + H]⁺. | Intermediate A6c: 5-[(6-amino-3-methyl-2-oxo-benzimidazol-1-yl)methyl]-5-ethyl-oxazolidin-2-one and 2,4,5-trichloro pyrimidine |

TABLE 22-continued

Compounds prepared by a method analogous to that used for the preparation of Example 22a

| Intermediate | Data | Starting from |
| --- | --- | --- |
| Intermediate D3f: 6-[(2,5-dichloropyrimidin-4-yl)amino]-5-fluoro-1-(3-hydroxy-3-methyl-butyl)-3-methyl-benzimidazol-2-one | LCMS (Method T2): Rt 1.41 min; m/z 414.08 [M + H]+. | Intermediate A6a: 6-amino-5-fluoro-1-(3-hydroxy-3-methyl-butyl)-3-methyl-benzimidazol-2-one and 2,4,5-trichloro pyrimidine |
| Intermediate D3g: 5-[(5-bromo-2-chloro-pyrimidin-4-yl)amino]-3-(3-hydroxy-3-methyl-butyl)-1-methyl-benzimidazol-2-one | LCMS (Method X4) Rt 2.62 min; m/z 440.05 and 442.05 [M + H]+. | Intermediate A1: 5-amino-3-(3-hydroxy-3-methyl-butyl)-1-methyl-benzimidazol-2-one and 5-bromo-2,4-dichloropyrimidine |
| Intermediate D3h: 5-[(2,5-dichloro-6-methyl-pyrimidin-4-yl)amino]-3-(3-hydroxy-3-methyl-butyl)-1-methyl-benzimidazol-2-one | LCMS (Method X4) Rt 2.72 min; m/z 410.11 and 412.11 [M + H]+. | Intermediate A1: 5-amino-3-(3-hydroxy-3-methyl-butyl)-1-methyl-benzimidazol-2-one and 2,4,5-trichloro-6-methylpyrimidine |

TABLE 22-continued

Compounds prepared by a method analogous to that used for the preparation of Example 22a

| Intermediate | Data | Starting from |
|---|---|---|
| Intermediate D3i: 5-chloro-7-[[3-(3-hydroxy-3-methyl-butyl)-1-methyl-2-oxo-benzimidazol-5-yl]amino]pyrazolo[1,5-a]pyrimidine-3-carbonitrile | LCMS (Method X2) Rt 1.26 min; m/z 426.14 [M + H]+. | Intermediate A1: 5-amino-3-(3-hydroxy-3-methyl-butyl)-1-methyl-benzimidazol-2-one and 5,7-dichloropyrazolo[1,5-a]pyrimidine-3-carbonitrile |
| Intermediate D3j: 5-((6-((2,5-dichloropyrimidin-4-yl)amino)-3-methyl-2-oxo-2,3-dihydro-1H-benzo[d]imidazol-1-yl)methyl)-5-(2-hydroxypropan-2-yl)-3-methyloxazolidin-2-one | LCMS (Method T2): Rt 1.31 min, m/z 481.11 [M + H]+. | Intermediate A6e: 5-((6-amino-3-methyl-2-oxo-2,3-dihydro-1H-benzo[d]imidazol-1-yl)methyl)-5-(2-hydroxypropan-2-yl)-3-methyloxazolidin-2-one and 2,4,5-trichloro pyrimidine |
| Intermediate D3k: 4-chloro-6-((2,5-dichloropyrimidin-4-yl)amino)-1,3-bis(3-hydroxy-3-methylbutyl)-1,3-dihydro-2H-benzo[d]imidazol-2-one | LCMS (Method T2) Rt 1.47 min, m/z 524.10 [M + Na]+ | Intermediate A6i: 6-amino-4-chloro-1,3-bis(3-hydroxy-3-methylbutyl)-1,3-dihydro-2H-benzo[d]imidazol-2-one |

TABLE 22-continued

Compounds prepared by a method analogous to that used for the preparation of Example 22a

| Intermediate | Data | Starting from |
|---|---|---|
| Intermediate D3l: 6-((2,5-dichloropyrimidin-4-yl)amino)-1,3-bis(3-hydroxy-3-methylbutyl)-1,3-dihydro-2H-imidazo[4,5-b]pyridin-2-one 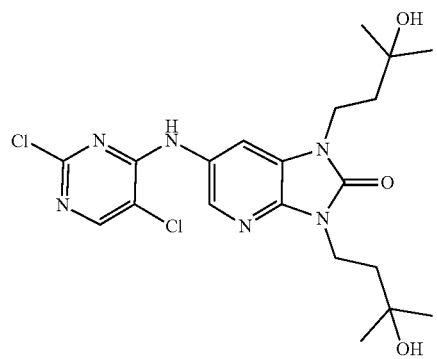 [SMILES: CC(C)(O)CCn1c(=O)n(CCC(C)(C)O)c2ncc(Nc3nc(Cl)ncc3Cl)cc21] | LCMS (Method X2) Rt 1.30 min; m/z 491.1349 [M + Na]$^+$. | Intermediate A6h: 6-amino-1,3-bis(3-hydroxy-3-methylbutyl)-1,3-dihydro-2H-imidazo[4,5-b]pyridin-2-one |

Intermediate D4: 5-[(2,5-dichloropyrimidin-4-yl)amino]-3-(3,5-dihydroxy-3-methyl-pentyl)-1-methyl-benzimidazol-2-one

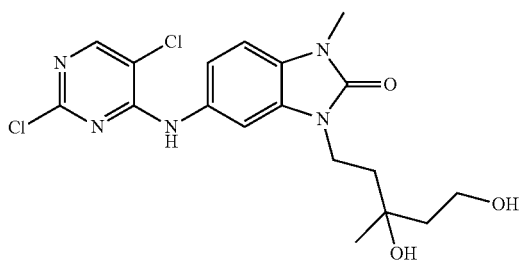 [SMILES: Cn1c(=O)n(CCC(C)(O)CCO)c2cc(Nc3nc(Cl)ncc3Cl)ccc21]

To a solution of 5-[(2,5-dichloropyrimidin-4-yl)amino]-1-methyl-3-[2-(4-methyl-2-phenyl-1,3-dioxan-4-yl)ethyl]benzimidazol-2-one (intermediate D3b, 60 mg, 0.12 mmol) in DCM (2.3 mL) was added trifluoroacetic acid (0.01 mL, 0.14 mmol) dropwise at room temperature. The mixture was stirred for 1 h, and then it was cooled to 0° C. and 2 M NaOH (2.5 mL) was added dropwise. The mixture was stirred for 20 min at room temperature, then the layers were separated and the aqueous layer was extracted with further DCM. Purification by reverse phase chromatography (12 g column, gradient 30 to 80% MeOH in water, both modified with 0.1% formic acid) gave the title compound (28 mg, 56%, 0.0657 mmol) as a white solid. LCMS (Method T2): Rt 1.33 min, m/z 426.11 [M+H]$^+$.

Intermediate E1: 4,6-Dichloro-5-cyano-N-methyl-pyridine-2-carboxamide

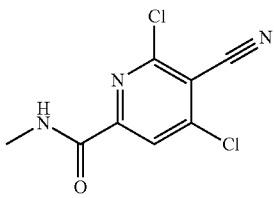

4,6-Dichloro-5-cyano-pyridine-2-carboxylic acid (310 mg, 1.43 mmol) was suspended in DCM (15 mL) and DMF (0.06 mL) under argon and cooled to 0° C. Oxalyl chloride 2M in DCM (1.50 mL, 3 mmol) was added dropwise over 15 minutes. The mixture was stirred at room temperature for 1h under nitrogen, after which time all material was in solution, then cooled again to 0° C. Methanamine 2M in THF (3.50 mL, 7 mmol) was added dropwise over 10 mins and the resulting mixture continued to stir at 0° C. for 1.5h, then warmed to room temperature and opened to air. After 1h, pH was adjusted to pH6 using 10% citric acid/sat sodium bicarbonate solution as required, then the resulting mixture extracted with DCM, using a phase separator cartridge to separate and dry aqueous. Resulting solution was evaporated under reduced pressure to give 4,6-dichloro-5-cyano-N-methyl-pyridine-2-carboxamide as beige solid (280 mg). $^1$H NMR (500 MHz, DMSO-d$_6$) δ 8.98 (q, J=4.4 Hz, 1H), 8.25 (s, 1H), 2.82 (d, J=4.7 Hz, 3H).

Intermediate E2: 4,5-Dichloro-N-ethyl-pyridine-2-carboxamide

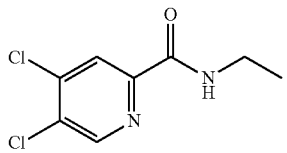

A mixture of 4,5-dichloropyridine-2-carboxylic acid (90 mg, 0.47 mmol), HATU (250 mg, 0.66 mmol) and ethylamine (106 mg, 2.34 mmol) in DMF (3 mL) was stirred at rt overnight. Water was added and the resulting solution was stirred at rt overnight. Precipitate was collected by filtration and dried to give the title compound (24 mg). $^1$H NMR (500 MHz, DMSO-$d_6$) δ 8.93 (br m, 1H), 8.83 (s, 1H), 8.17 (s, 1H), 3.38-3.27 (m, 2H), 1.11 (t, J=7.2 Hz, 3H).

Intermediate E3a: 5-chloro-2-[(3S,5R)-3,5-dimethyl-1-piperidyl]-4-iodo-pyridine

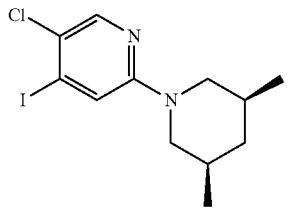 [SMILES: C[C@@H]1C[C@H](C)CN(c2cc(I)c(Cl)cn2)C1]

A solution of cis-3,5-dimethylpiperidine (0.23 g, 2.0 mmol), 5-chloro-2-fluoro-4-iodo-pyridine (0.53 g, 2.0 mmol) and N,N-diisopropylethylamine (0.53 mL, 3.1 mmol) in THF (8 mL) was heated in a sealed vial to 100° C. for 16h. When cooled, water was added to the THF solution and extracted with EtOAc. The combined organic layers were washed with water twice and dried with $Na_2SO_4$. Flash column chromatography (4% ethyl acetate in cyclohexane) gave 5-chloro-2-[(3S,5R)-3,5-dimethyl-1-piperidyl]-4-iodo-pyridine (488 mg) as a white solid. LCMS (Method T2) Rt=1.48 mins, m/z 351.0 [M+H]$^+$.

The following tabulated intermediates were prepared by a method analogous to that used for the preparation of intermediate E3a. Extended heating times were used as follows: 32h for intermediate E3b, 56h for Intermediate E3c, and 5 days for Intermediate E3d.

TABLE 23

Compounds prepared by a method analogous to that used for the preparation of Intermediate E3a.

| Intermediate | Data |
| --- | --- |
| Intermediate E3b: 5-chloro-2-(4,4-difluoro-1-piperidyl)-4-iodo-pyridine | LCMS (Method T2) Rt = 1.63 mins, m/z 359.0 [M + H]$^+$. |

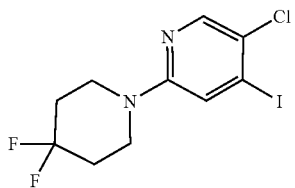 [SMILES: FC1(F)CCN(c2cc(I)c(Cl)cn2)CC1]

TABLE 23-continued

Compounds prepared by a method analogous to that used for the preparation of Intermediate E3a.

| Intermediate | Data |
| --- | --- |
| Intermediate E3c: (2S,6R)-4-(5-chloro-4-iodo-2-pyridyl)-2,6-dimethyl-morpholine | LCMS (Method T2) Rt = 1.63 mins, m/z 353.0 [M + H]$^+$. |
| Intermediate E3d: 1-(5-chloro-4-iodo-2-pyridyl)-N,N-dimethyl-piperidine-4-carboxamide | LCMS (Method T2) Rt = 1.49 mins, m/z 394.0 [M + H]$^+$. |

Intermediate F1: 2-(Oxiran-2-yl)propan-2-ol

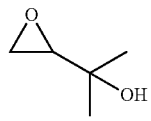

To a stirred solution of 2-methylbut-3-en-2-ol (1.05 mL, 10.0 mmol) in DCM (25 mL) at 0° C. was added portionwise m-CPBA (2.50 g, 11.2 mmol) and the resulting mixture stirred at room temperature overnight. White precipitate was removed by filtration, washing with DCM. Combined filtrate and washings were washed with a 10% aq solution of sodium sulfite (3×15 mL), sat. sodium bicarbonate (2×15 mL), passed through a phase separator and evaporated under reduced pressure (water bath 25° C., 500 mbar, then 2 mins at 300 mbar) to give the title compound as a 1:1 mixture with DCM (560 mg, clear liquid). $^1$H NMR (500 MHz, chloroform-d) 2.96 (dd, J=4.0, 2.8 Hz, 1H), 2.82 (dd, J=5.0, 2.8 Hz, 1H), 2.74 (dd, J=5.0, 4.0 Hz, 1H), 1.69 (s, 1H), 1.35 (s, 3H), 1.25 (s, 3H). Also 5.31 (2H, residual DCM).

Intermediate F2: tert-butyl-dimethyl-[2-(2-methyl-oxiran-2-yl)ethoxy]silane

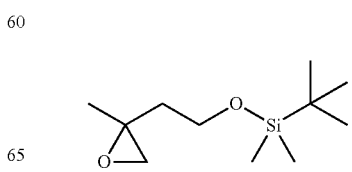

Step 1: tert-butyl-dimethyl-(3-methylbut-3-enoxy)silane

A mixture of 3-methylbut-3-en-1-ol (3.52 mL, 34.83 mmol), tert-butyldimethylsilyl chloride (6.3 g, 41.80 mmol) and Imidazole (4.75 g, 69.66 mmol) in DCM (113 mL) was stirred at room temperature for 18 h. The reaction was quenched with aqueous NH$_4$Cl, the layers were separated and the aqueous layer was extracted with DCM. Purification by column chromatography (100g column, 1 to 10% EtOAc in cHex, 15 CV) gave the title compound (6.85 g, 98%, 34.18 mmol) as a colourless oil. $^1$H NMR (Chloroform-d, 500 MHz): δ 4.77 (1H, s), 4.71 (1H, s), 3.73 (2H, t, J 7.3 Hz), 2.26 (2H, t, J 7.3 Hz), 1.75 (3H, s), 0.91 (9H, s), 0.07 (6H, s).

Step 2: tert-butyl-dimethyl-[2-(2-methyloxiran-2-yl)ethoxy]silane

To a solution of tert-butyl-dimethyl-(3-methylbut-3-enoxy)silane (from previous step, 2.0 g, 10 mmol) in DCM (100 mL) was added m-CPBA (2.58 g, 15 mmol) at room temperature, then it was quenched by the addition of saturated aqueous Na$_2$S$_2$O$_3$ (100 mL). The layers were separated, the organic layer was washed with saturated aqueous NaHCO$_3$ and the combined aqueous layers were extracted with DCM. The organic layers were combined, dried over MgSO$_4$ and concentrated under reduced pressure, giving the title compound (2.1 g, 97%, 9.7 mmol) as an oil. $^1$H NMR (Chloroform-d, 500 MHz): δ 3.78-3.70 (2H, m), 2.70 (1H, d, J 5.0 Hz), 2.60 (1H, d, J 5.0 Hz), 1.88 (1H, m), 1.71 (1H, m), 1.36 (3H, s), 0.90 (9H, s), 0.06 (6H, s).

Intermediate G1a: 1-[tert-butyl(dimethyl)silyl]oxy-3-methyl-pentan-3-ol

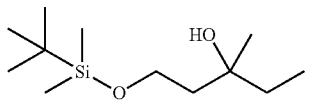

Step 1: 4-[tert-butyl(dimethyl)silyl]oxybutan-2-one

A mixture of 4-hydroxy-2-butanone (1.0 g, 11.35 mmol), tert-butyldimethylsilyl chloride (2.05 g, 13.62 mmol) and Imidazole (1.55 g, 22.70 mmol) in DCM (100 mL) was stirred at room temperature for 18 h. The reaction was quenched with aqueous NH$_4$Cl, the layers were separated and the aqueous layer was extracted with DCM. Purification by column chromatography (50g column, 5 to 15% EtOAc in cHex, 15 CV) gave 4-[tert-butyl(dimethyl)silyl]oxybutan-2-one (2.29 g, 100%, 11.32 mmol) as a colourless oil. $^1$H NMR (Chloroform-d, 500 MHz): δ 3.90 (2H, t, J 6.1 Hz), 2.63 (2H, t, J 6.1 Hz), 2.19 (3H, s), 0.89 (9H, s), 0.06 (6H, s).

Step 2: 1-[tert-butyl(dimethyl)silyl]oxy-3-methyl-pentan-3-ol

A solution of 4-[tert-butyl(dimethyl)silyl]oxybutan-2-one (from previous step, 560 mg, 2.77 mmol) in THF (25 mL) under a N$_2$ atmosphere was cooled to 0 C and ethylmagnesium chloride (2 M in THF, 2.08 mL, 4.15 mmol) was added dropwise. The mixture was stirred for 3 h at 0 C. The reaction was quenched with saturated aqueous NH$_4$Cl, EtOAc was added and the layers were separated. The aqueous layer was extracted with further EtOAc, the organic layers were combined, dried over MgSO$_4$ and concentrated under reduced pressure. Purification by column chromatography (50g column, 5-25% EtOAc in cHex, 13 CV) gave 1-[tert-butyl(dimethyl)silyl]oxy-3-methyl-pentan-3-ol (570 mg, 80%, 2.21 mmol) as a clear oil. $^1$H NMR (Chloroform-d, 500 MHz): δ 3.95-3.87 (2H, m), 1.75 (1H, m), 1.64 (1H, m), 1.59-1.50 (2H, m), 1.19 (3H, s), 0.93-0.90 (12H, m), 0.10 (6H, s).

Intermediate G1b: 1-((tert-butyldimethylsilyl)oxy)-3,4-dimethylpentan-3-ol

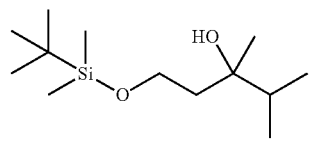 [SMILES: CC(C)C(C)(O)CCO[Si](C)(C)C(C)(C)C]

Prepared by a 2 step method by analogy to intermediate G1a. $^1$H NMR (Chloroform-d, 500 MHz) d 3.95-3.88 (2H, m), 1.85-1.75 (2H, m), 1.62 (1H, ddd, J 14.5, 5.6, 4.2 Hz), 1.12 (3H, s), 0.96 (3H, d, J 7.2 Hz), 0.93-0.91 (12H, m), 0.10 (6H, s).

Intermediate G2: 1-((tert-butyldimethylsilyl)oxy)-3-methyl-6-(trimethylsilyl)hex-5-yn-3-ol

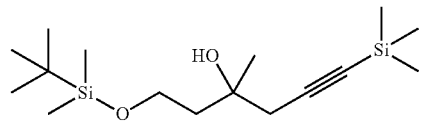 [SMILES: CC(O)(CC#C[Si](C)(C)C)CCO[Si](C)(C)C(C)(C)C]

To a solution of 2-trimethylsilylethylene (0.32 mL, 2.31 mmol) in THF (8 mL) at −78 C was added n-BuLi (1.44 mL, 2.31 mmol) dropwise. The mixture was stirred at −78 C for 30 min, then tert-butyl-dimethyl-[2-(2-methyloxiran-2-yl)ethoxy]silane (intermediate F2, 250 mg, 1.16 mmol) was added dropwise (dissolved in 2 mL THF), followed by BF$_3$-Et$_2$O (0.21 mL, 1.73 mmol). The mixture was stirred for 1 h at −78 C. The reaction was quenched with saturated aqueous NH$_4$Cl, EtOAc was added and the layers were separated. The aqueous layer was extracted with EtOAc. The organic layers were combined, dried over MgSO$_4$ and concentrated under reduced pressure. Purification by column chromatography (25g column, 5 to 50% EtOAc in cHex) gave the title compound (246 mg, 68%, 0.78 mmol) as a colourless oil. $^1$H NMR (Chloroform-d, 500 MHz): δ 3.97-3.89 (2H, m), 2.50 (1H, d, J 16.7 Hz), 2.46 (1H, d, J 16.7 Hz), 1.90 (1H, ddd, J 14.1, 6.4, 4.9 Hz), 1.81 (1H, ddd, J 14.1, 7.0, 5.1 Hz), 1.33 (3H, s), 0.91 (9H, s), 0.16 (9H, s), 0.11 (6H, s).

Intermediate G3: 2-(4-methyl-2-phenyl-1,3-dioxan-4-yl)ethanol

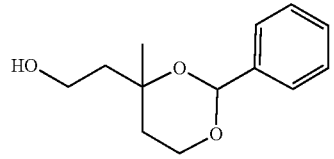 [SMILES: CC1(CCO)CCOC(c2ccccc2)O1]

A solution of 3-Methyl-1,3,5-pentanetriol (1.0 g, 0.89 mL, 7.45 mmol), benzaldehyde (2.27 mL, 22.36 mmol) and p-toluenesulfonic acid monohydrate (14 mg, 0.07 mmol) in toluene (35 mL) was heated to 60 C for 18 h 2M NaOH and EtOAc were added, the layers were separated and the aqueous layer was extracted with further EtOAc. The organic layers were combined, dried over MgSO₄ and concentrated under reduced pressure, to give the title compound (1.65 g, 100%, 7.45 mmol) as a clear oil. ¹H NMR (Chloroform-d, 500 MHz): δ 7.48-7.45 (2H, m), 7.38-7.33 (3H, m), 5.75 (1H, s), 4.19-4.10 (2H, m), 3.94-3.85 (2H, m), 2.28-2.03 (4H, m), 1.54 (3H, s).

Intermediate G4a: [(2S)-1-(2,2,2-trifluoroethyl)pyrrolidin-2-yl]methanol N5104-51 bbellenie

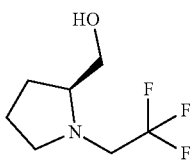 [SMILES: OC[C@@H]1CCCN1CC(F)(F)F]

To a solution of (S)-(+)-2-(hydroxymethyl)pyrrolidine (0.1 mL, 1.0 mmol) [L-prolinol] in acetonitrile (2 mL) was added potassium carbonate (150 mg, 1.1 mmol). The resulting mixture was cooled in an ice bath under nitrogen, then 2,2,2-trifluoroethyl trifluoromethanesulphonate (0.15 mL, 1.04 mmol) was added dropwise and the resulting mixture stirred at 0° C. for 1h, then allowed to warm to room temperature and stirred overnight. Added water (~2 mL) and extracted with DCM (3×2 mL), using a phase separator to separate and dry. Organics evaporated and purified by flash column chromatography (10g KP-SIL, 10-40% ethyl acetate in cyclohexane) to give a clear oil [(2S)-1-(2,2,2-trifluoroethyl)pyrrolidin-2-yl]methanol (106 mg, 51%). ¹H NMR (600 MHz, Chloroform-d) δ 3.63 (dd, J=11.3, 3.5 Hz, 1H), 3.49-3.43 (m, 1H), 3.41-3.21 (m, 2H), 3.08 (dq, J=14.7, 8.8 Hz, 1H), 2.86 (m, 1H), 2.56 (app q, J=8.3 Hz, 1H), 2.32 (s, 1H, OH), 1.98-1.86 (m, 1H), 1.88-1.76 (m, 3H).

The following tabulated intermediates were prepared by a method analogous to that used for the preparation of intermediate G4a, using the intermediates shown in Table 24. For the preparation of intermediate G4g, the reaction was heated to 60° C. overnight.

TABLE 24

Compounds prepared by a method analogous to that used for the preparation of Intermediate G4a

| Intermediate | Data | Starting from |
|---|---|---|
| Intermediate G4b: [4-(2,2,2-trifluoroethyl)morpholin-3-yl]methanol | ¹H NMR (600 MHz, Chloroform-d) δ 3.87-3.75 (m, 3H), 3.69-3.61 (m, 3H), 3.40 (dq, J = 15.4, 9.8 Hz, 1H), 3.14-2.99 (m, 2H), 2.77-2.68 (m, 2H), 1.95 (br, 1H). | 3-hydroxymethyl morpholine, 2,2,2-trifluoroethyl trifluoromethane-sulfonate |
| Intermediate G4c: [1-(2,2,2-trifluoroethyl)-2-piperidyl]methanol | ¹H NMR (600 MHz, Chloroform-d) δ 3.65 (br m, 2H), 3.32 (dq, J = 15.5, 9.8 Hz, 1H), 3.18-3.08 (m, 1H), 3.11-3.04 (m, 1H), 2.67 (m, 1H), 2.60 (ddd, J = 12.4, 8.7, 3.2 Hz, 1H), 2.22 (t, J = 5.3 Hz, 1H, OH), 1.77-1.62 (m, 2H), 1.58 (m, 1H), 1.55-1.36 (m, 3H). | 2-piperidine methanol, 2,2,2-trifluoroethyl trifluoromethane-sulfonate |
| Intermediate G4d: [(2S,4S)-4-fluoro-1-(2,2,2-trifluoroethyl)pyrrolidin-2-yl]methanol | ¹H NMR (600 MHz, Chloroform-d) δ 5.17 (dm, J = 54 Hz, 1H), 3.70 (dd, J = 11.5, 3.2 Hz, 1H), 3.64-3.56 (m, 1H), 3.55 (m, 1H), 3.38 (dq, J = 14.9, 10.1 Hz, 1H), 3.07 (dq, J = 14.8, 8.7 Hz, 1H), 2.99 (m, 1H), 2.77 (m, 1H), 2.32 (m, 1H), 2.15 (m, 1H), | ((2S,4S)-4-fluoropyrrolidin-2-yl)methanol hydrochloride, 2,2,2-trifluoroethyl-trifluoromethane-sulfonate |

TABLE 24-continued

Compounds prepared by a method analogous to that used for the preparation of Intermediate G4a

| Intermediate | Data | Starting from |
|---|---|---|
| Intermediate G4e: [(2S)-1-(2,2-difluoroethyl)pyrrolidin-2-yl]methanol | $^1$H NMR (600 MHz, Chloroform-d) δ 5.86 (tt, J = 56.0, 4.2 Hz, 1H), 3.63 (dd, J = 11.1, 3.5 Hz, 1H), 3.45 (dd, J = 11.1, 3.1 Hz, 1H), 3.29 (m, 1H), 3.12 (m, 1H), 2.83 (m, 1H), 2.81-2.75 (m, 1H), 2.49 (app q, J = 8.4 Hz, 1H), 1.96-1.86 (m, 1H), 1.85-1.74 (m, 3H). | (S)-(+)-2-(hydroxymethyl)-pyrrolidine, 2,2-difluoroethyl-trifluoromethane-sulfonate |
| Intermediate G4f: [(2S)-1-[2-[tert-butyl(dimethyl)silyl]oxyethyl]-pyrrolidin-2-yl]methanol | $^1$H NMR (600 MHz, Chloroform-d) δ 3.76-3.70 (m, 2H), 3.63 (dd, J = 10.8, 3.5 Hz, 1H), 3.38 (dd, J = 10.8, 3.5 Hz, 1H), 3.23 (m, 1H, 5pyrr), 2.92 (dt, J = 13.1, 6.6 Hz, 1H), 2.72 (br m, 1H), 2.57-2.50 (m, 1H), 2.40 (app q, J = 8.5 Hz, 1H), 1.92-1.83 (m, 1H), 1.80-1.75 (m, 1H), 1.78-1.69 (m, 2H), 0.92 (s, 9H), 0.09 (s, 6H). | (S)-(+)-2-(hydroxymethyl)-pyrrolidine, 2-bromoethoxy-t-butyl dimethylsilane |
| Intermediate G4g: [(2S)-1-(2-fluoroethyl)pyrrolidin-2-yl]methanol | $^1$H NMR (600 MHz, Chloroform-d) δ 4.59 (dm, J = 47.4Hz, 2H), 3.64 (dd, J = 10.9, 3.6 Hz, 1H), 3.43 (dd, J = 10.9, 2.9 Hz, 1H), 3.27 (m, 1H), 3.08 (dddd, J = 27.9, 14.0, 6.6, 4.1 Hz, 1H), 2.75-2.64 (m, 2H), 2.46-2.36 (m, 1H), 1.97-1.85 (m, 1H), 1.85-1.74 (m, 3H). | (S)-(+)-2-(hydroxymethyl)-pyrrolidine, 2-fluoroethyl 4-methylbenzene-sulfonate |

Intermediate G5: tert-butyl N-ethyl-N-(3-hydroxy-1-methyl-propyl)carbamate

To a solution of 3-(ethylamino)-1-butanol (500 mg, 4.3 mmol) in DCM (5 mL) under nitrogen was added triethylamine (0.7 mL, 5 mmol). The resulting mixture was cooled to 0° C. and a solution of di-tert-butyl dicarbonate (1.15g, 5.1 mmol) in DCM (2 mL) was added dropwise, and the resulting mixture stirred at room temperature for 2 days, then quenched by addition of a saturated solution of sodium bicarbonate. The organic layer was separated, dried over sodium sulfate, filtered and concentrated in vacuo. The residue was purified by flash column chromatography (25g KP-SIL, 5-40% ethyl acetate in cyclohexane) to give tert-butyl N-ethyl-N-(3-hydroxy-1-methyl-propyl)carbamate (750 mg, 81%, 3.4513 mmol) as clear oil. $^1$H NMR (500 MHz, Chloroform-d) δ 4.45 (br m, 1H), 3.58 (dt, J=12.0, 4.1 Hz, 1H), 3.42 (br m, 1H), 3.18 (dq, J=14.0, 7.0 Hz, 1H), 2.96 (br m, 1H), 1.71 (m, 1H), 1.51 (s, 9H) overlapping with ~1.5 (br m, 1H), 1.22 (d, J=7.0 Hz, 3H), 1.16 (t, J=7.0 Hz, 3H).

Intermediate G6a: 2,3-dimethylbutane-1,3-diol

Lithium aluminium hydride 1M in THF (3.5 mL, 3.5 mmol) under nitrogen at 0° C. was diluted with dry diethyl ether (5 mL). A solution of ethyl 3-hydroxy-2,3-dimethyl-butanoate (250 mg, 1.56 mmol) in dry diethyl ether (5 mL) was added dropwise over 20 minutes, resulting mixture allowed to warm to room temperature and stirred for 2 hours. Cooled to OC and very carefully quenched by addition of water (0.13 mL); 2M aq sodium hydroxide solution (0.13 mL); and water (0.4 mL). Stirred for 30 mins at room temperature then filtered to remove white precipitate, washing with diethyl ether. Solvents evaporated under reduced pressure to obtain the title compound as a clear liquid (214 mg). $^1$H NMR (500 MHz, Chloroform-d) δ 3.80-3.68 (m, 2H), 2.88 (s, 1H, OH), 2.55 (s, 1H, OH), 1.91-1.78 (m, 1H), 1.29 (s, 3H), 1.21 (s, 3H), 0.89 (d, J=7.1 Hz, 3H).

Intermediate G6b:
4,4,4-trifluoro-3-methyl-butane-1,3-diol

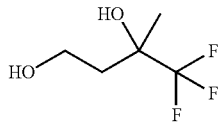

Prepared from ethyl 4,4,4-trifluoro-3-hydroxy-3-methyl-butanoate by analogy to Intermediate G6a. $^1$H NMR (500 MHz, Chloroform-d) δ 4.02 (m, 2H), 2.14-2.04 (m, 1H), 1.92-1.81 (m, 1H), 1.43 (s, 3H).

Intermediate G7:
3-methyl-2-methylene-butane-1,3-diol

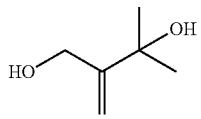

Step 1: ethyl 2-(hydroxymethyl)prop-2-enoate

A solution of ethyl acrylate (1.08 mL, 10 mmol), formaldehyde (37% in H$_2$O, 2.5 mL, 30 mmol) and DABCO (3.36 g, 30 mmol) in H$_2$O:Dioxane 1:1 (50 ML total) was stirred at room temperature for 3 days. Aqueous NH$_4$Cl and Et$_2$O were added and the layers were separated. The aqueous layer was extracted with further Et$_2$O. The organic layers were combined, dried over MgSO$_4$ and concentrated under reduced pressure. Purification by column chromatography (50 g column, 10 to 50% EtOAc in cHex) gave the title compound (1.0 g, 77%, 7.68 mmol) as a clear oil. $^1$H NMR (Chloroform-d, 500 MHz): δ 6.27 (1H, s), 5.84 (1H, q, J 1.3 Hz), 4.36-4.33 (2H, m), 4.26 (2H, q, J 7.2 Hz), 1.33 (3H, t, J 7.2 Hz).

Step 2: 3-methyl-2-methylene-butane-1,3-diol

A solution of ethyl 2-(hydroxymethyl)prop-2-enoate (from previous step, 900 mg, 6.92 mmol) in THF (40 mL) under a N$_2$ atmosphere was cooled to 0 C and methylmagnesium bromide (3 M in Et$_2$O, 8.07 mL, 24.21 mmol) was added dropwise. The mixture was stirred for 18 h, slowly warming to room temperature. Water and EtOAc were added, the layers were separated and the aqueous layer was extracted with further EtOAc. The organic layers were combined, dried over MgSO$_4$ and concentrated under reduced pressure. Purification by column chromatography (25 g column, 20 to 80% EtOAc in cHex) gave the title compound (312 mg, 39%, 2.69 mmol) as a clear oil. $^1$H NMR (Chloroform-d, 500 MHz): δ 5.13 (1H, s), 5.09 (1H, s), 4.31 (2H, s), 1.44 (6H, s).

Intermediate G8:
4-methoxy-3-methyl-butane-1,3-diol

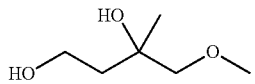

To tert-butyl-dimethyl-[2-(2-methyloxiran-2-yl)ethoxy] silane (intermediate F2, 500 mg, 2.31 mmol) was added NaOMe (0.5 M in MeOH, 11.55 mL, 5.78 mmol). The mixture was heated to 65 C for 18 h. EtOAc and aqueous NH4Cl were added, the layers were separated and the aqueous layer was extracted with further EtOAc. The organic layers were combined, dried over MgSO$_4$ and concentrated under reduced pressure, to give the title compound (300 mg, 97%, 2.24 mmol) as a clear oil. $^1$H NMR (Chloroform-d, 500 MHz): δ 3.90 (1H, m), 3.80 (1H, m), 3.42 (3H, s), 3.33 (1H, d, J 9.1 Hz), 3.27 (1H, d, J 9.1 Hz), 1.83 (1H, m), 1.69 (1H, m), 1.26 (3H, s).

Intermediate H1: 2-(5-(((5-chloro-2-((3S,5R)-4,4-difluoro-3,5-dimethylpiperidin-1-yl)pyrimidin-4-yl) amino)-3-(3-hydroxy-3-methylbutyl)-2-oxo-2,3-dihydro-1H-benzo[d]imidazol-1-yl)acetaldehyde

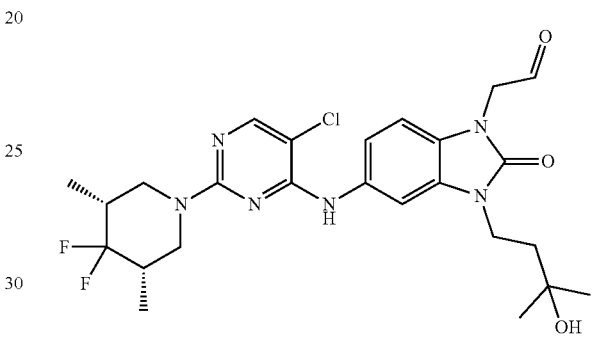

TFA (3.00 mL, 0.5008 mmol) was added dropwise to a solution of 5-((5-chloro-2-((3S,5R)-4,4-difluoro-3,5-dimethylpiperidin-1-yl)pyrimidin-4-yl)amino)-1-(2,2-dimethoxyethyl)-3-(3-hydroxy-3-methylbutyl)-1,3-dihydro-2H-benzo[d]imidazol-2-one (Example 41a, 292 mg, 0.5 mmol) in THF (4 mL) and water (2 mL). The solution was stirred at rt for 1 hour then at 70° C. for 2.5 hours. LCMS (Method T2) Rt=1.58 mins, m/z The mixture was concentrated in vacuo to remove the excess TFA and THF. The residue was then taken up in water and DCM then washed with sat. aq. NaHCO$_3$ to quenched residual TFA. The mixture was extracted with DCM and the combined organic extracts washed with brine then dried over MgSO$_4$, filtered and concentrated. The product was used without further purification. LCMS (Method T2) Rt=1.58 mins, m/z 537.21 [M+H]$^+$ and 569.23 [M+MeOH$_2$]$^+$.

HTRF Assay

Each 15 µL HTRF reaction in a 384-well black Proxiplate (Perkin Elmer) contained either 1 nM (data in table 1b) or 10 nM (data in table 1a) Trx-6×His-BCL6 (in house-produced, human BCL6 BTB domain covering amino-acid sequence 5-129), 300 nM BCOR-AF633 peptide (RSEISTAPSS-WVVPGP-Cys-AlexaFluor 633-amide, Cambridge Research Biochemical) and 0.5 nM (data in table 1b) or 1 nM (data in table 1a) anti-6×His-Terbium cryptate (CisBio Bioassays, France), in assay buffer (25 mM Hepes pH8, 100 mM NaCl, 0.05% Tween20, 0.5 mM TCEP, 0.05% bovine serum albumin). Test compounds in DMSO or DMSO alone were added to the wells using an ECHO550 acoustic dispenser (Labcyte Inc) to give the appropriate test concentration in 0.7% v/v DMSO final. After 2 hours incubation at room temperature the plate was read on an Envision plate reader (Perkin Elmer) with 337 nm laser excitation, a first emission filter APC 665 nm and a second emission filter Europium 615 nm. The % inhibition at each concentration was calculated by normalising FRET ratio to the appropriate high (DMSO with all reagents) and low (DMSO without BCL6) controls. The compound $IC_{50}$s were determined using GraphPad Prism 6.0 or Dotmatics (Bishops Stortford, UK) software by fitting the normalised data to a sigmoidal four-parameter logistic fit equation.

The results of this assay are shown in Table 1a and Table 1b above.

NanoBRET Assay

A cellular nano-Bioluminescence Resonance Energy Transfer (nanoBRET) assay (Promega NanoBRET Nano-Glo Detection System, catalogue number N1662) was used to detect inhibition of the BCL6-NCOR2(SMRT) corepressor protein-protein interaction. DNA encoding full length BCL6 and NCOR2 were inserted into pFC32K.NanoLuc and pFC14K.HaloTag vectors (Promega) to produce C-terminal tagged fusion proteins BCL6-nanoLuc and NCOR2-HaloTag, respectively. HEK293T cells were plated ($5 \times 10^5$) in T75 tissue culture flask and bulk transfected 48 hours later with Fugene 6 (Promega cat. #E2691) reagent and 18 µg total DNA plasmids encoding BCL6-nanoLuc as donor and NCOR2-HaloTag as acceptor, at a donor:acceptor DNA ratio of 1:25. At 24 hr post-transfection, HEK293T cells were collected and stored in liquid nitrogen in 90% FBS (PAN Biotech UK) and 10% DMSO. At the time of assay, compounds (100 nL/well) and NanoBRET 618 ligand (10 nL of 1 mg/ml stock solution per well) were dispensed in a dry 384-well NUNC white assay plate (ThermoScientific NUNC cat. #10080681) using Echo550 acoustic dispensing (Labcyte Inc.). Frozen transfected HEK293T cells were thawed, centrifuged and freezing medium was replaced by phenol red-free OptiMEM+4% FBS (Life Technology). The cell density was adjusted to $3 \times 10^5$ cells/ml and 20 µL (6000 cells) were plated in each well containing test compounds (0.0125-50 µM) in DMSO or DMSO alone and 0.5 µg/ml NanoBRET 618 fluorescence ligand, in 0.55% v/v DMSO final concentration. Cells were incubated for 6 hr at 37° C./5% C02 then NanoBRET furimazine substrate (Promega) was added to give a final concentration of 10 µM. After a short centrifugation the plates were read on an Envision (Perkin Elmer) plate reader equipped with a LUM/D600 Dual mirror, Lum 450/40 nm bandpass and D605 nm longpass filters, with a 0.2 sec reading to determine the BRET ratio. The % inhibition at each test concentration was calculated by normalising the BRET ratio to the appropriate high and low controls. The compound $IC_{50}$s were determined using Graphpad Prism 6.0 or Dotmatics software by fitting the normalised data to a sigmoidal four-parameter logistic fit equation.

The results obtained using this assay are shown in Tables 2a and 2b above.

Immunofluorescence-Based BCL6 Degradation Assay $DC_{50}$ values (compound concentration at which 50% of endogenous BCL6 protein is degraded) were determined in SUDHL-4 cells (American Type Culture Collection) in an immunofluorescence-based assay using an InCell2200 high content imaging system (GE Healthcare). Briefly, 40 µL of lymphoma suspension cells cultured in RPMI 1640-10% FBS (Sigma-Aldrich or PAN Biotech UK Ltd) were platted on fibronectin (Sigma catalogue F1141)-coated 384 well Cell Carrier Ultra plate (Perkin Elmer catalogue 6057300) at 1.2 104 cells/well. After 20 hours cell culture at 37° C./CO2 incubator, compounds were dispensed in the cell culture plate using ECHO550 acoustic dispenser (Labcyte, Inc.), as 8 point-concentration response (ranging from 5 nM to 10 µM) in 0.67% final DMSO concentration. Cells were incubated with compound for 2 hours at 37° C./CO2 incubator followed by fixation in 4.5% formaldehyde (37% formaldehyde solution, Sigma catalogue F8775) at room temperature for 15 min. After fixing, cells were washed in 1×TBS (Tris Buffer Saline) using a Power Washer 384 (Tecan Group Ltd). Blocking and cell permeabilisation were performed by incubating the fixed cells for 1 hour at room temperature in 1×TBS, 5% BSA, 1% Triton X100, followed by three washes on PW384 plate washer. Primary and secondary antibodies were prepared in 1×TBS, 1% BSA, 0.2% Triton X100. BCL6 expression was detected by incubating the cells for 1h30 with BCL6 rabbit polyclonal antibody (Sigma Catalogue HPA004899) at 1:250, 0.8 µg/ml, followed by 1 hour in chicken anti-Rabbit Alexa 488 conjugated antibody (Life Technology) at 1:500. After incubation in each antibody, cells were washes four times in 1×TBS-0.05% tween on PW384 plate washer. Cells were finally incubated for 60 min with nuclear staining RedDot2 dye (Biotium) at 0.5× the stock concentration in 1×TBS. BCL6 expression in the absence or presence of compound was detected on InCell2200 with 20× objective and quantified on InCell Analyser 3.7.2 workstation (GE Healthcare). The % response at each concentration was calculated by normalising BCL6 expression in the presence of compound to the appropriate high (DMSO) and low (DMSO with 7 µM CCT369260) controls. The compound DC50s were determined using GraphPad Prism 6.0 or Dotmatics (Bishops Stortford, UK) software by fitting the normalised data to a sigmoidal four-parameter logistic fit equation.

14-Day Cell Proliferation Assay

SU-DHL-4 cells were seeded in 96-well culture plates at a density of 2000 cells/well in RPMI-1640 medium (Sigma-Aldrich) supplemented with 10% FBS (Gibco). Compounds were initially dispensed into 96-well U-bottom plates using an Echo 550 acoustic dispenser (Labcyte Inc.), then diluted in RPMI-1640 medium and transferred onto the cells. Cells were treated with 8 compound concentrations in duplicate, ranging from 1 nM to 10 µM, in a final DMSO concentration of 0.1% and final volume of 100 µl. Cells were incubated with compound for 14 days, with medium changes at days 3, 7 and 10 carried out as follows: fresh 96-well cell culture plates were prepared containing 100 µl medium plus compound at the assay concentrations (white plates were used on day 10 to optimise luminescence measurement). Assay plates containing cells were vortexed to mix and cell density in one control well was counted using a Coulter Z2 cell counter (Beckman Coulter). The volume of medium containing 2000 cells in the control well was calculated and this volume of cells was transferred from every well of the assay plates to the corresponding well of the fresh plates containing compound. After 14 days, CellTiter Glo reagent (Promega) was added to the medium in each well of the assay plate at a ratio of 1:2, mixed on a plate shaker, then incubated at room temperature for 10 minutes. Luminescence was measured using an Envision plate reader (Perkin Elmer) and the relative luminescence at each compound concentration, compared to DMSO alone, was calculated. G150 were determined using a 4-parameter curve fit in Dotmatics (Bishops Stortford, UK).

While specific embodiments of the invention have been described herein for the purpose of reference and illustration, various modifications will be apparent to a person skilled in the art without departing from the scope of the invention as defined by the appended claims.

The invention claimed is:
1. A compound of Formula (I), or a pharmaceutically acceptable salt or solvate thereof, as shown below:

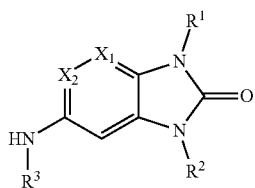

Formula (I)

wherein:
- $X_1$ is selected from N or $CR^a$, wherein $R^a$ is selected from hydrogen, (1-2C)alkyl, halogen, hydroxy, (1-2C)alkoxy, (1-2C)haloalkyl, (1-2C)haloalkoxy, (2-4C)alkenyl, (2-4C)alkynyl, nitro, cyano or $NR^bR^c$, wherein $R^b$ and $R^c$ are independently selected from hydrogen or (1-2C)alkyl;
- X2 is selected from N or $CR^d$, wherein $R^d$ is selected from hydrogen, (1-2C)alkyl, fluoro, chloro, bromo, hydroxy, (1-2C)alkoxy, (1-2C)haloalkyl or (1-2C)haloalkoxy;
- $R^1$ is a group of the formula:

-L-Z wherein:
- L is absent or (1-2C)alkylene; and
- Z is (1-6C)alkyl, (3-6C)cycloalkyl or 4 to 7 membered heterocyclyl; wherein Z is optionally further substituted by one or more substituent groups independently selected from oxo, (1-2C)alkyl, halo, (1-2C)haloalkyl, (1-2C)haloalkoxy, amino, (1-2C)aminoalkyl, cyano, hydroxy, $NR^gR^h$ or $OR^g$; wherein $R^g$ and $R^h$ are each independently selected from hydrogen or (1-2C)alkyl;
- $R^2$ is selected from:
  (i) a group of the formula:

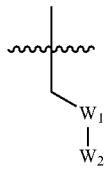

wherein:

denotes the point of attachment;
$W_1$ is selected from $CR^4R^5$ or C(O), wherein $R^4$ and $R^5$ are independently selected from hydrogen, (1-2C)alkyl, fluoro, hydroxy, cyano, nitro, (1-2C)alkoxy, (1-2C)haloalkyl, (1-2C)haloalkoxy or $NR^jR^k$, wherein $R^j$ and $R^k$ are independently selected from hydrogen or (1-2C)alkyl; or
$R^4$ and $R^5$ can be linked such that, together with the carbon atom to which they are attached, they form a 3-6-membered carbocyclic ring or a 3-6-membered heterocyclic ring, which is optionally substituted by one or more substituents selected from (1-2C)alkyl, halo, (1-2C)haloalkyl, (1-2C)haloalkoxy, (1-2C)alkoxy, (1-2C)alkylamino, amino, cyano or hydroxy;
$W_2$ is selected from cyano, a 5- or 6-membered heteroaryl, phenyl, $C(O)R^1$, $SO_2R^1$, $C(O)OCH_3$, $C(O)N(H)CH_3$, $CR^6R^7R^8$ or $NR^lR^m$, wherein $R^l$ and $R^m$ are independently selected from hydrogen or (1-4C)alkyl, and wherein:
- $R^6$ is selected from hydroxy, amino, or (1-2C)alkoxy;
- $R^7$ is selected from hydrogen, (1-2C)alkyl, fluoro, chloro, bromo, hydroxy, cyano, nitro, (1-2C)alkoxy, (1-2C)haloalkyl, (1-2C)haloalkoxy or a group of the formula:

—$Y_2$-$L_2$-$Z_2$ wherein:
- $Y_2$ is absent or selected from O, N(R″), S, SO, $SO_2$, C(O), C(O)O, OC(O), C(O)N(R″), N(R″)C(O), S(O)$_2$N(R″), or N(R″)SO$_2$, wherein R″ is selected from hydrogen or (1-2C)alkyl;
- $L_2$ is absent or (1-2C)alkylene; and
- $Z_2$ is hydrogen, (1-6C)alkyl, (2-4C)alkenyl, (2-4C)alkynyl, phenyl, (3-6C)cycloalkyl, 5-6 membered heteroaryl or a 4-6-membered heterocyclyl; wherein $Z_2$ is optionally substituted by one or more substituents selected from (1-4C)alkyl, halo, (1-4C)haloalkyl, (1-4C)haloalkoxy, (1-4C)alkoxy, (1-4C)alkylamino, amino, cyano, nitro, hydroxy, $C(O)R^o$, $C(O)OR^o$, $OC(O)R^o$, $C(O)N(R^o)R^p$, or $NR^oC(O)R^p$, wherein $R^o$ and $R^p$ are independently selected from hydrogen or (1-4C)alkyl; and
- $R^8$ is selected from (1-2C)alkyl, —$C(O)OR^q$, $OR^q$, or a 5-membered heteroaryl, wherein $R^q$ is selected from hydrogen or (1-2C)alkyl;
or $R^6$ and $R^7$ can be linked such that, together with the carbon atom to which they are attached, they form a 3-6-membered carbocyclic ring or a 3-6-membered heterocyclic ring, which is optionally substituted by one or more substituents selected from (1-2C)alkyl, halo, (1-2C)haloalkyl, (1-2C)haloalkoxy, (1-2C)alkoxy, (1-2C)alkylamino, amino, cyano or hydroxyl; or (ii) a group of the formula:

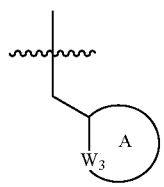

wherein:

denotes the point or attachment;

ring A is a 4 to 6 membered cycloalkyl or heterocyclyl ring, optionally substituted with one or more substituent groups selected from (1-2C)alkyl, halo, hydroxy, cyano or (1-2C)alkoxy;

$W_3$ is selected from $NR^{100}$ or $CR^{101}R^{102}$, wherein $R^{100}$ is selected from hydrogen, (1-2C)alkyl, (1-4C)haloalkyl, (1-4C)hydroxyalkyl, —C(O)—CH$_3$ or —C(O)OR$^{ab}$, wherein R$^{ab}$ is (1-4C)alkyl, $R^{101}$ and $R^{102}$ are each independently selected from hydrogen, (1-2C)alkyl, cyclopropyl, fluoro, chloro, bromo, hydroxy, amino, cyano, nitro, (1-2C)alkoxy, (1-2C)haloalkyl, (1-2C)haloalkoxy, —C(O)OR$^{ac}$, —NR$^{ac}$R$^{ad}$, phenyl or a 5-membered heteroaryl, wherein R$^{ac}$ and R$^{ad}$ are independently selected from hydrogen or (1-2C)alkyl; and $R^3$ is selected from:

i) a group of Formula A shown below:

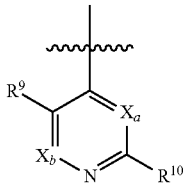

Formula A wherein:

denotes the point of attachment, $X_a$ and $X_b$ are independently selected from N or $CR^{x1}$, wherein $R^{x1}$ is selected from hydrogen, fluoro, chloro, bromo, (1-2C)alkyl, (1-2C)alkoxy, cyano, nitro, acetylenyl, CH$_2$F, CF$_2$H or CF$_3$;

$R^9$ is selected from hydrogen, fluoro, chloro, bromo, (1-2C)alkyl, (1-2C)alkoxy, cyano, nitro, acetylenyl, CH$_2$F, CF$_2$H or CF$_3$;

$R^{10}$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

-$Y_3$-$Z_3$ wherein:

$Y_3$ is absent or O, N(R$^s$)(CR$^s$R$^t$)$_{q1}$ (where $q_1$ is 0, 1 or 2), S, SO, SO$_2$, C(O), C(O)O, OC(O), C(O)N(R$^s$), N(R$^s$)C(O), N(R$^s$)C(O)N(R$^t$), N(R$^s$)C(O)O, OC(O)N(R$^s$), S(O)$_2$N(R$^s$), or N(R$^s$)SO$_2$, wherein R$^s$ and R$^t$ are each independently selected from hydrogen or (1-4C)alkyl; and $Z_3$ is hydrogen, (1-6C)alkyl, aryl, (3-6C)cycloalkyl, (2-4C)alkenyl, (2-4C)alkynyl, (3-6C)cycloalkenyl, heteroaryl or 4 to 11-membered heterocyclyl; wherein $Z_3$ is optionally further substituted by one or more substituent groups independently selected from oxo, (1-4C)alkyl, (3-6C)cycloalkyl, halo, (1-4C)haloalkyl, (1-4C)haloalkoxy, (1-4C)hydroxyalkyl, amino, cyano, hydroxy, amido, carboxy, carbamoyl, sulphamoyl, mercapto, C(O)NR$^u$R$^v$, NR$^u$R$^v$ or OR$^u$, wherein R$^u$ and R$^v$ are each independently selected from hydrogen, (1-4C)alkyl or (3-6C)cycloalkyl; and/or $Z^3$ is optionally further substituted by a group of the formula:

-$L_Z$-$W_Z$ wherein:

$L_Z$ is absent or a (1-5C)alkylene optionally substituted by one or more substituents selected from (1-2C)alkyl or oxo; and $W_Z$ is aryl, heteroaryl, 4- to 7-membered heterocyclyl, 3- to 6-membered carbocyclyl, halo, (1-4C)haloalkyl, (1-4C)haloalkoxy, cyano, hydroxy, (1-4C)alkoxy, C(O)R$^{xa}$, COOR$^{xa}$, C(O)NR$^{xa}$R$^{xb}$ or NR$^{xa}$R$^{xb}$, wherein R$^{xa}$ and R$^{xb}$ are each independently selected from hydrogen or (1-4C)alkyl; and wherein each aryl, heteroaryl, 4- to 7-membered heterocyclyl or 3- to 6-membered carbocyclyl is optionally further substituted by one or more substituent groups independently selected from (1-4C)alkyl, halo, (1-4C)haloalkyl, amino, cyano or hydroxy;

ii) a group of Formula B shown below:

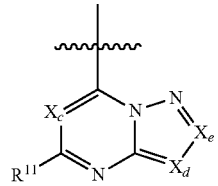

Formula B wherein:

denotes the point of attachment;

$X_c$, $X_d$ and $X_e$ are independently selected from N, CH, CF, CCl, C—CN or CCH$_3$;

$R^{11}$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

-$Y_5$-$Z_5$ wherein:

$Y_5$ is absent or O, N(R$^w$), C(O), C(O)O, OC(O), C(O)N(R$^w$), N(R$^w$)C(O), N(R$^w$)C(O)N(R$^x$), N(R$^w$)C(O)O, OC(O)N(R$^w$), S(O)$_2$N(R$^w$), or N(R$^w$)SO$_2$, wherein R$^w$ and R$^x$ are each independently selected from hydrogen or (1-4C) alkyl; and $Z_5$ is hydrogen, (1-6C)alkyl, aryl, (3-8C)cycloalkyl, (3-8C)cycloalkenyl, heteroaryl or heterocyclyl; wherein $Z_5$ is optionally further substituted by one or more substituent groups independently selected from (1-4C)alkyl, halo, (1-4C)haloalkyl, (1-4C)haloalkoxy, (1-4C)hydroxyalkyl, amino, cyano, hydroxy, amido, carboxy, carbamoyl, sulphamoyl, mercapto, NR$^y$R$^z$, or OR$^y$, wherein R$^y$ and R$^z$ are each independently selected from hydrogen, (1-4C) alkyl or (3-6C)cycloalkyl; or iii) a group of Formula C shown below:

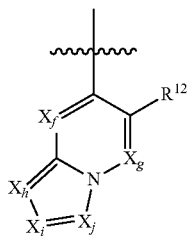

Formula C wherein:

denotes the point of attachment;

R$^{12}$ is selected from fluoro, chloro, bromo, (1-2C) alkyl, (1-2C)alkoxy, cyano, nitro, (2-4C)alkenyl, (2-4C)alkynyl, CH$_2$F, CF$_2$H or CF$_3$;

X$_f$ and X$_g$ are independently selected from N or CR$^{13}$, wherein R$^{13}$ is selected from hydrogen, fluoro, chloro, (1-2C)alkyl, (1-2C)haloalkyl or (1-2C)haloalkoxy;

X$_h$, X$_i$ and X$_j$ are independently selected from N or CR$^{14}$, wherein R$^{14}$ is selected from hydrogen, halo, (1-2C)alkyl, (1-2C)alkoxy, (1-2C)haloalkyl or (1-2C)haloalkoxy;

with the proviso that:
(i) when R3 is a group of Formula B, no more than two of X$_c$, X$_d$ and X$_e$ are nitrogen; and
(ii) when R3 is a group of Formula C, no more than three of X$_f$, X$_g$, X$_h$, X$_i$ and X$_j$ are nitrogen.

2. A compound of Formula (I), or a pharmaceutically acceptable salt or solvate thereof, according to claim 1, wherein X$_1$ is selected from N or CR$^a$, wherein R$^a$ is selected from hydrogen, methyl, fluoro, chloro, hydroxy, OCH$_3$, CH$_2$F, CHF$_2$, CF$_3$, OCF$_3$, acetylenyl, cyano or NH$_2$.

3. A compound of Formula (I), or a pharmaceutically acceptable salt or solvate thereof, according to claim 1, wherein X$_2$ is selected from N or CH.

4. A compound of Formula (I), or a pharmaceutically acceptable salt or solvate thereof, according to claim 1, wherein X$_1$ is CH and X$_2$ is CH.

5. A compound of Formula (I), or a pharmaceutically acceptable salt or solvate thereof, according to claim 1, wherein R$^1$ is (1-6C)alkyl or (3-6C)cycloalkyl; wherein each (1-6C)alkyl or (3-6C)cycloalkyl is optionally further substituted by one or more substituent groups independently selected from oxo, (1-2C)alkyl, halo, (1-2C)haloalkyl, (1-2C)haloalkoxy, amino, (1-2C)aminoalkyl, cyano, hydroxy or NH$_2$.

6. A compound of Formula (I), or a pharmaceutically acceptable salt or solvate thereof, according to claim 5, wherein R$^1$ is (1-4C)alkyl.

7. A compound of Formula (I), or a pharmaceutically acceptable salt or solvate thereof, according to claim 1, wherein R$^2$ is selected from:

(i) a group of the formula:

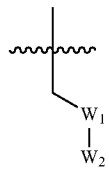

wherein:

denotes the point of attachment;

W$_1$ is selected from CR$^4$R$^5$ or C(O), wherein R$^4$ and R$^5$ are independently selected from hydrogen, (1-2C) alkyl, fluoro, hydroxy, cyano, (1-2C)alkoxy, CH$_2$F, CF$_2$H or amino; or R$^4$ and R$^5$ can be linked such that, together with the carbon atom to which they are attached, they form a 3-6-membered carbocyclic ring or a 3-6-membered heterocyclic ring, which is optionally substituted by one or more substituents selected from methyl, fluoro, chloro, OCH$_3$, amino, cyano or hydroxy;

W$_2$ is selected from cyano, a 5- or 6-membered heteroaryl, phenyl, C(O)OCH$_3$, C(O)N(H)CH$_3$, CR$^6$R$^7$R$^8$ or NR$^l$R$^m$, wherein R$^l$ and R$^m$ are independently selected from hydrogen or (1-2C)alkyl, and wherein:

R$^6$ is selected from hydroxy, amino, or (1-2C)alkoxy;

R$^7$ is selected from hydrogen, (1-2C)alkyl, fluoro, chloro, hydroxy, cyano, (1-2C)alkoxy, (1-2C)haloalkyl, (1-2C)haloalkoxy or a group of the formula:

-Y$_2$-L$_2$-Z$_2$ wherein:

Y$_2$ is absent or selected from O, C(O), C(O)O, OC(O), C(O)N(R$''$) or N(R$''$)C(O, wherein R$''$ is selected from hydrogen or (1-2C)alkyl;

L$_2$ is absent or (1-2C)alkylene; and

Z$_2$ is hydrogen, (1-6C)alkyl, (2-4C)alkenyl, (2-4C) alkynyl, phenyl, (3-6C)cycloalkyl, 5-6 membered heteroaryl or a 4-6-membered heterocyclyl; wherein Z$_2$ is optionally substituted by one or more substituents selected from (1-2C)alkyl, halo, (1-2C)haloalkyl, (1-2C)haloalkoxy, (1-2C)alkoxy, (1-2C)alkylamino, amino, cyano, nitro or hydroxy; and R$^8$ is selected from (1-2C)alkyl, —C(O)OR$^q$, OR$^q$, or a 5-membered heteroaryl, wherein R$^q$ is selected from hydrogen or (1-2C)alkyl; or (ii) a group of the formula:

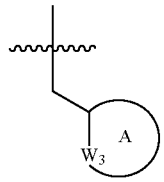

wherein:

denotes the point of attachment;
ring A is a 5-membered cycloalkyl or heterocyclyl ring;
$W_3$ is selected from $NR^{100}$ or $CR^{101}R^{102}$, wherein $R^{100}$ is selected from hydrogen, (1-2C)alkyl or —C(O)OR$^{ab}$, wherein R$^{ab}$ is (1-2C)alkyl, $R^{101}$ and $R^{102}$ are each independently selected from hydrogen, (1-2C)alkyl, fluoro, chloro, hydroxy, (1-2C)alkoxy, CH$_2$F, CF$_2$H, CF$_3$, —C(O)OR$^{ac}$ or —NR$^{ac}$R$^{ad}$, and wherein R$^{ac}$ and R$^{ad}$ are independently selected from hydrogen or (1-2C)alkyl.

8. A compound of Formula (I), or a pharmaceutically acceptable salt or solvate thereof, according to claim 1, wherein $R^2$ is selected from:
(i) a group of the formula:

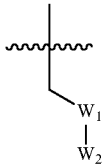

wherein:

denotes the point or attachment;
$W_1$ is selected from CHR$^4$ or C(O), wherein R4 is selected from hydrogen, (1-2C)alkyl, fluoro, hydroxy, cyano, (1-2C)alkoxy, CH$_2$F, CF$_2$H or amino;
$W_2$ is selected from cyano, a 5- or 6-membered heteroaryl, phenyl, C(O)OCH$_3$, C(O)N(H)CH$_3$, CR$^6$R$^7$R$^8$ or NR$^l$R$^m$, wherein R$^l$ and R$^m$ are independently selected from hydrogen or (1-2C)alkyl, and wherein:
$R^6$ is selected from hydroxy, amino, or (1-2C)alkoxy;
$R^7$ is selected from hydrogen, (1-2C)alkyl, fluoro, chloro, hydroxy, cyano, (1-2C)alkoxy, (1-2C)haloalkyl, (1-2C)haloalkoxy or a group of the formula:

-Y$_2$-L$_2$-Z$_2$ wherein:
Y$_2$ is absent or selected from O, C(O)O, C(O)N(R″) or N(R″)C(O), wherein R″ is selected from hydrogen or (1-2C)alkyl;
L$_2$ is absent or (1-2C)alkylene; and
Z$_2$ is hydrogen, (1-6C)alkyl, (2-4C)alkenyl, (2-4C)alkynyl, phenyl, (3-6C)cycloalkyl, 5-6 membered heteroaryl or a 4-6-membered heterocyclyl; wherein Z$_2$ is optionally substituted by one or more substituents selected from (1-2C)alkyl, halo, (1-2C)haloalkyl, (1-2C)haloalkoxy, (1-2C)alkoxy, (1-2C)alkylamino, amino, cyano or hydroxy; and $R^8$ is selected from (1-2C)alkyl, —C(O)OR$^q$, OR$^q$, or a 5-membered heteroaryl, wherein R$^q$ is selected from hydrogen or (1-2C)alkyl; or
$R^6$ and $R^7$ can be linked such that, together with the carbon atom to which they are attached, they form a 4-6 membered carbocyclic ring or a 4-6 membered heterocyclic ring; or
(ii) a group of the formula:

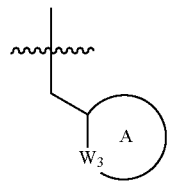

wherein:

denotes the point or attachment;
ring A is a 5-membered cycloalkyl or heterocyclyl ring;
$W_3$ is selected from NR$^{100}$ or CR$^{101}$R$^{102}$, wherein R$^{100}$ is selected from hydrogen, (1-2C)alkyl or —C(O)OR$^{ab}$, wherein R$^{ab}$ is (1-2C)alkyl, $R^{101}$ is selected from hydrogen or methyl and $R^{102}$ is selected from (1-2C)alkyl, hydroxy, (1-2C)alkoxy, C(O)OR$^{ac}$ or —NR$^{ac}$R$^{ad}$, and wherein R$^{ac}$ and R$^{ad}$ are independently selected from hydrogen or (1-2C)alkyl.

9. A compound of Formula (I), or a pharmaceutically acceptable salt or solvate thereof, according to claim 1, wherein R$^3$ is selected from:
i) a group of Formula A shown below:

Formula A

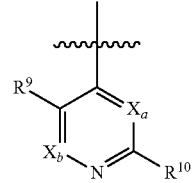

wherein:

denotes the point of attachment,
$X_a$ and $X_b$ are independently selected from N or CR$^{x1}$, wherein R$^{x1}$ is selected from hydrogen, fluoro, chloro, bromo, (1-2C)alkyl, (1-2C)alkoxy, cyano, nitro, acetylenyl, CH$_2$F, CF$_2$H or CF$_3$;
$R^9$ is selected from hydrogen, fluoro, chloro, bromo, (1-2C)alkyl, (1-2C)alkoxy, cyano, nitro, acetylenyl, CH$_2$F, CF$_2$H or CF$_3$;

R¹⁰ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

-Y₃-Z₃ wherein:
Y₃ is absent or N(R$^s$)(CR$^s$R$^t$)$_{q1}$ (where q₁ is 0, 1 or 2), S, C(O), C(O)O, C(O)N(R$^s$), N(R$^s$)C(O), S(O)₂N(R$^s$) or N(R$^s$)SO₂, wherein R$^s$ is selected from hydrogen or (1-4C)alkyl; and
Z₃ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or 4 to 11-membered heterocyclyl; wherein Z₃ is optionally further substituted by one or more substituent groups independently selected from oxo, (1-4C)alkyl, (3-6C)cycloalkyl, halo, (1-4C)haloalkyl, (1-4C)haloalkoxy, amino, cyano, hydroxy, amido, carboxy, carbamoyl, sulphamoyl, mercapto, C(O)NR$^u$R$^v$, NR$^u$R$^v$ or OR$^u$, wherein R$^u$ and R$^v$ are each independently selected from hydrogen, (1-4C)alkyl or (3-6C)cycloalkyl; and/or Z³ is optionally further substituted by a group of the formula:

-L$_Z$-W$_Z$ wherein:
L$_Z$ is absent or a (1-3C)alkylene; and
W$_Z$ is phenyl, 5- or 6-membered heteroaryl, 6-membered heterocyclyl, halo, (1-4C)haloalkyl, (1-4C)haloalkoxy, cyano, hydroxy, (1-4C)alkoxy, C(O)R$^{xa}$, COOR$^{xb}$, C(O)NR$^{xa}$R$^{xb}$ or NR$^{xa}$R$^{xb}$, wherein R$^{xa}$ and R$^{xb}$ are each independently selected from hydrogen or (1-4C)alkyl;

ii) a group of Formula B shown below:

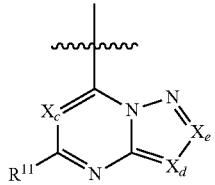

Formula B wherein:

denotes the point of attachment;
X$_c$, X$_d$ and X$_e$ are independently selected from N, CH, CF, CCl, C—CN or CCH₃;
R¹¹ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

-Y₅-Z₅ wherein:
Y₅ is absent or O, N(R$^w$), C(O), C(O)O, C(O)N(R$^w$) or S(O)₂N(R$^w$), wherein R$^w$ is selected from hydrogen or (1-4C)alkyl; and Z₅ is hydrogen, (1-6C)alkyl, aryl, (3-8C)cycloalkyl, (3-8C)cycloalkenyl, heteroaryl or heterocyclyl; wherein Z⁵ is optionally further substituted by one or more substituent groups independently selected from (1-4C)alkyl, halo, (1-4C)haloalkyl, (1-4C)haloalkoxy, amino, cyano, hydroxy, amido, carboxy, carbamoyl, sulphamoyl, mercapto, NR$^y$R$^z$, or OR$^y$, wherein R$^y$ and R$^z$ are each independently selected from hydrogen, (1-4C)alkyl or (3-6C)cycloalkyl; or iii) a group of Formula C shown below:

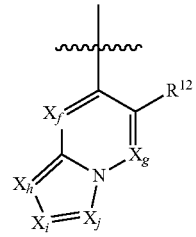

Formula C wherein:

denotes the point of attachment;
R¹² is selected from fluoro, chloro, bromo, (1-2C)alkyl, (1-2C)alkoxy, cyano, nitro, (2-4C)alkynyl, CH₂F, CF₂H or CF₃;
X$_f$ and X$_g$ are independently selected from N or CR¹³, wherein R¹³ is selected from hydrogen, fluoro, chloro, methyl, CH₂F, CF₂H or CF₃;
X$_h$, X$_i$ and X$_j$ are independently selected from N or CR¹⁴, wherein R¹⁴ is selected from hydrogen, halo, (1-2C)alkyl, (1-2C)alkoxy, (1-2C)haloalkyl or (1-2C)haloalkoxy.

10. A compound of Formula (I), or a pharmaceutically acceptable salt or solvate thereof, according to claim 1, wherein R³ is selected from:
i) a group of Formula A shown below:

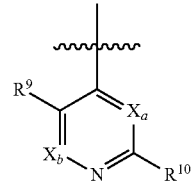

Formula A wherein:

denotes the point of attachment;
X$_a$ and X$_b$ are independently selected from N or CR$^{x1}$, wherein R$^{x1}$ is selected from hydrogen, fluoro, chloro, bromo, (1-2C)alkyl, (1-2C)alkoxy, cyano, nitro, acetylenyl, CH$_2$F, CF$_2$H or CF$_3$;

R$^9$ is selected from hydrogen, fluoro, chloro, bromo, (1-2C)alkyl, (1-2C)alkoxy, cyano, nitro, acetylenyl, CH$_2$F, CF$_2$H or CF$_3$;

R$^{10}$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

-Y$_3$-Z$_3$ wherein:

Y$_3$ is absent or N(R$^s$)(CR$^s$R$^t$)$_{q1}$ (where q$_1$ is 0, 1 or 2), S, C(O), C(O)O, C(O)N(R$^s$), N(R$^s$)C(O) or S(O)$_2$N(R$^s$), wherein R$^s$ is selected from hydrogen or (1-4C)alkyl; and Z$_3$ is hydrogen, (1-6C)alkyl, aryl, (3-6C)cycloalkyl, (2-4C)alkenyl, (2-4C)alkynyl, (3-6C)cycloalkenyl, heteroaryl or 4 to 11-membered heterocyclyl; wherein Z$_3$ is optionally further substituted by one or more substituent groups independently selected from oxo, (1-4C)alkyl, (3-6C)cycloalkyl, halo, (1-4C)haloalkyl, (1-4C) haloalkoxy, amino, cyano, hydroxy, amido, carboxy, carbamoyl, sulphamoyl, mercapto, C(O) NR$^u$R$^v$, NR$^u$R$^v$ or OR$^u$, wherein R$^u$ and R$^v$ are each independently selected from hydrogen, (1-4C)alkyl or (3-6C)cycloalkyl; and/or Z$^3$ is optionally further substituted by a group of the formula:

-L$_Z$-W$_Z$ wherein:

L$_Z$ is absent or a (1-5C)alkylene optionally substituted by one or more substituents selected from (1-2C)alkyl or oxo; and W$_Z$ is phenyl, 5- or 6-membered heteroaryl, 6-membered heterocyclyl, halo, (1-4C)haloalkyl, (1-4C)haloalkoxy, cyano, hydroxy, (1-4C) alkoxy, C(O)R$^{xa}$, COOR$^{xa}$, C(O)NR$^{xa}$R$^{xb}$ or NR$^{xa}$R$^{xb}$, wherein R$^{xa}$ and R$^{xb}$ are each independently selected from hydrogen or (1-4C) alkyl; or ii) a group of Formula B shown below:

Formula B

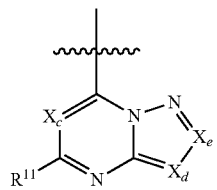

wherein:

denotes the point of attachment;

X$_c$, X$_d$ and X$_e$ are independently selected from N, CH, CF, CCl, C—CN or CCH$_3$;

R$^{11}$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

-Y$_5$-Z$_5$ wherein:

Y$_5$ is absent or O, N(R$^w$), C(O), C(O)O, C(O)N (R$^w$) or S(O)$_2$N(R$^w$), wherein R$^w$ is selected from hydrogen or (1-4C)alkyl; and Z$_5$ is hydrogen, (1-6C)alkyl, aryl, (3-8C)cycloalkyl, (3-8C)cycloalkenyl, heteroaryl or heterocyclyl; wherein Z$_5$ is optionally further substituted by one or more substituent groups independently selected from (1-4C)alkyl, halo, (1-4C)haloalkyl, (1-4C)haloalkoxy, amino, cyano, hydroxy, amido, carboxy, carbamoyl, sulphamoyl, mercapto, NR$^y$R$^z$, or OR$^y$, wherein R$^y$ and R$^z$ are each independently selected from hydrogen, (1-4C)alkyl or cyclopropyl.

11. A compound of Formula (I), or a pharmaceutically acceptable salt or solvate thereof, according to claim 1, wherein R$^3$ is a group of Formula A shown below:

Formula A

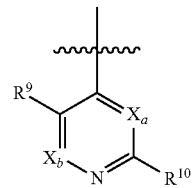

wherein:

denotes the point of attachment;

X$_a$ is CH or N;

X$_b$ is selected from N or CR$^{x1}$, wherein R$^{x1}$ is selected from hydrogen, fluoro, chloro, bromo, methyl, OCH$_3$, cyano or acetylenyl;

R$^9$ is selected from chloro or cyano;

R$^{10}$ is selected from hydrogen, halo, (1-4C)alkyl, (1-4C)alkoxy, (1-4C)haloalkyl, (1-4C)haloalkoxy, cyano or a group of the formula:

-Y$_3$-Z$_3$ wherein:

Y$_3$ is absent or N(R$^s$)(CH$_2$)$_{q1}$ (where q$_1$ is 0 or 1), C(O), C(O)O or C(O)N(R$^s$), wherein R$^s$ is selected from hydrogen or methyl; and Z$_3$ is hydrogen, (1-6C)alkyl, aryl, (3-6C)cycloalkyl, 5- or 6-membered heteroaryl or 4 to 9-membered heterocyclyl; wherein Z$_3$ is optionally further substituted by one or more substituent groups independently selected from oxo, (1-3C)alkyl, cyclopropyl, halo, (1-2C)haloalkyl, (1-2C)haloalkoxy, amino, cyano, hydroxy, amido, carboxy, C(O)NR$^u$R$^v$, NR$^u$R$^v$ or OR$^u$, wherein R$^u$ and R$^v$ are each independently selected from hydrogen or methyl; or $Z^3$ is optionally further substituted by a group of the formula:

$$-L_Z\text{-}W_Z$$

wherein:
L$_Z$ is absent or a (1-3C)alkylene; and
W$_Z$ is phenyl, 5- or 6-membered heteroaryl, 6-membered heterocyclyl, halo, (1-2C)haloalkyl, (1-2C)haloalkoxy, cyano, hydroxy, (1-2C)alkoxy, C(O)R$^{xa}$, COOR$^{xa}$, C(O)NR$^{xa}$R$^{xb}$ or NR$^{xa}$R$^{xb}$, wherein R$^{xa}$ and R$^{xb}$ are each independently selected from hydrogen or methyl.

12. A compound, or a pharmaceutically acceptable salt or solvate thereof, selected from one of the following:

6-Chloro-5-cyano-4-[[3-(3-hydroxy-3-methyl-butyl)-1-methyl-2-oxo-benzimidazol-5-yl]amino]-N-methyl-pyridine-2-carboxamide;
2-chloro-4-[[3-(3-hydroxy-3-methyl-butyl)-1-methyl-2-oxo-benzimidazol-5-yl]amino]-6-methyl-pyridine-3-carbonitrile;
6-chloro-5-cyano-4-[(1,3-dimethyl-2-oxo-benzimidazol-5-yl)amino]pyridine-2-carboxylic acid;
6-chloro-5-cyano-N-methyl-4-[[1-methyl-2-oxo-3-[(3S)-3-pyrazol-1-ylbutyl]benzimidazol-5-yl]amino]pyridine-2-carboxamide;
6-chloro-5-cyano-4-[[3-[(3R)-3-hydroxybutyl]-1-methyl-2-oxo-benzimidazol-5-yl]amino]pyridine-2-carboxylic acid;
6-chloro-5-cyano-N-methyl-4-[(1-methyl-2-oxo-3H-benzimidazol-5-yl)amino]pyridine-2-carboxamide;
6-chloro-5-cyano-4-[[3-(3-hydroxy-3-methyl-butyl)-2-oxo-1-(tetrahydropyran-4-ylmethyl)benzimidazol-5-yl]amino]-N-methyl-pyridine-2-carboxamide;
Ethyl 7-[[3-(3-hydroxy-3-methyl-butyl)-1-methyl-2-oxo-benzimidazol-5-yl]amino]pyrazolo[1,5-a]pyrimidine-5-carboxylate;
2-chloro-4-[[3-(3-hydroxy-3-methyl-butyl)-1-methyl-2-oxo-benzimidazol-5-yl]amino]pyridine-3-carbonitrile;
Methyl 4-[6-[(2-chloro-3-cyano-4-pyridyl)amino]-3-methyl-2-oxo-benzimidazol-1-yl]-2-methyl-butanoate;
2-bromo-4-[[3-(3-hydroxy-3-methyl-butyl)-1-methyl-2-oxo-benzimidazol-5-yl]amino]pyridine-3-carbonitrile;
2-chloro-4-[[3-[(3R)-3-hydroxybutyl]-1-methyl-2-oxo-benzimidazol-5-yl]amino]-6-methyl-pyridine-3-carbonitrile;
5-[(2,5-dichloro-4-pyridyl)amino]-3-[(3R)-3-hydroxybutyl]-1-methyl-benzimidazol-2-one;
5-[(2,5-dichloropyrimidin-4-yl)amino]-3-(3-hydroxy-3-methyl-butyl)-1-methyl-benzimidazol-2-one;
Ethyl 7-[3-[(3R)-3-hydroxybutyl]-1-methyl-2-oxo-benzimidazol-5-yl]amino]pyrazolo[1,5-a]pyrimidine-5-carboxylate;
4-chloro-6-[[3-(3-hydroxy-3-methyl-butyl)-1-methyl-2-oxo-benzimidazol-5-yl]amino]pyrimidine-5-carbonitrile;
5-[(2,3-dichloro-4-pyridyl)amino]-3-[(3R)-3-hydroxybutyl]-1-methyl-benzimidazol-2-one;
Ethyl 3-fluoro-7-((3-(2-hydroxybutyl)-1-methyl-2-oxo-2,3-dihydro-1H-benzo[d]imidazol-5-yl)amino)pyrazolo[1,5-a]pyrimidine-5-carboxylate;
Methyl 6-chloro-5-cyano-4-[[3-(4-methoxy-3-methyl-4-oxo-butyl)-1-methyl-2-oxo-benzimidazol-5-yl]amino]pyridine-2-carboxylate;
Ethyl 6-chloro-5-cyano-4-[[3-(4-methoxy-3-methyl-4-oxo-butyl)-1-methyl-2-oxo-benzimidazol-5-yl]amino]pyridine-2-carboxylate;
Isopropyl 6-chloro-5-cyano-4-[[3-(4-methoxy-3-methyl-4-oxo-butyl)-1-methyl-2-oxo-benzimidazol-5-yl]amino]pyridine-2-carboxylate;
Ethyl 6-chloro-5-cyano-4-[[3-[(3R)-3-hydroxybutyl]-1-methyl-2-oxo-benzimidazol-5-yl]amino]pyridine-2-carboxylate;
6-Chloro-5-cyano-4-[[3-(4-methoxy-3-methyl-4-oxo-butyl)-1-methyl-2-oxo-benzimidazol-5-yl]amino]pyridine-2-carboxylic acid;
Methyl 3-[6-[(2-chloro-3-cyano-4-pyridyl)amino]-3-methyl-2-oxo-benzimidazol-1-yl]-2-methyl-propanoate;
Methyl 4-[6-[(5-chloro-2-methyl-pyrimidin-4-yl)amino]-3-methyl-2-oxo-benzimidazol-1-yl]-2-methyl-butanoate;
6-Chloro-5-cyano-4-[[3-[(3R)-3-hydroxybutyl]-1-methyl-2-oxo-benzimidazol-5-yl]amino]-N-methyl-pyridine-2-carboxamide;
Methyl 4-[6-[[2-chloro-3-cyano-6-(3-methyl-1,2,4-oxadiazol-5-yl)-4-pyridyl]amino]-3-methyl-2-oxo-benzimidazol-1-yl]-2-methyl-butanoate;
Methyl (2S)-2-amino-4-[6-[(2-chloro-3-cyano-4-pyridyl)amino]-3-methyl-2-oxo-benzimidazol-1-yl]butanoate;
Methyl 4-[6-[[2-chloro-3-cyano-6-(methylcarbamoyl)-4-pyridyl]amino]-3-methyl-2-oxo-benzimidazol-1-yl]-2-methyl-butanoate;
Methyl 4-[6-[[6-(but-3-ynylcarbamoyl)-2-chloro-3-cyano-4-pyridyl]amino]-3-methyl-2-oxo-benzimidazol-1-yl]-2-methyl-butanoate;
Methyl 4-[6-[[2-chloro-3-cyano-6-(dimethylcarbamoyl)-4-pyridyl]amino]-3-methyl-2-oxo-benzimidazol-1-yl]-2-methyl-butanoate;
6-Chloro-5-cyano-N-[2-(dimethylamino)ethyl]-4-[(1,3-dimethyl-2-oxo-benzimidazol-5-yl)amino]pyridine-2-carboxamide;
Ethyl 7-[3-(4-methoxy-3-methyl-4-oxo-butyl)-1-methyl-2-oxo-benzimidazol-5-yl]amino]pyrazolo[1,5-a]pyrimidine-5-carboxylate;
Methyl 4-[6-[(2-chloro-3-cyano-4-pyridyl)amino]-3-methyl-2-oxo-benzimidazol-1-yl]-2-hydroxy-butanoate;
2-Chloro-4-[[3-(2,3-dihydroxy-3-methyl-butyl)-1-methyl-2-oxo-benzimidazol-5-yl]amino]pyridine-3-carbonitrile;
Methyl 4-[6-[(2-chloro-3-cyano-4-pyridyl)amino]-3-methyl-2-oxo-benzimidazol-1-yl]-2-methoxy-butanoate;
Methyl 4-[6-[(2-chloro-3-cyano-4-pyridyl)amino]-3-methyl-2-oxo-benzimidazol-1-yl]-2-ethoxy-butanoate;
Methyl 4-[6-[(2-chloro-3-cyano-4-pyridyl)amino]-3-methyl-2-oxo-benzimidazol-1-yl]butanoate;
methyl 4-[6-[(2-chloro-3-cyano-4-pyridyl)amino]-3-methyl-2-oxo-benzimidazol-1-yl]-2-(cyclopropylmethoxy)butanoate;
2-chloro-4-[[3-(2-hydroxy-3-pyrazol-1-yl-propyl)-1-methyl-2-oxo-benzimidazol-5-yl]amino]pyridine-3-carbonitrile;
2-chloro-4-[[3-(2-cyanobutyl)-1-methyl-2-oxo-benzimidazol-5-yl]amino]pyridine-3-carbonitrile;
2-chloro-4-[[3-[(3S)-3-hydroxybutyl]-1-methyl-2-oxo-benzimidazol-5-yl]amino]pyridine-3-carbonitrile;
Methyl 2-[[6-[(2-chloro-3-cyano-4-pyridyl)amino]-3-methyl-2-oxo-benzimidazol-1-yl]methyl]cyclopentanecarboxylate;
Methyl (2R)-2-amino-4-[6-[(2-chloro-3-cyano-4-pyridyl)amino]-3-methyl-2-oxo-benzimidazol-1-yl]butanoate;

N-[3-[6-[(2-Chloro-3-cyano-4-pyridyl)amino]-3-methyl-2-oxo-benzimidazol-1-yl]-1-methyl-propyl]acetamide;

5-Chloro-N-ethyl-4-[[3-(3-hydroxy-3-methyl-butyl)-1-methyl-2-oxo-benzimidazol-5-yl]amino]pyridine-2-carboxamide;

5-[[5-Chloro-2-(3,5-dimethylpyrazol-1-yl)pyrimidin-4-yl]amino]-3-(3-hydroxy-3-methyl-butyl)-1-methyl-benzimidazol-2-one;

5-((5-chloro-2-((3R,5S)-4,4-difluoro-3,5-dimethylpiperidin-1-yl)pyrimidin-4-yl)amino)-3-(3-hydroxy-3-methylbutyl)-1-methyl-1,3-dihydro-2H-benzo[d]imidazol-2-one;

Ethyl 1-(5-chloro-4-((3-(3-hydroxy-3-methylbutyl)-1-methyl-2-oxo-2,3-dihydro-1H-benzo[d]imidazol-5-yl)amino)pyrimidin-2-yl)-1H-pyrazole-4-carboxylate;

Ethyl 1-(5-chloro-4-((3-(3-hydroxy-3-methylbutyl)-1-methyl-2-oxo-2,3-dihydro-1H-benzo[d]imidazol-5-yl)amino)pyrimidin-2-yl)-3,5-dimethyl-1H-pyrazole-4-carboxylate;

5-((5-chloro-2-(3-(trifluoromethyl)-1H-pyrazol-1-yl)pyrimidin-4-yl)amino)-3-(3-hydroxy-3-methylbutyl)-1-methyl-1,3-dihydro-2H-benzo[d]imidazol-2-one;

5-((5-chloro-2-(3,5-dimethyl-1H-pyrazol-1-yl)pyrimidin-4-yl)amino)-3-(3,5-dihydroxy-3-methylpentyl)-1-methyl-1,3-dihydro-2H-benzo[d]imidazol-2-one;

5-((5-chloro-2-(3,5-dimethyl-1H-pyrazol-1-yl)pyrimidin-4-yl)amino)-3-(3-hydroxy-3-methylpentyl)-1-methyl-1,3-dihydro-2H-benzo[d]imidazol-2-one;

5-((5-chloro-2-(dimethylamino)pyrimidin-4-yl)amino)-3-(3-hydroxy-3-methylbutyl)-1-methyl-1,3-dihydro-2H-benzo[d]imidazol-2-one;

5-((5-chloro-2-(3,5-dimethyl-1H-pyrazol-1-yl)pyrimidin-4-yl)amino)-1-methyl-1,3-dihydro-2H-benzo[d]imidazol-2-one;

1-(5-chloro-4-((3-(3-hydroxy-4-methoxy-3-methylbutyl)-1-methyl-2-oxo-2,3-dihydro-1H-benzo[d]imidazol-5-yl)amino)pyrimidin-2-yl)-N,N-dimethylpiperidine-4-carboxamide;

5-((5-chloro-2-(3,5-dimethyl-1H-pyrazol-1-yl)pyrimidin-4-yl)amino)-3-(3-hydroxy-4-methoxy-3-methylbutyl)-1-methyl-1,3-dihydro-2H-benzo[d]imidazol-2-one;

1-(5-chloro-4-((3-(3,5-dihydroxy-3-methylpentyl)-1-methyl-2-oxo-2,3-dihydro-1H-benzo[d]imidazol-5-yl)amino)pyrimidin-2-yl)-N,N-dimethylpiperidine-4-carboxamide;

1-(5-chloro-4-((3-(3-hydroxy-3-methylpentyl)-1-methyl-2-oxo-2,3-dihydro-1H-benzo[d]imidazol-5-yl)amino)pyrimidin-2-yl)-N,N-dimethylpiperidine-4-carboxamide;

5-((5-chloro-2-(1H-pyrazol-1-yl)pyrimidin-4-yl)amino)-3-(3-hydroxy-3-methylbutyl)-1-methyl-1,3-dihydro-2H-benzo[d]imidazol-2-one;

5-((5-chloro-2-(4-chloro-3,5-dimethyl-1H-pyrazol-1-yl)pyrimidin-4-yl)amino)-3-(3-hydroxy-3-methylbutyl)-1-methyl-1,3-dihydro-2H-benzo[d]imidazol-2-one;

6-(3,5-dimethyl-1H-pyrazol-1-yl)-4-((3-(3-hydroxy-3-methylbutyl)-1-methyl-2-oxo-2,3-dihydro-1H-benzo[d]imidazol-5-yl)amino)nicotinonitrile;

5-((5-chloro-2-(3,5-dimethyl-1H-pyrazol-1-yl)-6-methylpyrimidin-4-yl)amino)-3-(3-hydroxy-3-methylbutyl)-1-methyl-1,3-dihydro-2H-benzo[d]imidazol-2-one;

5-((5-bromo-2-(3,5-dimethyl-1H-pyrazol-1-yl)pyrimidin-4-yl)amino)-3-(3-hydroxy-3-methylbutyl)-1-methyl-1,3-dihydro-2H-benzo[d]imidazol-2-one;

5-((5-chloro-2-(3-methyl-1H-pyrazol-1-yl)pyrimidin-4-yl)amino)-3-(3-hydroxy-3-methylbutyl)-1-methyl-1,3-dihydro-2H-benzo[d]imidazol-2-one;

5-((5-chloro-2-(5-methyl-1H-pyrazol-1-yl)pyrimidin-4-yl)amino)-3-(3-hydroxy-3-methylbutyl)-1-methyl-1,3-dihydro-2H-benzo[d]imidazol-2-one;

5-((5-chloro-2-(1H-indazol-3-yl)pyrimidin-4-yl)amino)-3-(3-hydroxy-3-methylbutyl)-1-methyl-1,3-dihydro-2H-benzo[d]imidazol-2-one;

5-((5-chloro-2-(1H-indazol-1-yl)pyrimidin-4-yl)amino)-3-(3-hydroxy-3-methylbutyl)-1-methyl-1,3-dihydro-2H-benzo[d]imidazol-2-one;

2-chloro-4-((3-(2-(1-hydroxycyclobutyl)ethyl)-1-methyl-2-oxo-2,3-dihydro-1H-benzo[d]imidazol-5-yl)amino)nicotinonitrile;

2-chloro-4-((1-methyl-3-(2-(methylsulfonyl)ethyl)-2-oxo-2,3-dihydro-1H-benzo[d]imidazol-5-yl)amino)nicotinonitrile;

2-chloro-4-((1-methyl-2-oxo-3-(3-oxopentyl)-2,3-dihydro-1H-benzo[d]imidazol-5-yl)amino)nicotinonitrile;

2-chloro-4-((1-methyl-3-((2-methyltetrahydrofuran-3-yl)methyl)-2-oxo-2,3-dihydro-1H-benzo[d]imidazol-5-yl)amino)nicotinonitrile;

2-chloro-4-((1-methyl-3-(2-(2-methyl-1,3-dioxolan-2-yl)ethyl)-2-oxo-2,3-dihydro-1H-benzo[d]imidazol-5-yl)amino)nicotinonitrile;

tert-Butyl 2-((6-((2-chloro-3-cyanopyridin-4-yl)amino)-3-methyl-2-oxo-2,3-dihydro-1H-benzo[d]imidazol-1-yl)methyl)azetidine-1-carboxylate;

5-((6-((5-chloro-2-(2,2,6,6-tetramethylmorpholino)pyrimidin-4-yl)amino)-3-methyl-2-oxo-2,3-dihydro-1H-benzo[d]imidazol-1-yl)methyl)-5-(2-hydroxypropan-2-yl)-3-methyloxazolidin-2-one;

1-(5-chloro-4-((3-(3-hydroxy-3-methylbutyl)-1-methyl-2-oxo-2,3-dihydro-1H-benzo[d]imidazol-5-yl)amino)pyrimidin-2-yl)-N,N-dimethylpiperidine-4-carboxamide;

5-((5-chloro-2-(piperidin-1-yl)pyrimidin-4-yl)amino)-3-(3-hydroxy-3-methylbutyl)-1-methyl-1,3-dihydro-2H-benzo[d]imidazol-2-one;

5-((5-chloro-2-((3S,5R)-3,5-dimethylpiperidin-1-yl)pyrimidin-4-yl)amino)-3-(3-hydroxy-3-methylbutyl)-1-methyl-1,3-dihydro-2H-benzo[d]imidazol-2-one;

5-((5-chloro-2-(isopropylamino)pyrimidin-4-yl)amino)-3-(3-hydroxy-3-methylbutyl)-1-methyl-1,3-dihydro-2H-benzo[d]imidazol-2-one;

5-((5-chloro-2-(3-methylpiperidin-1-yl)pyrimidin-4-yl)amino)-3-(3-hydroxy-3-methylbutyl)-1-methyl-1,3-dihydro-2H-benzo[d]imidazol-2-one;

5-((5-chloro-2-(3-(trifluoromethyl)piperidin-1-yl)pyrimidin-4-yl)amino)-3-(3-hydroxy-3-methylbutyl)-1-methyl-1,3-dihydro-2H-benzo[d]imidazol-2-one;

5-((5-chloro-2-(ethyl(methyl)amino)pyrimidin-4-yl)amino)-3-(3-hydroxy-3-methylbutyl)-1-methyl-1,3-dihydro-2H-benzo[d]imidazol-2-one;

5-((5-chloro-2-((2R,6S)-2,6-dimethylmorpholino)pyrimidin-4-yl)amino)-3-(3-hydroxy-3-methylbutyl)-1-methyl-1,3-dihydro-2H-benzo[d]imidazol-2-one;

5-((5-chloro-2-(2,2-dimethyl-6-(trifluoromethyl)morpholino)pyrimidin-4-yl)amino)-3-(3-hydroxy-3-methylbutyl)-1-methyl-1,3-dihydro-2H-benzo[d]imidazol-2-one;

5-((6-((5-chloro-2-((2R,6S)-2,6-dimethylmorpholino)pyrimidin-4-yl)amino)-3-methyl-2-oxo-2,3-dihydro-1H-benzo[d]imidazol-1-yl)methyl)-5-ethyl-3-methyloxazolidin-2-one;

5-((6-((5-chloro-2-(3-(trifluoromethyl)-1H-pyrazol-1-yl)pyrimidin-4-yl)amino)-3-methyl-2-oxo-2,3-dihydro-1H-benzo[d]imidazol-1-yl)methyl)-5-ethyl-3-methyloxazolidin-2-one;

5-((6-((5-chloro-2-((2R,6S)-2,6-dimethylmorpholino)pyrimidin-4-yl)amino)-3-methyl-2-oxo-2,3-dihydro-1H-benzo[d]imidazol-1-yl)methyl)-5-ethyloxazolidin-2-one;

5-((6-((5-chloro-2-(3-(trifluoromethyl)-1H-pyrazol-1-yl)pyrimidin-4-yl)amino)-3-methyl-2-oxo-2,3-dihydro-1H-benzo[d]imidazol-1-yl)methyl)-5-ethyloxazolidin-2-one;

5-((5-chloro-2-((2R,6S)-2,6-dimethylmorpholino)pyrimidin-4-yl)amino)-6-fluoro-3-(3-hydroxy-3-methylbutyl)-1-methyl-1,3-dihydro-2H-benzo[d]imidazol-2-one;

5-((5-chloro-2-((3S,5R)-3,5-dimethylpiperidin-1-yl)pyrimidin-4-yl)amino)-6-fluoro-3-(3-hydroxy-3-methylbutyl)-1-methyl-1,3-dihydro-2H-benzo[d]imidazol-2-one;

5-((5-chloro-2-(3-(trifluoromethyl)-1H-pyrazol-1-yl)pyrimidin-4-yl)amino)-6-fluoro-3-(3-hydroxy-3-methylbutyl)-1-methyl-1,3-dihydro-2H-benzo[d]imidazol-2-one;

5-((5-chloro-2-(4-(trifluoromethyl)-1H-pyrazol-1-yl)pyrimidin-4-yl)amino)-3-(3-hydroxy-3-methylbutyl)-1-methyl-1,3-dihydro-2H-benzo[d]imidazol-2-one;

5-((5-chloro-2-morpholinopyrimidin-4-yl)amino)-3-(3-hydroxy-3-methylbutyl)-1-methyl-1,3-dihydro-2H-benzo[d]imidazol-2-one;

5-((5-chloro-2-((2S,6R)-2-cyclopropyl-6-methylmorpholino)pyrimidin-4-yl)amino)-3-(3-hydroxy-3-methylbutyl)-1-methyl-1,3-dihydro-2H-benzo[d]imidazol-2-one;

5-((5-chloro-2-((2R,6R)-2-cyclopropyl-6-methylmorpholino)pyrimidin-4-yl)amino)-3-(3-hydroxy-3-methylbutyl)-1-methyl-1,3-dihydro-2H-benzo[d]imidazol-2-one;

5-((5-chloro-2-(methylthio)pyrimidin-4-yl)amino)-3-(3-hydroxy-3-methylbutyl)-1-methyl-1,3-dihydro-2H-benzo[d]imidazol-2-one;

5-((2-bromo-5-chloropyridin-4-yl)amino)-3-(3-hydroxy-3-methylbutyl)-1-methyl-1,3-dihydro-2H-benzo[d]imidazol-2-one;

2-chloro-4-((3-((5-ethyl-2-oxooxazolidin-5-yl)methyl)-1-methyl-2-oxo-2,3-dihydro-1H-benzo[d]imidazol-5-yl)amino)nicotinonitrile;

4-chloro-6-((6-fluoro-3-(3-hydroxy-3-methylbutyl)-1-methyl-2-oxo-2,3-dihydro-1H-benzo[d]imidazol-5-yl)amino)pyrimidine-5-carbonitrile;

2-chloro-4-((3-((5-ethyl-3-methyl-2-oxooxazolidin-5-yl)methyl)-1-methyl-2-oxo-2,3-dihydro-1H-benzo[d]imidazol-5-yl)amino)nicotinonitrile;

2-chloro-4-((6-fluoro-3-(3-hydroxy-3-methylbutyl)-1-methyl-2-oxo-2,3-dihydro-1H-benzo[d]imidazol-5-yl)amino)nicotinonitrile;

5-((2,5-dichloropyrimidin-4-yl)amino)-3-(3-hydroxy-3-methylpentyl)-1-methyl-1,3-dihydro-2H-benzo[d]imidazol-2-one;

5-((5-chloropyrazolo[1,5-a]pyrimidin-7-yl)amino)-3-(3-hydroxy-3-methylbutyl)-1-methyl-1,3-dihydro-2H-benzo[d]imidazol-2-one;

3-(3-hydroxy-3-methylbutyl)-1-methyl-5-((2,5,6-trichloropyrimidin-4-yl)amino)-1,3-dihydro-2H-benzo[d]imidazol-2-one;

(R)-6-chloro-5-cyano-4-((3-(3-methoxybutyl)-1-methyl-2-oxo-2,3-dihydro-1H-benzo[d]imidazol-5-yl)amino)-N-methylpicolinamide;

4-((3-(3-acetamido-3-methylbutyl)-1-methyl-2-oxo-2,3-dihydro-1H-benzo[d]imidazol-5-yl)amino)-6-chloro-5-cyano-N-methylpicolinamide;

5-((5,6-dichloropyrimidin-4-yl)amino)-3-(3-hydroxy-3-methylbutyl)-1-methyl-1,3-dihydro-2H-benzo[d]imidazol-2-one;

2-chloro-4-((3-(((1S,2S)-2-ethyl-2-hydroxycyclopentyl)methyl)-1-methyl-2-oxo-2,3-dihydro-1H-benzo[d]imidazol-5-yl)amino)nicotinonitrile;

2-chloro-4-((3-(((1S,2S)-2-hydroxy-2-methylcyclopentyl)methyl)-1-methyl-2-oxo-2,3-dihydro-1H-benzo[d]imidazol-5-yl)amino)nicotinonitrile;

5-((5-chloro-2-(1-methyl-1H-pyrazol-3-yl)pyrimidin-4-yl)amino)-3-(3-hydroxy-3-methylbutyl)-1-methyl-1,3-dihydro-2H-benzo[d]imidazol-2-one;

5-((5-chloro-2-(1,3-dimethyl-1H-pyrazol-5-yl)pyrimidin-4-yl)amino)-3-(3-hydroxy-3-methylbutyl)-1-methyl-1,3-dihydro-2H-benzo[d]imidazol-2-one;

5-((5-chloro-2-(2,4-dimethylthiazol-5-yl)pyrimidin-4-yl)amino)-3-(3-hydroxy-3-methylbutyl)-1-methyl-1,3-dihydro-2H-benzo[d]imidazol-2-one;

5-((5-chloro-2-(thiophen-2-yl)pyrimidin-4-yl)amino)-3-(3-hydroxy-3-methylbutyl)-1-methyl-1,3-dihydro-2H-benzo[d]imidazol-2-one;

5-((5-chloro-2-(1-methyl-1H-imidazol-2-yl)pyrimidin-4-yl)amino)-3-(3-hydroxy-3-methylbutyl)-1-methyl-1,3-dihydro-2H-benzo[d]imidazol-2-one;

2-chloro-4-((1-methyl-2-oxo-3-((4-(2,2,2-trifluoroethyl)morpholin-3-yl)methyl)-2,3-dihydro-1H-benzo[d]imidazol-5-yl)amino)nicotinonitrile;

2-chloro-4-((3-(2-(dimethylamino)butyl)-1-methyl-2-oxo-2,3-dihydro-1H-benzo[d]imidazol-5-yl)amino)nicotinonitrile;

(S)-2-chloro-4-((3-((1-ethylpyrrolidin-2-yl)methyl)-1-methyl-2-oxo-2,3-dihydro-1H-benzo[d]imidazol-5-yl)amino)nicotinonitrile;

2-chloro-4-((1-methyl-2-oxo-3-((1-(2,2,2-trifluoroethyl)piperidin-2-yl)methyl)-2,3-dihydro-1H-benzo[d]imidazol-5-yl)amino)nicotinonitrile;

(S)-2-chloro-4-((3-((1-(2-fluoroethyl)pyrrolidin-2-yl)methyl)-1-methyl-2-oxo-2,3-dihydro-1H-benzo[d]imidazol-5-yl)amino)nicotinonitrile;

(S)-2-chloro-4-((3-((1-(2-hydroxyethyl)pyrrolidin-2-yl)methyl)-1-methyl-2-oxo-2,3-dihydro-1H-benzo[d]imidazol-5-yl)amino)nicotinonitrile;

2-chloro-4-((3-(((2R,4S)-4-fluoro-1-(2,2,2-trifluoroethyl)pyrrolidin-2-yl)methyl)-1-methyl-2-oxo-2,3-dihydro-1H-benzo[d]imidazol-5-yl)amino)nicotinonitrile;

2-chloro-4-((3-(3-(ethylamino)butyl)-1-methyl-2-oxo-2,3-dihydro-1H-benzo[d]imidazol-5-yl)amino)nicotinonitrile;

2-chloro-4-((3-(3-hydroxy-3-methylhex-5-yn-1-yl)-1-methyl-2-oxo-2,3-dihydro-1H-benzo[d]imidazol-5-yl)amino)nicotinonitrile;

2-chloro-4-((3-(3-hydroxy-4-methoxy-3-methylbutyl)-1-methyl-2-oxo-2,3-dihydro-1H-benzo[d]imidazol-5-yl)amino)nicotinonitrile;

2-chloro-4-((3-(3-hydroxy-3-methylpentyl)-1-methyl-2-oxo-2,3-dihydro-1H-benzo[d]imidazol-5-yl)amino)nicotinonitrile;

2-chloro-4-((1-methyl-2-oxo-3-(4,4,4-trifluoro-3-hydroxy-3-methylbutyl)-2,3-dihydro-1H-benzo[d]imidazol-5-yl)amino)nicotinonitrile;

2-chloro-4-((3-(3-hydroxy-2,3-dimethylbutyl)-1-methyl-2-oxo-2,3-dihydro-1H-benzo[d]imidazol-5-yl)amino)nicotinonitrile;

2-chloro-4-((3-(3-hydroxy-3,4-dimethylpentyl)-1-methyl-2-oxo-2,3-dihydro-1H-benzo[d]imidazol-5-yl)amino)nicotinonitrile;

5-((5-chloro-2-(2,2,6,6-tetramethylmorpholino)pyrimidin-4-yl)amino)-3-(3-hydroxy-3-methylbutyl)-1-methyl-1,3-dihydro-2H-benzo[d]imidazol-2-one;

5-((5-chloro-2-(2-(trifluoromethyl)morpholino)pyrimidin-4-yl)amino)-3-(3-hydroxy-3-methylbutyl)-1-methyl-1,3-dihydro-2H-benzo[d]imidazol-2-one;

5-((3-chloro-2-fluoropyridin-4-yl)amino)-3-(3-hydroxy-3-methylbutyl)-1-methyl-1,3-dihydro-2H-benzo[d]imidazol-2-one;

5-((2,3-dichloropyridin-4-yl)amino)-3-(3-hydroxy-3-methylbutyl)-1-methyl-1,3-dihydro-2H-benzo[d]imidazol-2-one;

5-((3-bromopyridin-4-yl)amino)-3-(3-hydroxy-3-methylbutyl)-1-methyl-1,3-dihydro-2H-benzo[d]imidazol-2-one;

5-((5-chloro-2-(trifluoromethyl)pyridin-4-yl)amino)-3-(3-hydroxy-3-methylbutyl)-1-methyl-1,3-dihydro-2H-benzo[d]imidazol-2-one;

5-((3-chloropyridin-4-yl)amino)-3-(3-hydroxy-3-methylbutyl)-1-methyl-1,3-dihydro-2H-benzo[d]imidazol-2-one;

5-((5-chloro-2-(3,5-dimethyl-1H-pyrazol-1-yl)pyridin-4-yl)amino)-3-(3-hydroxy-3-methylbutyl)-1-methyl-1,3-dihydro-2H-benzo[d]imidazol-2-one;

5-((5-chloro-2-(2-oxopyrrolidin-1-yl)pyrimidin-4-yl)amino)-3-(3-hydroxy-3-methylbutyl)-1-methyl-1,3-dihydro-2H-benzo[d]imidazol-2-one;

(S)-5-((5-chloro-2-(2-(hydroxymethyl)pyrrolidin-1-yl)pyrimidin-4-yl)amino)-3-(3-hydroxy-3-methylbutyl)-1-methyl-1,3-dihydro-2H-benzo[d]imidazol-2-one;

(S)-7-((3-(3-hydroxy-3-methylbutyl)-1-methyl-2-oxo-2,3-dihydro-1H-benzo[d]imidazol-5-yl)amino)-5-(2-(hydroxymethyl)pyrrolidin-1-yl)pyrazolo[1,5-a]pyrimidine-3-carbonitrile;

2-chloro-4-((1-methyl-3-(2-(2-methyloxiran-2-yl)ethyl)-2-oxo-2,3-dihydro-1H-benzo[d]imidazol-5-yl)amino)nicotinonitrile;

2-chloro-4-((3-(2-(3,5-dimethyl-2-oxooxazolidin-5-yl)ethyl)-1-methyl-2-oxo-2,3-dihydro-1H-benzo[d]imidazol-5-yl)amino)nicotinonitrile;

2-chloro-4-((1-methyl-3-((5-methyl-2-oxooxazolidin-4-yl)methyl)-2-oxo-2,3-dihydro-1H-benzo[d]imidazol-5-yl)amino)nicotinonitrile;

(S)-5-((5-chloro-2-(2,2,6,6-tetramethylmorpholino)pyrimidin-4-yl)amino)-1-methyl-3-((1-(2,2,2-trifluoroethyl)pyrrolidin-2-yl)methyl)-1,3-dihydro-2H-benzo[d]imidazol-2-one;

5-((5-chloro-2-((3R,5S)-4,4-difluoro-3,5-dimethylpiperidin-1-yl)pyrimidin-4-yl)amino)-1,3-bis(3-hydroxy-3-methylbutyl)-1,3-dihydro-2H-benzo[d]imidazol-2-one;

5-((5-chloro-2-(2,2,6,6-tetramethylmorpholino)pyrimidin-4-yl)amino)-1,3-bis(3-hydroxy-3-methylbutyl)-1,3-dihydro-2H-benzo[d]imidazol-2-one;

5-((5-chloro-2-(4,4-difluoropiperidin-1-yl)pyrimidin-4-yl)amino)-3-(3-hydroxy-3-methylbutyl)-1-methyl-1,3-dihydro-2H-benzo[d]imidazol-2-one;

5-((5-chloro-2-(3,3-difluoro-8-azabicyclo[3.2.1]octan-8-yl)pyrimidin-4-yl)amino)-3-(3-hydroxy-3-methylbutyl)-1-methyl-1,3-dihydro-2H-benzo[d]imidazol-2-one;

5-((5-chloro-2-(2,2-difluoro-7-azaspiro[3.5]nonan-7-yl)pyrimidin-4-yl)amino)-3-(3-hydroxy-3-methylbutyl)-1-methyl-1,3-dihydro-2H-benzo[d]imidazol-2-one;

5-((5-chloro-2-(4-(trifluoromethyl)piperidin-1-yl)pyrimidin-4-yl)amino)-3-(3-hydroxy-3-methylbutyl)-1-methyl-1,3-dihydro-2H-benzo[d]imidazol-2-one;

5-((5-chloro-2-(4,4-difluoropiperidin-1-yl)pyridin-4-yl)amino)-3-(3-hydroxy-3-methylbutyl)-1-methyl-1,3-dihydro-2H-benzo[d]imidazol-2-one;

5-((5-chloro-2-((2R,6S)-2,6-dimethylmorpholino)pyridin-4-yl)amino)-3-(3-hydroxy-3-methylbutyl)-1-methyl-1,3-dihydro-2H-benzo[d]imidazol-2-one;

1-(5-chloro-4-((3-(3-hydroxy-3-methylbutyl)-1-methyl-2-oxo-2,3-dihydro-1H-benzo[d]imidazol-5-yl)amino)pyridin-2-yl)-N,N-dimethylpiperidine-4-carboxamide;

(R)-2-chloro-4-((3-(3-hydroxybutyl)-1-methyl-2-oxo-2,3-dihydro-1H-benzo[d]imidazol-5-yl)amino)nicotinonitrile;

(S)-2-chloro-4-((3-((1-(2,2-difluoroethyl)pyrrolidin-2-yl)methyl)-1-methyl-2-oxo-2,3-dihydro-1H-benzo[d]imidazol-5-yl)amino)nicotinonitrile;

5-((5-chloro-2-(4,4-difluoro-3-(hydroxymethyl)piperidin-1-yl)pyrimidin-4-yl)amino)-3-(3-hydroxy-3-methylbutyl)-1-methyl-1,3-dihydro-2H-benzo[d]imidazol-2-one;

5-((5-chloro-2-(4,4-difluoro-3-(methoxymethyl)piperidin-1-yl)pyrimidin-4-yl)amino)-3-(3-hydroxy-3-methylbutyl)-1-methyl-1,3-dihydro-2H-benzo[d]imidazol-2-one;

5-((5-chloro-2-(4,4-difluoro-3-methylpiperidin-1-yl)pyrimidin-4-yl)amino)-3-(3-hydroxy-3-methylbutyl)-1-methyl-1,3-dihydro-2H-benzo[d]imidazol-2-one;

5-((5-chloro-2-(4-(trifluoromethyl)piperidin-1-yl)pyrimidin-4-yl)amino)-3-(3-hydroxy-3-methylbutyl)-1-methyl-1,3-dihydro-2H-benzo[d]imidazol-2-one;

5-((5-chloro-2-((3R,4S)-3,4-difluoropyrrolidin-1-yl)pyrimidin-4-yl)amino)-3-(3-hydroxy-3-methylbutyl)-1-methyl-1,3-dihydro-2H-benzo[d]imidazol-2-one;

5-((5-chloro-2-((3S,5R)-3,4,5-trimethylpiperazin-1-yl)pyrimidin-4-yl)amino)-3-(3-hydroxy-3-methylbutyl)-1-methyl-1,3-dihydro-2H-benzo[d]imidazol-2-one;

5-((2-((1R,5S)-8-azabicyclo[3.2.1]octan-8-yl)-5-chloropyrimidin-4-yl)amino)-3-(3-hydroxy-3-methylbutyl)-1-methyl-1,3-dihydro-2H-benzo[d]imidazol-2-one;

5-((2-((1R,5S)-3-azabicyclo[3.2.1]octan-3-yl)-5-chloropyrimidin-4-yl)amino)-3-(3-hydroxy-3-methylbutyl)-1-methyl-1,3-dihydro-2H-benzo[d]imidazol-2-one;

5-((5-chloro-2-((3aR,7aS)-octahydro-2H-isoindol-2-yl)pyrimidin-4-yl)amino)-3-(3-hydroxy-3-methylbutyl)-1-methyl-1,3-dihydro-2H-benzo[d]imidazol-2-one;

5-((5-chloro-2-((3R,4S)-3,4-dimethylpyrrolidin-1-yl)pyrimidin-4-yl)amino)-3-(3-hydroxy-3-methylbutyl)-1-methyl-1,3-dihydro-2H-benzo[d]imidazol-2-one;

6-((5-chloro-2-(2,2,6,6-tetramethylmorpholino)pyrimidin-4-yl)amino)-1,3-bis(3-hydroxy-3-methylbutyl)-1,3-dihydro-2H-imidazo[4,5-b]pyridin-2-one;

6-((5-chloro-2-((3R,5S)-4,4-difluoro-3,5-dimethylpiperidin-1-yl)pyrimidin-4-yl)amino)-1,3-bis(3-hydroxy-3-methylbutyl)-1,3-dihydro-2H-imidazo[4,5-b]pyridin-2-one;

5-((5-chloro-2-(8,8-difluoro-3-azabicyclo[3.2.1]octan-3-yl)pyrimidin-4-yl)amino)-3-(3-hydroxy-3-methylbutyl)-1-methyl-1,3-dihydro-2H-benzo[d]imidazol-2-one;

5-((2-((1r,3r,5r,7r)-2-azaadamantan-2-yl)-5-chloropyrimidin-4-yl)amino)-3-(3-hydroxy-3-methylbutyl)-1-methyl-1,3-dihydro-2H-benzo[d]imidazol-2-one;

4-chloro-6-((5-chloro-2-(2,2,6,6-tetramethylmorpholino)pyrimidin-4-yl)amino)-1,3-bis(3-hydroxy-3-methylbutyl)-1,3-dihydro-2H-benzo[d]imidazol-2-one;

5-((5-chloro-2-(3-(methoxymethyl)piperidin-1-yl)pyrimidin-4-yl)amino)-3-(3-hydroxy-3-methylbutyl)-1-methyl-1,3-dihydro-2H-benzo[d]imidazol-2-one;

5-((5-chloro-2-(6,6-difluoro-3-azabicyclo[3.1.1]heptan-3-yl)pyrimidin-4-yl)amino)-3-(3-hydroxy-3-methylbutyl)-1-methyl-1,3-dihydro-2H-benzo[d]imidazol-2-one;

5-((5-chloro-2-((3S,5R)-3-hydroxy-5-methylpiperidin-1-yl)pyrimidin-4-yl)amino)-3-(3-hydroxy-3-methylbutyl)-1-methyl-1,3-dihydro-2H-benzo[d]imidazol-2-one;

5-((5-chloro-2-((3R,5S)-3,5-dimethylazepan-1-yl)pyrimidin-4-yl)amino)-3-(3-hydroxy-3-methylbutyl)-1-methyl-1,3-dihydro-2H-benzo[d]imidazol-2-one;

5-((5-chloro-2-(3-phenylpiperidin-1-yl)pyrimidin-4-yl)amino)-3-(3-hydroxy-3-methylbutyl)-1-methyl-1,3-dihydro-2H-benzo[d]imidazol-2-one;

5-((2-(4-((1H-pyrazol-1-yl)methyl)piperidin-1-yl)-5-chloropyrimidin-4-yl)amino)-3-(3-hydroxy-3-methylbutyl)-1-methyl-1,3-dihydro-2H-benzo[d]imidazol-2-one;

5-((5-chloro-2-((3S,5R)-3,5-dimethylpiperidin-1-yl)pyridin-4-yl)amino)-3-(3-hydroxy-3-methylbutyl)-1-methyl-1,3-dihydro-2H-benzo[d]imidazol-2-one;

5-((5-chloro-2-((3R,5S)-3,5-dimethylpiperidine-1-carbonyl)pyridin-4-yl)amino)-3-(3-hydroxy-3-methylbutyl)-1-methyl-1,3-dihydro-2H-benzo[d]imidazol-2-one;

5-((5-chloro-2-((3S,5R)-4,4-difluoro-3,5-dimethylpiperidine-1-carbonyl)pyridin-4-yl)amino)-3-(3-hydroxy-3-methylbutyl)-1-methyl-1,3-dihydro-2H-benzo[d]imidazol-2-one;

5-((5-chloro-2-((3S,5R)-4,4-difluoro-3,5-dimethylpiperidin-1-yl)pyrimidin-4-yl)amino)-1-(2-(dimethylamino)ethyl)-3-(3-hydroxy-3-methylbutyl)-1,3-dihydro-2H-benzo[d]imidazol-2-one;

5-((5-chloro-2-((3S,5R)-4,4-difluoro-3,5-dimethylpiperidin-1-yl)pyrimidin-4-yl)amino)-3-(3-hydroxy-3-methylbutyl)-1-(2-morpholinoethyl)-1,3-dihydro-2H-benzo[d]imidazol-2-one;

Ethyl (E)-4-(5-((5-chloro-2-((3S,5R)-4,4-difluoro-3,5-dimethylpiperidin-1-yl)pyrimidin-4-yl)amino)-3-(3-hydroxy-3-methylbutyl)-2-oxo-2,3-dihydro-1H-benzo[d]imidazol-1-yl)but-2-enoate;

5-((5-Chloro-2-(2,2,2-trifluoroethoxy)pyrimidin-4-yl)amino)-3-(3-hydroxy-3-methylbutyl)-1-methyl-1,3-dihydro-2H-benzo[d]imidazol-2-one;

5-[[5-chloro-2-[(3S,5R)-4,4-difluoro-3,5-dimethyl-1-piperidyl]pyrimidin-4-yl]amino]-1-(2-hydroxyethyl)-3-(3-hydroxy-3-methyl-butyl)benzimidazol-2-one;

5-((5-chloro-2-((3S,5R)-4,4-difluoro-3,5-dimethylpiperidin-1-yl)pyrimidin-4-yl)amino)-1-(2,2-dimethoxyethyl)-3-(3-hydroxy-3-methylbutyl)-1,3-dihydro-2H-benzo[d]imidazol-2-one;

1-(5-chloro-4-((3-(3-hydroxy-3-methylbutyl)-1-methyl-2-oxo-2,3-dihydro-1H-benzo[d]imidazol-5-yl)amino)pyrimidin-2-yl)piperidine-4-carbonitrile;

1-(5-chloro-4-((3-(3-hydroxy-3-methylbutyl)-1-methyl-2-oxo-2,3-dihydro-1H-benzo[d]imidazol-5-yl)amino)pyrimidin-2-yl)piperidine-3-carbonitrile;

5-((5-chloro-2-(4-(morpholinomethyl)piperidin-1-yl)pyrimidin-4-yl)amino)-3-(3-hydroxy-3-methylbutyl)-1-methyl-1,3-dihydro-2H-benzo[d]imidazol-2-one;

5-((5-chloro-2-(3-(morpholinomethyl)piperidin-1-yl)pyrimidin-4-yl)amino)-3-(3-hydroxy-3-methylbutyl)-1-methyl-1,3-dihydro-2H-benzo[d]imidazol-2-one;

5-((5-chloro-2-(2-methyl-2,4,5,7-tetrahydro-6H-pyrazolo[3,4-c]pyridin-6-yl)pyrimidin-4-yl)amino)-3-(3-hydroxy-3-methylbutyl)-1-methyl-1,3-dihydro-2H-benzo[d]imidazol-2-one;

5-((5-chloro-2-(1-methyl-1,4,5,7-tetrahydro-6H-pyrazolo[3,4-c]pyridin-6-yl)pyrimidin-4-yl)amino)-3-(3-hydroxy-3-methylbutyl)-1-methyl-1,3-dihydro-2H-benzo[d]imidazol-2-one;

5-((5-chloro-2-(3-(hydroxymethyl)piperidin-1-yl)pyrimidin-4-yl)amino)-3-(3-hydroxy-3-methylbutyl)-1-methyl-1,3-dihydro-2H-benzo[d]imidazol-2-one;

5-((5-chloro-2-(4-morpholinopiperidin-1-yl)pyrimidin-4-yl)amino)-3-(3-hydroxy-3-methylbutyl)-1-methyl-1,3-dihydro-2H-benzo[d]imidazol-2-one;

5-((2-(4-(1H-pyrazol-1-yl)piperidin-1-yl)-5-chloropyrimidin-4-yl)amino)-3-(3-hydroxy-3-methylbutyl)-1-methyl-1,3-dihydro-2H-benzo[d]imidazol-2-one; or 5-((5-chloro-2-(2-(hydroxymethyl)morpholino)pyrimidin-4-yl)amino)-3-(3-hydroxy-3-methylbutyl)-1-methyl-1,3-dihydro-2H-benzo[d]imidazol-2-one.

13. A pharmaceutical composition comprising a compound according to claim 1, or a pharmaceutically acceptable salt or hydrate thereof and a pharmaceutically acceptable carrier or excipient.

14. A method for the treatment of cancer in a subject in need of such treatment, said method comprising administering a therapeutically effective amount of i) a compound according to claim 1 or a pharmaceutically acceptable salt or hydrate thereof, or ii) a pharmaceutical composition comprising a compound according to claim 1, or a pharmaceutically acceptable salt or hydrate thereof and a pharmaceutically acceptable carrier or excipient.

15. The method according to claim 14, wherein said cancer is diffuse large B-cell lymphoma (DLBCL), follicular lymphoma (FL), Burkitt lymphoma (BL), angioimmunoblastic T-cell lymphoma (AITL), acute lymphoblastic leukaemia (ALL), chronic myeloid leukaemia (CML), multiple myeloma, breast cancer, non-small cell lung cancer (NSCLC) or squamous cell carcinomas (SCC) of the head and neck, oesophagus, lung or ovary.

\* \* \* \* \*